United States Patent
Santora et al.

(10) Patent No.: US 11,685,745 B2
(45) Date of Patent: Jun. 27, 2023

(54) SUBSTITUTED BENZOXAZOLE AND BENZOFURAN COMPOUNDS AS PDE7 INHIBITORS

(71) Applicant: Dart NeuroScience, LLC, San Diego, CA (US)

(72) Inventors: Vincent John Santora, San Diego, CA (US); Mi Chen, San Diego, CA (US); DeMichael Chung, San Diego, CA (US)

(73) Assignee: Dart Neuroscience, LLC, Dallas, TX (US)

( * ) Notice: Subject to any disclaimer, the term of this patent is extended or adjusted under 35 U.S.C. 154(b) by 243 days.

(21) Appl. No.: 16/629,922

(22) PCT Filed: Jul. 11, 2018

(86) PCT No.: PCT/US2018/041565
§ 371 (c)(1),
(2) Date: Jan. 9, 2020

(87) PCT Pub. No.: WO2019/014305
PCT Pub. Date: Jan. 17, 2019

(65) Prior Publication Data
US 2022/0267351 A1 Aug. 25, 2022

Related U.S. Application Data

(60) Provisional application No. 62/531,802, filed on Jul. 12, 2017.

(51) Int. Cl.
*C07D 498/10* (2006.01)
*C07D 519/00* (2006.01)

(52) U.S. Cl.
CPC ........ *C07D 498/10* (2013.01); *C07D 519/00* (2013.01)

(58) Field of Classification Search
CPC ................ C07D 498/10; C07D 519/00
See application file for complete search history.

(56) References Cited

U.S. PATENT DOCUMENTS

| | | |
|---|---|---|
| 6,531,498 B1 | 3/2003 | Eggenweiler et al. |
| 6,613,778 B1 | 9/2003 | Eggenweiler et al. |
| 6,737,436 B1 | 5/2004 | Eggenweiler et al. |
| 6,884,800 B1 | 4/2005 | Eggenweiler et al. |
| 7,491,742 B2 | 2/2009 | Eggenweiler et al. |
| 7,507,742 B2 | 3/2009 | Rawson et al. |
| 7,932,250 B2 | 4/2011 | Inoue et al. |
| 2002/0091134 A1 | 7/2002 | Beck et al. |
| 2002/0193365 A1 | 12/2002 | Stack et al. |
| 2002/0198198 A1 | 12/2002 | Bernardelli et al. |
| 2004/0106631 A1 | 6/2004 | Bernardelli et al. |
| 2007/0129388 A1 | 6/2007 | Rawson et al. |
| 2009/0111837 A1 | 4/2009 | Cox et al. |
| 2010/0216823 A1 | 8/2010 | Rawson et al. |

FOREIGN PATENT DOCUMENTS

| | | |
|---|---|---|
| JP | 2004502774 A | 1/2004 |
| WO | WO 2001/098274 | 12/2001 |
| WO | WO 2002/074754 | 9/2002 |
| WO | WO 2007/063391 | 6/2007 |

OTHER PUBLICATIONS

Cancer and Metastasis Reviews (1998), 17(1), 91-106.*
Science (1999), vol. 286, 531-537.*
Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003], Retrieved from the internet, URL;http;//www.cnn/com/2003/HEALTH/conditions/09/24/alzheimers.drug.ap/index.html>.*
Huff, Joel R., Journal of Medicinal Chemistry, vol. 34, No. 8, Aug. 1991, pp. 2305-2314.*
Banerjee et al., 2012, Isothiazole and isoxazole fused pyrimidones as PDE7 inhibitors: SAR and pharmacokinetic evaluation. Bioorg Med Chem Lett. 22, 3223-3228.
Banerjee et al., 2012, Imidazopyridazinones as novel PDE7 inhibitors: SAR and in vivo studies in Parkinson's disease model. Bioorg Med Chem Lett. 22(19):6286-6291.

(Continued)

*Primary Examiner* — Rebecca L Anderson
(74) *Attorney, Agent, or Firm* — Knobbe, Martens, Olson & Bear LLP

(57) ABSTRACT

Substituted benzoxazole and benzofuran chemical entities of Formula (I): wherein, V, W, X, Y, Z, and m have any of the values described herein and compositions comprising such chemical entities; processes for making them; and their use in a wide range of methods, including metabolic and reaction kinetic studies; detection and imaging techniques; radioactive treatments; and the treatment of one or more disorders, including neurological, cognitive, immunological, and inflammatory disorders, as well as other conditions and diseases involving PDE7 or cyclic nucleotide signaling.

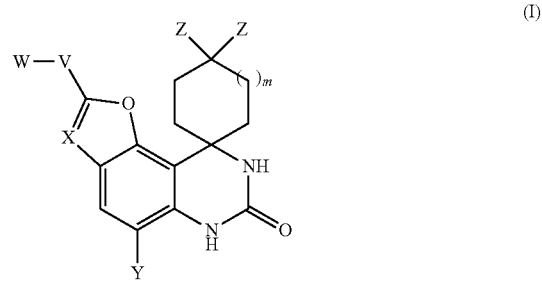

(I)

32 Claims, No Drawings

(56) References Cited

OTHER PUBLICATIONS

Barnes et al., 2001, Synthesis and structure-activity relationships of guanine analogues as phosphodiesterase 7 (PDE7) inhibitors. Bioorg Med Chem Lett. 11(8):1081-1083.

Bernardelli et al., 2004, Spiroquinazolinones as novel, potent, and selective PDE7 inhibitors. Part 2: Optimization of 5,8-disubstituted derivatives. Bioorg Med Chem Lett. 14(18):4627-4631.

Castro et al., 2001, CoMFA of benzyl derivatives of 2,1,3-benzo and benzothieno[3,2-a]thiadiazine 2,2-dioxides: clues for the design of phosphodiesterase 7 inhibitors. Eur J Med Chem. 36(4):333-338.

Endo et al., 2015, Discovery and SAR study of 2-(4-pyridylamino)thieno[3,2-d]pyrimidin-4(3H)-ones as soluble and highly potent PDE7 inhibitors. Bioorg Med Chem Lett. 25(3):649-653.

Garcia et al., 2014, Modulation of cAMP-specific PDE without emetogenic activity: new sulfide-like PDE7 inhibitors. J Med Chem. 57(2):8590-8607.

Gewald et al., 2011, Synthesis and structure-activity relationship studies of dihydronaphthyridinediones as a novel structural class of potent and selective PDE7 inhibitors. Bioorg Med Chem Lett. 21(22):6652-6656.

Jankowska et al., 2017, PDE7-Selective and Dual Inhibitors: Advances in Chemical and Biological Research. Curr Med Chem. 24(7):673-700.

Kempson et al., 2005, Fused pyrimidine based inhibitors of phosphodiesterase 7 (PDE7): synthesis and initial structure-activity relationships. Bioorg Med Chem Lett. 15(7):1829-1833.

Lorthiois et al., 2004, Spiroquinazolinones as novel, potent, and selective PDE7 inhibitors. Part 1. Bioorg Med Chem Lett. 14(18):4623-4626.

Pitts et al., 2004, Identification of purine inhibitors of phosphodiesterase 7 (PDE7). Bioorg Med Chem Lett. 14(11):2955-2958.

Redondo et al., 2012, Effect of phosphodiesterase 7 (PDE7) inhibitors in experimental autoimmune encephalomyelitis mice. Discovery of a new chemically diverse family of compounds. J Med Chem. 55(7):3274-3284 in 48 pages.

Sánchez et al., 2014, Microwave-assisted synthesis of potent PDE7 inhibitors containing a thienopyrimidin-4-amine scaffold. Org Biomol Chem. 12(24):4233-4242.

Vergne et al., 2004, Discovery of thiadiazoles as a novel structural class of potent and selective PDE7 inhibitors. Part 1: design, synthesis and structure-activity relationship studies. Bioorg Med Chem Lett. 14(18):4607-4613.

Vergne et al., 2004, Discovery of thiadiazoles as a novel structural class of potent and selective PDE7 inhibitors. Part 2: metabolism-directed optimization studies towards orally bioavailable derivatives. Bioorg Med Chem Lett. 14, 4615-4621.

International Search Report and Written Opinion dated Aug. 31, 2018 for corresponding PCT/US2018/041565.

Dong et al. (2010) Inhibition of PDE3, PDE4 and PDE7 potentiates glucocorticoid induced apoptosis and overcomes glucocorticoid resistance in CEM T leukemic cells. Biochem Pharmacol. 79(3): 321-329.

\* cited by examiner

SUBSTITUTED BENZOXAZOLE AND BENZOFURAN COMPOUNDS AS PDE7 INHIBITORS

CROSS REFERENCE TO RELATED APPLICATIONS

This application is U.S. National Phase under 35 U.S.C. § 371 of International Application No. PCT/US2018/041565, filed Jul. 11, 2018, designating the U.S. and published in English as International Pub. No. WO 2019/014305, which claims the benefit of U.S. Provisional Application No. 62/531,802, filed Jul. 12, 2017.

BACKGROUND

Field

The present disclosure relates to certain substituted benzoxazole and benzofuran compounds, and related chemical entities; compositions containing them; processes for making them; and their use in various methods and therapies, including the enhancement of neuroplasticity, and the treatment of neurological, cognitive, allergic, immunological, inflammatory disorders, and other conditions and diseases involving PDE7 or cyclic nucleotide signaling.

Description of the Related Technology

The cyclic nucleotides, adenosine and guanosine 3',5'-cyclic monophosphate (cAMP and cGMP) are ubiquitous second messengers in cellular signaling cascades activated by diverse transduction pathways, such as those triggered by neurotransmitters and hormones. See, e.g., Kelly and Brandon, 2009, *Prog. Brain Res.* 179, 67-73; Schmidt, 2010, *Curr. Top. Med. Chem.* 10, 222-230. Once generated, cAMP and cGMP transmit their signals through various tertiary effectors, such as cAMP dependent protein kinase (PKA), cGMP dependent protein kinase (PKG), and other proteins. In turn, these effectors modulate additional targets in downstream cascades, such as enzymes and transcription factors, ultimately resulting in cellular changes that impact numerous physiological processes, including neuronal plasticity, muscle contraction, sensory transduction, cell division, and inflammation.

Cyclic nucleotide levels are subject to tight regulatory controls, including the action of phosphodiesterases (PDEs), a superfamily of intracellular enzymes that hydrolyze cAMP and cGMP to their inactive non-cyclic forms, 5'-AMP and 5'-GMP. See, e.g., Bender and Beavo, 2006, *Pharmacol. Rev.* 58, 488-520. Mammalian PDEs can be divided into 11 families, PDE1-11, based on structural, biochemical, and pharmacological properties. Some are cAMP-selective hydrolases (PDE4, 7, and 8), some are cGMP-selective hydrolases (PDE5, 6, and 9), and some hydrolyze both cAMP and cGMP (PDE1, 2, 3, 10, and 11). By regulating cAMP and cGMP levels, PDEs play a key role in modulating cyclic nucleotide cascades, and they have become desirable targets for treating various diseases and disorders due to their different tissue distribution and functional properties. See, e.g., Keravis and Lugnier, 2001, *Br. J. Pharmacol.* 165, 1288-1305. Alterations in cyclic nucleotide concentrations, for example, can impact biochemical and physiological process linked to cognitive function (Kelly and Brandon, 2009, *Prog. Brain Res.* 179, 67-73; Schmidt, 2010, *Curr. Top. Med. Chem.* 10, 222-230; Perez-Gonzalez et al., 2013, *Neurobiol. Aging.* 34, 2133-2145; Lipina et al., 2013, *Neuropharmacology* 64, 295-214; Morales-Garcia et al., 2016, *Stem Cells.* 35, 458-472).

The PDE7 family specifically hydrolyzes cAMP, is insensitive to rolipram—a specific inhibitor of the cAMP PDE4 family, and includes two genes, PDE7A and PDE7B, which give rise to multiple isoforms and show overlapping but distinct expression patterns throughout the body. See, e.g., Jankowska et al., 2017, *Curr. Med. Chem.* 24, 1-28. In the brain, PDE7 is expressed in neuronal and non-neuronal cells, with elevated levels observed in multiple regions, including the hippocampus, cerebral cortex, basal ganglia, midbrain, and temporal lobe. Outside the brain, PDE7 is expressed in numerous areas, including skeletal muscle, heart, kidney, pancreas, lungs, and bronchi, as well as the immune system, where it is found in lymphocytes and elevated in activated T-cells.

Such expression patterns implicate PDE7 in numerous biological processes. PDE7 inhibition can reduce inflammatory responses following various insults in vivo and in vitro, suggesting therapeutic approaches for treating CNS and peripheral disorders, including neurodegenerative, traumatic, and immunological disorders. Moreover, by modulating cAMP levels, PDE7 can regulate cognitive processes, such as those underlying memory formation, which involve cAMP activation of PKA, which in turn can phosphorylate cAMP response element-binding protein (CREB). Phosphorylated CREB is an activated transcription factor that binds to specific DNA loci and initiates transcription of multiple genes involved in neuronal plasticity and memory formation.

These and other studies highlight the interest in PDE7 as a target for treating numerous disorders and modulating physiological processes, such as cognition. There is a substantial need for PDE7 inhibitors with desirable pharmacological and therapeutic properties, such as effective potency, exposure, selectivity, and safety. The present invention addresses these and other needs in the art by disclosing substituted benzoxazole and benzofuran chemical entities as potent, selective, and well-tolerated PDE7 inhibitors.

SUMMARY

The present disclosure relates to substituted benzoxazole and benzofuran chemical entities, compositions including such entities, processes for making them, and their use in various methods, including the treatment of neurological and peripheral disorders associated with phosphodiesterase 7 (PDE7).

Some embodiments provide a chemical entity of Formula (I), and more specifically, a compound, or pharmaceutically acceptable salt of a compound of Formula (I):

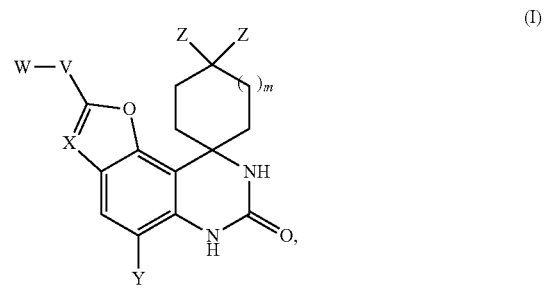

wherein, V, W, X, Y, Z, and m have any of the values described herein.

In some embodiments, a chemical entity of Formula (I) is a chemical entity of Formula (Ia), or more specifically, a compound or a pharmaceutically acceptable salt of a compound of Formula (Ia):

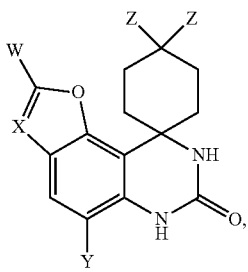
(Ia)

wherein W, X, Y, and Z have any of the values described herein.

In some embodiments, a chemical entity of Formula (I) is a chemical entity of Formula (Ib), or more specifically, a compound or a pharmaceutically acceptable salt of a compound of Formula (Ib):

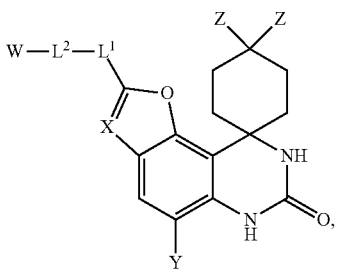
(Ib)

wherein W, $L^1$, $L^2$, X, Y, and Z have any of the values described herein.

Some embodiments provide a chemical entity of Formula (II), or more specifically, a compound, or pharmaceutically acceptable salt of a compound of Formula (II):

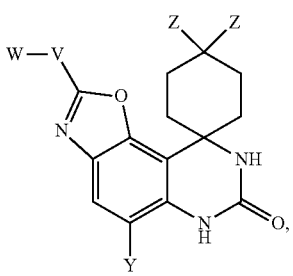
(II)

wherein V, W, Y, and Z have any of the values described herein.

In some embodiments, a chemical entity of Formula (II) is a chemical entity of Formula (IIa) or Formula (IIb), or more specifically, a compound or a pharmaceutically acceptable salt of a compound of Formula (IIa) or Formula (IIb):

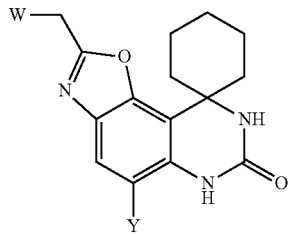
(IIa)

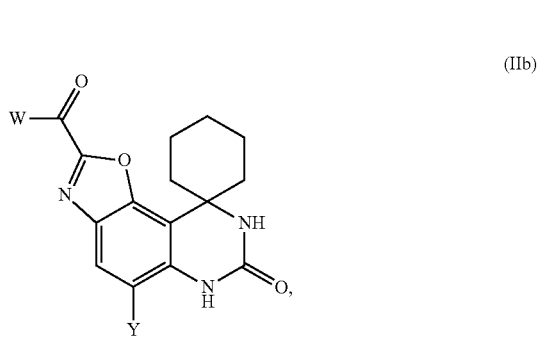
(IIb)

wherein W and Y have any of the values described herein.

Some embodiments provide a chemical entity of Formula (III), or more specifically, a compound, or pharmaceutically acceptable salt of a compound of Formula (III):

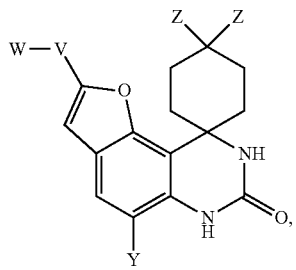
(III)

wherein V, W, Y, and Z have any of the values described herein.

In some embodiments, a chemical entity of Formula (III) is a chemical entity of Formula (IIIa) or Formula (IIIb), or more specifically, a compound or a pharmaceutically acceptable salt of a compound of Formula (IIIa) or Formula (IIIb):

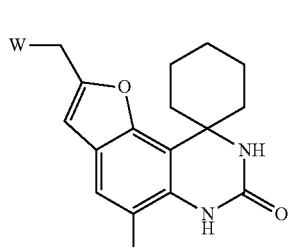
(IIIa)

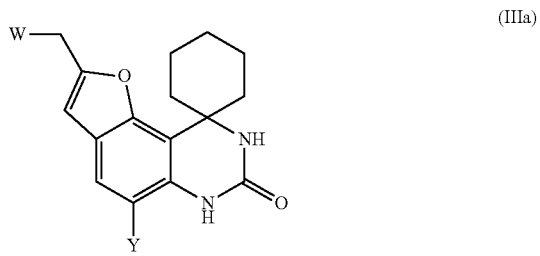

-continued

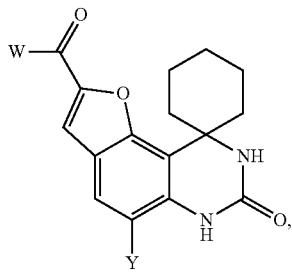

(IIIb)

wherein W and Y have any of the values described herein.

In certain embodiments, a chemical entity is selected from any of the species described or exemplified herein, and more particularly, is a compound, or pharmaceutically acceptable salt thereof.

In some embodiments, the chemical entities, and compositions including such entities, are used in a wide range of methods, as described herein. In some embodiments, the methods include metabolic and reaction kinetic studies, detection and imaging techniques, and radioactive treatments. In some embodiments, the methods include inhibiting PDE7, treating disorders mediated by PDE7, enhancing neuronal plasticity, conferring neuroprotection, and reducing inflammation. In some embodiments, the methods include treating neurological disorders, particularly CNS disorders, and more particularly, mental and psychiatric disorders, cognitive disorders, movement disorders, and neurodegenerative disorders. In some embodiments, the methods are directed to treating peripheral disorders, including infectious diseases, hematological disorders, cardiovascular diseases, gastroenterological disorders, dermatological disorders, immunological and inflammatory disorders, and fertility disorders.

In some embodiments, the chemical entities, and compositions including such entities, are useful as augmenting agents to increase the efficiency of cognitive and motor training, including training during post-stroke rehabilitation or post-traumatic brain injury (TBI) rehabilitation; and to increase the efficiency of non-human animal training protocols.

The disclosure is further directed to the general and specific embodiments defined, respectively, and by the independent and dependent claims appended hereto, which are incorporated by reference herein. Additional embodiments, features, and advantages of the disclosure will be apparent from the following detailed description and through practice of the exemplary embodiments.

DETAILED DESCRIPTION

The embodiments may be more fully appreciated by reference to the following description, including the examples. Unless otherwise defined, all technical and scientific terms used herein have the same meaning as commonly understood by one of ordinary skill in the art. Although methods and materials similar or equivalent to those described herein can be used in the practice or testing of the present embodiments, suitable methods and materials are described herein. In addition, the materials, methods, and examples are illustrative only and not intended to be limiting.

For the sake of brevity, all publications, including patent applications, patents, and other citations mentioned herein, are incorporated by reference in their entirety. Citation of any such publication, however, is not to be construed as an admission that it is prior art to the present embodiments.

Terms and Definitions

The use of headings and subheadings provided in the sections of this specification is solely for convenience of reference and does not limit the various embodiments herein, which are to be construed by reference to the specification as a whole.

General

As used herein, the term "about" or "approximately" means within an acceptable range for a particular value as determined by one skilled in the art, and may depend in part on how the value is measured or determined, e.g., the limitations of the measurement system or technique. For example, "about" can mean a range of up to 20%, up to 10%, up to 5%, or up to 1% or less on either side of a given value. To provide a more concise description, some of the quantitative expressions given herein are not qualified with the term "about." It is understood that, whether the term "about" is used explicitly or not, every quantity given herein is meant to refer to both the actual given value and the approximation of such given value that would reasonably be inferred based on the ordinary skill in the art, including equivalents and approximations due to the experimental and/or measurement conditions for such given value. Accordingly, for any embodiment of the invention in which a numerical value is prefaced by "about" or "approximately", the disclosure includes an embodiment in which the exact value is recited. Conversely, for any embodiment of the invention in which a numerical value is not prefaced by "about" or "approximately", the disclosure includes an embodiment in which the value is prefaced by "about" or "approximately".

As used herein, the terms "a," "an," and "the" are to be understood as meaning both singular and plural, unless explicitly stated otherwise. Thus, "a," "an," and "the" (and grammatical variations thereof where appropriate) refer to one or more. Furthermore, although items, elements or components of the embodiments may be described or claimed in the singular, the plural is contemplated to be within the scope thereof, unless limitation to the singular is explicitly stated.

The terms "comprising" and "including" are used herein in their open, non-limiting sense. Other terms and phrases used in this document, and variations thereof, unless otherwise expressly stated, should be construed as open ended, as opposed to limiting. As examples of the foregoing: the term "example" is used to provide exemplary instances of the item in discussion, not an exhaustive or limiting list thereof; adjectives such as "conventional", "normal", "known", and terms of similar meaning should not be construed as limiting the item described to a given time period or to an item available as of a given time, but instead should be read to encompass conventional, or normal technologies that may be available or known now or at any time in the future. Likewise, where this document refers to technologies that would be apparent or known to one of ordinary skill in the art, such technologies encompass those apparent or known to the skilled artisan now or at any time in the future.

As will become apparent to one of ordinary skill in the art after reading this document, the illustrated embodiments and their various alternatives may be implemented without confinement to the illustrated examples.

Chemical Terms

The term "alkyl" refers to a fully saturated aliphatic hydrocarbon group (i.e., contains no double or triple bonds). The alkyl moiety may be a straight- or branched-chain alkyl group having from 1 to 12 carbon atoms in the chain. Examples of alkyl groups include, but are not limited to, methyl (Me, which also may be structurally depicted by the symbol, " ▬ "), ethyl (Et), n-propyl, isopropyl, butyl, isobutyl, sec-butyl, tert-butyl (tBu), pentyl, isopentyl, tert-pentyl, hexyl, and isohexyl. Alkyl groups may be optionally substituted with one or more substituents including, but not limited to, hydroxyl, alkoxy, thioalkoxy, amino, aminoalkyl, and cyano.

The term "alkenyl" refers to unsaturated acyclic aliphatic moieties having at least one carbon-carbon double bond. The term alkenyl includes all possible geometric isomers, including E and Z isomers of said alkenyl moiety, unless specifically indicated. Examples of alkenyl radicals include ethenyl, propenyl, butenyl, 1,4-butadienyl, and the like.

The term "alkynyl" refers to optionally substituted unsaturated acyclic aliphatic moieties having at least one carbon-carbon triple bond. Examples of alkynyl radicals include ethynyl, propynyl, butynyl and the like.

The term "haloalkyl" refers to a straight- or branched-chain alkyl group having from 1 to 12 carbon atoms in the chain substituting one or more hydrogens with halogens. Examples of haloalkyl groups include, but are not limited to, —CF$_3$, —CHF$_2$, —CH$_2$F, —CH$_2$CF$_3$, —CH$_2$CHF$_2$, —CH$_2$CH$_2$F, —CH$_2$CH$_2$Cl, and —CH$_2$CF$_2$CF$_3$.

The term "alkoxy" includes a straight chain or branched alkyl group with an oxygen atom linking the alkyl group to the rest of the molecule. Examples of alkoxy groups include, but are not limited to, methoxy, ethoxy, propoxy, isopropoxy, butoxy, t-butoxy, and pentoxy. "Aminoalkyl," "thioalkyl," and "sulfonylalkyl" are analogous to alkoxy, replacing the terminal oxygen atom of alkoxy with, respectively, NH (or NR), S, and SO$_2$ where R is selected from hydrogen, C$_{1-6}$alkyl, C$_{2-6}$alkenyl, C$_{2-6}$ alkynyl, C$_{3-7}$cycloalkyl, phenyl, 5-, 6-, 9-, or 10-membered heteroaryl, and 5-10 membered heterocycloalkyl, as defined herein.

The term "haloalkoxy" refers to alkoxy groups substituting one or more hydrogens with halogens. Examples of haloalkoxy groups include, but are not limited to, —OCF$_3$, —OCHF$_2$, —OCH$_2$F, —OCH$_2$CF$_3$, —OCH$_2$CHF$_2$, —OCH$_2$CH$_2$Cl, —OCH$_2$CF$_2$CF$_3$, and —OCH(CH$_3$)CHF$_2$.

The term "amino group" refers to an —NH$_2$ group.

The term "cyano" refers to the group —CN.

The term "aryl" refers to a monocyclic, or fused or spiro polycyclic, aromatic carbocycle (ring structure having ring atoms that are all carbon), having from 3 to 15 ring atoms per ring (carbon atoms in aryl groups are sp$^2$ hybridized). Illustrative examples of aryl groups include the following moieties:

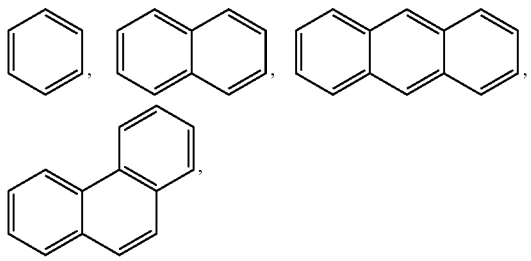

and the like.

The term "phenyl" represents the following moiety:

The term "aryloxy" refers to a group having the formula, —O—R, wherein R is an aryl group.

The term "cycloalkyl" refers to a fully saturated or partially saturated carbocycle, such as monocyclic, fused polycyclic, bridged monocyclic, bridged polycyclic, spirocyclic, or spiro polycyclic carbocycle having from 3 to 15 ring atoms per carbocycle. Where the term cycloalkyl is qualified by a specific characterization, such as monocyclic, fused polycyclic, bridged polycyclic, spirocyclic, and spiro polycyclic, then such term cycloalkyl refers only to the carbocycle so characterized. Illustrative examples of cycloalkyl groups include the following entities, in the form of properly bonded moieties:

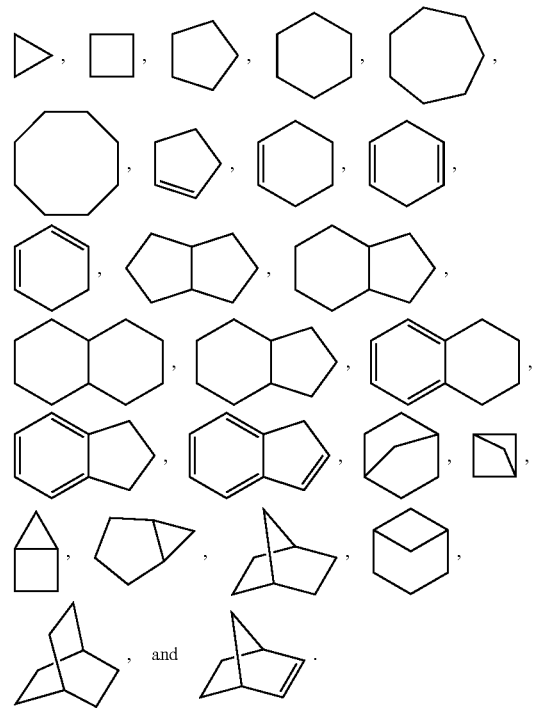

A "heterocycloalkyl" refers to a monocyclic, or fused, bridged, or spiro polycyclic ring structure that is fully saturated or partially saturated and at least one heteroatom selected from nitrogen, oxygen, and sulfur in the ring backbone. A heterocycloalkyl may have any degree of saturation provided that at least one ring in the ring system is not aromatic. The heteroatom(s) may be present in either a non-aromatic or aromatic ring in the ring system. The heterocycloalkyl group may have 3 to 20 ring members (i.e., the number of atoms making up the ring backbone, including carbon atoms and heteroatoms), although the present definition also covers the occurrence of the term "heterocycloalkyl" where no numerical range is designated. The heterocycloalkyl group may be designated as "3-15 membered heterocycloalkyl," "4-10 membered heterocycloalkyl," "3-15 membered C$_{2-14}$heterocycloalkyl," "5-9 membered C$_{4-8}$heterocycloalkyl," "5-10 membered C$_{4-9}$heterocycloalkyl," "5-membered C$_{3-4}$heterocycloalkyl," "6-membered C$_{4-5}$heterocycloalkyl," "7-membered C$_{5-6}$heterocycloalkyl," or similar designations. The heterocycloalkyl may be a 5-10 membered ring or ring system comprising one to four heteroatoms each independently selected from nitrogen, oxygen, and sulfur. The heterocycloalkyl may be a monocyclic five-membered ring comprising one to three heteroatoms each independently selected from nitrogen, oxygen, and sulfur. The heterocycloalkyl may be a monocyclic six-membered ring comprising one to three heteroatoms each independently selected from nitrogen, oxygen, and sulfur. The heterocycloalkyl may be a bicyclic nine-membered ring comprising one to three heteroatoms each independently selected from nitrogen, oxygen, and sulfur. The heterocycloalkyl may be a bicyclic ten-membered ring comprising one to three heteroatoms each independently selected from nitrogen, oxygen, and sulfur. The heterocycloalkyl may be optionally substituted. Illustrative unsubstituted heterocycloalkyl entities, in the form of properly bonded moieties, include:

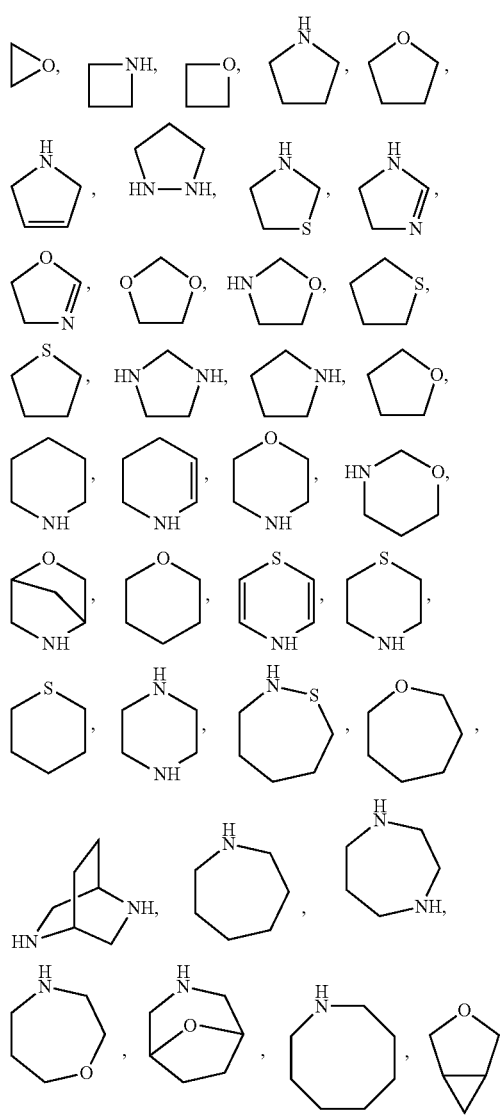

-continued

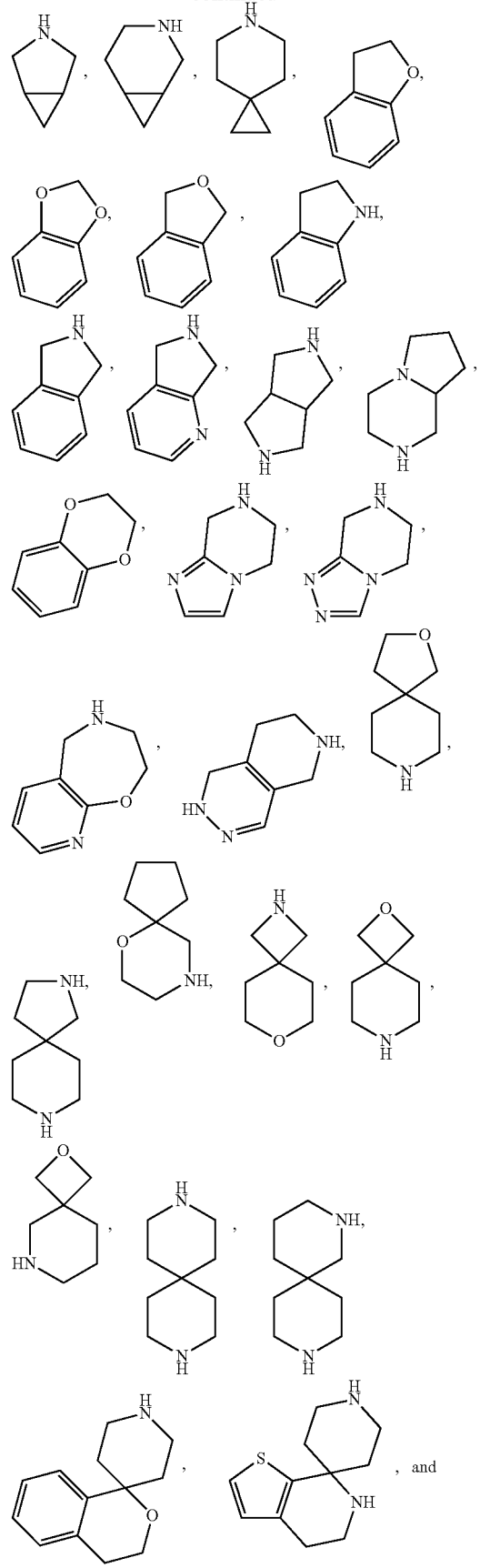

, and

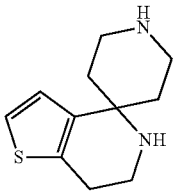

Illustrative carbon or sulfur oxo-substituted heterocycloalkyl entities, in the form of properly bonded moieties, include:

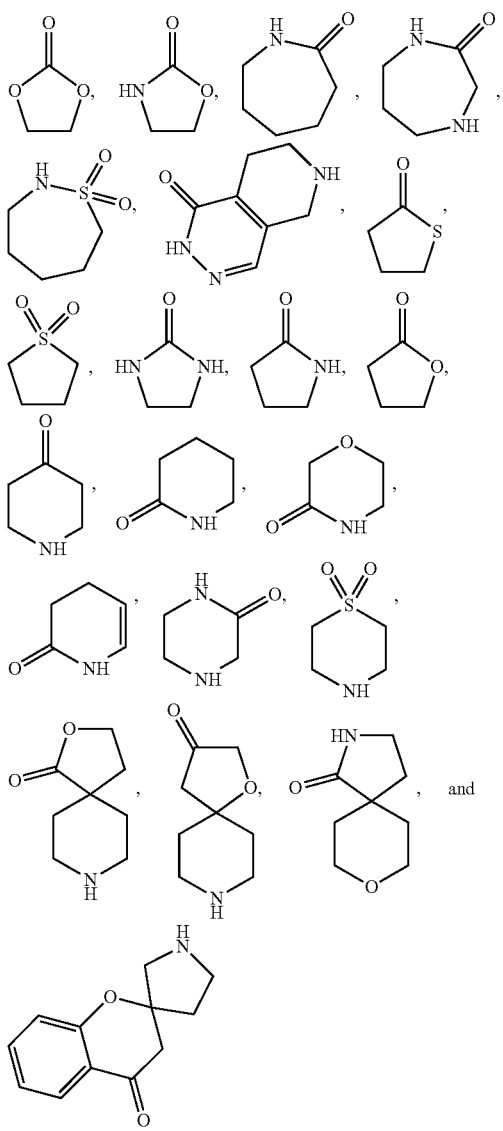

and

The term "heteroaryl" refers to an aromatic monocyclic, fused bicyclic, or fused polycyclic ring or ring system having one or more heteroatoms selected from nitrogen, oxygen, and sulfur in the ring backbone. When the heteroaryl is a ring system each ring in the ring system is fully unsaturated. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members. The heteroaryl group may be designated as "5-9 membered heteroaryl," "5-10 membered heteroaryl," "5-9 membered $C_{4-8}$heteroaryl," "5-10 membered $C_{4-9}$heteroaryl," or similar designations. The heteroaryl may be a 5-10 membered ring or ring system comprising one to four heteroatoms each independently selected from nitrogen, oxygen, and sulfur. The heteroaryl may be a monocyclic five-membered ring comprising one to four heteroatoms each independently selected from nitrogen, oxygen, and sulfur. The heteroaryl may be a monocyclic six-membered ring comprising one to four heteroatoms each independently selected from nitrogen, oxygen, and sulfur. The heteroaryl may be a bicyclic nine-membered ring comprising one to four heteroatoms each independently selected from nitrogen, oxygen, and sulfur. The heteroaryl may be a bicyclic ten-membered ring comprising one to four heteroatoms each independently selected from nitrogen, oxygen, and sulfur. In some embodiments, the heteroaryl may be a tautomer of a heterocycloalkyl where the heteroaryl is the predominate form under equilibrium conditions. Illustrative examples of heteroaryl groups include the following entities, in the form of properly bonded moieties:

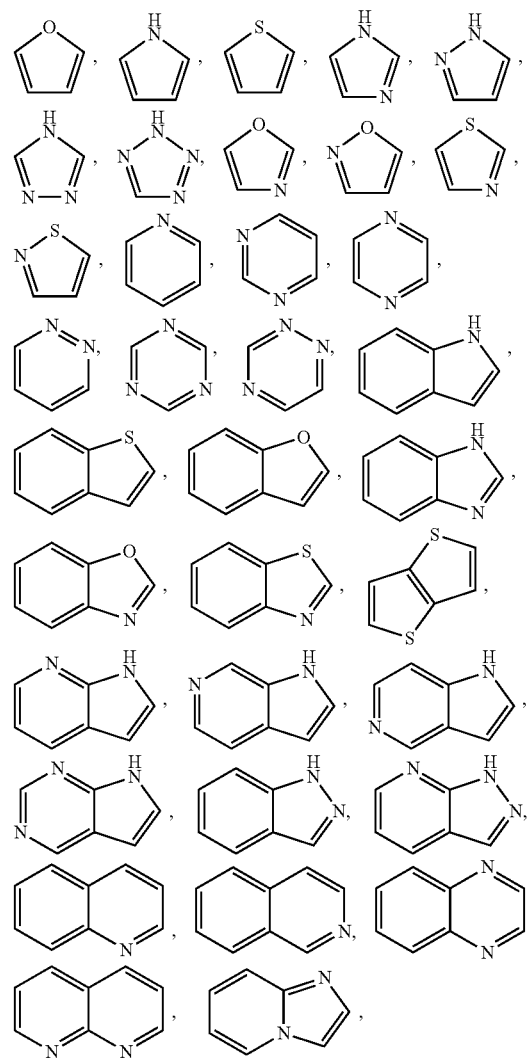

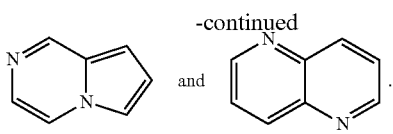

Those skilled in the art will recognize that the species of aryl, cycloalkyl, heterocycloalkyl, and heteroaryl groups listed or illustrated above are not exhaustive, and that additional species within the scope of these defined terms may also be selected.

The term "halogen" represents chlorine, fluorine, bromine or iodine. The term "halo" represents chloro, fluoro, bromo or iodo.

The term "heteroatom" used herein refers to, for example, O (oxygen), S (sulfur), or N (nitrogen).

By "optional" or "optionally" is meant that the subsequently described event or circumstance may or may not occur, and that the description includes instances where the event or circumstance occurs and instances or circumstances where it does not. For example, "optionally substituted alkyl" encompasses both "unsubstituted alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

The term "substituted" means that the specified group or moiety bears one or more substituents. A substituted group is derived from the unsubstituted parent group in which there has been an exchange of one or more hydrogen atoms for another atom or group or derived from the unsubstituted parent group in which there has been an addition of one or more atoms or group to a carbon, nitrogen or sulfur. Where the term "substituted" is used to describe a structural system, unless specified otherwise, the substitution is meant to occur at any valency-allowed position on the system. The term "unsubstituted" means that the specified group bears no substituents.

Any formula given herein is intended to represent compounds having structures depicted by the structural formula as well as certain variations or forms. In particular, compounds of any formula given herein may have asymmetric centers and therefore exist in different enantiomeric forms. All optical isomers and stereoisomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers.

As used herein, "tautomer" refers to the migration of protons between adjacent single and double bonds. The tautomerization process is reversible. Compounds described herein can undergo any possible tautomerization that is within the physical characteristics of the compound. The following is an example tautomerization that can occur in compounds described herein:

The symbols ▬▬ and ▬▬◀ are used as meaning the same spatial arrangement in chemical structures shown herein. Analogously, the symbols ⋅⋅⋅⋅⋅⋅ and ⋅⋅⋅⋅⋅⋅ are used as meaning the same spatial arrangement in chemical structures shown herein.

The term "chiral" refers to molecules, which have the property of non-superimposability of the mirror image partner.

"Stereoisomers" are compounds, which have identical chemical constitution, but differ with regard to the arrangement of the atoms or groups in space.

A "diastereomer" is a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis, crystallization in the presence of a resolving agent, or chromatography, using, for example a chiral HPLC column.

"Enantiomers" refer to two stereoisomers of a compound, which are non-superimposable mirror images of one another. A 50:50 mixture of enantiomers is referred to as a racemic mixture or a racemate, which may occur where there has been no stereoselection or stereospecificity in a chemical reaction or process.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., Stereochemistry of Organic Compounds (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory.

A "racemic mixture" or "racemate" is an equimolar (or 50:50) mixture of two enantiomeric species, devoid of optical activity. A racemic mixture may occur where there has been no stereoselection or stereospecificity in a chemical reaction or process.

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

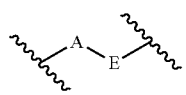

includes the substituent being oriented such that the A is attached at the leftmost attachment point of the molecule as well as the case in which A is attached at the rightmost attachment point of the molecule.

Chemical Entities

As used herein, the term "chemical entity" collectively refers to a compound, along with all pharmaceutically acceptable forms thereof, including pharmaceutically acceptable salts, chelates, solvates, conformers, crystalline forms/polymorphs, tautomers, prodrugs, metabolites, and mixtures thereof. In some embodiments, the chemical entity is selected from the group consisting of a compound and pharmaceutically acceptable salts thereof.

Chelates

The term "chelate" refers to the chemical entity formed by the coordination of a compound to a metal ion at two (or more) points.

Solvates

Additionally, any formula given herein is intended to refer also to hydrates and solvates of compounds herein, and mixtures thereof, even if such forms are not listed explicitly. Some embodiments provide a solvate of a compound of Formula (I), (II), or (III), and the use of such solvates in methods described herein. Certain compounds of Formula (I), (II), or (III), or pharmaceutically acceptable salts of compounds of Formula (I), (II), or (III), may be obtained as solvates. In some embodiments, the solvent is water and the solvates are hydrates.

More particularly, solvates include those formed from the interaction or complexes of compounds of the embodiments with one or more solvents, either in solution or as a solid or crystalline form. Such solvent molecules are those commonly used in the pharmaceutical art, which are known to be innocuous to the recipient, e.g., water, ethanol, ethylene glycol, and the like. Other solvents may be used as intermediate solvates in the preparation of more desirable solvates, such as methanol, methyl t-butyl ether, ethyl acetate, methyl acetate, (S)-propylene glycol, (R)-propylene glycol, 1,4-butyne-diol, and the like. Hydrates include a molecule of a compound associated with one or more water molecules.

Conformers and Crystalline Forms/Polymorphs

Some embodiments provide conformer and crystalline forms of a compound of Formula (I), (II), or (III), and their use in methods of the present disclosure. A conformer is a structure that is a conformational isomer.

Conformational isomerism is the phenomenon of molecules with the same structural formula but different conformations (conformers) of atoms about a rotating bond.

A polymorph is solid material of a specific chemical formula that can exist in more than one form, where each form is different from the other form(s). In certain embodiments, compounds of Formula (I), (II), or (III), are obtained in crystalline form. In addition, certain crystalline forms of compounds of Formula (I), (II), or (III), or pharmaceutically acceptable salts of compounds of Formula (I), (II), or (III), may be obtained as co-crystals. In still other embodiments, compounds of Formula (I), (II), or (III), may be obtained in one of several polymorphic forms, as a mixture of crystalline forms, as a polymorphic form, or as an amorphous form.

Compounds

As used herein, a "compound" refers to any one of: (a) the actually recited form of such compound; and (b) any of the forms of such compound in the medium in which the compound is being considered when named. For example, reference herein to a compound such as R—COOH encompasses reference to any one of, for example, R—COOH(s), R—COOH(sol), and R—COO-(sol). In this example, R—COOH(s) refers to the solid compound, as it could be for example in a tablet or some other solid pharmaceutical composition or preparation; R—COOH(sol) refers to the undissociated form of the compound in a solvent; and R—COO-(sol) refers to the dissociated form of the compound in a solvent, such as the dissociated form of the compound in an aqueous environment, whether such dissociated form derives from R—COOH, from a salt thereof, or from any other entity that yields R—COO— upon dissociation in the medium being considered.

In another example, an expression such as "exposing an entity to a compound of formula R—COOH" refers to the exposure of such entity to the form, or forms, of the compound R—COOH that exists, or exist, in the medium in which such exposure takes place. In still another example, an expression such as "reacting an entity with a compound of formula R—COOH" refers to the reacting of (a) such entity in its chemically relevant form (or forms) that exists in the medium in which such reacting takes place, with (b) the chemically relevant form (or forms) of the compound R—COOH that exists in the medium in which such reacting takes place. In this regard, if such entity is, for example, in an aqueous environment, it is understood that the compound R—COOH is in the same such medium, and therefore the entity is being exposed to species such as R—COOH(aq) and/or R—COO-(aq), where the subscript "(aq)" stands for "aqueous" according to its conventional meaning in chemistry and biochemistry. A carboxylic acid functional group has been chosen in these nomenclature examples; this choice is not intended, however, as a limitation but is merely an illustration. It is understood that analogous examples can be provided in terms of other functional groups, including, but not limited to, hydroxyl, basic nitrogen members, such as those in amines, and any other group that interacts or transforms according to known manners in the medium that contains the compound. Such interactions and transformations include, but are not limited to, dissociation, association, tautomerism, solvation, including hydration, protonation and deprotonation. No further examples in this regard are provided herein because these interactions and transformations in a given medium are known by any one of ordinary skill in the art.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of species for the same variable elsewhere in the formula, unless otherwise stated.

Salts

Embodiments include pharmaceutically acceptable salts of the compounds represented by Formula (I), (II), or (III), and methods using such salts.

A "pharmaceutically acceptable salt" is intended to mean a salt of a free acid or base of a compound represented by Formula (I), (II), or (III), that is non-toxic, biologically tolerable, or otherwise biologically suitable for administration to the subject. See, generally, G. S. Paulekuhn et al., 2007, *J. Med. Chem.* 50, 6665-6672; Berge et al., 1977, *J. Pharm. Sci.* 66, 1-19; Stahl and Wermuth (eds), Pharmaceutical Salts: Properties, Selection, and Use: 2nd Revised Edition, Wiley-VCS, Zurich, Switzerland (2011). Examples of pharmaceutically acceptable salts are those that are pharmacologically effective and suitable for contact with the tissues of patients without undue toxicity, irritation, or allergic response. A compound of Formula (I), (II), or (III), may possess a sufficiently acidic group, a sufficiently basic group, or both types of functional groups, and accordingly react with a number of inorganic or organic bases, and inorganic and organic acids, to form pharmaceutically acceptable salt bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, borate, nitrate, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methanesulfonates, propanesulfonates, naphthalene-1-sulfonates, naphthalene-2-sulfonates, besylates, mesylates and mandelates.

When the compound of Formula (I), (II), or (III), contains a basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid, glutaric acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

When the compound of Formula (I), (II), or (III), is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as N-methyl-O-glucamine, lysine, choline, glycine and arginine, ammonia, carbonates, bicarbonates, primary, secondary, and tertiary amines, and cyclic amines, such as tromethamine, benzylamines, pyrrolidines, piperidine, morpholine, and piperazine, and inorganic salts derived from sodium, calcium, potassium, magnesium, manganese, iron, copper, zinc, aluminum, and lithium.

Prodrugs

Some embodiments provide prodrugs of the compounds of Formula (I), (II), or (III), and the use of such pharmaceutically acceptable prodrugs in methods of the present disclosure, particularly therapeutic methods.

The term "prodrug" means a precursor of a designated compound that is initially inactive or partially inactive, and that following administration to a subject, yields the compound in vivo via a chemical or physiological process such as solvolysis or enzymatic cleavage, or under physiological conditions (e.g., a prodrug on being brought to physiological pH is converted to an active pharmacological compound of Formula (I), (II), or (III)).

A "pharmaceutically acceptable prodrug" is a prodrug that is preferably non-toxic, biologically tolerable, and otherwise biologically suitable for administration to the subject. Prodrugs are often useful because, in some situations, they can be easier to administer than the parent drug. They can, for instance, be bioavailable by oral administration whereas the parent is not. The prodrug can also have improved solubility in pharmaceutical compositions over the parent drug. Illustrative procedures for the selection and preparation of suitable prodrug derivatives are described, for example, in "Design of Prodrugs", ed. H. Bundgaard, Elsevier, 1985.

Exemplary prodrugs include compounds having an amino acid residue, or a polypeptide chain of two or more (e.g., two, three or four) amino acid residues, covalently joined through an amide or ester bond to a free amino, hydroxy, or carboxylic acid group of a compound of Formula (I), (II), or (III). Examples of amino acid residues include the twenty naturally occurring amino acids, commonly designated by three letter symbols, as well as 4-hydroxyproline, hydroxylysine, demosine, isodemosine, 3-methylhistidine, norvaline, beta-alanine, gamma-aminobutyric acid, citrulline homocysteine, homoserine, ornithine and methionine sulfone.

Prodrugs may be determined using routine techniques known or available in the art (e.g., Bundgaard (ed.), 1985, Design of prodrugs, Elsevier; Krogsgaard-Larsen et al., (eds.), 1991, Design and Application of Prodrugs, Harwood Academic Publishers). Prodrugs may be produced, for instance, by derivatizing free carboxyl groups of structures of Formula (I), (II), or (III), as amides or alkyl esters. Examples of amides include those derived from ammonia, primary $C_{1-6}$ alkyl amines and secondary di($C_{1-6}$alkyl) amines. Secondary amines include 5- or 6-membered heterocycloalkyl or heteroaryl ring moieties. Examples of amides include those that are derived from ammonia, $C_{1-3}$ alkyl primary amines, and di($C_{1-6}$alkyeamines. Examples of esters include $C_{1-6}$alkyl, $C_{1-6}$cycloalkyl, phenyl, and phenyl ($C_{1-6}$alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in Fleisher et al., 1996, *Adv. Drug Delivery Rev.* 19, 115-130.

Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy) methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in Robinson et al., 1996, *J. Med. Chem.* 39, 10-18. Free amines can also be derivatized as amides, sulfonamides or phosphonamides. All of these prodrug moieties may incorporate groups including ether, amine, and carboxylic acid functionalities.

Tautomers

Some embodiments provide tautomers of compounds of Formula (I), (II), or (III), as defined further herein, which may also be used in the methods of the disclosure.

Metabolites

Some embodiments provide pharmaceutically active metabolites of the compounds of Formula (I), (II), or (III), which may also be used in the methods of the disclosure. A "pharmaceutically active metabolite" means a pharmacologically active product of metabolism in the body of a compound of Formula (I), (II), or (III), or salt thereof. Preferably, the metabolite is in an isolated form outside the body.

Active metabolites of a compound may be determined using routine techniques known or available in the art. For example, isolated metabolites can be enzymatically and synthetically produced (e.g., Bertolini et al., 1997, *J. Med. Chem.* 40, 2011-2016; Shan et al., 1997, *J. Pharm. Sci.* 86, 765-767; Bagshawe, 1995, *Drug Dev. Res.* 34, 220-230; and Bodor, 1984, *Adv Drug Res.* 13, 224-231).

Isotopes

Isotopes may be present in the compounds described. Each chemical element present in a compound either specifically or generically described herein may include any isotope of the element. Any formula given herein is also intended to represent unlabeled forms as well as isotopically-labeled forms of the compounds. Isotopically-labeled compounds have structures depicted by the formulas given herein except that one or more atoms are replaced by an atom having a selected atomic mass or mass number. Examples of isotopes that can be incorporated into compounds of the embodiments include isotopes of hydrogen, carbon, nitrogen, oxygen, phosphorus, sulfur, fluorine, chlorine, and iodine, such as $^2$H, $^3$H, $^{11}$C, $^{13}$C, $^{14}$C, $^{15}$N, $^{18}$O, $^{17}$O $^{31}$P, $^{32}$P, $^{35}$S, $^{18}$F, $^{36}$Cl, and $^{125}$I, respectively.

Compositions

The term "composition," as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation, or aggregation of any two or more of the ingredients, or from dissociation of one or more of the ingredients, or from other types of reactions or interactions of one or more of the ingredients. Accordingly, the pharmaceutical compositions of the present embodiments encompass any composition made by admixing a compound of Formula (I), (II), or (III), and a pharmaceutically acceptable excipient.

The term "pharmaceutically acceptable," as used in connection with compositions of the disclosure, refers to molecular entities and other ingredients of such compositions that are physiologically tolerable and do not typically produce untoward reactions when administered to an animal (e.g., human). The term "pharmaceutically acceptable" may also mean approved by a regulatory agency of the Federal or a state government or listed in the U.S. Pharmacopeia or other generally recognized pharmacopeia for use in animals (e.g. mammals), and more particularly in humans.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluents to facilitate administration of an agent and that is compatible therewith. Examples of excipients include calcium carbonate, calcium phosphate, various sugars and types of starch, cellulose derivatives, gelatin, vegetable oils, and polyethylene glycols. Suitable pharmaceutical carriers include those described in Remington: The Science and Practice of Pharmacy, 21$^{st}$ Ed., Lippincott Williams & Wilkins (2005).

The term "carrier" refers to an adjuvant, vehicle, or excipients, with which the compound is administered. In preferred embodiments, the carrier is a solid carrier. Suitable pharmaceutical carriers include those described in Remington: The Science and Practice of Pharmacy, 21$^{st}$ Ed., Lippincott Williams & Wilkins (2005).

The term "dosage form," as used herein, is the form in which the dose is to be administered to the subject or patient. The drug is generally administered as part of a formulation that includes nonmedical agents. The dosage form has unique physical and pharmaceutical characteristics. Dosage forms, for example, may be solid, liquid or gaseous. "Dosage forms" may include for example, a capsule, tablet, caplet, gel caplet (gelcap), syrup, a liquid composition, a powder, a concentrated powder, a concentrated powder admixed with a liquid, a chewable form, a swallowable form, a dissolvable form, an effervescent, a granulated form, and an oral liquid solution. In a specific embodiment, the dosage form is a solid dosage form, and more specifically, comprises a tablet or capsule.

As used herein, the term "inert" refers to any inactive ingredient of a described composition. The definition of "inactive ingredient" as used herein follows that of the U.S. Food and Drug Administration, as defined in 21 C.F.R. 201.3(b)(8), which is any component of a drug product other than the active ingredient.

As used herein, "suitable for oral administration" refers to a sterile, pharmaceutical product produced under good manufacturing practices (GMP) that is prepared and presented in a manner such that the composition not likely to cause any untoward or deleterious effects when orally administered to a subject. Unless specified otherwise, all of the compositions disclosed herein are suitable for oral administration.

Methods and Uses

As used herein, the term "disorder" is used interchangeably with "disease" or "condition". For example, a CNS disorder also means a CNS disease or a CNS condition.

As used herein, the term "cognitive impairment" is used interchangeably with "cognitive dysfunction" or "cognitive deficit," all of which are deemed to cover the same therapeutic indications.

The terms "treating," "treatment," and "treat" cover therapeutic methods directed to a disease-state in a subject and include: (i) preventing the disease-state from occurring, in particular, when the subject is predisposed to the disease-state but has not yet been diagnosed as having it; (ii) inhibiting the disease-state, e.g., arresting its development (progression) or delaying its onset; and (iii) relieving the disease-state, e.g., causing regression of the disease state until a desired endpoint is reached. Treating also includes ameliorating a symptom of a disease (e.g., reducing the pain, discomfort, or deficit), wherein such amelioration may be directly affecting the disease (e.g., affecting the disease's cause, transmission, or expression) or not directly affecting the disease.

As used in the present disclosure, the term "effective amount" is interchangeable with "therapeutically effective amount" and means an amount or dose of a compound or composition effective in treating the particular disease, condition, or disorder disclosed herein, and thus "treating" includes producing a desired preventative, inhibitory, relieving, or ameliorative effect. In methods of treatment according to the embodiments, "an effective amount" of at least one compound according to the embodiments is administered to a subject (e.g., a mammal). An "effective amount" also means an amount or dose of a compound or composition effective to modulate activity of PDE7 or an associated signaling pathway. The "effective amount" will vary, depending on the compound, the disease, the type of treatment desired, and its severity, and age, weight, etc.

As used herein, the term "PDE7" refers to all translation products coded by transcripts of either or both of the two genes, PDE7A and PDE7B. The amino acid and nucleotide sequences that encode PDE7 of various species are known to those skilled in the art and can be found, for example, in GenBank under accession numbers AB057409, U77880, AB038040, L12052, AK035385, AY007702.

The term "animal" is interchangeable with "subject" and may be a vertebrate, in particular, a mammal, and more particularly, a human, and includes a laboratory animal or patient in the context of a clinical trial or screening or activity experiment. Thus, as can be readily understood by one of ordinary skill in the art, the compositions and methods of the present embodiments are particularly suited to administration to any vertebrate, particularly a mammal, and more particularly, a human.

As used herein, a "control animal" or a "normal animal" is an animal that is of the same species as, and otherwise comparable to (e.g., similar age, sex), the animal that is trained under conditions sufficient to induce transcription-dependent memory formation in that animal.

By "enhance," "enhancing" or "enhancement" is meant the ability to potentiate, increase, improve or make greater or better, relative to normal, a biochemical or physiological action or effect. For example, enhancing long term memory formation refers to the ability to potentiate or increase long term memory formation in an animal relative to (or "compared to") the normal long term memory formation of the animal or controls. As a result, long term memory acquisition is faster or better retained. Enhancing performance of a cognitive task refers to the ability to potentiate or improve performance of a specified cognitive task by an animal relative to the normal performance of the cognitive task by the animal or controls.

As used herein, the term "training protocol," or "training," refers to either "cognitive training" or "motor training."

Reference will now be made to the embodiments of the present disclosure, examples of which are illustrated by and described in conjunction with the accompanying examples. While certain embodiments are described herein, it is understood that the described embodiments are not intended to limit the scope of the invention. On the contrary, the present disclosure is intended to cover alternatives, modifications, and equivalents that can be included within the invention as defined by the appended claims.

Chemical Entities

Some embodiments provide certain substituted benzoxazole and benzofuran chemical entities, which are useful, for example, as inhibitors of PDE7 enzymatic activity.

In some embodiments, the chemical entities include the compounds disclosed herein and pharmaceutically acceptable chelates, solvates, conformers, crystalline forms/polymorphs, salts, tautomers, and mixtures thereof. In some embodiments, the chemical entities include the compounds disclosed herein and pharmaceutically acceptable salts thereof.

Formula (I)

Some embodiments provide a chemical entity of Formula (I), or, more specifically, a compound of Formula (I), or a pharmaceutically acceptable salt of a compound of Formula (I):

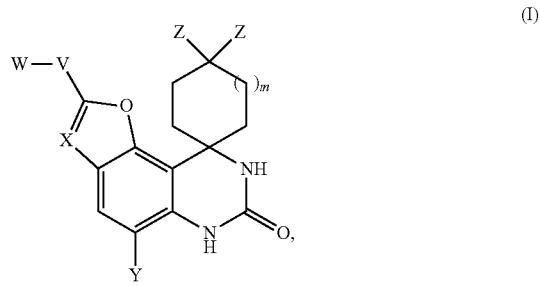

wherein,

X is —CH or —N;

Y is selected from the group consisting of: —H, halo, and —$C_{1-4}$alkyl;

each Z is independently selected from the group consisting of: —H, halo, and —$C_{1-4}$alkyl;

V is selected from the group consisting of: a bond, —$(CH_2)_m$—, —$(CH_2)_mO(CH_2)_m$—, —$(CH_2)_mO(CH_2)_nC(O)$—, —$(CH_2)_mN[(CH_2)_nR^{1A}]$—, —$(CH_2)_mC(O)O$—, —$(CH_2)_mC(O)$—, —$(CH_2)_mC(O)N[(CH_2)_nR^{1A}]$—, -$L^1$-$L^2$-$L^3$-$L^4$-, and -$L^1$-$L^5$;

each m is independently 0, 1, 2 or 3;

each n is independently 0, 1, 2 or 3;

$L^1$ is —$C(O)(CH_2)_m$—, —$[C(R^{1A})_2]_m$— or —$(CH_2)_m$—;

$L^2$ is —$N[(CH_2)_nR^{1A}]$— or —$N((CH_2)_nR^{1A})(CH_2)_p$—;

$L^3$ is selected from the group consisting of: —$(CH_2)_m$—$C_{3-7}$cycloalkyl, —$[C((CH_2)_nR^{1B})_2]_m[C((CH_2)_nR^{1C})_2]_n$—, —$[N[(CH_2)_mR^{1A}](CH_2)_n]$—, —$[(CH_2)_mN((CH_2)_nR^{1A})(CH_2)_p]$—, —$[(CH_2)_mC(O)N((CH_2)_nR^{1B})(CH_2)_p]$—, —$(CH_2)_mC(O)$—, —$[C(R^{1A})_2]_m$— and —$[(CH_2)_pO]$—;

$L^4$ is selected from the group consisting of: —$(CH_2)_mC(O)$—, —$(CH_2)_mO$—, —$C_{1-6}$ alkyl, —$C_{3-7}$cycloalkyl, heteroaryl, aryl, 3-10 membered heterocycloalkyl and —CH(OH)—, said —$C_{1-6}$ alkyl, —$C_{3-7}$cycloalkyl, heteroaryl, aryl, and 3-10 membered heterocycloalkyl each optionally substituted with one to four $R^{2A}$;

$L^5$ is selected from the group consisting of: —$C(O)(CH_2)_m$ $N[(CH_2)_nR^{1B}]$—, —$C(O)(CH_2)_m$, —$CH(OH)$—, and —$(CH_2)_mC(O)O$—;

each p is independently 0, 1, 2 or 3;

each $R^{1A}$ is independently selected from the group consisting of: —H, —OH, —CN, halo, —$C_{1-6}$ alkyl, —$C_{2-6}$ alkenyl, —$C_{2-6}$ alkynyl, —$C_{3-7}$cycloalkyl, aryl, heteroaryl, 3-15 membered heterocycloalkyl, —$C_{1-6}$haloalkyl, and —$C_{1-6}$ alkoxy, said —$C_{3-7}$cycloalkyl, aryl, heteroaryl, 3-15 membered heterocycloalkyl, —$C_{1-6}$haloalkyl, and —$C_{1-6}$alkoxy each optionally substituted with one to four $R^{2A}$;

each $R^{1B}$ is independently selected from the group consisting of: —H, —OH, —CN, halo, —$C_{1-6}$ alkyl, —$C_{2-6}$ alkenyl, —$C_{2-6}$ alkynyl, —$C_{3-7}$cycloalkyl, aryl, heteroaryl, 3-15 membered heterocycloalkyl, —$C_{1-6}$ haloalkyl, —$C_{3-7}$cycloalkyl and —$C_{1-6}$alkoxy, said —$C_{3-7}$cycloalkyl, aryl, heteroaryl, 3-15 membered heterocycloalkyl, —$C_{1-6}$ haloalkyl, and —$C_{3-7}$cycloalkyl each optionally substituted with one to four $R^{2A}$;

each $R^{1C}$ is independently selected from the group consisting of: —H, —OH, —CN, halo, —$C_{1-6}$ alkyl, —$C_{2-6}$ alkenyl, —$C_{2-6}$ alkynyl, —$C_{3-7}$cycloalkyl, aryl, heteroaryl, 3-15 membered heterocycloalkyl, —$C_{1-6}$ haloalkyl, and —$C_{1-6}$ alkoxy, said —$C_{3-7}$cycloalkyl, aryl, heteroaryl, 3-15 membered heterocycloalkyl, —$C_{1-6}$haloalkyl, and —$C_{1-6}$alkoxy each optionally substituted with one to four $R^{2A}$;

W is selected from the group consisting of: —H, halo, —OH, —CN, —$C_{1-6}$ alkyl, —$C_{1-6}$ haloalkyl, aryl, heteroaryl, 3-15 membered heterocycloalkyl, —$C_{3-7}$cycloalkyl, —$SO_2C_{1-6}$alkyl, —$(CH_2)_mR^{1A}$, —$(CH_2)_mN(R^{1B})_2$, —$(CH_2)_mO(CH_2)_6R^{1A}$, —$(CH_2)_mS(CH_2)_6R^{1A}$, —$(CH_2)_m$ $C(O)C_{1-6}$alkyl, —$(CH_2)_mC(O)$heterocycloalkyl, —$(CH_2)_m$ C(O)OH, —$(CH_2)_mC(O)OC_{1-6}$ alkyl, —$(CH_2)_m$ $C(O)NH_2$, —$(CH_2)_mC(O)N(C_{1-4}$alkyl$)_2$, and —$(CH_2)_mC(O)NH(C_{1-4}$alkyl), said aryl, heteroaryl, 3-15 membered heterocycloalkyl, and —$C_{3-7}$cycloalkyl, each optionally substituted with one to five $R^{3A}$;

each $R^{2A}$ is independently selected from the group consisting of: halo, —CN, =O, —OH, —$SO_2C_{1-6}$ alkyl, —$C_{1-6}$alkyl, —$C_{1-6}$alkoxy, —$C_{1-6}$ halo alkyl, aryl, heteroaryl, 3-15 membered heterocycloalkyl, —$C_{3-7}$cycloalkyl, —$(CH_2)_mN(C_{1-4}$alkyl$)_2$, —$OCH_2(CH_2)_m$ $R^{2AA}$, —$CH_2(CH_2)_mR^{2AA}$, —$C_{1-6}$ alkyl-OH, —$C_{1-6}$ haloalkylOH, —$C_{1-6}$haloalkyl-$C_{3-7}$cycloalkyl, —$C_{3-7}$ cycloalkyl, —$C_{2-6}$ alkenyl, —$C_{2-6}$alkynyl, —C(O)C $(CH_3)_3$, —$OC_{3-7}$cycloalkyl, —$C(O)C_{1-6}$ alkyl, —C(O) aryl, —C(O)heterocycloalkyl, —$C(O)OC_{1-6}$ alkyl, —$C(O)R^{2AA}$, —$NHC(O)R^{2AA}$, —$C(O)NH(C_{1-4}$alkyl), —$C(O)N(C_{1-4}$alkyl$)_2$, —$CH_2CH(OH)C_{3-7}$cycloalkyl, —$C(CH_3)_2OH$, —$N(R^{2AA})_2$, —$C(CH_3)_2CH_2OCH_3$, —$CH(CH_3)C(O)N(C_{1-4}$alkyl$)_2$, and —$CH_2CF_2C_{3-7}$cycloalkyl, said aryl, heteroaryl, 3-15 membered heterocycloalkyl, and —$C_{3-7}$cycloalkyl, each optionally substituted with one to five substituents each independently selected from the group consisting of: —CN, =O, —OH, —$SO_2C_{1-6}$ alkyl, —$C_{1-6}$alkyl, —$C_{1-6}$ alkoxy, —$C_{1-6}$haloalkyl, aryl, heteroaryl, 3-membered heterocycloalkyl, —$C_{3-7}$cycloalkyl, —$N(C_{1-4}$alkyl$)_2$, —$NH(C_{1-4}$alkyl), —$C_{2-6}$ alkenyl, —$C_{2-6}$ alkynyl, —$C(O)C(CH_3)_3$, —$OC_{3-7}$cycloalkyl, —$C(O)C_{1-6}$alkyl, —C(O)aryl, —C(O)heterocycloalkyl, —$C(O)OC_{1-6}$ alkyl, —$C(O)N(C_{1-4}$alkyl$)_2$, —$CH_2CH(OH)C_{3-7}$cycloalkyl, and —$C(CH_3)_2OH$;

each $R^{3A}$ is independently selected from the group consisting of: halo, —CN, =O, —OH, —$SO_2C_{1-6}$ alkyl, —$C_{1-6}$alkyl, —$C_{1-6}$alkoxy, —$C_{1-6}$ halo alkyl, aryl, heteroaryl, 3-15 membered heterocycloalkyl, —$C_{3-7}$cycloalkyl, —$(CH_2)_mN(C_{1-4}$alkyl$)_2$, —$OCH_2(CH_2)_m$ $R^{3AA}$, —$CH_2(CH_2)_mR^{3AA}$, —$C_{1-6}$ alkyl-OH, —$C_{1-6}$ haloalkylOH, —$C_{1-6}$haloalkyl-$C_{3-7}$cycloalkyl, —$C_{2-6}$ alkenyl, —$C_{2-6}$ alkynyl, —$C(O)C(CH_3)_3$, —$OC_{3-7}$cycloalkyl, —$C(O)C_{1-6}$ alkyl, —C(O)aryl, —C(O)heterocycloalkyl, —$C(O)OC_{1-6}$ alkyl, —$C(O)R^{3AA}$, —$NHC(O)R^{3AA}$, —$C(O)NH(C_{1-4}$alkyl), —$C(O)N(C_{1-4}$alkyl$)_2$, —$CH_2CH(OH)C_{3-7}$cycloalkyl, —$C(CH_3)_2OH$, —$N(R^{3AA})_2$, —$C(CH_3)_2CH_2OCH_3$, —$CH(CH_3)C(O)N(C_{1-4}$alkyl$)_2$, and —$CH_2CF_2C_{3-7}$cycloalkyl, said aryl, heteroaryl, 3-15 membered heterocycloalkyl and —$C_{3-7}$ cycloalkyl, each optionally substituted with one to five substituents each independently selected from the group consisting of: —CN, =O, —OH, —$SO_2C_{1-6}$ alkyl, —$C_{1-6}$alkyl, —$C_{1-6}$ alkoxy, —$C_{1-6}$haloalkyl, aryl, heteroaryl, 3-15 membered heterocycloalkyl, —$C_{3-7}$cycloalkyl, —$N(C_{1-4}$alkyl$)_2$, —$NH(C_{1-4}$alkyl), —$NH_2$, aryl, heteroaryl, 3-15 membered heterocycloalkyl, —$C_{2-6}$ alkenyl, —$C_{2-6}$ alkynyl, —$C(O)C(CH_3)_3$, —$OC_{3-7}$cycloalkyl, —$C(O)C_{1-6}$alkyl, —C(O)aryl, —C(O)heterocycloalkyl, —$C(O)OC_{1-6}$ alkyl, —C(O) $N(C_{1-4}$alkyl$)_2$, —$CH_2CH(OH)C_{3-7}$cycloalkyl, and —$C(CH_3)_2OH$;

each $R^{2AA}$ is independently selected from the group consisting of: —H, —OH, —$SO_2C_{1-6}$alkyl, -halo, —CN, —$C_{1-6}$ alkoxy, —$C_{1-6}$haloalkyl, —$N(C_{1-4}$alkyl$)_2$, —$NH(C_{1-4}$alkyl), —$NH_2$, aryl, heteroaryl, 3-15 membered heterocycloalkyl, —$C_{2-6}$ alkenyl, —$C_{2-6}$ alkynyl, —$C_{3-7}$cycloalkyl, —$C(O)C_{1-6}$ alkyl, —C(O)heterocycloalkyl, —$C(O)OC_{1-6}$ alkyl, —$C(O)N(C_{1-4}$alkyl$)_2$, and —C(O)aryl; and each $R^{3AA}$ is independently selected from the group consisting of: —H, —OH, —$SO_2C_{1-6}$ alkyl, halo, —CN, —$C_{1-6}$ alkoxy, —$C_{1-6}$haloalkyl, —$N(C_{1-4}$alkyl$)_2$, —$NH(C_{1-4}$alkyl), —$NH_2$, aryl, heteroaryl, 3-15 membered heterocycloalkyl, —$C_{2-6}$alkenyl, —$C_{2-6}$alkynyl, —$C_{3-7}$cycloalkyl, —$C(O)C_{1-6}$ alkyl, —C(O)heterocycloalkyl, —$C(O)OC_{1-6}$ alkyl, —$C(O)N(C_{1-4}$alkyl$)_2$, and —C(O)aryl.

In some embodiments, V is selected from the group consisting of: a bond, —$(CH_2)_m$—, —$(CH_2)_mO(CH_2)_n$—, —$(CH_2)_mO(CH_2)_nC(O)$—, —C(O)O—, —C(O)—, —$(CH_2)_mC(O)O$—, and —$(CH_2)_mC(O)$—; and m is 1, 2 or 3.

In some embodiments, V is selected from the group consisting of:
—$C(O)(CH_2)_mN[(CH_2)_nR^{1A}][C(R^{1B})_2]_m[C(R^{1C})_2]_n$—, —$[C(R^{1A})_2]_mN[(CH_2)_nR^{1A}][C(R^{1B})_2]_m[C(R^{1C})_2]$, and —$[(CH_2)_mN((CH_2)_nR^{1A})(CH_2)_p][C(R^{1B})_2]_m[C(R^{1C})_2]_n$—.

In some embodiments, V is selected from the group consisting of:
—$C(O)(CH_2)_mN(CH_2)_nR^{1A})(CH_2)_p[N[(CH_2)_mR^{1A}](CH_2)_n]$—, —$[C(R^{1A})_2]_mN((CH_2)_nR^{1A})(CH_2)_p[N[(CH_2)_m R^{1A}](CH_2)_n]$—, and —$[(CH_2)_mN((CH_2)_nR^{1A})(CH_2)_p[N[(CH_2)_mR^{1A}](CH_2)_n]$—.

In some embodiments, V is selected from the group consisting of:
—$C(O)(CH_2)_mN[(CH_2)_nR^{1A}][(CH_2)_mN((CH_2)_nR^{1A})(CH_2)_p]$—, —$[C(R^{1A})_2]_mN[(CH_2)_nR^{1A}][(CH_2)_mN((CH_2)_n R^{1A})(CH_2)_p]$—, and —$[(CH_2)_mN((CH_2)_nR^{1A})(CH_2)_p[N[(CH_2)_mR^{1A}](CH_2)_n]$—.

In some embodiments, V is selected from the group consisting of:
—$C(O)(CH_2)_mN[(CH_2)$—$R^{1A}(CH_2)_pO$—, —$[C(R^{1A})_2]_mN[(CH_2)_nR^{1A}][(CH_2)_pO]$—, and —$[(CH_2)_mN((CH_2)_nR^{1A})(CH_2)_p][(CH_2)_pO]$—.

In some embodiments, V is selected from the group consisting of:
—$C(O)(CH_2)_mN[(CH_2)_nR^{1A}][N[(CH_2)_mR^{A1}](CH_2)_n]CH$ (OH)—, —$[C(R^{1A})_2]_mN[(CH_2)_nR^{1A}][N[(CH_2)_mR^{1A}](CH_2)_n]CH(OH)$—, —$[(CH_2)_mN((CH_2)_nR^{1A})(CH_2)_p][N[(CH_2)_mR^a](CH_2)_n]CH(OH)$—, —$C(O)(CH_2)_mN[(CH_2)_n R^{1A}][(CH_2)_mN((CH_2)_nR^{1A})(CH_2)_p]CH(OH)$—, —$[C(R^{1A})_2]_mN[(CH_2)_nR^{1A}][(CH_2)_mN((CH_2)_nR^{1A})(CH_2)_p]CH(OH)$—, —$[(CH_2)_mN((CH_2)_nR^{1A})(CH_2)_p][(CH_2)_mN((CH_2)_n R^{1A})(CH_2)_p]CH(OH)$—, —$C(O)(CH_2)_mN[(CH_2)_n R^{1A}][(CH_2)_pO]CH(OH)$—, —$[C(R^{1A}_2]_mN[(CH_2)_n R^{1A}][(CH_2)_pO]CH(OH)$—, and —$[(CH_2)_mN((CH_2)_nR^{1A})(CH_2)_p][(CH_2)_pO]CH(OH)$—.

In some embodiments, V is selected from the group consisting of: —CH$_2$—, —C(O)—, —C(O)O—, —CH$_2$C(O)—, —CH$_2$OCH$_2$—, and —CH$_2$C(O)O—.

In some embodiments, V is selected from the group consisting of:

—C(O)(CH$_2$)$_m$N[(CH$_2$)$_n$R$^{1.4}$]CH$_2$CF$_2$CH(OH)—, —C(O)(CH$_2$)$_m$N[(CH$_2$)$_n$R$^{1.4}$]CH$_2$CH(OH)CH$_2$—, —C(O)(CH$_2$)$_m$ N[(CH$_2$)$_n$R$^{1.4}$]CH$_2$CH$_2$CH(OH)—, —C(O)(CH$_2$)$_m$ N[(CH$_2$)$_n$R$^{1.4}$]CH$_2$CH(OH)—, —C(O)(CH$_2$)$_m$N[(CH$_2$)$_n$R$^{1.4}$][(CH$_2$)$_m$C(O)]—, —(CH$_2$)$_m$N[(CH$_2$)$_n$R$^{1.4}$][(CH$_2$)$_n$N((CH$_2$)$_n$R$^{1.4}$)(CH$_2$)$_n$]—, —(CH$_2$)$_m$N[(CH$_2$)$_n$R$^{1.4}$](CH$_2$)$_n$(CF$_2$)$_n$—, and —(CH$_2$)$_m$N[(CH$_2$)$_n$R$^{1.4}$](CH$_2$)$_n$ (CF$_2$)$_n$CH(OH)—.

In some embodiments, V is selected from the group consisting of:

—C(O)N[(CH$_2$)$_n$R$^{1.4}$]CH$_2$CF$_2$CH(OH)—, —C(O)N[(CH$_2$)$_n$ R$^{1.4}$]CH$_2$CH(OH)CH$_2$—, —C(O)N[(CH$_2$)$_n$R$^{1.4}$]CH$_2$CH$_2$CH(OH)—, —C(O)N[(CH$_2$)$_n$R$^{1.4}$]CH$_2$CH(OH)—, —C(O)N[(CH$_2$)$_n$R$^{1.4}$][(CH$_2$)$_m$C(O)]—, —CH$_2$N[(CH$_2$)$_n$R$^{1.4}$][(CH$_2$)$_n$N((CH$_2$)$_n$R$^{1.4}$)(CH$_2$)$_n$]—, —CH$_2$N[(CH$_2$)$_n$R$^{1.4}$](CH$_2$)$_n$(CF$_2$)$_n$—, and —CH$_2$N[(CH$_2$)$_n$R$^{1.4}$](CH$_2$)$_n$(CF$_2$)$_n$CH(OH)—.

In some embodiments, V is selected from the group consisting of: —CH$_2$—, —CH$_2$C(O)—, —CH$_2$OCH$_2$—, and —CH$_2$C(O)O—.

In some embodiments, V is selected from the group consisting of:

—CH$_2$—, —C(O)NR$^{1.4}$—, —C(O)NR$^{1.4}$CH$_2$—, —C(O)NR$^{1.4}$CH$_2$CF$_2$CH$_2$—, —N[CH$_2$CH$_2$R$^{1.4}$]CH$_2$CH$_2$—, —C(O)NR$^{1.4}$CH$_2$CH$_2$NR$^{1.4}$CH$_2$—, —CH$_2$NR$^{1.4}$CH$_2$—, —CH$_2$NR$^{1.4}$CH$_2$CH$_2$—, —CH$_2$NR$^{1.4}$CH$_2$CF$_2$—, —C(O)—, —CH$_2$NR$^{1.4}$—, —CH$_2$NR$^{1.4}$CH(CH$_3$)—, —CH$_2$NR$^{1.4}$CH$_2$CH(OH)—, —CH$_2$NR$^{1.4}$CH$_2$C(O)—, —CH$_2$NR$^{1.4}$CH$_2$CH$_2$C(O)—, —CH$_2$NR$^{1.4}$CH(CH$_3$)C(O)—, —CH$_2$NR$^{1.4}$CH$_2$CH$_2$O—, —C(O)NR$^{1.4}$CH$_2$CH$_2$—, —C(O)NR$^{1.4}$C(CH$_3$)$_2$CH$_2$—, —C(O)N[CH$_2$R$^{1.4}$]CH$_2$CH$_2$—, —C(O)N[CH$_2$R$^{1.4}$]CH$_2$—, —C(O)NR$^{1.4}$CH$_2$C(CH$_3$)$_2$—, —C(O)NR$^{1.4}$CH$_2$CH$_2$CH$_2$—, —CH$_2$OCH$_2$C(O)—, —C(O)NR$^{1.4}$CH$_2$CH$_2$CH$_2$CH$_2$—, —C(O)NR$^{1.4}$CH(R$^{1.4}$)CH$_2$—, —C(O)NR$^{1.4}$CH$_2$CH$_2$O—, —C(O)NR$^{1.4}$CH$_2$CH(OH)CH$_2$—, —C(O)NR$^{1.4}$CH$_2$CH$_2$CH(OH)—, C(O)NR$^{1.4}$CH$_2$CH$_2$C(O)—, —C(O)NR$^{1.4}$CH$_2$CH(OH)—, —C(O)NR$^{1.4}$ [CH$_2$C(O)O]—, —CH$_2$OCH$_2$CH$_2$C(O)—, —C(O)NR$^{1.4}$CH$_2$CH$_2$C(O)NR$^{1.4}$CH$_2$—, —CH$_2$NR$^{1.4}$[(CH$_2$)$_n$N((CH$_2$)$_n$R$^{1.4}$)(CH$_2$)$_n$]— CH$_2$NR$^{1.4}$CH$_2$CH$_2$CH$_2$—, —CH$_2$N[CH$_2$R$^{1.4}$)]CH$_2$CH$_2$—, —C(O)NR$^{1.4}$CH$_2$CF$_2$—, —C(O)NR$^{1.4}$CH$_2$C(O)—, —C(O)NR$^{1.4}$CH(CH$_2$OH)CH$_2$—, —C(O)N[CH$_2$R$^{1.4}$]CH$_2$CH$_2$CH$_2$—, —C(O)N[CH$_2$R$^{1.4}$]CH$_2$CH$_2$O—, —CH$_2$NR$^{1.4}$CH$_2$CH$_2$CH$_2$NR$^{1.4}$—, —CH$_2$NR$^{1.4}$C(CH$_3$)$_2$CH$_2$CH$_2$O—, —CH$_2$NR$^{1.4}$CH$_2$C(O)O—, —CH$_2$NR$^{1.4}$CH$_2$CH$_2$NR$^{1.4}$C(O)—, and —CH$_2$NR$^{1.4}$(CH$_2$)$_m$(CF$_2$)$_n$CH(OH)—.

In certain embodiments, a chemical entity of Formula (I) is a chemical entity of Formula (Ia), and more particularly, is a compound of Formula (Ia), or a pharmaceutically acceptable salt of a compound of Formula (Ia):

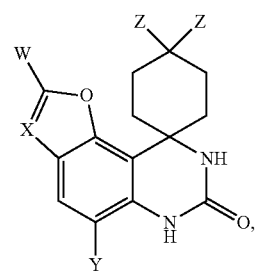

(Ia)

wherein W, X, Y, and Z have any of the values described herein.

In certain embodiments of a chemical entity of Formula (Ia),

W is selected from the group consisting of: —H, —C$_{1-6}$ alkyl, —C$_{1-6}$haloalkyl, aryl, heteroaryl, heterocycloalkyl, —C$_{3-7}$cycloalkyl, —(CH$_2$)$_m$R$^{1.4}$, —(CH$_2$)$_m$N(R$^{1B}$)$_2$, —(CH$_2$)$_m$O(CH$_2$)$_n$R$^{1.4}$, —(CH$_2$)$_m$S(CH$_2$)$_n$R$^{1.4}$, —CH$_2$C(O)C$_{1-6}$alkyl, —C(O)C$_{1-6}$alkyl, —C(O)heterocycloalkyl, —C(O)OH, —C(O)OC$_{1-6}$ alkyl, —C(O)NH$_2$, —C(O)NH(C$_{1-4}$alkyl), and —C(O)N(C$_{1-4}$alkyl)$_2$, said aryl, heteroaryl, 3-15 membered heterocycloalkyl and —C$_{3-7}$cycloalkyl, each optionally substituted with one to three R$^{3.4}$; and each R$^{1.4}$ is independently selected from the group consisting of: —H, —OH, —CN, halo, —C$_{3-7}$cycloalkyl, aryl, heteroaryl, 3-15 membered heterocycloalkyl —C$_{1-6}$haloalkyl, and —C$_{1-6}$ alkoxy, said —C$_{3-7}$cycloalkyl, aryl, heteroaryl, 3-15 membered heterocycloalkyl, —C$_{1-6}$haloalkyl, and —C$_{1-6}$ alkoxy each optionally substituted with one to three R$^{2.4}$.

In certain embodiments, the chemical entity of Formula (I) is a chemical entity of Formula (Ib), and more particularly, is a compound of Formula (Ib), or a pharmaceutically acceptable salt of a compound of Formula (Ib):

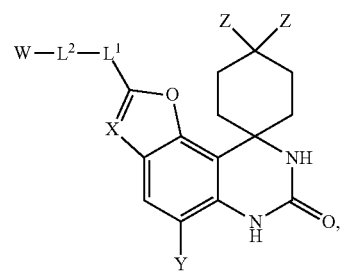

(Ib)

wherein W, X, Y, Z, L$^2$, and L$^1$ have any of the values described herein.

In certain embodiments of a chemical entity of Formula (Ib),

L$^1$ is —C(O)(CH$_2$)$_m$—, —[C(R$^{1.4}$)$_2$]$_m$—, or —(CH$_2$)$_m$—;

L$^2$ is —N[(CH$_2$)—R$^{1.4}$]— or —N((CH$_2$)$_n$R$^{1.4}$)(CH$_2$)$_p$—;

W is selected from the group consisting of: —C$_{1-6}$alkyl, —C$_{1-6}$haloalkyl, aryl, heteroaryl, 3-15 membered heterocycloalkyl, —C$_{3-7}$cycloalkyl, —(CH$_2$)$_m$R$^{1.4}$, —(CH$_2$)$_m$N(R$^{1B}$)$_2$, —(CH$_2$)$_m$O(CH$_2$)$_m$R$^{1.4}$, —(CH$_2$)$_m$S(CH$_2$)$_6$R$^{1.4}$, —C(O)C$_{1-6}$alkyl, —C(O)heterocycloalkyl, —(CH$_2$)$_m$C(O)OC$_{1-6}$ alkyl, and —C(O)N(C$_{1-4}$alkyl)$_2$, said aryl, heteroaryl, 3-15 membered heterocycloalkyl, and —C$_{3-7}$cycloalkyl, each optionally substituted with one to three R$^{3.4}$; and each $R^{1A}$ is independently selected from the group consisting of: —H, —OH, —CN, halo, —$C_{3-7}$cycloalkyl, aryl, heteroaryl, 3-15 membered heterocycloalkyl, —$C_{1-6}$haloalkyl, and —$C_{1-6}$ alkoxy, said —$C_{3-7}$cycloalkyl, aryl, heteroaryl, 3-15 membered heterocycloalkyl, and —$C_{1-6}$ haloalkyl each optionally substituted with one to three $R^{2A}$;

each $R^{3A}$ is independently selected from the group consisting of: halo, —CN, =O, —OH, —SO$_2$C$_{1-6}$alkyl, —C$_{1-6}$ alkyl, —C$_{1-6}$alkoxy, —C$_{1-6}$haloalkyl, aryl, heteroaryl, 3-15 membered heterocycloalkyl, —C$_{3-7}$cycloalkyl, —(CH$_2$)$_m$N (C$_{1-4}$alkyl)$_2$, —OCH$_2$(CH$_2$)$_m$R$^{3AA}$, —CH$_2$(CH$_2$)$_m$R$^{3AA}$, —C$_{1-6}$ alkyl-OH, —C$_{1-6}$haloalkylOH, —C$_{1-6}$haloalkyl-C$_{3-7}$ cycloalkyl, —C$_{2-6}$ alkenyl, —C$_{2-6}$ alkynyl, —C(O)C(CH$_3$)$_3$, —OC$_{3-7}$cycloalkyl, —C(O)C$_{1-6}$ alkyl, —C(O)aryl, —C(O) heterocycloalkyl, —C(O)OC$_{1-6}$ alkyl, —C(O)R$^{3AA}$, —NHC (O)R$^{3AA}$, —C(O)NH(C$_{1-4}$alkyl), —C(O)N(C$_{1-4}$alkyl)$_2$, —CH$_2$CH(OH)C$_{3-7}$cycloalkyl, —C(CH$_3$)$_2$OH, —N (R$^{3AA}$)$_2$, —C(CH$_3$)$_2$CH$_2$OCH$_3$, —CH(CH$_3$)C(O)N(C$_{1-4}$alkyl)$_2$, and —CH$_2$CF$_2$C$_{3-7}$cycloalkyl, said aryl, heteroaryl, 3-15 membered heterocycloalkyl, and —C$_{3-7}$cycloalkyl, each optionally substituted with one to five substituents each independently selected from the group consisting of: —CN, =O, halo, —OH, —SO$_2$C$_{1-6}$ alkyl, —C$_{1-6}$ alkyl, —C$_{1-6}$ alkoxy, —C$_{1-6}$ haloalkyl, aryl, heteroaryl, 3-15 membered heterocycloalkyl, —C$_{3-7}$cycloalkyl, —N(C$_{1-4}$alkyl)$_2$, —NH (C$_{1-4}$alkyl), —C$_{2-6}$ alkenyl, —C$_{2-6}$ alkynyl, —C(O)C (CH$_3$)$_3$, —OC$_{3-7}$cycloalkyl, —C(O)C$_{1-6}$ alkyl, —C(O)aryl, —C(O)heterocycloalkyl, —C(O)OC$_{1-6}$ alkyl, —C(O)N (C$_{1-4}$ alkyl)$_2$, —CH$_2$CH(OH)C$_{3-7}$cycloalkyl, and —C(CH$_3$)$_2$ OH; and each $R^{3AA}$ is independently selected from the group consisting of: —H, —OH, —SO$_2$C$_{1-6}$ alkyl, halo, —CN, —C$_{1-6}$alkoxy, —C$_{1-6}$haloalkyl, —N(C$_{1-4}$alkyl)$_2$, —NH(C$_{1-4}$alkyl), —NH$_2$, aryl, heteroaryl, 3-15 membered heterocycloalkyl, —C$_{2-6}$ alkenyl, —C$_{2-6}$ alkynyl, —C$_{3-7}$cycloalkyl, —C(O)C$_{1-6}$ alkyl, —C(O)heterocycloalkyl, —C(O)OC$_{1-6}$ alkyl, —C(O)N(C$_{1-4}$alkyl)$_2$, and —C(O)aryl.

In some embodiments of a chemical entity of Formula (I), (Ia), or (Ib) disclosed herein: each $R^{3A}$ is independently selected from the group consisting of: halo, —CN, =O, —OH, —SO$_2$C$_{1-6}$alkyl, —C$_{1-6}$alkyl, —C$_{1-6}$alkoxy, —C$_{1-6}$ haloalkyl, aryl, heteroaryl, 4-12 membered heterocycloalkyl, —C$_{3-7}$cycloalkyl, —OCH$_2$(CH$_2$)$_m$R$^{3AA}$, —CH$_2$(CH$_2$)$_m$ R$^{3AA}$, —C(O)C$_{1-6}$alkyl, —C(O)heterocycloalkyl, —C(O) OC$_{1-6}$ alkyl, —C(O)R$^{3AA}$, —NHC(O)R$^{3AA}$, —C(O)NH (C$_{1-4}$ alkyl), —C(O)N(C$_{1-4}$alkyl)$_2$, and —N(R$^{3AA}$)$_2$, said aryl, heteroaryl, 4-12 membered heterocycloalkyl and —C$_{3-7}$ cycloalkyl, each optionally substituted with one to five substituents each independently selected from the group consisting of: —CN, —OH and —C$_{1-6}$ alkoxy; and each $R^{3AA}$ is independently selected from the group consisting of: —H, —OH, —N(C$_{1-4}$alkyl)$_2$, —NH$_2$, heteroaryl, —C$_{3-7}$cycloalkyl, - and —C(O)OC$_{1-6}$alkyl.

In some embodiments of a chemical entity of Formula (I), (Ia), or (Ib) disclosed herein: each $R^{3A}$ is independently selected from the group consisting of: halo, —CN, —OH, —C$_{1-6}$alkyl, —C$_{1-6}$alkoxy, —C$_{1-6}$haloalkyl, aryl, heteroaryl, 4-12 membered heterocycloalkyl, —C$_{3-7}$cycloalkyl, —C(O)NH(C$_{1-4}$alkyl), and —C(O)N(C$_{1-4}$alkyl)$_2$, said aryl, heteroaryl, 4-12 membered heterocycloalkyl and —C$_{3-7}$cycloalkyl, each optionally substituted with one to five substituents each independently selected from the group consisting of: —CN, —OH and —C$_{1-6}$alkoxy.

In some embodiments of a chemical entity of Formula (I), (Ia), or (Ib) disclosed herein: at least one of W, $R^{1B}$, $R^{1C}$, $R^{3A}$ and $R^{3AA}$ is a 4-12 membered C$_{3-11}$heterocycloalkyl or a 5-10 membered C$_{4-9}$heteroaryl.

In some embodiments of a chemical entity of Formula (I), (Ia), or (Ib) disclosed herein: at least one of W, $R^{1B}$, $R^{1C}$, $R^{3A}$ and $R^{3AA}$ is a 4-12 membered C$_{3-11}$heterocycloalkyl.

In some embodiments of a chemical entity of Formula (I), (Ia), or (Ib) disclosed herein: Y is chloro.

In some embodiments of a chemical entity of Formula (I), (Ia), or (Ib) disclosed herein: each Z is H or fluoro.

In some embodiments of a chemical entity of Formula (I), (Ia), or (Ib) disclosed herein: each Z is H.

In some embodiments of a chemical entity of Formula (I), (Ia), or (Ib) disclosed herein: W is selected from the group consisting of: azetidinyl, tetrahydropyranyl, tetrahydrofuranyl, piperazinyl, piperidinyl, oxetanyl, pyrrolidinyl, morpholinyl, pyrazolyl, triazolyl, furanyl, thiazolyl, pyridyl, phenyl, thienyl, imidazolyl, 1,3-oxazolyl, 1,2-oxazolyl, pyrrolyl, 2-oxa-8-azaspiro[4.5]decan-8-yl, 7-oxa-2-azaspiro [3.5]nonan-2-yl, 1-oxa-8-azaspiro[4.5]decan-8-yl, 5',6'-dihydro-4'H-spiro[piperidine-4,7'-thieno[2,3-c]pyridine], cyclopentyl, 6',7'-dihydro-5'H-spiro[piperidine-4,4'-thieno [3,2-c]pyridine]-1-yl, 3,4-dihydrospiro[2-benzopyran-1,4'-piperidine]-3-azabicyclo[4.1.0]heptan-3-yl, 2-oxa-6-azaspiro[2.5]octan-6-yl, 2-oxa-6-azaspiro[2.5]octan-6-yl, 6-azaspiro[2.5]octan-6-yl, 6-aza spiro[3.5]nonan-6-yl, 6-oxa-9-azaspiro[4.5]decan-9-yl, 2-oxa-5-azabicyclo[2.2.1] heptan-5-yl, 2,3-dihydro-1-benzofuranyl, 1,3-dihydro-2-benzofuranyl, bicyclo[1.1.1]pentan-1-yl, azepanyl, octahydropyrrolo[3,4-c]pyrrol-2-yl, octahydropyrrolo[1,2-a] piperazin-2-yl, 3,4-dihydrospiro[1-benzopyran-2,3'-pyrrolidinyl, 2,9-diazaspiro[5.5]undecanyl, 2,3-dihydro-1,4-benzodioxinyl, 3-azabicyclo[3.1.0]hexanyl, 3-oxabicyclo [3.1.0]hexan-6-yl, 2H,3H,4H,5H-pyrido[3,2-f][1,4] oxazepinyl, 5H,6H,7H,8H-imidazo[1,2-a]pyrazin-7-yl, 5H,6H,7H-pyrrolo[3,4-b]pyridine-6-yl, 1,3-benzodiazol-2-yl, bicyclo[3.1.0]hexan-3-yl, 2H-1,3-benzodioxolyl, 2,3-dihydro-1H-indol-1-yl, 5H,6H,7H,8H-[1,2,4]triazolo[4,3-a] pyrazin-7-yl, 1,4-diazepan-1-yl, oxepanyl, pyrimidinyl, each optionally substituted with one to three $R^{3A}$.

In some embodiments of a chemical entity of Formula (I), (Ia), or (Ib), disclosed herein: each $R^{1A}$ is independently —H, —OH, fluoro, or methyl.

In some embodiments of a chemical entity of Formula (I), (Ia), or (Ib), disclosed herein: each $R^{1B}$ is independently —H, —OH, fluoro, or methyl.

In some embodiments of a chemical entity of Formula (I), (Ia), or (Ib), disclosed herein: each $R^{1C}$ is independently —H, —OH, fluoro, or methyl.

Formula (II) and Formula (III)

Some embodiments provide a chemical entity of Formula (II), or, more specifically, a compound of Formula (II), or a pharmaceutically acceptable salt of a compound of Formula (II):

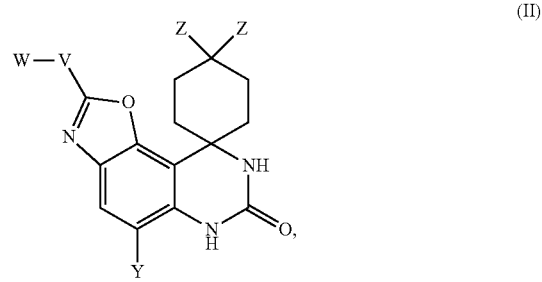

(II)

wherein: V, W, Y and Z have any of the values described herein.

Some embodiments provide a chemical entity of Formula (III), or, more specifically, a compound of Formula (III), or a pharmaceutically acceptable salt of a compound of Formula (III):

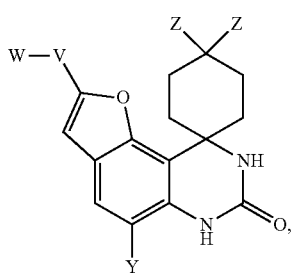

(III)

wherein: V, W, Y and Z have any of the values described herein.

In some embodiments of Formula (II) or (III),

Y is selected from the group consisting of: —H, —F, —Cl, —Br, and —$C_{1-4}$alkyl;

Z is selected from the group consisting of: —H, —F, and —$C_{1-4}$alkyl;

V is selected from the group consisting of: a bond, —$CH_2$—, —C(O)—, and —$NR^a$—, where $R^a$ is —H, —$C_{1-6}$ alkyl, —$C_{1-6}$haloalkyl, —$C_{3-7}$cycloalkyl, or —$CH_2CH_2OC_{1-6}$ alkyl; and W is selected from the group consisting of: —H, halo, —$C_{1-6}$ alkyl, —$C_{1-6}$ haloalkyl, —$CH_2OC_{1-5}$alkyl, —$CH_2OH$, —$CH_2CH_2OH$, —$CH_2CH_2OCH_3$, —C(O)$C_{1-6}$ alkyl, —C(O)$C_{3-7}$cycloalkyl, —C(O)O$C_{1-4}$alkyl, —$C_{3-7}$cycloalkyl, said —$C_{3-7}$cycloalkyl optionally substituted with one or more -halo or —$C_{1-6}$ alkyl, —$C_{1-6}$ aryl, —$C_{1-6}$ heteroaryl, said aryl or heteroaryl optionally substituted, —OH, —O$C_{1-6}$ alkyl, —$OCH_2CH_2OCH_3$, —$OCH_2C(O)N(CH_3)_2$, —Otetrahydropyranyl, —Opiperidinyl, optionally substituted heterocycloalkyl, and —$N(R^b)_2$, where each $R^b$ is independently selected from the group consisting of: —H, —$C_{1-6}$alkyl, —$C_{1-6}$alkyl-OH, —$C_{1-6}$haloalkyl, —$C_{1-6}$haloalkylOH, —$C_{1-6}$haloalkyl-$C_{3-7}$cycloalkyl, —$C_{3-7}$cycloalkyl, —$CH_2$-alkenyl, —$CH_2$-alkynyl, —$CH_2C_{3-7}$cycloalkyl, —$CH_2C(O)C(CH_3)_3$, —$CH_2C(O)C_{1-6}$ alkyl, —$CH_2C(O)$heterocycloalkyl, —$CH_2C(O)OC_{1-6}$ alkyl, —$CH_2C(O)N(C_{1-4}$ alkyl)$_2$, —$CH_2CH(OH)C_{3-7}$cycloalkyl, —$C(CH_3)_2OH$, —$C(CH_3)_2CH_2OCH_3$, —$CH(CH_3)C(O)N(C_{1-4}$alkyl)$_2$, —$CH_2CF_2C_{3-7}$cycloalkyl, —$CH_2CH_2$—$R^c$, and —$(CH_2)R^d$, where $R^c$ is —$C_{2-6}$ alkynyl, —$C_{3-7}$cycloalkyl, —OH, —O—$C_{1-6}$ alkyl, —$OC(CH_3)_2$, —O—$C_{1-6}$ haloalkyl, —Ophenyl, —Opyridyl, —$CH_2N(CH_3)_2$, —C(O)NHCH$_3$, —C(O)N(CH$_3$)$_2$, —CN, —NHCH$_3$, —N(CH$_3$)$_2$, —NHC(O)CH$_3$, or —SO$_2$CH$_3$, where $R^d$ is —$C_{3-7}$cycloalkyl, —$C_{3-7}$ halocycloalkyl, heterocycloalkyl, aryl, or heteroaryl, each optionally substituted with up to 4 substituents each independently selected from the group consisting of: halo, —$C_{1-6}$alkyl, —$C_{1-6}$haloalkyl, —$C_{3-7}$cycloalkyl, —OH, —O$C_{1-6}$ alkyl, —O—$C_{1-6}$ haloalkyl, —O-phenyl, —O-pyridyl, —$CH_2OH$, —$CH_2OCH_3$, —$CH_2OCH_2CH_3$, —CN, —$N(CH_3)_2$, —$N(CH_3)$benzyl, heteroaryl, heterocycloalkyl, morpholine, phenyl, or benzyl, where n is 0, 1, 2 or 3;

or, alternatively, both $R^b$ come together to form a 4-15-membered, monocyclic, bicyclic or tricyclic ring, optionally containing up to 3 additional heteroatoms each independently selected from O (oxygen), N (nitrogen) and S (sulfur), said 4-15-membered monocyclic, bicyclic or tricyclic ring optionally substituted with one to 4 $R^{b1}$ where each $R^{b1}$ is independently selected from the group consisting of: -halo, —$C_{1-6}$alkyl, —$C_{1-6}$haloalkyl, —$C_{1-6}$ haloalkyl-$C_{3-7}$cycloalkyl, —$C_{3-7}$cycloalkyl, bicyclo[2.2.1]heptane, —$C_{1-6}$alkyl-OH, —$C(CH_3)_2OH$, —$CH_2OC_{1-6}$ alkyl, —$CH_2C(O)OCH_2CH_3$, —$CH_2CH_2OC_{1-6}$ alkyl, —$CH_2CH_2OC_{1-6}$ haloalkyl, —$CH_2CH_2C(O)OCH_3$, —OH, —O$C_{1-6}$ alkyl, —$OCH_2$—$C_{3-7}$cycloalkyl, —$OCH_2CH_2OCH_3$, =O, —$CH_2N(CH_3)_2$, —$CH_2CH_2N(CH_3)_2$, —$C(O)C_{1-6}$ alkyl, —C(O)H, —C(O)OH, —$C(O)OC_{1-6}$ alkyl, —$C(O)CH_3$, —$C(O)NH_2$, —$C(O)NHCH_3$, —$C(O)N(CH_3)_2$, —CN, —$NH_2$, —$NHC(O)CH_3$, —$N(CH_3)_2$, —$SO_2CH_3$, oxetane, pyrrolidine, morpholine, furan, thiazole, pyridyl, phenyl, thiophene, —$CH_2$imidazole, —$CH_2$furan, —$CH_2$-thiophene, —$CH_2$pyridyl, benzyl, —C(O)-tetrahydrofuran, —C(O)pyrrole, and —C(O)phenyl.

In some embodiments of a compound of Formula (II) or (III), W is —$N(R^b)_2$, where each W is independently selected from the group consisting of: —H, —$C_{1-6}$ alkyl, —$C_{1-6}$alkyl-OH, —$C_{1-6}$haloalkyl, —$C_{1-6}$haloalkyl OH, —$C_{1-6}$ haloalkyl-$C_{3-7}$cycloalkyl, —$C_{3-7}$cycloalkyl, —$CH_2$-alkenyl, —$CH_2$-alkynyl, —$CH_2C_{3-7}$cycloalkyl, —$CH_2C(O)C(CH_3)_3$, —$CH_2C(O)C_{1-6}$ alkyl, —$CH_2C(O)$heterocycloalkyl, —$CH_2C(O)OC_{1-6}$ alkyl, —$CH_2C(O)N(C_{1-4}$ alkyl)$_2$, —$CH_2CH(OH)C_{3-7}$cycloalkyl, —$C(CH_3)_2OH$, —$C(CH_3)_2CH_2OCH_3$, —$CH(CH_3)C(O)N(C_{1-4}$alkyl)$_2$, —$CH_2CF_2C_{3-7}$cycloalkyl, —$CH_2CH_2$—$R^c$, and —$(CH_2)_n$—$R^d$, where W is —$C_{2-6}$ alkynyl, —$C_{3-7}$cycloalkyl, —OH, —O—$C_{1-6}$ alkyl, —$OC(CH_3)_2$, —O—$C_{1-6}$ haloalkyl, —Ophenyl, —Opyridyl, —$CH_2N(CH_3)_2$, —C(O)NHCH$_3$, —C(O)N(CH$_3$)$_2$, —CN, —NHCH$_3$, —N(CH$_3$)$_2$, —NHC(O)CH$_3$, or —SO$_2$CH$_3$, where $R^d$ is cyclopropyl, cyclobutyl, cyclopentyl, cyclohexyl, bicyclo[1.1.1]pentane, bicyclo[3.1.0]hexane, —$C_{3-7}$halocycloalkyl, oxetane, pyrrolidine, pyrrolidinone, piperidine, piperidinone, tetrahydropyranyl, tetrahydrofuranyl, oxepane, morpholine, 3-azabicyclo[3.1.0]hexane, tetrahydrothiophene-1,1-dioxide, tetrahydro-2H-thiopyran-1,1-dioxide, thiomorpholine-1,1-dioxide, tetrahydrothiophene-1,1-dioxide, 1,3-dihydroisobenzofuran, benzofuran, indoline, benzodioxine, benzodioxole, phenyl, benzyl, —$CH_2CH_2$phenyl, —$CH_2CH_2CH_2$phenyl, furan, pyrrole, pyrazole, imidazole, triazole, isoxazole, oxazole, thiazole, pyridine, pyrimidine, thiophene, pyrrolopyridine, or benzimidazole, said $R^d$ optionally substituted with up to 4 substituents each independently selected from the group consisting of: halo, —$C_{1-6}$alkyl, —$C_{1-6}$ haloalkyl, cyclopropyl, —OH, —O$C_{1-6}$ alkyl, —O—$C_{1-6}$ haloalkyl, —O-phenyl, —O-pyridyl, —$CH_2OH$, —$CH_2OCH_3$, —$CH_2OCH_2CH_3$, —CN, —$N(CH_3)_2$, —$N(CH_3)$ benzyl, heteroaryl, heterocycloalkyl, phenyl, or benzyl, where n is 0, 1, 2 or 3;

or, alternatively, both W come together to form a monocyclic, bicyclic or tricyclic ring selected from the group consisting of: azetidine, pyrrole, pyrrolidine, pyrrolidinone, piperazine, piperazinone, piperidine, piperidinone, azepane, morpholine, 1-oxa-8-azaspiro[4.5]decan-3-one, 2-oxa-5-azabicyclo[2.2.1]heptane, 2-oxa-7-azaspiro[3.5]nonane, 2-oxa-8-azaspiro[4.5]decane, -2-oxa-8-azaspiro[4.5]decan-1-one, 6-oxa-9-azaspiro[4.5]decane, 7-oxa-2-azaspiro[3.5]nonane, octahydropyrrolo[3,4-c]pyrrole, octahydropyrrolo[1,2-a]pyrazine, oxaazabicyclo[2.2.1]heptane, thiomorpholine-1,1-dioxide, diazepane, 2,3,4,5-tetrahydropyrido[2,3-f][1,4]oxazepine, 5,6,7,8-tetrahydro[1,2,4]triazolo[4,3-a]pyrazine, 5,6,7,8-tetrahydroimidazo[1,2-a]pyrazine, 5,6,7,8-tetrahydropyrido[3,4-d]pyridazin-1(2H)-one, azaspiro[2.5]octane, azabicyclo[3.1.0]hexane, azabicyclo[4.1.0]heptane, diazaspiro[5.5]undecane, tetrahydroimidazopyrazine, dihydropyrrolopyridine, spiro[chroman-2,3'-pyrrolidin]-4-one, spiro[isochroman-1,4'-piperidine], 6',7'-dihydro-5'H-spiro[piperidine-4,4'-thieno[3,2-c]pyridine], and 5',6'-dihydro-4'H-spiro[piperidine-4,7'-thieno[2,3-c]pyridine]), each optionally substituted with up to 4 substituents each independently selected from the group consisting of: halo, —$C_{1-6}$alkyl, —$C_{1-6}$haloalkyl, —$C_{1-6}$haloalkyl-$C_{3-7}$cycloalkyl, —$C_{3-7}$cycloalkyl, -bicyclo[2.2.1]heptane, —$C_{1-6}$alkyl-OH, —C(CH$_3$)$_2$OH, —CH$_2$OC$_{1-6}$ alkyl, —CH$_2$C(O) OCH$_2$CH$_3$, —CH$_2$CH$_2$OC$_{1-6}$alkyl, —CH$_2$CH$_2$OC$_{1-6}$ haloalkyl, —CH$_2$CH$_2$C(O)OCH$_3$, —OH, —OC$_{1-6}$ alkyl, —OCH$_2$—C$_{3-7}$cycloalkyl, —OCH$_2$CH$_2$OCH$_3$, =O, —CH$_2$N(CH$_3$)$_2$, —CH$_2$CH$_2$N(CH$_3$)$_2$, —C(O)C$_{1-6}$ alkyl, —C(O)H, —C(O)OH, —C(O)OC$_{1-6}$alkyl, —C(O)CH$_3$, —C(O)NH$_2$, —C(O)NHCH$_3$, —C(O)N(CH$_3$)$_2$, —CN, —NH$_2$, —NHC(O)CH$_3$, —N(CH$_3$)$_2$, —SO$_2$CH$_3$, oxetane, pyrrolidine, morpholine, furan, thiazole, pyridyl, phenyl, thiophene, —CH$_2$imidazole, —CH$_2$furan, —CH$_2$-thiophene, —CH$_2$pyridyl, benzyl, —C(O)-tetrahydrofuran, —C(O)pyrrole, or —C(O)phenyl.

In certain embodiments, a chemical entity of Formula (II) is a chemical entity of Formula (IIa), or, more specifically, a compound of Formula (IIa), or a pharmaceutically acceptable salt of a compound of Formula (IIa):

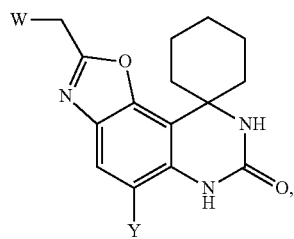

(IIa)

wherein:
W and Y have any of the values described herein.

In certain embodiments, a chemical entity of Formula (II) is a chemical entity of Formula (IIa), or, more specifically, a compound of Formula (IIb), or a pharmaceutically acceptable salt of a compound of Formula (IIb):

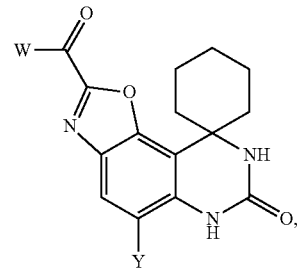

(IIb)

wherein:
W and Y have any of the values described herein.

In some embodiments of a chemical entity of Formula (IIa) or (IIb),

Y is selected from the group consisting of: —H, —F, —C$_1$, —Br, and —CH$_3$; and W is —N(R$^b$)$_2$, where each W is independently selected from the group consisting of: —H, —C$_{1-6}$ alkyl, —C$_{1-6}$ alkylOH, —C$_{1-6}$ haloalkyl, —C$_{1-6}$ haloalkylOH, —C$_{1-6}$ haloalkyl-C$_{3-7}$cycloalkyl, —C$_{3-7}$cycloalkyl, —CH$_2$-alkenyl, —CH$_2$-alkynyl, —CH$_2$C$_{3-7}$cycloalkyl, —CH$_2$C(O)C(CH$_3$)$_3$, —CH$_2$C(O)C$_{1-6}$ alkyl, —CH$_2$C(O)heterocycloalkyl, —CH$_2$C(O)OC$_{1-6}$ alkyl, —CH$_2$C(O)N(C$_{1-4}$ alkyl)$_2$, —CH$_2$CH(OH)C$_{3-7}$cycloalkyl, —C(CH$_3$)$_2$OH, —C(CH$_3$)$_2$CH$_2$OCH$_3$, —CH(CH$_3$)C(O)N(C$_{1-4}$alkyl)$_2$, —CH$_2$CF$_2$C$_{3-7}$cycloalkyl, —CH$_2$CH$_2$—R$^c$, and —(CH$_2$)R$^d$, where W is —C$_{2-6}$ alkynyl, —C$_{3-7}$cycloalkyl, —OH, —O—C$_{1-6}$ alkyl, —OC(CH$_3$)$_2$, —O—C$_{1-6}$haloalkyl, —Ophenyl, —Opyridyl, —CH$_2$N(CH$_3$)$_2$, —C(O)NHCH$_3$, —C(O)N(CH$_3$)$_2$, —CN, —NHCH$_3$, —N(CH$_3$)$_2$, —NHC(O)CH$_3$, or —SO$_2$CH$_3$, where R$^d$ is —C$_{3-7}$cycloalkyl, —C$_{3-7}$ halocycloalkyl, heterocycloalkyl, aryl, or heteroaryl, each optionally substituted with up to 4 substituents each independently selected from the group consisting of: halo, —C$_{1-6}$ alkyl, —C$_{1-6}$haloalkyl, —C$_{3-7}$cycloalkyl, —OH, —OC$_{1-6}$ alkyl, —O—C$_{1-6}$ haloalkyl, —O-phenyl, —O-pyridyl, —CH$_2$OH, —CH$_2$OCH$_3$, —CH$_2$OCH$_2$CH$_3$, —CN, —N(CH$_3$)$_2$, —N(CH$_3$) benzyl, heteroaryl, heterocycloalkyl, morpholine, phenyl, or benzyl, where n is 0, 1, 2 or 3;

or, alternatively, both R$^b$ come together to form a 4-15-membered, monocyclic, bicyclic or tricyclic ring, optionally containing up to 3 additional heteroatoms each independently selected from O (oxygen), N (nitrogen) and S (sulfur), said 4-15-membered monocyclic, bicyclic or tricyclic ring optionally substituted with up to 4 substituents each independently selected from the group consisting of: halo, —C$_{1-6}$ alkyl, —C$_{1-6}$ haloalkyl, —C$_{1-6}$ haloalkyl-cycloalkyl, —C$_{3-7}$cycloalkyl, bicyclo[2.2.1]heptane, —C$_{1-6}$ alkyl-OH, —C(CH$_3$)$_2$OH, —CH$_2$OC$_{1-6}$ alkyl, —CH$_2$C(O)OCH$_2$CH$_3$, —CH$_2$CH$_2$OC$_{1-6}$ alkyl, —CH$_2$CH$_2$OC$_{1-6}$ haloalkyl, —CH$_2$CH$_2$C(O)OCH$_3$, —OH, —OC$_{1-6}$ alkyl, —OCH$_2$—C$_{3-7}$cycloalkyl, —OCH$_2$CH$_2$OCH$_3$, =O, —CH$_2$N(CH$_3$)$_2$, —CH$_2$CH$_2$N(CH$_3$)$_2$, —C(O)C$_{1-6}$ alkyl, —C(O)H, —C(O)OH, —C(O)OC$_{1-6}$ alkyl, —C(O)CH$_3$, —C(O)NH$_2$, —C(O)NHCH$_3$, —C(O)N(CH$_3$)$_2$, —CN, —NH$_2$, —NHC(O)CH$_3$, —N(CH$_3$)$_2$, —SO$_2$CH$_3$, oxetane, pyrrolidine, morpholine, furan, thiazole, pyridyl, phenyl, thiophene, —CH$_2$imidazole, —CH$_2$furan, —CH$_2$-thiophene, —CH$_2$pyridyl, benzyl, —C(O)-tetrahydrofuran, —C(O)pyrrole, or —C(O)phenyl.

In certain embodiments, a chemical entity of Formula (III) is a chemical entity of Formula (IIIa), or, more specifically, a compound of Formula (IIIa), or a pharmaceutically acceptable salt of a compound of Formula (IIIa):

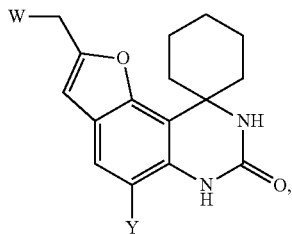

(IIIa)

wherein:
W and Y have any of the values described herein.
In some embodiments of a chemical entity of formula (IIIa),
Y is selected from the group consisting of: —H, —F, —C$_1$, —Br, and —CH$_3$; and
W is —N(R$^b$)$_2$,
  where each R$^b$ is independently selected from the group consisting of: —H, —C$_{1-6}$alkyl, —C$_{1-6}$ alkyl-OH, —C$_{1-6}$ haloalkyl, —C$_{1-6}$ haloalkylOH, —C$_{1-6}$ haloalkyl-C$_{3-7}$cycloalkyl, —C$_{3-7}$cycloalkyl, —CH$_2$-alkenyl, —CH$_2$-alkynyl, —CH$_2$C$_{3-7}$cycloalkyl, —CH$_2$C(O)C(CH$_3$)$_3$, —CH$_2$C(O)C$_{1-6}$ alkyl, —CH$_2$C(O)heterocycloalkyl, —CH$_2$C(O)OC$_{1-6}$ alkyl, —CH$_2$C(O)N(C$_{1-4}$alkyl)$_2$, —CH$_2$CH(OH)C$_{3-7}$cycloalkyl, —C(CH$_3$)$_2$OH, —C(CH$_3$)$_2$CH$_2$OCH$_3$, —CH(CH$_3$)C(O)N(C$_{1-4}$alkyl)$_2$, —CH$_2$CF$_2$C$_{3-7}$cycloalkyl, —CH$_2$CH$_2$—R$^c$, and —(CH$_2$)R$^d$,
    where R$^c$ is —C$_{2-6}$alkynyl, —C$_{3-7}$cycloalkyl, —OH, —O—C$_{1-6}$alkyl, —OC(CH$_3$)$_2$, —O—C$_{1-6}$haloalkyl, —Ophenyl, —Opyridyl, —CH$_2$N(CH$_3$)$_2$, —C(O)NHCH$_3$, —C(O)N(CH$_3$)$_2$, —CN, —NHCH$_3$, —N(CH$_3$)$_2$, —NHC(O)CH$_3$, or —SO$_2$CH$_3$,
    where R$^d$ is —C$_{3-7}$cycloalkyl, —C$_{3-7}$ halocycloalkyl, heterocycloalkyl, aryl, or heteroaryl, each optionally substituted with up to 4 substituents each independently selected from the group consisting of: halo, —C$_{1-6}$ alkyl, —C$_{1-6}$haloalkyl, —C$_{3-7}$cycloalkyl, —OH, —OC$_{1-6}$ alkyl, —O—C$_{1-6}$ haloalkyl, —O-phenyl, —O-pyridyl, —CH$_2$OH, —CH$_2$OCH$_3$, —CH$_2$OCH$_2$CH$_3$, —CN, —N(CH$_3$)$_2$, —N(CH$_3$)benzyl, heteroaryl, heterocycloalkyl, phenyl, or benzyl,
  where n is 0, 1, 2 or 3;
  or, alternatively, both R$^b$ come together to form a 4-15-membered, monocyclic, bicyclic or tricyclic ring, optionally containing up to 3 additional heteroatoms each independently selected from O (oxygen), N (nitrogen) and S (sulfur), said 4-15-membered monocyclic, bicyclic or tricyclic ring optionally substituted with up to 4 substituents each independently selected from the group consisting of: halo, —C$_{1-6}$alkyl, —C$_{1-6}$haloalkyl, —C$_{1-6}$ haloalkyl-C$_{3-7}$cycloalkyl, —C$_{3-7}$cycloalkyl, bicyclo[2.2.1]heptane, —C$_{1-6}$alkyl-OH, —C(CH$_3$)$_2$ OH, —CH$_2$OC$_{1-6}$ alkyl, —CH$_2$C(O)OCH$_2$CH$_3$, —CH$_2$CH$_2$OC$_{1-6}$ alkyl, —CH$_2$CH$_2$OC$_{1-6}$ haloalkyl, —CH$_2$CH$_2$C(O) OCH$_3$, —OH, —OC$_{1-6}$ alkyl, —OCH$_2$—C$_{3-7}$cycloalkyl, —OCH$_2$CH$_2$OCH$_3$, =O, —CH$_2$N(CH$_3$)$_2$, —CH$_2$CH$_2$N(CH$_3$)$_2$, —C(O)C$_{1-6}$ alkyl, —C(O)H, —C(O)OH, —C(O)OC$_{1-6}$ alkyl, —C(O)CH$_3$, —C(O)NH$_2$, —C(O)NHCH$_3$, —C(O)N(CH$_3$)$_2$, —CN, —NH$_2$, —NHC(O)CH$_3$, —N(CH$_3$)$_2$, —SO$_2$CH$_3$, oxetane, pyrrolidine, morpholine, furan, thiazole, pyridyl, phenyl, thiophene, —CH$_2$imidazole, —CH$_2$furan, —CH$_2$-thiophene, —CH$_2$pyridyl, benzyl, —C(O)-tetrahydrofuran, —C(O)pyrrole or —C(O)phenyl.

In certain embodiments, a chemical entity of Formula (III) is a chemical entity of Formula (IIIb), or, more specifically, a compound of Formula (IIIb), or a pharmaceutically acceptable salt of a compound of Formula (IIIb):

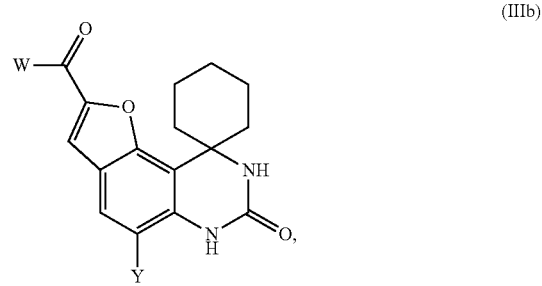

(IIIb)

wherein: W and Y have any of the values described herein.
In some embodiments of a chemical entity of Formula (IIIb),
Y is selected from the group consisting of: —H, —F, —C$_1$, —Br, and —CH$_3$; and
W is —C$_{1-6}$ aryl, —C$_{1-6}$heteroaryl, said aryl or heteroaryl optionally substituted, or —N(R$^b$)$_2$,
  where each R$^b$ is independently selected from the group consisting of: —H, —C$_{1-6}$alkyl, —C$_{1-6}$alkyl-OH, —C$_{1-6}$haloalkyl, —C$_{1-6}$haloalkyl OH, —C$_{1-6}$ haloalkyl-C$_{3-7}$cycloalkyl, —C$_{3-7}$cycloalkyl, —CH$_2$-alkenyl, —CH$_2$-alkynyl, —CH$_2$C$_{3-7}$cycloalkyl, —CH$_2$C(O)C(CH$_3$)$_3$, —CH$_2$C(O)C$_{1-6}$ alkyl, —CH$_2$C(O)heterocycloalkyl, —CH$_2$C(O)OC$_{1-6}$ alkyl, —CH$_2$C(O)N(C$_{1-4}$alkyl)$_2$, —CH$_2$CH(OH)C$_{3-7}$cycloalkyl, —C(CH$_3$)$_2$OH, —C(CH$_3$)$_2$CH$_2$OCH$_3$, —CH(CH$_3$)C(O)N(C$_{1-4}$alkyl)$_2$, —CH$_2$CF$_2$C$_{3-7}$cycloalkyl, —CH$_2$CH$_2$—R$^c$, and —(CH$_2$)R$^d$,
    where R$^c$ is —C$_{2-6}$alkynyl, —C$_{3-7}$cycloalkyl, —OH, —O—C$_{1-6}$alkyl, —OC(CH$_3$)$_2$, —O—C$_{1-6}$haloalkyl, —Ophenyl, —Opyridyl, —CH$_2$N(CH$_3$)$_2$, —C(O)NHCH$_3$, —C(O)N(CH$_3$)$_2$, —CN, —NHCH$_3$, —N(CH$_3$)$_2$, —NHC(O)CH$_3$, or —SO$_2$CH$_3$,
    where R$^d$ is —C$_{3-7}$cycloalkyl, —C$_{3-7}$ halocycloalkyl, heterocycloalkyl, aryl, or heteroaryl, each optionally substituted with up to 4 substituents each independently selected from the group consisting of: halo, —C$_{1-6}$ alkyl, —C$_{1-6}$haloalkyl, —C$_{3-7}$cycloalkyl, —OH, —OC$_{1-6}$ alkyl, —O—C$_{1-6}$ haloalkyl, —O-phenyl, —O-pyridyl, —CH$_2$OH, —CH$_2$OCH$_3$, —CH$_2$OCH$_2$CH$_3$, —CN, —N(CH$_3$)$_2$, —N(CH$_3$)benzyl, heteroaryl, heterocycloalkyl, phenyl, or benzyl,
  where n is 0, 1, 2 or 3;
  or, alternatively, both R$^b$ come together to form a 4-15-membered, monocyclic, bicyclic or tricyclic ring, optionally containing up to 3 additional heteroatoms each independently selected from O (oxygen), N (nitrogen) and S (sulfur), said 4-15-membered monocyclic, bicyclic or tricyclic ring optionally substituted with up to 4 substituents each independently selected from the group consisting of: halo, —$C_{1-6}$ alkyl, —$C_{1-6}$ haloalkyl, —$C_{1-6}$ haloalkyl-$C_{3-7}$cycloalkyl, —$C_{3-7}$cycloalkyl, -bicyclo[2.2.1]heptane, —$C_{1-6}$ alkyl-OH, —$C(CH_3)_2OH$, —$CH_2OC_{1-6}$ alkyl, —$CH_2C(O)OCH_2CH_3$, —$CH_2CH_2OC_{1-6}$alkyl, —$CH_2CH_2OC_{1-6}$ haloalkyl, —$CH_2CH_2C(O)$ $OCH_3$, —OH, —$OC_{1-6}$ alkyl, —$OCH_2$—$C_{3-7}$cycloalkyl, —$OCH_2CH_2OCH_3$, =O, —$CH_2N(CH_3)_2$, —$CH_2CH_2N(CH_3)_2$, —$C(O)C_{1-6}$ alkyl, —C(O)H, —C(O)OH, —$C(O)OC_{1-6}$ alkyl, —$C(O)CH_3$, —$C(O)NH_2$, —$C(O)NHCH_3$, —$C(O)N(CH_3)_2$, —CN, —$NH_2$, —$NHC(O)CH_3$, —$N(CH_3)_2$, —$SO_2CH_3$, oxetane, pyrrolidine, morpholine, furan, thiazole, pyridyl, phenyl, thiophene, —$CH_2$imidazole, —$CH_2$furan, —$CH_2$-thiophene, —$CH_2$pyridyl, benzyl, —C(O)-tetrahydrofuran, —C(O)pyrrole or —C(O)phenyl.

In some embodiments of a chemical entity of Formula (II), (III), (IIa), (IIb), (IIIa), or (IIIb), W is selected from the group consisting of: azetidine, pyrrole, pyrrolidine, pyrrolidinone, piperazine, piperazinone, piperidine, piperidinone, azepane, morpholine, 1-oxa-8-azaspiro[4.5]decan-3-one, 2-oxa-5-azabicyclo[2.2.1]heptane, 2-oxa-7-azaspiro[3.5] nonane, 2-oxa-8-azaspiro[4.5]decane, 2-oxa-8-azaspiro[4.5] decan-1-one, 6-oxa-9-azaspiro[4.5]decane, 7-oxa-2-azaspiro[3.5]nonane, octahydropyrrolo[3,4-c]pyrrole, octahydropyrrolo[1,2-a]pyrazine, oxaazabicyclo[2.2.1]heptane, thiomorpholine-1,1-dioxide, diazepane, 2,3,4,5-tetrahydropyrido[2,3-f][1,4]oxazepine, 5,6,7,8-tetrahydro[1,2,4]triazolo[4,3-a]pyrazine, 5,6,7,8-tetrahydroimidazo[1,2-a]pyrazine, 5,6,7,8-tetrahydropyrido[3,4-d]pyridazin-1(2H)-one, azaspiro[2.5]octane, azabicyclo[3.1.0]hexane, azabicyclo[4.1.0]heptane, diazaspiro[5.5]undecane, tetrahydroimidazopyrazine, dihydropyrrolopyridine, spiro[chroman-2,3'-pyrrolidin]-4-one, spiro[isochroman-1,4'-piperidine], 6',7'-dihydro-5'H-spiro[piperidine-4,4'-thieno[3,2-c]pyridine], and 5',6'-dihydro-4'H-spiro[piperidine-4,7'-thieno[2,3-c]pyridine], each optionally substituted with up to 4 substituents each independently selected from the group consisting of: halo, —$C_{1-6}$ alkyl, —$C_{1-6}$haloalkyl, —$C_{1-6}$ haloalkyl-$C_{3-7}$cycloalkyl, —$C_{3-7}$cycloalkyl, bicyclo[2.2.1] heptane, —$C_{1-6}$ alkyl-OH, —$C(CH_3)_2OH$, —$CH_2OC_{1-6}$alkyl, —$CH_2C(O)OCH_2CH_3$, —$CH_2CH_2OC_{1-6}$ alkyl, —$CH_2CH_2OC_{1-6}$ halo alkyl, —$CH_2CH_2C(O)OCH_3$, —OH, —$OC_{1-6}$alkyl, —$OCH_2$—$C_{3-7}$cycloalkyl, —$OCH_2CH_2OCH_3$, =O, —$CH_2N(CH_3)_2$, —$CH_2CH_2N(CH_3)_2$, —$C(O)C_{1-6}$ alkyl, —C(O)H, —C(O)OH, —$C(O)OC_{1-6}$ alkyl, —$C(O)CH_3$, —$C(O)NH_2$, —$C(O)NHCH_3$, —$C(O)N(CH_3)_2$, —CN, —$NH_2$, —$NHC(O)CH_3$, —$N(CH_3)_2$, —$SO_2CH_3$, oxetane, pyrrolidine, morpholine, furan, thiazole, pyridyl, phenyl, thiophene, —$CH_2$imidazole, —$CH_2$furan, —$CH_2$-thiophene, —$CH_2$pyridyl, benzyl, —C(O)-tetrahydrofuran, —C(O)pyrrole, or —C(O)phenyl.

In some embodiments of a chemical entity of Formula (II), (III), (IIa), (IIb), (IIIa), or (IIIb), W is -halo, —$C_{1-6}$ alkyl, —$C_{1-6}$haloalkyl, or —$C_{3-7}$cycloalkyl; said —$C_{3-7}$cycloalkyl optionally substituted with one or more halo or —$C_{1-6}$ alkyl.

In some embodiments of a chemical entity of Formula (II), (III), (IIa), (IIb), (IIIa), or (IIIb), W is halo, —$C_{1-6}$ alkyl, —$C_{1-6}$haloalkyl, —$CH_2OC_{1-5}$alkyl, —$CH_2OH$, —$CH_2CH_2OH$, —$CH_2CH_2OCH_3$, —$C(O)C_{1-6}$ alkyl, —$C(O)C_{3-7}$cycloalkyl, —$C(O)OC_{1-4}$alkyl, —$C_{3-7}$cycloalkyl, said —$C_{3-7}$cycloalkyl optionally substituted with one or more halo or —$C_{1-6}$ alkyl, —$C_{1-6}$ aryl, —$C_{1-6}$heteroaryl, said aryl or heteroaryl optionally substituted, —OH, —$OC_{1-6}$ alkyl, —$OCH_2CH_2OCH_3$, —$OCH_2C(O)N(CH_3)_2$, —O-tetrahydropyranyl, —O-piperidinyl, and —$N(R^b)_2$, where each $R^b$ is independently selected from the group consisting of: —H, —$C_{1-6}$alkyl, —$C_{1-6}$alkyl-OH, —$C_{1-6}$ haloalkyl, —$C_{1-6}$haloalkylOH, —$C_{1-6}$haloalkyl-$C_{3-7}$cycloalkyl, —$C_{3-7}$cycloalkyl, —$CH_2$-alkenyl, —$CH_2$-alkynyl, —$CH_2C_{3-7}$cycloalkyl, —$CH_2C(O)C(CH_3)_3$, —$CH_2C(O)$ $C_{1-6}$ alkyl, —$CH_2C(O)$heterocycloalkyl, —$CH_2C(O)OC_{1-6}$ alkyl, —$CH_2C(O)N(C_{1-4}alkyl)_2$, —$CH_2CH(OH)C_{3-7}$cycloalkyl, —$C(CH_3)_2OH$, —$C(CH_3)_2CH_2OCH_3$, —$CH(CH_3)C(O)N(C_{1-4}alkyl)_2$, —$CH_2CF_2C_{3-7}$cycloalkyl, —$CH_2CH_2$—Re (where $R^c$ is —$C_{2-6}$ alkynyl, —$C_{3-7}$cycloalkyl, —OH, —O—$C_{1-6}$ alkyl, —$OC(CH_3)_2$, —O—$C_{1-6}$ haloalkyl, —Ophenyl, —Opyridyl, —$CH_2N(CH_3)_2$, —C(O) $NHCH_3$, —$C(O)N(CH_3)_2$, —CN, —$NHCH_3$, —$N(CH_3)_2$, —$NHC(O)CH_3$, or —$SO_2CH_3$), and —$(CH_2)_n$—$R^d$ (where $R^d$ is —$C_{3-7}$cycloalkyl, —$C_{3-7}$halocycloalkyl, heterocycloalkyl, aryl, or heteroaryl, each optionally substituted with up to 4 substituents each independently selected from the group consisting of: -halo, —$C_{1-6}$alkyl, —$C_{1-6}$haloalkyl, —$C_{3-7}$cycloalkyl, —OH, —$OC_{1-6}$alkyl, —O—$C_{1-6}$haloalkyl, —O-phenyl, —O-pyridyl, —$CH_2OH$, —$CH_2OCH_3$, —$CH_2OCH_2CH_3$, —CN, —$N(CH_3)_2$, —$N(CH_3)$benzyl, heteroaryl, heterocycloalkyl, phenyl, or benzyl, where n is 0, 1, 2 or 3); or, alternatively, both $R^b$ come together to form a 4-15-membered, monocyclic, bicyclic or tricyclic ring, optionally containing up to 3 additional heteroatoms each independently selected from O (oxygen), N (nitrogen) and S (sulfur), said 4-15-membered monocyclic, bicyclic or tricyclic ring optionally substituted with up to 4 substituents each independently selected from the group consisting of: halo, —$C_{1-6}$alkyl, —$C_{1-6}$ haloalkyl, —$C_{1-6}$haloalkyl-$C_{3-7}$cycloalkyl, —$C_{3-7}$cycloalkyl, -bicyclo[2.2.1]heptane, —$C_{1-6}$alkyl-OH, —$C(CH_3)_2OH$, —$CH_2OC_{1-6}$ alkyl, —$CH_2C(O)OCH_2CH_3$, —$CH_2CH_2OC_{1-6}$ alkyl, —$CH_2CH_2OC_{1-6}$ haloalkyl, —$CH_2CH_2C(O)OCH_3$, —OH, —$OC_{1-6}$ alkyl, —$OCH_2$—$C_{3-7}$cycloalkyl, —$OCH_2CH_2OCH_3$, =O, —$CH_2N(CH_3)_2$, —$CH_2CH_2N(CH_3)_2$, —$C(O)C_{1-6}$ alkyl, —C(O)H, —C(O)OH, —$C(O)OC_{1-6}$ alkyl, —$C(O)CH_3$, —$C(O)NH_2$, —$C(O)NHCH_3$, —$C(O)N(CH_3)_2$, —CN, —$NH_2$, —$NHC(O)CH_3$, —$N(CH_3)_2$, —$SO_2CH_3$, oxetane, pyrrolidine, morpholine, furan, thiazole, pyridyl, phenyl, thiophene, —$CH_2$imidazole, —$CH_2$furan, —$CH_2$-thiophene, —$CH_2$pyridyl, benzyl, —C(O)-tetrahydrofuran, —C(O)pyrrole or —C(O)phenyl.

In some embodiments of a chemical entity of Formula (II), (III), (IIa), (IIb), (IIIa), or (IIIb), W is selected from the group consisting of: halo, —$C_{1-6}$ alkyl, —$C_{1-6}$ haloalkyl, —$CH_2OC_{1-5}$alkyl, —$CH_2OH$, —$CH_2CH_2OH$, —$CH_2CH_2OCH_3$, —$C(O)C_{1-6}$ alkyl, —$C(O)C_{3-7}$cycloalkyl, —$C(O)OC_{1-4}$alkyl, —$C_{3-7}$cycloalkyl, said $C_{3-7}$cycloalkyl optionally substituted with one or more halo or —$C_{1-6}$ alkyl, —$C_{1-6}$ aryl, —$C_{1-6}$ heteroaryl, said aryl or heteroaryl optionally substituted, —OH, —$OC_{1-6}$ alkyl, —$OCH_2CH_2OCH_3$, —$OCH_2C(O)N(CH_3)_2$, —O-tetrahydropyranyl, —Opiperidinyl, and —$N(R^b)_2$, where each $R^b$ is independently selected from the group consisting of: —H, —$C_{1-6}$alkyl, —$C_{1-6}$alkyl-OH, —$C_{1-6}$haloalkyl, —$C_{1-6}$haloalkylOH, —$C_{1-6}$haloalkyl-$C_{3-7}$cycloalkyl, —$C_{3-7}$cycloalkyl, —$CH_2$-alkenyl, —$CH_2$-alkynyl, —$CH_2C_{3-7}$cycloalkyl, —$CH_2C(O)C(CH_3)_3$, —$CH_2C(O)C_{1-6}$ alkyl, —$CH_2C(O)$piperidine, —$CH_2C(O)OC_{1-6}$ alkyl, —$CH_2C(O)N(C_{1-4}$alkyl$)_2$, —$CH_2CH(OH)C_{3-7}$cycloalkyl, —$C(CH_3)_2OH$, —$C(CH_3)_2CH_2OCH_3$, —$CH(CH_3)C(O)N(C_{1-4}alkyl)_2$, —$CH_2CF_2C_{3-7}$cycloalkyl, —$CH_2CH_2$—Re (where $R^c$ is —$C_{2-6}$ alkynyl, —$C_{3-7}$cycloalkyl, —OH, —O—$C_{1-6}$ alkyl, —OC(CH$_3$)$_2$, —O—$C_{1-6}$ haloalkyl, —Ophenyl, —Opyridyl, —CH$_2$N(CH$_3$)$_2$, —C(O)NHCH$_3$, —C(O)N (CH$_3$)$_2$, —CN, —NHCH$_3$, —N(CH$_3$)$_2$, —NHC(O)CH$_3$, or —SO$_2$CH$_3$, and —(CH$_2$)R$^d$ (where R$^d$ is cyclopropyl, cyclobutyl, cyclopentyl, cyclohexyl, bicyclo[1.1.1]pentane, bicyclo[3.1.0]hexane, —$C_{3-7}$halocycloalkyl, oxetane, pyrrolidine, pyrrolidinone, piperidine, piperidinone, tetrahydropyranyl, tetrahydrofuranyl, oxepane, morpholine, 3-azabicyclo[3.1.0]hexane, tetrahydrothiophene-1,1-dioxide, tetrahydro-2H-thiopyran-1,1-dioxide, thiomorpholine-1,1-dioxide, tetrahydrothiophene-1,1-dioxide, 1,3-dihydroisobenzofuran, benzofuran, indoline, benzodioxine, benzodioxole, phenyl, benzyl, —CH$_2$CH$_2$phenyl, —CH$_2$CH$_2$CH$_2$phenyl, furan, pyrrole, pyrazole, imidazole, triazole, isoxazole, oxazole, thiazole, pyridine, pyrimidine, thiophene, pyrrolopyridine, or benzimidazole, said R$^d$ optionally substituted with up to 4 substituents each independently selected from the group consisting of: —F, cyclopropyl, —OH, —O—$C_{1-6}$haloalkyl, —O— phenyl, —O-pyridyl, —CH$_2$OH, —CH$_2$OCH$_3$, —CH$_2$OCH$_2$CH$_3$, —CN, —N(CH$_3$)$_2$, —N(CH$_3$)benzyl, heteroaryl, heterocycloalkyl, morpholine, pyrrolidinone, hydroxypiperidine, phenyl, benzyl, imidazole, or pyridine, where n is 0, 1, 2 or 3); or, alternatively, both R$^b$ come together to form a monocyclic, bicyclic or tricyclic ring selected from the group consisting of: azetidine, pyrrole, pyrrolidine, pyrrolidinone, piperazine, piperazinone, piperidine, piperidinone, azepane, morpholine, 1-oxa-8-azaspiro[4.5]decan-3-one, 2-oxa-5-azabicyclo [2.2.1]heptane, 2-oxa-7-azaspiro[3.5]nonane, 2-oxa-8-azaspiro[4.5]decane, 2-oxa-8-azaspiro[4.5]decan-1-one, 6-oxa-9-azaspiro[4.5]decane, 7-oxa-2-azaspiro[3.5]nonane, octahydropyrrolo[3,4-c]pyrrole, octahydropyrrolo[1,2-a] pyrazine, oxaazabicyclo[2.2.1]heptane, thiomorpholine-1,1-dioxide, diazepane, 2,3,4,5-tetrahydropyrido[2,3-f][1,4] oxazepine, 5,6,7,8-tetrahydro[1,2,4]triazolo[4,3-a]pyrazine, 5,6,7,8-tetrahydroimidazo[1,2-a]pyrazine, 5,6,7,8-tetrahydropyrido[3,4-d]pyridazin-1(2H)-one, azaspiro[2.5]octane, azabicyclo[3.1.0]hexane, azabicyclo[4.1.0]heptane, diazaspiro[5.5]undecane, tetrahydroimidazopyrazine, dihydropyrrolopyridine, spiro[chroman-2,3'-pyrrolidin]-4-one, spiro[isochroman-1,4'-piperidine]6',7'-dihydro-5'H-spiro [piperidine-4,4'-thieno[3,2-c]pyridine], and 5',6'-dihydro-4'H-spiro[piperidine-4,7'-thieno[2,3-c]pyridine], said 4-15-membered monocyclic, bicyclic or tricyclic ring optionally substituted with up to 4 substituents each independently selected from the group consisting of: halo, —$C_{1-6}$ alkyl, —$C_{1-6}$ haloalkyl-$C_{3-7}$cycloalkyl, —$C_{3-7}$cycloalkyl, bicyclo [2.2.1]heptane, —$C_{1-6}$ alkyl-OH, —C(CH$_3$)$_2$OH, —CH$_2$OC$_{1-6}$ alkyl, —CH$_2$C(O)OCH$_2$CH$_3$, —CH$_2$CH$_2$OC$_{1-6}$ alkyl, —CH$_2$CH$_2$OC$_{1-6}$ haloalkyl, —CH$_2$CH$_2$C(O)OCH$_3$, —OH, —OC$_{1-6}$ alkyl, —OCH$_2$—$C_{3-7}$cycloalkyl, —OCH$_2$CH$_2$OCH$_3$, =O, —CH$_2$N(CH$_3$)$_2$, —CH$_2$CH$_2$N(CH$_3$)$_2$, —C(O)C$_{1-6}$ alkyl, —C(O)H, —C(O) OH, —C(O)OC$_{1-6}$ alkyl, —C(O)CH$_3$, —C(O)NH$_2$, —C(O) NHCH$_3$, —C(O)N(CH$_3$)$_2$, —CN, —NH$_2$, —NHC(O)CH$_3$, —N(CH$_3$)$_2$, —SO$_2$CH$_3$, oxetane, pyrrolidine, morpholine, furan, thiazole, pyridyl, phenyl, thiophene, —CH$_2$imidazole, —CH$_2$furan, —CH$_2$-thiophene, —CH$_2$pyridyl, benzyl, —C(O)-tetrahydrofuran, —C(O)pyrrole or —C(O)phenyl.

In some embodiments of a chemical entity of Formula (II), (III), (IIa), (IIb), (IIIa), or (IIIb), W is —N(R$^b$)$_2$, where both R$^b$ come together to form a monocyclic, bicyclic or tricyclic ring selected from the group consisting of: azetidine, pyrrole, pyrrolidine, pyrrolidinone, piperazine, piperazinone, piperidine, piperidinone, azepane, morpholine, 1-oxa-8-azaspiro[4.5]decan-3-one, 2-oxa-5-azabicyclo [2.2.1]heptane, 2-oxa-7-azaspiro[3.5]nonane, 2-oxa-8-azaspiro[4.5]decane, 2-oxa-8-azaspiro[4.5]decan-1-one, 6-oxa-9-azaspiro[4.5]decane, 7-oxa-2-azaspiro[3.5]nonane, octahydropyrrolo[3,4-c]pyrrole, octahydropyrrolo[1,2-a] pyrazine, oxaazabicyclo[2.2.1]heptane, thiomorpholine-1,1-dioxide, diazepane, 2,3,4,5-tetrahydropyrido[2,3-f][1,4] oxazepine, 5,6,7,8-tetrahydro[1,2,4]triazolo[4,3-a]pyrazine, 5,6,7,8-tetrahydroimidazo[1,2-a]pyrazine, 5,6,7,8-tetrahydropyrido[3,4-c]pyridazin-1(2H)-one, azaspiro[2.5]octane, azabicyclo[3.1.0]hexane, azabicyclo[4.1.0]heptane, diazaspiro[5.5]undecane, tetrahydroimidazopyrazine, dihydropyrrolopyridine, spiro[chroman-2,3'-pyrrolidin]-4-one, spiro[isochroman-1,4'-piperidine], 6',7'-dihydro-5'H-spiro [piperidine-4,4'-thieno[3,2-c]pyridine], and 5',6'-dihydro-4'H-spiro[piperidine-4,7'-thieno[2,3-c]pyridine], said monocyclic, bicyclic or tricyclic ring optionally substituted with up to 4 substituents each independently selected from the group consisting of: halo, —$C_{1-6}$ alkyl, —$C_{1-6}$haloalkyl, —$C_{1-6}$ halo alkyl-$C_{3-7}$cycloalkyl, —$C_{3-7}$cycloalkyl, bicyclo[2.2.1]heptane, —$C_{1-6}$ alkyl-OH, —C(CH$_3$)$_2$OH, —CH$_2$OC$_{1-6}$ alkyl, —CH$_2$C (O)OCH$_2$CH$_3$, —CH$_2$CH$_2$OC$_{1-6}$ alkyl, —CH$_2$CH$_2$OC$_{1-6}$ haloalkyl, —CH$_2$CH$_2$C(O)OCH$_3$, —OH, —OC$_{1-6}$ alkyl, —OCH$_2$—$C_{3-7}$cycloalkyl, —OCH$_2$CH$_2$OCH$_3$, =O, —CH$_2$N(CH$_3$)$_2$, —CH$_2$CH$_2$N(CH$_3$)$_2$, —C(O)C$_{1-6}$ alkyl, —C(O)H, —C(O)OH, —C(O)OC$_{1-6}$ alkyl, —C(O)CH$_3$, —C(O)NH$_2$, —C(O)NHCH$_3$, —C(O)N(CH$_3$)$_2$, —CN, —NH$_2$, —NHC(O)CH$_3$, —N(CH$_3$)$_2$, —SO$_2$CH$_3$, oxetane, pyrrolidine, morpholine, furan, thiazole, pyridyl, phenyl, -thiophene, —CH$_2$imidazole, —CH$_2$furan, —CH$_2$-thiophene, —CH$_2$pyridyl, benzyl, —C(O)-tetrahydrofuran, —C(O)pyrrole or —C(O)phenyl.

In some embodiments of a chemical entity of Formula (II), (III), (IIa), (IIb), (IIIa), or (IIIb), W is selected from the group consisting of: —$C_{1-6}$ alkyl, —$C_{1-6}$ haloalkyl, —$C_{3-7}$ cycloalkyl, —C(O)C$_{1-6}$ alkyl, —C(O)C$_{3-7}$cycloalkyl, and —CH$_2$CH$_2$OCH$_3$.

In some embodiments of a chemical entity of Formula (II) or (III), wherein V is a bond and W is halo, —$C_{1-6}$ alkyl, —$C_{1-6}$ haloalkyl, or —$C_{3-7}$cycloalkyl, said —$C_{3-7}$cycloalkyl optionally substituted with one or more halo or —$C_{1-6}$ alkyl.

In some embodiments of a chemical entity of Formula (II) or (III), wherein V is —CH$_2$—, and W is selected from the group consisting of: halo, —$C_{1-6}$alkyl, —$C_{1-6}$haloalkyl, —CH$_2$OC$_{1-5}$alkyl, —CH$_2$OH, —CH$_2$CH$_2$OH, —CH$_2$CH$_2$OCH$_3$, —C(O)C$_{1-6}$ alkyl, —C(O)C$_{3-7}$cycloalkyl, —C(O)OC$_{1-4}$alkyl, —$C_{3-7}$cycloalkyl, said —$C_{3-7}$cycloalkyl optionally substituted with one or more halo or —$C_{1-6}$alkyl, —$C_{1-6}$ aryl, —$C_{1-6}$heteroaryl, said aryl or heteroaryl optionally substituted, —OH, —OC$_{1-6}$ alkyl, —OCH$_2$CH$_2$OCH$_3$, —OCH$_2$C(O)N(CH$_3$)$_2$, —O-tetrahydropyranyl, —Opiperidinyl, and —N(R$^b$)$_2$, where each R$^b$ is independently selected from the group consisting of: —H, —$C_{1-6}$alkyl, —$C_{1-6}$alkyl-OH, —$C_{1-6}$ haloalkyl, —$C_{1-6}$ haloalkylOH, —$C_{1-6}$ haloalkyl-$C_{3-7}$cycloalkyl, —$C_{3-7}$cycloalkyl, —CH$_2$-alkenyl, —CH$_2$-alkynyl, —CH$_2$C$_{3-7}$cycloalkyl, —CH$_2$C(O)C(CH$_3$)$_3$, —CH$_2$C(O)C$_{1-6}$ alkyl, —CH$_2$C(O)heterocycloalkyl, —CH$_2$C(O)OC$_{1-6}$ alkyl, —CH$_2$C(O)N(C$_{1-4}$alkyl)$_2$, —CH$_2$CH(OH)C$_{3-7}$cycloalkyl, —C(CH$_3$)$_2$OH, —C(CH$_3$)$_2$CH$_2$OCH$_3$, —CH(CH$_3$)C(O)N (C$_{1-4}$alkyl)$_2$, —CH$_2$CF$_2$C$_{3-7}$cycloalkyl, —CH$_2$CH$_2$—R$^e$, where R$^e$ is —$C_{2-6}$ alkynyl, —$C_{3-7}$cycloalkyl, —OH, —O—$C_{1-6}$ alkyl, —OC(CH$_3$)$_2$, —O—$C_{1-6}$haloalkyl, —Ophenyl, —Opyridyl, —CH$_2$N(CH$_3$)$_2$, —C(O)NHCH$_3$, —C(O)N(CH$_3$)$_2$, —CN, —NHCH$_3$, —N(CH$_3$)$_2$, —NHC (O)CH$_3$, or —SO$_2$CH$_3$, —(CH$_2$)$_n$—R$^d$, where R$^d$ is —C$_{3-7}$ cycloalkyl, —C$_{3-7}$halocycloalkyl, heterocycloalkyl, aryl, and heteroaryl, each optionally substituted with up to 4 substituents each independently selected from the group consisting of: halo,
—C$_{1-6}$ alkyl, —C$_{1-6}$ haloalkyl, —C$_{3-7}$cycloalkyl, —OH, —OC$_{1-6}$ alkyl, —O—C$_{1-6}$ haloalkyl, —O-phenyl, —O-pyridyl, —CH$_2$OH, —CH$_2$OCH$_3$, —CH$_2$OCH$_2$CH$_3$, heteroaryl, heterocycloalkyl, morpholine, phenyl, —CN, —N(CH$_3$)$_2$, —N(CH$_3$)benzyl, heterocycloalkyl, aryl, or heteroaryl, where n is 0, 1, 2 or 3; or, alternatively, both R$^b$ come together to form a 4-15-membered, monocyclic, bicyclic or tricyclic ring, optionally containing up to 3 additional heteroatoms each independently selected from O (oxygen), N (nitrogen) and S (sulfur), said 4-15-membered monocyclic, bicyclic or tricyclic ring optionally substituted with up to 4 substituents each independently selected from the group consisting of: halo, —C$_{1-6}$ alkyl, —C$_{1-6}$halo alkyl, —C$_{1-6}$haloalkyl-C$_{3-7}$cycloalkyl, —C$_{3-7}$cycloalkyl, bicyclo[2.2.1]heptane, —C$_{1-6}$alkyl-OH, —C(CH$_3$)$_2$OH, —CH$_2$OC$_{1-6}$alkyl, —CH$_2$C(O)OCH$_2$CH$_3$, —CH$_2$CH$_2$OC$_{1-6}$ alkyl, —CH$_2$CH$_2$OC$_{1-6}$ halo alkyl, —CH$_2$CH$_2$C(O)OCH$_3$, —OH, —OC$_{1-6}$alkyl, —OCH$_2$—C$_{3-7}$cycloalkyl, —OCH$_2$CH$_2$OCH$_3$, =O, —CH$_2$N(CH$_3$)$_2$, —CH$_2$CH$_2$N(CH$_3$)$_2$, —C(O)C$_{1-6}$ alkyl, —C(O)H, —C(O)OH, —C(O)OC$_{1-6}$ alkyl, —C(O)CH$_3$, —C(O)NH$_2$, —C(O)NHCH$_3$, —C(O)N(CH$_3$)$_2$, —CN, —NH$_2$, —NHC(O)CH$_3$, —N(CH$_3$)$_2$, —SO$_2$CH$_3$, oxetane, pyrrolidine, morpholine, furan, thiazole, pyridyl, phenyl, thiophene, —CH$_2$imidazole, —CH$_2$furan, —CH$_2$-thiophene, —CH$_2$pyridyl, benzyl, —C(O)-tetrahydrofuran, —C(O)pyrrole or —C(O)phenyl.

In some embodiments of a chemical entity of Formula (II) or (III), W is selected from the group consisting of: halo, —C$_{1-6}$alkyl, —C$_{1-6}$haloalkyl, —CH$_2$OC$_{1-5}$ alkyl, —CH$_2$OH, —CH$_2$CH$_2$OH, —CH$_2$CH$_2$OCH$_3$, —C(O)C$_{1-6}$ alkyl, —C(O)C$_{3-7}$cycloalkyl, —C(O)OC$_{1-4}$alkyl, —C$_{3-7}$cycloalkyl, said —C$_{3-7}$cycloalkyl optionally substituted with one or more halo or —C$_{1-6}$alkyl, optionally substituted —C$_{1-6}$aryl, optionally substituted —C$_{1-6}$ hetero aryl, —OH, —OC$_{1-6}$ alkyl, —OCH$_2$CH$_2$OCH$_3$, —OCH$_2$C(O)N(CH$_3$)$_2$, —O-tetrahydropyranyl, —Opiperidinyl, and —N(R$^b$)$_2$, where each R$^b$ is independently selected from the group consisting of: —H, —C$_{1-6}$alkyl, —C$_{1-6}$alkyl-OH, —C$_{1-6}$ haloalkyl, —C$_{1-6}$ haloalkylOH, —C$_{1-6}$ haloalkyl-C$_{3-7}$cycloalkyl, —C$_{3-7}$cycloalkyl, —CH$_2$-alkenyl, —CH$_2$-alkynyl, —CH$_2$C$_{3-7}$cycloalkyl, —CH$_2$C(O)C(CH$_3$)$_3$, —CH$_2$C(O)C$_{1-6}$ alkyl, —CH$_2$C(O)piperidine, —CH$_2$C(O)OC$_{1-6}$ alkyl, —CH$_2$C(O)N(C$_{1-4}$alkyl)$_2$, —CH$_2$CH(OH)C$_{3-7}$cycloalkyl, —C(CH$_3$)$_2$OH, —C(CH$_3$)$_2$CH$_2$OCH$_3$, —CH(CH$_3$)C(O)N(C$_{1-4}$alkyl)$_2$, —CH$_2$CF$_2$C$_{3-7}$cycloalkyl, —CH$_2$CH$_2$—Re (where R$^c$ is —C$_{2-6}$ alkynyl, —C$_{3-7}$cycloalkyl, —OH, —O—C$_{1-6}$ alkyl, —OC(CH$_3$)$_2$, —O—C$_{1-6}$ haloalkyl, —Ophenyl, —Opyridyl, —CH$_2$N(CH$_3$)$_2$, —C(O)NHCH$_3$, —C(O)N(CH$_3$)$_2$, —CN, —NHCH$_3$, —N(CH$_3$)$_2$, —NHC(O)CH$_3$, or —SO$_2$CH$_3$), and —(CH$_2$)R$^d$ (where R$^d$ is cyclopropyl, cyclobutyl, cyclopentyl, cyclohexyl, bicyclo[1.1.1]pentane, bicyclo[3.1.0]hexane, —C$_{3-7}$halocycloalkyl, oxetane, pyrrolidine, pyrrolidinone, piperidine, piperidinone, tetrahydropyranyl, tetrahydrofuranyl, oxepane, morpholine, 3-azabicyclo[3.1.0]hexane, tetrahydrothiophene-1,1-dioxide, tetrahydro-2H-thiopyran-1,1-dioxide, thiomorpholine-1,1-dioxide, tetrahydrothiophene-1,1-dioxide, 1,3-dihydroisobenzofuran, benzofuran, indoline, benzodioxine, benzodioxole, phenyl, benzyl, —CH$_2$CH$_2$phenyl, —CH$_2$CH$_2$CH$_2$phenyl, furan, pyrrole, pyrazole, imidazole, triazole, isoxazole, oxazole, thiazole, pyridine, pyrimidine, thiophene, pyrrolopyridine, benzimidazole, said R$^d$ optionally substituted with up to 4 substituents each independently selected from the group consisting of: —F, C$_{1-6}$alkyl, cyclopropyl, —OH, —O—C$_{1-6}$ halo alkyl, —O-phenyl, —O-pyridyl, —CH$_2$OH, —CH$_2$OCH$_3$, —CH$_2$OCH$_2$CH$_3$, —CN, or —N(CH$_3$)$_2$, —N(CH$_3$)benzyl, heteroaryl, heterocycloalkyl, morpholine, phenyl, pyrrolidinone, hydroxypiperidine, benzyl, imidazole, or pyridine, where n is 0, 1, 2 or 3; or, alternatively, both R$^b$ come together to form a monocyclic, bicyclic or tricyclic ring selected from the group consisting of: azetidine, pyrrole, pyrrolidine, pyrrolidinone, piperazine, piperazinone, piperidine, piperidinone, azepane, morpholine, 1-oxa-8-azaspiro[4.5]decan-3-one, 2-oxa-5-azabicyclo[2.2.1]heptane, 2-oxa-7-azaspiro[3.5]nonane, 2-oxa-8-azaspiro[4.5]decane, 2-oxa-8-azaspiro[4.5]decan-1-one, 6-oxa-9-azaspiro[4.5]decane, 7-oxa-2-azaspiro[3.5]nonane, octahydropyrrolo[3,4-c]pyrrole, -octahydropyrrolo[1,2-a]pyrazine, oxaazabicyclo[2.2.1]heptane, thiomorpholine-1,1-dioxide, diazepane, 2,3,4,5-tetrahydropyrido[2,3-f][1,4]oxazepine, 5,6,7,8-tetrahydro[1,2,4]triazolo[4,3-a]pyrazine, 5,6,7,8-tetrahydroimidazo[1,2-a]pyrazine, 5,6,7,8-tetrahydropyrido[3,4-d]pyridazin-1(2H)-one, azaspiro[2.5]octane, azabicyclo[3.1.0]hexane, azabicyclo[4.1.0]heptane, diazaspiro[5.5]undecane, tetrahydroimidazopyrazine, dihydropyrrolopyridine, spiro[chroman-2,3'-pyrrolidin]-4-one, spiro[isochroman-1,4'-piperidine]6',7'-dihydro-5'H-spiro[piperidine-4,4'-thieno[3,2-c]pyridine], and 5',6'-dihydro-4'H-spiro[piperidine-4,7'-thieno[2,3-c]pyridine], said monocyclic, bicyclic or tricyclic ring optionally substituted with up to 4 substituents each independently selected from the group consisting of: halo, —C$_{1-6}$alkyl, —C$_{1-6}$haloalkyl-C$_{3-7}$cycloalkyl, —C$_{3-7}$cycloalkyl, bicyclo[2.2.1]heptane, —C$_{1-6}$alkyl-OH, —C(CH$_3$)$_2$OH, —CH$_2$OC$_{1-6}$ alkyl, —CH$_2$C(O)OCH$_2$CH$_3$, —CH$_2$CH$_2$OC$_{1-6}$ alkyl, —CH$_2$CH$_2$OC$_{1-6}$ haloalkyl, —CH$_2$CH$_2$C(O)OCH$_3$, —OH, —OC$_{1-6}$ alkyl, —OCH$_2$—C$_{3-7}$cycloalkyl, —OCH$_2$CH$_2$OCH$_3$, =O, —CH$_2$N(CH$_3$)$_2$, —CH$_2$CH$_2$N(CH$_3$)$_2$, —C(O)C$_{1-6}$ alkyl, —C(O)H, —C(O)OH, —C(O)OC$_{1-6}$ alkyl, —C(O)CH$_3$, —C(O)NH$_2$, —C(O)NHCH$_3$, —C(O)N(CH$_3$)$_2$, —CN, —NH$_2$, —NHC(O)CH$_3$, —N(CH$_3$)$_2$, —SO$_2$CH$_3$, oxetane, pyrrolidine, morpholine, furan, thiazole, pyridyl, phenyl, thiophene, —CH$_2$imidazole, —CH$_2$furan, —CH$_2$-thiophene, —CH$_2$pyridyl, benzyl, —C(O)-tetrahydrofuran, —C(O)pyrrole or —C(O)phenyl.

In some embodiments of a chemical entity of Formula (II) or (III), W is —N(R$^b$)$_2$, where each R$^b$ is independently selected from the group consisting of: —H, —C$_{1-6}$alkyl, —C$_{1-6}$alkyl-OH, —C$_{1-6}$haloalkyl, —C$_{1-6}$haloalkylOH, —C$_{1-6}$haloalkyl-C$_{3-7}$cycloalkyl, —C$_{3-7}$cycloalkyl, —CH$_2$-alkenyl, —CH$_2$-alkynyl, —CH$_2$C$_{3-7}$cycloalkyl, —CH$_2$C(O)C(CH$_3$)$_3$, —CH$_2$C(O)C$_{1-6}$ alkyl, —CH$_2$C(O)piperidine, —CH$_2$C(O)OC$_{1-6}$alkyl, —CH$_2$C(O)N(C$_{1-4}$alkyl)$_2$, —CH$_2$CH(OH)C$_{3-7}$cycloalkyl, —C(CH$_3$)$_2$OH, —C(CH$_3$)$_2$CH$_2$OCH$_3$, —CH(CH$_3$)C(O)N(C$_{1-4}$alkyl)$_2$, —CH$_2$CF$_2$C$_{3-7}$cycloalkyl, —CH$_2$CH$_2$—Re (where R$^c$ is —C$_{2-6}$ alkynyl, —C$_{3-7}$cycloalkyl, —OH, —O—C$_{1-6}$ alkyl, —OC(CH$_3$)$_2$, —O—C$_{1-6}$ haloalkyl, —Ophenyl, —Opyridyl, —CH$_2$N(CH$_3$)$_2$, —C(O)NHCH$_3$, —C(O)N(CH$_3$)$_2$, —CN, —NHCH$_3$, —N(CH$_3$)$_2$, —NHC(O)CH$_3$, or —SO$_2$CH$_3$), and —(CH$_2$)R$^d$ (where R$^d$ is cyclopropyl, cyclobutyl, cyclopentyl, cyclohexyl, bicyclo[1.1.1]pentane, bicyclo[3.1.0]hexane, —C$_{3-7}$ halocycloalkyl, oxetane, pyrrolidine, pyrrolidinone, piperidine, piperidinone, tetrahydropyranyl, tetrahydrofuranyl, oxepane, morpholine, 3-azabicyclo[3.1.0]hexane, tetrahydrothiophene-1,1-dioxide, tetrahydro-2H-thiopyran-1,1-dioxide, thiomorpholine-1,1-dioxide, tetrahydrothiophene-1,1-dioxide, 1,3-dihydroisobenzofuran, benzofuran, indoline, benzodioxine, benzodioxole, phenyl, benzyl, —CH$_2$CH$_2$phenyl, —CH$_2$CH$_2$CH$_2$phenyl, furan, pyrrole, pyrazole, imidazole, triazole, isoxazole, oxazole, thiazole, pyridine, pyrimidine, thiophene, pyrrolopyridine, or benzimidazole, said R$^d$ optionally substituted with up to 4 substituents each independently selected from the group consisting of: —F, —C$_{1-6}$alkyl, —C$_{1-6}$haloalkyl, cyclopropyl, —OH, —OC$_{1-6}$alkyl, —O—C$_{1-6}$haloalkyl, —O—phenyl, —O-pyridyl, —CH$_2$OH, —CH$_2$OCH$_3$, —CH$_2$OCH$_2$CH$_3$, —CN, —N(CH$_3$)$_2$, —N(CH$_3$)benzyl, heteroaryl, heterocycloalkyl, morpholine, pyrrolidinone, hydroxypiperidine, phenyl, benzyl, imidazole, or pyridine, where n is 0, 1, 2 or 3).

In some embodiments of a chemical entity of Formula (II) or (III), W is N(R$^b$)$_2$, where both R$^b$ come together to form a monocyclic, bicyclic or tricyclic ring selected from the group consisting of: azetidine, pyrrole, pyrrolidine, pyrrolidinone, piperazine, piperazinone, piperidine, piperidinone, azepane, morpholine, 1-oxa-8-azaspiro[4.5]decan-3-one, 2-oxa-5-azabicyclo[2.2.1]heptane, 2-oxa-7-azaspiro[3.5]nonane, 2-oxa-8-azaspiro[4.5]decane, 2-oxa-8-azaspiro[4.5]decan-1-one, 6-oxa-9-azaspiro[4.5]decane, 7-oxa-2-azaspiro[3.5]nonane, octahydropyrrolo[3,4-c]pyrrole, octahydropyrrolo[1,2-a]pyrazine, oxaazabicyclo[2.2.1]heptane, thiomorpholine-1,1-dioxide, -diazepane, 2,3,4,5-tetrahydropyrido[2,3-f][1,4]oxazepine, 5,6,7,8-tetrahydro[1,2,4]triazolo[4,3-a]pyrazine, 5,6,7,8-tetrahydroimidazo[1,2-a]pyrazine, 5,6,7,8-tetrahydropyrido[3,4-d]pyridazin-1(2H)-one, azaspiro[2.5]octane, azabicyclo[3.1.0]hexane, azabicyclo[4.1.0]heptane, diazaspiro[5.5]undecane, tetrahydroimidazopyrazine, dihydropyrrolopyridine, spiro[chroman-2,3'-pyrrolidin]-4-one, spiro[isochroman-1,4'-piperidine], 6',7'-dihydro-5'H-spiro[piperidine-4,4'-thieno[3,2-c]pyridine], and 5',6'-dihydro-4'H-spiro[piperidine-4,7'-thieno[2,3-c]pyridine], said monocyclic, bicyclic or tricyclic ring optionally substituted with up to 4 substituents each independently selected from the group consisting of: halo, —C$_{1-6}$alkyl, —C$_{1-6}$haloalkyl-C$_{3-7}$cycloalkyl, —C$_{3-7}$cycloalkyl, bicyclo[2.2.1]heptane, —C$_{1-6}$ alkyl-OH, —C(CH$_3$)$_2$OH, —CH$_2$OC$_{1-6}$alkyl, —CH$_2$C(O)OCH$_2$CH$_3$, —CH$_2$CH$_2$OC$_{1-6}$ alkyl, —CH$_2$CH$_2$OC$_{1-6}$ haloalkyl, —CH$_2$CH$_2$C(O)OCH$_3$, —OH, —OC$_{1-6}$ alkyl, —OCH$_2$—C$_{3-7}$cycloalkyl, —OCH$_2$CH$_2$OCH$_3$, =O, —CH$_2$N(CH$_3$)$_2$, —CH$_2$CH$_2$N(CH$_3$)$_2$, —C(O)C$_{1-6}$ alkyl, —C(O)H, —C(O)OH, —C(O)OC$_{1-6}$ alkyl, —C(O)NH$_2$, —C(O)NHCH$_3$, —C(O)N(CH$_3$)$_2$, —CN, —NH$_2$, —NHC(O)CH$_3$, —N(CH$_3$)$_2$, —SO$_2$CH$_3$, oxetane, pyrrolidine, morpholine, furan, thiazole, pyridyl, phenyl, thiophene, —CH$_2$imidazole, —CH$_2$furan, —CH$_2$-thiophene, —CH$_2$pyridyl, benzyl, —C(O)-tetrahydrofuran, —C(O)pyrrole or —C(O)phenyl.

In some embodiments of a chemical entity of Formula (II) or (III), W is selected from the group consisting of: -halo, —C$_{1-6}$alkyl, —CH$_2$OC$_{1-5}$alkyl, —CH$_2$OH, —CH$_2$CH$_2$OH, —CH$_2$CH$_2$OCH$_3$, —C(O)C$_{1-6}$ alkyl, —C(O)C$_{3-7}$cycloalkyl, —C(O)OC$_{1-4}$alkyl, —C$_{3-7}$cycloalkyl, said —C$_{3-7}$cycloalkyl optionally substituted with one or more -halo or —C$_{1-6}$alkyl, optionally substituted —C$_{1-6}$aryl, optionally substituted —C$_{1-6}$hetero aryl, —OH, —OCH$_2$CH$_2$OCH$_3$, —OCH$_2$C(O)N(CH$_3$)$_2$, —O-tetrahydropyranyl, —Opiperidinyl, and —N(R$^b$)$_2$, where each R$^b$ is independently selected from the group consisting of: —H, —C$_{1-6}$ haloalkylOH, —C$_{1-6}$ haloalkyl-C$_{3-7}$cycloalkyl, —C$_{3-7}$cycloalkyl, —CH$_2$-alkenyl, —CH$_2$-alkynyl, —CH$_2$C$_{3-7}$cycloalkyl, —CH$_2$C(O)C(CH$_3$)$_3$, —CH$_2$C(O)C$_{1-6}$ alkyl, —CH$_2$C(O)heterocycloalkyl, —CH$_2$C(O)OC$_{1-6}$ alkyl, —CH$_2$C(O)N(C$_{1-4}$alkyl)$_2$, —CH$_2$CH(OH)C$_{3-7}$cycloalkyl, —C(CH$_3$)$_2$OH, —C(CH$_3$)$_2$CH$_2$OCH$_3$, —CH(CH$_3$)C(O)N(C$_{1-4}$alkyl)$_2$, —CH$_2$CF$_2$C$_{3-7}$cycloalkyl, —CH$_2$CH$_2$—R$^c$, where R$^c$ is —C$_{2-6}$ alkynyl, —C$_{3-7}$cycloalkyl, —OH, —O—C$_{1-6}$ alkyl, —OC(CH$_3$)$_2$, —Ophenyl, —Opyridyl, —CH$_2$N(CH$_3$)$_2$, —C(O)NHCH$_3$, —C(O)N(CH$_3$)$_2$, —CN, —NHCH$_3$, —N(CH$_3$)$_2$, —NHC(O)CH$_3$, or —SO$_2$CH$_3$, and —(CH$_2$)$_n$—R$^d$, where R$^d$ is —C$_{3-7}$cycloalkyl, —C$_{3-7}$ halocycloalkyl, heterocycloalkyl, aryl, and heteroaryl, each optionally substituted with up to 4 substituents each independently selected from the group consisting of: halo, —C$_{1-6}$alkyl, —C$_{3-7}$cycloalkyl, —OH, —O—C$_{1-6}$haloalkyl, —O-phenyl, —O-pyridyl, —CH$_2$OH, —CH$_2$OCH$_3$, —CH$_2$OCH$_2$CH$_3$, —CN, or —N(CH$_3$)$_2$, —N(CH$_3$)benzyl, heteroaryl, heterocycloalkyl, phenyl, or benzyl, where n is 0, 1, 2 or 3; or, alternatively, both R$^b$ come together to form a 4-15-membered, monocyclic, bicyclic or tricyclic ring, optionally containing up to 3 additional heteroatoms each independently selected from O (oxygen), N (nitrogen) and S (sulfur), said 4-15-membered monocyclic, bicyclic or tricyclic ring optionally substituted with up to 4 substituents each independently selected from the group consisting of: halo, —C$_{1-6}$ alkyl, —C$_{1-6}$ halo alkyl, —C$_{1-6}$ haloalkyl-C$_{3-7}$cycloalkyl, —C$_{3-7}$cycloalkyl, bicyclo[2.2.1]heptane, —C$_{1-6}$ alkyl-OH, —C(CH$_3$)$_2$OH, —CH$_2$OC$_{1-6}$alkyl, —CH$_2$C(O)OCH$_2$CH$_3$, —CH$_2$CH$_2$OC$_{1-6}$ alkyl, —CH$_2$CH$_2$OC$_{1-6}$ haloalkyl, —CH$_2$CH$_2$C(O)OCH$_3$, —OH, —OC$_{1-6}$alkyl, —OCH$_2$—C$_{3-7}$cycloalkyl, —OCH$_2$CH$_2$OCH$_3$, =O, —CH$_2$N(CH$_3$)$_2$, —CH$_2$CH$_2$N(CH$_3$)$_2$, —C(O)C$_{1-6}$ alkyl, —C(O)H, —C(O)OH, —C(O)OC$_{1-6}$ alkyl, —C(O)NH$_2$, —C(O)NHCH$_3$, —C(O)N(CH$_3$)$_2$, —CN, —NH$_2$, —NHC(O)CH$_3$, —N(CH$_3$)$_2$, —SO$_2$CH$_3$, oxetane, pyrrolidine, morpholine, furan, thiazole, pyridyl, phenyl, thiophene, —CH$_2$imidazole, —CH$_2$furan, —CH$_2$-thiophene, —CH$_2$pyridyl, benzyl, —C(O)-tetrahydrofuran, —C(O)pyrrole or —C(O)phenyl.

In some embodiments of compounds of Formula (II), (IIa), (IIb), (III), (IIIa), and (IIIb), Y is selected from the group consisting of: —H, —F, —C$_1$, —Br, and —CH$_3$;

Z is selected from the group consisting of: —H, —F and —CH$_3$;

m is 0, 1 or 2;

V is —CH$_2$— or —C(O)—; and

W is —N(R$^b$)$_2$, where each R$^b$ is independently selected from the group consisting of: —H, —C$_{1-6}$haloalkyl, —C$_{1-6}$haloalkylOH, —C$_{1-6}$haloalkyl-C$_{3-7}$cycloalkyl, —C$_{3-7}$cycloalkyl, —CH$_2$-alkenyl, —CH$_2$-alkynyl, —CH$_2$C$_{3-7}$cycloalkyl, —CH$_2$C(O)C(CH$_3$)$_3$, —CH$_2$C(O)C$_{1-6}$ alkyl, —CH$_2$C(O)heterocycloalkyl, —CH$_2$C(O)OC$_{1-6}$ alkyl, —CH$_2$C(O)N(C$_{1-4}$alkyl)$_2$, —CH$_2$CH(OH)C$_{3-7}$cycloalkyl, —C(CH$_3$)$_2$OH, —C(CH$_3$)$_2$CH$_2$OCH$_3$, —CH(CH$_3$)C(O)N(C$_{1-4}$alkyl)$_2$, —CH$_2$CF$_2$C$_{3-7}$cycloalkyl, —CH$_2$CH$_2$—R$^c$ (where R$^c$ is —C$_{2-6}$ alkynyl, —C$_{3-7}$cycloalkyl, —OH, —OC(CH$_3$)$_2$, —Ophenyl, —Opyridyl, —CH$_2$N(CH$_3$)$_2$, —C(O)NHCH$_3$, —C(O)N(CH$_3$)$_2$, —CN, —NHCH$_3$, —N(CH$_3$)$_2$, —NHC(O)CH$_3$, or —SO$_2$CH$_3$), and —(CH$_2$)$_n$R$^d$ (where R$^d$ is cyclopropyl, cyclobutyl, cyclopentyl, cyclohexyl, bicyclo[1.1.1]pentane, bicyclo[3.1.0]hexane, —C$_{3-7}$ halocycloalkyl, oxetane, pyrrolidine, pyrrolidinone, piperidine, piperidinone, tetrahydropyranyl, tetrahydrofuranyl, oxepane, morpholine, 3-azabicyclo[3.1.0]hexane, tetrahydrothiophene-1,1-dioxide, tetrahydro-2H-thiopyran-1,1-dioxide, thiomorpholine-1,1-dioxide, tetrahydrothiophene-1,1-dioxide, 1,3-dihydroisobenzofuran, benzofuran, indoline, benzodioxine, benzodioxole, phenyl, benzyl, —CH$_2$CH$_2$phenyl, —CH$_2$CH$_2$CH$_2$phenyl, furan, pyrrole, pyrazole, imidazole, triazole, isoxazole, oxazole, thiazole, pyridine, pyrimidine, thiophene, pyrrolopyridine, benzimidazole, said $R^d$ optionally substituted with up to 4 substituents each independently selected from the group consisting of: halo, —$C_{1-6}$alkyl, —$C_{1-6}$haloalkyl, cyclopropyl, —OH, —$OC_{1-6}$alkyl, —O—$C_{1-6}$ haloalkyl, —O-phenyl, —O-pyridyl, —$CH_2OH$, —$CH_2OCH_3$, —$CH_2OCH_2CH_3$, —CN, —$N(CH_3)_2$, —$N(CH_3)$benzyl, heteroaryl, heterocycloalkyl, phenyl, or benzyl, where n is 0, 1, 2 or 3); or, alternatively, both $R^b$ come together to form a monocyclic, bicyclic or tricyclic ring selected from the group consisting of: azetidine, pyrrole, pyrrolidine, pyrrolidinone, piperazine, piperazinone, piperidine, piperidinone, azepane, morpholine, 1-oxa-8-azaspiro[4.5]decan-3-one, 2-oxa-5-azabicyclo[2.2.1]heptane, 2-oxa-7-azaspiro[3.5]nonane, 2-oxa-8-azaspiro[4.5]decane, 2-oxa-8-azaspiro[4.5]decan-1-one, 6-oxa-9-azaspiro[4.5]decane, 7-oxa-2-azaspiro[3.5]nonane, octahydropyrrolo[3,4-c]pyrrole, octahydropyrrolo[1,2-a]pyrazine, oxaazabicyclo[2.2.1]heptane, thiomorpholine-1,1-dioxide, diazepane, 2,3,4,5-tetrahydropyrido[2,3-f][1,4]oxazepine, 5,6,7,8-tetrahydro[1,2,4]triazolo[4,3-a]pyrazine, 5,6,7,8-tetrahydroimidazo[1,2-a]pyrazine, 5,6,7,8-tetrahydropyrido[3,4-d]pyridazin-1 (2H)-one, azaspiro[2.5]octane, azabicyclo[3.1.0]hexane, azabicyclo[4.1.0]heptane, diazaspiro[5.5]undecane, tetrahydroimidazopyrazine, dihydropyrrolopyridine, spiro[chroman-2,3'-pyrrolidin]-4-one, spiro[isochroman-1,4'-piperidine], 6',7'-dihydro-5'H-spiro[piperidine-4,4'-thieno[3,2-c]pyridine], and 5',6'-dihydro-4'H-spiro[piperidine-4,7'-thieno[2,3-c]pyridine]), said monocyclic, bicyclic or tricyclic ring optionally substituted with up to 4 substituents each independently selected from the group consisting of: halo, —$C_{1-6}$alkyl, —$C_{1-6}$haloalkyl, —$C_{1-6}$haloalkyl-$C_{3-7}$cycloalkyl, —$C_{3-7}$cycloalkyl, bicyclo[2.2.1]heptane, —$C_{1-6}$ alkyl-OH, —$C(CH_3)_2OH$, —$CH_2OC_{1-6}$ alkyl, —$CH_2C(O)OCH_2CH_3$, —$CH_2CH_2OC_{1-6}$ alkyl, —$CH_2CH_2OC_{1-6}$ haloalkyl, —$CH_2CH_2C(O)OCH_3$, —OH, —$OC_{1-6}$ alkyl, —$OCH_2$—$C_{3-7}$cycloalkyl, —$OCH_2CH_2OCH_3$, =O, —$CH_2N(CH_3)_2$, —$CH_2CH_2N(CH_3)_2$, —$C(O)C_{1-6}$ alkyl, —$C(O)H$, —$C(O)OH$, —$C(O)OC_{1-6}$ alkyl, —$C(O)NH_2$, —$C(O)NHCH_3$, —$C(O)N(CH_3)_2$, —CN, —$NH_2$, —NHC(O)$CH_3$, —$N(CH_3)_2$, —$SO_2CH_3$, oxetane, pyrrolidine, morpholine, furan, thiazole, pyridyl, phenyl, thiophene, —$CH_2$imidazole, —$CH_2$furan, —$CH_2$-thiophene, —$CH_2$pyridyl, benzyl, —C(O)-tetrahydrofuran, —C(O)pyrrole, or —C(O)phenyl;

In some embodiments of compounds of Formula (II), (IIa), (IIb), (III), (IIIc), and (IIId), Y is a member selected from the group consisting of: —H, —F, —$C_1$, —Br, and —$CH_3$;

Z is a member selected from the group consisting of: —H, —F and —$CH_3$;

m is 0, 1 or 2;

V is —$CH_2$— or —C(O)—; and

W is —$N(R^b)_2$, where each $R^b$ is independently selected from the group consisting of: —H, —$C_{1-6}$alkyl, —$C_{1-6}$alkyl-OH, —$C_{1-6}$haloalkyl, —$C_{1-6}$haloalkylOH, —$C_{1-6}$haloalkyl-$C_{3-7}$cycloalkyl, —$C_{3-7}$cycloalkyl, —$CH_2$-alkenyl, —$CH_2$-alkynyl, —$CH_2C_{3-7}$cycloalkyl, —$CH_2C(O)C(CH_3)_3$, —$CH_2C(O)C_{1-6}$ alkyl, —$CH_2C(O)$heterocycloalkyl, —$CH_2C(O)OC_{1-6}$ alkyl, —$CH_2C(O)N(C_{1-4}$alkyl)$_2$, —$CH_2CH(OH)C_{3-7}$cycloalkyl, —$C(CH_3)_2OH$, —$C(CH_3)_2CH_2OCH_3$, —$CH(CH_3)C(O)N(C_{1-4}$alkyl)$_2$, —$CH_2CF_2C_{3-7}$cycloalkyl, —$CH_2CH_2$—$R^c$ (where $R^c$ is —$C_{2-6}$ alkynyl, —$C_{3-7}$cycloalkyl, —OH, —O—$C_{1-6}$ alkyl, —$OC(CH_3)_2$, —O—$C_{1-6}$haloalkyl, —Ophenyl, —Opyridyl, —$CH_2N(CH_3)_2$, —$C(O)NHCH_3$, —$C(O)N(CH_3)_2$, —CN, —$NHCH_3$, —$N(CH_3)_2$, —NHC(O)$CH_3$, or —$SO_2CH_3$), and —$(CH_2)_n$—$R^d$ (where $R^d$ is cyclopropyl, cyclobutyl, cyclopentyl, cyclohexyl, bicyclo[1.1.1]pentane, bicyclo[3.1.0]hexane, —$C_{3-7}$halocycloalkyl, oxetane, pyrrolidine, pyrrolidinone, piperidine, piperidinone, tetrahydropyranyl, tetrahydrofuranyl, oxepane, morpholine, 3-azabicyclo[3.1.0]hexane, tetrahydrothiophene-1,1-dioxide, tetrahydro-2H-thiopyran-1,1-dioxide, thiomorpholine-1,1-dioxide, tetrahydrothiophene-1,1-dioxide, 1,3-dihydroisobenzofuran, benzofuran, indoline, benzodioxine, benzodioxole, phenyl, benzyl, —$CH_2CH_2$phenyl, —$CH_2CH_2CH_2$phenyl, furan, pyrrole, pyrazole, imidazole, triazole, isoxazole, oxazole, thiazole, pyridine, pyrimidine, thiophene, pyrrolopyridine, or benzimidazole, said $R^d$ optionally substituted with up to 4 substituents each independently selected from the group consisting of: halo, —$C_{1-6}$alkyl, —$C_{1-6}$haloalkyl, cyclopropyl, —OH, —$OC_{1-6}$alkyl, —O—$C_{1-6}$ haloalkyl, —O-phenyl, —O-pyridyl, —$CH_2OH$, —$CH_2OCH_3$, —$CH_2OCH_2CH_3$, —CN, —$N(CH_3)_2$, —$N(CH_3)$benzyl, heteroaryl, heterocycloalkyl, phenyl, or benzyl, where n is 0, 1, 2 or 3).

In some embodiments of compounds of Formula (II), (IIa), (IIb), (III), (IIIa), and (IIIb), Y is selected from the group consisting of: —H, —F, —$C_1$, —Br, and —$CH_3$;

Z is selected from the group consisting of: —H, —F and —$CH_3$;

m is 0, 1 or 2;

V is —$CH_2$— or —C(O)—; and

W is —$N(R^b)_2$, where both $R^b$ come together to form a monocyclic, bicyclic or tricyclic ring selected from the group consisting of: azetidine, pyrrole, pyrrolidine, pyrrolidinone, piperazine, piperazinone, piperidine, piperidinone, azepane, morpholine, 1-oxa-8-azaspiro[4.5]decan-3-one, 2-oxa-5-azabicyclo[2.2.1]heptane, 2-oxa-7-azaspiro[3.5]nonane, 2-oxa-8-azaspiro[4.5]decane, 2-oxa-8-azaspiro[4.5]decan-1-one, 6-oxa-9-azaspiro[4.5]decane, 7-oxa-2-azaspiro[3.5]nonane, octahydropyrrolo[3,4-c]pyrrole, octahydropyrrolo[1,2-a]pyrazine, oxaazabicyclo[2.2.1]heptane, thiomorpholine-1,1-dioxide, diazepane, 2,3,4,5-tetrahydropyrido[2,3-f][1,4]oxazepine, 5,6,7,8-tetrahydro[1,2,4]triazolo[4,3-a]pyrazine, 5,6,7,8-tetrahydroimidazo[1,2-a]pyrazine, 5,6,7,8-tetrahydropyrido[3,4-d]pyridazin-1 (2H)-one, azaspiro[2.5]octane, azabicyclo[3.1.0]hexane, azabicyclo[4.1.0]heptane, diazaspiro[5.5]undecane, tetrahydroimidazopyrazine, dihydropyrrolopyridine, spiro[chroman-2,3'-pyrrolidin]-4-one, spiro[isochroman-1,4'-piperidine], 6',7'-dihydro-5'H-spiro[piperidine-4,4'-thieno[3,2-c]pyridine], and 5',6'-dihydro-4'H-spiro[piperidine-4,7'-thieno[2,3-c]pyridine], said monocyclic, bicyclic or tricyclic ring optionally substituted with up to 4 substituents each independently selected from the group consisting of: halo, —$C_{1-6}$ alkyl, —$C_{1-6}$ haloalkyl, —$C_{1-6}$haloalkyl-$C_{3-7}$cycloalkyl, —$C_{3-7}$cycloalkyl, -bicyclo[2.2.1]heptane, —$C_{1-6}$alkyl-OH, —$C(CH_3)_2OH$, —$CH_2OC_{1-6}$alkyl, —$CH_2C(O)OCH_2CH_3$, —$CH_2CH_2OC_{1-6}$ alkyl, —$CH_2CH_2OC_{1-6}$ haloalkyl, —$CH_2CH_2C(O)OCH_3$, —OH, —$OC_{1-6}$ alkyl, —$OCH_2$—$C_{3-7}$cycloalkyl, —$OCH_2CH_2OCH_3$, =O, —$CH_2N(CH_3)_2$, —$CH_2CH_2N(CH_3)_2$, —$C(O)C_{1-6}$ alkyl, —$C(O)H$, —$C(O)OH$, —$C(O)OC_{1-6}$ alkyl, —$C(O)CH_3$, —$C(O)NH_2$, —$C(O)NHCH_3$, —$C(O)N(CH_3)_2$, —CN, —$NH_2$, —NHC(O)CH$_3$, —N(CH$_3$)$_2$, —SO$_2$CH$_3$, oxetane, pyrrolidine, morpholine, furan, thiazole, pyridyl, phenyl, thiophene, —CH$_2$imidazole, —CH$_2$furan, —CH$_2$-thiophene, —CH$_2$pyridyl, benzyl, —C(O)-tetrahydrofuran, —C(O)pyrrole or —C(O)phenyl.

In certain embodiments, X is —CH.

In certain embodiments, X is —N.

In certain embodiments of compounds of Formula (II), (IIa), (IIb), (III), (IIIa), and (IIIb), Y is —F, —C$_1$, or —Br.

In certain embodiments, Y is —H or —CH$_3$.

In certain embodiments, Z is —H.

In certain embodiments, Z is —F or —CH$_3$.

In certain embodiments, m is 1.

In certain embodiments, V is —CH$_2$—.

In certain embodiments, V is —C(O)—.

In certain embodiments, W is —N(R$^b$)$_2$, where each R$^b$ is independently selected from the group consisting of: —H, —C$_{1-6}$alkyl, —C$_{1-6}$alkyl-OH, —C$_{1-6}$ haloalkyl, —C$_{1-6}$haloalkylOH, —C$_{1-6}$haloalkyl-C$_{3-7}$cycloalkyl, —C$_{3-7}$cycloalkyl, —CH$_2$-alkenyl, —CH$_2$-alkynyl, —CH$_2$C$_{3-7}$cycloalkyl, —CH$_2$C(O)C(CH$_3$)$_3$, —CH$_2$C(O)C$_{1-6}$ alkyl, —CH$_2$C(O)heterocycloalkyl, —CH$_2$C(O)OC$_{1-6}$ alkyl, —CH$_2$C(O)N(C$_{1-4}$alkyl)$_2$, —CH$_2$CH(OH)C$_{3-7}$cycloalkyl, —C(CH$_3$)$_2$OH, —C(CH$_3$)$_2$CH$_2$OCH$_3$, —CH(CH$_3$)C(O)N(C$_{1-4}$alkyl)$_2$, —CH$_2$CF$_2$C$_{3-7}$cycloalkyl, —CH$_2$CH$_2$—R$^e$ (where R$^e$ is —C$_{2-6}$ alkynyl, —C$_{3-7}$cycloalkyl, —OH, —O—C$_{1-6}$ alkyl, —OC(CH$_3$)$_2$, —O—C$_{1-6}$ haloalkyl, —Ophenyl, —Opyridyl, —CH$_2$N(CH$_3$)$_2$, —C(O)NHCH$_3$, —C(O)N(CH$_3$)$_2$, —CN, —NHCH$_3$, —N(CH$_3$)$_2$, —NHC(O)CH$_3$, or —SO$_2$CH$_3$), and —(CH$_2$)$_n$—R$^d$ (where R$^d$ is —C$_{3-7}$cycloalkyl, —C$_{3-7}$halocycloalkyl, heterocycloalkyl, aryl, or heteroaryl, each optionally substituted with up to 4 substituents each independently selected from the group consisting of: halo, —C$_{1-6}$alkyl, —C$_{1-6}$haloalkyl, —C$_{3-7}$cycloalkyl, —OH, —OC$_{1-6}$alkyl, —O—C$_{1-6}$haloalkyl, —O-phenyl, —O-pyridyl, —CH$_2$OH, —CH$_2$OCH$_3$, —CH$_2$OCH$_2$CH$_3$, —CN, —N(CH$_3$)$_2$, —N(CH$_3$)benzyl, heteroaryl, heterocycloalkyl, phenyl, or benzyl, where n is 0, 1, 2 or 3); or, alternatively, both R$^b$ come together to form a 4-15-membered, monocyclic, bicyclic or tricyclic ring, optionally containing up to 3 additional heteroatoms each independently selected from O (oxygen), N (nitrogen) and S (sulfur), said 4-15-membered monocyclic, bicyclic or tricyclic ring optionally substituted with up to 4 substituents each independently selected from the group consisting of: halo, —C$_{1-6}$ alkyl, —C$_{1-6}$ halo alkyl, —C$_{1-6}$ haloalkyl-C$_{3-7}$cycloalkyl, —C$_{3-7}$cycloalkyl, bicyclo[2.2.1]heptane, —C$_{1-6}$alkyl-OH, —C(CH$_3$)$_2$OH, —CH$_2$OC$_{1-6}$alkyl, —CH$_2$C(O)OCH$_2$CH$_3$, —CH$_2$CH$_2$OC$_{1-6}$ alkyl, —CH$_2$CH$_2$OC$_{1-6}$halo alkyl, —CH$_2$CH$_2$C(O)OCH$_3$, —OH, —OCH$_2$—C$_{3-7}$cycloalkyl, —OCH$_2$CH$_2$OCH$_3$, =O, —CH$_2$N(CH$_3$)$_2$, —CH$_2$CH$_2$N(CH$_3$)$_2$, —C(O)C$_{1-6}$ alkyl, —C(O)H, —C(O)OH, —C(O)OC$_{1-6}$alkyl, —C(O)CH$_3$, —C(O)NH$_2$, —C(O)NHCH$_3$, —C(O)N(CH$_3$)$_2$, —CN, —NH$_2$, —NHC(O)CH$_3$, —N(CH$_3$)$_2$, —SO$_2$CH$_3$, oxetane, pyrrolidine, morpholine, furan, thiazole, pyridyl, phenyl, thiophene, —CH$_2$imidazole, —CH$_2$furan, —CH$_2$-thiophene, —CH$_2$pyridyl, benzyl, —C(O)-tetrahydrofuran, —C(O)pyrrole or —C(O)phenyl.

Some embodiments provide one or more compounds of Examples 1-583, and all pharmaceutically acceptable forms thereof, including pharmaceutically acceptable chelates, solvates, conformers, crystalline forms/polymorphs, salts, prodrugs, and pharmaceutically active metabolites. Some embodiments provide one or more compounds of Examples 1-583 and pharmaceutically acceptable salts thereof. Some embodiments provide one or more compounds of Examples 1-583.

Isotopically-Labeled Compounds

Compounds of the present disclosure (and all forms of such compounds) may include any isotope where one or more atoms are replaced by an atom having an atomic mass or mass number different from the atomic mass or mass number usually found in nature. For example, the isotopes may be isotopes of carbon, chlorine, fluorine, hydrogen, iodine, nitrogen, oxygen, phosphorous, sulfur, and technetium, including $^{11}$C, $^{13}$C, $^{14}$C, $^{36}$Cl, $^{18}$F, $^{2}$H, $^{3}$H, $^{123}$I, $^{125}$I, $^{13}$N, $^{15}$N, $^{15}$O, $^{17}$O, $^{18}$O, $^{31}$P, $^{32}$P, $^{35}$S, and $^{99m}$Tc.

Compounds of the present disclosure (and all forms of such compounds, such as pharmaceutically acceptable salts) that contain the aforementioned isotopes or other isotopes of other atoms are within the scope of the invention. Isotopically-labeled compounds of the present embodiments are useful in drug and substrate tissue distribution and target occupancy assays. For example, isotopically labeled compounds are particularly useful in SPECT (single photon emission computed tomography) and in PET (positron emission tomography), as discussed further herein. In addition, isotopically labelled compounds are useful for improving the absorption, distribution, metabolism and/or excretion (ADME) properties of drugs. For instance, replacement of one or more hydrogen atoms with deuterium ($^{2}$H) can modify the metabolism of a drug and improve the metabolic profile by decreasing the metabolic clearance in vivo, extending the half-life, reducing C. or reducing levels of potentially toxic metabolites.

Compositions

In some embodiments, the chemical entities disclosed herein, and more particularly, compounds and pharmaceutically acceptable salts thereof, are used, alone or in combination with one or more additional active ingredients, to formulate pharmaceutical compositions.

In some embodiments, a pharmaceutical composition can comprise: (a) an effective amount of at least one chemical entity of the present disclosure; and (b) a pharmaceutically acceptable carrier.

In some embodiments, a pharmaceutical composition comprises a compound, or pharmaceutically acceptable salt thereof, of any of the embodiments and examples disclosed herein; and a pharmaceutically acceptable carrier. In specific embodiments, a pharmaceutical composition comprises a compound of any one of Examples 1-583, or pharmaceutically acceptable salt thereof; and a pharmaceutically acceptable carrier.

Formulations and Administration

Numerous standard references are available that describe procedures for preparing various formulations suitable for administering the compounds according to the embodiments.

Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Osol, ed.), 1980, 1553-1593.

Any suitable route of administration may be employed for providing an animal, especially a human, with an effective dosage of a compound of the present embodiments. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent, or excipient used will depend upon the means and purpose for which the compound of the present embodiments is being applied. Solvents are generally selected based on solvents recognized by persons skilled in the art as safe (GRAS) to be administered to an animal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present embodiments or pharmaceutical composition thereof) or aid in the manufacturing of the pharmaceutical product (i.e., medicament).

The formulations may be prepared using conventional dissolution and mixing procedures. For example, the bulk drug substance (i.e., a compound of the present embodiments or stabilized form of the compound (e.g., complex with a cyclodextrin derivative or other known complexation agent)) is dissolved in a suitable solvent in the presence of one or more of the excipients described above. The compound of the present embodiments is typically formulated into pharmaceutical dosage forms to provide an easily controllable and appropriate dosage of the drug.

The pharmaceutical composition (or formulation) for application may be packaged in a variety of ways, depending upon the method used to administer the drug. Generally, an article for distribution includes a container having deposited therein the pharmaceutical formulation in an appropriate form. Suitable containers are well-known to those skilled in the art and include materials such as bottles (plastic and glass), sachets, ampules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Dosage Forms

The present compounds may be systemically administered, e.g., orally, in combination with a pharmaceutically acceptable vehicle such as an inert diluent or an assimilable edible carrier. Hence in some embodiments, chemical entities of the present embodiments are suitable for oral administration. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be in a range from 1% to 65% or 2% to 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid, and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are typically prepared by incorporating the active compound in the required amount in the appropriate solvent with a variety of the other ingredients enumerated above, as required, followed by filter sterilization. In the case of sterile powders for the preparation of sterile injectable solutions, common methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina, and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Dosages

Useful dosages of the chemical entities and compounds (active agents) of the present disclosure can be determined by comparing their in vitro activity and in vivo activity in animal models. Methods for the extrapolation of effective dosages in mice, and other animals, to humans are known to the art. Useful dosages of the active agents can be determined by comparing their in vitro activity, and in vivo activity in animal models. Methods for the extrapolation of effective dosages in mice, and other animals, to humans are known to the art (e.g., U.S. Pat. No. 4,938,949).

Effective amounts or doses of the active agents of the present invention may be ascertained by routine methods such as modeling, dose escalation studies or clinical trials, and by taking into consideration routine factors, e.g., the mode or route of administration or drug delivery, the pharmacokinetics of the agent, the severity and course of the disease, disorder, or condition, the subject's previous or ongoing therapy, the subject's health status and response to drugs, concomitant medications, and the judgment of the treating physician. An exemplary dose can be in the range from 0.0001 to 200 mg of active agent per day, from 0.001 to 200 mg per day, from 0.05 to 100 mg per day, from 0.1 to 10 mg per day, from 1 to 200 mg per day, or from 5 to 50 mg per day.

In some embodiments, the desired dose may be presented in a unit dosage form; for example, a composition containing from 0.01 to 1000 mg, from 0.1 to 200 mg, from 0.5 to 100 mg, or from 1 to 50 mg, of active ingredient per unit dosage form.

In other embodiments, the desired dose may be presented in divided doses administered at appropriate intervals, for example, as two, three, four, or more sub-doses per day. (e.g., BID, TID, QID). The sub-dose itself may be further divided, e.g., into a number of temporally-distinct administrations used according to the compositions and methods of the present invention.

Methods and Uses

Uses of Isotopically-Labeled Compounds

In some embodiments, the present disclosure provides methods of using isotopically labeled compounds and chemical entities of the present invention in: (i) metabolic studies (with, for example, $^{14}C$), reaction kinetic studies (with, for example $^{2}H$ or $^{3}H$); (ii) detection or imaging techniques [such as positron emission tomography (PET) or single-photon emission computed tomography (SPECT)] including drug or substrate tissue distribution assays; or (iii) in radioactive treatment of patients.

Isotopically labeled compounds and chemical entities of the present disclosure can generally be prepared by carrying out the procedures disclosed in the schemes or in the examples and preparations described below by substituting a readily available isotopically labeled reagent for a non-isotopically labeled reagent. Compounds labeled with $^{18}F$ or $^{11}C$ may be particularly preferred for PET, and an $^{123}I$ labeled compound may be particularly preferred for SPECT studies. Further substitution of compounds of Formula (I) with heavier isotopes such as deuterium (i.e., $^{2}H$) may afford certain therapeutic advantages resulting from greater metabolic stability, for example increased in vivo half-life or reduced dosage requirements.

Therapeutic Methods

Generally

Chemical entities and compositions of the present disclosure are useful in various therapeutic methods (or in the manufacture of a medicament for use in such methods), comprising administering to a subject in need thereof a chemical entity or composition herein. In a specific aspect, the chemical entity is a compound of Formula (I) or a pharmaceutically acceptable salt thereof. Such therapeutic methods can be directed to a wide range of indications, as described further herein, including cognitive or motor deficits associated with neurological disorders, neurodegenerative disorders, immunological and inflammatory disorders, and numerous peripheral disorders.

In some embodiments, chemical entities and compositions herein are useful in methods of inhibiting PDE7 activity, comprising exposing PDE7 to an effective amount of a chemical entity or composition of any one of the embodiments disclosed herein. In some embodiments, the PDE7 is in an animal, and more particularly, is in a human subject.

In some embodiments, chemical entities and compositions herein are useful in methods of treating a subject suffering from or diagnosed with a disorder mediated by PDE7 activity, comprising administering to a subject in need thereof an effective amount of a chemical entity or composition of any one of the embodiments herein. In one aspect, the subject is diagnosed with a disorder mediated by PDE7 activity. In another aspect, the subject is suffering from a disorder mediated by PDE7 activity.

In some embodiments, chemical entities and compositions herein are useful in methods of enhancing neuronal plasticity, an essential property of the brain that can be impaired in numerous CNS disorders and augmented in healthy animals. Without being limited by mechanism, such chemical entities can enhance cyclic adenosine monophosphate (cAMP) response element binding protein (CREB) pathway function in cells, modulating transcription of multiple genes involved in synaptic plasticity (see, e.g., Tully et al., 2003, *Nat. Rev. Drug Discov.* 2, 267-277; Alberini, 2009,

*Physiol. Rev.* 89, 121-145). Accordingly, in some embodiments, the present disclosure provides methods of enhancing neuronal plasticity, comprising administering to a subject in need thereof an effective amount of a chemical entity or composition of any one of the embodiments herein. In specific embodiments, chemical entities of the present disclosure are useful in methods of enhancing cognitive or motor function, comprising administering to a subject in need thereof an effective amount of a chemical entity of any one of the embodiments disclosed herein.

In some embodiments, chemical entities and compositions herein are used as neuroprotective agents. Accordingly, the present disclosure provides methods of conferring neuroprotection, comprising administering to a subject in need thereof an effective amount of a chemical entity of Formula (I).

In some embodiments, chemical entities and compositions herein are used as anti-inflammatory agents, including in the treatment of neurological and peripheral disorders. Accordingly, the present disclosure provides methods of treating or reducing inflammation, comprising administering to a subject in need thereof an effective amount of a chemical entity of Formula (I).

In some embodiments, chemical entities and compositions are used as "agents" (or "augmenting agents") to increase the efficiency of training protocols that facilitate functional reorganization in targeted "domains" (or "functions") in the brain.

In some embodiments, chemical entities and compositions are used in combination with other therapies or with other active agents, as described further herein.

Neurological Disorders

In some embodiments the present disclosure provides methods of treating neurological disorders, comprising administering to a subject in need thereof a chemical entity or composition described herein.

In some embodiments, the method is directed to a neurological impairment ("neurological deficit") associated with the neurological disorder, including a cognitive impairment ("cognitive deficit") or a motor impairment ("motor deficit") associated with ("due to") the pathology of the neurological disorder.

A cognitive impairment can manifest, for example, as a deficit in: attention (e.g., sustained attention, divided attention, selective attention, processing speed); executive function (e.g., planning, decision, and working memory); memory (e.g., immediate memory; recent memory, including free recall, cued recall, and recognition memory; and long-term memory, which can be divided into explicit memory (declarative memory), such as episodic, semantic, and autobiographical memory, and into implicit memory (procedural memory)); expressive language, including naming, word recall, fluency, grammar, and syntax; understanding speech or writing (e.g., aphasia); perceptual-motor functions (e.g., abilities encompassed under visual perception, visual-constructional, perceptual-motor praxis, and gnosis); and social cognition (e.g., recognition of emotions, theory of mind). In certain embodiments, the cognitive deficit is a deficit in memory and more particularly, a deficit in long-term memory.

A motor impairment can manifest, for example, as weakness or paralysis, deficits in upper and lower extremity function, problems with balance or coordination, impairments of gross motor skills, and deficits in fine motor skills.

A neurological disorder (or condition or disease) is any disorder of the body's nervous system. Neurological disorders can be categorized according to the primary location affected, the primary type of dysfunction involved, and the primary type of cause. The broadest division is between disorders of the central nervous system (CNS), which comprises the nerves in the brain and spinal cord, and disorders of the peripheral nervous system (PNS), which comprises the nerves outside the brain and spinal cord.

Many CNS disorders are amenable for treatment with chemical entities and compositions, including those discussed herein. The terms "Neurodevelopment disorders," "Schizophrenia spectrum and other psychotic disorders," "Bipolar and related disorders," "Depressive disorders," "Anxiety disorders," "Obsessive-compulsive and related disorders," "Dissociative disorders," "Disruptive, impulse-control, and conduct disorders," "Trauma- and stressor-related disorders," "Feeding and eating disorders," "Sleep disorders," "Sexual disorders," "Substance-related and addictive disorders," "Personality disorders," "Neurodegenerative disorders," "Neurocognitive disorders," "Delirium," "Dementias," "Age-associated cognitive deficits," "and "Trauma" include the diagnosis and classification of these CNS conditions and disorders (and related CNS conditions and disorders) as described in the Diagnostic and Statistical Manual of Mental Disorders (DSM-5; 5th ed., 2013, American Psychiatric Association). The skilled artisan will recognize that there are alternative nomenclature and classification systems for these CNS disorders, and that these systems evolve with medical and scientific progress. Thus, these terms in this paragraph are intended to include like disorders that are described in other diagnostic sources.

Mental and Psychiatric Disorders:

In certain embodiments, chemical entities and compositions herein are useful in treating mental or psychiatric disorders, and more particularly, a cognitive impairment associated with the pathology of such disorders. Mental and psychiatric disorders are well known in the art, and include, but are not limited to, one or more of the following:

Neurodevelopmental (or "developmental" disorders), such as intellectual disability disorders (e.g., Rubinstein-Taybi syndrome, Down syndrome); communication disorders; autism-spectrum disorders; attention-deficit/hyperactivity disorders; specific learning, language, or reading (e.g., dyslexia) disorders; motor disorders; fetal alcohol spectrum disorders (FASD); and other neurodevelopmental disorders;

Schizophrenia spectrum and other psychotic disorders, such as schizophrenia, schizotypal (personality) disorder, delusional disorder, brief psychotic disorder, schizoaffective disorder, substance/medication-induced psychotic disorder, psychotic disorder due to another medical condition, catatonia, catatonia associated with another mental disorder (catatonia specifier), catatonic disorder due to another medical condition, unspecified catatonia, schizophreniform disorder, and other schizophrenia spectrum and psychotic disorders;

Bipolar and related disorders, such as Bipolar I and II disorders, cyclothymic disorders, and other bipolar and related disorders;

Depressive disorders, such as major depressive disorder, persistent depressive disorder (dysthymia), a major depressive episode of the mild, moderate, or severe type, a depressive episode with melancholic features, a depressive episode with catatonic features, seasonal depression (seasonal affective disorder), disruptive mood dysregulation disorder, premenstrual dysphoric disorder, substance/medication-induced depressive disorder, depressive disorder due to another medical condition, mood disorders due to a general medical conditions, and other depressive disorder;

Anxiety disorders, such as specific phobia, agoraphobia, social anxiety disorder (social phobia), panic attack, panic disorder, acute stress disorder, generalized anxiety disorder, posttraumatic stress disorder (PTSD), and other anxiety disorders;

Obsessive-compulsive and related disorders, such as obsessive-compulsive disorder (OCD), body dysmorphic disorder, hoarding disorder, trichotillomania (hair-pulling disorder), excoriation (skin-picking) disorder, substance/medication-induced obsessive-compulsive and related disorder, obsessive-compulsive and related disorder due to another medical condition, and other specified obsessive-compulsive and related disorder and unspecified obsessive-compulsive and related disorder (e.g., body-focused repetitive behavior disorder, obsessional jealousy), and other obsessive-compulsive and related disorders;

Dissociative disorders, such as dissociative identity disorder, dissociative amnesia, depersonalization/derealization disorder, dissociative subtypes (in conjunction with other disorders), and other dissociative disorders;

Disruptive, impulse-control, and conduct disorders, such as conduct disorder, antisocial personality disorder, pyromania, kleptomania, and other disruptive, impulse-control, and conduct disorders;

Trauma- and stressor-related disorders, such as reactive attachment disorder, disinhibited social engagement disorder, posttraumatic stress disorder, acute stress disorder, adjustment disorders, and other trauma- and stressor-related disorders;

Feeding and eating disorders, such as pica, rumination disorder, avoidant/restrictive food intake disorder, anorexia, bulimia, binge-eating disorder, and other feeding and eating disorders;

Sleep disorders, such as sleep-wake disorders, insomnia disorder, hypersomnolence disorder, narcolepsy, breathing-related sleep disorders, sleep apnea, circadian rhythm sleep-wake disorders, non-rapid eye movement (NREM) sleep arousal disorders, nightmare disorder, rapid eye movement (REM) sleep behavior disorder, restless legs syndrome, and substance/medication-induced sleep disorder, parasomnias, and other sleep-wake disorders;

Sexual disorders, such as arousal disorders, desire disorders, dysfunctions, substance- and medication-induced dysfunctions, impotence and other sexual disorders;

Substance-related and addictive disorders, such as those involving alcohol, drugs, stimulants, opioids, tobacco, and non-substance-related addictive disorders; and other substance-related and addictive disorders;

Personality disorders, such as antisocial personality disorder, borderline personality disorder, histrionic personality disorder, narcissistic personality disorder, avoidant personality disorder, dependent personality disorder, obsessive-compulsive personality disorder, paranoid personality disorder, schizoid personality disorder, schizotypal personality disorder, personality change due to another medical condition, and other personality disorders; and Somatic symptom and related disorders, such as somatic symptom disorder, illness anxiety disorder (hypochondriasis), factitious disorder, factitious disorder imposed on another, pain disorders, conversion disorder, and other somatic symptom and related disorders.

Schizophrenia:

In specific embodiments, the mental or psychiatric disorder is a schizophrenia spectrum or psychotic disorder, and, in particular, is schizophrenia. Schizophrenia is a devastating neurological disorder, characterized by a combination of symptoms, which may include negative, positive, or cognitive symptoms. Negative symptoms can include flat affect (lack or decline in emotional response), alogia (lack or decline in speech), avolition (lack or decline in motivation), anhedonia (the inability to experience pleasure from activities usually found enjoyable), and asociality (lack of motivation to engage in social interaction, or a preference for solitary activities). Positive symptoms include paranoia, hallucinations, and delusions. Cognitive symptoms can include impairments in such functions as attention, memory, reasoning, and processing speed. See, e.g., Keefe and Harvey, 2012, *Handb. Exp. Pharamacol.* 213, 11-23. PDE7 inhibitors have been shown to ameliorate various cognitive functions associated with schizophrenia, such as deficits in working memory, short-term memory, spatial memory, and cued memory. (e.g., Lipan et al., 2013, *Neuropharmacology.* 64, 205-214.)

Accordingly, the present invention provides a method of treating schizophrenia, comprising administering to a subject in need thereof an effective amount of a chemical entity or composition herein. In some embodiments, the treatment is directed to a positive symptom of schizophrenia. In some embodiments, treatment is directed to a negative symptom of schizophrenia. In some embodiments, treatment is directed to a cognitive impairment associated with schizophrenia (CIAS). In some embodiments, the treatment also include a cognitive training protocol.

Addictive Disorders:

In specific embodiments, the disclosure provides a method of treating an addictive disorder, comprising administering to a subject in need thereof an effective amount of a chemical entity or composition herein. In one aspect, the subject is addicted to an addictive agent selected from the group consisting of alcohol, nicotine, marijuana, a marijuana derivative, an opioid agonist (such as morphine, methadone, fentanyl, sufentanil, or heroin), a benzodiazepine, a barbiturate, and a psychostimulant, such as cocaine or amphetamine. In another aspect, the addiction is associated with an obsessive-compulsive disorder. In another aspect, the disorder is associated with a primary impulse-control disorder, such as binge eating, pathological gambling, addiction to pornography, sex addiction, compulsive spending, anorexia, bulimia, kleptomania, pyromania, trichotillomania, compulsive over-exercising, or compulsive overworking.

Cognitive Disorders:

In specific embodiments, the present disclosure provides a method of treating a cognitive disorder, and more particularly, a neurological impairment associated with the disorder, comprising administering to a subject in need thereof a chemical entity or composition described herein. A "cognitive disorder" (or "neurocognitive disorder") is one in which the primary clinical feature is impaired cognition, i.e., a disorder in which the primary cognitive deficit has not been present since birth or very early life and therefore represents a decline from a previously attained level of functioning. Such disorders, include one or more of the following:

Delirium, such as substance-intoxication (or withdrawal) delirium, medication-induced delirium, and other forms of delirium;

Dementias and other cognitive impairments due to acquired diseases, such as HIV infection, or transmissible encephalopathies; or due to neurodegenerative or progressive nervous system diseases, such as Alzheimer's disease, Parkinson's disease (in particular Parkinson's Disease Dementia (PDD)), Huntington's disease, Lewy body disease, Pick's disease, a prion disease (e.g., Creutzfeldt-Jakob disease), Amyotrophic lateral sclerosis (ALS), multiple sclerosis (MS), frontotemporal lobar degeneration (FTLD), and corticobasal degeneration; dementia due to a vascular disease ("vascular disease"); autoimmune disorders; and other dementias and neurodegenerative diseases.

Age-associated cognitive decline, including age-associated memory impairment (AAMI), also referred to as age-related memory impairment (AMI) (see, e.g., Crook et al., 1986, Devel. Neuropsychol. 2, 261-276); and cognitive decline affecting patients in early stages of cognitive decline, as in Mild Cognitive Impairment (MCI) (see, e.g., Arnáiz and Almkvist, 2003, Acta Neurol. Scand. Suppl. 179, 34-41);

Trauma-dependent losses of function, including vascular diseases, such as stroke (e.g., ischemic or hemorrhagic stroke) or ischemia; infarction, including cerebral and myocardial; microvascular or macrovascular disease arising from diabetes or arthrosclerosis; traumatic brain injury (TBI), such as brain trauma including subdural hematoma and brain tumor; head trauma (closed and penetrating); head injury; tumors, such as nervous system cancers, including cerebral tumors affecting the thalamic or temporal lobe; hypoxia, and viral, fungal, or bacterial infection (e.g., encephalitis, or meningitis); excitotoxicity; and seizures; and Cognitive impairments due to chemotherapy, such as post-chemotherapy cognitive impairments (PCCI); chemotherapy-induced cognitive dysfunction or impairments; chemo brain; or chemo fog.

Such cognitive disorders can include neurological impairments other than cognitive impairments. For example, trauma-dependent losses of function, such as stroke, traumatic brain injury, head trauma, and head injury, can include impairments in multiple neurological functions, such as impairments in motor functions.

Age Associated Cognitive Decline:

In specific embodiments, the cognitive disorder is age-associated cognitive decline.

In one aspect, the age-related cognitive decline is age-associated memory impairment (AAMI). AAMI is a decline in various cognitive abilities, in particular memory abilities, associated with normal aging. For example, AAMI subjects show a decline in the ability to encode new memories of events or facts, as well as in working memory (Hedden and Gabrieli, 2004, Nat. Rev. Neurosci. 5, 87-96). In addition, AAMI subjects, when compared with age-matched controls, appeared to be impaired in tests of executive functions associated with frontal lobe function. These and other studies suggest an important role for frontal lobe dysfunction in the memory loss of elderly people. (Nilsson, 2003, Acta Scand. Suppl. 179, 7-13). In general, an AAMI diagnosis identifies persons with subjectively and objectively evidenced memory loss without cognitive decline impaired enough to warrant the diagnosis of dementia. For example, the NIH working group has established multiple criteria for a diagnosis of AAMI in a person aged 50 or older, including the presence of subjective memory decline, objective evidence of memory loss, evidence of adequate intellectual function, and the absence of dementia (or other memory-affecting disease) (Crook et al., 1986, Devel. Neuropsychol. 2, 261-276). Individuals with AAMI have been shown to have a three-fold greater risk for development of dementia than individuals who do not meet AAMI criteria (Goldman and Morris, 2002, Alzheimer Dis. Assoc. Disord. 75, 72-79).

In another aspect, the age-associated cognitive decline is Mild Cognitive Impairment, which may be diagnosed when an individual's memory declines below the level considered normal for that age group. In other words, MCI is a condition in which people face memory problems more often than that of the average person their age. Symptoms often include misplacing items, forgetting events or appointments, and having trouble thinking of desired words (e.g., Arnaiz and Almkvist, Acta Neurol. Scand. Suppl. 2003, 179, 34-41). MCI can represent a transitional state between cognitive changes of normal aging and Alzheimer's disease (AD). Many people who experience mild cognitive impairment are at a high risk of developing Alzheimer's disease. About 12% of people aged 65 or older diagnosed with MCI go on to develop Alzheimer's disease within a year, and about 40% develop Alzheimer's within three years. This is a much higher rate than in the general population, in which only about 1% of people aged 65 or older develop Alzheimer's each year. Thus, people with MCI are considered at heightened risk to develop Alzheimer's disease. Some patients with MCI, however, never progress to AD.

Accordingly, the disclosure includes methods of treating age-associated cognitive decline, and more particularly, age-related memory impairment or mild cognitive impairment, comprising administering to a subject in need thereof an effective amount of a chemical entity or composition disclosed herein.

Trauma-Dependent Loss of Function:

In specific embodiments, the cognitive disorder is a trauma-dependent loss of function, and more particularly, stroke or TBI. Accordingly, the disclosure includes methods of treating a trauma-dependent loss of function, and more particularly, stroke or TBI, comprising administering to a subject in need thereof an effective amount of a chemical entity or composition disclosed herein.

Movement Disorders:

In certain embodiments, the present disclosure provides methods of treating movement and motor disorders, and more particularly, a movement or motor impairment associated with the pathology of such disorders, comprising administering to a subject in need thereof a chemical entity or composition described herein. PDE7B is highly expressed in striatal neurons of the basal ganglia, where it appears to modulate dopaminergic neurotransmission. In primary striatal neurons, PDE7B is transcriptionally activated by dopamine receptor stimulation through the cAMP/PKA/CREB pathway. Loss of dopaminergic neurotransmission in striatum is a central cause of neurodegenerative diseases leading to movement disorders, such as Parkinson's disease and Huntington's disease. See, e.g., Sasaki et al., 2004, J. Neurochem. 89, 474-483; Morales-Garcia et al., 2014, Neurobiol. Aging. 36, 1160-1173; Banerjee et al., 2012, Bioorg. Med. Chem. Lett. 22, 6286-6291.

Movement disorders include, but are not limited to, basal ganglia disorders, Parkinson's disease, Post-Encephalitic Parkinsonism, Dopamine-Responsive Dystonia, Hallervorden-Spatz Syndrome (HSS), Restless Leg Syndromes, Wilson's Disease, Shy-Drager Syndrome, Periodic Limb Movement Disorder (PLMD), Periodic Limb Movements in Sleep (PLMS), Tourette's Syndrome, Restless Leg(s) Syndrome (RLS); chorea, such as that in Huntington's disease; myoclonus (including generalized myoclonus and focal myoclonus); tics (including simple tics, complex tics and symptomatic tics); and hyperkinetic, hypokinetic, and dyskinetic disorders; movement disorders induced by drugs, diseases associated with striatal hypofunction; and other movement and motor disorders.

In specific embodiments, the dyskinetic disorder is a drug-induced dyskinesia. More particularly, the dyskinetic disorder is levodopa induced dyskinesia (LID) or tardive dyskinesia (TD), which represent the most common forms of drug-induced dyskinesias. For example, uncontrolled stimulation of supersensitized dopamine D1 receptors in the direct striatonigral pathway are thought to mediate LIDs. In addition, long-term blockade of dopamine D2 receptors in the basal ganglia by dopamine D2 antagonists (e.g., neuroleptics) may produce compensatory supersensitivity of dopamine receptors and TD. Accordingly, in specific embodiments, then present disclosure provides methods of treating LID (or TD), comprising administering to a subject in need therefor an effective amount of a chemical entity of any of the embodiments disclosed herein.

In certain embodiments, the movement disorder is a basal ganglia disorder.

In other embodiments, the movement disorder includes kinesias and akinetic-rigid syndromes, such as Parkinson's disease or corticobasal degeneration; Tourette's syndrome, epilepsy, muscular spasms, and disorders associated with muscular spasticity or weakness; dyskinesias, including tremors, such as rest tremor, postural tremor and intention tremor.

In specific embodiments, the movement disorder is Parkinson's disease or Huntington's disease, as discussed further herein.

In some embodiments, the methods are directed to a specific movement abnormality associated with the pathology of a movement or motor disorder. Movement abnormalities include, but are not limited to, tremors, resting tremors, rigidity, bradykinesia, and deficient postural reflexes.

Neurodegenerative Disorders:

In specific embodiments, the disclosure provides methods of treating a neurodegenerative disorder, and more particularly treating a neurological impairment associated with the pathology of a neurodegenerative disorder, comprising administering to a subject in need thereof a chemical entity or composition described herein.

Neurodegenerative disorders can result from a primary nervous system disease or a primary nervous system injury. Chronic neuroinflammation is a hallmark of neurodegenerative disorders, and in animal and cellular models, PDE7 inhibition shows neuroprotective and anti-inflammatory effects that are expected to be beneficial in treating neuroinflammation and other hallmarks of such disorders.

Accordingly, in some embodiments, the therapeutic methods are directed to neurodegenerative disorders resulting from a primary nervous system disease. Such diseases include, but are not limited to, Parkinson's disease, Alzheimer's disease, Huntington's disease, Lewy body disease, Pick's disease, a prion disease (e.g., Creutzfeldt-Jakob disease), Amyotrophic lateral sclerosis (ALS), multiple sclerosis (MS), frontotemporal lobar degeneration (FTLD), and corticobasal degeneration.

In other embodiments, the therapeutic methods are directed to a neurodegenerative disorder resulting from a primary nervous system injury. Such primary injuries can include, but are not limited to, stroke, including hemorrhagic stroke and ischemic stroke; a traumatic brain injury (TBI), which can include closed head injuries and blunt trauma, including those caused by participation in sports, and penetrating trauma, such as gunshot wounds; spinal cord injuries; glaucoma, cerebral ischemia, or damages caused by surgery such as tumor excision.

Parkinson's Disease:

In specific embodiments, the present disclosure provides methods of treating Parkinson's disease, comprising administering to a subject in need thereof a chemical entity or composition described herein. Parkinson's disease (PD), also known as Parkinson's, idiopathic Parkinsonism, or primary Parkinsonism, is a degenerative disorder of the CNS estimated to afflict more than 5 million people worldwide. It is a slowly progressive neurological condition, characterized by tremors, stiffness, slowness of movement (bradykinesia) and impaired balance. PDE7 inhibitors improve motor function and promote neurogenesis in animal models of PD, demonstrate neuroprotective effects in dopaminergic neurons in vitro and in vivo, can show synergistic effects in combination with L-DOPA. Morales-Garcia et al., 2012, *PLoS One.* 6, e17240; Morales-Garcia et al., 2014, *ACS Chem. Neurosci.* 19, 194-204; Morales-Garcia et al., 2015, *Neurobiol. Aging.* 36, 1160-1173.

While Parkinson's disease has been defined by its motor hallmarks, non-motor features such as cognitive impairment and dementia have been increasingly recognized. For example, MCI is common in a significant fraction (with estimates ranging from 20%-50%) of non-demented PD patients. While diagnostic criteria are not completely uniform, PD patients with MCI (PD-MCI patients) typically exhibit non-amnestic deficits in cognitive domains such as executive function, attention, and visuospatial function. The cognitive phenotype of PD-MCI is heterogeneous, however, with some patients demonstrating amnestic deficits. Certain PD-MCI patients may be at high risk for developing dementia. (e.g., Goldman and Litvan, 2011, *Minerva Med.* 102, 441-459).

Alzheimer's Disease:

In specific embodiments, the present disclosure provides methods of treating Alzheimer's disease (AD), comprising administering to an animal in need thereof an effective amount of a chemical entity or composition disclosed herein Alzheimer's disease is a neurodegenerative disorder that involves the progressive loss of memory and other cognitive functions. Although the pathogenesis of AD is not well known, its etiology is associated with the presence of β-amyloid (or senile) plaques; deficiencies in neurotransmission; loss of neurons, especially in the cortex and hippocampus; neurofibrillary tangles; and the hyperphosphorylation and intraneuronal deposition of the microtubule-associated protein tau in the form of filaments; intraneuronal deposition of aggregated tau filaments. PDE7 mediated pathways that impact cAMP and CREB signaling have been implicated in AD etiology. See, e.g., Perez-Torres et al., 2003, *Exp. Neurol.* 182, 322-334; Perez-Gonzales et al., 2013, Neurobiol. Aging 34, 2133-2145.

Huntington's Disease:

In specific embodiments, the disclosure provides a method of treating Huntington's disease (or "Huntington's chorea"), comprising administering to a subject in need thereof an effective amount of a chemical entity or compound disclosed herein. There are two forms of Huntington's disease: adult-onset Huntington's disease, which is the most common form and usually begins in subjects aged in the mid 30's and 40's, and early-onset Huntington's disease, which accounts for a small number of cases and begins in childhood or adolescence. Symptoms of Huntington's disease include behavioral changes, abnormal and unusual movements, and worsening dementia (e.g., Dumas et al., 2013, *Front. Biosci.* (Schol. Ed) 5, 1-18). Huntington's disease (HD, or Huntington chorea) is a genetic disorder, whose pathology includes degeneration of striatal neurons in the basal ganglia responsible for movement and coordination. PDE7 variants are upregulated in striatal neurons in response to dopamine receptor agonists acting through the cAMP/PKA/CREB pathway. A detailed set of criteria for the diagnosis of Huntington's disease is set forth in the Diagnostic and Statistical Manual of Mental Disorders (DSM-5; 5$^{th}$ ed., 2013, American Psychiatric Association).

Multiple Sclerosis:

In specific embodiments, the disclosure provides methods of treating multiple sclerosis (MS), comprising administering to a subject in need thereof an effective amount of a chemical entity or composition disclosed herein. MS is a complex CNS disease associated with demyelination and axonal damage that impair normal neurotransmission, leading to deficits in sensory function and motor coordination. MS etiology is not fully understood but is regarded as an autoimmune disease that includes neuroinflammatory and neurodegenerative components (Kipp et al., 2012, *CNS Neurol. Disord. Drug Targets* 11, 506-617).

Because nerves in any part of the brain or spinal cord may be damaged, patients with multiple sclerosis can have variable symptoms in many parts of the body. Symptomatic episodes can vary in frequency and severity and typically alternate with periods of reduced or no symptoms (remissions). Muscle symptoms associated with MS include loss of balance; muscle spasms; numbness, tingling, or abnormal sensation in any area; problems moving arms or legs; problems walking; problems with coordination and making small movements; tremor in one or more arms or legs; and weakness in one or more arms or legs. PDE7 inhibition has been shown to play a general role in modulating inflammatory responses and to reduce symptoms in animal models of primary progressive multiple sclerosis (Mestre et al., 2015, *Br. J. Pharmacol.* 172, 4277-4290; Redondo et al., 2012, *J. Med. Chem.* 55, 3274-84; Gonzalez-Garcia et al., 2013, *Brit. J. Pharm.* 170, 602-613; Redondo et al., 2012, *ACS Chemical Neuroscience* 3, 793-803; Medina-Rodriguez et al., 2017, *Sci Rep.* 7, 43545; Medina-Rodriguez et al., 2013, *Cell Mol. Life Sci.* 70, 3449-3462).

Spinal Cord Injury:

In specific embodiments, the disclosure provides methods of treating a spinal cord injury (SCI), comprising administering to a subject in need thereof an effective amount of a chemical entity or composition disclosed herein. An excessive inflammatory response plays an important role in the secondary injury processes that lead to continued death of neurons following the primary injury. This neuroinflammatory response is modulated by cAMP levels, highlighting a role for cAMP PDEs, and more particularly, PDE7, which is expressed on leukocytes and in the brain. See, e.g., Paterniti et al., 2011, *PLoS One* 6, e15937.

Augmented Training

In some embodiments, chemical entities, and compositions thereof, of the present disclosure are used as augmenting agents in methods to increase the efficiency of training protocols for enhancing a neurological function or treating a neurological impairment associated with a neurological disorder. Such methods are known as "augmented training," and more particularly, in the case of cognitive impairments, "augmented cognitive training," and in the case of motor impairments, "augmented motor training." Augmenting agents can act by shortening the time that methods of rehabilitating (or enhancing) a cognitive or motor function result in improved performance or a functional gain. Such augmented training therefore comprises a specific training protocol for a particular brain function, such as that underlying declarative memory, performance of a fine motor skill, a specific locomotor function, language acquisition, executive function, etc.; and a general administration of an augmenting agent of the present disclosure.

Training (or a "training protocol") generally requires many sessions to attain the desired benefits, for example, to rehabilitate a motor deficit or language deficit following stroke. This can be costly and time-consuming, deterring subject compliance and the realization of real world benefits that endure over time. The efficiency of such training protocols can be improved by administering certain agents (known as augmenting agents) in conjunction with the training protocol (see, e.g., U.S. Pat. Nos. 7,868,015; 7,947,731; U.S. 2008-0188525). When administered in combination with training protocols (or "training"), augmenting agents enhance functional reorganization in targeted domains (or "functions") in the brain.

Cognitive domains (or "functions") that can be targeted by training protocols include, but are not limited to, the following: attention (e.g., sustained attention, divided attention, selective attention, processing speed); executive function (e.g., planning, decision, and working memory); learning and memory (e.g., immediate memory; recent memory, including free recall, cued recall, and recognition memory; and long-term memory, which can be divided into explicit memory (declarative memory) memory, such as episodic, semantic, and autobiographical memory, and into implicit memory (procedural memory)); language (e.g., expressive language, including naming, word recall, fluency, grammar, and syntax; and receptive language); perceptual-motor functions (e.g., abilities encompassed under visual perception, visuo-constructional, perceptual-motor praxis, and gnosis); and social cognition (e.g., recognition of emotions, theory of mind). In specific embodiments, the cognitive function is learning and memory, and more particularly, long term memory.

Motor domains (or functions) that can be targeted by training protocols include, but are not limited to, those involved in gross body control, coordination, posture, and balance; bilateral coordination; upper and lower limb coordination; muscle strength and agility; locomotion and movement; motor planning and integration; manual coordination and dexterity; gross and fine motor skills; and eye-hand coordination.

Training Protocols:

Training protocols (or "modules") include cognitive training and motor training protocols. Training protocols are well-known in the art and typically comprise a set of distinct exercises that can be process-specific or skill-based: See, e.g., Kim et al., 2014, *J. Phys. Ther. Sci.* 26, 1-6; Allen et al., 2012, *Parkinson's Dis.* 2012, 1-15; Jaeggi et al., 2011, *Proc. Natl. Acad. Sci. USA* 108, 10081-10086; Chein et al., 2010, *Psychon. Bull. Rev.* 17, 193-199; Klingberg, 2010, *Trends Cogn. Sci.* 14, 317-324; Owen et al., 2010, *Nature* 465, 775-778; Tsao et al., 2010, *J. Pain* 11, 1120-1128; Lustig et al., 2009, *Neuropsychol. Rev.* 19, 504-522; Park and Reuter-Lorenz, 2009, *Ann. Rev. Psych.* 60, 173-196; Oujamaa et al., 2009, *Ann. Phys. Rehabil. Med.* 52, 269-293; Frazzitta et al., 2009, *Mov. Disord.* 8, 1139-1143; Jaeggi et al., 2008, *Proc. Natl. Acad. Sci. USA* 105, 6829-6833; Volpe et al., 2008, *Neurorehabil. Neural Repair* 22, 305-310; Fischer et al., 2007, *Top. Stroke Rehab.* 14, 1-12; Jonsdottir et al., 2007, *Neurorehabil. Neural Repair* 21, 191-194; Stewart et al., 2006, *J. Neurol. Sci.* 244, 89-95; Krakauer, 2006, *Curr. Opin. Neurol.* 19, 84-90; Belleville et al., 2006, *Dement. Geriatr. Cogn. Disord.* 22, 486-499; Klingberg et al., 2005,

*J. Am. Acad. Child. Adolesc. Psychiatry* 44, 177-186; Dean et al., 2000, *Arch. Phys. Med. Rehabil.* 81, 409-417; Whitall et al., 2000, *Stroke* 31, 2390-2395; Hummelsheim and Eickhof, 1999, *Scand. J. Rehabil. Med.* 31, 250-256; Merzenich et al., 1996, *Science* 271, 77-81; Merzenich et al., 1996, *Cold Spring Harb. Symp. Quant. Biol.* 61, 1-8; Rider and Abdulahad, 1991, *Percept. Mot. Skills* 73, 219-224.

Process-specific training focuses on improving a particular domain such as attention, memory, language, executive function, or motor function. Here the goal of training is to obtain a general improvement that transfers from the trained activities to untrained activities based on the same cognitive or motor function or domain.

Skill-based training is aimed at improving performance of a particular activity or ability, such as learning a new language, performing a musical instrument, improving memory, or learning a fine motor skill. The different exercises within such a protocol will focus on core components within one or more domains underlying the skill. Modules for increasing memory, for example, may include tasks directed to specific domains involved in memory processing, e.g., the recognition and use of facts, and the acquisition and comprehension of explicit knowledge rules.

In some embodiments, the battery of exercises is administered as part of a single training session. In one aspect, the training protocol comprises multiple training sessions, each separated by a discrete interval. In another aspect, the number of training sessions sufficient to improve performance is reduced compared to that produced by training alone.

In a further aspect, the augmenting agent is a PDE7 inhibitor, and more particularly, is a chemical entity of the present disclosure, and is administered in conjunction with training. The phrase "in conjunction with" means that the augmenting agent enhances CREB pathway function during training. In some embodiments, the deficit is a motor deficit. In other embodiments, the deficit is a cognitive deficit. In still other embodiments, the deficit may include both a cognitive and motor deficit. In other aspects, the compound is administered before and during each training session. In one aspect, the subject is a human. In some embodiments, the subject is a non-human, and more particularly, is a primate or a canine. In one aspect, a compound or composition of the present disclosure can be used as an augmenting agent in conjunction with any psychotherapeutic approach intended to modulate cognitive function in the brain, thereby enhancing the efficacy of such therapy by reducing the number of sessions necessary to attain benefits.

Accordingly, in some embodiments, the disclosure provides the use of a compound or composition herein in a method of augmented training to treat a neurological disorder, the method comprising: (a) providing training to an animal in need of treatment of a neurological impairment associated with the neurological disorder under conditions sufficient to produce an improvement in performance by said animal of a neurological function whose deficit is associated with said neurological impairment; (b) administering the compound or composition to the animal in conjunction with said training; (c) repeating said providing and administering steps one or more times; and (d) reducing the number of training sessions sufficient to produce the improvement in performance, relative to the improvement in performance produced by training alone. In some aspects, the augmented training is augmented cognitive training. In some aspects, the neurological impairment is a cognitive impairment. In some aspects, the neurological impairment is a motor impairment. In a specific aspect, the neurological disorder is stroke or traumatic brain injury. In some aspects, the augmented training is provided to a stroke patient during post-stroke rehabilitation, as described further herein.

Animal Skill Protocols:

In some embodiments, chemical entities of the present invention are used to enhance the efficiency of training protocols directed to cognitive and motor skills in an animal. Such augmented training (augmenting agent and training) reduces the time necessary to acquire a cognitive or motor skill, and/or enhance function or cognitive ability beyond what would be possible by training alone in the non-human animal.

In particular embodiments, the animal is a non-human animal, and more particularly, is a service animal, a category that includes, but is not limited to, dogs, miniature horses, and capuchin monkeys. Service animals may be involved in public service or private service, and the training protocols will be appropriately matched to these objections. For example, training protocols directed to public service include public order maintenance, search and rescue, and contraband detection, and training protocols directed to private service include private security, handicap assistance, health care, psychiatric assistance, and pest control.

The training protocol may be directed to a single skill, such as the detection of a specific contraband category by a service animal. In other embodiments, the training protocol may be directed to a complex set of skills, such as those underlying search and rescue training of a service animal; for a complex set of skills, training will therefore comprise more than one tasks.

Accordingly, in some embodiments, the present invention provides a method of teaching a non-human animal one or more skills, comprising (a) administering to a non-human animal in need thereof a PDE7 inhibitor; (b) providing training to the animal under conditions sufficient to improve performance of the one or more skills; and (c) repeating steps (a) and (b) one or more times, whereby the amount of training sufficient to improve the performance is reduced compared to that produced by training alone.

Stroke

In certain embodiments, chemical entities and compositions of the present disclosure are useful in methods of treating a trauma-dependent loss of function, and more particularly, stroke. Stroke is a leading cause of serious long-term disability in adults and is the second leading cause of death worldwide (e.g., Go et al., 2014, *Circulation* 129, e28-e92). Stroke is comprises two main types: 1) ischemic stroke which occurs when blood vessels supplying the brain are blocked by clot formation (85% of all strokes) and 2) hemorrhagic stroke which occurs when blood vessels rupture within the brain (13-15% of all strokes). Stroke care is a temporal continuum that includes medical intervention during the acute phase of stroke and subsequent rehabilitative therapy directed to restoring function during the post-stroke phase of stroke.

Acute Treatments:

Treatments following the onset of stroke directly target the initial damage triggered by ischemic or hemorrhagic stroke. Acute treatment options for ischemic stroke include pharmacotherapy with intravenous recombinant tissue plasminogen activator (r-tPA) to thrombolyze the clot, or the use of endovascular procedures or mechanical thrombectomy to physically remove the clot. Acute treatment options for hemorrhagic stroke typically involve endovascular or surgical procedures to physically repair the rupture via.

PDE7 inhibition has been shown to reduce the infarct size, as well as behavioral impairments, in animal stroke models, and more generally, PDE7 inhibitors can prevent glial cell activation and neuronal cell death in KA models of neurodegeneration (Redondo et al., 2012, *Eur. J. Med. Chem.* 47, 175-185; Susin et al., 2012, *J. Neurochem.* 122, 1193-1202). Accordingly, in some embodiments, the present disclosure provides methods of treating stroke during the acute stage, comprising administering to a subject in need thereof a chemical entity or composition disclosed herein. Thus, in some embodiments, the subject is an acute stage stroke patient, and PDE7 inhibitors herein are administered to treat neuroinflammatory and neurodegenerative events resulting from the primary stroke injury. In one aspect, the stroke is ischemic stroke. In another aspect, the stroke is hemorrhagic stroke.

Post-stroke rehabilitation:

Following the acute phase of stroke—and typically after the patient has been medically stabilized—the focus of stroke treatment shifts to restoring function by rehabilitation. Depending on the severity and location of the stroke as well as the timing and effectiveness of acute interventions, post-stroke symptoms may persist and can include motor deficits (e.g., hemiparesis, apraxia), speech impairment (e.g., aphasia), visual impairments (e.g., visual field loss), emotional and behavioral changes (e.g., depression, anxiety), and mental and cognitive changes (e.g., confusion, apathy, cognitive impairment) (Winstein et al., 2016, *Stroke* 47, e98-e169). Rehabilitation (also referred to as "stroke rehabilitation" or "post-stroke rehabilitation") is directed to post-stroke deficits, such as cognitive and motor deficits that persist after the initial stroke injury. The goal is to restore and recover neurological functions, e.g., physical, intellectual, psychological, and social functions, as much as possible to compensate for the permanent tissue loss (e.g., 1995 Clinical Guideline by the Department of Health and Human Services on Post-Stroke Rehabilitation).

Stroke rehabilitation is typically a comprehensive program coordinated by a team of medical professionals, which may include occupational, speech, and physical therapists. A physical therapist on the team, for example, may focus on maintaining and restoring range of motion and strength in affected limbs, maximizing mobility in walking, improving manual dexterity, and rehabilitating other motor and sensorimotor functions. A mental health professional may be involved in the treatment of loss of cognitive skills. Rehabilitation services can occur in multiple environments, such as a rehabilitation hospital, long-term care facility, outpatient clinic, or at home.

Neurological functions impacted by stroke (and which can be targeted during rehabilitation) include impairments in cognitive and motor functions. Cognitive function impairments, for example, can manifest as deficits in understanding speech or writing (aphasia); knowing the right words but having trouble saying them clearly (dysarthria); as well as deficits in other cognitive functions, such as attention, reasoning, planning, execution, and learning and memory. Motor function impairments, for example, can manifest as weakness (hemiparesis) or paralysis (hemiplegia) on one side of the body that may affect the whole side or just the arm or leg; as problems with balance or coordination; as deficits in gross motor skills such as gait and walking speed; as deficits in fine motor skills or manual dexterity; and as deficits in upper and lower extremity function.

In the United States, more than 700,000 people suffer a stroke each year, two-thirds of these survive and require rehabilitation. Unfortunately, recovery is generally only partial and considerable deficits persist in many patients (e.g., Gordon et al., 2004, *Stroke* 35, 1230-1240). For example, after standard rehabilitation, approximately 30% to 60% of patients are left without functional use of their paretic/plegic arm (Gowland, 1982, *Physiother. Can.* 34, 77-84; Kwakkel et al., *Age Ageing* 25, 479-489), and despite intensive rehabilitation efforts, only approximately 5% to 20% reach complete functional recovery of their arm (Nakayama et al., 1994, *Arch. Phys. Med. Rehabil.* 75, 394-398).

As discussed herein, chemical entities, and compositions thereof, of the present disclosure are used as augmenting agents to increase the efficiency of training protocols for treating a neurological impairment, which encompasses impairments due to traumatic events such as stroke. Accordingly, in some embodiments, the present disclosure provides methods of treating a neurological deficit during post-stroke rehabilitation comprising: (a) administering to a subject in need thereof a PDE7 inhibitor disclosed herein during recovery of the subject from stroke; (b) providing training to the subject under conditions sufficient to improve performance of a neurological function whose impairment is due to the deficit; and (c) repeating steps (a) and (b) one or more times, In some embodiments, administration can begin during the acute stage. In other embodiments, the PDE7 inhibitor is administered only after the acute stage, i.e., during post-stroke rehabilitation, which may include sub-acute and chronic stages. In some embodiments, administration occurs during the acute stage and post-stroke stage. In some embodiments, the PDE7 inhibitor is administered chronically, meaning that it is indicated for long-term use after the acute stage of the stroke has ended and the patient has been medically stabilized.

In other embodiments, the subject is a post-stroke patient, and PDE7 inhibitors are administered during stroke rehabilitation to treat stroke deficits (or "post-stroke deficits") resulting from impaired neurological functions. In some embodiments, the deficit is a motor deficit, including upper or lower extremity motor deficit. In other embodiments, the deficit is a cognitive deficit, such as such as aphasia, apraxia, and mental and cognitive changes, particularly, a deficit in memory formation, and more specifically, a deficit in long-term memory formation. In still other embodiments, the deficit may include a cognitive and motor deficit. In another aspect, training comprises a battery of tasks directed to the neurological function. In a specific aspect, the reduction in the amount of training is a reduction in the number of training sessions.

In a further embodiment, the administering step (a) is in conjunction with the training step (b). In one aspect, the subject is a human. In another aspect, the subject has undergone neuronal stem cell manipulation. In other aspects, the compound is administered before and during each training session.

Traumatic Brain Injury

In some embodiments, chemical entities and compositions are useful in methods of treating traumatic brain injury (TBI), and in more specific embodiments, treating motor or cognitive impairments during rehabilitation of TBI after the initial trauma.

TBI, also known as intracranial injury, occurs when an external force injures the brain. TBI can be classified based on severity, mechanism (closed or penetrating head injury), or other features (e.g., occurring in a specific location or over a widespread area). TBI can result in physical, cognitive, social, emotional, and behavioral symptoms. Causes include falls, vehicle collisions, gunshot injuries, and explosives. Outcomes can range from complete recovery to permanent disability or death.

Like stroke care, TBI case is a temporal continuum that includes acute (or sub-acute) treatments directed to the injury itself and subsequent rehabilitative therapy directed to restoring function.

Accordingly, in some embodiments, the chemical entities and compositions of the present disclosure are useful during the acute (or sub-acute) stage of TBI, during which their administration can treat neuroinflammatory and neurodegenerative events following the primary injury.

Some embodiments provide the use of a PDE7 inhibitor disclosed during TBI rehabilitation to treat TBI deficits (or "post-TBI deficits") resulting from impaired neurological functions. Some embodiments provide methods of treating a neurological deficit during post-TBI rehabilitation comprising: (a) administering to a subject in need thereof a PDE7 inhibitor during recovery of the subject from TBI; (b) providing training to the subject under conditions sufficient to improve performance of a neurological function whose impairment is due to the deficit; and (c) repeating steps (a) and (b) one or more times, whereby the amount of training sufficient to improve the performance is reduced compared to that produced by training alone.

In one aspect, the PDE7 inhibitor is a chemical entity of the present disclosure, and more specifically, is a compound, or pharmaceutically acceptable salt thereof, of Formula (I). In some embodiments, the deficit is a motor deficit. In other embodiments, the deficit is a cognitive deficit, particularly, a deficit in memory formation, and more specifically, a deficit in long-term memory formation. In still other embodiments, the deficit may include a cognitive and motor deficit. In another aspect, training comprises a battery of tasks directed to the neurological function. In a specific aspect, the reduction in the amount of training is a reduction in the number of training sessions.

In a further embodiment, the administering step (a) is in conjunction with the training step (b). In one aspect, the subject is a human. In another aspect, the subject has undergone neuronal stem cell manipulation. In other aspects, the compound is administered before and during each training session.

Peripheral Disorders

In some embodiments, the present disclosure provides methods of treating a peripheral disorder (i.e., a disorder other than a primary neurological disorder), comprising administering to a subject in need thereof an effective amount of a chemical entity or composition disclosed herein. Peripheral disorders involving PDE7 include a wide variety of diseases, based on numerous biological studies and the expression of PDE7 subtypes in peripheral tissues, such as heart, ovary, pituitary gland, kidney, liver, small intestine, thymus, skeletal muscle, colon, bladder, uterus, prostate, stomach, adrenal gland, thyroid gland, as well as T-cells, B-cells, lung mast cells, and bronchial epithelial cells. See, e.g., Michaeli et al., 1993, *Biol. Chem.* 268, 12925-12932; Gardner et al., 2000, *Biochem. Biophys. Res. Commun.* 272, 186-192; Hetman et al., 2000, *Proc. Natl. Acad. Sci. USA* 97, 472-476; Glavas et al., 2001, *Proc. Natl. Acad. Sci. USA* 98, 6319-6324; Bloom et al., 1996, *Proc. Natl. Acad. Sci. USA* 93, 14188-14192; Smith et al., 2003, *Cell. Mol. Physiol.* 284, L279-L289; Smith et al., 2004, *Mol. Pharmacol.* 66, 1679-1689; Reyes-Irisarri et al., 2005, *Neuroscience* 132, 1173-1185; Pekkinen et al., 2008, *Bone* 43, 84-91; Fortin et al., 2009, *Respir. Res.* 10, 39-49; Goto et al., 2009, *Int. Immunopharmacol.* 9, 1347-1351; Dong et al., 2010, *Biochem. Pharmacol.* 79, 321-329; Goto et al., 2010, *Eur. J. Pharmacol.* 633, 93-97; Johansson et al., 2012, *Neurosci. Lett.* 525, 1-6; Fang et al., 2013, *Leuk. Res.* 37, 536-540; Brooks et al., 2014, *PLoS One.* 9, e107397; Dong et al., 2015, *Breast Cancer Res. Treat.* 152, 17-28; Yamamoto et al., 2015, *International Journal of Oncology*, 46, 325-334; Jankowska et al., 2017, *Curr. Med. Chem.* 24, 1-28.

In some embodiments, the peripheral disorder is an infectious disease, which can include bacterial, fungal, protozoan, and viral infections.

In some embodiments, the peripheral disorder is a cancer or hematological disease, which can include anemias, myeloproliferative disorders, hemorrhagic disorders, leukopenias, eosinophilic disorders, leukemias such as chronic lymphocytic leukemia (CLL), lymphomas such as mantle cell lymphoma, plasma cell dyscrasias, breast cancer, endometrial cancer, and glioblastomas.

In some embodiments, the peripheral disorder is a cardiovascular disease, which can include congestive heart failure, myocardial infarction, ischemic diseases, atrial and ventricular arrhythmias, pulmonary hypertension, hypertensive vascular diseases, and atherosclerosis. A peripheral disorder may also include disorders that have a likely vascular component, such as migraine disorders.

In some embodiments, the peripheral disorder is a gastroenterological disorder, which can include diseases of the esophagus, stomach, duodenum, pancreas, bowel, and liver.

In some embodiments, the peripheral disorder is a dermatological disorder, which can include psoriasis, dermatitis, impetigo, folliculitis, melanoma, and skin cancers.

In some embodiments, the peripheral disorder is a renal disease, such as kidney failure.

In some embodiments, peripheral disorders includes inflammatory disorders and immunological disorders (which can include autoimmune and allergic diseases). Such immunological or inflammatory disorders include, but are not limited to, allergic rhinitis; atopic dermatitis (or eczema); dermatitis herpetiformis; celiac disease; skin disorders, such as psoriasis; conjunctivitis; myalgic encephalomyelitis (ME); chronic fatigue syndrome (CFS); encephalomyelitis; systemic lupus erythematosus (SLE or lupus); inflammatory bowel disease (IBD); Crohn's disease; ulcerative colitis; arthritic diseases, such as rheumatoid arthritis, osteoarthritis, and psoriatic arthritis; respiratory and pulmonary illnesses, such as bronchial asthma, chronic bronchitis, and chronic obstructive pulmonary disease (COPD); hepatitis; pancreatitis; sepsis; human immunodeficiency virus (HIV) infection; and acquired immune deficiency syndrome (AIDS).

In other embodiments, the peripheral disorder is a fertility disorder (e.g., WO0183772) or bone disorder, such as osteopenia, and more particularly, osteoporosis (Ahlstrom et al., 2005, *Cell. Mol. Biol. Lett.* 10, 305-319).

In some embodiments, the peripheral disorder is associated with inflammation. Increasing cAMP levels can promote inflammatory and immunological processes, and PDE7 shows widespread expression, including in proinflammatory and immune cells, and is involved in activation of T-cell proliferation. See, e.g., Li et al., 1999, *Science* 283, 848-851; Lee et al., 2002, *Cell Signal.* 14, 277-284; Smith et al., 2003, *Am. J. Physiol Lung Cell. Mol. Physiol.* 284, L279-L289. Accordingly, the present disclosure provides methods of reducing inflammation, comprising administering to a subject in need thereof an effective amount of a chemical entity or composition herein.

Treatment Combinations

Chemical entities and compositions of the present disclosure can be administered as a monotherapy or as part of a combination therapy. "Monotherapy" refers to a treatment regimen based on the delivery of at least therapeutically effective chemical entity or composition thereof.

In a combination therapy, one or more chemical entities or compositions of the present invention can be co-administered or used in combination with one or more additional agents (or therapies) known in the art. Such administration may be simultaneous, sequential, or staggered.

In some embodiments, the combination is administered as part of an adjunct (or adjunctive) therapy, in which one agent is given in addition to a primary agent to assist or maximize the effectiveness of the primary agent.

In specific embodiments, the combination is administered to treat schizophrenia, Parkinson's disease, Alzheimer's disease, Huntington's disease, anxiety and depressive disorders, or stroke.

Exemplary agents for treating schizophrenia include, but are not limited to, clozapine, aripiprazole, brexpiprazole, cariprazine, lurasidone, paliperidone, quetiapine, risperidone, olanzapine, ziprasidone, and iloperidone.

Exemplary agents for treating Parkinson's disease include, but are not limited to, dopamine preparations, dopamine agonists, or COMT agents (drugs that inhibit the action of catechol-methyl transferase).

Exemplary agents for treating Alzheimer's disease include, but are not limited to, donepezil, rivastigmine, galantamine, marijuana-like cannabinoids, and memantine.

Exemplary agents for treating Huntington's disease (or other motor disorders) may include, but are not limited to, tetrabenazine, as well as antipsychotic drugs such as haloperidol, chlorpromazine, risperidone, and quetiapine, and anti-epileptic drugs such as levetiracetam and clonazepam, which may be beneficial in treating chorea or related motor disorders.

Exemplary agents for treating anxiety or depression include, but are not limited to, benzodiazepines and other anxiolytics; serotonin reuptake inhibitors (SSRIs), such as sertraline, fluoxetine, citalopram, escitalopram, paroxetine, fluvoxamine, and trazodone; serotonin and norepinephrine reuptake inhibitors (SNRIs), such as desvenlafaxine, duloxetine, levomilnacipran, and venlafaxine; tricyclic antidepressants (TCAs), such as amitriptyline, amoxapine, clomipramine, desipramine, doxepin, imipramine, nortriptyline, protriptyline, and trimipramine; monoamine oxidase inhibitors (MAOIs), such as isocarboxazid, phenelzine, selegiline, and tranylcypromine; and other classes of drugs, such as maprotiline, bupropion, vilazodone, nefazodone, trazodone, vortioxetine, and mirtazapine Exemplary agents for treating stroke include, but are not limited to, a thrombolytic agent (e.g., streptokinase, acylated plasminogen-streptokinase activator complex (APSAC), urokinase, single-chain urokinase-plasminogen activator (scu-PA), anti-inflammatory agents, thrombin-like enzymes, tissue plasminogen activator (t-PA); an anticoagulant (e.g., warfarin or heparin); an antiplatelet drug (e.g., aspirin); a glycoprotein IIb/IIIa inhibitor; a glycosaminoglycan; coumarin; GCSF; melatonin; an apoptosis inhibitor (e.g., caspase inhibitor), an anti-oxidant (e.g., NXY-059); and a neuroprotectant (e.g., an NMDA receptor antagonists or a cannabinoid antagonist).

The preceding list of additional active agents is meant to be exemplary rather than fully inclusive. Additional active agents not included in the above list may be administered in combination with a compound of Formula (I), such as those know for treating peripheral disorders described herein. The additional active agent will be dosed according to its approved prescribing information, though in some embodiments the additional active agent may be dosed at less the typically prescribed dose.

EXAMPLES

The present disclosure will be further illustrated by the following non-limiting Examples. These Examples are understood to be exemplary only, and they are not to be construed as limiting the scope of the one or more embodiments, and as defined by the appended claims.

PREPARATIVE EXAMPLES

Exemplary compounds will now be described by reference to the illustrative synthetic schemes for their general preparation below and the specific examples to follow.

One skilled in the art will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I). Reactions may be performed between −100° C. and the reflux temperature of the solvent. Reactions may be heated employing conventional heating or microwave heating. Reactions may also be conducted in sealed pressure vessels above the normal reflux temperature of the solvent.

Abbreviations

The specification includes numerous abbreviations, whose meanings are listed in the following Table:

TABLE 1

| Abbreviation | Definition |
| --- | --- |
| ACN | Acetonitrile |
| AcOH or HOAc | Acetic Acid |
| $Ac_2O$ | Acetic Anhydride |
| APCI | Atmospheric pressure chemical ionization |
| $BBr_3$ | Boron tribromide or tribromoborane |
| CELITE ® | Diatomaceous earth |
| $CHCl_3$ | Chloroform |
| $CO_2$ | Carbon dioxide |
| $Cs_2CO_3$ | Cesium Carbonate |
| DCM, $CH_2Cl_2$ | Dichloromethane |
| DIBAL | Diisobutylaluminum hydride |
| DIPEA, DIEA | N,N-ethyl-diisopropylamine or N,N-Diisopropyl-ethyl amine or N-ethyl-N-isopropylpropan-2-amine |
| DMA | N,N-Dimethylacetamide |
| DMF | N,N-Dimethylformamide |
| DMSO | Dimethylsulfoxide |
| Eaton's reagent | Phosphorus pentoxide, 7.7 wt. % in methanesulfonic acid |
| EtOAc, or EA | Ethyl Acetate |
| EtOH | Ethanol |
| ESI | Electrospray ionization |
| FCC | Flash column chromatography |
| HATU | 1-[Bis(dimethylamino)nethylene]-1H-1,2,3-triazolo[4,5-b]pyridinium 3-oxide hexafluorophosphate |
| HBr | Hydrobromic acid |
| HCl | Hydrochloric acid |
| HCOOH | Formic acid |

TABLE 1-continued

| Abbreviation | Definition |
|---|---|
| HNO$_3$ | Nitric Acid |
| H$_2$O | Water |
| HPLC | High-performance liquid chromatography |
| K$_2$CO$_3$ | Potassium carbonate |
| KOCN | Potassium cyanate |
| KOtBu | Potassium tert-butoxide |
| LAH, LiAlH$_4$ | Lithium aluminum hydride |
| LCMS, LC/MS | Liquid chromatography-mass spectrometry |
| LDA | Lithium diisopropylamide |
| LiHMDS, LHMDS | Lithium bis(trimethylsilyl)amide |
| LiOH | Lithium hydroxide |
| MeOH | Methanol |
| MgSO$_4$ | Magnesium sulfate |
| NaBH$_4$ | Sodium borohydride |
| NaCl, brine | Sodium chloride |
| NaHCO$_3$ | Sodium bicarbonate |
| Na$_2$SO$_4$ | Sodium sulfate |
| NH$_4$Cl | Ammonium chloride |
| NH$_4$OH | Ammonium hydroxide |
| NMP | 1-Methyl-2-pyrrolidinone |
| NMR | Nuclear magnetic resonance |
| P$_2$O$_5$ | Phosphorous pentoxide |
| iPrOH | Isopropyl alcohol |
| PtO$_2$ | Platinum (IV) Oxide |
| SiO$_2$ | Silicon dioxide |
| SFC | Super-critical fluid chromatography |
| pTsOH, PTSA | p-Toluenesulfonic acid, 4-Methylbenzene-1-sulfonic acid |
| TEA, Et$_3$N | Triethylamine |
| TFA | Trifluoroacetic acid |
| THF | Tetrahydrofuran |
| UPLC | Ultra-performance liquid chromatography |

Synthetic Schemes temperatures ranging from room temperature to 60° C., sometimes 40° C., provides compounds of formula (III). Subsequent treatment with a cyclohexanone in the presence of Eaton's reagent, with heat, under conditions known to one of skill in the art, provides a hydroxy-1'H-spiro[cycloalkane-1,4'-quinazolin]-2'(3'H)-one of formula (VIII). For example, treatment of compounds of formula (III) with a substituted cyclohexanone and Eaton's Reagent, at a temperature ranging from 40° C. to 100° C., provides compounds of formula (VIII), where Y is —H, —F, —Cl, —Br, or —C$_{1-4}$alkyl, Z is —H, —F, or —C$_{1-4}$alkyl, and m is 0, 1 or 2. Subsequent nitration, using methods known to one skilled in the art, provides a substituted nitrophenol of formula (IX). For example, nitration of compounds of formula (VIII) with nitric acid, in the presence of an acid such as trifluoroacetic acid, sulfuric acid or the like, provides compounds of formula (IX), Y is —H, —F, —Cl, —Br, or —C$_{1-4}$alkyl, Z is —H, —F, or —C$_{1-4}$alkyl and m is 0, 1 or 2.

Alternatively, compounds of formula (IX) can be synthesized using a similar synthetic route, starting with a methyl ether of formula (V). A substituted 3-methoxyaniline of formula (V) can be treated with potassium cyanate and acetic acid, followed by treatment with a cyclohexanone in the presence of Eaton's reagent, with heat, under conditions described above, to give tricyclic compounds of formula (VII) where Y is —H, —F, —Cl, —Br, or —C$_{1-4}$alkyl, Z is —H, —F, or —C$_{1-4}$alkyl and m is 0, 1 or 2. Next, deprotection of the methyl ether and nitration, in either order, provides a nitrophenol of formula (IX). In one embodiment, initial deprotection of the methyl ether, followed by nitration

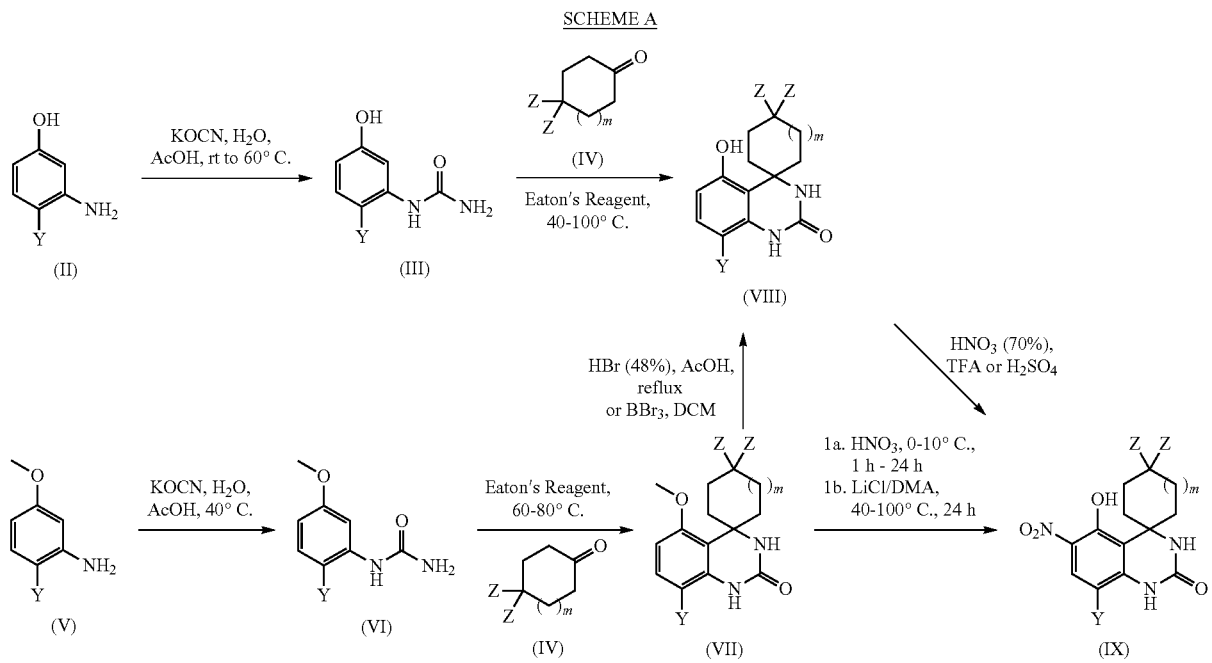

Substituted 3-hydroxyphenyl ureas of formula (III) can be prepared from the corresponding substituted 3-hydroxyphenyl aniline and potassium cyanate, under acidic conditions known to one of skill in the art. For example, treatment of compounds of formula (II), where Y is —H, —F, —C$_1$, —Br or —C$_{1-4}$alkyl, with potassium cyanate in the presence of an acid, such as acetic acid, in a solvent, such as water, at using nitric acid, in the presence of another strong acid such as trifluoroacetic or sulfuric acid, provides a nitrophenol compound of formula (IX). For example, treatment of compounds of formula (VII) with HBr (48%), in the presence of another acid, such as acetic acid, at temperatures near or at reflux, in a solvent such as dichloromethane or the like, provides a hydroxy-1'H-spiro[cycloalkane-1,4'-quinazolin]-2'(3'H)-one of formula (VIII). Alternatively, treatment of compounds of formula (VII) with boron tribromide in a solvent such as dichloromethane, or the like, also provides a hydroxy-1'H-spiro[cycloalkane-1,4'-quinazolin]-2'(3'H)-one of formula (VIII) where Y is —H, —F, —Cl, —Br, or —C$_{1-4}$alkyl, Z is —H, —F, or —C$_{1-4}$alkyl and m is 0, 1 or 2. Subsequent treatment with nitric acid, as described above, provides a compound of formula (IX), where Y is —H, —F, —Cl, —Br, or —C$_{1-4}$alkyl, Z is —H, —F, or —C$_{1-4}$alkyl and m is 0, 1 or 2. In another embodiment, nitration followed by cleavage of the methyl ether is achieved by treatment of compounds with nitric acid followed by addition of LiCl in a solvent such as DMA, or the like, to provide compounds of formula (IX). For example, treatment of compounds of formula (VII) with nitric acid, at a temperature of 0° C. to 10° C. for 1 hour, followed by treatment with LiCl, in a solvent such as DMA or the like, heated to a temperature ranging from 40° C. to 80° C., ideally 70° C., overnight, provides a nitrophenol of formula (IX).

acidic conditions, such as in the presence of an like acetic acid, in a solvent mixture, such as tetrahydrofuran and water or DMA and water, preferably DMA and water, provides an aminophenol compound of formula (X). Alternatively, treatment of compounds of formula (IX) with a catalyst, such as platinum(IV) oxide, or the like, in the presence of hydrogen gas, in a solvent such as tetrahydrofuran or the like, at room temperature, followed by treatment with sulfuric acid, provides the hemi sulfate salt of compounds of formula (X), where Y is —H, —F, —Cl, —Br, or —C$_{1-4}$alkyl, Z is —H, —F, or —C$_{1-4}$alkyl and m is 0, 1 or 2.

Treatment of compounds of formula (X) with methyl 2,2,2-trichloroacetimidate in the presence of an acid, such as acetic acid, for several hours, followed by addition of potassium carbonate in a solvent, such as methanol, heated to a temperature ranging from 40° C. to 60° C., sometimes 50° C., for several hours, gives an ester of formula (XI). Alternatively, compounds of formula (X) can be treated with methyl 2,2,2-trimethoxyacetate in the presence of an acid,

SCHEME B

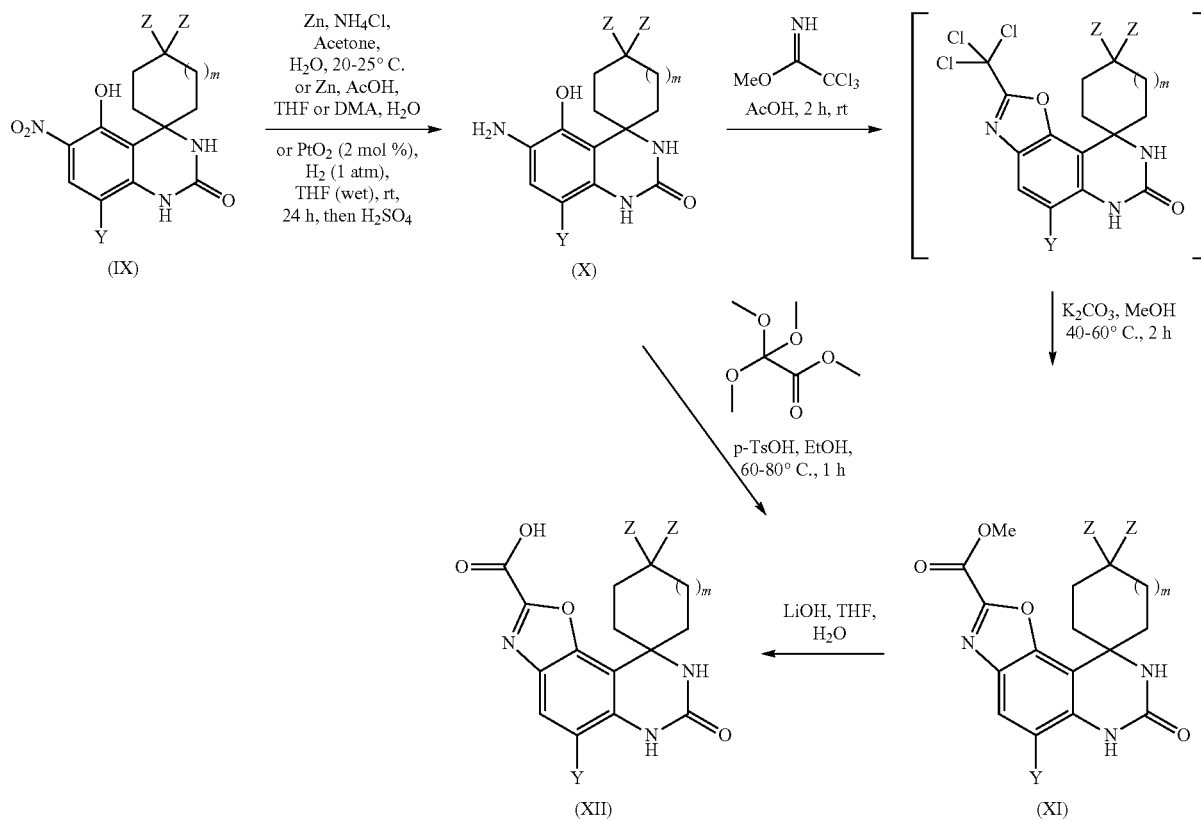

According to Scheme B, compounds of formula (XII) can be prepared in three or four steps from compounds of formula (IX). Reduction of compounds of formula (IX), under various conditions known to one skilled in the art, provides a 6'-amino-5'-hydroxy-FH-spiro[cycloalkane-1,4'-quinazolin]-2'(3'H)-one of formula (X). For instance, employing a reducing agent, such as Zn, under acidic conditions such as, in the presence of an acid such as ammonium chloride, in a solvent mixture such as acetone and water, provides an aminophenol compound of formula (X). Also, employing a reducing agent, such as Zn, under such as p-toluenesulfonic acid, in a solvent, such as ethanol, at a temperature ranging from 60° C. to 80° C. to give an ester of formula (XI). Hydrolysis of the ester to the carboxylic acid is achieved under basic or acidic conditions. For example, treatment of an ester of formula (XI) with lithium hydroxide, in a solvent mixture, such as tetrahydrofuran and water, for several hours, with or without heat, provides a 2-carboxylic acid benzoxazole of formula (XII), where Y is —H, —F, —Cl, —Br, or —C$_{1-4}$alkyl, Z is —H, —F, or —C$_{1-4}$alkyl and m is 0, 1 or 2.

SCHEME C

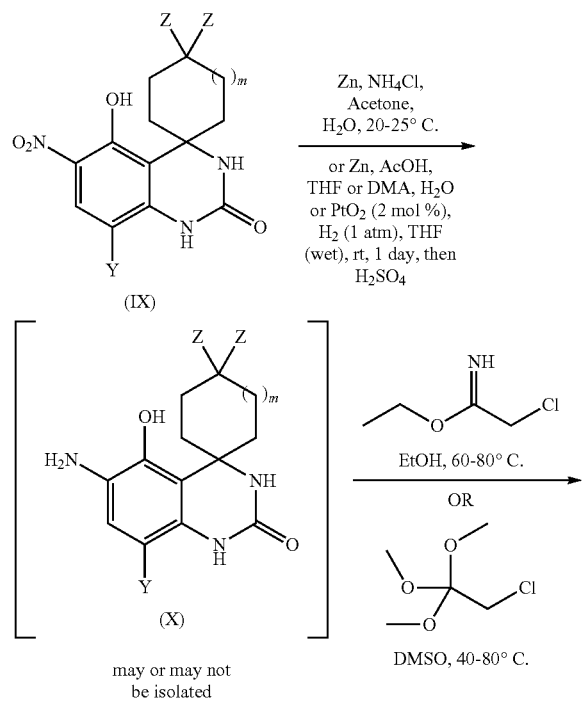

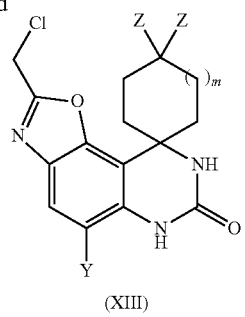

Compounds of formula (XIII) are prepared in two steps from compounds of formula (IX). Reduction of a nitrophenol of formula (IX) to give an aminophenol of formula (X) is achieved using one of several methods previously described in Scheme B. Subsequent treatment of an aminophenol of formula (X) with a chloroacetimidate, such as ethyl 2-chloroacetimidate, in a solvent such as ethanol, at a temperature ranging from 60° C. to 80° C., provides a 2-(chloromethyl)benzoxazole of formula (XIII), where Y is —H, —F, —Cl, —Br, or —$C_{1-4}$alkyl, Z is —H, —F, or —$C_{1-4}$alkyl and m is 0, 1 or 2. Alternatively, treatment of an aminophenol of formula (X) with 2-chloro-1,1,1-trimethoxyethane, in a solvent such as DMSO or the like, at a temperature ranging from 40° C. to 80° C., sometimes 50° C., provides a 2-(chloromethyl)benzoxazole of formula (XIII).

SCHEME D

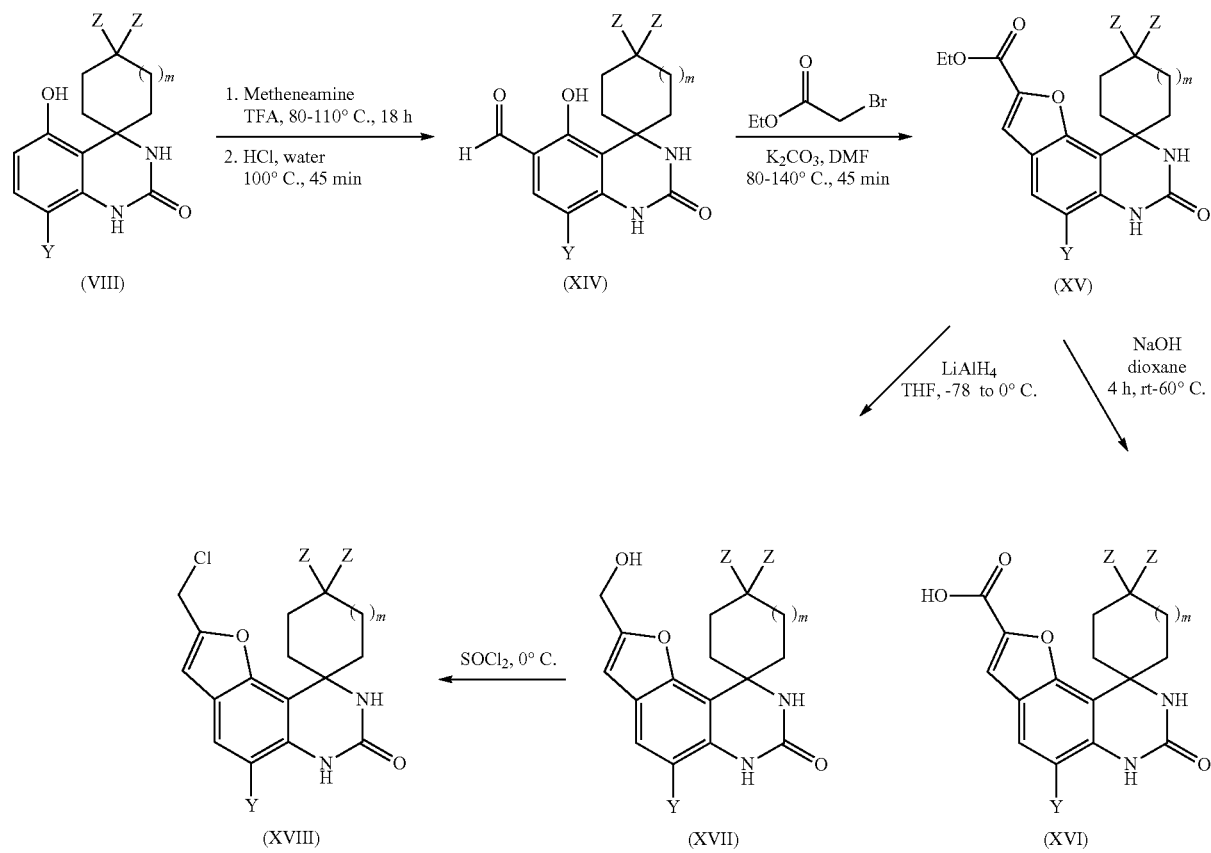

According to Scheme D, benzofuran-2-carboxylic acid compounds of formula (XVI) can be synthesized in three steps from a phenol of formula (VIII). Treatment of a phenol of formula (VIII) with metheneamine, in the presence of an acid, such as TFA, at a temperature ranging from 80° C. to 110° C., sometimes 100° C., followed by addition of HCl and water and further heating at a temperature ranging from 80° C. to 110° C., sometimes 100° C., provides an aldehyde of formula (XIV). Formation of an ester of formula (XV) is achieved by further treatment with ethyl bromoacetate, under conditions known to one of skill in the art, in the presence of a base, such as $K_2CO_3$ or $Cs_2CO_3$ or the like, in a solvent such as DMF or DMA or the like, at a temperature ranging from 80° C. to 140° C., sometimes 125° C. Hydrolysis of the ester intermediate in the presence of a base, such as NaOH or LiOH or the like, in a solvent such as dioxane, at a temperature ranging from room temperature to 60° C. provides a carboxylic acid compound of formula (XVI), where Y is —H, —F, —Cl, —Br, or —$C_{1-4}$alkyl, Z is —H, —F, or —$C_{1-4}$alkyl and m is 0, 1 or 2.

A 2-(chloromethyl)benzofuran of formula (XVIII) is prepared in two steps, using methods known to one of skill in the art, from an ester compound of formula (XV). Reduction of compounds of formula (XV), under conditions known to one skilled in the art, such as, employing a reducing agent, such as LAH, DIBAL, $NaBH_4$ and the like, preferably LAH, in a solvent such as THF, at a temperature ranging from −78° C. to 0° C., sometimes −78° C., provides a hydroxymethyl compound of formula (XVII). Subsequent halogenation, under conditions known to one skilled in the art, such as chlorination using thionyl chloride, or the like, at 0° C., with or without a solvent, provides a 2-(chloromethyl)benzofuran of formula (XVIII), Y is —H, —F, —Cl, —Br, or —$C_{1-4}$ alkyl, Z is —H, —F, or —$C_{1-4}$alkyl and m is 0, 1 or 2.

formula (XIX) with an amine, in a solvent, such as dichloromethane or the like, at a temperature between room temperature and 40° C., provides a 2-substituted methanamine compound of formula (XX), where X is —C or —N, Y is —H, —F, —Cl, —Br, or —$C_{1-4}$alkyl, Z is —H, —F, or —$C_{1-4}$alkyl, m is 0, 1 or 2, and $R^1$ and $R^2$ are independently —H, —$C_{1-6}$alkyl, —$C_{1-6}$alkyl-OH, —$C_{1-6}$haloalkyl, —$C_{1-6}$haloalkylOH, —$C_{1-6}$haloalkyl-$C_{3-7}$cycloalkyl, —$C_{3-7}$cycloalkyl, —$CH_2$-alkenyl, —$CH_2$-alkynyl, —$CH_2C_{3-7}$cycloalkyl, —$CH_2C(O)C(CH_3)_3$, —$CH_2C(O)C_{1-6}$ alkyl, —$CH_2C(O)$heterocycloalkyl, —$CH_2C(O)OC_{1-6}$alkyl, —$CH_2C(O)N(C_{1-4}$alkyl$)_2$, —$CH_2CH(OH)C_{3-7}$cycloalkyl, —$C(CH_3)_2OH$, —$C(CH_3)_2CH_2OCH_3$, —$CH(CH_3)C(O)N(C_{1-4}$alkyl$)_2$, —$CH_2CF_2C_{3-7}$cycloalkyl, —$CH_2CH_2$—Re, or —$(CH_2)_n$—$R^d$, or both $R^1$ and $R^2$ together form a monocyclic, bicyclic or tricyclic ring; n is 0, 1, 2, or 3; $R^c$ is —$C_{2-6}$ alkynyl, —$C_{3-7}$cycloalkyl, —OH, —O—$C_{1-6}$ alkyl, —OC$(CH_3)_2$, —O—$C_{1-6}$ haloalkyl, —Ophenyl, —Opyridyl, —$CH_2N(CH_3)_2$, —$C(O)NHCH_3$, —$C(O)N(CH_3)_2$, —CN, —$NHCH_3$, —$N(CH_3)_2$, —NHC(O)$CH_3$, or —$SO_2CH_3$; and $R^d$ is —$C_{3-7}$cycloalkyl, —$C_{3-7}$ halocycloalkyl, heterocycloalkyl, aryl, or heteroaryl.

Alternatively, treatment of a compound of formula (XIX) with an amine, in the presence of a base such as DIEA or the like, in a solvent such as DMSO or the like, at a temperature ranging from 60° C. to 110° C., sometimes 90° C., for several hours, provides a 2-substituted methanamine compound of formula (XX). Also, treatment with an amine, or the hydrochloride salt of an amine, in the presence of as base such as $K_3PO_4$ or the like, in a solvent such as DMA or DMF or the like, at a temperature ranging from 50° C. to 120° C., sometimes 80° C., for several hours, also provides a compound of formula (XX). In another embodiment, treatment of 2-(chloromethyl)benzoxazoles of formula (XIX) with an

SCHEME E

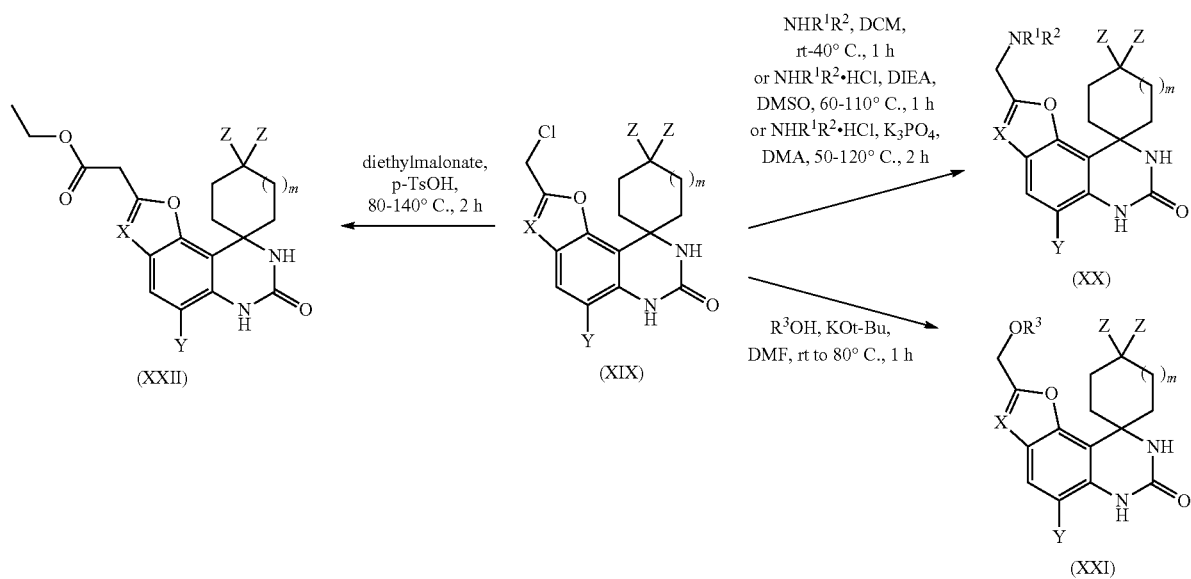

A nucleophilic substitution reaction of compounds of formula (XIX), in the presence of an amine or an alcohol, using conditions known to one of skill in the art, provides 2-substituted methanamine compounds of formula (XX) or substituted ether compounds of formula (XXI), respectively. For instance, treatment of 2-(chloromethyl)benzoxazoles of alcohol, in the presence of a base, such as potassium tert-butoxide or the like, in a solvent such as DMF or DMA, at a temperature ranging from room temperature to 80° C., provides compounds of formula (XXI), where X is —C or —N, Y is —H, —F, —Cl, —Br, or —$C_{1-4}$alkyl, Z is —H, —F, or —$C_{1-4}$alkyl, $R^3$ is —H, —$C_{1-6}$ alkyl, —CH$_2$CH$_2$OCH$_3$, —CH$_2$C(O)N(CH$_3$)$_2$, tetrahydropyranyl, or piperidinyl, and m is 0, 1 or 2.

Similarly, a nucleophilic substitution reaction of compounds of formula (XIX), in the presence of a diester, such as diethylmalonate, under conditions known to one of skill in the art, provides analogs of formula (XXII). For example, treatment of compounds of formula (XIX) with diethylmalonate, in the presence of an acid, such as p-toluenesulfonic acid, at a temperature ranging from 80° C. to 140° C., sometimes 120° C., provides an ethyl ester of formula (XXII), where X is —C or —N, Y is —H, —F, —Cl, —Br, or —C$_{1-4}$alkyl, Z is —H, —F, or —C$_{1-4}$alkyl and m is 0, 1 or 2.

cloalkyl, —C$_{3-7}$cycloalkyl, —CH$_2$-alkenyl, —CH$_2$-alkynyl, —CH$_2$C$_{3-7}$cycloalkyl, —CH$_2$C(O)C(CH$_3$)$_3$, —CH$_2$C(O)C$_{1-6}$alkyl, —CH$_2$C(O)heterocycloalkyl, —CH$_2$C(O)OC$_{1-6}$alkyl, —CH$_2$C(O)N(C$_{1-4}$alkyl)$_2$, —CH$_2$CH(OH)C$_{3-7}$cycloalkyl, —C(CH$_3$)$_2$OH, —C(CH$_3$)$_2$CH$_2$OCH$_3$, —CH(CH$_3$)C(O)N(C$_{1-4}$alkyl)$_2$, —CH$_2$CF$_2$C$_{3-7}$cycloalkyl, —CH$_2$CH$_2$—R$^c$, or —(CH$_2$)R$^d$, or both R$^4$ and R$^5$ together form a monocyclic, bicyclic or tricyclic ring; n is 0, 1, 2 or 3; R$^c$ is —C$_{2-6}$ alkynyl, —C$_{3-7}$cycloalkyl, —OH, —O—C$_{1-6}$alkyl, —OC(CH$_3$)$_2$, —O—C$_{1-6}$haloalkyl, —Ophenyl, —Opyridyl, —CH$_2$N(CH$_3$)$_2$, —C(O)NHCH$_3$, —C(O)N(CH$_3$)$_2$, —CN, —NHCH$_3$, —N(CH$_3$)$_2$, —NHC(O)CH$_3$, or

SCHEME F

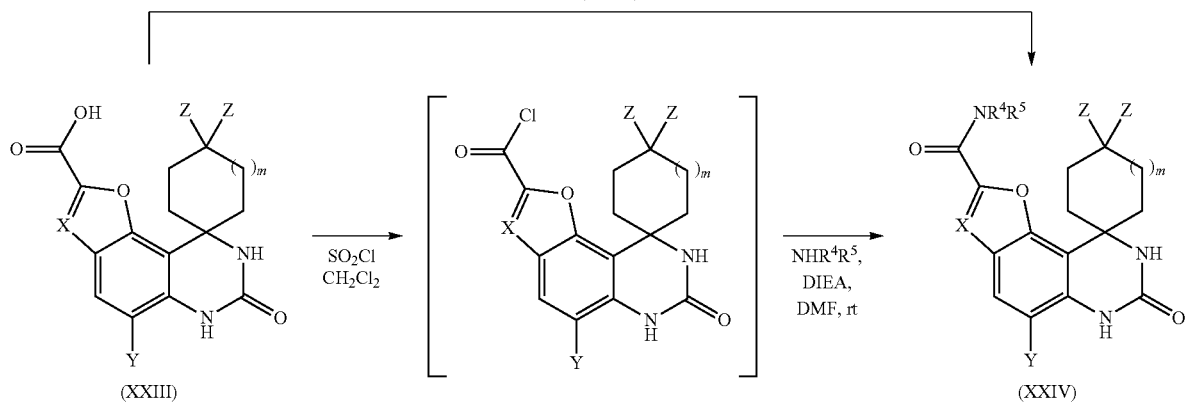

Treatment of carboxylic acids of formula (XXIII) with an amine in an amide coupling reaction, in the presence of a base, using conditions known to one skilled in the art, provides an amide of formula (XXIV). For instance, treatment of compounds of formula (XXIII) with an amine, and a coupling reagent, such as 1-[bis(dimethylamino)methylene]-1H-1,2,3-triazolo[4,5-b]pyridinium 3-oxide hexafluorophosphate or the like, in the presence of a base, such as N,N-diisopropylethyl amine or the like, in a solvent such as DMF or DMA, provides analogs of formula (XXIV), where X is —C or —N, Y is —H, —F, —Cl, —Br, or —C$_{1-4}$alkyl, Z is —H, —F, or —C$_{1-4}$alkyl, m is 0, 1 or 2, and R$^4$ and R$^5$ are independently —H, —C$_{1-6}$alkyl, —C$_{1-6}$alkyl-OH, —C$_{1-6}$haloalkyl, —C$_{1-6}$ haloalkylOH, —C$_{1-6}$ haloalkyl-C$_{3-7}$cycloalkyl, —C$_{3-7}$cycloalkyl, heterocycloalkyl, aryl, or heteroaryl.

Alternatively, conversion of carboxylic acid compounds of formula (XXIII) into an acid chloride, under conditions known to one skilled in the art, followed by treatment with an amine, provides an amide of formula (XXIV). For example, treatment of compounds of formula (XXIII) with a chlorinating reagent such as thionyl chloride or oxalyl chloride or the like, neat or in a solvent such as dichloromethane or the like, provides the acyl chloride intermediate. Subsequent addition of an amine, in the presence of a base such as DIEA or the like, in a solvent such as DMF or DMA or the like provides an amide of formula (XXIV).

SCHEME G

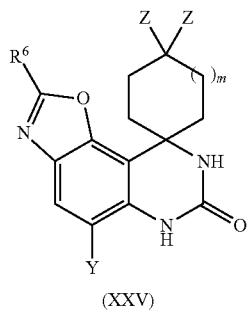

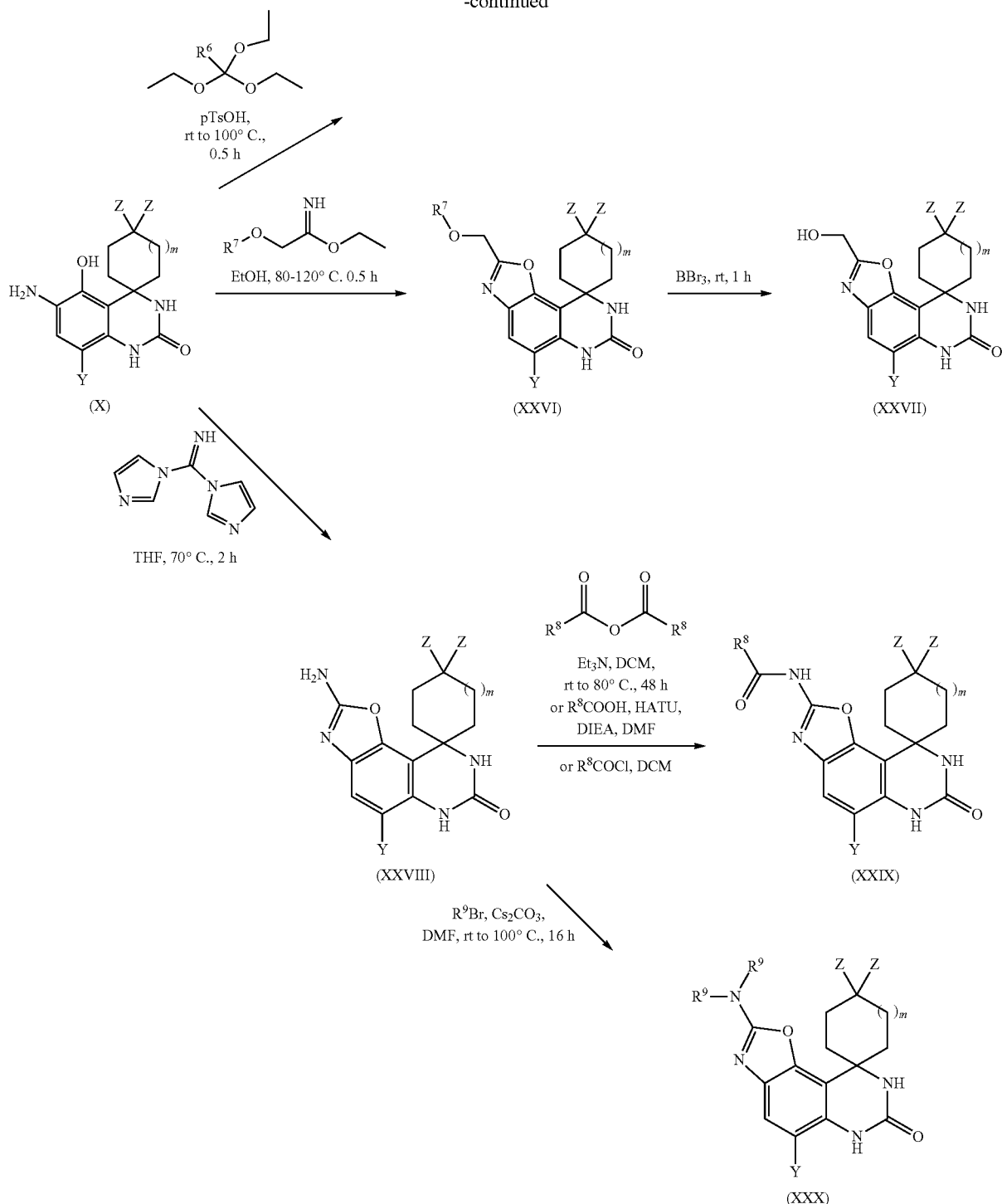

Multiple benzoxazoles, with varying substitution on the 2-position of the benzoxazole, are synthetically accessible from aminophenol compounds of formula (X), according to Scheme G. In one embodiment, a compound of formula (XXV), where $R^6$ is —H, —$C_{1-6}$ alkyl, —$C_{3-7}$cycloalkyl, or —$C_{1-6}$ alkyl-O—$C_{1-6}$ alkyl, all optionally substituted, can be synthesized by treating a compound of formula (X) with the corresponding trimethoxyalkane. For example, treatment of a compound of formula (X) with 1,1,1-trimethoxypropane, in the presence of an acid, such as p-toluenesulfonic acid, with or without a solvent such as THF, or the like, at a temperature ranging from rt to 100° C., provides a compound of formula (XXV) where $R^6$ is -ethyl, Y is —H, —F, —$C_1$, —Br, or —$C_{1-4}$alkyl, Z is —H, —F, or —$C_{1-4}$alkyl and m is 0, 1 or 2. In a similar manner, treatment of a compound of formula (X) with 1,1,1-triethoxy-3-methoxy-propane, in the presence of an acid, such as p-toluenesulfonic acid, with or without a solvent, at rt, provides a compound of formula (XXV) where $R^6$ is —$CH_2CH_2OCH_3$, Y is —H, —F, —Cl, —Br, or —$C_{1-4}$alkyl, Z is —H, —F, or —$C_{1-4}$alkyl and m is 0, 1 or 2. Other analogs of formula (XXV), where $R^6$ is —H, -alkyl, —$C_{3-7}$cycloalkyl, or -6alkyl-O—$C_{1-6}$ alkyl, can be synthesized in a similar manner, using the appropriate starting material substitutions.

In another embodiment, ethers of formula (XXVI) are prepared in one-step from compounds of formula (X). Treatment of an aminophenol compound of formula (X) with an ethyl 2-alkoxyacetimidate, in a solvent, such as ethanol, at a temperature ranging from 80° C. to 120° C., sometimes 110° C., provides analogs of formula (XXVI), where $R^7$ is -alkyl or —$C_{3-7}$cycloalkyl, Y is —H, —Cl, —Br, or —$CH_3$, Z is —H, —F, or —$CH_3$, and m is 0, 1 or 2. For example, treatment of the aminophenol with ethyl 2-methoxyacetimidate, in ethanol, affords an analog of formula (XXVI) where $R^7$ is methyl. Further, cleavage of the methyl ether of formula (XXVI) provides a methyl alcohol of formula (XXVII). For example, treatment of a methyl ether compound of formula (XXVI) with boron tribromide provides the alcohol of formula (XXVII), where Y is —H, —F, —Cl, —Br, or —$C_{1-4}$alkyl, Z is —H, —F, or —$C_{1-4}$alkyl and m is 0, 1 or 2.

2-aminobenzoxazole compounds of formula (XXVIII) are synthetically accessible from an amino phenol compound using conditions known to those skilled in the art. Treatment of aminophenol compounds of formula (X) with (1H-imidazol-1-yl)(1H-pyrazol-1-yl)methanimine provides an aminobenzoxazole of formula (XXVIII), where Y is —H, —Cl, —Br, or —$CH_3$, Z is —H, —F, or —$CH_3$, and m is 0, 1 or 2. Acylation of the aminobenzoxazole analog can be accomplished by reaction with an anhydride, carboxylic acid or acid chloride, using conditions known to one skilled in the art. For example, treatment of an aminobenzoxazole compound of formula (XXVIII) with acetic anhydride, in a solvent such as dichloromethane or the like, in the presence of a base such as trimethylamine or the like, at a temperature ranging from room temperature to 80° C., preferably 80° C., provides a compound of formula (XXIX) where $R^8$ is methyl and Y is —H, —F, —Cl, —Br, or —$C_{1-4}$alkyl, Z is —H, —F, or —$C_{1-4}$alkyl and m is 0, 1 or 2. Additional analogs of formula (XXIX), where $R^8$ is —$C_{1-6}$alkyl or —$C_{3-8}$cycloalkyl can be synthesized using the appropriate starting material substitutions. Similarly, treatment of compounds of formula (XXVIII) with a carboxylic acid, under conditions known to one skilled in the art, in the presence of a coupling reagent, such as HATU or the like, and a base, such as DIEA or the like, in an appropriate solvent, such as DMF or DMA, also provides compounds of formula (XXIX). Additionally, treatment of an aminobenzoxazole of formula (XXVIII) with an acid chloride, under conditions known to one skilled in the art, in the presence of a base, in a solvent such as DCM, also provides a compound of formula (XXIX).

Further, aminobenzoxazole compounds of formula (XXVIII) can be alkylated, using conditions known to one skilled in the art. Treatment with an alkyl halide, such as an alkyl bromide or alkyl chloride, under basic conditions, in a solvent such as DMF, DMA or the like, at a temperature ranging from room temperature to 100° C., sometimes 60° C., provides a monoalkylated or bisalkylated compound. For example, treatment with an alkyl bromide, in the presence of a base such as cesium carbonate, potassium carbonate or the like, in DMF, at 100° C. provides compounds of formula (XXX), where $R^9$ is independently —H, —$C_{3-7}$cycloalkyl, or —$C_{1-6}$alkyl-O—$C_{1-6}$alkyl, Y is —H, —F, —Cl, —Br, or —$C_{1-4}$alkyl, Z is —H, —F, or —$C_{1-4}$alkyl and m is 0, 1 or 2.

SCHEME H

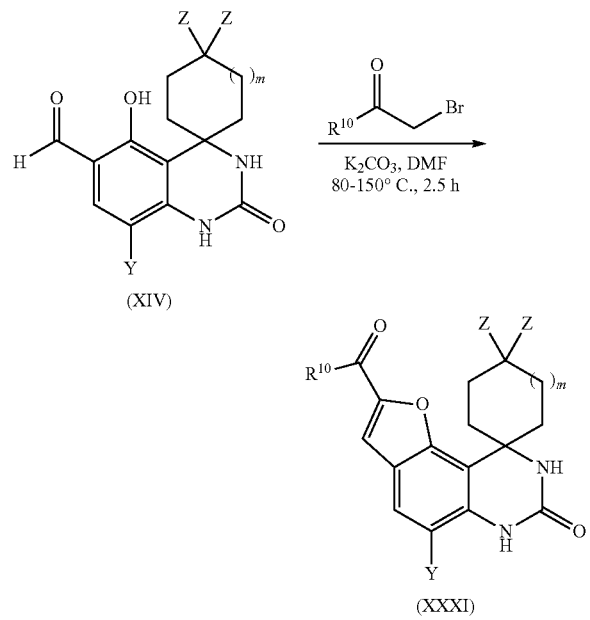

According to Scheme H, compounds of formula (XIV) can be converted to a 2-substituted benzofuran of formula (XXXI), where $R^{19}$ is an aryl or heteroaryl ring, by O-alkylation followed by subsequent cyclization to form the furan ring. Treatment of the aldehyde of formula (XIV) with a substituted bromoacetate, under conditions known to one of skill in the art, in the presence of a base, such as $K_2CO_3$ or $Cs_2CO_3$ or the like, in a solvent such as DMF or DMA or the like, at a temperature ranging from 80° C. to 150° C., sometimes 135° C., for a time period of several hours, provides a benzofuran of formula (XXXI), where $R^{19}$ is an aryl or heteroaryl ring, Y is —H, —F, —Cl, —Br, or —$C_{1-4}$alkyl, Z is —H, —F, or —$C_{1-4}$alkyl and m is 0, 1 or 2.

EXAMPLES

Chemistry:

In obtaining the compounds described in the examples below, and the corresponding analytical data, the following experimental and analytical protocols were followed, unless otherwise indicated.

Unless otherwise stated, reaction mixtures were magnetically stirred at room temperature (rt) under nitrogen atmosphere. Where solutions were "dried," they were generally dried over a drying agent such as $Na_2SO_4$ or $MgSO_4$. Where mixtures, solutions, and extracts were "concentrated," they were typically concentrated on a rotary evaporator under reduced pressure.

Reactions under microwave irradiation conditions were carried out in a CEM Discover-SP with Activent microwave reaction apparatus, model number 909150, or Biotage Initiator, model number 355302.

Normal-phase flash column chromatography (FCC) was performed on Silica ($SiO_2$) using packed or prepackaged cartridges, eluting with the indicated solvents.

The mass spectra (m/z) were recorded using either electrospray ionization (ESI) or atmospheric pressure chemical ionization (APCI). LC/MS were obtained on a Waters 2695 Separations Unit, 2487 Dual Absorbance Detector, Micromass ZQ fitted with ESI Probe, or a Waters Acquity™ Ultra performance LC (UPLC) with PDA eλ and SQ detectors.

Analytical LC-MS was performed on a Waters Acquity UPLC-MS instrument equipped with a Acquity UPLC BEH C18 column (1.7 µm, 2.1×50 mm) and the solvent system A: 0.1% HCOOH in $H_2O$ and B: 0.1% HCOOH in ACN. Column temperature was 45° C. All compounds were run using the same elution gradient, i.e., 5% to 95% solvent B in 0.75 min with a flow rate of 1 mL/min.

Analytical SFC-MS was performed on a Waters $UPC^2$-MS instrument equipped with a Acquity $UPC^2$BEH 2-ethylpyridine column (1.7 µm, 2.1×50 mm) and the solvent system A: $CO_2$ and B: 0.1% $NH_4OH$ in MeOH. Column temperature was 55° C. All compound were run using the same elution gradient, i.e., 3% to 35% solvent B in 0.75 min with a flow rate of 2.5 mL/min.

Preparative HPLC was performed on a Shimadzu SIL-10AP system using a Waters SunFire™ OBD (5 lam, 30×100 mm) C18 column with a 15-minute gradient of 10-100% acetonitrile in water and 0.05% trifluoroacetic acid added as a modifier to both phases. Elution profiles were monitored by UV at 254 and 220 nm.

Some compounds were purified using a Waters Fractionlynx system equipped with a XBridge Prep C18 OBD column (5 µm, 19×50 mm) and the solvent system: $H_2O$: AcCN and 2% TFA in $H_2O$. Specific elution gradients were based on retention times obtained with an analytical UPLC-MS, however, in general all elution gradients of $H_2O$ and ACN were run over a 5.9 min run time with a flow rate of 40 mL/min. An autoblend method was used to ensure a concentration of 0.1% TFA throughout each run.

Some compounds were purified using a Waters Fractionlynx system equipped with a XBridge Prep C18 OBD column (5 µm, 30×100 mm) and the solvent system: $H_2O$: AcCN and 2% TFA in $H_2O$. Specific elution gradients were based on retention times obtained with an analytical UPLC-MS, however, in general all elution gradients of $H_2O$ and ACN were run over a 9 min run time with a flow rate of 60 mL/min. An autoblend method was used to ensure a concentration of 0.1% TFA throughout each run.

Preparative SFC-MS was performed using a Waters Prep100 SFC-MS system equipped with a Viridis 2-ethylpyridine OBD column (5 µm, 30×100 mm) and the solvent system: $CO_2$:MeOH with 0.2% $NH_4OH$ in MeOH as a co-solvent. Specific elution gradients were based on retention times obtained with an analytical $UPC^2$-MS, however, in general all elution gradients of $CO_2$ and MeOH were run over a 3.6 min run time with a flow rate of 100 mL/min and a column temperature of 55° C. An autoblend method was used to ensure a concentration of 0.2% $NH_4OH$ throughout each run.

Nuclear magnetic resonance (NMR) spectra were obtained in a Varian 400 MHz or Bruker 400 MHz NMR. Samples were analyzed in either deuterated acetone ($(CD_3)_2CO$), chloroform ($CDCl_3$), methanol-$d_4$ ($CD_3OD$), or dimethyl sulfoxide-$d_6$ (DMSO-d6). For $CDCl_3$ samples, the residual central resonance peak at 7.26 for $^1H$ was used for chemical shift assignment for $^1H$ NMR spectra. For $CD_3OD$ the residual central resonance peak at 3.31 for $^1H$ was used for chemical shift assignment and for DMSO-d6 the residual central resonance peak at 2.50 ppm for $^1H$ was used for chemical shift assignment. The format of the $^1H$ NMR data below is: chemical shift in ppm downfield the tetramethylsilane reference (multiplicity, coupling constant J in Hz, integration, using conventional abbreviations for designation of major peaks: e.g. s, singlet; d, doublet; t, triplet; q, quartet; p, pentet; m, multiplet; br, broad.

Chemical names were generated using ChemDraw Ultra 12.0 (CambridgeSoft Corp., Cambridge, Mass.), ChemDraw Professional 15.1 (CambridgeSoft Corp., Cambridge, Mass.) or ChemAxon.

Intermediate 1. 8'-Chloro-5'-hydroxy-6'-nitro-1'H-spiro[cyclohexane-1,4'-quinazolin]-2'(3'H)-one

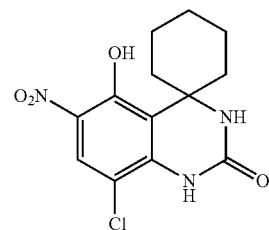 [SMILES: O=C1Nc2c(Cl)cc([N+](=O)[O-])c(O)c2C2(CCCCC2)N1]

Step 1. (2-chloro-5-methoxy-phenyl) urea. A solution of potassium cyanate (124 g, 1.52 mol) in water (850 mL) was added over 2 h to a solution of 2-chloro-5-methoxy-aniline (200 g, 1.27 mol) in water (100 mL) and AcOH (800 mL) at 30° C. The reaction mixture was stirred for 1 h at 40° C., and then cooled to rt. The suspension was filtered using a medium frit and rinsed with water. The resulting solid was dried in a vacuum oven at 60° C. for 48 h to provide the title compound (240 g, 95%) as a solid. $^1H$ NMR (400 MHz, DMSO) δ 8.00 (s, 1H), 7.85 (d, J=3.0 Hz, 1H), 7.27 (d, J=8.8 Hz, 1H), 6.54 (dd, J=8.8, 3.0 Hz, 1H), 6.42 (s, 2H), 3.71 (s, 3H). [M+H]=201.1.

Step 2. 8-chloro-5-methoxy-spiro[1,3-dihydroquinazoline-4,1'-cyclohexane]-2-one. A solution of (2-chloro-5-methoxy-phenyl) urea (155 g, 125 mmol) in Eaton's reagent (2.0 L; 7% w/w solution of $P_2O_5$ in methanesulfonic acid) was heated at 60° C. Cyclohexanone (160 mL, 155 mmol) was added dropwise over 1 h and the reaction mixture was heated to 80° C. for 2 h. The solution was then cooled to rt and the mixture was added dropwise to cold water (2.0 L) over 2 h. The suspension was filtered and the aqueous layer was extracted with DCM (2×1.0 L). The solid was dissolved in DCM (1.0 L) and the combined organic layers were dried over $MgSO_4$, filtered and evaporated under reduced pressure. To the material, 2-propanol (1.5 L) was added and the suspension was stirred for 2 h at 0° C. The resulting solid was collected by filtration, washed with cold 2-propanol (2×150 mL), and then dried for 18 h in a vacuum oven at 50° C. to afford the title compound (158 g, 73%) as a solid. $^1H$ NMR (400 MHz, DMSO) δ 7.96 (d, J=1.0 Hz, 1H), 7.28 (d, J=8.9 Hz, 1H), 7.02 (s, 1H), 6.66 (d, J=9.0 Hz, 1H), 3.80 (s, 3H), 2.42 (td, J=13.5, 4.5 Hz, 2H), 1.80 (qt, J=13.6, 3.4 Hz, 2H), 1.60 (t, J=15.8 Hz, 3H), 1.47 (d, J=13.5 Hz, 2H), 1.19 (qt, J=13.1, 3.6 Hz, 1H). [M+H]=281.2.

Step 3. 8-chloro-5-hydroxy-spiro[1,3-dihydroquinazoline-4,1'-cyclohexane]-2-one. 8-chloro-5-methoxy-spiro[1,3-dihydroquinazoline-4,1'-cyclohexane]-2-one (153 g, 545 mmol) was added to a mixture of hydrobromic acid (48%, 1.2 L) and glacial AcOH (1.5 L) at rt. The reaction mixture was heated to reflux and stirred for 94 h. The reaction mixture was cooled to 100° C. and water (1.2 L) was added dropwise over 2 h. The stirred reaction mixture was cooled in a cold water bath then in an ice bath to −5° C. The resulting solid was filtered, washed with cold water (2×200 mL), air-dried for 2 h (~149 g) and then dried for 18 h in a vacuum oven at 40° C. to afford the acetic acid solvate (~130 g). To the material, acetone (320 mL) was added and the suspension was stirred for 5 h (mechanical stirrer). The solid was filtered, washed with cold acetone (120 mL) and then dried for 18 h in a vacuum oven at 60° C. to afford the title compound (105 g, 72%). ¹H NMR (400 MHz, DMSO) δ 9.96 (s, 1H), 7.77 (s, 1H), 7.07 (d, J=8.7 Hz, 1H), 6.96 (s, 1H), 6.43 (d, J=8.8 Hz, 1H), 2.60-2.51 (m, 2H), 1.84-1.71 (m, 2H), 1.60 (d, J=12.8 Hz, 1H), 1.54 (d, J=12.6 Hz, 2H), 1.46 (d, J=13.6 Hz, 2H), 1.23-1.11 (m, 1H). [M+H]=267.1.

Step 4. 8'-chloro-5'-hydroxy-6'-nitro-1'H-spiro[cyclohexane-1,4'-quinazolin]-2'(3'H)-one. Nitric acid (70%, 9.23 mL, 155 mmol) was added dropwise over 60 min to a suspension of 8-chloro-5-hydroxyspiro[benzo[d][1,3] oxazine-4,1'-cyclohexan]-2(1H)-one (32.0 g, 119 mmol) in TFA (350 mL) at 0° C. During the addition, the temperature was maintained between 0° C. and 4° C. The mixture was warmed to 10° C. over 30 min, then cooled to 0° C. The mixture was slowly poured into ice water (2000 mL) and the suspension was filtered. The solid was rinsed with water and dried in a vacuum oven at 50° C. for 48 h to provide the title compound (33.2 g, 88%). ¹H NMR (400 MHz, CDCl₃) δ 11.75 (s, 1H), 8.19 (s, 1H), 7.59 (br, 1H), 2.52 (td, J=13.9, 4.7 Hz, 2H), 2.06-1.99 (m, 2H), 1.99-1.87 (m, 2H), 1.85-1.77 (m, 1H), 1.71-1.61 (m, 2H), 1.38 (tdd, J=16.9, 10.3, 6.6 Hz, 1H). [M+H₂O]=330.1.

Alternate Route:

Step 1. 1-(2-chloro-5-methoxyphenyl)urea. Deionized water (7 L, 7V), 2-chloro-5-methoxyaniline hydrogen chloride (1000 g, 5.15 mol) and acetic acid (4 L, 4V) were added to a dry 20 L glass vessel under nitrogen. The mixture was warmed to 30° C. until the raw materials were completely dissolved. A solution of potassium cyanate (627 g, 7.73 mol) in water (2 L, 2V) was slowly added dropwise to the vessel over 2 h at a rate sufficient to keep the reaction temperature below 35° C. After addition, the internal temperature was slowly increased to 38-40° C. and the resulting mixture was then heated at 40° C. for 1 h. The HPLC assay showed that approximately 2.4% of the starting material remained. The reaction mixture was slowly cooled to below 20° C. and stirring was continued for 1 h, then the resulting solid was collected by filtration and dried at 55° C. under vacuum over the weekend. The title compound was obtained as white solid powder (943 g, 91%). ¹H NMR (400 MHz, DMSO) δ 8.00 (s, 1H), 7.85 (d, J=3.0 Hz, 1H), 7.27 (d, J=8.8 Hz, 1H), 6.54 (dd, J=8.8, 3.0 Hz, 1H), 6.42 (s, 2H), 3.71 (s, 3H). [M+H]=201.1.

Step 2. 8'-chloro-5'-methoxy-6'-nitro-1'H-spiro[cyclohexane-1,4'-quinazolin]-2'(3'H)-one. 1-(2-chloro-5-methoxyphenyl)urea (943 g) was taken up in Eaton's reagent (12.7 L, 7.00% w/w) and heated to an internal temperature of 70° C. over 1 hour. Cyclohexanone (691 g, 7.04 mol) was then added dropwise via a dropping funnel over ~1 hr. while keeping the internal temperature between 68-72° C., then the reaction was heated at 70° C. overnight. HPLC analysis showed complete conversion to the non-isolated intermediate 8'-chloro-5'-methoxy-FH-spiro[cyclohexane-1,4'-quinazolin]-2'(3'H)-one. The reaction was cooled to 0-5° C. over 1.5 hour. Nitric acid (1013.2 g, 16.08 mol) was then charged into the addition funnel and nitric acid was carefully added dropwise while keeping the internal temperature below 10° C. The reaction mixture was natural slowly warmed to 20° C. and stirred overnight. The HPLC analysis showed complete conversion to the title compound. Deionized water (17 L) was then added dropwise by using a dropping funnel and the internal temperature was maintained at 20° C. and stirred overnight. The product was isolated by filtration and the solid was charged into the reactor and re-slurried in water (10 V) for 3 hours. The reaction mixture was filtered and the resulting solid that was collected by filtration was dried at 45° C. under vacuum over the weekend to afford the title compound as a brown powder (1654 g). ¹H NMR (400 MHz, DMSO-d6) δ 8.95 (s, 1H), 8.12-7.99 (m, 1H), 7.30 (s, 1H), 3.76 (s, 3H), 2.28-2.16 (m, 2H), 1.88-1.75 (m, 4H), 1.65 (d, J=12.0 Hz, 1H), 1.52 (d, J=13.7 Hz, 2H), 1.30-1.17 (m, 1H). [M+H]=326.2.

Step 3. 8'-chloro-5'-hydroxy-6'-nitro-1'H-spiro[cyclohexane-1,4'-quinazolin]-2'(3'H)-one. Dimethyl acetamide (7.5 L, 4.5 V) and 8'-chloro-5'-methoxy-6'-nitro-1'H-spiro [cyclohexane-1,4'-quinazolin]-2'(3'H)-one (1654 g, 5.07 mol) were added to a dry 30 L glass vessel under nitrogen, then lithium chloride (646 g, 15.23 mol) was added. The reaction mixture was heated to an internal temperature of 70° C. over 1 hour, then stirred at that temperature overnight. The reaction was determined to be complete by HPLC and was cooled to 25° C., filtered and then water (13 L, 8 V) was added dropwise using a dropping funnel to maintain the internal temperature at 10° C. After addition was complete, the reaction was stirred overnight. Brine (1.5 L) was charged into the reaction mixture with stirring to assist in product precipitation and the mixture was stirred at 10° C. overnight. The reaction mixture was filtered and washed with water and the solid then re-charged directly into the reactor and re-slurried in ethanol (1 V) and acetic acid (2 V) at 20° C. for 1 hour. The suspension was filtered and washed with ethanol, resulting in a yellow solid that was dried in a vacuum oven at 50° C. overnight to afford 1280 g (80% yield, 94.0% purity by UPLC) of the product. The solid was pulverized into a powder and re-slurried in ethanol (3 V) at 20° C. for 8 hours. The mixture was filtered and washed with ethanol to give a brown solid that was dried under vacuum overnight (8-10 h) at 50° C. to provide the title compound as a yellowish-brown powder (1060 g). ¹H NMR (400 MHz, DMSO-d6) δ 11.95 (br s, 1H), 11.47 (br s, 1H), 8.96 (s, 1H), 8.11 (s, 1H), 7.44 (s, 1H), 2.60 (dt, J=4.5, 13.5 Hz, 2H), 1.90-1.78 (m, 2H), 1.66 (d, J=12.2 Hz, 3H), 1.50 (d, J=13.4 Hz, 2H), 1.27-1.15 (m, 1H). [M+H]=312.2.

Intermediate 2. 6'-Amino-8'-chloro-5'-hydroxy-1'H-spiro[cyclohexane-1,4'-quinazolin]-2'(3'H)-one

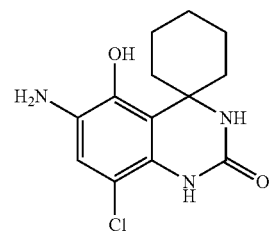

6'-amino-8'-chloro-5'-hydroxy-1'H-spiro[cyclohexane-1, 4'-quinazolin]-2'(3'H)-one. To a suspension of 8-chloro-5-hydroxy-6-nitrospiro[benzo[d][1,3]oxazine-4,1'-cyclohexan]-2(1H)-one (35.0 g, 0.112 mol) and NH₄Cl (59.9 g, 1.10 mol) in acetone (1.0 L) and water (222 mL) was added zinc dust (36.6 g, 0.560 mol) over a period of 30 min while the internal temperature was maintained between 20° C. and 25° C. using an ice-water bath. The suspension was stirred for 10 min at rt and filtered over a pad of celite. The filtrate was concentrated under reduced pressure to ~250 mL and EtOAc (500 mL) was added to the residue. The layers were separated and the aqueous layer was extracted with EtOAc (×2). The combined organic layers were washed with brine, dried over Na$_2$SO$_4$ and concentrated under reduced pressure to provide the title compound (18.3 g, 58%). $^1$H NMR (400 MHz, DMSO-d6) δ 9.02 (s, 1H), 6.66 (s, 1H), 5.92 (br, 2H), 2.42 (td, J=13.8, 4.6 Hz, 2H), 1.82 (d, J=13.5 Hz, 2H), 1.76-1.64 (m, 4H), 1.59-1.51 (m, 2H), 1.33-1.21 (m, 1H). [M+H]=283.2.

Alternate Route:

6'-amino-8'-chloro-5'-hydroxy-1'H-spiro[cyclohexane-1, 4'-quinazolin]-2'(3'H)-one hemi sulfate. In a 2-L 3-neck round bottom flask with a stir bar, J-KEM internal temperature probe, N$_2$ inlet and septum, 8'-chloro-5'-hydroxy-6'-nitro-2',3'-dihydro-1'H-spiro[cyclohexane-1,4'-quinazoline]-2'-one (40 g, 128 mmol) was taken up in tetrahydrofuran (1.20 L) and water (20 mL), then platinum (IV) oxide (583 mg, 2.57 mmol) was added, then the vessel was evacuated and backfilled with N$_2$ (×3). Then the reaction was charged with a hydrogen balloon (1 atm) and stirred vigorously at rt. The reaction was a yellow-brown suspension that slowly turned to a dark green thin suspension-solution. The temperature rose only slightly after H$_2$ was added, as the internal temperature was still <20° C. After stirring overnight, LCMS analysis showed ~80% conversion to the desired product (UV 254 nm). The reaction vessel was evacuated and re-charged with a fresh H$_2$ balloon and allowed to stir. After 5 h, LCMS analysis showed ~90% conversion. Another H$_2$ balloon was added and the reaction was stirred at rt overnight. Then, the amber-colored suspension was analyzed by LCMS to show >98% conversion (UV+ELSD) to the desired product. The reaction mixture was then diluted with DMSO (200 mL), filtered through a tightly packed pad of celite, and rinsed with EtOH (7.5 V, 300 mL). The dark purple filtrate was transferred to 3-L round bottom flask under N$_2$, rinsed with EtOH and charged with sulfuric acid (7.52 mL, 141 mmol). Within minutes, a light-colored solid formed. Another portion of EtOH (2.5 V, 100 mL) was added and the suspension was rapidly stirred at rt for several hours, then cooled in an ice-water bath. The solid was collected by filtration and washed with ethanol (2×400 mL) to give a white solid. The solid was dried in a vacuum oven (35° C.) overnight, to afford the hemi sulfate salt of the title compound as an off-white powder (34.1 g, 78%). $^1$H NMR (400 MHz, DMSO-d6) δ 7.82 (s, 1H), 6.93 (s, 1H), 6.87 (s, 1H), 2.61-2.53 (m, 3H), 1.79 (q, J=13.6 Hz, 2H), 1.67-1.54 (m, 3H), 1.48 (d, J=13.0 Hz, 2H), 1.21 (q, J=13.1 Hz, 1H). [M+H]=282.3.

Intermediate 3. Methyl 5'-chloro-7'-oxo-7',8'-dihydro-6'H-spiro[cyclohexane-1,9'-oxazolo[5,4-f]quinazoline]-2'-carboxylate

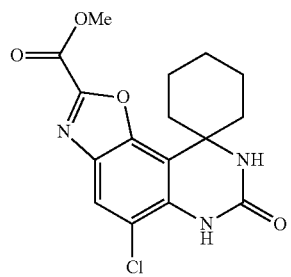 [SMILES: COC(=O)c1nc2cc(Cl)c3c(c2o1)C1(CCCCC1)NC(=O)N3]

To a solution of 6-amino-8-chloro-5-hydroxyspiro[benzo [d][1,3]oxazine-4,1'-cyclohexan]-2(1H)-one (Intermediate 1, 11.0 g, 38.9 mmol) in AcOH (800 mL) at rt was added methyl 2,2,2-trichloroacetimidate (5.06 mL, 40.9 mmol), dropwise. The reaction mixture was stirred for 2 h, then water (1.0 L) was added. The resulting solid was filtered, rinsed with water (400 mL) and dried under reduced pressure. The material was taken up in MeOH (1.1 L) and K$_2$CO$_3$ (6.45 g, 46.7 mmol) was added at rt. The mixture was heated to 52° C., stirred for 2 h, and then cooled to rt. The solvent was concentrated under reduced pressure to a volume of ~300 mL. Water (700 mL) was added and the aqueous layer was extracted with DCM (3×400 mL). The combined organic layers were washed with brine, dried over Na$_2$SO$_4$, filtered and concentrated under reduced pressure. The material was purified by flash chromatography (silica gel, 100% DCM (2% AcOH) to 7% EtOAc in DCM (2% AcOH)). The organic solvent containing product was then triturated into a mixture of ether/hexanes (100 mL/600 mL) and the resulting solid was filtered, rinsed with hexane and dried under reduced pressure to provide the title compound (Intermediate 3 and Example 1, 2.70 g, 20%). $^1$H NMR (400 MHz, CDCl$_3$) δ 7.85 (s, 1H), 7.61 (br, 1H), 4.10 (s, 3H), 2.23 (dd, J=9.2, 3.6 Hz, 3H), 2.03-1.93 (m, 2H), 1.89-1.82 (m, 1H), 1.77-1.70 (m, 2H), 1.51-1.41 (m, 2H). [M+H]=351.2.

Intermediate 4. 5'-Chloro-7'-oxo-7',8'-dihydro-6'H-spiro[cyclohexane-1,9'-oxazolo[5,4-f]quinazoline]-2'-carboxylic acid

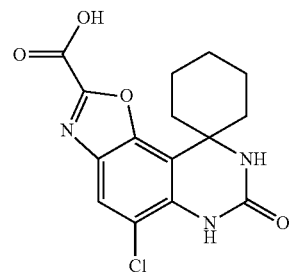 [SMILES: O=C1Nc2c(Cl)cc3nc(C(=O)O)oc3c2C2(CCCCC2)N1]

LiOH (581 mg, 6.93 mmol) was added to a mixture of methyl 5'-chloro-7'-oxo-7',8'-dihydro-6'H-spiro[cyclohexane-1,9'-oxazolo[5,4-f]quinazoline]-2'-carboxylate (Intermediate 3, 2.43 g, 6.93 mmol) in THF (71 mL) and water (18 mL). The mixture was stirred at rt for 15 min, then cooled to 0° C. Water (500 mL) was added and the pH was adjusted to ~3 by adding concentrated HCl. The resulting suspension was filtered, rinsed with water (500 mL) and dried under reduced pressure to provide the title compound (Intermediate 4 and Example 2, 1.80 g, 58% yield corrected at 75% purity) as a solid. $^1$H NMR (400 MHz, DMSO) δ 10.17 (s, 1H), 8.08 (s, 1H), 2.19-2.09 (m, 4H). 1.81-1.63 (m, 5H), 1.41-1.33 (m, 1H).

Intermediate 5. 5'-Chloro-2'-(chloromethyl)-6'H-spiro[cyclohexane-1,9'-oxazolo[5,4-f]quinazolin]-7'(8'H)-one

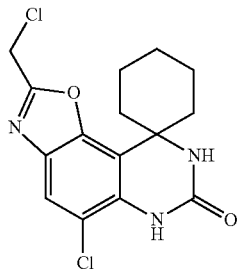

A solution of 6'-amino-8'-chloro-5'-hydroxy-1'H-spiro[cyclohexane-1,4'-quinazolin]-2'(3'H)-one (Intermediate 1, 2.07 g, 7.35 mmol) and ethyl 2-chloroethanecarboximidate (1.39 g, 8.82 mmol) in ethanol (20.7 mL) was stirred at 80° C. for 1 hour, then cooled to room temperature. The reaction mixture was diluted with i-PrOH/DCM (1:3), washed with water and brine, then concentrated to give the title compound as a dark brown solid (2.32 g, 92.8%). $^1$H NMR (400 MHz, DMSO-d6) δ 8.63-8.39 (m, 1H), 7.84 (s, 1H), 7.47-7.38 (m, 1H), 5.07 (s, 2H), 2.25-2.10 (m, 2H), 1.88 (br s, 4H), 1.78-1.67 (m, 1H), 1.63-1.51 (m, 2H), 1.40-1.17 (m, 1H). [M+H]=340.1.

Intermediate 6. 6'-Amino-8'-fluoro-5'-hydroxy-1'H-spiro[cyclohexane-1,4'-quinazolin]-2'(3'H)-one

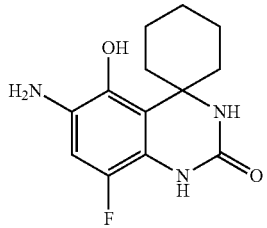

Step 1. 1-(2-Fluoro-5-methoxyphenyl) urea. 2-Fluoro-5-methoxyaniline (2.32 g, 16.4 mmol) was dissolved in acetic acid (11.6 mL) and water (1.16 mL), then a solution of potassium cyanate (1.33 g, 16.4 mmol) in water (1 mL) was added dropwise and the mixture was stirred at rt for 3 h. The reaction mixture was filtered, the filter cake was washed with water and ether and was dried under vacuum to give the title compound as an off-white solid. [M+H]=185.1.

Step 2. 8'-Fluoro-5'-methoxy-1'H-spiro[cyclohexane-1,4'-quinazolin]-2'(3'H)-one. 1-(2-Fluoro-5-methoxyphenyl)urea (520 mg, 2.82 mmol) was added to Eaton's reagent (11.2 mL, 7.70% w/w, 5.36 mmol), heated to 60° C., then cyclohexanone (585 µL, 5.65 mmol) was added slowly, and the mixture was warmed to 80° C. with stirring, then held at 80° C. for 2 hours. The reaction mixture was then cooled to 0° C., ice-cold water was added and the mixture was extracted with DCM. The combined organics were concentrated to give the crude product as a brown solid. [M+H]=265.0.

Step 3. 8'-Fluoro-5'-hydroxy-1'H-spiro[cyclohexane-1,4'-quinazolin]-2'(3'H)-one. To a suspension of 8'-fluoro-5'-methoxy-1'H-spiro[cyclohexane-1,4'-quinazolin]-2'(3'H)-one (650 mg, 2.46 mmol) in acetic acid (1.50 mL), was slowly added hydrogen bromide (48%, 0.90 mL) and the mixture was stirred at reflux (~145° C.) for 4 days. The reaction was cooled to 100° C. and H$_2$O was added slowly. The mixture was cooled to rt, then to 0° C. in an ice bath. Vacuum filtration provided the title compound as a grey powder, which was washed with H$_2$O, then dried under vacuum overnight. [M+H]=251.0.

Step 4. 8'-Fluoro-5'-hydroxy-6'-nitro-1'H-spiro[cyclohexane-1,4'-quinazolin]-2'(3'H)-one. To a solution of 8'-fluoro-5'-hydroxy-1'H-spiro[cyclohexane-1,4'-quinazolin]-2'(3'H)-one (450 mg, 1.80 mmol) in sulfuric acid (1.80 mL) was added nitric acid (180 µL, 4.05 mmol) dropwise at 0° C. After addition, the reaction was warmed to room temperature and stirred for 1 h then LCMS showed that the reaction had gone to completion. Ice was added to the reaction mixture. After the ice melted, EtOAc was added, and the solid was collected by filtration and washed with EtOAc (249 mg). The filtrate was transferred to a separatory funnel, the two layers were separated and the aqueous layer was extracted with EtOAc (×2). The combined organic layers were washed with brine, dried over MgSO$_4$, concentrated and purified by flash chromatography (0 % to 50% EtOAc/Heptane) to yield the title compound as a yellow solid, which was combined with the previously isolated solid (354 mg, 66.7%). [M+H]=296.0.

Step 5. 6'-Amino-8'-fluoro-5'-hydroxy-1'H-spiro[cyclohexane-1,4'-quinazolin]-2'(3'H)-one. 8'-Fluoro-5'-hydroxy-6'-nitro-1'H-spiro[cyclohexane-1,4'-quinazolin]-2'(3'H)-one (249 mg, 0.84 mmol) was suspended in a mixture of tetrahydrofuran (3.49 mL), water (0.35 mL) and acetic acid (1.49 mL), the solution was cooled to 0° C. then zinc (221 mg, 3.37 mmol) was added. After addition, the reaction mixture was warmed to room temperature and stirred for 2 hours, at which time analysis by LC/MS showed that the reaction had reached completion. The mixture was filtered and the isolated solid was washed with EtOAc. The filtrate was transferred to a separatory funnel and extracted with EtOAc, and then the organic layer was washed with water and brine, dried over MgSO$_4$ and concentrated to give the title compound as a dark brown solid, which was combined with the earlier isolated solid. [M+H]=266.0.

Intermediate 7. 2'-(Chloromethyl)-5'-fluoro-6'H-spiro[cyclohexane-1,9'-oxazolo[5,4-f]quinazolin]-7'(8'H)-one

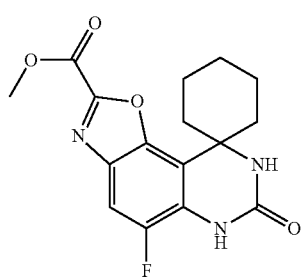 [SMILES: COC(=O)c1nc2cc(F)c3c(c2o1)C1(CCCCC1)NC(=O)N3]

A solution of 6'-amino-8'-fluoro-5'-hydroxy-1'H-spiro[cyclohexane-1,4'-quinazolin]-2'(3'H)-one (Intermediate 5, 150 mg, 0.57 mmol) and ethyl 2-chloroacetimidate (107 mg, 0.68 mmol) in ethanol (1.50 mL) was stirred at 80° C. for 1 hour, then cooled to room temperature. The solvent was evaporated to afford the title compound as a dark brown solid. The crude product was used in subsequent reactions without further purification. [M+4]=324.0

Intermediate 8. 2'-(Chloromethyl)-5'-fluoro-6'H-spiro[cyclohexane-1,9'-oxazolo[5,4-f]quinazolin]-7'(8'H)-one

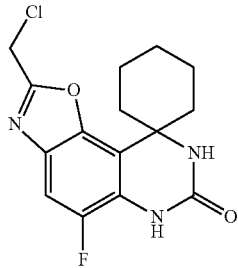

Intermediate 8 was synthesized in a manner analogous to Intermediate 5, with the appropriate starting material substitutions. [M+H]=324.0.

Intermediate 9. 6'-Amino-8'-chloro-4,4-difluoro-5'-hydroxy-1'H-spiro[cyclohexane-1,4'-quinazolin]-2'(3'H)-one

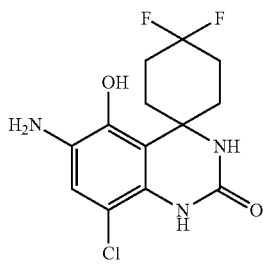

Step 1. 1-(2-chloro-5-hydroxyphenyl) urea. 3-amino-4-chlorophenol (10.0 g, 69.7 mmol) was dissolved in acetic acid (40.0 mL) and water (10.0 mL), a solution of potassium cyanate (6.78 g, 83.6 mmol) in water (40.0 mL) was added dropwise and the mixture was stirred at rt for 3 h. The reaction mixture was filtered then the filter cake was washed with water and a small amount of DCM, and then dried to give the title compound as an off-white solid (8.4 g, 64%). $^1$H NMR (400 MHz, DMSO-d6) δ 9.61 (br s, 1H), 7.88 (s, 1H), 7.73 (d, J=2.7 Hz, 1H), 7.13 (d, J=8.7 Hz, 1H), 6.50-6.28 (m, 3H). [M+H]=187.4.

Step 2. 8'-Chloro-4,4-difluoro-5'-hydroxy-1'H-spiro[cyclohexane-1,4'-quinazolin]-2'(3'H)-one. 1-(2-Chloro-5-hydroxyphenyl) urea (1.74 g, 9.32 mmol) was added to Eaton's reagent (7.7 wt. % diphosphooxidane in methanesulfonic acid, 6.8 mL, 17.7 mmol), the mixture was heated to 60° C., then 4,4-difluorocyclohexanone (2.50 g, 18.6 mmol) was added slowly, and the mixture was stirred at this temperature for 1 hour until the reaction had reached completion as measured by LC/MS. The reaction mixture was then cooled to 0° C., ice was added and the mixture was extracted with DCM. The combined organics were concentrated to give the crude mixture as a brown solid. The crude product was purified by flash chromatography (0 % to 40% EtOAc/Hexanes) to yield the title compound as an off-white solid (1.2 g, 42.5%). $^1$H NMR (400 MHz, CDCl$_3$) δ 7.15 (d, J=8.7 Hz, 2H), 6.43 (d, J=8.7 Hz, 1H), 6.05 (br s, 1H), 3.02 (dt, J=5.7, 13.3 Hz, 2H), 2.21-2.10 (m, 4H), 1.92 (d, J=15.3 Hz, 2H).

Step 3. 8'-Chloro-4,4-difluoro-5'-hydroxy-6'-nitro-1'H-spiro[cyclohexane-1,4'-quinazolin]-2'(3'H)-one. To a solution of 8'-Chloro-4,4-difluoro-5'-hydroxy-1'H-spiro[cyclohexane-1,4'-quinazolin]-2'(3'H)-one (6.40 g, 21.1 mmol) in TFA (44.8 mL) at 0° C. was added nitric acid (2.13 mL, 47.6 mmol) dropwise. After the addition was complete, the reaction was warmed to rt, stirred for 1 h, then cooled to 5° C., and water was added dropwise. The reaction mixture was extracted with DCM, washed with water and brine, and then dried over MgSO$_4$ to give the title compound as a brown solid. [M+H]=348.1.

Step 4. 6'-Amino-8'-chloro-4,4-difluoro-5'-hydroxy-1'H-spiro[cyclohexane-1,4'-quinazolin]-2'(3'H)-one. To a suspension of 8'-chloro-4,4-difluoro-5'-hydroxy-6'-nitro-1'H-spiro[cyclohexane-1,4'-quinazolin]-2'(3'H)-one (556 mg, 1.60 mmol) in tetrahydrofuran (7.79 mL), water (0.78 mL) and acetic acid (3.34 mL) at 0° C. was added zinc (418 mg, 6.40 mmol). After addition, the reaction mixture was warmed to room temperature, stirred for 2 hours, and then monitored by LC/MS to determine that the reaction had gone to completion. A mixture of i-PrOH and DCM (1:3) was added to the reaction mixture, the layers were separated and the combined organics were washed with water and brine, dried over MgSO$_4$ and concentrated to give the title compound as a dark brown solid. $^1$H NMR (400 MHz, DMSO-d6) δ 7.72 (s, 1H), 7.35 (s, 1H), 6.79 (s, 1H), 2.99-2.87 (m, 3H), 2.47-2.27 (m, 4H), 1.88 (br s, 2H), 1.67 (d, J=12.0 Hz, 2H). [M+H]=318.0.

Intermediate 10. Methyl 5'-chloro-4,4-difluoro-7'-oxo-7',8'-dihydro-6'H-spiro[cyclohexane-1,9'-oxazolo[5,4-f]quinazoline]-2'-carboxylate (XXVII and Example 9)

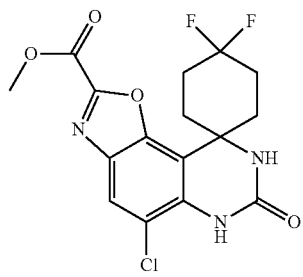 [SMILES: COC(=O)c1nc2cc(Cl)c3c(c2o1)C1(CCC(F)(F)CC1)NC(=O)N3]

6'-Amino-8'-chloro-4,4-difluoro-5'-hydroxy-1'H-spiro[cyclohexane-1,4'-quinazolin]-2'(3'H)-one (1.00 g, 3.15 mmol), 4-methylbenzenesulfonic acid (27.1 mg, 0.16 mmol) and methyl 2,2,2-trimethoxyacetate (4.58 mL, 31.5 mmol) were combined and stirred at 80° C. for 2 hours. The reaction mixture was cooled to room temperature, diluted with a mixture of i-PrOH/DCM (1:3), washed with a saturated solution of NaHCO$_3$ and brine, and then concentrated to give the title compound as a brown solid. The crude product was used in subsequent reactions without further purification. $^1$H NMR (400 MHz, CDCl$_3$) δ 7.90 (s, 1H), 7.50 (s, 1H), 6.70 (br s, 1H), 4.11 (s, 3H), 2.85-2.70 (m, 2H), 2.34-1.76 (m, 6H). [M+H]=386.0.

Intermediate 11. 5'-Chloro-4,4-difluoro-7'-oxo-7',8'-dihydro-6'H-spiro[cyclohexane-1,9'-oxazolo[5,4-f]quinazoline]-2'-carboxylic acid

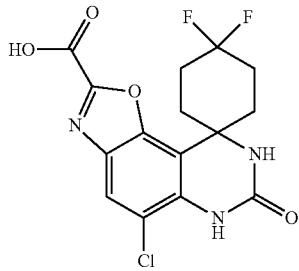 [SMILES: O=C1Nc2c(Cl)cc3nc(C(=O)O)oc3c2C2(CCC(F)(F)CC2)N1]

A mixture of methyl 5'-chloro-4,4-difluoro-7'-oxo-7',8'-dihydro-6'H-spiro[cyclohexane-1,9'-oxazolo[5,4-f]quinazoline]-2'-carboxylate (1.16 g, 3.00 mmol) and lithium hydroxide (0.22 g, 9.0 mmol) was suspended in tetrahydrofuran (18.5 mL) and water (4.63 mL), then stirred at room temperature for 0.5 h. Water was added to the reaction mixture, then the reaction mixture was washed with EtOAc. The aqueous layer was acidified using 2N HCl, extracted with EtOAc (×2), then the combined organic layers were washed with brine, dried over MgSO$_4$ and concentrated to give the title compound as a dark brown solid (221 mg). [M+H]=372.0.

Intermediate 12. 5'-Chloro-2'-(chloromethyl)-4,4-difluoro-6'H-spiro[cyclohexane-1,9'-oxazolo[5,4-f]quinazolin]-7'(8'H)-one

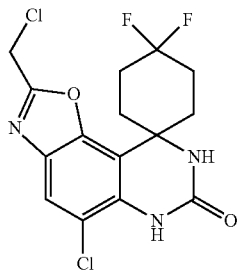 [SMILES: O=C1Nc2c(Cl)cc3nc(CCl)oc3c2C2(CCC(F)(F)CC2)N1]

Intermediate 12 was synthesized in a manner analogous to Intermediate 5, with the appropriate starting material substitutions. [M+H]=376.4.

Intermediate 13. 6'-Amino-8'-chloro-5'-hydroxy-4,4-dimethyl-1'H-spiro[cyclohexane-1,4'-quinazolin]-2'(3'H)-one

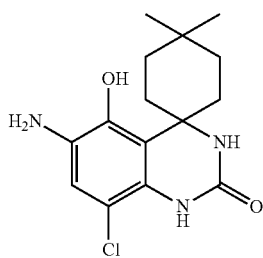 [SMILES: CC1(C)CCC2(CC1)NC(=O)Nc1c(Cl)cc(N)c(O)c12]

Intermediate 13 was synthesized according to Intermediate 9, with the appropriate starting material substitutions. [M+H]=310.1.

Intermediate 14. Ethyl 5'-chloro-7'-oxo-7',8'-dihydro-6'H-spiro[cyclohexane-1,9'-furo[2,3-f]quinazoline]-2'-carboxylate

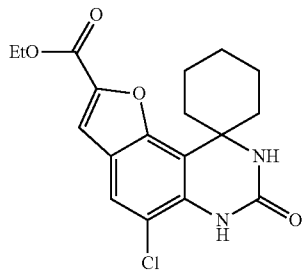 [SMILES: CCOC(=O)c1cc2cc(Cl)c3c(c2o1)C1(CCCCC1)NC(=O)N3]

Step 1. 8'-Chloro-5'-hydroxy-2'-oxo-2',3'-dihydro-1'H-spiro[cyclohexane-1,4'-quinazoline]-6'-carbaldehyde. Hexamine (20.3 g, 144 mmol) was added portion-wise to a suspension of 8'-chloro-5'-hydroxy-1'H-spiro[cyclohexane-1,4'-quinazolin]-2'(3'H)-one (35.0 g, 131 mmol) in TFA (140 mL) and the reaction mixture was heated to 100° C. for 18 h. The mixture was cooled to 0° C., and then water (700 mL) was added followed by concentrated HCl (50 mL). The mixture was heated to 100° C. and vigorously stirred for 45 min. The mixture was cooled to room temperature and the solid was collected by filtration, washed with water (2×300 mL), then dried in a vacuum oven at 45° C. for 18 h to provide the title compound (38 g, 98%). $^1$H NMR (400 MHz, CDCl$_3$) δ 12.22 (s, 1H), 9.66 (s, 1H), 7.62 (br, 1H), 7.48 (s, 1H), 6.60 (br, 1H), 2.69 (td, J=13.6, 4.3 Hz, 2H), 1.86-1.76 (m, 3H), 1.76-1.66 (m, 2H), 1.65-1.51 (m, 2H), 1.42-1.29 (m, 1H). [M+H]=295.2.

Step 2. Ethyl 5'-Chloro-7'-oxo-7',8'-dihydro-6'H-spiro[cyclohexane-1,9'-furo[2,3-f]quinazoline]-2'-carboxylate.
Ethyl bromoacetate (19.1 mL, 173 mmol) was added to a mixture of 8'-chloro-5'-hydroxy-2'-oxo-2',3'-dihydro-1'H-spiro[cyclohexane-1,4'-quinazoline]-6'-carbaldehyde (30.0 g, 102 mmol) and K$_2$CO$_3$ (49.2 g, 356 mmol) in DMF (1.0 L). The reaction mixture was heated to 100° C. for 30 min, then heated to 125° C. for 90 min. The mixture was cooled to room temperature and water (6.0 L) was added. The mixture was cooled to 0° C. and stirred for 1 h. The solid was collected by filtration, rinsed with water, and then dried in a vacuum oven at 60° C. for 18 h. The material was dissolved in DCM (1.5 L), silica gel was added and the solvent was concentrated under reduced pressure. The material was purified by flash chromatography on silica gel (100% hexanes (contains 2% AcOH) to 20% EtOAc in hexanes (contains 2% AcOH)) to provide the title compound (20 g, 54%). $^1$H NMR (400 MHz, CDCl$_3$) δ 7.59 (s, 1H), 7.45 (br, 1H), 7.39 (s, 1H), 6.38 (br, 1H), 4.48-4.34 (m, 2H), 2.53 (td, J=13.6, 4.4 Hz, 2H), 1.99 (d, J=12.4 Hz, 2H), 1.89-1.71 (m, 3H), 1.72-1.59 (m, 2H), 1.51-1.39 (m, 4H). [M+H]=363.0.

Intermediate 15. 5'-Chloro-7'-oxo-7',8'-dihydro-6'H-spiro[cyclohexane-1,9'-furo[2,3-f]quinazoline]-2'-carboxylic acid

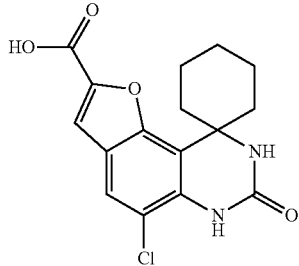

To a solution of ethyl 5'-chloro-7'-oxo-7',8'-dihydro-6'H-spiro[cyclohexane-1,9'-furo[2,3-f]quinazoline]-2'-carboxylate (Intermediate 14, 16.0 g, 44.1 mmol) in dioxane (600 mL) was added a 1M solution of NaOH (132 mL, 132 mmol) and the reaction mixture was heated to 40° C. for 3 h. The mixture was cooled and the solvent was concentrated under reduced pressure. The aqueous phase was extracted with EtOAc, then acidified by dropwise addition of concentrated HCl until a persistent pH of 2 was obtained. The resulting solid was collected by filtration, washed with water and dried in a vacuum oven at 50° C. for 18 h to afford the title compound (14 g, 95%). $^1$H NMR (400 MHz, DMSO-d6) δ 13.52 (br, 1H), 8.46 (d, J=1.4 Hz, 1H), 7.78 (s, 1H), 7.54 (s, 1H), 7.37 (d, J=1.4 Hz, 1H), 2.35 (td, J=13.3, 4.1 Hz, 2H), 1.91-1.77 (m, 4H), 1.70 (d, J=12.5 Hz, 1H), 1.56 (d, J=13.3 Hz, 2H), 1.26 (tdd, J=12.9, 9.2, 3.6 Hz, 1H). [M+H]=335.0.

Intermediate 16. 5'-Chloro-2'-(hydroxymethyl)-6'H-spiro[cyclohexane-1,9'-furo[2,3-f]quinazolin]-7'(8'H)one

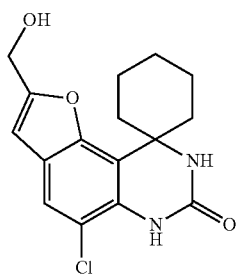 [SMILES: O=C1Nc2c(Cl)cc3cc(CO)oc3c2C2(CCCCC2)N1]

To a solution of ethyl 5'-chloro-7'-oxo-7',8'-dihydro-6'H-spiro[cyclohexane-1,9'-furo[2,3-f]quinazoline]-2'-carboxylate (Intermediate 14, 37.6 g, 104 mmol) in THF (1.0 L) at 0° C. was added LiAlH$_4$ (2M in THF, 104 mL, 207 mmol), dropwise, and the reaction mixture was stirred at room temperature for 2 h. The mixture was cooled to 0° C., then the pH was adjusted to 3 by adding a 2M HCl solution. The resulting solid was filtered and the solid was rinsed with water and dried in a vacuum oven at 55° C. for 24 h to provide the title compound (29 g, 87%). $^1$H NMR (400 MHz, DMSO-d6) δ 8.17 (br, 1H), 7.58 (s, 1H), 7.23 br, 1H), 6.65 (s, 1H), 5.46 (t, J=5.9 Hz, 1H), 4.54 (d, J=5.9 Hz, 2H), 2.35 (td, J=13.2, 4.1 Hz, 2H), 1.91-1.73 (m, 4H), 1.68 (d, J=13.0 Hz, 1H), 1.54 (d, J=13.7 Hz, 2H), 1.35-1.25 (m, 1H). [M+H]=321.2.

Intermediate 17. 5'-Chloro-2'-(chloromethyl)-6'H-spiro[cyclohexane-1,9'-furo[2,3-f]quinazolin]-7'(8'H)-one

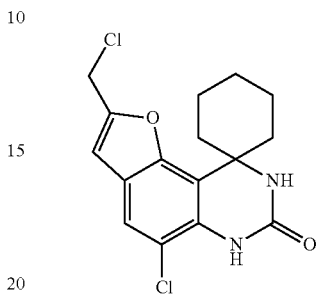

5'-Chloro-2'-(hydroxymethyl)-6'H-spiro[cyclohexane-1,9'-furo[2,3-f]quinazolin]-7'(8'H)-one (29.0 g, 90.4 mmol) was added portion-wise to thionyl chloride (500 mL) at 0° C. The reaction mixture was warmed to room temperature, stirred for 2 h, and then concentrated under reduced pressure without heating. The material was purified by flash chromatography on silica gel (hexanes (contains 1% AcOH) to 20% EtOAc in hexanes (contains 1% AcOH)) then the resulting material was triturated in hexanes (500 mL), filtered and dried under reduced pressure to provide the title compound (7.9 g, 26%). $^1$H NMR (400 MHz, DMSO-d6) δ 8.27 (s, 1H), 7.65 (s, 1H), 7.29 (s, 1H), 6.91 (s, 1H), 4.98 (s, 2H), 2.39-2.27 (m, 2H), 1.94-1.75 (m, 4H), 1.70 (d, J=12.6 Hz, 1H), 1.55 (d, J=14.0 Hz, 2H), 1.28 (dd, J=14.8, 11.0 Hz, 1H). [M+H]=339.1.

Example 1. Methyl 5'-chloro-7'-oxo-7',8'-dihydro-6'H-spiro[cyclohexane-1,9'-oxazolo[5,4-f]quinazoline]-2'-carboxylate

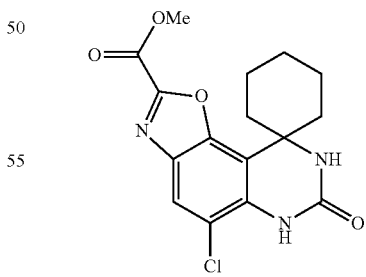

The structure of Example 1 is the same as Intermediate 3. The synthesis of Example 1 is that described for Intermediate 3. $^1$H NMR (400 MHz, CDCl$_3$) δ 7.85 (s, 1H), 7.61 (br, 1H), 4.10 (s, 3H), 2.23 (dd, J=9.2, 3.6 Hz, 3H), 2.03-1.93 (m, 2H), 1.89-1.82 (m, 1H), 1.77-1.70 (m, 2H), 1.51-1.41 (m, 2H). [M+H]=351.2.

Example 2. 5'-Chloro-7'-oxo-7',8'-dihydro-6'H-spiro[cyclohexane-1,9'-oxazolo[5,4-f]quinazoline]-2'-carboxylic acid

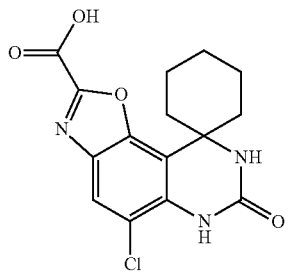 [SMILES: O=C1Nc2c(Cl)cc3nc(C(=O)O)oc3c2C2(CCCCC2)N1]

The structure of Example 2 is the same as Intermediate 4. The synthesis of Example 2 is that described for Intermediate 4. ¹H NMR (400 MHz, DMSO) δ 10.17 (s, 1H), 8.08 (s, 1H), 2.19-2.09 (m, 4H), 1.81-1.63 (m, 5H), 1.41-1.33 (m, 1H).

Example 3. 5'-Chloro-2'-(chloromethyl)-6'H-spiro[cyclohexane-1,9'-oxazolo[5,4-f]quinazolin]-7'(8'H)-one

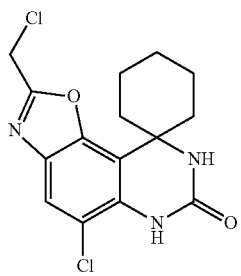

The structure of Example 3 is the same as Intermediate 5. The synthesis of Example 3 is that described for Intermediate 5. ¹H NMR (400 MHz, DMSO-d6) δ 8.63-8.39 (m, 1H), 7.84 (s, 1H), 7.47-7.38 (m, 1H), 5.07 (s, 2H), 2.25-2.10 (m, 2H), 1.88 (br s, 4H), 1.78-1.67 (m, 1H), 1.63-1.51 (m, 2H), 1.40-1.17 (m, 1H). [M+H]=340.1.

Example 4. 5'-Chloro-2'-(((2-methoxyethyl)amino)methyl)-6'H-spiro[cyclohexane-1,9'-oxazolo[5,4-f]quinazolin]-7'(8'H)-one

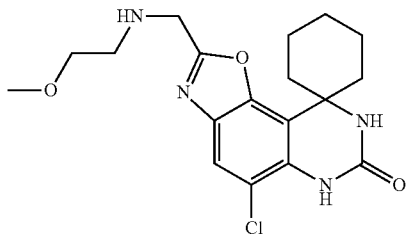

To a solution of 5'-chloro-2'-(chloromethyl)-6'H-spiro[cyclohexane-1,9'-oxazolo[5,4-f]quinazolin]-7'(8'H)-one (Intermediate 5, 250 mg, 0.73 mmol) in dichloromethane (2.50 mL) was added 2-methoxyethanamine (0.32 mL, 3.67 mmol) and the reaction mixture was stirred at rt for 1 hour. The reaction mixture was diluted with MeOH (1 mL), filtered and purified by prep. HPLC (5-95% ACN—H₂O). The desired fraction was lyophilized to afford the title compound as a brown powder. The product was purified again by flash chromatography (O % to 5% MeOH/EtOAc) using an ISCO amine column to yield the title compound as an off-white solid (54.2 mg, 19.5%). ¹H NMR (400 MHz, CDCl₃) δ 7.61 (s, 1H), 7.23 (s, 1H), 5.83 (s, 1H), 4.14 (s, 2H), 3.63-3.51 (m, 2H), 3.38 (s, 3H), 3.02-2.91 (m, 2H), 2.34-2.21 (m, 3H), 2.01 (d, J=12.8 Hz, 2H), 1.91-1.74 (m, 3H), 1.70-1.53 (m, 2H), 1.49-1.37 (m, 1H). [M+H]=379.1.

Example 5. 5'-Chloro-2'-((2-methoxyethoxy)methyl)-6'H-spiro[cyclohexane-1,9'-oxazolo[5,4-f]quinazolin]-7'(8'H)-one

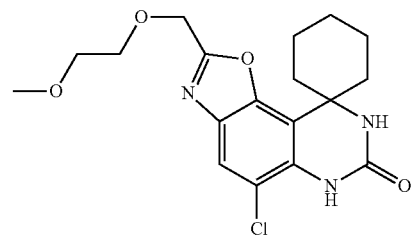

To a suspension of potassium tert-butoxide (19.8 mg, 0.18 mmol) in DMF (0.99 ml), was added methoxyethanol (13.9 µL, 0.18 mmol), the mixture was stirred at room temperature for 10 minutes, then a solution of 5'-Chloro-2'-(chloromethyl)-6'H-spiro[cyclohexane-1,9'-oxazolo[5,4-f]quinazolin]-7'(8'H)-one (Intermediate 5, 30 mg, 0.09 mmol) in DMF was added. The reaction mixture was stirred at room temperature for 15 minutes, and then heated to 80° C. for 1 hour. The reaction mixture was cooled to room temperature, diluted with MeOH (1 mL), filtered and purified by prep. HPLC (5-95% ACN in H₂O). The desired fraction was lyophilized to afford the title product as a gray powder (4.0 mg, 12%). ¹H NMR (400 MHz, DMSO-d6) δ 8.45 (s, 1H), 7.80 (s, 1H), 7.39 (s, 1H), 4.78 (s, 2H), 3.75-3.68 (m, 2H), 3.57-3.48 (m, 2H), 3.25 (s, 3H), 2.26-2.11 (m, 2H), 1.85 (d, J=11.2 Hz, 4H), 1.71 (d, J=11.4 Hz, 1H), 1.56 (d, J=15.2 Hz, 2H), 1.27 (d, J=13.9 Hz, 1H). [M+H]=380.1.

Example 6. Ethyl 2-(5'-chloro-7'-oxo-7',8'-dihydro-6'H-spiro[cyclohexane-1,9'-oxazolo[5,4-f]quinazolin]-2'-yl)acetate

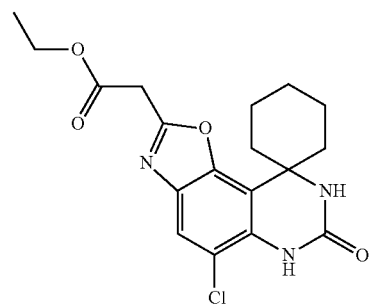 [SMILES: CCOC(=O)Cc1nc2cc(Cl)c3c(c2o1)C1(CCCCC1)NC(=O)N3]

5'-Chloro-2'-(chloromethyl)-6'H-spiro[cyclohexane-1,9'-oxazolo[5,4-f]quinazolin]-7'(8'H)-one (Intermediate 5, 30 mg, 0.11 mmol), p-toluenesulfonic acid (1.83 mg, 0.01 mmol), and diethyl malonate (80.8 µL, 0.53 mmol) were mixed together, then stirred at 120° C. for 2 hours. The reaction mixture was cooled to room temperature, diluted with MeOH, filtered and purified by Prep. HPLC (5-95% ACN in H$_2$O). The desired fraction was lyophilized to afford the title compound as an off-white powder. $^1$H NMR (400 MHz, DMSO-d6) δ 8.44 (s, 1H), 7.77 (s, 1H), 7.39 (s, 1H), 4.24-4.09 (m, 4H), 2.25-2.10 (m, 2H), 1.97-1.78 (m, 4H), 1.70 (d, J=12.0 Hz, 1H), 1.54 (d, J=13.8 Hz, 2H), 1.33-1.14 (m, 4H). [M+H]=378.1.

Example 7. 5'-Chloro-2'-(4-methoxypiperidine-1-carbonyl)-6'H-spiro[cyclohexane-1,9'-oxazolo[5,4-f]quinazolin]-7'(8'H)-one

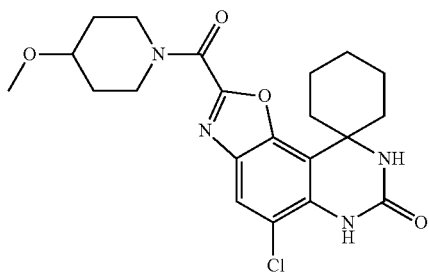 [SMILES: COC1CCN(C(=O)c2nc3cc(Cl)c4c(c3o2)C2(CCCCC2)NC(=O)N4)CC1]

To a mixture of 5'-chloro-7'-oxo-7',8'-dihydro-6'H-spiro[cyclohexane-1,9'-oxazolo[5,4-f]quinazoline]-2'-carboxylic acid (Intermediate 4, 175 mg, 0.52 mmol) and 4-methoxypiperidine (90 mg, 0.78 mmol) in N,N-dimethylformamide (3.50 mL), was added 1-[bis(dimethylamino) methylene]-1H-1,2,3-triazolo[4,5-b]pyridinium-3-oxide hexafluorophosphate (297 mg, 0.78 mmol), followed by N,N-diisopropylethylamine (273 µL, 1.56 mmol). The reaction was stirred at room temperature for 1 hour, and then water was added followed by EtOAc. The layers were separated and the organics were washed with brine, dried over MgSO$_4$ and concentrated. SFC purification provided the title compound as an off-white solid (225 mg, 44.8%). $^1$H NMR (400 MHz, CDCl$_3$) δ 7.75 (s, 1H), 7.24 (s, 1H), 5.67 (br s, 1H), 4.28-4.18 (m, 1H), 4.03-3.89 (m, 2H), 3.80-3.71 (m, 1H), 3.59 (tt, J=3.4, 6.8 Hz, 1H), 3.42 (s, 3H), 2.37 (tt, J=3.7, 13.3 Hz, 2H), 2.08-1.94 (m, 4H), 1.87-1.74 (m, 4H), 1.69-1.41 (m, 4H). [M+H]=433.6.

Example 8. 5'-Fluoro-2'-((3-methoxyazetidin-1-yl)methyl)-6'H-spiro[cyclohexane-1,9'-oxazolo[5,4-f]quinazolin]-7'(8'H)-one

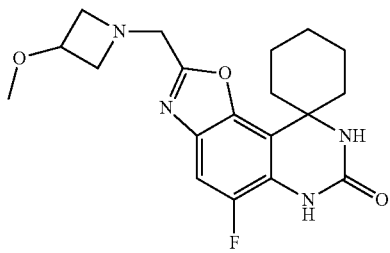 [SMILES: COC1CN(Cc2nc3cc(F)c4c(c3o2)C2(CCCCC2)NC(=O)N4)C1]

To a solution of 2'-(chloromethyl)-5'-fluoro-6'H-spiro[cyclohexane-1,9'-oxazolo[5,4-f]quinazolin]-7'(8'H)-one (Intermediate 8, 25 mg, 0.08 mmol) in N,N-dimethylformamide (0.45 ml) was added 3-methoxyazetidine (19.1 mg, 0.15 mmol) followed by triethylamine (38 µL, 0.27 mmol) and the reaction mixture was stirred at 40° C. for 1 h. The crude material was diluted with MeOH, filtered and purified by Prep. HPLC (5-95% ACN in H$_2$O). The desired fraction was lyophilized to afford the desired product as a TFA salt. The product was dissolved in EtOAc, washed with a saturated solution of NaHCO$_3$, dried over MgSO$_4$, and then concentrated to give the title compound as a free base (7.44 mg, 25.7%). $^1$H NMR (400 MHz, CDCl$_3$) δ 7.35 (d, J=9.5 Hz, 1H), 7.26 (br s, 1H), 5.72 (br s, 1H), 4.23-4.09 (m, 1H), 3.95 (s, 2H), 3.87 (dd, J=6.2, 8.1 Hz, 2H), 3.29 (s, 3H), 3.23 (dd, J=5.9, 8.1 Hz, 2H), 2.29 (dt, J=4.1, 13.5 Hz, 2H), 2.02 (br s, 2H), 1.92-1.74 (m, 3H), 1.63 (q, J=13.7 Hz, 2H), 1.47-1.34 (m, 1H). [M+H]=375.1.

Example 9. Methyl 5'-chloro-4,4-difluoro-7'-oxo-7',8'-dihydro-6'H-spiro[cyclohexane-1,9'-oxazolo[5,4-f]quinazoline]-2'-carboxylate

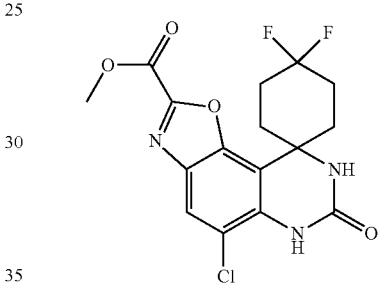

6'-Amino-8'-chloro-4,4-difluoro-5'-hydroxy-1'H-spiro[cyclohexane-1,4'-quinazolin]-2'(3'H)-one (Intermediate 9, 1.00 g, 3.15 mmol), 4-methylbenzenesulfonic acid (27.1 mg, 0.16 mmol) and methyl 2,2,2-trimethoxyacetate (4.58 mL, 31.5 mmol) were combined, then stirred at 80° C. for 2 hours. The reaction mixture was cooled to room temperature, diluted with i-PrOH/DCM (1:3), washed with a saturated solution of NaHCO$_3$ and brine, and then concentrated to give the title compound as a brown solid. $^1$H NMR (400 MHz, CDCl$_3$) δ 7.90 (s, 1H), 7.50 (s, 1H), 6.70 (br s, 1H), 4.11 (s, 3H), 2.85-2.70 (m, 2H), 2.34-1.76 (m, 6H). [M+H]=386.0.

Example 10. 5'-Chloro-4,4-difluoro-2'-((4-methylpiperazin-1-yl)methyl)-6'H-spiro[cyclohexane-1,9'-oxazolo[5,4-f]quinazolin]-7'(8'H)-one

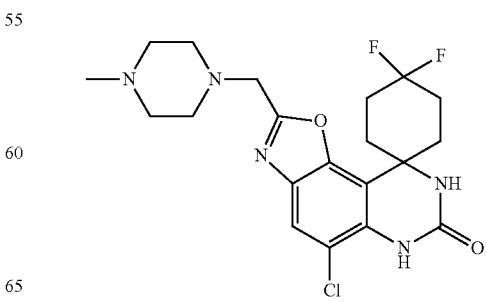

To a solution of 5'-chloro-2'-(chloromethyl)-4,4-difluoro-6'H-spiro[cyclohexane-1,9'-oxazolo[5,4-f]quinazolin]-7'(8'H)-one (Intermediate 12, 30 mg, 0.08 mmol) in DMF (0.60 mL, 20 V) was added 1-methylpiperazine (16 mg, 0.16 mmol) followed by triethylamine (28 µL, 0.20 mmol). The reaction mixture was stirred at room temperature for 5 hours then diluted with MeOH, filtered and purified by prep. HPLC (5-95% ACN—H$_2$O). The desired fraction was lyophilized to afford the title compound as a TFA salt (5.3 mg, 10%). $^1$H NMR (400 MHz, DMSO-d6) δ 9.41 (br s, 1H), 8.64 (s, 1H), 7.86 (s, 1H), 7.83 (s, 1H), 4.01 (s, 2H), 3.40 (d, J=13.0 Hz, 4H), 3.19-2.99 (m, 5H), 2.79 (br s, 3H), 2.66-2.55 (m, 2H), 2.00 (d, J=8.1 Hz, 4H). [M+H]=440.3.

Example 11. 5'-Chloro-4,4-difluoro-2'-methyl-6'H-spiro[cyclohexane-1,9'-oxazolo[5,4-f]quinazolin]-7'(8'H)-one

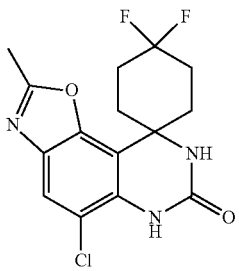 [SMILES: Cc1nc2cc(Cl)c3c(c2o1)C1(CCC(F)(F)CC1)NC(=O)N3]

6'-Amino-8'-chloro-4,4-difluoro-5'-hydroxy-1'H-spiro[cyclohexane-1,4'-quinazolin]-2'(3'H)-one (Intermediate 9, 30 mg, 0.09 mmol), 4-methylbenzenesulfonic acid (0.81 mg, 0.005 mmol) and 1,1,1-triethoxyethane (0.30 mL, 1.64 mmol, 10 V) were combined and stirred at 140° C. for 1 hour. The reaction mixture was cooled to room temperature. The crude material was diluted with MeOH, filtered and purified by Prep. HPLC (5-95% ACN—H$_2$O). The desired fraction was lyophilized to afford the title compound as a brown solid (1.8 mg, 5.6%). $^1$H NMR (400 MHz, CDCl$_3$) δ 7.64 (s, 1H), 7.35 (br s, 1H), 6.70 (br s, 1H), 2.77-2.64 (m, 5H), 2.28-2.09 (m, 6H).

Example 12. 5-Chloro-2,4',4'-trimethyl-7,8-dihydro-6H-spiro[[1,3]oxazolo[5,4-f]quinazoline-9,1'-cyclohexane]-7-one

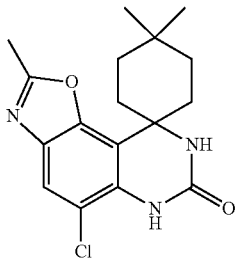 [SMILES: Cc1nc2cc(Cl)c3c(c2o1)C1(CCC(C)(C)CC1)NC(=O)N3]

6'-Amino-8'-chloro-5'-hydroxy-4,4-dimethyl-1'H-spiro[cyclohexane-1,4'-quinazolin]-2'(3'H)-one (Intermediate 13, 70 mg, 0.23 mmol), 4-methylbenzenesulfonic acid (2.0 mg, 0.01 mmol) and 1,1,1-triethoxyethane (0.70 ml, 1.64 mmol, 10 V) were mixed together, then stirred at 100° C. for 1 hour. The reaction mixture was cooled to room temperature. The crude material was diluted with MeOH, filtered and purified by Prep. HPLC (5-95% ACN in H$_2$O). The desired fraction was lyophilized to afford the title compound as a brown solid (5.5 mg, 7.3%). $^1$H NMR (400 MHz, CDCl$_3$) δ 7.62-7.58 (m, 1H), 7.33 (br s, 1H), 6.47 (br s, 1H), 2.68 (s, 3H), 2.58-2.48 (m, 2H), 1.88 (d, J=13.6 Hz, 2H), 1.61 (dt, J=3.4, 14.2 Hz, 2H), 1.48-1.40 (m, 2H), 1.15 (s, 3H), 1.08 (s, 3H). [M+H]=334.1.

Example 13. 5'-Chloro-6'H-spiro[cyclohexane-1,9'-oxazolo[5,4-f]quinazolin]-7'(8'H)-one

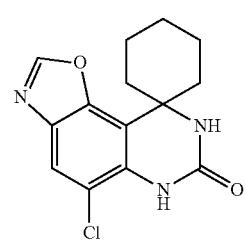 [SMILES: O=C1Nc2c(Cl)cc3ncoc3c2C2(CCCCC2)N1]

6'-Amino-8'-chloro-5'-hydroxy-1'H-spiro[cyclohexane-1,4'-quinazolin]-2'(3'H)-one (Intermediate 2, 32.0 mg, 0.11 mmol), 4-methylbenzenesulfonic acid (0.98 mg, 0.01 mmol) and triethoxymethane (0.32 mL, 1.91 mmol) were combined and stirred at rt for 1 hour. The crude material was diluted with MeOH, filtered and purified by prep. HPLC (5-95% ACN—H$_2$O). The desired fraction was lyophilized to afford the title compound as an off-white powder (7.5 mg, 23%). $^1$H NMR (400 MHz, CDCl$_3$) δ 8.07 (s, 1H), 7.76 (s, 1H), 7.41 (br s, 1H), 6.37 (br s, 1H), 2.34 (dt, J=4.3, 13.6 Hz, 2H), 2.05 (d, J=13.1 Hz, 2H), 1.95-1.75 (m, 3H), 1.73-1.53 (m, 2H), 1.44 (q, J=13.2 Hz, 1H). [M+H]=292.0.

Example 14. 5'-Chloro-2'-methyl-6'H-spiro[cyclohexane-1,9'-oxazolo[5,4-f]quinazolin]-7'(8'H)-one

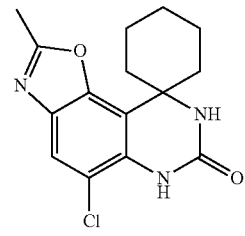

6'-Amino-8'-chloro-5'-hydroxy-1'H-spiro[cyclohexane-1,4'-quinazolin]-2'(3'H)-one (Intermediate 2, 21.4 mg, 0.08 mmol), 4-methylbenzenesulfonic acid (0.65 mg, 0.004 mmol) and 1,1,1-triethoxyethane (214 µL, 1.17 mmol) were mixed together, then stirred at 100° C. for 1 hour. The reaction mixture was cooled to room temperature. The crude material was diluted with MeOH, filtered and purified by prep. HPLC (5-95% ACN—H$_2$O). The desired fraction was lyophilized to afford the title compound as an off-white powder (3.8 mg, 16.4%). $^1$H NMR (400 MHz, CDCl$_3$) δ 7.58 (s, 1H), 7.16 (br s, 1H), 5.61 (br s, 1H), 2.67 (s, 3H), 2.30 (dt, J=4.1, 13.3 Hz, 2H), 2.02 (d, J=13.2 Hz, 2H), 1.81 (d, J=17.5 Hz, 3H), 1.56 (br s, 1H), 1.51-1.37 (m, 2H). [M+H]=306.1.

Example 15. 5'-Chloro-2'-ethyl-6'H-spiro[cyclohexane-1,9'-oxazolo[5,4-f]quinazolin]-7'(8'H)-one

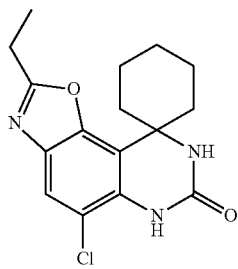 [SMILES: CCc1nc2cc(Cl)c3c(c2o1)C1(CCCCC1)NC(=O)N3]

6'-Amino-8'-chloro-5'-hydroxy-1'H-spiro[cyclohexane-1,4'-quinazolin]-2'(3'H)-one (Intermediate 2, 30 mg, 0.11 mmol), 4-methylbenzenesulfonic acid (0.92 mg, 0.01 mmol) and 1,1,1-triethoxypropane (0.30 ml, 1.5 mmol) were combined and stirred at 100° C. for 30 minutes. The reaction mixture was cooled to room temperature, then diluted with MeOH (1 mL), filtered and purified by prep. HPLC (5-95% ACN—H₂O). The desired fraction was lyophilized to afford the title compound as a white powder (4.2 mg, 12%). $^1$H NMR (400 MHz, CDCl₃) δ 7.60 (s, 1H), 7.15 (br s, 1H), 5.59 (br s, 1H), 2.99 (q, J=7.6 Hz, 2H), 2.38-2.23 (m, 2H), 2.02 (d, J=13.1 Hz, 2H), 1.92-1.74 (m, 3H), 1.57-1.53 (m, 1H), 1.52-1.43 (m, 5H). [M+H]=320.2.

Example 16. 5'-Chloro-2'-propyl-6'H-spiro[cyclohexane-1,9'-oxazolo[5,4-f]quinazolin]-7'(8'H)-one

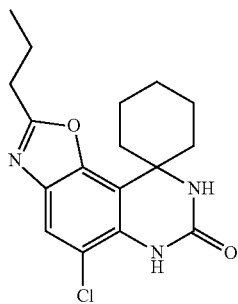 [SMILES: CCCc1nc2cc(Cl)c3c(c2o1)C1(CCCCC1)NC(=O)N3]

6'-Amino-8'-chloro-5'-hydroxy-1'H-spiro[cyclohexane-1,4'-quinazolin]-2'(3'H)-one (Intermediate 2, 30 mg, 0.11 mmol), 4-methylbenzenesulfonic acid (0.92 mg, 0.01 mmol) and 1,1,1-triethoxybutane (0.30 mL, 1.4 mmol) were mixed together and stirred at 100° C. for 0.5 hour. The reaction mixture was cooled to room temperature and the crude material was diluted with MeOH (1 mL), filtered and purified by prep. HPLC (5-95% ACN—H₂O). The desired fraction was lyophilized to afford the title compound as an off-white powder (7.4 mg, 21%). $^1$H NMR (400 MHz, CDCl₃) δ 7.59 (s, 1H), 7.15 (br s, 1H), 5.60 (br s, 1H), 2.93 (t, J=7.5 Hz, 2H), 2.30 (dt, J=4.0, 13.5 Hz, 2H), 2.10-1.75 (m, 8H), 1.54-1.26 (m, 2H), 1.10 (t, J=7.4 Hz, 3H). [M+H]=334.2.

Example 17. 5'-Chloro-2'-isopropyl-6'H-spiro[cyclohexane-1,9'-oxazolo[5,4-f]quinazolin]-7'(8'H)-one

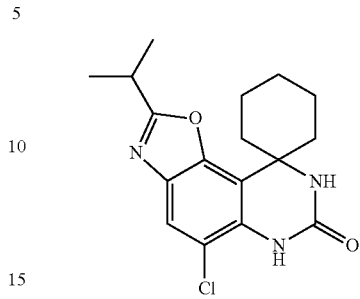

A solution of 6'-amino-8'-chloro-5'-hydroxy-1'H-spiro[cyclohexane-1,4'-quinazolin]-2'(3'H)-one (Intermediate 2, 30 mg, 0.11 mmol) and methyl 2-methylpropanecarboximidate (17 mg, 0.13 mmol) in ethanol (300 μL) was stirred at 90° C. for a half hour, then cooled to room temperature. The crude material was diluted with MeOH (1 mL), filtered and purified by prep. HPLC (5-95% ACN—H₂O). The desired fraction was lyophilized to afford the title compound as a white powder (9.1 mg, 26%). $^1$H NMR (400 MHz, CDCl₃) δ 7.61 (s, 1H), 7.34-7.29 (m, 1H), 6.10 (br s, 1H), 3.27 (td, J=7.0, 13.9 Hz, 1H), 2.30 (dt, J=4.1, 13.5 Hz, 2H), 2.04 (d, J=13.1 Hz, 2H), 1.94-1.78 (m, 3H), 1.73-1.56 (m, 2H), 1.49 (d, J=7.0 Hz, 6H), 1.45-1.38 (m, 1H). [M+H]=334.2.

Example 18. 5'-Chloro-2'-cyclopropyl-6'H-spiro[cyclohexane-1,9'-oxazolo[5,4-f]quinazolin]-7'(8'H)-one

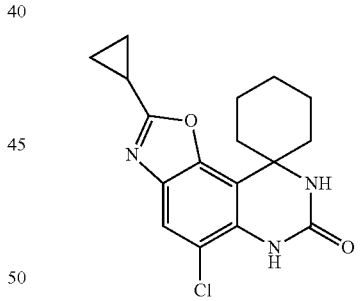

A solution of 6'-amino-8'-chloro-5'-hydroxy-1'H-spiro[cyclohexane-1,4'-quinazolin]-2'(3'H)-one (Intermediate 2, 32 mg, 0.11 mmol), 4-methylbenzenesulfonic acid (1.9 mg, 0.01 mmol) and (triethoxymethyl)cyclopropane (25 μL, 0.12 mmol) in ethanol (0.32 mL) was stirred at 90° C. for 0.5 hours, then cooled to room temperature. The crude material was diluted with DMSO, filtered and purified by prep. HPLC (5-95% ACN—H₂O). The desired fraction was lyophilized to afford the title compound as a white powder (5.1 mg, 14%). $^1$H NMR (400 MHz, CDCl₃) δ 7.54 (s, 1H), 7.33-7.29 (m, 1H), 6.18 (br s, 1H), 2.39-2.16 (m, 2H), 2.03 (d, J=13.3 Hz, 2H), 1.94-1.74 (m, 3H), 1.71-1.56 (m, 2H), 1.41 (q, J=13.1 Hz, 1H), 1.30-1.11 (m, 5H). [M+H]=332.1.

Example 19. 5'-Chloro-2'-(methoxymethyl)-6'H-spiro[cyclohexane-1,9'-oxazolo[5,4-f]quinazolin]-7'(8'H)-one

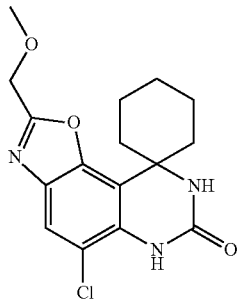 [SMILES: COCc1nc2cc(Cl)c3c(c2o1)C1(CCCCC1)NC(=O)N3]

A suspension of 6'-amino-8'-chloro-5'-hydroxy-1'H-spiro[cyclohexane-1,4'-quinazolin]-2'(3'H)-one (Intermediate 2, 30 mg, 0.11 mmol) and ethyl 2-methoxyacetimidate (24 mg, 0.16 mmol) in ethanol (300 μL) was microwaved at 110° C. for 30 minutes. The crude material was diluted with MeOH (1 mL), filtered and purified by prep. HPLC (5-95% ACN—H$_2$O). The desired fraction was lyophilized to give the title compound as a white powder (4.8 mg, 13.2%). $^1$H NMR (400 MHz, CDCl$_3$) δ 7.68 (s, 1H), 7.24 (br s, 1H), 5.76 (br s, 1H), 4.72 (s, 2H), 3.56 (s, 3H), 2.41-2.23 (m, 2H), 2.04 (d, J=13.3 Hz, 2H), 1.94-1.77 (m, 4H), 1.51-1.37 (m, 2H). [M+H]=336.1.

Example 20. 5'-Chloro-2'-(hydroxymethyl)-6'H-spiro[cyclohexane-1,9'-oxazolo[5,4-f]quinazolin]-7'(8'H)-one

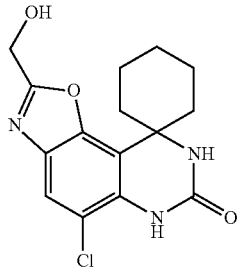

5'-Chloro-2'-(methoxymethyl)-6'H-spiro[cyclohexane-1,9'-oxazolo[5,4-f]quinazolin]-7'(8'H)-one (34 mg, 0.10 mmol) in a solution of 1N boron tribromide (2.03 mL, 2.03 mmol) was stirred at room temperature for 1 hour. The solvent was evaporated and the crude material was diluted with MeOH, filtered and purified by prep. HPLC (5-95% ACN—H$_2$O). The desired fraction was lyophilized to afford the title compound as a white powder (13 mg, 40%). $^1$H NMR (400 MHz, DMSO-d6) δ 8.42 (s, 1H), 7.77 (s, 1H), 7.37 (s, 1H), 4.68 (s, 2H), 2.30-2.14 (m, 2H), 1.96-1.79 (m, 4H), 1.75-1.42 (m, 4H), 1.36-1.17 (m, 1H). [M+H]=322.1.

Example 21. 5'-Chloro-2'-(2-methoxyethyl)-6'H-spiro[cyclohexane-1,9'-oxazolo[5,4-f]quinazolin]-7'(8'H)-one

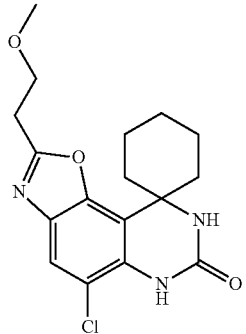 [SMILES: COCCc1nc2cc(Cl)c3c(c2o1)C1(CCCCC1)NC(=O)N3]

6'-Amino-8'-chloro-5'-hydroxy-1'H-spiro[cyclohexane-1,4'-quinazolin]-2'(3'H)-one (Intermediate 2, 60 mg, 0.21 mmol), 4-methylbenzenesulfonic acid (1.8 mg, 0.01 mmol) and 1,1,1-triethoxy-3-methoxypropane (0.51 mL, 2.2 mmol) were combined and stirred at rt for 1 hour. The crude material was diluted with MeOH, filtered and purified by prep. HPLC (5-95% ACN—H$_2$O). The desired fraction was lyophilized to afford the title compound as an off-white powder (20 mg, 27%). $^1$H NMR (400 MHz, CDCl$_3$) δ 7.61 (s, 1H), 7.21 (br s, 1H), 5.81 (br s, 1H), 3.91 (t, J=6.5 Hz, 2H), 3.43 (s, 3H), 3.23 (t, J=6.5 Hz, 2H), 2.30 (dt, J=4.1, 13.6 Hz, 2H), 2.03 (d, J=13.4 Hz, 2H), 1.93-1.76 (m, 3H), 1.62 (q, J=14.0 Hz, 2H), 1.42 (q, J=12.8 Hz, 1H). [M+H]=350.1.

Example 22. 5'-Chloro-2'-(2-hydroxyethyl)-6'H-spiro[cyclohexane-1,9'-oxazolo[5,4-f]quinazolin]-7'(8'H)-one

5'-Chloro-2'-(2-methoxyethyl)-6'H-spiro[cyclohexane-1,9'-oxazolo[5,4-f]quinazolin]-7'(8'H)-one (15 mg, 0.04 mmol) in 1N boron tribromide (0.42 mL, 0.42 mmol) was stirred at room temperature for 1 hour. The solvent was evaporated and the crude material was dissolved in MeOH, filtered and purified by prep. HPLC (5-95% ACN—H$_2$O). The desired fraction was lyophilized to afford the title compound as a white powder (2.9 mg, 21%). $^1$H NMR (400 MHz, CDCl$_3$) δ 7.62 (s, 1H), 7.24 (br s, 1H), 5.88 (br s, 1H), 4.17 (t, J=5.6 Hz, 2H), 3.20 (t, J=5.6 Hz, 2H), 2.40-2.22 (m, 2H), 2.03 (d, J=13.6 Hz, 2H), 1.92-1.76 (m, 4H), 1.63 (q, J=13.5 Hz, 2H), 1.50-1.39 (m, 1H). [M+H]=336.1.

Example 23. N-(5'-Chloro-7'-oxo-7',8'-dihydro-6'H-spiro[cyclohexane-1,9'-oxazolo[5,4-f]quinazolin]-2'-yl)acetamide

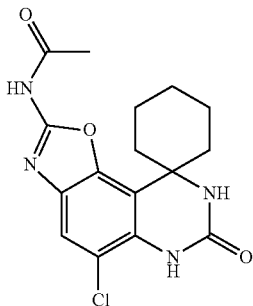 [SMILES: CC(=O)Nc1nc2cc(Cl)c3c(c2o1)C1(CCCCC1)NC(=O)N3]

Step 1. 6'-Amino-8'-chloro-5'-hydroxy-1'H-spiro[cyclohexane-1,4'-quinazolin]-2'(3'H)-one (Intermediate 2, 300 mg, 1.06 mmol) and di(1H-imidazol-1-yl)$_m$ethanimine (309 mg, 1.92 mmol) were dissolved in dry tetrahydrofuran (9.0 mL) and heated at 70° C. for 2 hours. The reaction was cooled to room temperature then the reaction mixture was diluted with EtOAc, washed with a saturated solution of NaHCO$_3$, filtered, then the organic layer was concentrated. The crude product was purified by flash chromatography (20% to 100% EtOAc/Hexanes) to yield 2'-amino-5'-chloro-6'H-spiro[cyclohexane-1,9'-oxazolo[5,4-f]quinazolin]-7'(8'H)-one as a light brown solid (139 mg, 42.5%). [MAI]= 307.1.

Step 2. Acetic anhydride (26 µL, 0.27 mmol) was added to the above solution of 2'-amino-5'-chloro-6'H-spiro[cyclohexane-1,9'-oxazolo[5,4-f]quinazolin]-7'(8'H)-one (17 mg, 0.05 mmol) in dichloromethane (336 µL) at rt, followed by triethylamine (23 µL, 0.16 mmol). The reaction mixture became clear, then was stirred at room temperature for 1 hour, then heated to 80° C. for 3 days. Upon completion of the reaction, the crude material was diluted with MeOH (1 mL), then filtered and purified by Prep. HPLC (5-95% ACN—H$_2$O). The desired fraction was lyophilized to afford the title compound as a white powder (8.8 mg, 46%). $^1$H NMR (400 MHz, DMSO-d6) δ 11.64 (s, 1H), 8.33 (s, 1H), 7.58 (s, 1H), 7.32 (s, 1H), 2.25-2.13 (m, 5H), 1.94-1.77 (m, 4H), 1.70 (d, J=13.2 Hz, 1H), 1.54 (d, J=13.3 Hz, 2H), 1.27 (d, J=13.4 Hz, 1H). [M+H]=335.1.

Example 24. 2'-(Bis(2-methoxyethyl)amino)-5'-chloro-6'H-spiro[cyclohexane-1,9'-oxazolo[5,4-f]quinazolin]-7'(8'H)-one

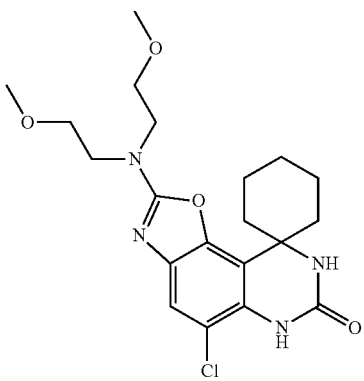 [SMILES: COCCN(CCOC)c1nc2cc(Cl)c3c(c2o1)C1(CCCCC1)NC(=O)N3]

To a solution of 2'-amino-5'-chloro-6'H-spiro[cyclohexane-1,9'-oxazolo[5,4-f]quinazolin]-7'(8'H)-one (20 mg, 0.07 mmol) and cesium carbonate (53 mg, 0.16 mmol) in DMF (400 µL), was added 2-bromoethyl methyl ether (7.4 µL, 0.08 mmol) and the reaction mixture was stirred at room temperature for 1 hour, then heated at 60° C. overnight. The reaction mixture was cooled to room temperature and was diluted with MeOH (1 mL), filtered and purified by prep. HPLC (5-95% ACN—H$_2$O). The fraction containing the desired product was lyophilized to afford the title compound as a light brown powder. $^1$H NMR (400 MHz, CDCl$_3$) δ 7.25 (s, 1H), 7.03 (s, 1H), 5.56 (s, 1H), 3.84-3.74 (m, 4H), 3.71-3.62 (m, 4H), 3.38 (s, 6H), 2.30-2.14 (m, 2H), 2.02 (d, J=12.8 Hz, 2H), 1.91-1.70 (m, 3H), 1.59 (q, J=13.8 Hz, 2H), 1.43-1.20 (m, 1H). [M+H]=423.1.

Example 25. 5'-Chloro-7'-oxo-7',8'-dihydro-6'H-spiro[cyclohexane-1,9'-oxazolo[5,4-f]quinazoline]-2'-carboxamide

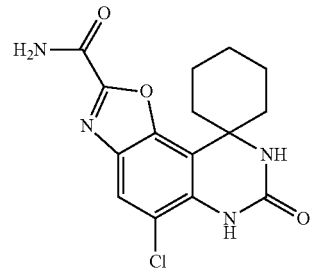

6'-Amino-8'-chloro-5'-hydroxy-1'H-spiro[cyclohexane-1,4'-quinazolin]-2'(3'H)-one (Intermediate 2, 35 mg, 0.12 mmol), 4-methylbenzenesulfonic acid (1.1 mg, 0.01 mmol) and trimethoxyacetamide (56 mg, 0.37 mmol) were mixed together, stirred at 100° C. for 0.5 hours, then the reaction mixture was cooled to room temperature. The crude material was diluted with MeOH, then filtered and purified by prep. HPLC (5-95% ACN—H$_2$O). The desired fraction was lyophilized to afford the title compound as an off-white powder (4.1 mg, 10%). $^1$H NMR (400 MHz, CDCl$_3$) δ 7.77 (s, 1H), 7.32 (br s, 1H), 7.15-6.88 (m, 1H), 6.07-5.53 (m, 2H), 2.56-2.23 (m, 2H), 2.05 (d, J=16.4 Hz, 2H), 1.83 (d, J=12.5 Hz, 4H), 1.71-1.38 (m, 2H). [M+H]=335.1.

Example 26. 5'-Chloro-2'-(hydroxymethyl)-6'H-spiro[cyclohexane-1,9'-furo[2,3-f]quinazolin]-7'(8'H)one

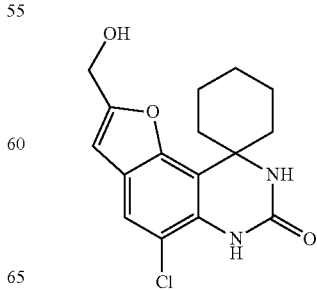

The structure of Example 26 is the same as Intermediate 16. The synthesis of Example 26 is that described for Intermediate 16. ¹H NMR (400 MHz, DMSO-d6) δ 8.17 (br, 1H), 7.58 (s, 1H), 7.23 (br, 1H), 6.65 (s, 1H), 5.46 (t, J=5.9 Hz, 1H), 4.54 (d, J=5.9 Hz, 2H), 2.35 (td, J=13.2, 4.1 Hz, 2H), 1.91-1.73 (m, 4H), 1.68 (d, J=13.0 Hz, 1H), 1.54 (d, J=13.7 Hz, 2H), 1.35-1.25 (m, 1H). [M+H]=321.2.

Example 27. 5'-Chloro-2'-(4-(2-fluoroethyl)piperazine-1-carbonyl)-6'H-spiro[cyclohexane-1,9'-furo[2,3-f]quinazolin]-7'(8'H)-one

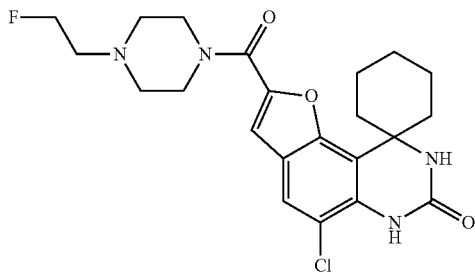 [SMILES: O=C1Nc2c(Cl)cc3cc(C(=O)N4CCN(CCF)CC4)oc3c2C2(CCCCC2)N1]

To a mixture of 5'-chloro-7'-oxo-7',8'-dihydro-6'H-spiro[cyclohexane-1,9'-furo[2,3-f]quinazoline]-2'-carboxylic acid (Intermediate 15, 50 mg, 0.15 mmol) and 1-(2-fluoroethyl) piperazine hydrochloride in DMF (5 mL) was added a solution of N-ethyl-N-isopropylpropan-2-amine (0.08 mL, 0.45 mmol) and 2-(3H-[1,2,3]triazolo[4,5-b]pyridin-3-yl)-1,1,3,3-tetramethylisouronium hexafluorophosphate (HATU, 68 mg, 0.18 mmol) in DMF (1 mL). The vial was sealed and the reaction mixture was stirred at room temperature for 3.5 h. The reaction mixture was diluted with water and EtOAc. A precipitate formed in the biphasic mixture, which was filtered, rinsed with H₂O and dried under vacuum to give the title compound as a white solid (19 mg, 28%). ¹H NMR (400 MHz, DMSO-d6) δ 8.42 (s, 1H), 7.75 (s, 1H), 7.37 (s, 1H), 7.34 (s, 1H), 4.67-4.47 (m, 2H), 3.70 (br s, 4H), 2.77-2.63 (m, 2H), 2.59-2.54 (m, 4H), 2.36-2.25 (m, 2H), 1.95-1.81 (m, 4H), 1.72 (d, J=12.7 Hz, 1H), 1.56 (d, J=14.2 Hz, 2H), 1.35-1.22 (m, 1H). [M+H]=449.0.

Example 28. N-(2-(Benzyl(methyl)amino)ethyl)-5'-chloro-N-methyl-7'-oxo-7',8'-dihydro-6'H-spiro[cyclohexane-1,9'-furo[2,3-f]quinazoline]-2'-carboxamide

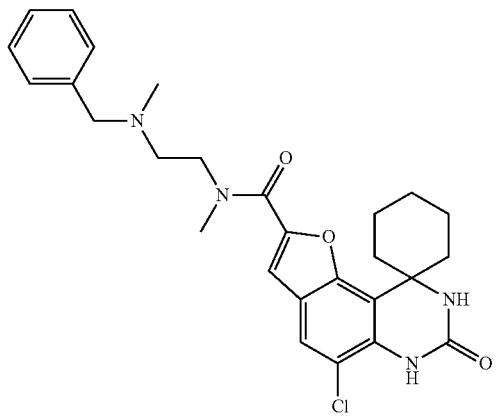 [SMILES: CN(CCN(C)C(=O)c1cc2cc(Cl)c3c(c2o1)C1(CCCCC1)NC(=O)N3)Cc1ccccc1]

To a suspension of 5'-chloro-7'-oxo-7',8'-dihydro-6'H-spiro[cyclohexane-1,9'-furo[2,3-f]quinazoline]-2'-carboxylic acid (Intermediate 15, 34 mg, 0.10 mol) in N,N-dimethylacetamide (0.1 mL) was added a solution of 2-(3H-[1,2,3]triazolo[4,5-b]pyridin-3-yl)-1,1,3,3-tetramethylisouronium hexafluorophosphate(V) (HATU, 0.2 mL of a 0.5 M solution in N,N-dimethylacetamide, 0.1 mmol) followed by N-ethyl-N-isopropylpropan-2-amine (35 μL, 0.20 mmol). The resulting solution was added to a solution of N¹-benzyl-N¹,N²-dimethylethane-1,2-diamine (21 mg, 0.12 mmol) in N,N-dimethylacetamide (0.12 mL) and the sealed reaction was shaken at 270 rpm at room temperature for 16 h. The reaction mixture was diluted with N,N-dimethylacetamide (0.3 mL), filtered, and the filter frit rinsed with additional N,N-dimethylacetamide (0.1 mL). The filtered crude product solution was purified by preparative HPLC-MS to afford the title compound (30 mg, 49%). [M+H]=495.5.

Example 29. 5'-Chloro-2'-((4-isopropylpiperazin-1-yl)methyl)-6'H-spiro[cyclohexane-1,9'-furo[2,3-f]quinazolin]-7'(8'H)-one

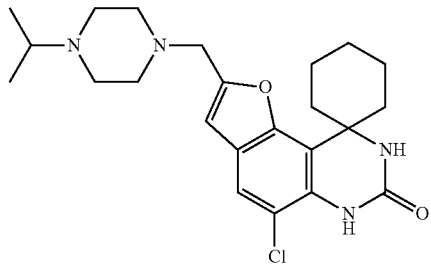 [SMILES: CC(C)N1CCN(Cc2cc3cc(Cl)c4c(c3o2)C2(CCCCC2)NC(=O)N4)CC1]

To a solution of 5'-chloro-2'-(chloromethyl)-6'H-spiro[cyclohexane-1,9'-furo[2,3-f]quinazolin]-7'(8'H)-one (Intermediate 17, 30 mg, 0.09 mmol) in DMF (5 mL) was added 1-isopropylpiperazine (22 mg, 0.18 mmol) followed by N,N'-Diisopropyl ethylamine (0.05 mL, 0.27 mmol) and the reaction mixture was stirred at 60° C. for 4 h. The reaction mixture was cooled to room temperature, diluted with H₂O (15 mL) then extracted with EtOAc. The combined organics were washed with H₂O, dried with Na₂SO₄ and concentrated under vacuum to give the title compound as an off-white solid (22 mg, 58%). ¹H NMR (400 MHz, DMSO-d6) δ 8.16 (s, 1H), 7.57 (s, 1H), 7.26 (br s, 1H), 6.64 (s, 1H), 3.69 (s, 3H), 2.44 (br s, 10H), 1.91-1.80 (m, 5H), 1.69 (br s, 1H), 1.56 (br s, 2H), 1.32-1.25 (m, 1H), 0.94 (d, J=6.4 Hz, 6H). [M+H]=431.0.

Example 30. 5'-Chloro-2'-((((4-isopropyl-4H-1,2,4-triazol-3-yl)methyl)(methyl)amino)methyl)-6'H-spiro[cyclohexane-1,9'-furo[2,3-f]quinazolin]-7'(8'H)-one

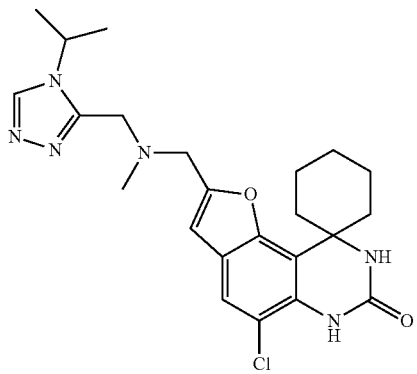 [SMILES: CC(C)n1cnnc1CN(C)Cc1cc2cc(Cl)c3c(c2o1)C1(CCCCC1)NC(=O)N3]

To a solution of 1-(4-isopropyl-4H-1,2,4-triazol-3-yl)-N-methylmethanamine (30.8 mg, 0.2 mmol) and N-ethyl-N-isopropylpropan-2-amine (52 μL, 0.30 mmol) in N,N-dimethylacetamide (0.2 mL) was added a solution of 5'-chloro-2'-(chloromethyl)-6'H-spiro[cyclohexane-1,9'-furo[2,3-f]quinazolin]-7'(8'H)-one (Intermediate 17, 34 mg, 0.10 mmol) in N,N-dimethylacetamide (0.4 mL) and the reaction was shaken at 60° C. After shaking for 16 hours at 60° C. the reaction mixture was filtered, and the filter frit rinsed with additional N,N-dimethylacetamide (0.2 mL). The filtered crude product solution was purified by preparative SFC-MS to afford the title compound (24 mg, 42%). [M+H]=457.2.

Example 31.-Example 175. were prepared in a manner analogous to Example 4, with the appropriate starting material substitutions.

Example 31. 5-Chloro-2-[(dimethylamino)methyl]-7,8-dihydro-6H-spiro[[1,3]oxazolo[5,4-f]quinazoline-9,1'-cyclohexane]-7-one

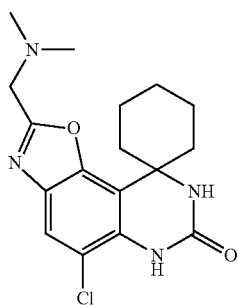 [SMILES: CN(C)Cc1nc2cc(Cl)c3c(c2o1)C1(CCCCC1)NC(=O)N3]

$^1$H NMR (400 MHz, CDCl$_3$) δ 7.73 (s, 1H), 7.33 (s, 1H), 5.89 (s, 1H), 4.54 (s, 2H), 3.00 (s, 6H), 2.32-2.18 (m, 2H), 2.03 (d, J=13.3 Hz, 2H), 1.92-1.75 (m, 3H), 1.62 (q, J=13.6 Hz, 2H), 1.51-1.36 (m, 1H). [M+H]=349.3.

Example 32. 5-Chloro-2-[(4-methylpiperazin-1-yl)methyl]-7,8-dihydro-6H-spiro[[1,3]oxazolo[5,4-f]quinazoline-9,1'-cyclohexane]-7-one

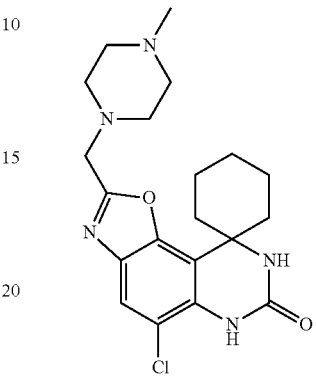

$^1$H NMR (400 MHz, CDCl$_3$) δ 7.66 (s, 1H), 7.36 (s, 1H), 6.18 (s, 1H), 3.99 (s, 2H), 3.60 (br s, 2H), 3.18 (br s, 2H), 3.02 (br s, 4H), 2.85 (s, 3H), 2.25 (dt, J=4.0, 13.4 Hz, 2H), 2.04 (d, J=13.2 Hz, 2H), 1.92-1.75 (m, 3H), 1.65 (q, J=13.6 Hz, 2H), 1.41 (q, J=12.8 Hz, 1H). [M+H]=404.2.

Example 33. 5-Chloro-2-(morpholin-4-ylmethyl)-7,8-dihydro-6H-spiro[[1,3]oxazolo[5,4-f]quinazoline-9,1'-cyclohexane]-7-one

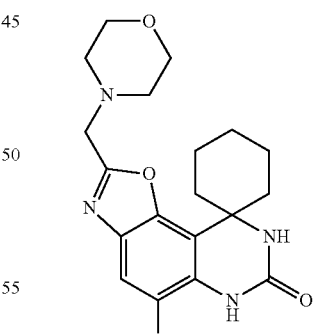

$^1$H NMR (400 MHz, CDCl$_3$) δ 7.71 (s, 1H), 7.39 (s, 1H), 6.15 (br s, 1H), 4.37 (s, 2H), 4.04-3.92 (m, 4H), 3.29-3.18 (m, 4H), 2.25 (dt, J=4.3, 13.8 Hz, 2H), 2.04 (d, J=12.6 Hz, 2H), 1.90-1.90 (m, 1H), 1.92-1.77 (m, 3H), 1.63 (q, J=13.7 Hz, 2H), 1.51-1.32 (m, 1H). [M+H]=391.2.

Example 34. 5-Chloro-2-[(4-hydroxypiperidin-1-yl)methyl]-7,8-dihydro-6H-spiro[[1,3]oxazolo[5,4-f]quinazoline-9,1'-cyclohexane]-7-one Example 36. 5-Chloro-2-[(cyclopropylamino)methyl]-7,8-dihydro-6H-spiro[[1,3]oxazolo[5,4-f]quinazoline-9,1'-cyclohexane]-7-one

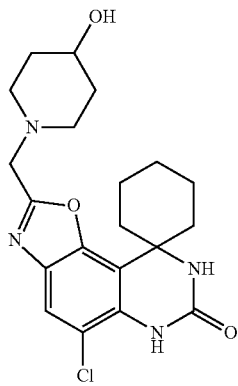 [SMILES: O=C1Nc2c(Cl)cc3nc(CN4CCC(O)CC4)oc3c2C2(CCCCC2)N1]

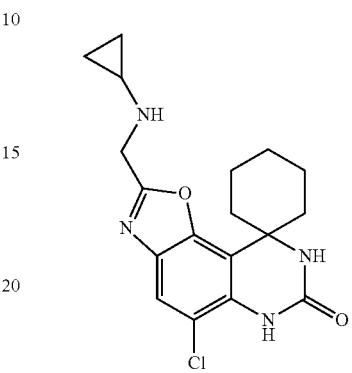

$^1$H NMR (400 MHz, DMSO-d6) δ 8.57 (s, 1H), 7.91 (s, 1H), 7.44 (s, 1H), 4.79 (br s, 3H), 4.17-3.59 (m, 3H), 3.20-2.95 (m, 1H), 2.26-2.12 (m, 2H), 2.05-1.80 (m, 7H), 1.72 (d, J=13.6 Hz, 2H), 1.56 (d, J=14.2 Hz, 3H), 1.38-1.21 (m, 1H). [M+H]=405.3.

$^1$H NMR (400 MHz, CDCl$_3$) δ 7.66 (s, 1H), 7.35 (s, 1H), 6.15 (s, 1H), 4.53 (s, 2H), 2.83 (td, J=3.5, 7.2 Hz, 2H), 2.25 (dt, J=4.2, 13.2 Hz, 2H), 2.02 (d, J=13.4 Hz, 2H), 1.95-1.72 (m, 3H), 1.64 (q, J=14.0 Hz, 2H), 1.48-1.28 (m, 1H), 1.12-0.99 (m, 2H), 0.90-0.76 (m, 2H). [M+H]=361.3.

Example 35. 5-Chloro-2-[(methylamino)methyl]-7,8-dihydro-6H-spiro[[1,3]oxazolo[5,4-f]quinazoline-9,1'-cyclohexane]-7-one Example 37. 5-Chloro-2-(piperazin-1-ylmethyl)-7,8-dihydro-6H-spiro[[1,3]oxazolo[5,4-f]quinazoline-9,1'-cyclohexane]-7-one

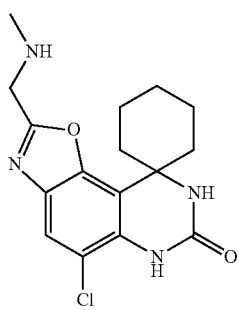 [SMILES: CNCc1nc2cc(Cl)c3c(c2o1)C1(CCCCC1)NC(=O)N3]

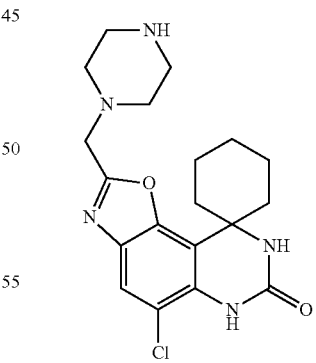

$^1$H NMR (400 MHz, DMSO-d6) δ 9.39 (br s, 1H), 8.55 (s, 1H), 7.89 (s, 1H), 7.43 (s, 1H), 4.64 (s, 2H), 2.76 (s, 3H), 2.28-2.14 (m, 2H), 2.00-1.80 (m, 4H), 1.71 (d, J=11.5 Hz, 1H), 1.56 (d, J=13.9 Hz, 2H), 1.39-1.20 (m, 1H). [M+H]=335.2.

$^1$H NMR (400 MHz, DMSO-d6) δ 8.54 (br s, 1H), 8.47 (d, J=1.2 Hz, 1H), 7.78 (s, 1H), 7.40 (s, 1H), 4.02 (s, 2H), 3.13 (br s, 4H), 2.86-2.76 (m, 4H), 2.26-2.11 (m, 2H), 1.96-1.81 (m, 4H), 1.71 (d, J=12.5 Hz, 1H), 1.56 (d, J=13.1 Hz, 2H), 1.33-1.20 (m, 1H). [M+H]=390.3.

Example 38. 5-Chloro-2-(pyrrolidin-1-ylmethyl)-7,8-dihydro-6H-spiro[[1,3]oxazolo[5,4-f]quinazoline-9,1'-cyclohexane]-7-one

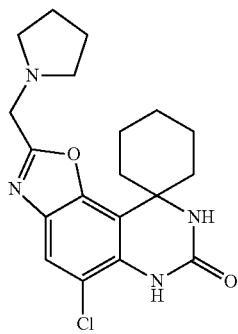 [SMILES: O=C1Nc2c(Cl)cc3nc(CN4CCCC4)oc3c2C2(CCCCC2)N1]

$^1$H NMR (400 MHz, CDCl$_3$) δ 7.63 (s, 1H), 7.20 (br s, 1H), 5.73 (br s, 1H), 4.02 (s, 2H), 2.80 (br s, 4H), 2.31 (dt, J=4.0, 13.5 Hz, 2H), 2.12-1.98 (m, 2H), 1.95-1.75 (m, 7H), 1.63 (q, J=13.7 Hz, 2H), 1.51-1.33 (m, 1H). [M+H]=375.2.

Example 39. 5-Chloro-2-{[(propan-2-yl)amino]methyl}-7,8-dihydro-6H-spiro[[1,3]oxazolo[5,4-f]quinazoline-9,1'-cyclohexane]-7-one

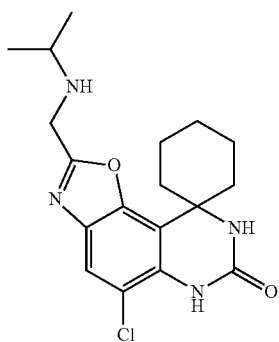 [SMILES: CC(C)NCc1nc2cc(Cl)c3c(c2o1)C1(CCCCC1)NC(=O)N3]

$^1$H NMR (400 MHz, CDCl$_3$) δ 7.62 (s, 1H), 7.20 (br s, 1H), 5.74 (br s, 1H), 4.12 (s, 2H), 2.98 (td, J=6.2, 12.4 Hz, 1H), 2.28 (dt, J=4.3, 13.5 Hz, 2H), 2.03 (d, J=12.5 Hz, 3H), 1.90-1.75 (m, 3H), 1.70-1.55 (m, 2H), 1.50-1.35 (m, 1H), 1.17 (d, J=6.2 Hz, 6H). [M+H]=362.0.

Example 40. 5-Chloro-2-[(ethylamino)methyl]-7,8-dihydro-6H-spiro[[1,3]oxazolo[5,4-f]quinazoline-9,1'-cyclohexane]-7-one

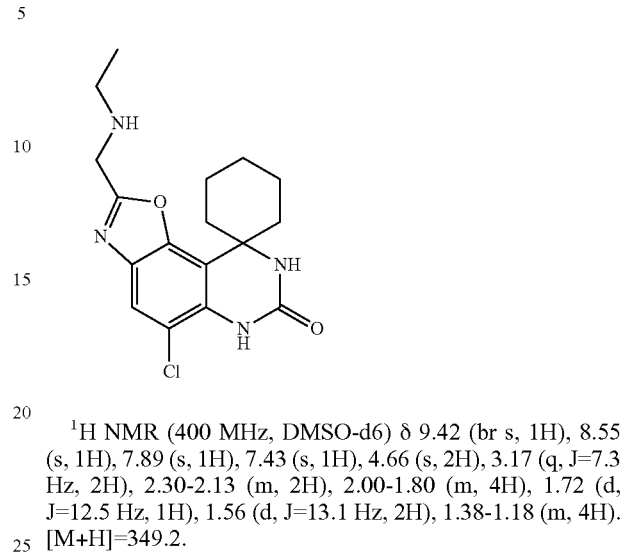

$^1$H NMR (400 MHz, DMSO-d6) δ 9.42 (br s, 1H), 8.55 (s, 1H), 7.89 (s, 1H), 7.43 (s, 1H), 4.66 (s, 2H), 3.17 (q, J=7.3 Hz, 2H), 2.30-2.13 (m, 2H), 2.00-1.80 (m, 4H), 1.72 (d, J=12.5 Hz, 1H), 1.56 (d, J=13.1 Hz, 2H), 1.38-1.18 (m, 4H). [M+H]=349.2.

Example 41. 5-Chloro-2-{[(2-hydroxyethyl)amino]methyl}-7,8-dihydro-6H-spiro[[1,3]oxazolo[5,4-f]quinazoline-9,1'-cyclohexane]-7-one

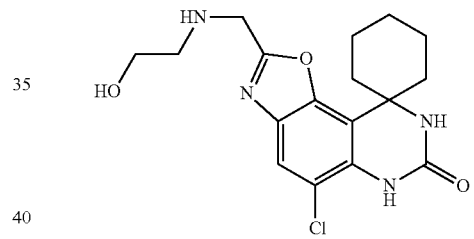

$^1$H NMR (400 MHz, DMSO-d6) δ 9.50 (br s, 2H), 8.53 (s, 1H), 7.88 (s, 1H), 7.42 (s, 1H), 5.30 (br s, 1H), 4.66 (s, 2H), 3.73 (t, J=5.2 Hz, 2H), 3.23 (t, J=5.1 Hz, 2H), 2.30-2.13 (m, 2H), 1.98-1.78 (m, 4H), 1.71 (d, J=11.6 Hz, 1H), 1.56 (d, J=12.8 Hz, 2H), 1.32 (d, J=13.1 Hz, 1H). [M+H]=365.2.

Example 42. 5-Chloro-2-[(4,4-difluoropiperidin-1-yl)methyl]-7,8-dihydro-6H-spiro[[1,3]oxazolo[5,4-f]quinazoline-9,1'-cyclohexane]-7-one

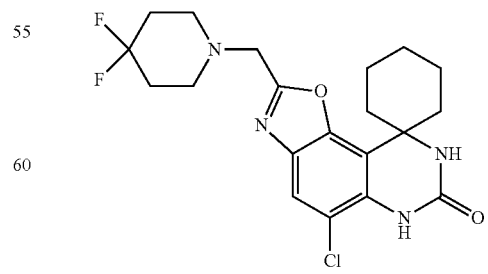

$^1$H NMR (400 MHz, CDCl$_3$) δ 7.65 (s, 1H), 7.18 (s, 1H), 5.61 (br s, 1H), 3.99 (s, 2H), 2.85 (br s, 4H), 2.37-2.21 (m,

2H), 2.17-1.95 (m, 4H), 1.92-1.76 (m, 4H), 1.71-1.53 (m, 3H), 1.47-1.32 (m, 1H). [M+H]=425.1.

Example 43. 5-Chloro-2-{[(2,2,2-trifluoroethyl)amino]methyl}-7,8-dihydro-6H-spiro[[1,3]oxazolo[5,4-f]quinazoline-9,1'-cyclohexane]-7-one

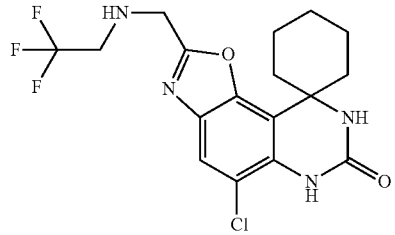 [SMILES: O=C1Nc2c(Cl)cc3nc(CNCC(F)(F)F)oc3c2C2(CCCCC2)N1]

$^1$H NMR (400 MHz, CDCl$_3$) δ 7.10 (s, 1H), 6.96 (s, 1H), 5.50 (s, 1H), 4.82 (br s, 1H), 4.44 (s, 2H), 4.20 (q, J=9.1 Hz, 2H), 2.38 (dt, J=4.3, 13.5 Hz, 2H), 1.94-1.46 (m, 7H), 1.40-1.20 (m, 1H). [M+H]=403.1.

Example 44. 5-Chloro-2-{[(2-hydroxyethyl)(methyl)amino]methyl}-7,8-dihydro-6H-spiro[[1,3]oxazolo[5,4-f]quinazoline-9,1'-cyclohexane]-7-one

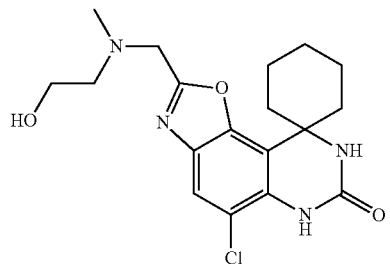 [SMILES: CN(CCO)Cc1nc2cc(Cl)c3c(c2o1)C1(CCCCC1)NC(=O)N3]

$^1$H NMR (400 MHz, CDCl$_3$) δ 7.67 (s, 1H), 7.18 (br s, 1H), 5.59 (br s, 1H), 4.21 (s, 2H), 3.88-3.72 (m, 2H), 3.00 (t, J=4.6 Hz, 2H), 2.70 (s, 3H), 2.28 (dt, J=3.9, 13.4 Hz, 2H), 2.04 (d, J=12.8 Hz, 2H), 1.95-1.74 (m, 4H), 1.61 (q, J=13.7 Hz, 2H), 1.43 (d, J=13.0 Hz, 1H). [M+H]=379.1.

Example 45. 5-Chloro-2-[(3,3-difluoroazetidin-1-yl)methyl]-7,8-dihydro-6H-spiro[[1,3]oxazolo[5,4-f]quinazoline-9,1'-cyclohexane]-7-one

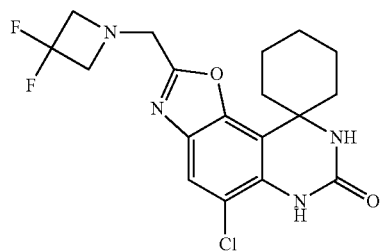 [SMILES: O=C1Nc2c(Cl)cc3nc(CN4CC(F)(F)C4)oc3c2C2(CCCCC2)N1]

$^1$H NMR (400 MHz, CDCl$_3$) δ 7.65 (s, 1H), 7.19 (br s, 1H), 5.66 (br s, 1H), 4.06 (s, 2H), 3.89 (t, J=12.0 Hz, 4H), 2.27 (dt, J=4.2, 13.5 Hz, 2H), 2.04 (d, J=12.7 Hz, 2H), 1.93-1.76 (m, 3H), 1.72-1.53 (m, 2H), 1.50-1.34 (m, 1H). [M+H]=397.0.

Example 46. 5-Chloro-2-[(3,3-difluoropyrrolidin-1-yl)methyl]-7,8-dihydro-6H-spiro[[1,3]oxazolo[5,4-f]quinazoline-9,1'-cyclohexane]-7-one

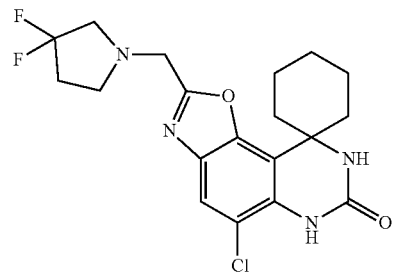 [SMILES: O=C1Nc2c(Cl)cc3nc(CN4CCC(F)(F)C4)oc3c2C2(CCCCC2)N1]

$^1$H NMR (400 MHz, CDCl$_3$) δ 7.65 (s, 1H), 7.19 (s, 1H), 5.64 (br s, 1H), 4.03 (s, 2H), 3.20 (t, J=13.3 Hz, 2H), 3.02 (t, J=7.0 Hz, 2H), 2.45-2.22 (m, 4H), 2.04 (d, J=12.5 Hz, 2H), 1.93-1.75 (m, 3H), 1.72-1.54 (m, 2H), 1.50-1.31 (m, 1H). [M+H]=411.1.

Example 47. 2-[(4-Acetylpiperazin-1-yl)methyl]-5-chloro-7,8-dihydro-6H-spiro[[1,3]oxazolo[5,4-f]quinazoline-9,1'-cyclohexane]-7-one

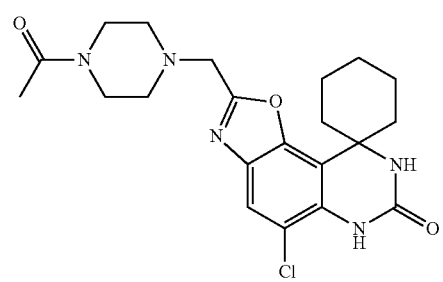

$^1$H NMR (400 MHz, CDCl$_3$) δ 7.71 (s, 1H), 7.50 (s, 1H), 6.50 (s, 1H), 4.28 (s, 2H), 3.90 (br s, 2H), 3.75 (t, J=4.7 Hz, 2H), 3.16-3.04 (m, 4H), 2.33-2.19 (m, 2H), 2.16 (s, 3H), 2.05 (d, J=13.1 Hz, 2H), 1.90 (d, J=12.6 Hz, 1H), 1.85-1.76 (m, 2H), 1.66 (q, J=13.7 Hz, 2H), 1.49-1.36 (m, 1H). [M+H]=432.2.

Example 48. 5-Chloro-2-[(4-propanoylpiperazin-1-yl)methyl]-7,8-dihydro-6H-spiro[[1,3]oxazolo[5,4-f]quinazoline-9,1'-cyclohexane]-7-one

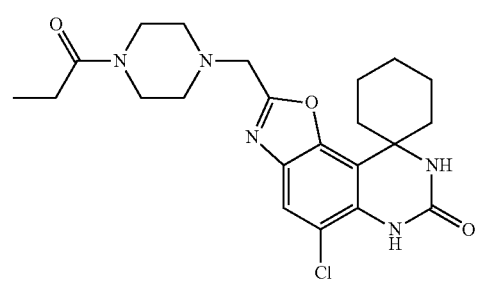

¹H NMR (400 MHz, CDCl₃) δ 7.70 (s, 1H), 7.45 (s, 1H), 6.36 (s, 1H), 4.28 (s, 2H), 3.90 (br s, 2H), 3.75 (br s, 2H), 3.09 (d, J=17.1 Hz, 4H), 2.28-2.18 (m, 4H), 2.05 (d, J=12.8 Hz, 2H), 1.89 (d, J=13.8 Hz, 1H), 1.85-1.75 (m, 2H), 1.65 (q, J=13.5 Hz, 2H), 1.50-1.33 (m, 1H), 1.18 (t, J=7.4 Hz, 3H). [M+H]=446.3.

Example 49. 5-Chloro-2-{2-oxa-8-azaspiro[4.5]decan-8-ylmethyl}-7,8-dihydro-6H-spiro[[1,3]oxazolo[5,4-f]quinazoline-9,1'-cyclohexane]-7-one

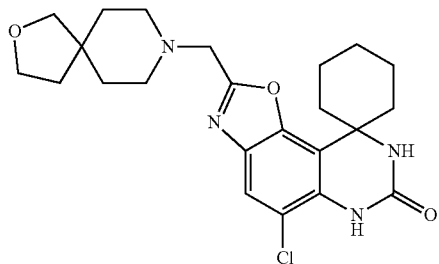 [SMILES: O=C1Nc2c(Cl)cc3nc(CN4CCC5(CCOC5)CC4)oc3c2C2(CCCCC2)N1]

¹H NMR (400 MHz, CDCl₃) δ 7.73 (s, 1H), 7.46 (s, 1H), 6.26 (s, 1H), 4.58 (s, 2H), 3.93 (t, J=7.2 Hz, 2H), 3.64 (s, 2H), 2.34-2.19 (m, 3H), 2.14-1.95 (m, 6H), 1.94-1.75 (m, 6H), 1.70-1.32 (m, 5H). [M+H]=445.3.

Example 50. 5-Chloro-2-{[4-(oxetan-3-yl)piperazin-1-yl]methyl}-7,8-dihydro-6H-spiro[[1,3]oxazolo[5,4-f]quinazoline-9,1'-cyclohexane]-7-one

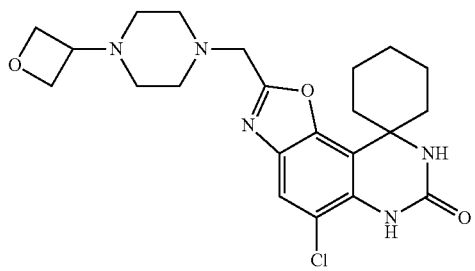 [SMILES: O=C1Nc2c(Cl)cc3nc(CN4CCN(C5COC5)CC4)oc3c2C2(CCCCC2)N1]

¹H NMR (400 MHz, CDCl₃) δ 7.77-7.64 (m, 1H), 7.58-7.47 (m, 1H), 6.56 (s, 1H), 5.06-4.94 (m, 2H), 4.81 (t, J=7.5 Hz, 2H), 4.17-4.11 (m, 1H), 4.10 (s, 2H), 3.58 (q, J=7.2 Hz, 1H), 3.20 (br s, 5H), 2.32-2.17 (m, 2H), 2.05 (d, J=13.2 Hz, 2H), 1.90 (d, J=13.1 Hz, 1H), 1.85-1.75 (m, 2H), 1.74-1.58 (m, 2H), 1.54 (t, J=7.2 Hz, 2H), 1.48-1.32 (m, 1H). [M+H]=446.3.

Example 51. 2-({5-Chloro-7-oxo-7,8-dihydro-6H-spiro[[1,3]oxazolo[5,4-f]quinazoline-9,1'-cyclohexane]-2-ylmethyl}amino)-N,N-dimethylacetamide

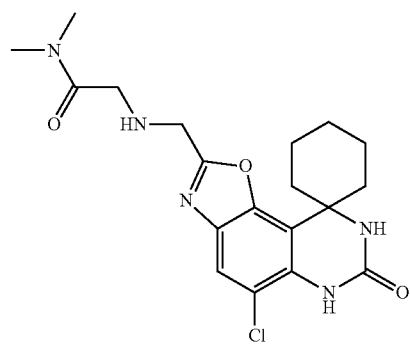 [SMILES: CN(C)C(=O)CNCc1nc2cc(Cl)c3c(c2o1)C1(CCCCC1)NC(=O)N3]

¹H NMR (400 MHz, DMSO-d6) δ 9.80 (br s, 1H), 8.55 (s, 1H), 7.89 (s, 1H), 7.43 (s, 1H), 4.59 (s, 2H), 4.24 (s, 2H), 2.93 (d, J=13.9 Hz, 6H), 2.29-2.15 (m, 2H), 1.99-1.80 (m, 4H), 1.71 (d, J=12.3 Hz, 1H), 1.55 (d, J=13.6 Hz, 2H), 1.32 (d, J=12.8 Hz, 1H). [M+H]=406.2.

Example 52. Tert-Butyl 2-[({5-chloro-7-oxo-7,8-dihydro-6H-spiro[[1,3]oxazolo[5,4-f]quinazoline-9,1'-cyclohexane]-2-ylmethyl}amino)methyl]piperidine-1-carboxylate

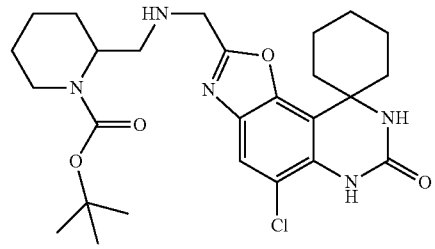 [SMILES: CC(C)(C)OC(=O)N1CCCCC1CNCc1nc2cc(Cl)c3c(c2o1)C1(CCCCC1)NC(=O)N3]

¹H NMR (400 MHz, CDCl₃) δ 7.66 (s, 1H), 7.48 (s, 1H), 6.41 (s, 1H), 4.71-4.42 (m, 2H), 3.95 (br s, 1H), 3.79 (t, J=11.8 Hz, 1H), 3.29 (dd, J=2.7, 12.6 Hz, 1H), 3.04 (br s, 1H), 2.39-2.16 (m, 2H), 2.03 (d, J=13.2 Hz, 2H), 1.93-1.61 (m, 10H), 1.53-1.49 (m, 2H), 1.48-1.41 (m, 11H). [M+H]=518.3.

Example 53. 5-Chloro-2-({[(3,5-difluoropyridin-2-yl)methyl]amino}methyl)-7,8-dihydro-6H-spiro[[1,3]oxazolo[5,4-f]quinazoline-9,1'-cyclohexane]-7-one

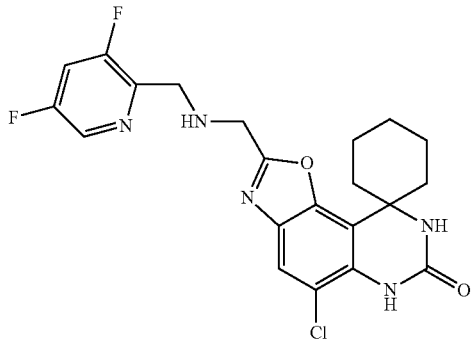 [SMILES: O=C1Nc2c(Cl)cc3nc(CNCc4ncc(F)cc4F)oc3c2C2(CCCCC2)N1]

¹H NMR (400 MHz, CDCl₃) δ 8.32 (d, J=2.3 Hz, 1H), 7.62 (s, 1H), 7.26-7.13 (m, 2H), 5.65 (s, 1H), 4.24 (s, 2H), 4.20 (d, J=1.0 Hz, 2H), 2.29 (dt, J=4.2, 13.5 Hz, 3H), 2.07-1.96 (m, 2H), 1.90-1.74 (m, 3H), 1.69-1.53 (m, 2H), 1.51-1.31 (m, 1H). [M+H]=448.1.

Example 54. 5-Chloro-2-{[(piperidin-2-ylmethyl)amino]methyl}-7,8-dihydro-6H-spiro[[1,3]oxazolo[5,4-f]quinazoline-9,1'-cyclohexane]-7-one

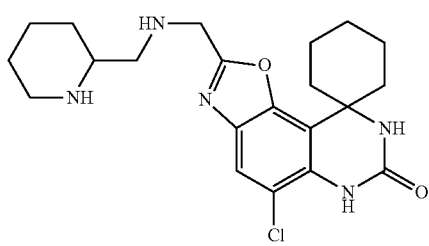 [SMILES: O=C1Nc2c(Cl)cc3nc(CNCC4CCCCN4)oc3c2C2(CCCCC2)N1]

¹H NMR (400 MHz, CDCl₃) δ 7.55 (s, 1H), 7.17 (br s, 1H), 6.94-6.84 (m, 1H), 5.74-5.48 (m, 2H), 4.91 (d, J=11.5 Hz, 1H), 4.27 (d, J=17.4 Hz, 1H), 4.07 (d, J=17.5 Hz, 1H), 3.89-3.45 (m, 4H), 3.30-3.11 (m, 3H), 3.03-2.93 (m, 2H), 2.85-2.75 (m, 2H), 2.64-2.56 (m, 2H), 2.37-2.11 (m, 3H), 2.06-1.27 (m, 4H). [M+H]=418.1.

Example 55. 5-Chloro-2-({[2-oxo-2-(piperidin-1-yl)ethyl]amino}methyl)-7,8-dihydro-6H-spiro[[1,3]oxazolo[5,4-f]quinazoline-9,1'-cyclohexane]-7-one

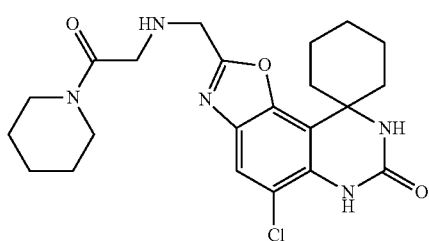 [SMILES: O=C1Nc2c(Cl)cc3nc(CNCC(=O)N4CCCCC4)oc3c2C2(CCCCC2)N1]

¹H NMR (400 MHz, DMSO-d6) δ 9.68 (br s, 1H), 8.55 (s, 1H), 7.89 (s, 1H), 7.43 (s, 1H), 4.58 (s, 2H), 4.24 (s, 2H), 3.56-3.46 (m, 3H), 2.29-2.15 (m, 2H), 2.02-1.79 (m, 4H), 1.71 (d, J=13.3 Hz, 1H), 1.66-1.39 (m, 9H), 1.32 (d, J=13.1 Hz, 1H). [M+H]=446.4.

Example 56. 2-({5-Chloro-7-oxo-7,8-dihydro-6H-spiro[[1,3]oxazolo[5,4-f]quinazoline-9,1'-cyclohexane]-2-ylmethyl}amino)-N-ethyl-N-methylacetamide

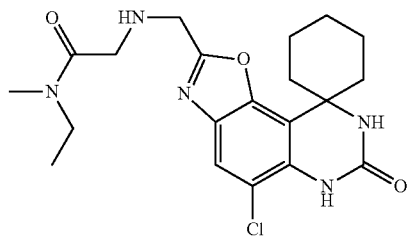 [SMILES: CCN(C)C(=O)CNCc1nc2cc(Cl)c3c(c2o1)C1(CCCCC1)NC(=O)N3]

¹H NMR (400 MHz, DMSO-d6) δ 8.55 (s, 1H), 7.89 (s, 1H), 7.43 (s, 1H), 4.60 (d, J=5.9 Hz, 2H), 4.24 (d, J=14.5 Hz, 2H), 3.41-3.34 (m, 1H), 3.27 (q, J=7.0 Hz, 1H), 2.90 (d, J=15.4 Hz, 3H), 2.30-2.15 (m, 2H), 1.96-1.80 (m, 4H), 1.71 (d, J=12.1 Hz, 1H), 1.55 (d, J=13.2 Hz, 2H), 1.42-1.28 (m, 2H), 1.17-0.98 (m, 3H). [M+H]=420.1.

Example 57. 5-Chloro-2-[(4-methyl-3-oxopiperazin-1-yl)methyl]-7,8-dihydro-6H-spiro[[1,3]oxazolo[5,4-f]quinazoline-9,1'-cyclohexane]-7-one

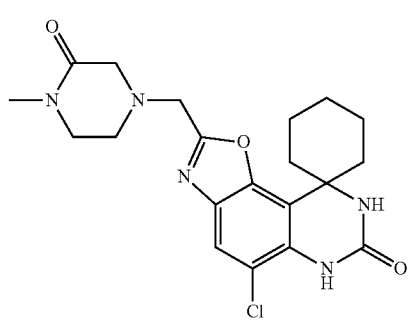 [SMILES: CN1CCN(Cc2nc3cc(Cl)c4c(c3o2)C2(CCCCC2)NC(=O)N4)CC1=O]

¹H NMR (400 MHz, DMSO-d6) δ 8.45 (s, 1H), 7.80 (s, 1H), 7.39 (s, 1H), 4.06 (s, 2H), 3.34-3.26 (m, 4H), 2.93 (t, J=5.4 Hz, 2H), 2.83 (s, 3H), 2.25-2.11 (m, 2H), 1.86 (d, J=10.8 Hz, 4H), 1.71 (d, J=12.2 Hz, 1H), 1.55 (d, J=14.1 Hz, 2H), 1.33-1.18 (m, 1H). [M+H]=418.1.

Example 58. 5-Chloro-2-[(4-ethyl-3-oxopiperazin-1-yl)methyl]-7,8-dihydro-6H-spiro[[1,3]oxazolo[5,4-f]quinazoline-9,1'-cyclohexane]-7-one

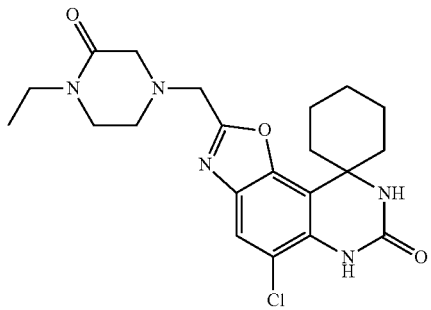 [SMILES: CCN1CCN(Cc2nc3cc(Cl)c4c(c3o2)C2(CCCCC2)NC(=O)N4)CC1=O]

¹H NMR (400 MHz, DMSO-d6) δ 8.44 (s, 1H), 7.79 (s, 1H), 7.39 (s, 1H), 4.05 (s, 2H), 3.35-3.25 (m, 6H), 2.91 (t, J=5.3 Hz, 2H), 2.25-2.11 (m, 2H), 1.86 (d, J=11.5 Hz, 4H), 1.71 (d, J=12.6 Hz, 1H), 1.55 (d, J=13.6 Hz, 2H), 1.35-1.16 (m, 1H), 1.02 (t, J=7.2 Hz, 3H). [M+H]=432.2.

Example 59. 5-Chloro-2-{[(pyridin-2-ylmethyl)amino]methyl}-7,8-dihydro-6H-spiro[[1,3]oxazolo[5,4-f]quinazoline-9,1'-cyclohexane]-7-one

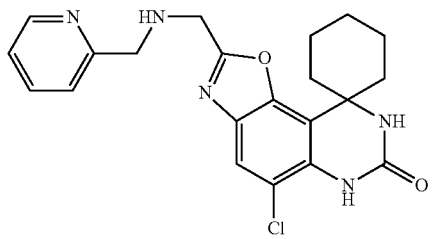 [SMILES: O=C1Nc2c(Cl)cc3nc(CNCc4ccccn4)oc3c2C2(CCCCC2)N1]

¹H NMR (400 MHz, DMSO-d6) δ 8.65 (d, J=4.2 Hz, 1H), 8.55 (s, 1H), 7.97-7.86 (m, 2H), 7.53 (d, J=7.8 Hz, 1H), 7.48-7.39 (m, 2H), 4.72 (s, 2H), 4.55 (s, 2H), 2.28-2.11 (m, 2H), 2.01-1.78 (m, 4H), 1.76-1.62 (m, 1H), 1.60-1.41 (m, 3H), 1.40-1.17 (m, 1H). [M+H]=412.1.

Example 60. 5-Chloro-2-{[(pyrimidin-2-ylmethyl)amino]methyl}-7,8-dihydro-6H-spiro[[1,3]oxazolo[5,4-f]quinazoline-9,1'-cyclohexane]-7-one

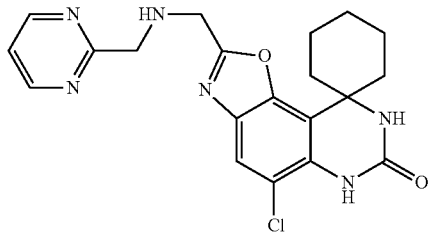 [SMILES: O=C1Nc2c(Cl)cc3nc(CNCc4ncccn4)oc3c2C2(CCCCC2)N1]

¹H NMR (400 MHz, DMSO-d6) δ 8.91 (d, J=5.0 Hz, 2H), 8.56 (s, 1H), 7.90 (s, 1H), 7.58 (t, J=5.0 Hz, 1H), 7.44 (s, 1H), 4.79 (s, 2H), 4.71 (s, 2H), 2.55 (s, 1H), 2.28-2.11 (m, 2H), 1.99-1.80 (m, 4H), 1.71 (d, J=12.0 Hz, 1H), 1.55 (d, J=13.2 Hz, 2H), 1.30 (d, J=13.6 Hz, 1H). [M+H]=413.1.

Example 61. 5-Chloro-2-({[(5-methoxypyridin-3-yl)methyl]amino}methyl)-7,8-dihydro-6H-spiro[[1,3]oxazolo[5,4-f]quinazoline-9,1'-cyclohexane]-7-one

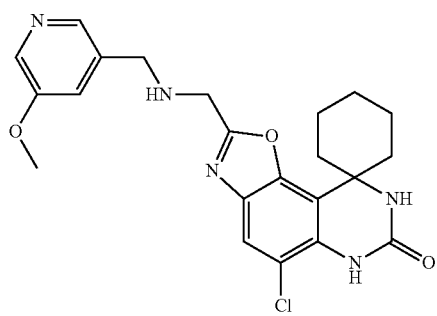 [SMILES: COc1cncc(CNCc2nc3cc(Cl)c4c(c3o2)C2(CCCCC2)NC(=O)N4)c1]

¹H NMR (400 MHz, DMSO-d6) δ 8.56 (d, J=1.2 Hz, 1H), 8.36 (d, J=2.8 Hz, 1H), 8.30 (d, J=1.7 Hz, 1H), 7.89 (s, 1H), 7.65-7.57 (m, 1H), 7.43 (s, 1H), 4.66 (s, 2H), 4.40 (s, 2H), 3.88-3.83 (m, 4H), 2.28-2.12 (m, 2H), 1.98-1.80 (m, 4H), 1.70 (d, J=12.2 Hz, 1H), 1.55 (d, J=13.6 Hz, 2H), 1.30 (q, J=12.6 Hz, 1H). [M+H]=442.1.

Example 62. 5-Chloro-2-[(2,4-dimethyl-3-oxopiperazin-1-yl)methyl]-7,8-dihydro-6H-spiro[[1,3]oxazolo[5,4-f]quinazoline-9,1'-cyclohexane]-7-one

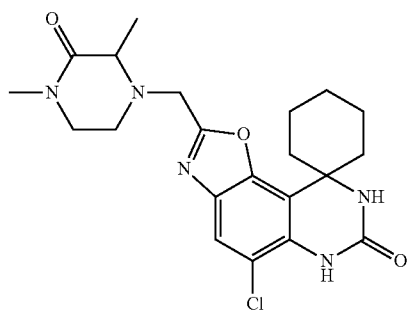 [SMILES: CC1C(=O)N(C)CCN1Cc1nc2cc(Cl)c3c(c2o1)C1(CCCCC1)NC(=O)N3]

¹H NMR (400 MHz, DMSO-d6) δ 8.43 (s, 1H), 7.79 (s, 1H), 7.40 (s, 1H), 4.16 (s, 2H), 3.39-3.31 (m, 1H), 3.26-3.11 (m, 2H), 2.89-2.74 (m, 4H), 2.27-2.10 (m, 2H), 1.85 (d, J=11.4 Hz, 4H), 1.75-1.49 (m, 4H), 1.37 (d, J=6.8 Hz, 3H), 1.30-1.12 (m, 1H). [M+H]=432.1.

Example 63. Ethyl 1-{5-chloro-7-oxo-7,8-dihydro-6H-spiro[[1,3]oxazolo[5,4-f]quinazoline-9,1'-cyclohexane]-2-ylmethyl}piperidine-4-carboxylate

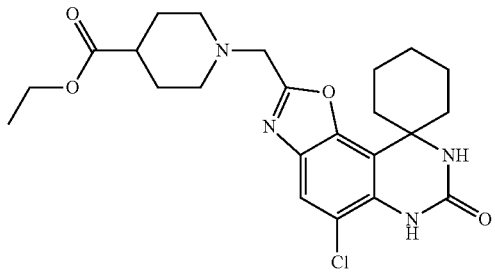 [SMILES: CCOC(=O)C1CCN(Cc2nc3cc(Cl)c4c(c3o2)C2(CCCCC2)NC(=O)N4)CC1]

¹H NMR (400 MHz, DMSO-d6) δ 8.54 (s, 1H), 7.88 (s, 1H), 7.43 (s, 1H), 4.57 (br s, 2H), 4.09 (q, J=6.6 Hz, 2H), 3.12-2.61 (m, 4H), 2.29-2.11 (m, 2H), 2.02-1.78 (m, 6H), 1.77-1.37 (m, 6H), 1.28 (d, J=12.3 Hz, 1H), 1.18 (t, J=7.1 Hz, 3H). [M+H]=461.2.

Example 64. 5-Chloro-2-({1-oxo-2-oxa-8-azaspiro[4.5]decan-8-yl}methyl)-7,8-dihydro-6H-spiro[[1,3]oxazolo[5,4-f]quinazoline-9,1'-cyclohexane]-7-one

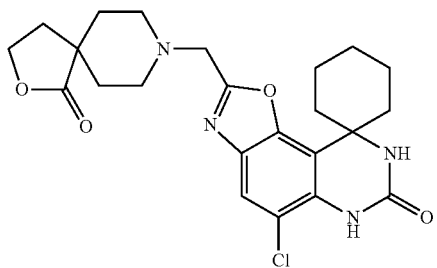 [SMILES: O=C1Nc2c(Cl)cc3nc(CN4CCC5(CCOC5=O)CC4)oc3c2C2(CCCCC2)N1]

¹H NMR (400 MHz, DMSO-d6) δ 8.57 (s, 1H), 7.90 (s, 1H), 7.44 (s, 1H), 4.72 (br s, 2H), 4.32 (t, J=7.0 Hz, 2H), 3.22 (br s, 2H), 2.34-2.14 (m, 5H), 2.08-1.80 (m, 9H), 1.72 (d, J=12.8 Hz, 1H), 1.56 (d, J=13.1 Hz, 2H), 1.41-1.18 (m, 1H). [M+H]=459.2.

Example 65. 2-[(4-Acetylpiperidin-1-yl)methyl]-5-chloro-7,8-dihydro-6H-spiro[[1,3]oxazolo[5,4-f]quinazoline-9,1'-cyclohexane]-7-one

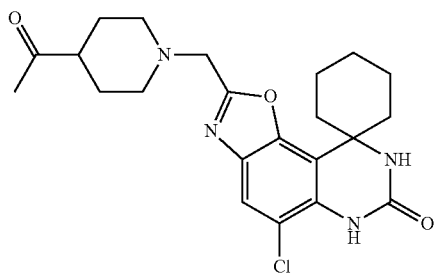

¹H NMR (400 MHz, DMSO-d6) δ 8.58 (s, 1H), 7.91 (s, 1H), 7.44 (s, 1H), 4.74 (br s, 2H), 3.13 (br s, 1H), 2.78-2.58 (m, 1H), 2.27-2.00 (m, 8H), 1.97-1.80 (m, 5H), 1.77-1.48 (m, 5H), 1.39-1.18 (m, 2H). [M+H]=431.1.

Example 66. Methyl 1-{5-chloro-7-oxo-7,8-dihydro-6H-spiro[[1,3]oxazolo[5,4-f]quinazoline-9,1'-cyclohexane]-2-ylmethyl}piperidine-4-carboxylate

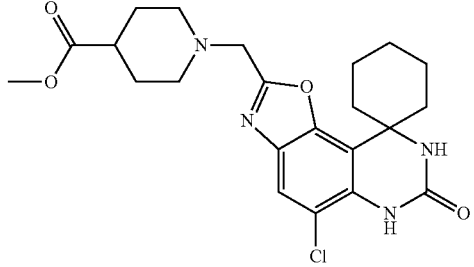 [SMILES: COC(=O)C1CCN(Cc2nc3cc(Cl)c4c(c3o2)C2(CCCCC2)NC(=O)N4)CC1]

¹H NMR (400 MHz, DMSO-d6) δ 8.57 (s, 1H), 7.90 (s, 1H), 7.44 (s, 1H), 4.68 (br s, 2H), 3.64 (s, 3H), 3.20-2.96 (m, 1H), 2.66 (d, J=16.0 Hz, 1H), 2.29-1.99 (m, 5H), 1.96-1.66 (m, 8H), 1.56 (d, J=14.4 Hz, 2H), 1.42-1.19 (m, 2H). [M+H]=447.2.

Example 67. 5-Chloro-2-({[(5-fluoropyridin-2-yl)methyl]amino}methyl)-7,8-dihydro-6H-spiro[[1,3]oxazolo[5,4-f]quinazoline-9,1'-cyclohexane]-7-one

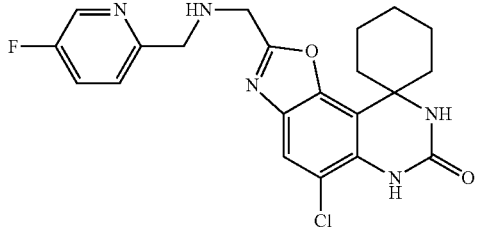 [SMILES: O=C1Nc2c(Cl)cc3nc(CNCc4ccc(F)cn4)oc3c2C2(CCCCC2)N1]

¹H NMR (400 MHz, DMSO-d6) δ 8.67 (d, J=2.9 Hz, 1H), 8.55 (s, 1H), 7.91-7.82 (m, 2H), 7.63 (dd, J=4.5, 8.7 Hz, 1H), 7.43 (s, 1H), 4.71 (s, 2H), 4.54 (s, 2H), 3.86 (s, 1H), 2.28-2.13 (m, 2H), 2.02-1.79 (m, 4H), 1.70 (d, J=11.9 Hz, 1H), 1.55 (d, J=13.4 Hz, 2H), 1.41-1.22 (m, 1H). [M+H]=430.1.

Example 68. 5-Chloro-2-{[3-(2-methylpropoxy)azetidin-1-yl]methyl}-7,8-dihydro-6H-spiro[[1,3]oxazolo[5,4-f]quinazoline-9,1'-cyclohexane]-7-one

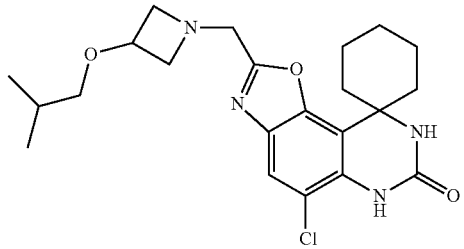 [SMILES: CC(C)COC1CN(Cc2nc3cc(Cl)c4c(c3o2)C2(CCCCC2)NC(=O)N4)C1]

¹H NMR (400 MHz, CDCl₃) δ 7.63 (s, 1H), 7.16 (s, 1H), 5.58 (s, 1H), 4.19 (t, J=6.0 Hz, 1H), 3.94 (s, 2H), 3.90-3.78 (m, 2H), 3.26-3.16 (m, 2H), 3.13 (d, J=6.6 Hz, 2H), 2.30 (dt, J=4.2, 13.5 Hz, 2H), 2.03 (d, J=12.8 Hz, 2H), 1.92-1.75 (m, 4H), 1.69-1.55 (m, 1H), 1.49-1.33 (m, 1H), 0.92 (d, J=6.7 Hz, 7H). [M+H]=433.1.

Example 69. 5-Chloro-2-[(4-ethoxypiperidin-1-yl)methyl]-7,8-dihydro-6H-spiro[[1,3]oxazolo[5,4-f]quinazoline-9,1'-cyclohexane]-7-one

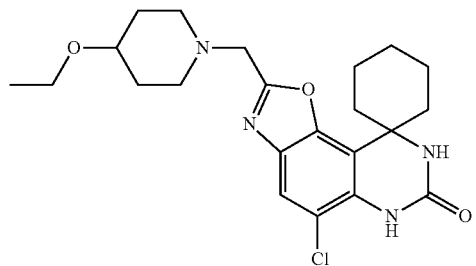 [SMILES: CCOC1CCN(Cc2nc3cc(Cl)c4c(c3o2)C2(CCCCC2)NC(=O)N4)CC1]

¹H NMR (400 MHz, CDCl₃) δ 7.64 (s, 1H), 7.15 (s, 1H), 5.54 (s, 1H), 3.89 (s, 2H), 3.51 (q, J=7.0 Hz, 2H), 3.34 (td, J=4.4, 8.4 Hz, 1H), 2.98-2.87 (m, 2H), 2.49-2.38 (m, 2H), 2.31 (dt, J=4.2, 13.6 Hz, 2H), 2.10-2.00 (m, 2H), 1.95 (dd, J=3.0, 14.0 Hz, 2H), 1.82 (d, J=18.0 Hz, 3H), 1.76-1.65 (m, 2H), 1.64-1.52 (m, 2H), 1.49-1.36 (m, 1H), 1.21 (t, J=7.0 Hz, 3H). [M+H]=433.2.

Example 70. 5-Chloro-2-{[4-(cyclopropylmethoxy)piperidin-1-yl]methyl}-7,8-dihydro-6H-spiro[[1,3]oxazolo[5,4-f]quinazoline-9,1'-cyclohexane]-7-one

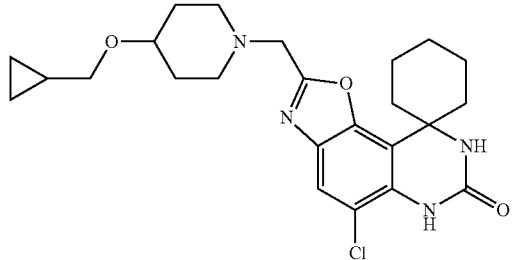 [SMILES: O=C1Nc2c(Cl)cc3nc(CN4CCC(OCC5CC5)CC4)oc3c2C2(CCCCC2)N1]

¹H NMR (400 MHz, CDCl₃) δ 7.64 (s, 1H), 7.15 (s, 1H), 5.57 (s, 1H), 3.89 (s, 2H), 3.36 (t, J=4.0 Hz, 1H), 3.29 (d, J=6.8 Hz, 2H), 3.01-2.85 (m, 2H), 2.49-2.37 (m, 2H), 2.30 (dt, J=4.1, 13.5 Hz, 2H), 2.13-1.99 (m, 2H), 1.95 (dd, J=3.7, 13.3 Hz, 2H), 1.90-1.78 (m, 3H), 1.77-1.69 (m, 2H), 1.68-1.54 (m, 2H), 1.48-1.32 (m, 1H), 1.13-1.00 (m, 1H), 0.60-0.49 (m, 2H), 0.25-0.16 (m, 2H). [M+H]=459.2.

Example 71. 5-Chloro-2-{[4-hydroxy-4-(trifluoromethyl)piperidin-1-yl]methyl}-7,8-dihydro-6H-spiro[[1,3]oxazolo[5,4-f]quinazoline-9,1'-cyclohexane]-7-one

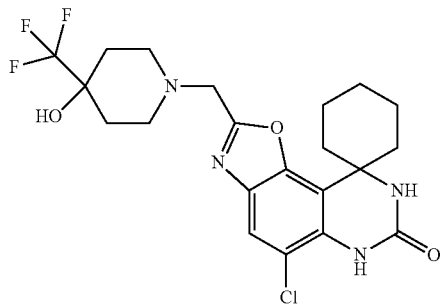 [SMILES: O=C1Nc2c(Cl)cc3nc(CN4CCC(O)(C(F)(F)F)CC4)oc3c2C2(CCCCC2)N1]

¹H NMR (400 MHz, CDCl₃) δ 7.65 (s, 1H), 7.16 (s, 1H), 5.56 (s, 1H), 3.94 (s, 2H), 2.98 (d, J=11.0 Hz, 2H), 2.70-2.57 (m, 3H), 2.29 (dt, J=4.1, 13.5 Hz, 2H), 2.14-1.98 (m, 4H), 1.91-1.73 (m, 6H), 1.69-1.54 (m, 1H), 1.48-1.32 (m, 1H). [M+H]=473.1.

Example 72. 5-Chloro-2-{[4-(propan-2-yloxy)piperidin-1-yl]methyl}-7,8-dihydro-6H-spiro[[1,3]oxazolo[5,4-f]quinazoline-9,1'-cyclohexane]-7-one

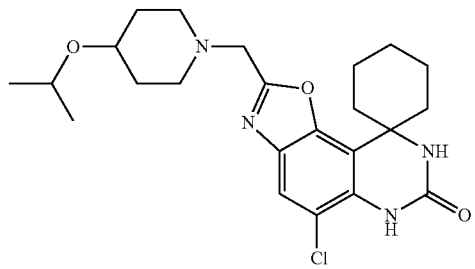 [SMILES: CC(C)OC1CCN(Cc2nc3cc(Cl)c4c(c3o2)C2(CCCCC2)NC(=O)N4)CC1]

¹H NMR (400 MHz, CDCl₃) δ 7.64 (s, 1H), 7.16 (s, 1H), 5.58 (s, 1H), 3.89 (s, 2H), 3.78-3.63 (m, 1H), 3.40 (td, J=4.3, 8.4 Hz, 1H), 2.99-2.85 (m, 2H), 2.49-2.37 (m, 2H), 2.31 (dt, J=4.2, 13.5 Hz, 2H), 2.03 (d, J=12.8 Hz, 2H), 1.95-1.76 (m, 5H), 1.73-1.51 (m, 4H), 1.42 (d, J=13.0 Hz, 1H), 1.15 (d, J=6.1 Hz, 6H). [M+H]=447.2.

Example 73. 5-Chloro-2-[(3-fluoroazetidin-1-yl)methyl]-7,8-dihydro-6H-spiro[[1,3]oxazolo[5,4-f]quinazoline-9,1'-cyclohexane]-7-one

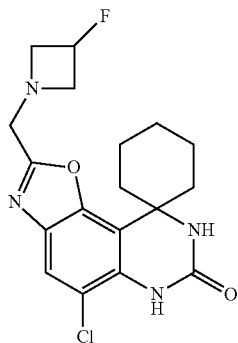 [SMILES: O=C1Nc2c(Cl)cc3nc(CN4CC(F)C4)oc3c2C2(CCCCC2)N1]

$^1$H NMR (400 MHz, CDCl$_3$) δ 7.64 (s, 1H), 7.18 (br s, 1H), 5.64 (br s, 1H), 5.34-5.09 (m, 1H), 4.02-3.85 (m, 4H), 3.55-3.38 (m, 2H), 2.29 (dt, J=4.2, 13.5 Hz, 2H), 2.09-1.98 (m, 2H), 1.91-1.76 (m, 3H), 1.69-1.54 (m, 2H), 1.49-1.32 (m, 1H). [M+H]=379.0.

Example 74. 5-Chloro-2-[(3-methoxyazetidin-1-yl)methyl]-7,8-dihydro-6H-spiro[[1,3]oxazolo[5,4-f]quinazoline-9,1'-cyclohexane]-7-one

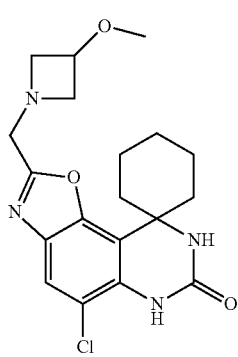 [SMILES: COC1CN(Cc2nc3cc(Cl)c4c(c3o2)C2(CCCCC2)NC(=O)N4)C1]

$^1$H NMR (400 MHz, CDCl$_3$) δ 7.63 (s, 1H), 7.18 (s, 1H), 5.67 (s, 1H), 4.14 (t, J=5.8 Hz, 1H), 3.94 (s, 2H), 3.89-3.81 (m, 2H), 3.29 (s, 3H), 3.24-3.15 (m, 2H), 2.29 (dt, J=4.0, 13.5 Hz, 2H), 2.02 (d, J=13.0 Hz, 2H), 1.90-1.79 (m, 2H), 1.71-1.55 (m, 3H), 1.49-1.32 (m, 1H). [M+H]=391.1.

Example 75. 5-Chloro-2-{[3-(methoxymethyl)azetidin-1-yl]methyl}-7,8-dihydro-6H-spiro[[1,3]oxazolo[5,4-f]quinazoline-9,1'-cyclohexane]-7-one

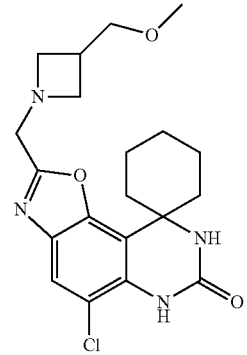

$^1$H NMR (400 MHz, CDCl$_3$) δ 7.63 (s, 1H), 7.17 (s, 1H), 5.64 (s, 1H), 3.89 (s, 2H), 3.61 (t, J=7.6 Hz, 2H), 3.54 (d, J=6.5 Hz, 2H), 3.37 (s, 3H), 3.26 (t, J=6.9 Hz, 2H), 2.89-2.76 (m, 1H), 2.30 (dt, J=4.1, 13.5 Hz, 2H), 2.02 (d, J=13.1 Hz, 2H), 1.90-1.75 (m, 3H), 1.65-1.54 (m, 2H), 1.49-1.36 (m, 1H). [M+H]=405.1.

Example 76. 5-Chloro-2-{7-oxa-2-azaspiro[3.5]nonan-2-ylmethyl}-7,8-dihydro-6H-spiro[[1,3]oxazolo[5,4-f]quinazoline-9,1'-cyclohexane]-7-one

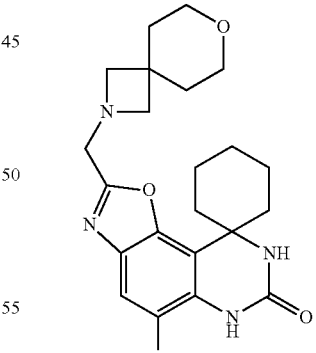

$^1$H NMR (400 MHz, DMSO-d6) δ 8.57 (s, 1H), 7.87 (s, 1H), 7.45 (s, 1H), 4.96 (s, 2H), 4.12 (s, 4H), 3.78-3.63 (m, 4H), 2.57-2.53 (m, 5H), 2.25-2.11 (m, 2H), 2.01-1.79 (m, 2H), 1.76-1.67 (m, 2H), 1.56 (d, J=12.6 Hz, 2H), 1.27 (d, J=13.0 Hz, 1H). [M+H]=431.2.

Example 77. 5-Chloro-2-[(4-methoxy-4-methylpiperidin-1-yl)methyl]-7,8-dihydro-6H-spiro[[1,3]oxazolo[5,4-f]quinazoline-9,1'-cyclohexane]-7-one

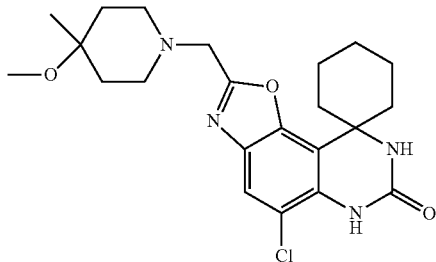 [SMILES: COC1(C)CCN(Cc2nc3cc(Cl)c4c(c3o2)C2(CCCCC2)NC(=O)N4)CC1]

¹H NMR (400 MHz, CDCl₃) δ 7.64 (s, 1H), 7.15 (s, 1H), 5.57 (s, 1H), 3.90 (s, 2H), 3.18 (s, 3H), 2.73 (d, J=10.5 Hz, 2H), 2.59 (t, J=10.3 Hz, 2H), 2.31 (dt, J=4.2, 13.4 Hz, 2H), 2.03 (d, J=13.4 Hz, 2H), 1.91-1.77 (m, 5H), 1.72-1.53 (m, 4H), 1.42 (d, J=13.0 Hz, 1H), 1.17 (s, 3H). [M+H]=433.2.

Example 78. 5-Chloro-2-({3-oxo-1-oxa-8-azaspiro[4.5]decan-8-yl}methyl)-7,8-dihydro-6H-spiro[[1,3]oxazolo[5,4-f]quinazoline-9,1'-cyclohexane]-7-one

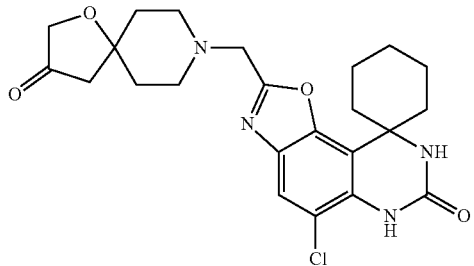 [SMILES: O=C1COC2(CCN(Cc3nc4cc(Cl)c5c(c4o3)C3(CCCCC3)NC(=O)N5)CC2)C1]

¹H NMR (400 MHz, DMSO-d6) δ 8.58 (s, 1H), 7.91 (s, 1H), 7.44 (s, 1H), 4.79 (br s, 2H), 4.04 (s, 2H), 3.45-3.04 (m, 2H), 2.55 (s, 2H), 2.27-2.17 (m, 2H), 2.08-1.81 (m, 8H), 1.72 (d, J=12.3 Hz, 1H), 1.56 (d, J=14.4 Hz, 2H), 1.39-1.23 (m, 3H). [M+H]=459.2.

Example 79. 2-({5-Chloro-7-oxo-7,8-dihydro-6H-spiro[[1,3]oxazolo[5,4-f]quinazoline-9,1'-cyclohexane]-2-ylmethyl}(methyl)amino)-N,N-dimethylacetamide

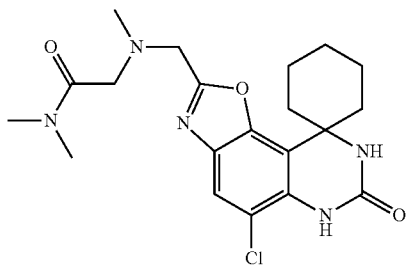 [SMILES: CN(CC(=O)N(C)C)Cc1nc2cc(Cl)c3c(c2o1)C1(CCCCC1)NC(=O)N3]

¹H NMR (400 MHz, DMSO-d6) δ 8.56 (s, 1H), 7.90 (s, 1H), 7.44 (s, 1H), 4.67 (br s, 2H), 4.31 (br s, 2H), 4.06-3.97 (m, 1H), 3.10 (dq, J=4.8, 7.3 Hz, 1H), 2.93 (s, 3H), 2.88 (s, 3H), 2.55 (s, 1H), 2.28-2.11 (m, 2H), 1.98-1.81 (m, 4H), 1.71 (d, J=12.0 Hz, 1H), 1.55 (d, J=13.2 Hz, 2H), 1.28 (d, J=12.3 Hz, 1H). [M+H]=420.1.

Example 80. 5-Chloro-2-({[(6-methylpyridin-3-yl)methyl]amino}methyl)-7,8-dihydro-6H-spiro[[1,3]oxazolo[5,4-f]quinazoline-9,1'-cyclohexane]-7-one

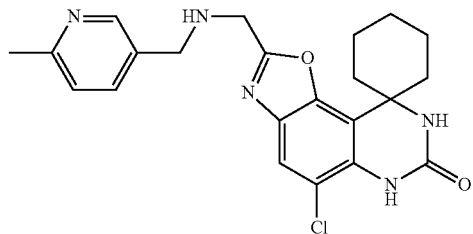 [SMILES: Cc1ccc(CNCc2nc3cc(Cl)c4c(c3o2)C2(CCCCC2)NC(=O)N4)cn1]

¹H NMR (400 MHz, DMSO-d6) δ 8.63 (d, J=2.0 Hz, 1H), 8.56 (s, 1H), 7.97 (dd, J=2.0, 7.9 Hz, 1H), 7.88 (s, 1H), 7.50-7.40 (m, 2H), 4.63 (s, 2H), 4.39 (s, 2H), 3.18-3.05 (m, 1H), 2.54 (s, 3H), 2.27-2.12 (m, 2H), 1.96-1.81 (m, 4H), 1.70 (d, J=12.0 Hz, 1H), 1.55 (d, J=13.3 Hz, 2H), 1.30 (q, J=13.0 Hz, 1H). [M+H]=426.1.

Example 81. 5-Chloro-2-{[methyl(oxan-4-ylmethyl)amino]methyl}-7,8-dihydro-6H-spiro[[1,3]oxazolo[5,4-f]quinazoline-9,1'-cyclohexane]-7-one

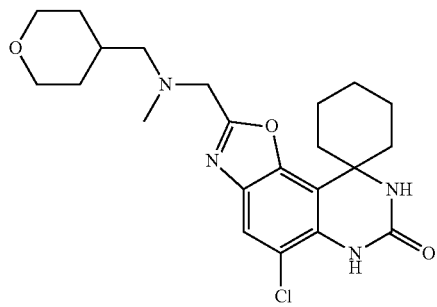 [SMILES: CN(Cc1nc2cc(Cl)c3c(c2o1)C1(CCCCC1)NC(=O)N3)CC1CCOCC1]

¹H NMR (400 MHz, DMSO-d6) δ 8.56 (s, 1H), 7.91 (s, 1H), 7.45 (s, 1H), 4.67 (br s, 2H), 3.85 (dd, J=2.6, 11.4 Hz, 2H), 3.36-3.26 (m, 2H), 3.02 (br s, 2H), 2.88-2.69 (m, 1H), 2.27-2.03 (m, 3H), 1.98-1.80 (m, 5H), 1.76-1.63 (m, 3H), 1.55 (d, J=13.2 Hz, 2H), 1.37-1.11 (m, 4H). [M+H]=433.2.

Example 82. 5-Chloro-2-({methyl[(3-methyloxetan-3-yl)methyl]amino}methyl)-7,8-dihydro-6H-spiro[[1,3]oxazolo[5,4-f]quinazoline-9,1'-cyclohexane]-7-one

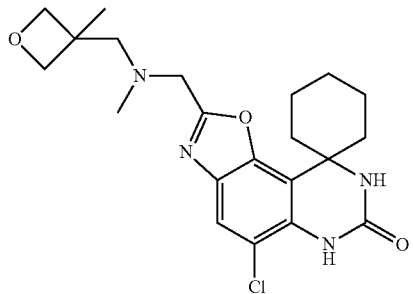 [SMILES: CN(Cc1nc2cc(Cl)c3c(c2o1)C1(CCCCC1)NC(=O)N3)CC1(C)COC1]

¹H NMR (400 MHz, DMSO-d6) δ 8.42 (s, 1H), 7.78 (s, 1H), 7.40 (s, 1H), 4.39 (d, J=5.6 Hz, 2H), 4.20 (d, J=5.7 Hz, 2H), 3.88 (s, 2H), 2.72 (s, 2H), 2.24 (s, 5H), 1.95-1.79 (m, 4H), 1.71 (d, J=12.3 Hz, 1H), 1.55 (d, J=13.4 Hz, 2H), 1.40-1.18 (m, 4H). [M+H]=419.1.

Example 83. 5-Chloro-2-({[(3-fluorooxetan-3-yl)methyl]amino}methyl)-7,8-dihydro-6H-spiro[[1,3]oxazolo[5,4-f]quinazoline-9,1'-cyclohexane]-7-one

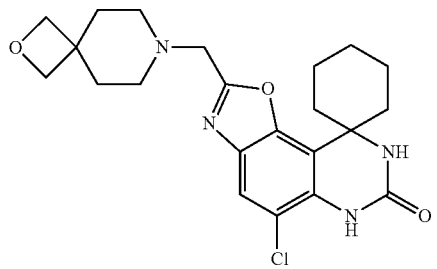 [SMILES: O=C1Nc2c(Cl)cc3nc(CN4CCC5(CC4)COC5)oc3c2C2(CCCCC2)N1]

¹H NMR (400 MHz, DMSO-d6) δ 8.40 (s, 1H), 7.75 (s, 1H), 7.36 (s, 1H), 4.66-4.48 (m, 4H), 4.07 (d, J=5.6 Hz, 2H), 3.22-3.05 (m, 2H), 2.85 (d, J=6.8 Hz, 1H), 2.28-2.13 (m, 2H), 1.97-1.79 (m, 4H), 1.70 (d, J=12.0 Hz, 1H), 1.55 (d, J=13.9 Hz, 2H), 1.38-1.22 (m, 1H). [M+H]=409.1.

Example 84. 5-Chloro-2-{[(oxan-4-ylmethyl)amino]methyl}-7,8-dihydro-6H-spiro[[1,3]oxazolo[5,4-f]quinazoline-9,1'-cyclohexane]-7-one

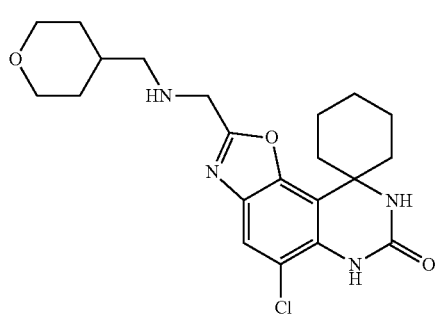 [SMILES: O=C1Nc2c(Cl)cc3nc(CNCC4CCOCC4)oc3c2C2(CCCCC2)N1]

¹H NMR (400 MHz, DMSO-d6) δ 8.39 (br s, 1H), 7.73 (s, 1H), 7.37 (s, 1H), 3.97 (s, 2H), 3.82 (dd, J=3.3, 11.0 Hz, 2H), 3.29-3.17 (m, 2H), 2.49 (br s, 2H), 2.27-2.12 (m, 2H), 1.99-1.77 (m, 4H), 1.75-1.44 (m, 7H), 1.39-1.21 (m, 1H), 1.19-1.02 (m, 2H). [M+H]=419.2.

Example 85. 5-Chloro-2-{2-oxa-7-azaspiro[3.5]nonan-7-ylmethyl}-7,8-dihydro-6H-spiro[[1,3]oxazolo[5,4-f]quinazoline-9,1'-cyclohexane]-7-one

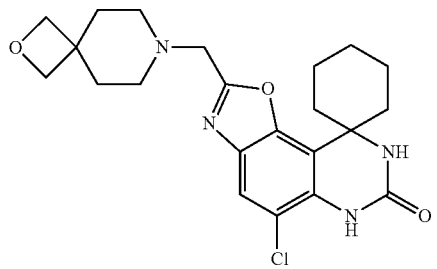 [SMILES: O=C1Nc2c(Cl)cc3nc(CN4CCC5(CC4)COC5)oc3c2C2(CCCCC2)N1]

¹H NMR (400 MHz, DMSO-d6) δ 8.41 (br s, 1H), 7.75 (s, 1H), 7.39 (s, 1H), 4.25 (s, 4H), 3.87 (s, 2H), 2.47 (br s, 3H), 2.26-2.10 (m, 2H), 1.99-1.62 (m, 10H), 1.55 (d, J=14.3 Hz, 2H), 1.32-1.15 (m, 1H). [M+H]=431.2.

Example 86. 5-Chloro-2-({[(3-methyloxetan-3-yl)methyl]amino}methyl)-7,8-dihydro-6H-spiro[[1,3]oxazolo[5,4-f]quinazoline-9,1'-cyclohexane]-7-one

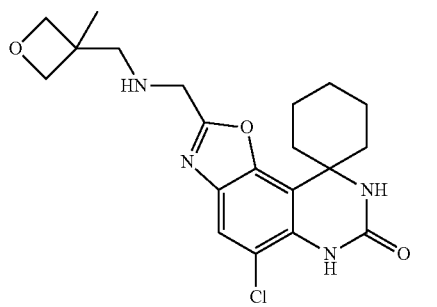 [SMILES: CC1(CNCc2nc3cc(Cl)c4c(c3o2)C2(CCCCC2)NC(=O)N4)COC1]

¹H NMR (400 MHz, DMSO-d6) δ 8.40 (s, 1H), 7.75 (s, 1H), 7.37 (s, 1H), 4.35 (d, J=5.6 Hz, 2H), 4.18 (d, J=5.6 Hz,

2H), 4.05 (br s, 2H), 2.80 (br s, 2H), 2.55 (s, 1H), 2.30-2.14 (m, 2H), 1.97-1.78 (m, 4H), 1.70 (d, J=12.1 Hz, 1H), 1.54 (d, J=13.3 Hz, 2H), 1.34-1.20 (m, 4H). [M+H]=405.1.

Example 87. 5-Chloro-2-{2-oxa-5-azabicyclo[2.2.1]heptan-5-ylmethyl}-7,8-dihydro-6H-spiro[[1,3]oxazolo[5,4-f]quinazoline-9,1'-cyclohexane]-7-one

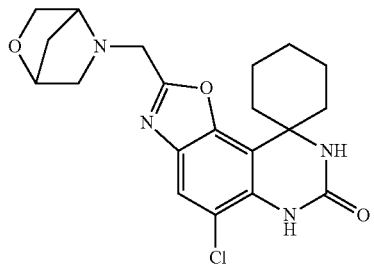

¹H NMR (400 MHz, DMSO-d6) δ 8.41 (s, 1H), 7.75 (s, 1H), 7.38 (s, 1H), 4.39 (s, 1H), 4.04 (d, J=2.4 Hz, 2H), 3.93-3.82 (m, 1H), 3.76-3.61 (m, 1H), 3.56 (dd, J=1.7, 7.7 Hz, 1H), 2.95 (dd, J=1.3, 9.9 Hz, 1H), 2.65 (d, J=10.1 Hz, 1H), 2.55 (s, 2H), 2.28-2.10 (m, 2H), 1.97-1.81 (m, 2H), 1.80-1.68 (m, 2H), 1.66-1.52 (m, 2H), 1.42-1.18 (m, 2H). [M+H]=403.1.

Example 88. 5-Chloro-2-{[methyl(2,2,2-trifluoroethyl)amino]methyl}-7,8-dihydro-6H-spiro[[1,3]oxazolo[5,4-f]quinazoline-9,1'-cyclohexane]-7-one

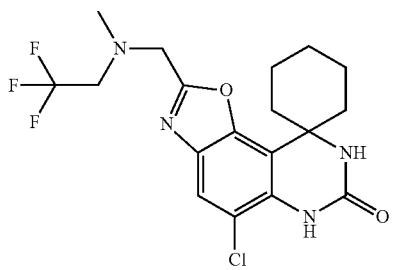 [SMILES: CN(Cc1nc2cc(Cl)c3c(c2o1)C1(CCCCC1)NC(=O)N3)CC(F)(F)F]

¹H NMR (400 MHz, DMSO-d6) δ 8.42 (s, 1H), 7.78 (s, 1H), 7.40 (s, 1H), 4.13 (s, 2H), 3.47 (q, J=10.0 Hz, 2H), 2.53 (s, 3H), 2.28-2.13 (m, 2H), 1.96-1.80 (m, 4H), 1.71 (d, J=12.7 Hz, 1H), 1.55 (d, J=13.9 Hz, 2H), 1.25 (d, J=13.1 Hz, 1H). [M+H]=417.0.

Example 89. 5-Chloro-2-{[(oxetan-3-ylmethyl)amino]methyl}-7,8-dihydro-6H-spiro[[1,3]oxazolo[5,4-f]quinazoline-9,1'-cyclohexane]-7-one

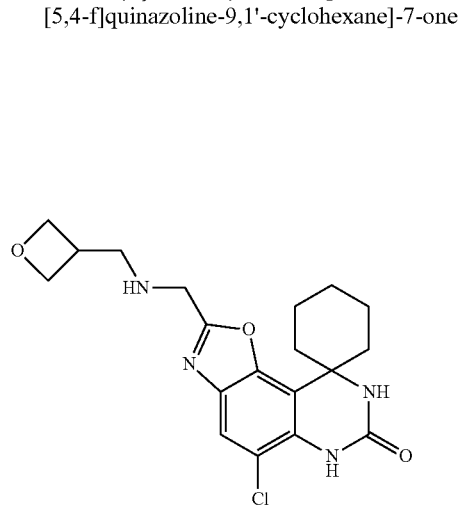

¹H NMR (400 MHz, CD₃OD) δ 7.78 (s, 1H), 4.92-4.89 (m, 2H), 4.76-4.65 (m, 2H), 4.54 (t, J=6.2 Hz, 1H), 3.67 (d, J=7.3 Hz, 2H), 3.54-3.45 (m, 1H), 3.37 (s, 1H), 3.23 (q, J=7.3 Hz, 1H), 2.43-2.27 (m, 2H), 2.02 (d, J=13.1 Hz, 2H), 1.91-1.80 (m, 3H), 1.78-1.70 (m, 2H), 1.33 (t, J=7.3 Hz, 3H). [M+H]=391.1.

Example 90. 5-Chloro-2-[(4-oxopiperidin-1-yl)methyl]-7,8-dihydro-6H-spiro[[1,3]oxazolo[5,4-f]quinazoline-9,1'-cyclohexane]-7-one

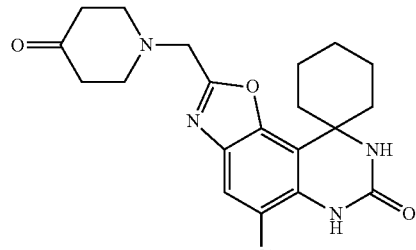

¹H NMR (400 MHz, DMSO-d6) δ 8.48 (s, 1H), 7.82 (s, 1H), 7.40 (s, 1H), 4.37 (br s, 2H), 3.20 (br s, 4H), 3.10 (dq, J=4.9, 7.3 Hz, 2H), 2.55 (s, 1H), 2.28-2.12 (m, 2H), 1.86 (d, J=11.0 Hz, 5H), 1.71 (d, J=12.5 Hz, 1H), 1.56 (d, J=14.1 Hz, 2H), 1.36-1.23 (m, 1H). [M+H]=403.1.

Example 91. 5-Chloro-2-({[(2-methoxyphenyl)methyl]amino}methyl)-7,8-dihydro-6H-spiro[[1,3]oxazolo[5,4-f]quinazoline-9,1'-cyclohexane]-7-one

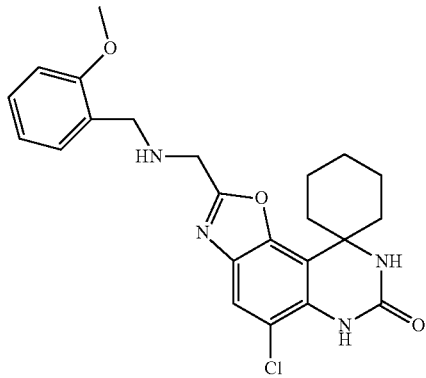 [SMILES: COc1ccccc1CNCc1nc2cc(Cl)c3c(c2o1)C1(CCCCC1)NC(=O)N3]

¹H NMR (400 MHz, CDCl₃) δ 7.63 (s, 1H), 7.44-7.37 (m, 1H), 7.35-7.31 (m, 1H), 7.01-6.93 (m, 3H), 6.06 (s, 1H), 4.47 (s, 2H), 4.44 (s, 2H), 3.91 (s, 3H), 3.22-3.11 (m, 1H), 2.28-2.14 (m, 2H), 1.99 (d, J=13.1 Hz, 2H), 1.90-1.72 (m, 3H), 1.69-1.53 (m, 2H), 1.41 (d, J=13.0 Hz, 1H). [M+H]=441.2.

Example 92. 5-Chloro-2-({[(2,4-dimethoxyphenyl)methyl]amino}methyl)-7,8-dihydro-6H-spiro[[1,3]oxazolo[5,4-f]quinazoline-9,1'-cyclohexane]-7-one

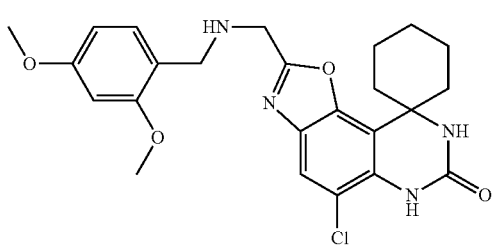 [SMILES: COc1ccc(CNCc2nc3cc(Cl)c4c(c3o2)C2(CCCCC2)NC(=O)N4)c(OC)c1]

¹H NMR (400 MHz, CDCl₃) δ 7.62 (s, 1H), 7.39 (s, 1H), 7.23 (d, J=8.6 Hz, 1H), 6.50-6.42 (m, 2H), 6.24 (s, 1H), 4.44 (s, 2H), 4.37 (s, 2H), 3.89-3.76 (m, 6H), 3.24-3.09 (m, 1H), 2.22 (dt, J=4.2, 13.4 Hz, 2H), 1.98 (d, J=12.6 Hz, 2H), 1.88-1.72 (m, 3H), 1.62 (q, J=13.7 Hz, 2H), 1.48-1.36 (m, 1H). [M+H]=471.2.

Example 93. 5-Chloro-2-{[4-(propan-2-yl)piperazin-1-yl]methyl}-7,8-dihydro-6H-spiro[[1,3]oxazolo[5,4-f]quinazoline-9,1'-cyclohexane]-7-one

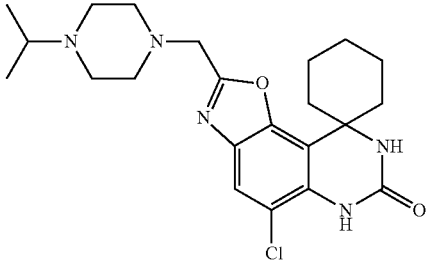

¹H NMR (400 MHz, CDCl₃) δ 7.61 (s, 1H), 7.23 (s, 1H), 5.83 (s, 1H), 4.14 (s, 2H), 3.63-3.51 (m, 2H), 3.38 (s, 3H), 3.02-2.91 (m, 2H), 2.34-2.21 (m, 3H), 2.01 (d, J=12.8 Hz, 2H), 1.91-1.74 (m, 3H), 1.70-1.53 (m, 2H), 1.49-1.37 (m, 1H). [M+H]=432.2.

Example 94. 5-Chloro-2-[(3,3,4-trimethylpiperazin-1-yl)methyl]-7,8-dihydro-6H-spiro[[1,3]oxazolo[5,4-f]quinazoline-9,1'-cyclohexane]-7-one

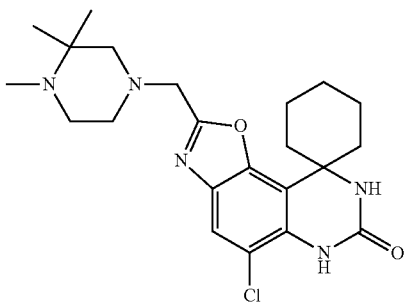 [SMILES: CN1CCN(Cc2nc3cc(Cl)c4c(c3o2)C2(CCCCC2)NC(=O)N4)CC1(C)C]

¹H NMR (400 MHz, CDCl₃) δ 7.66 (s, 1H), 7.36 (s, 1H), 6.18 (s, 1H), 3.94 (d, J=3.9 Hz, 2H), 3.52 (d, J=12.3 Hz, 1H), 3.25-3.07 (m, 2H), 3.05-2.78 (m, 3H), 2.74 (s, 3H), 2.34-2.20 (m, 2H), 2.04 (d, J=13.2 Hz, 2H), 1.95-1.76 (m, 3H), 1.72-1.50 (m, 3H), 1.47 (s, 6H). [M+H]=432.2.

Example 95. 5-Chloro-2-{[2-(hydroxymethyl)piperidin-1-yl]methyl}-7,8-dihydro-6H-spiro[[1,3]oxazolo[5,4-f]quinazoline-9,1'-cyclohexane]-7-one

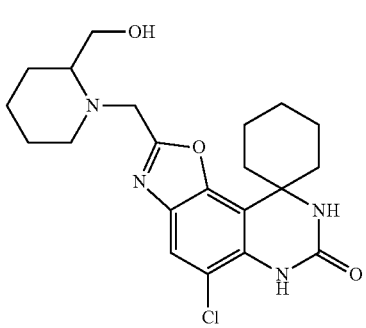 [SMILES: O=C1Nc2c(Cl)cc3nc(CN4CCCCC4CO)oc3c2C2(CCCCC2)N1]

¹H NMR (400 MHz, CDCl₃) δ 7.71 (s, 1H), 7.41 (s, 1H), 6.11 (s, 1H), 5.10-5.01 (m, 1H), 4.58 (d, J=16.1 Hz, 1H), 4.19 (dd, J=3.1, 13.4 Hz, 1H), 3.87 (dd, J=4.3, 13.5 Hz, 1H), 3.66-3.54 (m, 3H), 3.46-3.35 (m, 1H), 3.17 (dq, J=4.6, 7.3 Hz, 2H), 2.32-2.16 (m, 2H), 2.09-1.78 (m, 7H), 1.66-1.41 (m, 5H). [M+H]=419.2.

Example 96. 5-Chloro-2-({[1-(hydroxymethyl)cyclopentyl]amino}methyl)-7,8-dihydro-6H-spiro[[1,3]oxazolo[5,4-f]quinazoline-9,1'-cyclohexane]-7-one

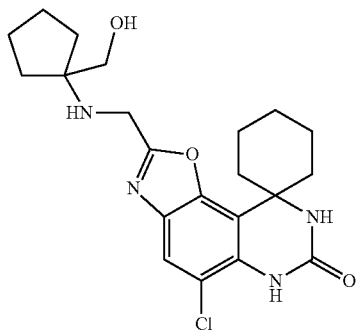 [SMILES: O=C1Nc2c(Cl)cc3nc(CNC4(CO)CCCC4)oc3c2C2(CCCCC2)N1]

¹H NMR (400 MHz, CDCl₃) δ 7.60 (s, 1H), 7.22 (s, 1H), 5.88 (s, 1H), 4.58 (s, 2H), 3.78 (s, 2H), 3.59 (q, J=7.3 Hz, 1H), 3.21-3.12 (m, 1H), 2.26-2.13 (m, 2H), 2.08-1.49 (m, 16H). [M+H]=419.16.

Example 97. 5-Chloro-2-{[(2R)-2-(hydroxymethyl)pyrrolidin-1-yl]methyl}-7,8-dihydro-6H-spiro[[1,3]oxazolo[5,4-f]quinazoline-9,1'-cyclohexane]-7-one

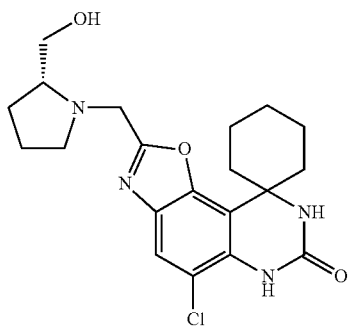 [SMILES: O=C1Nc2c(Cl)cc3nc(CN4CCC[C@@H]4CO)oc3c2C2(CCCCC2)N1]

¹H NMR (400 MHz, CDCl₃) δ 7.70 (s, 1H), 7.43 (s, 1H), 6.17 (s, 1H), 4.81 (s, 2H), 4.07-3.84 (m, 4H), 3.47 (td, J=7.7, 11.2 Hz, 1H), 3.17 (dq, J=4.7, 7.3 Hz, 1H), 2.33-2.13 (m, 5H), 2.06-1.75 (m, 6H), 1.69-1.56 (m, 2H), 1.51-1.41 (m, 1H). [M+H]=405.1.

Example 98. 5-Chloro-2-[(2-methylpiperidin-1-yl)methyl]-7,8-dihydro-6H-spiro[[1,3]oxazolo[5,4-f]quinazoline-9,1'-cyclohexane]-7-one

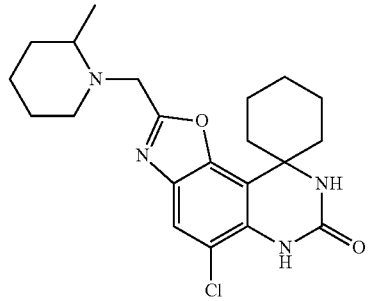 [SMILES: CC1CCCCN1Cc1nc2cc(Cl)c3c(c2o1)C1(CCCCC1)NC(=O)N3]

¹H NMR (400 MHz, CDCl₃) δ 7.75-7.69 (m, 1H), 7.44 (s, 1H), 6.19 (s, 1H), 4.88-4.58 (m, 2H), 3.71-3.07 (m, 4H), 2.22 (dd, J=4.0, 10.8 Hz, 2H), 2.11-1.75 (m, 9H), 1.71-1.39 (m, 7H). [M+H]=403.

Example 99. 5-Chloro-2-{[2-(2-methylpropyl)morpholin-4-yl]methyl}-7,8-dihydro-6H-spiro[[1,3]oxazolo[5,4-f]quinazoline-9,1'-cyclohexane]-7-one

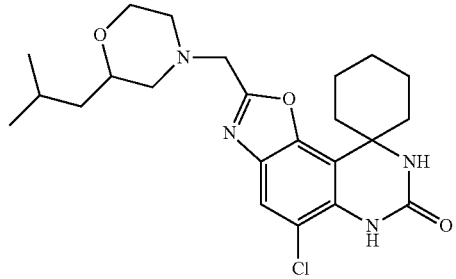 [SMILES: CC(C)CC1CN(Cc2nc3cc(Cl)c4c(c3o2)C2(CCCCC2)NC(=O)N4)CCO1]

¹H NMR (400 MHz, CDCl₃) δ 7.70 (s, 1H), 7.32 (br s, 1H), 5.93 (br s, 1H), 4.34 (s, 2H), 4.09-3.80 (m, 3H), 3.36 (d, J=11.5 Hz, 2H), 3.24-3.14 (m, 1H), 2.70-2.56 (m, 2H), 2.32-2.18 (m, 2H), 2.04 (d, J=13.1 Hz, 2H), 1.93-1.74 (m, 3H), 1.62 (q, J=13.7 Hz, 2H), 1.53-1.39 (m, 2H), 1.30-1.15 (m, 1H), 0.93 (t, J=6.3 Hz, 6H). [M+H]=447.3.

Example 100. 5-Chloro-2-{[(2-cyclobutyl-2,2-difluoroethyl)amino]methyl}-7,8-dihydro-6H-spiro[[1,3]oxazolo[5,4-f]quinazoline-9,1'-cyclohexane]-7-one

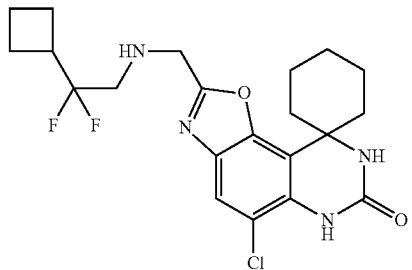 [SMILES: O=C1Nc2c(Cl)cc3nc(CNCC(F)(F)C4CCC4)oc3c2C2(CCCCC2)N1]

¹H NMR (400 MHz, CDCl₃) δ 7.66 (s, 1H), 7.45 (s, 1H), 6.46 (s, 1H), 4.34 (s, 2H), 3.26-3.16 (m, 2H), 2.97-2.78 (m, 1H), 2.38-1.59 (m, 16H), 1.51-1.38 (m, 1H). [M+H]=439.2.

Example 101. 5-Chloro-2-[(3-ethylmorpholin-4-yl)methyl]-7,8-dihydro-6H-spiro[[1,3]oxazolo[5,4-f]quinazoline-9,1'-cyclohexane]-7-one

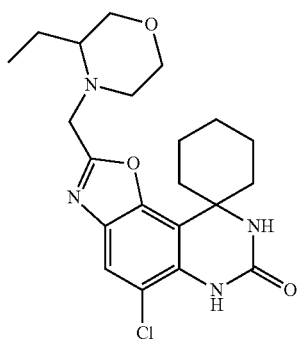 [SMILES: CCC1COCCN1Cc1nc2cc(Cl)c3c(c2o1)C1(CCCCC1)NC(=O)N3]

¹H NMR (400 MHz, CDCl₃) δ 7.73 (s, 1H), 7.44 (s, 1H), 6.25 (s, 1H), 4.70-4.50 (m, 2H), 4.11-3.93 (m, 3H), 3.77 (dd, J=9.2, 12.7 Hz, 1H), 3.51-3.33 (m, 2H), 3.31-3.13 (m, 2H), 2.28-2.18 (m, 2H), 2.11-2.02 (m, 2H), 1.96-1.81 (m, 2H), 1.66 (q, J=14.3 Hz, 2H), 1.47-1.30 (m, 3H), 1.03 (t, J=7.5 Hz, 3H). [M+H]=419.2.

Example 102. 5-Chloro-2-{[(2-cyclohexyl-2-hydroxyethyl)amino]methyl}-7,8-dihydro-6H-spiro[[1,3]oxazolo[5,4-f]quinazoline-9,1'-cyclohexane]-7-one

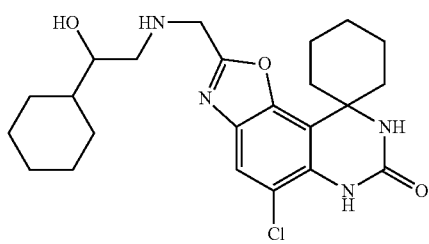 [SMILES: O=C1Nc2c(Cl)cc3nc(CNCC(O)C4CCCCC4)oc3c2C2(CCCCC2)N1]

¹H NMR (400 MHz, DMSO-d6) δ 8.55 (s, 1H), 7.89 (s, 1H), 7.44 (s, 1H), 5.36 (br s, 1H), 4.62 (s, 2H), 3.61 (br s, 1H), 3.28 (d, J=9.9 Hz, 1H), 3.15-3.01 (m, 2H), 2.29-2.15 (m, 2H), 1.97-1.80 (m, 4H), 1.72 (d, J=15.8 Hz, 3H), 1.66-1.52 (m, 4H), 1.39-1.27 (m, 2H), 1.23-1.08 (m, 4H), 1.07-0.93 (m, 2H). [M+H]=447.3.

Example 103. 5-Chloro-2-{6-oxa-9-azaspiro[4.5]decan-9-ylmethyl}-7,8-dihydro-6H-spiro[[1,3]oxazolo[5,4-f]quinazoline-9,1'-cyclohexane]-7-one

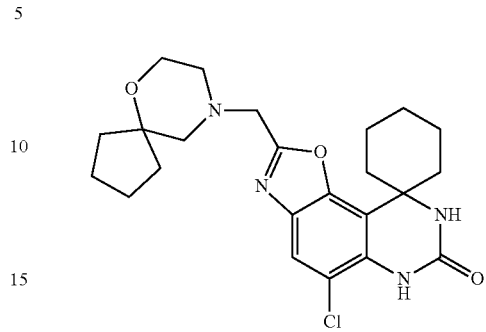

¹H NMR (400 MHz, CDCl₃) δ 7.72 (s, 1H), 7.49 (s, 1H), 6.37 (s, 1H), 4.46 (s, 2H), 3.95 (t, J=4.8 Hz, 2H), 3.27 (br s, 2H), 3.18-3.13 (m, 2H), 2.32-2.17 (m, 2H), 2.10-1.92 (m, 4H), 1.91-1.75 (m, 5H), 1.73-1.61 (m, 6H), 1.53-1.40 (m, 1H). [M+H]=445.1.

Example 104. 5-Chloro-2-({[1-(oxan-2-yl)ethyl]amino}methyl)-7,8-dihydro-6H-spiro[[1,3]oxazolo[5,4-f]quinazoline-9,1'-cyclohexane]-7-one

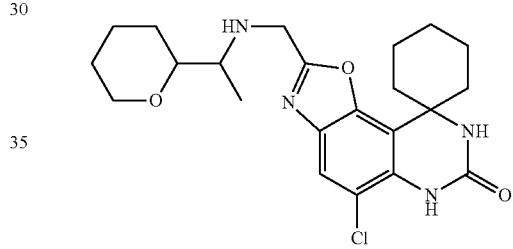

¹H NMR (400 MHz, CDCl₃) δ 7.71-7.61 (m, 1H), 7.32 (br s, 1H), 6.05 (s, 1H), 4.93-4.68 (m, 1H), 4.60-4.42 (m, 1H), 4.01 (d, J=10.1 Hz, 1H), 3.72 (d, J=10.4 Hz, 1H), 3.61-3.39 (m, 2H), 3.28-3.11 (m, 1H), 2.24 (dt, J=3.7, 13.4 Hz, 2H), 2.07-1.91 (m, 3H), 1.88-1.74 (m, 3H), 1.69-1.52 (m, 6H), 1.46-1.31 (m, 5H). [M+H]=433.2.

Example 105. 5-Chloro-2-{[(oxan-2-ylmethyl)amino]methyl}-7,8-dihydro-6H-spiro[[1,3]oxazolo[5,4-f]quinazoline-9,1'-cyclohexane]-7-one

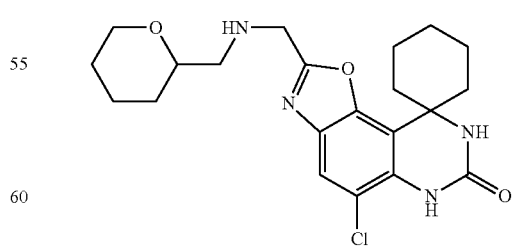

¹H NMR (400 MHz, CDCl₃) δ 7.69 (s, 1H), 7.27 (br s, 1H), 5.85 (s, 1H), 4.74-4.63 (m, 1H), 4.59-4.45 (m, 1H), 4.01 (d, J=10.1 Hz, 1H), 3.77 (t, J=10.5 Hz, 1H), 3.48 (t, J=7.0 Hz, 1H), 3.40-3.33 (m, 1H), 3.20-3.08 (m, 2H), 2.31-2.18 (m, 2H), 2.01 (d, J=12.7 Hz, 2H), 1.93-1.75 (m, 4H), 1.69-1.52 (m, 7H), 1.43 (d, J=13.0 Hz, 1H). [M+H]=419.2.

Example 106. 5-Chloro-2-{[(3-methyl-2-oxobutyl)amino]methyl}-7,8-dihydro-6H-spiro[[1,3]oxazolo[5,4-f]quinazoline-9,1'-cyclohexane]-7-one

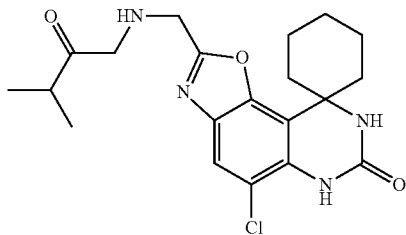

$^1$H NMR (400 MHz, DMSO-d6) δ 8.62 (s, 1H), 7.98 (s, 1H), 7.50 (s, 1H), 4.94 (s, 2H), 3.70 (br s, 1H), 3.40 (q, J=7.1 Hz, 2H), 3.10 (dq, J=4.9, 7.3 Hz, 1H), 2.28-2.11 (m, 2H), 1.88 (d, J=11.9 Hz, 4H), 1.74 (d, J=11.9 Hz, 1H), 1.56 (d, J=12.8 Hz, 2H), 1.36 (t, J=7.2 Hz, 7H). [M+H]=405.2.

Example 107. 5-Chloro-2-{[(4,4-difluorocyclohexyl)amino]methyl}-7,8-dihydro-6H-spiro[[1,3]oxazolo[5,4-f]quinazoline-9,1'-cyclohexane]-7-one

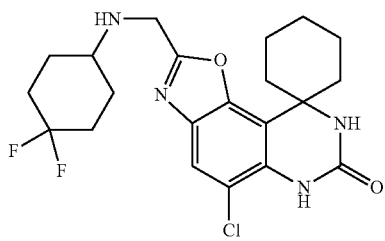 [SMILES: O=C1Nc2c(Cl)cc3nc(CNC4CCC(F)(F)CC4)oc3c2C2(CCCCC2)N1]

$^1$H NMR (400 MHz, CDCl3) δ 7.64 (s, 1H), 7.26 (s, 1H), 5.99 (s, 1H), 4.47 (s, 2H), 3.33 (br s, 1H), 3.23-3.13 (m, 1H), 2.66 (s, 1H), 2.31-2.12 (m, 5H), 2.04-1.73 (m, 8H), 1.70-1.48 (m, 3H), 1.40 (br s, 1H). [M+H]=439.2.

Example 108. 5-Chloro-2-({[(1R,4R)-4-methoxycyclohexyl]amino}methyl)-7,8-dihydro-6H-spiro[[1,3]oxazolo[5,4-f]quinazoline-9,1'-cyclohexane]-7-one

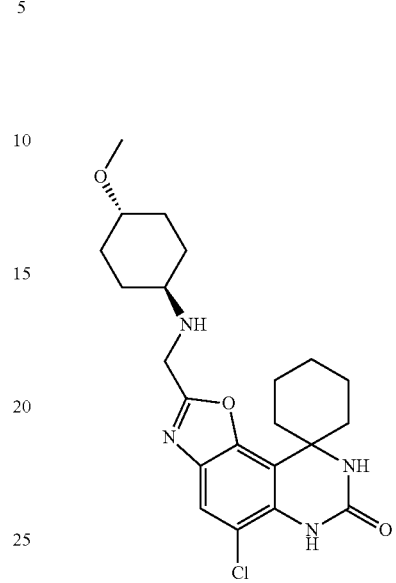

$^1$H NMR (400 MHz, CDCl3) δ 7.63 (s, 1H), 7.25 (s, 1H), 5.99 (s, 1H), 4.52 (s, 2H), 3.58 (q, J=6.9 Hz, 1H), 3.41-3.31 (m, 4H), 3.28-3.06 (m, 1H), 2.31-2.07 (m, 6H), 1.98 (d, J=13.1 Hz, 2H), 1.87-1.49 (m, 7H), 1.31-1.18 (m, 3H). [M+H]=433.2.

Example 109. 5-Chloro-2-[(1R,4R)-2-oxa-5-azabicyclo[2.2.1]heptan-5-ylmethyl]-7,8-dihydro-6H-spiro[[1,3]oxazolo[5,4-f]quinazoline-9,1'-cyclohexane]-7-one

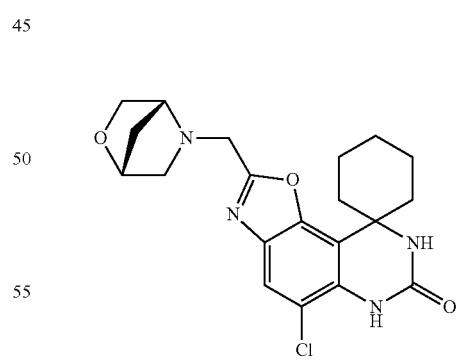

$^1$H NMR (400 MHz, CDCl3) δ 7.64 (s, 1H), 7.15 (br s, 1H), 5.54 (br s, 1H), 4.50 (s, 1H), 4.22-4.12 (m, 1H), 4.08 (d, J=3.8 Hz, 2H), 3.80-3.65 (m, 2H), 3.17 (d, J=10.1 Hz, 1H), 2.78 (d, J=10.3 Hz, 1H), 2.29 (dt, J=3.8, 13.5 Hz, 2H), 2.11-1.93 (m, 3H), 1.90-1.76 (m, 4H), 1.70-1.60 (m, 2H), 1.42 (q, J=12.9 Hz, 1H). [M+H]=403.1.

Example 110. 5-Chloro-2-[(1S,4S)-2-oxa-5-azabicyclo[2.2.1]heptan-5-ylmethyl]-7,8-dihydro-6H-spiro[[1,3]oxazolo[5,4-f]quinazoline-9,1'-cyclohexane]-7-one

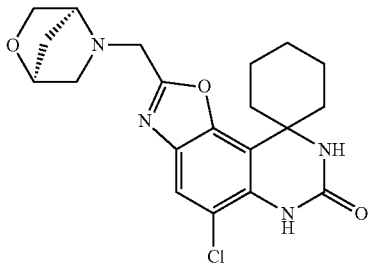 [SMILES: O=C1Nc2c(Cl)cc3nc(CN4C[C@@H]5C[C@H]4CO5)oc3c2C2(CCCCC2)N1]

$^1$H NMR (400 MHz, DMSO-d6) δ 11.20-10.61 (m, 1H), 8.58 (s, 1H), 7.90 (s, 1H), 7.46 (s, 1H), 4.96 (d, J=18.2 Hz, 2H), 4.79-4.51 (m, 2H), 4.44-3.94 (m, 1H), 3.80 (d, J=9.5 Hz, 1H), 3.75-3.61 (m, 1H), 2.46 (br s, 1H), 2.30 (s, 3H), 2.25-2.15 (m, 2H), 2.12 (d, J=13.2 Hz, 1H), 1.97-1.81 (m, 4H), 1.72 (d, J=12.2 Hz, 1H), 1.56 (d, J=13.9 Hz, 2H), 1.35-1.20 (m, 1H). [M+H]=403.4.

Example 111. 5-Chloro-2-[(3-methoxy-3-methylazetidin-1-yl)methyl]-7,8-dihydro-6H-spiro[[1,3]oxazolo[5,4-f]quinazoline-9,1'-cyclohexane]-7-one

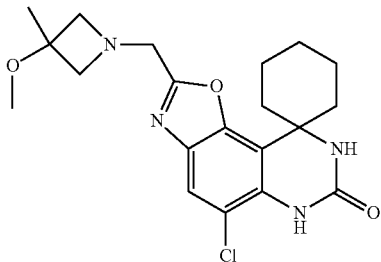

$^1$H NMR (400 MHz, CDCl$_3$) δ 7.70 (s, 1H), 7.28-7.24 (m, 1H), 5.81 (br s, 1H), 4.60 (s, 2H), 4.30 (d, J=11.0 Hz, 2H), 3.98 (d, J=10.9 Hz, 2H), 3.25 (s, 3H), 2.33-2.17 (m, 2H), 2.01 (d, J=12.1 Hz, 2H), 1.81 (d, J=16.6 Hz, 3H), 1.68-1.51 (m, 5H), 1.49-1.33 (m, 1H). [M+H]=405.2.

Example 112. 5-Chloro-2-[(4-methoxypiperidin-1-yl)methyl]-7,8-dihydro-6H-spiro[[1,3]oxazolo[5,4-f]quinazoline-9,1'-cyclohexane]-7-one

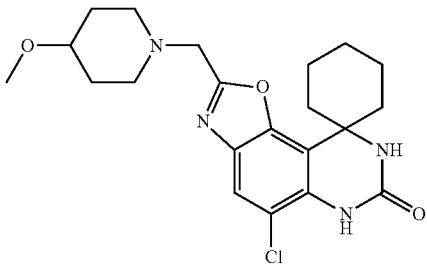 [SMILES: COC1CCN(Cc2nc3cc(Cl)c4c(c3o2)C2(CCCCC2)NC(=O)N4)CC1]

$^1$H NMR (400 MHz, CDCl$_3$) δ 7.73 (s, 1H), 7.41 (s, 1H), 6.14 (s, 1H), 4.53 (s, 2H), 3.59 (br s, 1H), 3.54-3.46 (m, 2H), 3.42-3.33 (m, 5H), 2.29-2.00 (m, 8H), 1.91-1.77 (m, 3H), 1.69-1.55 (m, 2H), 1.50-1.38 (m, 1H). [M+H]=418.0.

Example 113. 5-Chloro-2-{[4-(dimethylamino)piperidin-1-yl]methyl}-7,8-dihydro-6H-spiro[[1,3]oxazolo[5,4-f]quinazoline-9,1'-cyclohexane]-7-one

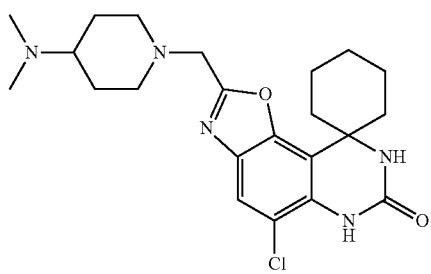 [SMILES: CN(C)C1CCN(Cc2nc3cc(Cl)c4c(c3o2)C2(CCCCC2)NC(=O)N4)CC1]

$^1$H NMR (400 MHz, CDCl$_3$) δ 7.64 (s, 1H), 7.15 (br s, 1H), 5.56 (s, 1H), 3.90 (s, 2H), 3.11 (d, J=11.6 Hz, 2H), 2.35-2.24 (m, 8H), 2.21-2.12 (m, 1H), 2.03 (d, J=13.3 Hz, 2H), 1.90-1.77 (m, 5H), 1.70-1.54 (m, 6H), 1.47-1.36 (m, 1H). [M+H]=432.2.

Example 114. 5-Chloro-2-({5-methyl-octahydropyrrolo[3,4-c]pyrrol-2-yl}methyl)-7,8-dihydro-6H-spiro[[1,3]oxazolo[5,4-f]quinazoline-9,1'-cyclohexane]-7-one

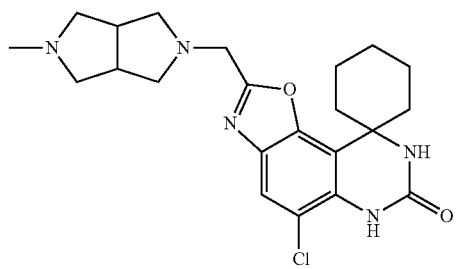 [SMILES: CN1CC2CN(Cc3nc4cc(Cl)c5c(c4o3)C3(CCCCC3)NC(=O)N5)CC2C1]

$^1$H NMR (400 MHz, CDCl$_3$) δ 7.69 (s, 1H), 7.43 (s, 1H), 6.31 (br s, 1H), 4.53-4.28 (m, 2H), 4.04-3.72 (m, 3H), 3.41 (d, J=8.9 Hz, 4H), 3.01 (s, 3H), 2.96 (br s, 3H), 2.33-2.17 (m, 2H), 2.10-1.98 (m, 2H), 1.94-1.76 (m, 3H), 1.65 (d, J=12.7 Hz, 2H), 1.41 (d, J=11.6 Hz, 1H). [M+H]=430.2.

Example 115. 5-Chloro-2-{[(2R)-2-(methoxymethyl)pyrrolidin-1-yl]methyl}-7,8-dihydro-6H-spiro[[1,3]oxazolo[5,4-f]quinazoline-9,1'-cyclohexane]-7-one

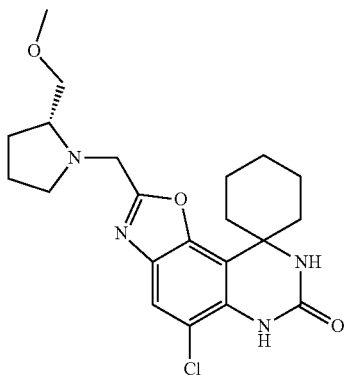 [SMILES: COC[C@H]1CCCN1Cc1nc2cc(Cl)c3c(c2o1)C1(CCCCC1)NC(=O)N3]

$^1$H NMR (400 MHz, CDCl$_3$) δ 7.69 (s, 1H), 7.41 (s, 1H), 6.17 (s, 1H), 4.97-4.81 (m, 2H), 4.09 (dd, J=2.8, 8.4 Hz, 1H), 3.98-3.82 (m, 2H), 3.76-3.44 (m, 2H), 3.42-3.36 (m, 3H), 2.37-2.18 (m, 4H), 2.16-1.75 (m, 7H), 1.64 (q, J=13.6 Hz, 2H), 1.51-1.35 (m, 1H). [M+H]=419.2.

Example 116. 5-Chloro-2-{[3-(hydroxymethyl)pyrrolidin-1-yl]methyl}-7,8-dihydro-6H-spiro[[1,3]oxazolo[5,4-f]quinazoline-9,1'-cyclohexane]-7-one

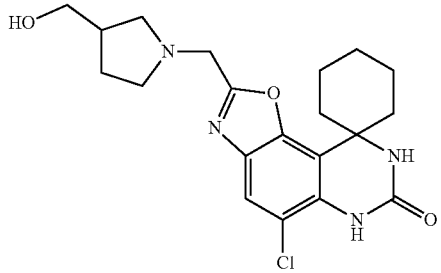 [SMILES: O=C1Nc2c(Cl)cc3nc(CN4CCC(CO)C4)oc3c2C2(CCCCC2)N1]

$^1$H NMR (400 MHz, CDCl$_3$) δ 7.71 (s, 1H), 7.40 (s, 1H), 6.12 (s, 1H), 4.64 (s, 2H), 3.84-3.53 (m, 7H), 2.79 (br s, 1H), 2.41-2.20 (m, 3H), 2.15-1.98 (m, 3H), 1.81 (d, J=17.2 Hz, 3H), 1.62 (d, J=13.9 Hz, 2H), 1.51-1.35 (m, 1H). [M+H]= 405.2.

Example 117. 5-Chloro-2-{[(3R)-3-methoxypiperidin-1-yl]methyl}-7,8-dihydro-6H-spiro[[1,3]oxazolo[5,4-f]quinazoline-9,1'-cyclohexane]-7-one

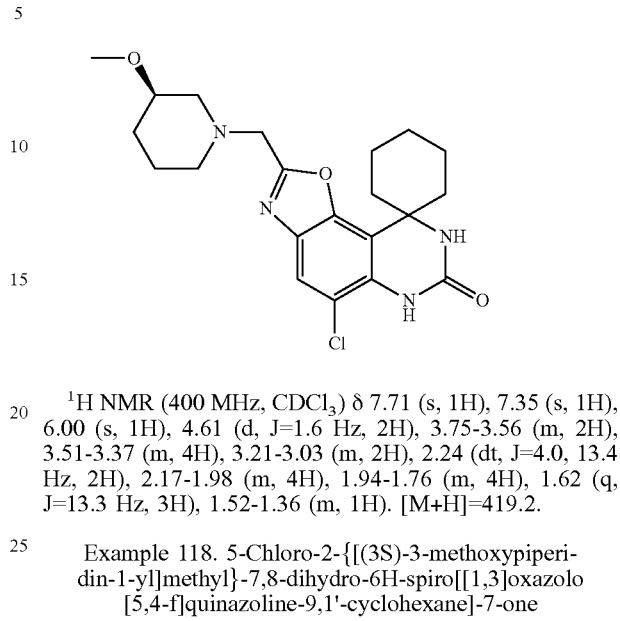

$^1$H NMR (400 MHz, CDCl$_3$) δ 7.71 (s, 1H), 7.35 (s, 1H), 6.00 (s, 1H), 4.61 (d, J=1.6 Hz, 2H), 3.75-3.56 (m, 2H), 3.51-3.37 (m, 4H), 3.21-3.03 (m, 2H), 2.24 (dt, J=4.0, 13.4 Hz, 2H), 2.17-1.98 (m, 4H), 1.94-1.76 (m, 4H), 1.62 (q, J=13.3 Hz, 3H), 1.52-1.36 (m, 1H). [M+H]=419.2.

Example 118. 5-Chloro-2-{[(3S)-3-methoxypiperidin-1-yl]methyl}-7,8-dihydro-6H-spiro[[1,3]oxazolo[5,4-f]quinazoline-9,1'-cyclohexane]-7-one

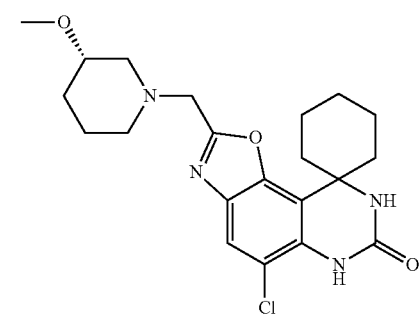 [SMILES: CO[C@H]1CCCN(Cc2nc3cc(Cl)c4c(c3o2)C2(CCCCC2)NC(=O)N4)C1]

$^1$H NMR (400 MHz, CDCl$_3$) δ 7.71 (s, 1H), 7.36 (s, 1H), 6.01 (s, 1H), 4.61 (d, J=1.8 Hz, 2H), 3.74-3.56 (m, 2H), 3.51-3.37 (m, 4H), 3.25-3.04 (m, 2H), 2.30-2.18 (m, 2H), 2.17-1.98 (m, 4H), 1.96-1.76 (m, 4H), 1.69-1.55 (m, 3H), 1.52-1.37 (m, 1H). [M+H]=419.2.

Example 119. 5-Chloro-2-{[(3R)-3-ethoxypyrrolidin-1-yl]methyl}-7,8-dihydro-6H-spiro[[1,3]oxazolo[5,4-f]quinazoline-9,1'-cyclohexane]-7-one

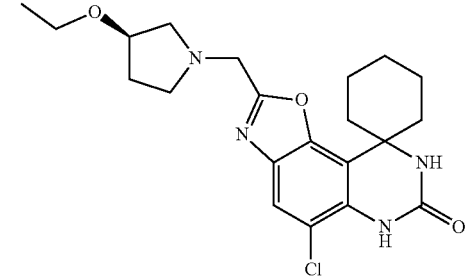 [SMILES: CCO[C@@H]1CCN(Cc2nc3cc(Cl)c4c(c3o2)C2(CCCCC2)NC(=O)N4)C1]

¹H NMR (400 MHz, CDCl₃) δ 7.71 (s, 1H), 7.33 (s, 1H), 5.93 (s, 1H), 4.72-4.57 (m, 2H), 4.24 (br s, 1H), 3.84 (dd, J=4.6, 12.8 Hz, 2H), 3.54-3.42 (m, 4H), 2.31-2.19 (m, 4H), 2.02 (d, J=13.2 Hz, 2H), 1.90-1.76 (m, 3H), 1.68-1.54 (m, 2H), 1.52-1.41 (m, 1H), 1.12 (t, J=7.0 Hz, 3H). [M+H]= 419.6.

Example 120. 5-Chloro-2-{[(3R)-3-(2-hydroxypropan-2-yl)pyrrolidin-1-yl]methyl}-7,8-dihydro-6H-spiro[[1,3]oxazolo[5,4-f]quinazoline-9,1'-cyclohexane]-7-one

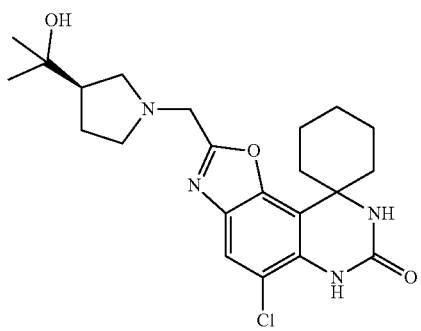 [SMILES: CC(C)(O)[C@@H]1CCN(Cc2nc3cc(Cl)c4c(c3o2)C2(CCCCC2)NC(=O)N4)C1]

¹H NMR (400 MHz, CD₃OD) δ 8.00 (s, 1H), 7.78 (s, 1H), 7.30 (s, 1H), 4.89 (d, J=2.6 Hz, 2H), 3.30-3.13 (m, 1H), 3.04-2.86 (m, 1H), 2.60 (t, J=8.6 Hz, 1H), 2.42-2.29 (m, 2H), 2.24-2.13 (m, 2H), 2.02 (d, J=12.5 Hz, 2H), 1.91-1.68 (m, 6H), 1.52-1.41 (m, 1H), 1.29-1.24 (m, 8H). [M+H]= 433.6.

Example 121. 5-Chloro-2-{[(3R)-3-hydroxypyrrolidin-1-yl]methyl}-7,8-dihydro-6H-spiro[[1,3]oxazolo[5,4-f]quinazoline-9,1'-cyclohexane]-7-one

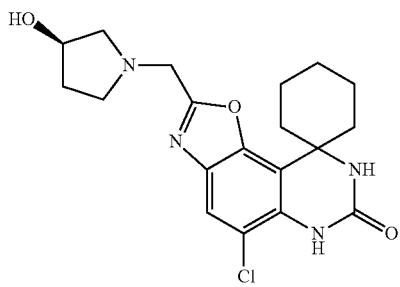 [SMILES: O=C1Nc2c(Cl)cc3nc(CN4CC[C@@H](O)C4)oc3c2C2(CCCCC2)N1]

¹H NMR (400 MHz, CD₃OD) δ 8.00 (s, 1H), 7.78 (s, 1H), 7.30 (s, 1H), 4.93 (s, 2H), 3.94-3.61 (m, 3H), 3.50-3.37 (m, 1H), 3.25 (s, 1H), 2.35 (dt, J=4.6, 13.3 Hz, 3H), 2.21-2.12 (m, 1H), 2.09-1.96 (m, 3H), 1.90-1.79 (m, 3H), 1.78-1.71 (m, 2H), 1.53-1.37 (m, 1H). [M+H]=391.5.

Example 122. 5-Chloro-2-({[2-(dimethylamino)ethyl](methyl)amino}methyl)-7,8-dihydro-6H-spiro[[1,3]oxazolo[5,4-f]quinazoline-9,1'-cyclohexane]-7-one

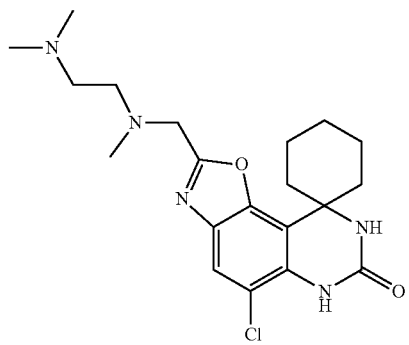 [SMILES: CN(C)CCN(C)Cc1nc2cc(Cl)c3c(c2o1)C1(CCCCC1)NC(=O)N3]

¹H NMR (400 MHz, DMSO-d6) δ 8.46 (s, 1H), 7.80 (s, 1H), 7.40 (s, 1H), 4.08 (s, 2H), 3.28 (t, J=5.9 Hz, 2H), 2.92-2.87 (m, 2H), 2.83 (s, 6H), 2.43 (s, 3H), 2.26-2.12 (m, 2H), 1.98-1.81 (m, 4H), 1.71 (d, J=12.1 Hz, 1H), 1.55 (d, J=13.9 Hz, 2H), 1.25 (d, J=13.1 Hz, 1H). [M+H]=406.4.

Example 123. 3-({5-Chloro-7-oxo-7,8-dihydro-6H-spiro[[1,3]oxazolo[5,4-f]quinazoline-9,1'-cyclohexane]-2-ylmethyl}(methyl)amino)-N,N-dimethyl-propanamide

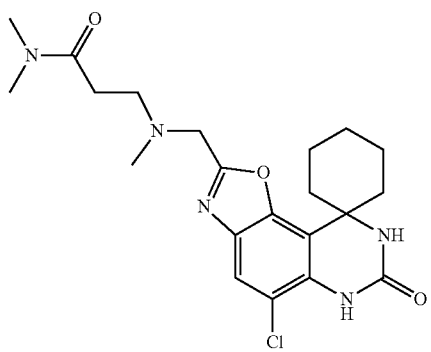 [SMILES: CN(CCC(=O)N(C)C)Cc1nc2cc(Cl)c3c(c2o1)C1(CCCCC1)NC(=O)N3]

¹H NMR (400 MHz, DMSO-d6) δ 8.57 (s, 1H), 7.91 (s, 1H), 7.44 (s, 1H), 4.81 (s, 2H), 3.46 (br s, 2H), 3.00-2.95 (m, 6H), 2.90 (t, J=7.0 Hz, 2H), 2.84 (s, 3H), 2.28-2.14 (m, 2H), 1.97-1.81 (m, 4H), 1.71 (d, J=12.5 Hz, 1H), 1.55 (d, J=13.8 Hz, 2H), 1.30 (d, J=12.6 Hz, 1H). [M+H]=434.3.

Example 124. 5-Chloro-2-({methyl[2-(morpholin-4-yl)ethyl]amino}methyl)-7,8-dihydro-6H-spiro[[1,3]oxazolo[5,4-f]quinazoline-9,1'-cyclohexane]-7-one

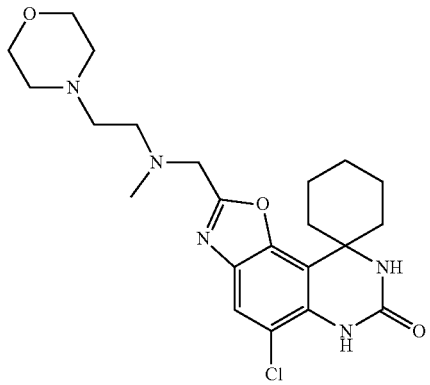 [SMILES: CN(CCN1CCOCC1)Cc1nc2cc(Cl)c3c(c2o1)C1(CCCCC1)NC(=O)N3]

$^1$H NMR (400 MHz, DMSO-d6) δ 8.46 (s, 1H), 7.79 (s, 1H), 7.40 (s, 1H), 4.12 (s, 2H), 3.91-3.79 (m, 6H), 3.38-3.23 (m, 4H), 2.94 (t, J=5.8 Hz, 2H), 2.46 (s, 3H), 2.28-2.10 (m, 2H), 1.97-1.81 (m, 4H), 1.72 (d, J=12.5 Hz, 1H), 1.55 (d, J=13.7 Hz, 2H), 1.25 (d, J=13.1 Hz, 1H). [M+H]=448.4.

Example 125. 5-Chloro-2-[(3-methoxypyrrolidin-1-yl)methyl]-7,8-dihydro-6H-spiro[[1,3]oxazolo[5,4-f]quinazoline-9,1'-cyclohexane]-7-one

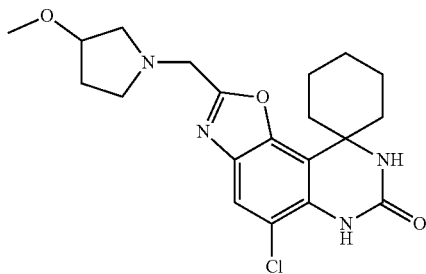 [SMILES: COC1CCN(Cc2nc3cc(Cl)c4c(c3o2)C2(CCCCC2)NC(=O)N4)C1]

$^1$H NMR (400 MHz, DMSO-d6) δ 8.56 (s, 1H), 7.89 (s, 1H), 7.44 (s, 1H), 4.87 (s, 2H), 4.17 (br s, 1H), 3.62-3.40 (m, 6H), 2.33-2.03 (m, 4H), 1.98-1.81 (m, 5H), 1.71 (d, J=12.2 Hz, 1H), 1.55 (d, J=13.8 Hz, 2H), 1.41-1.20 (m, 1H). [M+H]=405.3.

Example 126. 5-Chloro-2-{[4-(2,2,2-trifluoroethyl)piperazin-1-yl]methyl}-7,8-dihydro-6H-spiro[[1,3]oxazolo[5,4-f]quinazoline-9,1'-cyclohexane]-7-one

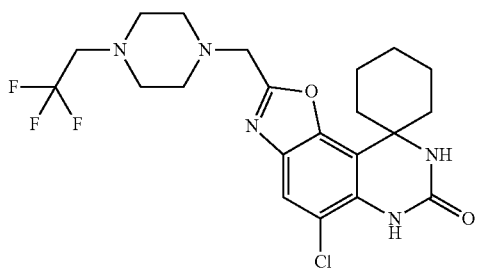

$^1$H NMR (400 MHz, DMSO-d6) δ 8.54 (s, 1H), 7.87 (s, 1H), 7.43 (s, 1H), 4.64-4.47 (m, 2H), 3.32-3.02 (m, 6H), 2.86 (br s, 4H), 2.26-2.13 (m, 2H), 1.97-1.82 (m, 4H), 1.71 (d, J=12.5 Hz, 1H), 1.56 (d, J=14.2 Hz, 2H), 1.28 (d, J=13.0 Hz, 1H). [M+H]=472.3.

Example 127. Methyl 2-({5-chloro-7-oxo-7,8-dihydro-6H-spiro[[1,3]oxazolo[5,4-f]quinazoline-9,1'-cyclohexane]-2-ylmethyl}(methyl)amino)acetate

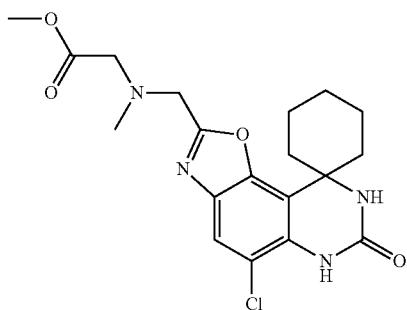 [SMILES: COC(=O)CN(C)Cc1nc2cc(Cl)c3c(c2o1)C1(CCCCC1)NC(=O)N3]

$^1$H NMR (400 MHz, DMSO-d6) δ 8.45 (s, 1H), 7.80 (s, 1H), 7.39 (s, 1H), 4.22 (s, 2H), 3.69 (br s, 2H), 3.63 (s, 3H), 2.57 (s, 3H), 2.28-2.11 (m, 2H), 1.96-1.81 (m, 4H), 1.71 (d, J=12.1 Hz, 1H), 1.55 (d, J=14.2 Hz, 2H), 1.35-1.20 (m, 1H). [M+H]=407.3.

Example 128. 2-[(8aR)-octahydropyrrolo[1,2-a]piperazin-2-ylmethyl]-5-chloro-7,8-dihydro-6H-spiro[[1,3]oxazolo[5,4-f]quinazoline-9,1'-cyclohexane]-7-one

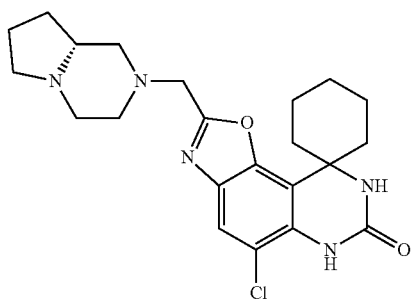 [SMILES: O=C1Nc2c(Cl)cc3nc(CN4CCN5CCC[C@@H]5C4)oc3c2C2(CCCCC2)N1]

$^1$H NMR (400 MHz, DMSO-d6) δ 8.47 (s, 1H), 7.78 (s, 1H), 7.40 (s, 1H), 3.77 (br s, 1H), 3.65-3.50 (m, 1H), 3.44-3.17 (m, 4H), 3.12-2.92 (m, 2H), 2.86-2.57 (m, 2H), 2.26-2.08 (m, 3H), 2.00 (br s, 2H), 1.86 (d, J=10.9 Hz, 5H), 1.72 (d, J=12.0 Hz, 1H), 1.56 (d, J=13.4 Hz, 3H), 1.26 (q, J=13.0 Hz, 1H). [M+H]=430.4.

Example 129. 5-Chloro-2-{[methyl(oxan-4-yl)amino]methyl}-7,8-dihydro-6H-spiro[[1,3]oxazolo[5,4-f]quinazoline-9,1'-cyclohexane]-7-one

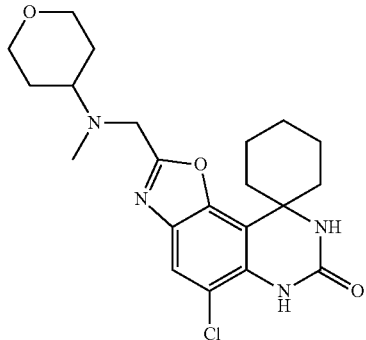 [SMILES: CN(Cc1nc2cc(Cl)c3c(c2o1)C1(CCCCC1)NC(=O)N3)C1CCOCC1]

¹H NMR (400 MHz, DMSO-d6) δ 8.58 (s, 1H), 7.91 (s, 1H), 7.46 (s, 1H), 4.79 (br s, 2H), 4.00 (dd, J=3.2, 11.4 Hz, 2H), 3.43-3.38 (m, 1H), 3.29 (t, J=11.2 Hz, 2H), 2.90 (br s, 3H), 2.24-2.14 (m, 2H), 2.02 (br s, 2H), 1.88 (d, J=10.1 Hz, 4H), 1.71 (br s, 3H), 1.55 (d, J=13.4 Hz, 2H), 1.31-1.15 (m, 1H). [M+H]=419.3.

Example 130. Methyl 1-{5-chloro-7-oxo-7,8-dihydro-6H-spiro[[1,3]oxazolo[5,4-f]quinazoline-9,1'-cyclohexane]-2-ylmethyl}piperidine-3-carboxylate

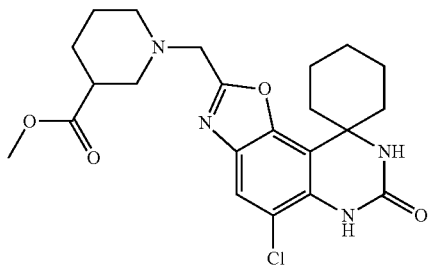

¹H NMR (400 MHz, DMSO-d6) δ 8.55 (s, 1H), 7.89 (s, 1H), 7.44 (s, 1H), 4.61 (br s, 2H), 3.64 (s, 5H), 3.08 (br s, 1H), 2.88 (d, J=10.8 Hz, 2H), 2.27-2.13 (m, 2H), 2.03-1.82 (m, 6H), 1.72 (d, J=12.6 Hz, 2H), 1.55 (d, J=13.6 Hz, 3H), 1.35-1.20 (m, 1H). [M+H]=447.4.

Example 131. Methyl 2-({5-chloro-7-oxo-7,8-dihydro-6H-spiro[[1,3]oxazolo[5,4-f]quinazoline-9,1'-cyclohexane]-2-ylmethyl}amino)acetate

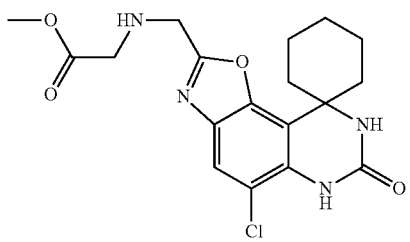 [SMILES: COC(=O)CNCc1nc2cc(Cl)c3c(c2o1)C1(CCCCC1)NC(=O)N3]

¹H NMR (400 MHz, DMSO-d6) δ 8.51 (s, 1H), 7.86 (s, 1H), 7.42 (s, 1H), 4.49 (s, 2H), 4.04 (s, 2H), 3.73 (s, 3H), 2.94 (s, 1H), 2.30-2.14 (m, 2H), 1.99-1.80 (m, 4H), 1.71 (d, J=12.5 Hz, 1H), 1.55 (d, J=13.6 Hz, 2H), 1.30 (d, J=12.7 Hz, 1H). [M+H]=393.2.

Example 132. 5-Chloro-2-{[(3S)-3-methoxypyrrolidin-1-yl]methyl}-7,8-dihydro-6H-spiro[[1,3]oxazolo[5,4-f]quinazoline-9,1'-cyclohexane]-7-one

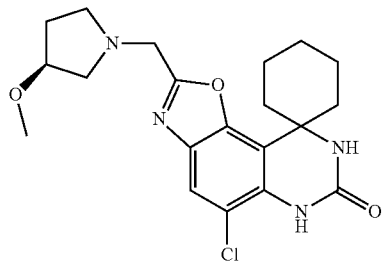 [SMILES: CO[C@H]1CCN(Cc2nc3cc(Cl)c4c(c3o2)C2(CCCCC2)NC(=O)N4)C1]

¹H NMR (400 MHz, CDCl₃) δ 7.63 (s, 1H), 7.19 (s, 1H), 5.71 (br s, 1H), 4.08-3.96 (m, 3H), 3.30 (s, 3H), 3.16-3.05 (m, 1H), 2.98-2.76 (m, 3H), 2.31 (dt, J=4.0, 13.5 Hz, 2H), 2.21-2.08 (m, 1H), 2.06-1.74 (m, 6H), 1.71-1.54 (m, 2H), 1.50-1.36 (m, 1H). [M+H]=405.4.

Example 133. 5-Chloro-2-{[(oxan-3-yl)amino]methyl}-7,8-dihydro-6H-spiro[[1,3]oxazolo[5,4-f]quinazoline-9,1'-cyclohexane]-7-one

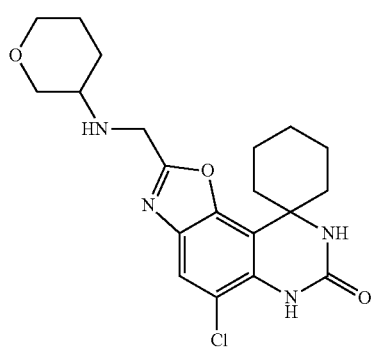

¹H NMR (400 MHz, DMSO-d6) δ 8.56 (s, 1H), 7.89 (s, 1H), 7.44 (s, 1H), 4.82 (br s, 2H), 4.15 (br s, 1H), 3.56-3.53 (m, 1H), 3.45 (br s, 4H), 2.36-2.01 (m, 5H), 1.97-1.81 (m, 5H), 1.72 (d, J=12.2 Hz, 1H), 1.56 (d, J=13.8 Hz, 2H), 1.39-1.19 (m, 1H). [M+H]=405.3.

Example 134. 5-Chloro-2-{[(3R)-3-methoxypyrrolidin-1-yl]methyl}-7,8-dihydro-6H-spiro[[1,3]oxazolo[5,4-f]quinazoline-9,1'-cyclohexane]-7-one

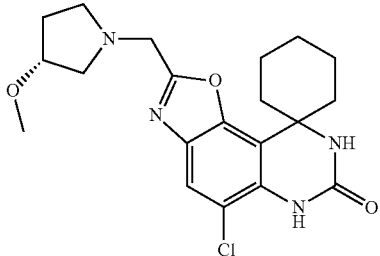 [SMILES: CO[C@@H]1CCN(Cc2nc3cc(Cl)c4c(c3o2)C2(CCCCC2)NC(=O)N4)C1]

¹H NMR (400 MHz, DMSO-d6) δ 8.57 (s, 1H), 7.90 (s, 1H), 7.45 (s, 1H), 4.71 (d, J=3.1 Hz, 2H), 3.96 (dd, J=2.6, 11.5 Hz, 1H), 3.74-3.64 (m, 1H), 3.59 (dd, J=7.4, 11.4 Hz, 1H), 3.52-3.26 (m, 5H), 2.27-2.09 (m, 3H), 1.95-1.69 (m, 6H), 1.61-1.50 (m, 2H), 1.36-1.24 (m, 1H). [M+H]=405.3.

Example 135. 5-Chloro-2-{[(3S)-3-(methoxymethyl)pyrrolidin-1-yl]methyl}-7,8-dihydro-6H-spiro[[1,3]oxazolo[5,4-f]quinazoline-9,1'-cyclohexane]-7-one

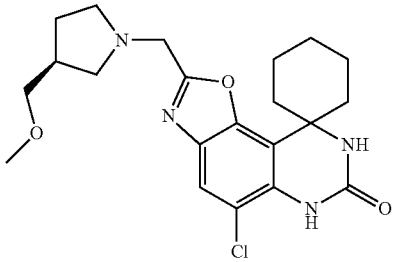 [SMILES: COC[C@H]1CCN(Cc2nc3cc(Cl)c4c(c3o2)C2(CCCCC2)NC(=O)N4)C1]

¹H NMR (400 MHz, CDCl₃) δ 7.63 (s, 1H), 7.19 (br s, 1H), 5.72 (br s, 1H), 4.00 (br s, 2H), 3.41-3.31 (m, 5H), 2.96 (br s, 1H), 2.81 (br s, 2H), 2.64-2.48 (m, 2H), 2.31 (dt, J=4.0, 13.5 Hz, 2H), 2.03 (d, J=13.1 Hz, 3H), 1.91-1.76 (m, 3H), 1.62 (q, J=13.5 Hz, 3H), 1.50-1.35 (m, 1H). [M+H]=419.3.

Example 136. 5-Chloro-2-{[(3R)-3-(methoxymethyl)pyrrolidin-1-yl]methyl}-7,8-dihydro-6H-spiro[[1,3]oxazolo[5,4-f]quinazoline-9,1'-cyclohexane]-7-one

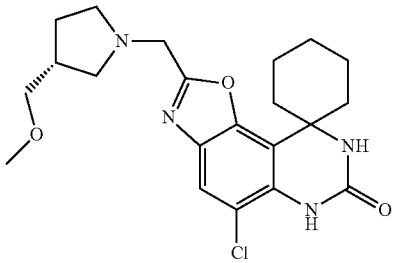 [SMILES: COC[C@@H]1CCN(Cc2nc3cc(Cl)c4c(c3o2)C2(CCCCC2)NC(=O)N4)C1]

¹H NMR (400 MHz, DMSO-d6) δ 8.57 (s, 1H), 7.90 (s, 1H), 7.45 (s, 1H), 4.89 (s, 2H), 3.44-3.30 (m, 6H), 3.26 (s, 3H), 2.68 (br s, 1H), 2.26-2.08 (m, 3H), 1.97-1.83 (m, 4H), 1.72 (d, J=13.1 Hz, 2H), 1.55 (d, J=13.6 Hz, 2H), 1.36-1.19 (m, 1H). [M+H]=419.3.

Example 137. Methyl (3R)-1-{5-chloro-7-oxo-7,8-dihydro-6H-spiro[[1,3]oxazolo[5,4-f]quinazoline-9,1'-cyclohexane]-2-ylmethyl}piperidine-3-carboxylate

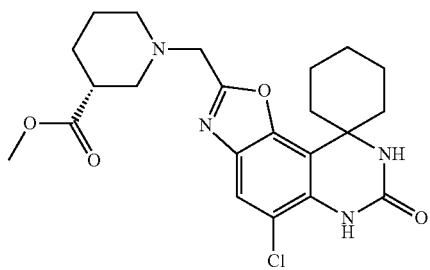 [SMILES: COC(=O)[C@@H]1CCCN(Cc2nc3cc(Cl)c4c(c3o2)C2(CCCCC2)NC(=O)N4)C1]

¹H NMR (400 MHz, DMSO-d6) δ 8.55 (s, 1H), 7.89 (s, 1H), 7.44 (s, 1H), 4.64 (br s, 2H), 3.64 (s, 4H), 3.24-2.77 (m, 4H), 2.28-2.11 (m, 2H), 2.00-1.82 (m, 6H), 1.72 (d, J=11.6 Hz, 2H), 1.55 (d, J=14.2 Hz, 3H), 1.37-1.19 (m, 1H). [M+H]=447.3.

Example 138. 5-Chloro-2-({[2-(trifluoromethoxy)ethyl]amino}methyl)-7,8-dihydro-6H-spiro[[1,3]oxazolo[5,4-f]quinazoline-9,1'-cyclohexane]-7-one

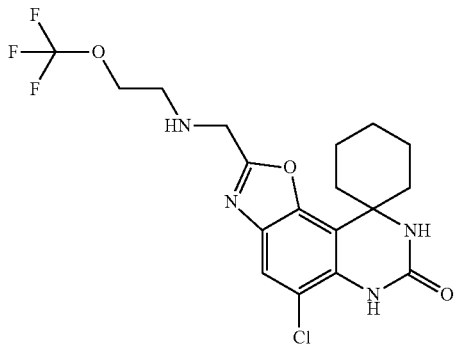 [SMILES: O=C1Nc2c(Cl)cc3nc(CNCCOC(F)(F)F)oc3c2C2(CCCCC2)N1]

¹H NMR (400 MHz, DMSO-d6) δ 8.56 (s, 1H), 7.89 (s, 1H), 7.44 (s, 1H), 4.67 (s, 2H), 4.42 (t, J=5.0 Hz, 2H), 3.62-3.50 (m, 3H), 2.27-2.15 (m, 2H), 1.97-1.82 (m, 4H), 1.71 (d, J=12.6 Hz, 1H), 1.56 (d, J=13.4 Hz, 2H), 1.39-1.21 (m, 1H). [M+H]=433.2.

Example 139. 5-Chloro-2-[(4-ethylpiperazin-1-yl)methyl]-7,8-dihydro-6H-spiro[[1,3]oxazolo[5,4-f]quinazoline-9,1'-cyclohexane]-7-one

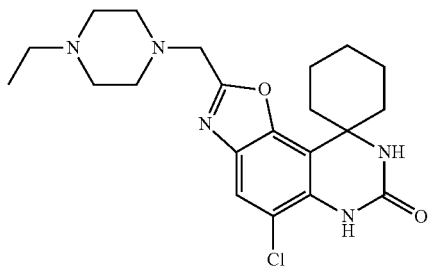

$^1$H NMR (400 MHz, DMSO-d6) δ 8.48 (s, 1H), 7.78 (s, 1H), 7.39 (s, 1H), 4.04 (s, 2H), 3.48 (d, J=11.6 Hz, 2H), 3.20-3.09 (m, 4H), 3.06-2.93 (m, 2H), 2.59 (t, J=11.7 Hz, 2H), 2.25-2.11 (m, 2H), 1.95-1.80 (m, 4H), 1.71 (d, J=11.7 Hz, 1H), 1.56 (d, J=13.8 Hz, 2H), 1.35-1.14 (m, 4H). [M+H]=418.3.

Example 140. 5-Chloro-2-{[3-(dimethylamino)pyrrolidin-1-yl]methyl}-7,8-dihydro-6H-spiro[[1,3]oxazolo[5,4-f]quinazoline-9,1'-cyclohexane]-7-one

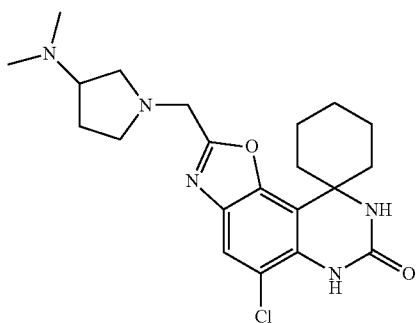 [SMILES: CN(C)C1CCN(Cc2nc3cc(Cl)c4c(c3o2)C2(CCCCC2)NC(=O)N4)C1]

$^1$H NMR (400 MHz, DMSO-d6) δ 8.47 (s, 1H), 7.79 (s, 1H), 7.40 (s, 1H), 4.20-4.05 (m, 2H), 3.94-3.86 (m, 1H), 3.16-3.01 (m, 2H), 2.99-2.90 (m, 1H), 2.80-2.69 (m, 7H), 2.32-2.12 (m, 3H), 2.09-1.97 (m, 1H), 1.95-1.80 (m, 4H), 1.71 (d, J=12.1 Hz, 1H), 1.55 (d, J=13.4 Hz, 2H), 1.35-1.18 (m, 1H). [M+H]=418.4.

Example 141. 2-({5-Chloro-7-oxo-7,8-dihydro-6H-spiro[[1,3]oxazolo[5,4-f]quinazoline-9,1'-cyclohexane]-2-ylmethyl}amino)-N,N-diethylacetamide

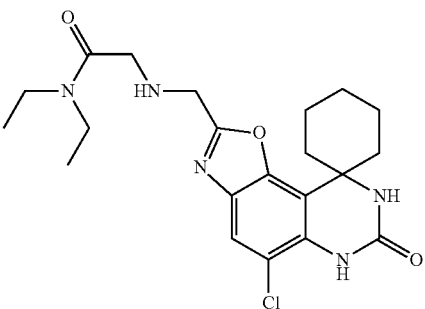 [SMILES: CCN(CC)C(=O)CNCc1nc2cc(Cl)c3c(c2o1)C1(CCCCC1)NC(=O)N3]

$^1$H NMR (400 MHz, DMSO-d6) δ 9.75 (br s, 1H), 8.54 (d, J=1.2 Hz, 1H), 7.88 (s, 1H), 7.43 (s, 1H), 4.60 (s, 2H), 4.25 (s, 2H), 3.38-3.22 (m, 4H), 2.32-2.16 (m, 2H), 2.01-1.80 (m, 4H), 1.71 (d, J=12.8 Hz, 1H), 1.55 (d, J=13.7 Hz, 2H), 1.33 (br s, 1H), 1.17-1.12 (m, 3H), 1.09-1.04 (m, 3H). [M+H]=434.4.

Example 142. (2S)-2-({5-Chloro-7-oxo-7,8-dihydro-6H-spiro[[1,3]oxazolo[5,4-f]quinazoline-9,1'-cyclohexane]-2-ylmethyl}amino)-N,N-dimethylpropanamide

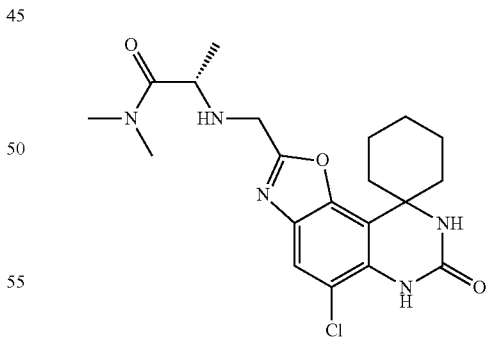

$^1$H NMR (400 MHz, DMSO-d6) δ 9.74 (br s, 1H), 8.56 (d, J=1.1 Hz, 1H), 7.90 (s, 1H), 7.43 (s, 1H), 4.67-4.45 (m, 3H), 3.02 (s, 3H), 2.88 (s, 3H), 2.29-2.16 (m, 2H), 1.99-1.81 (m, 4H), 1.71 (d, J=12.6 Hz, 1H), 1.56 (d, J=13.2 Hz, 2H), 1.43 (d, J=7.0 Hz, 3H), 1.38-1.25 (m, 1H). [M+H]=420.3.

Example 143. (2R)-2-({5-Chloro-7-oxo-7,8-dihydro-6H-spiro[[1,3]oxazolo[5,4-f]quinazoline-9,1'-cyclohexane]-2-ylmethyl}amino)-N,N-dimethylpropanamide

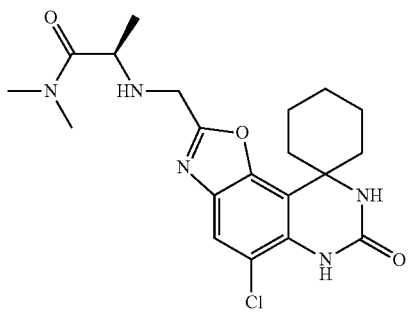 [SMILES: C[C@@H](NCc1nc2cc(Cl)c3c(c2o1)C1(CCCCC1)NC(=O)N3)C(=O)N(C)C]

¹H NMR (400 MHz, DMSO-d6) δ 9.80 (br s, 1H), 8.55 (d, J=1.1 Hz, 1H), 7.90 (s, 1H), 7.44 (s, 1H), 4.68-4.45 (m, 3H), 3.02 (s, 3H), 2.88 (s, 3H), 2.30-2.15 (m, 2H), 1.98-1.81 (m, 4H), 1.71 (d, J=12.5 Hz, 1H), 1.56 (d, J=13.7 Hz, 2H), 1.44 (d, J=7.0 Hz, 3H), 1.37-1.25 (m, 1H). [M+H]=420.3.

Example 144. 5-Chloro-2-({[2-oxo-2-(pyrrolidin-1-yl)ethyl]amino}methyl)-7,8-dihydro-6H-spiro[[1,3]oxazolo[5,4-f]quinazoline-9,1'-cyclohexane]-7-one

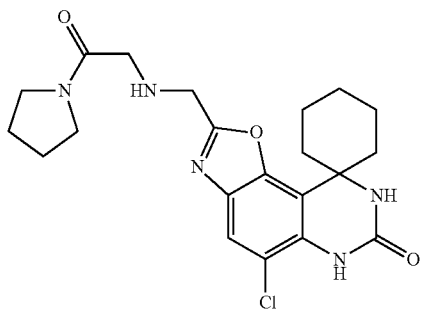 [SMILES: O=C1Nc2c(Cl)cc3nc(CNCC(=O)N4CCCC4)oc3c2C2(CCCCC2)N1]

¹H NMR (400 MHz, DMSO-d6) δ 9.76 (br s, 1H), 8.55 (s, 1H), 7.89 (s, 1H), 7.43 (s, 1H), 4.60 (s, 2H), 4.14 (s, 2H), 2.27-2.16 (m, 2H), 1.96-1.79 (m, 9H), 1.71 (d, J=12.2 Hz, 1H), 1.55 (d, J=13.6 Hz, 3H), 1.40-1.23 (m, 3H). [M+H]=432.3.

Example 145. 5-Chloro-2-{[(oxan-4-yl)amino]methyl}-7,8-dihydro-6H-spiro[[1,3]oxazolo[5,4-f]quinazoline-9,1'-cyclohexane]-7-one

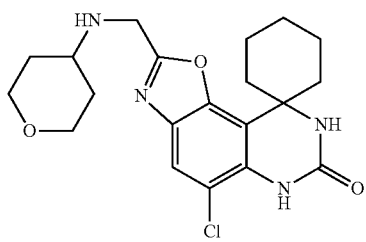 [SMILES: O=C1Nc2c(Cl)cc3nc(CNC4CCOCC4)oc3c2C2(CCCCC2)N1]

¹H NMR (400 MHz, CDCl₃) δ 7.63 (s, 1H), 7.18 (br s, 1H), 5.66 (br s, 1H), 4.26-4.13 (m, 2H), 4.02 (d, J=11.7 Hz, 2H), 3.42 (dt, J=1.9, 11.6 Hz, 2H), 2.91 (br s, 1H), 2.28 (dt, J=4.1, 13.5 Hz, 2H), 2.03 (d, J=13.0 Hz, 2H), 1.94-1.77 (m, 6H), 1.68-1.52 (m, 4H), 1.48-1.34 (m, 1H). [M+H]=405.3.

Example 146. 5-Chloro-2-[({3-oxabicyclo[3.1.0]hexan-6-yl}amino)methyl]-7,8-dihydro-6H-spiro[[1,3]oxazolo[5,4-f]quinazoline-9,1'-cyclohexane]-7-one

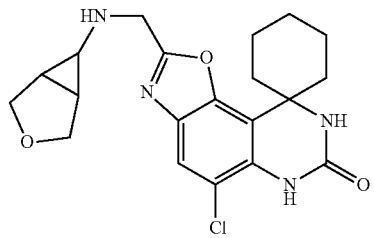 [SMILES: O=C1Nc2c(Cl)cc3nc(CNC4C5COCC54)oc3c2C2(CCCCC2)N1]

¹H NMR (400 MHz, DMSO-d6) δ 8.54 (s, 1H), 7.88 (s, 1H), 7.42 (s, 1H), 4.61 (br s, 2H), 3.78 (d, J=8.7 Hz, 2H), 3.60 (d, J=8.4 Hz, 3H), 2.56 (br s, 1H), 2.28-2.14 (m, 2H), 2.10 (br s, 2H), 1.96-1.81 (m, 4H), 1.71 (d, J=12.7 Hz, 1H), 1.56 (d, J=13.4 Hz, 2H), 1.31 (q, J=13.0 Hz, 1H). [M+H]=403.3.

Example 147. 5-Chloro-2-{[(oxepan-4-yl)amino]methyl}-7,8-dihydro-6H-spiro[[1,3]oxazolo[5,4-f]quinazoline-9,1'-cyclohexane]-7-one

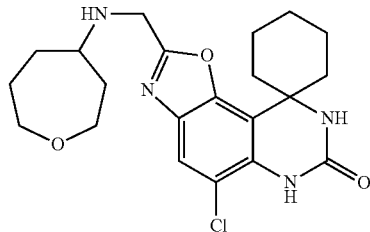 [SMILES: O=C1Nc2c(Cl)cc3nc(CNC4CCCOCC4)oc3c2C2(CCCCC2)N1]

¹H NMR (400 MHz, DMSO-d6) δ 9.57 (br s, 1H), 8.57 (d, J=1.1 Hz, 1H), 7.90 (s, 1H), 7.44 (s, 1H), 4.72 (br s, 2H), 3.83-3.64 (m, 2H), 3.61-3.54 (m, 2H), 2.28-2.12 (m, 4H), 1.99-1.50 (m, 11H), 1.42-1.20 (m, 2H). [M+H]=419.3.

Example 148. 5-Chloro-2-{[(oxolan-3-ylmethyl)amino]methyl}-7,8-dihydro-6H-spiro[[1,3]oxazolo[5,4-f]quinazoline-9,1'-cyclohexane]-7-one

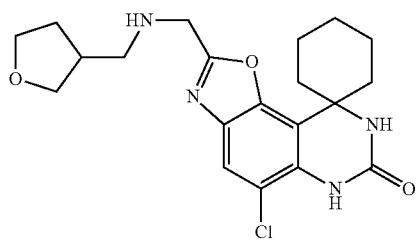 [SMILES: O=C1Nc2c(Cl)cc3nc(CNCC4CCOC4)oc3c2C2(CCCCC2)N1]

¹H NMR (400 MHz, DMSO-d6) δ 9.58 (br s, 1H), 8.56 (s, 1H), 7.90 (s, 1H), 7.44 (s, 1H), 4.68 (s, 2H), 3.85-3.72 (m, 2H), 3.64 (q, J=7.6 Hz, 1H), 3.48 (dd, J=5.7, 8.9 Hz, 1H), 3.17 (d, J=7.2 Hz, 2H), 2.60 (td, J=6.9, 14.1 Hz, 1H), 2.28-2.14 (m, 2H), 2.12-2.00 (m, 1H), 1.98-1.80 (m, 4H), 1.77-1.49 (m, 4H), 1.39-1.25 (m, 1H). [M+H]=405.2.

Example 149. 5-Chloro-2-{[(3,3-difluoro-2-hydroxypropyl)amino]methyl}-7,8-dihydro-6H-spiro[[1,3]oxazolo[5,4-f]quinazoline-9,1'-cyclohexane]-7-one

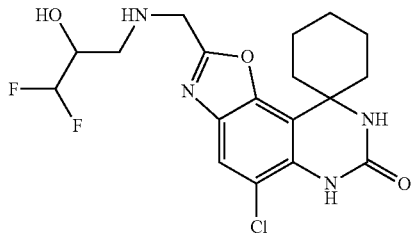

¹H NMR (400 MHz, DMSO-d6) δ 9.94-9.39 (m, 1H), 8.56 (s, 1H), 7.89 (s, 1H), 7.44 (s, 1H), 6.50 (br s, 1H), 6.21-5.85 (m, 1H), 4.68 (s, 2H), 4.14 (d, J=10.5 Hz, 1H), 3.26-3.16 (m, 1H), 2.28-2.13 (m, 2H), 1.99-1.80 (m, 4H), 1.71 (d, J=13.3 Hz, 1H), 1.55 (d, J=13.8 Hz, 2H), 1.44-1.23 (m, 2H). [M+H]=415.2.

Example 150. 5-Chloro-2-{[(4-cyclopropyloxan-4-yl)amino]methyl}-7,8-dihydro-6H-spiro[[1,3]oxazolo[5,4-f]quinazoline-9,1'-cyclohexane]-7-one

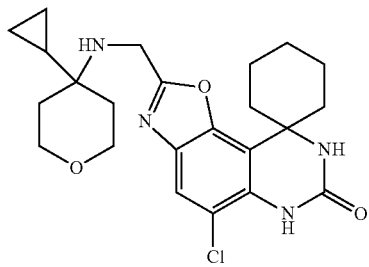 [SMILES: O=C1Nc2c(Cl)cc3nc(CNC4(C5CC5)CCOCC4)oc3c2C2(CCCCC2)N1]

¹H NMR (400 MHz, DMSO-d6) δ 9.34 (br s, 1H), 8.58 (s, 1H), 7.90 (s, 1H), 7.45 (s, 1H), 4.75 (br s, 2H), 3.86-3.76 (m, 2H), 3.55 (t, J=8.9 Hz, 2H), 2.28-2.17 (m, 2H), 1.87 (d, J=12.1 Hz, 6H), 1.71 (br s, 3H), 1.56 (d, J=13.4 Hz, 2H), 1.36-1.23 (m, 1H), 1.12 (br s, 1H), 0.71 (br s, 4H). [M+H]=445.3.

Example 151. 5-Chloro-2-{[(2,6-dimethyloxan-4-yl)amino]methyl}-7,8-dihydro-6H-spiro[[1,3]oxazolo[5,4-f]quinazoline-9,1'-cyclohexane]-7-one

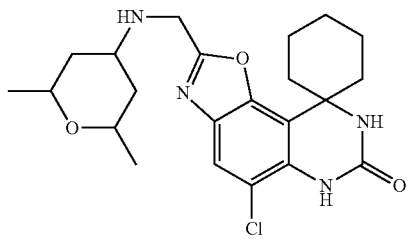 [SMILES: CC1CC(NCc2nc3cc(Cl)c4c(c3o2)C2(CCCCC2)NC(=O)N4)CC(C)O1]

¹H NMR (400 MHz, DMSO-d6) δ 9.66 (br s, 1H), 8.57 (s, 1H), 7.93-7.87 (m, 1H), 7.45 (s, 1H), 4.81-4.67 (m, 2H), 3.83 (dd, J=5.9, 10.9 Hz, 1H), 3.70 (br s, 1H), 3.48-3.37 (m, 1H), 2.28-1.83 (m, 8H), 1.72 (d, J=13.0 Hz, 1H), 1.56 (d, J=12.1 Hz, 2H), 1.50-1.41 (m, 1H), 1.39-1.19 (m, 2H), 1.18-1.05 (m, 6H). [M+H]=433.3.

Example 152. 5-Chloro-2-({[(3S)-oxan-3-yl]amino}methyl)-7,8-dihydro-6H-spiro[[1,3]oxazolo[5,4-f]quinazoline-9,1'-cyclohexane]-7-one

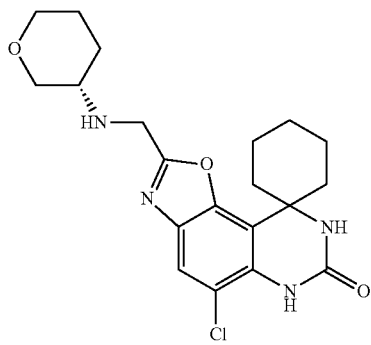 [SMILES: O=C1Nc2c(Cl)cc3nc(CN[C@H]4CCCOC4)oc3c2C2(CCCCC2)N1]

¹H NMR (400 MHz, DMSO-d6) δ 9.66 (br s, 1H), 8.57 (d, J=1.2 Hz, 1H), 8.00-7.85 (m, 1H), 7.45 (s, 1H), 4.72 (d, J=3.5 Hz, 1H), 3.97 (dd, J=2.4, 11.6 Hz, 1H), 3.67-3.54 (m, 2H), 3.51-3.45 (m, 1H), 3.44-3.37 (m, 2H), 2.28-2.07 (m, 3H), 1.96-1.65 (m, 7H), 1.61-1.46 (m, 3H), 1.36 (t, J=7.1 Hz, 2H). [M+H]=405.4.

Example 153. 5-Chloro-2-({[(3S)-oxolan-3-yl]methyl}-7,8-dihydro-6H-spiro[[1,3]oxazolo[5,4-f]quinazoline-9,1'-cyclohexane]-7-one

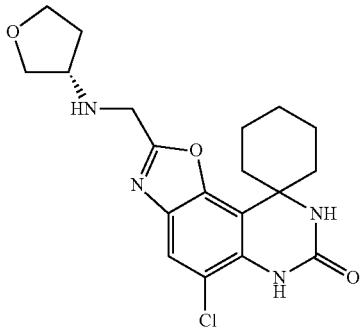 [SMILES: O=C1Nc2c(Cl)cc3nc(CN[C@H]4CCOC4)oc3c2C2(CCCCC2)N1]

¹H NMR (400 MHz, DMSO-d6) δ 9.72 (br s, 1H), 8.57 (s, 1H), 7.90 (s, 1H), 7.45 (s, 1H), 4.70 (s, 2H), 4.05 (br s, 1H), 3.99-3.88 (m, 2H), 3.80 (dd, J=6.1, 10.5 Hz, 1H), 3.72-3.62 (m, 1H), 2.37-2.14 (m, 3H), 2.13-2.01 (m, 1H), 1.98-1.80 (m, 4H), 1.72 (d, J=13.7 Hz, 1H), 1.56 (d, J=13.9 Hz, 2H), 1.38-1.21 (m, 1H). [M+H]=391.2.

Example 154. 5-Chloro-2-{[(3-methyloxolan-3-yl)amino]methyl}-7,8-dihydro-6H-spiro[[1,3]oxazolo[5,4-f]quinazoline-9,1'-cyclohexane]-7-one

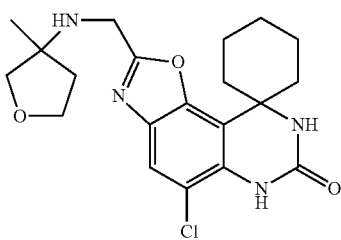 [SMILES: CC1(NCc2nc3cc(Cl)c4c(c3o2)C2(CCCCC2)NC(=O)N4)CCOC1]

¹H NMR (400 MHz, DMSO-d6) δ 9.83 (br s, 1H), 8.57 (d, J=1.1 Hz, 1H), 7.90 (s, 1H), 7.45 (s, 1H), 4.73 (br s, 2H), 4.09-3.96 (m, 2H), 3.85-3.74 (m, 1H), 3.65-3.56 (m, 1H), 2.40-2.28 (m, 1H), 2.27-2.14 (m, 2H), 2.02 (ddd, J=5.1, 8.3, 13.6 Hz, 1H), 1.96-1.82 (m, 4H), 1.72 (d, J=11.1 Hz, 1H), 1.62-1.49 (m, 5H), 1.39-1.24 (m, 1H). [M+H]=405.3.

Example 155. 5-Chloro-2-({[(3R)-oxolan-3-yl]amino}methyl)-7,8-dihydro-6H-spiro[[1,3]oxazolo[5,4-f]quinazoline-9,1'-cyclohexane]-7-one

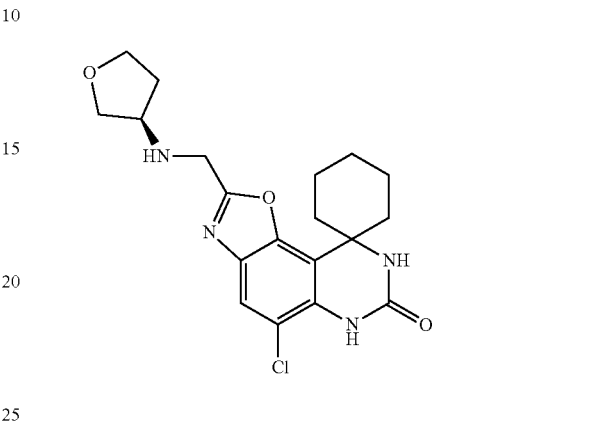

¹H NMR (400 MHz, DMSO-d6) δ 9.77 (br s, 1H), 8.56 (s, 1H), 7.90 (s, 1H), 7.44 (s, 1H), 4.70 (s, 2H), 4.04 (d, J=8.1 Hz, 1H), 3.99-3.89 (m, 2H), 3.80 (dd, J=6.1, 10.5 Hz, 1H), 3.71-3.64 (m, 1H), 2.36-2.16 (m, 3H), 2.13-2.02 (m, 1H), 1.96-1.82 (m, 4H), 1.72 (d, J=12.3 Hz, 1H), 1.56 (d, J=13.1 Hz, 2H), 1.39-1.23 (m, 1H). [M+H]=391.2.

Example 156. 5-Chloro-2-{[4-(2-methoxyethoxy)piperidin-1-yl]methyl}-7,8-dihydro-6H-spiro[[1,3]oxazolo[5,4-f]quinazoline-9,1'-cyclohexane]-7-one

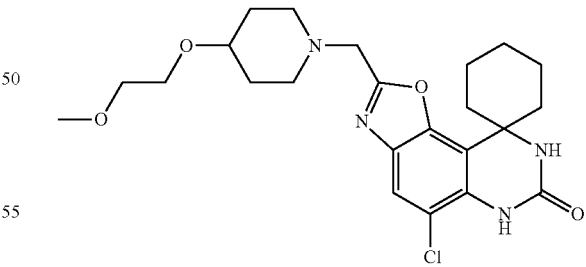

¹H NMR (400 MHz, DMSO-d6) δ 8.57 (s, 1H), 7.90 (s, 1H), 7.44 (s, 1H), 3.56-3.51 (m, 3H), 3.49-3.43 (m, 8H), 3.24 (s, 3H), 2.26-2.13 (m, 3H), 1.97-1.81 (m, 6H), 1.72 (d, J=12.8 Hz, 2H), 1.56 (d, J=12.7 Hz, 2H), 1.40-1.22 (m, 1H). [M+H]=463.4.

Example 157. 2-[(8aS)-Octahydropyrrolo[1,2-a]piperazin-2-ylmethyl]-5-chloro-7,8-dihydro-6H-spiro[[1,3]oxazolo[5,4-f]quinazoline-9,1'-cyclohexane]-7-one

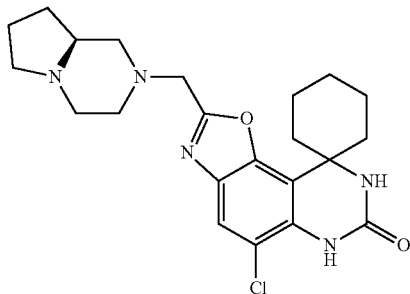 [SMILES: O=C1Nc2c(Cl)cc3nc(CN4CCN5CCC[C@H]5C4)oc3c2C2(CCCCC2)N1]

¹H NMR (400 MHz, DMSO-d6) δ 8.47 (br s, 1H), 7.78 (s, 1H), 7.40 (s, 1H), 4.16-3.98 (m, 2H), 3.40-3.28 (m, 3H), 3.18 (d, J=12.7 Hz, 2H), 3.12-2.87 (m, 2H), 2.80 (d, J=4.2 Hz, 1H), 2.74-2.58 (m, 1H), 2.25-2.10 (m, 3H), 2.00 (br s, 2H), 1.86 (d, J=10.9 Hz, 4H), 1.72 (d, J=13.2 Hz, 1H), 1.55 (d, J=13.4 Hz, 3H), 1.35-1.18 (m, 1H). [M+H]=430.4.

Example 158. Methyl (3R)-1-{5-chloro-7-oxo-7,8-dihydro-6H-spiro[[1,3]oxazolo[5,4-f]quinazoline-9,1'-cyclohexane]-2-ylmethyl}pyrrolidine-3-carboxylate

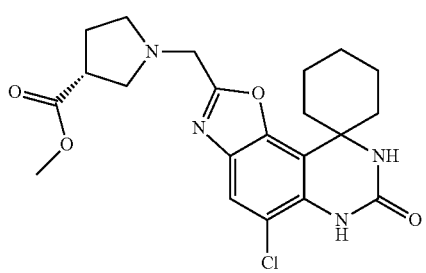 [SMILES: COC(=O)[C@@H]1CCN(Cc2nc3cc(Cl)c4c(c3o2)C2(CCCCC2)NC(=O)N4)C1]

¹H NMR (400 MHz, DMSO-d6) δ 8.56 (s, 1H), 7.89 (s, 1H), 7.44 (s, 1H), 4.82 (br s, 2H), 3.67 (s, 7H), 3.41-3.38 (m, 1H), 2.34 (br s, 1H), 2.24-2.14 (m, 3H), 1.96-1.83 (m, 4H), 1.72 (d, J=12.1 Hz, 1H), 1.56 (d, J=13.8 Hz, 2H), 1.28 (d, J=13.0 Hz, 1H). [M+H]=433.3.

Example 159. 5-Chloro-2-{[4-(2,2-difluoroethyl)piperazin-1-yl]methyl}-7,8-dihydro-6H-spiro[[1,3]oxazolo[5,4-f]quinazoline-9,1'-cyclohexane]-7-one

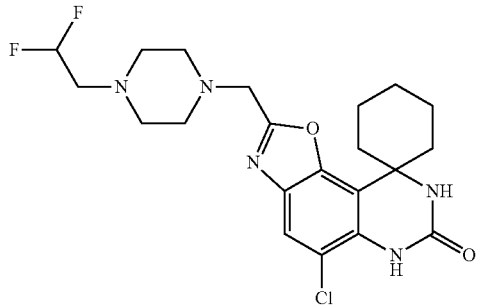 [SMILES: O=C1Nc2c(Cl)cc3nc(CN4CCN(CC(F)F)CC4)oc3c2C2(CCCCC2)N1]

¹H NMR (400 MHz, DMSO-d6) δ 8.53 (s, 1H), 7.85 (s, 1H), 7.42 (s, 1H), 6.46-6.06 (m, 1H), 4.42 (br s, 2H), 3.27-2.85 (m, 10H), 2.25-2.13 (m, 2H), 1.96-1.81 (m, 4H), 1.72 (d, J=12.6 Hz, 1H), 1.56 (d, J=13.4 Hz, 2H), 1.38-1.21 (m, 1H). [M+H]=454.3.

Example 160. 5-Chloro-2-({[(3-methyloxolan-3-yl)methyl]amino}methyl)-7,8-dihydro-6H-spiro[[1,3]oxazolo[5,4-f]quinazoline-9,1'-cyclohexane]-7-one

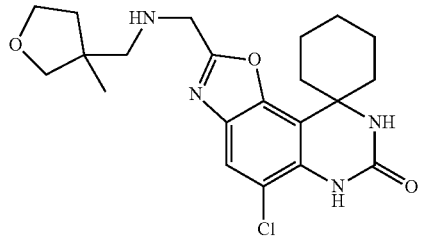 [SMILES: CC1(CNCc2nc3cc(Cl)c4c(c3o2)C2(CCCCC2)NC(=O)N4)CCOC1]

¹H NMR (400 MHz, DMSO-d6) δ 8.56 (s, 1H), 7.90 (s, 1H), 7.44 (s, 1H), 4.68 (s, 2H), 3.87-3.71 (m, 3H), 3.64 (d, J=8.8 Hz, 1H), 3.34 (d, J=8.8 Hz, 1H), 3.18 (br s, 2H), 2.26-2.14 (m, 2H), 1.97-1.82 (m, 5H), 1.76-1.65 (m, 2H), 1.56 (d, J=13.3 Hz, 2H), 1.42-1.31 (m, 1H), 1.18 (s, 3H). [M+H]=419.3.

Example 161. 5-Chloro-2-({[(3R)-oxan-3-yl]amino}methyl)-7,8-dihydro-6H-spiro[[1,3]oxazolo[5,4-f]quinazoline-9,1'-cyclohexane]-7-one

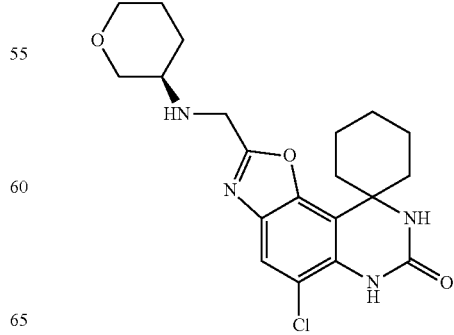

¹H NMR (400 MHz, DMSO-d6) δ 8.57 (s, 1H), 7.90 (s, 1H), 7.45 (s, 1H), 4.72 (d, J=3.3 Hz, 2H), 3.96 (dd, J=2.8, 11.7 Hz, 1H), 3.75-3.56 (m, 3H), 3.50 (br s, 1H), 2.27-2.09 (m, 3H), 1.98-1.97 (m, 1H), 1.96-1.84 (m, 4H), 1.82-1.67 (m, 3H), 1.61-1.49 (m, 3H), 1.39-1.27 (m, 1H). [M+H] =405.3.

Example 162. 5-Chloro-2-({[(3R)-oxolan-3-ylmethyl]amino}methyl)-7,8-dihydro-6H-spiro[[1,3]oxazolo[5,4-f]quinazoline-9,1'-cyclohexane]-7-one

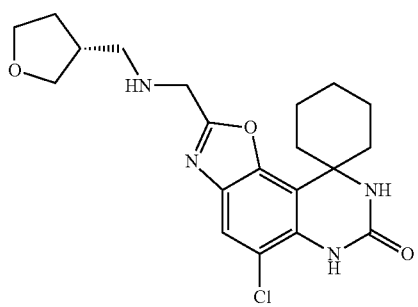 [SMILES: O=C1Nc2c(Cl)cc3nc(CNC[C@H]4CCOC4)oc3c2C2(CCCCC2)N1]

¹H NMR (400 MHz, DMSO-d6) δ 9.61 (br s, 1H), 8.55 (d, J=1.1 Hz, 1H), 7.89 (s, 1H), 7.41 (s, 1H), 4.67 (s, 2H), 3.80-3.72 (m, 2H), 3.69-3.61 (m, 2H), 3.18 (d, J=7.3 Hz, 2H), 2.65-2.55 (m, 1H), 2.28-2.15 (m, 2H), 2.14-2.00 (m, 1H), 1.85 (d, J=10.6 Hz, 4H), 1.76-1.48 (m, 4H), 1.40-1.23 (m, 1H). [M+H]=405.3.

Example 163. 5-Chloro-2-{[(3-fluorooxan-4-yl)amino]methyl}-7,8-dihydro-6H-spiro[[1,3]oxazolo[5,4-f]quinazoline-9,1'-cyclohexane]-7-one

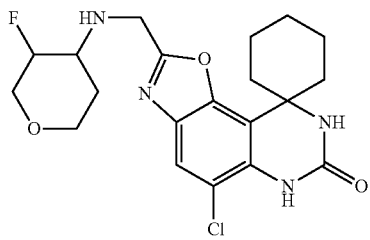

¹H NMR (400 MHz, DMSO-d6) δ 8.56 (s, 1H), 7.89 (s, 1H), 7.44 (s, 1H), 5.17-4.97 (m, 1H), 4.71 (s, 2H), 4.09 (t, J=13.2 Hz, 1H), 3.97 (dd, J=4.1, 11.3 Hz, 1H), 3.86-3.68 (m, 2H), 3.59 (d, J=13.6 Hz, 2H), 2.29-2.14 (m, 2H), 2.08-1.81 (m, 6H), 1.72 (d, J=12.1 Hz, 1H), 1.56 (d, J=14.1 Hz, 2H), 1.38-1.20 (m, 1H). [M+H]=423.3.

Example 164. 5-Chloro-2-{[(2,2-difluoro-3-hydroxypropyl)amino]methyl}-7,8-dihydro-6H-spiro[[1,3]oxazolo[5,4-f]quinazoline-9,1'-cyclohexane]-7-one

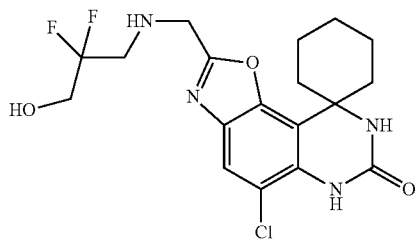 [SMILES: O=C1Nc2c(Cl)cc3nc(CNCC(F)(F)CO)oc3c2C2(CCCCC2)N1]

¹H NMR (400 MHz, DMSO-d6) δ 8.48 (s, 1H), 7.82 (s, 1H), 7.40 (s, 1H), 4.40 (br s, 2H), 3.92-3.29 (m, 6H), 2.29-2.14 (m, 2H), 1.98-1.78 (m, 4H), 1.70 (d, J=12.7 Hz, 1H), 1.55 (d, J=13.4 Hz, 2H), 1.31 (d, J=12.8 Hz, 1H). [M+H]=415.2.

Example 165. 5-Chloro-2-{[(2,2-difluorocyclopentyl)amino]methyl}-7,8-dihydro-6H-spiro[[1,3]oxazolo[5,4-f]quinazoline-9,1'-cyclohexane]-7-one

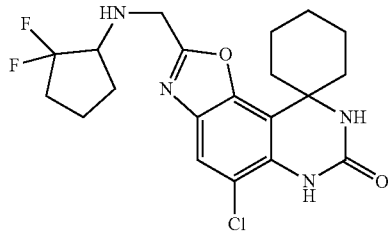 [SMILES: O=C1Nc2c(Cl)cc3nc(CNC4CCCC4(F)F)oc3c2C2(CCCCC2)N1]

¹H NMR (400 MHz, DMSO-d6) δ 8.49 (s, 1H), 7.83 (s, 1H), 7.41 (s, 1H), 4.42 (br s, 2H), 3.90-3.53 (m, 2H), 2.27-2.08 (m, 5H), 1.96-1.77 (m, 5H), 1.75-1.62 (m, 3H), 1.55 (d, J=13.7 Hz, 2H), 1.30 (q, J=12.4 Hz, 1H). [M+H]=425.3.

Example 166. 5-Chloro-2-({[4-(methoxymethyl)oxan-4-yl]amino}methyl)-7,8-dihydro-6H-spiro[[1,3]oxazolo[5,4-f]quinazoline-9,1'-cyclohexane]-7-one

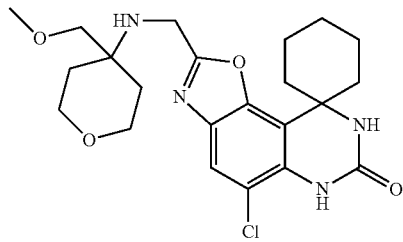 [SMILES: COCC1(NCc2nc3cc(Cl)c4c(c3o2)C2(CCCCC2)NC(=O)N4)CCOCC1]

¹H NMR (400 MHz, DMSO-d6) δ 8.57 (s, 1H), 7.89 (s, 1H), 7.44 (s, 1H), 4.61 (br s, 2H), 3.91-3.78 (m, 4H), 3.51-3.42 (m, 3H), 3.38 (s, 3H), 2.30-2.16 (m, 2H), 1.99-1.77 (m, 8H), 1.72 (d, J=12.5 Hz, 1H), 1.62-1.48 (m, 2H), 1.31 (d, J=12.8 Hz, 1H). [M+H]=449.4.

Example 167. 5-Chloro-2-({[(3S)-oxolan-3-ylmethyl]amino}methyl)-7,8-dihydro-6H-spiro[[1,3]oxazolo[5,4-f]quinazoline-9,1'-cyclohexane]-7-one

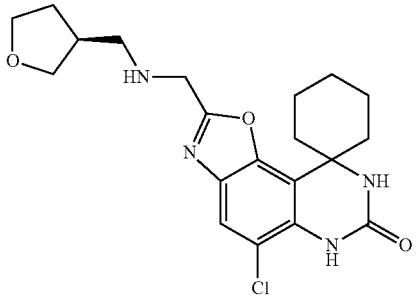 [SMILES: O=C1Nc2c(Cl)cc3nc(CNC[C@@H]4CCOC4)oc3c2C2(CCCCC2)N1]

¹H NMR (400 MHz, CDCl₃) δ 7.63 (s, 1H), 7.21 (s, 1H), 5.73 (s, 1H), 4.17-4.10 (m, 2H), 3.98-3.84 (m, 2H), 3.77 (q, J=7.6 Hz, 1H), 3.59 (dd, J=5.7, 8.7 Hz, 1H), 2.80 (dq, J=7.3, 11.4 Hz, 2H), 2.56-2.44 (m, 1H), 2.28 (dt, J=4.1, 13.5 Hz, 2H), 2.12-1.97 (m, 4H), 1.89-1.75 (m, 3H), 1.69-1.56 (m, 3H), 1.49-1.35 (m, 1H). [M+H]=405.2.

Example 168. 5-Chloro-4',4'-difluoro-2-[(1S,4S)-2-oxa-5-azabicyclo[2.2.1]heptan-5-ylmethyl]-7,8-dihydro-6H-spiro[[1,3]oxazolo[5,4-f]quinazoline-9,1'-cyclohexane]-7-one

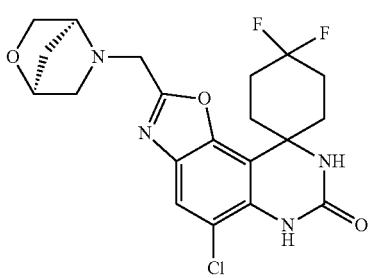 [SMILES: O=C1Nc2c(Cl)cc3nc(CN4C[C@@H]5C[C@H]4CO5)oc3c2C2(CCC(F)(F)CC2)N1]

¹H NMR (400 MHz, DMSO-d6) δ 8.74 (s, 1H), 7.94 (s, 1H), 7.90 (s, 1H), 5.06-4.82 (m, 2H), 4.70 (br s, 2H), 4.09 (br s, 2H), 3.78 (d, J=8.7 Hz, 2H), 2.81-2.65 (m, 1H), 2.48-2.37 (m, 2H), 2.33 (s, 1H), 2.10-1.89 (m, 6H). [M+H]=439.2.

Example 169. 5-Chloro-4',4'-difluoro-2-({[(3S)-oxolan-3-ylmethyl]amino}methyl)-7,8-dihydro-6H-spiro[[1,3]oxazolo[5,4-f]quinazoline-9,1'-cyclohexane]-7-one

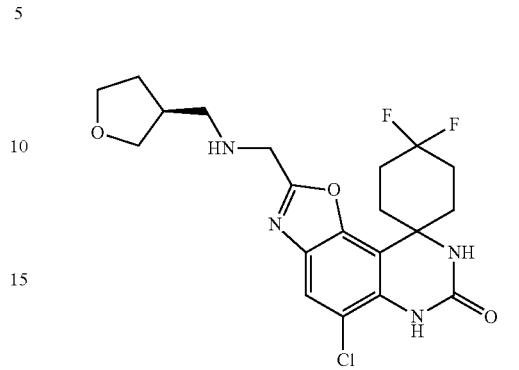

¹H NMR (400 MHz, DMSO-d6) δ 9.47 (br s, 1H), 8.75 (s, 1H), 7.95 (s, 1H), 7.90 (s, 1H), 4.66 (br s, 2H), 3.81-3.73 (m, 2H), 3.69-3.62 (m, 1H), 3.50-3.46 (m, 1H), 3.17 (d, J=6.8 Hz, 2H), 2.68 (s, 1H), 2.58 (d, J=6.4 Hz, 2H), 2.33 (d, J=1.7 Hz, 1H), 2.11-1.92 (m, 6H), 1.69-1.59 (m, 1H). [M+H]=441.2.

Example 170. 5-Chloro-2-{[(1,3-oxazol-2-ylmethyl)amino]methyl}-7,8-dihydro-6H-spiro[[1,3]oxazolo[5,4-f]quinazoline-9,1'-cyclohexane]-7-one

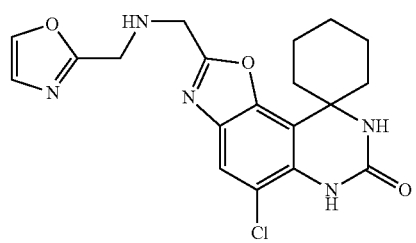 [SMILES: O=C1Nc2c(Cl)cc3nc(CNCc4ncco4)oc3c2C2(CCCCC2)N1]

¹H NMR (400 MHz, DMSO-d6) δ 8.50 (s, 1H), 8.19 (s, 1H), 7.84 (s, 1H), 7.41 (s, 1H), 7.29 (s, 1H), 4.54 (s, 2H), 4.44 (s, 2H), 2.27-2.14 (m, 2H), 1.98-1.80 (m, 4H), 1.70 (d, J=11.6 Hz, 1H), 1.55 (d, J=13.9 Hz, 2H), 1.41-1.22 (m, 2H). [M+H]=402.3.

Example 171. 5-Chloro-2-{[(1,3-oxazol-5-ylmethyl)amino]methyl}-7,8-dihydro-6H-spiro[[1,3]oxazolo[5,4-f]quinazoline-9,1'-cyclohexane]-7-one

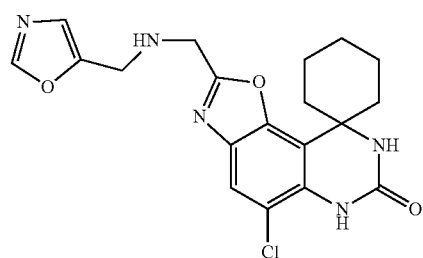 [SMILES: O=C1Nc2c(Cl)cc3nc(CNCc4cnco4)oc3c2C2(CCCCC2)N1]

¹H NMR (400 MHz, DMSO-d6) δ 8.54 (s, 1H), 8.48 (s, 1H), 7.87 (s, 1H), 7.42 (s, 1H), 7.31 (s, 1H), 4.57 (s, 2H), 4.47 (s, 2H), 2.27-2.14 (m, 2H), 1.99-1.80 (m, 5H), 1.71 (d, J=11.7 Hz, 1H), 1.56 (d, J=13.6 Hz, 2H), 1.37-1.26 (m, 1H). [M+H]=402.1.

Example 172. 5-Chloro-2-({[2-(1,2-oxazol-3-yl)ethyl]amino}methyl)-7,8-dihydro-6H-spiro[[1,3]oxazolo[5,4-f]quinazoline-9,1'-cyclohexane]-7-one

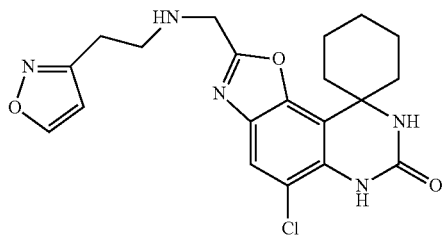 [SMILES: O=C1Nc2c(Cl)cc3nc(CNCCc4ccon4)oc3c2C2(CCCCC2)N1]

¹H NMR (400 MHz, DMSO-d6) δ 9.69 (br s, 1H), 8.91 (d, J=1.6 Hz, 1H), 8.57 (s, 1H), 7.90 (s, 1H), 7.44 (s, 1H), 6.60 (d, J=1.7 Hz, 1H), 4.73 (s, 2H), 3.53-3.36 (m, 2H), 3.14 (t, J=7.8 Hz, 2H), 2.29-2.12 (m, 2H), 1.92-1.82 (m, 4H), 1.70 (d, J=13.4 Hz, 1H), 1.55 (d, J=13.3 Hz, 2H), 1.36 (t, J=7.2 Hz, 1H). [M+H]=416.1.

Example 173. 5-Chloro-2-{[(1,3-oxazol-4-ylmethyl)amino]methyl}-7,8-dihydro-6H-spiro[[1,3]oxazolo[5,4-f]quinazoline-9,1'-cyclohexane]-7-one

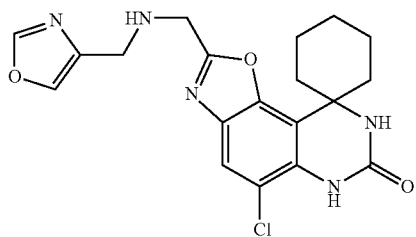 [SMILES: O=C1Nc2c(Cl)cc3nc(CNCc4cocn4)oc3c2C2(CCCCC2)N1]

¹H NMR (400 MHz, DMSO-d6) δ 10.19-9.84 (m, 1H), 8.57-8.52 (m, 2H), 8.26 (s, 1H), 7.88 (s, 1H), 7.43 (s, 1H), 4.66 (s, 2H), 4.35 (s, 2H), 2.27-2.14 (m, 2H), 1.97-1.80 (m, 4H), 1.70 (d, J=12.3 Hz, 1H), 1.55 (d, J=13.6 Hz, 2H), 1.32 (d, J=13.2 Hz, 1H). [M+H]=402.1.

Example 174. 5-Chloro-2-({[(1-methyl-1H-pyrazol-3-yl)methyl]amino}methyl)-7,8-dihydro-6H-spiro[[1,3]oxazolo[5,4-f]quinazoline-9,1'-cyclohexane]-7-one

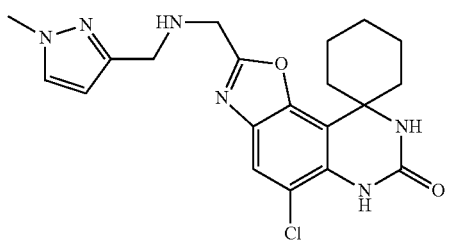 [SMILES: Cn1ccc(CNCc2nc3cc(Cl)c4c(c3o2)C2(CCCCC2)NC(=O)N4)n1]

¹H NMR (400 MHz, DMSO-d6) δ 9.98 (br s, 1H), 8.55 (s, 1H), 7.89 (s, 1H), 7.76 (d, J=2.2 Hz, 1H), 7.43 (s, 1H), 6.40 (d, J=2.2 Hz, 1H), 4.63 (s, 2H), 4.35 (s, 2H), 3.85 (s, 3H), 2.30-2.14 (m, 2H), 1.95-1.79 (m, 4H), 1.70 (d, J=12.5 Hz, 1H), 1.55 (d, J=13.3 Hz, 2H), 1.42-1.33 (m, 1H). [M+H]=415.1.

Example 175. 5-Chloro-2-{[(1,2-oxazol-5-ylmethyl)amino]methyl}-7,8-dihydro-6H-spiro[[1,3]oxazolo[5,4-f]quinazoline-9,1'-cyclohexane]-7-one

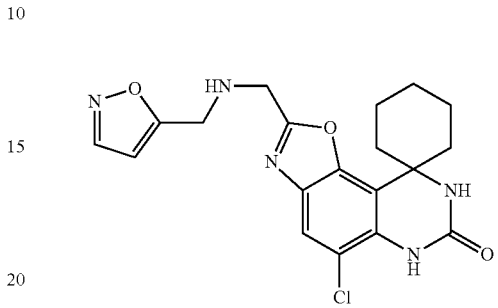

¹H NMR (400 MHz, DMSO-d6) δ 8.61 (d, J=1.6 Hz, 1H), 8.51 (s, 1H), 7.85 (s, 1H), 7.41 (s, 1H), 6.60 (s, 1H), 4.46 (d, J=12.1 Hz, 4H), 2.28-2.15 (m, 2H), 1.95-1.81 (m, 4H), 1.70 (d, J=12.5 Hz, 1H), 1.56 (d, J=13.9 Hz, 2H), 1.41-1.24 (m, 2H). [M+H]=402.1.

Example 176.-Example 178. were prepared in a manner analogous to Example 5, with the appropriate starting material substitutions.

Example 176. 2-{5-Chloro-7-oxo-7,8-dihydro-6H-spiro[[1,3]oxazolo[5,4-f]quinazoline-9,1'-cyclohexane]-2-ylmethoxy}-N,N-dimethylacetamide

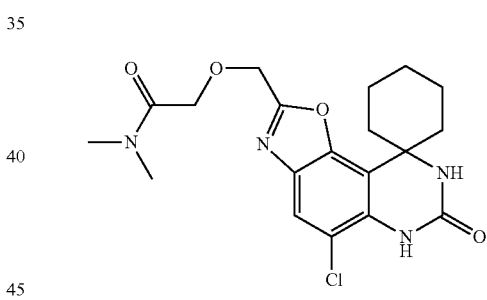

¹H NMR (400 MHz, CDCl₃) δ 7.68 (s, 1H), 7.34 (s, 1H), 6.10 (br s, 1H), 4.93 (s, 2H), 4.40 (s, 2H), 3.01 (d, J=8.6 Hz, 6H), 2.31 (dt, J=4.3, 13.5 Hz, 2H), 1.90-1.71 (m, 4H), 1.70-1.55 (m, 3H), 1.50-1.40 (m, 1H). [M+H]=407.2.

Example 177. 5-Chloro-2-[(oxan-4-yloxy)methyl]-7,8-dihydro-6H-spiro[[1,3]oxazolo[5,4-f]quinazoline-9,1'-cyclohexane]-7-one

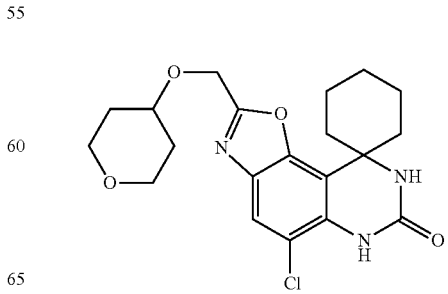

¹H NMR (400 MHz, CDCl₃) δ 7.68 (s, 1H), 7.44-7.33 (m, 1H), 6.31-6.19 (m, 1H), 4.82 (s, 2H), 4.00 (td, J=4.5, 11.7 Hz, 2H), 3.84-3.70 (m, 1H), 3.48 (ddd, J=2.7, 9.4, 11.8 Hz, 2H), 2.35-2.24 (m, 2H), 2.09-1.77 (m, 4H), 1.76-1.57 (m, 6H), 1.50-1.36 (m, 2H). [M+H]=406.2.

Example 178. 5-Chloro-2-{[(1-methylpiperidin-4-yl)oxy]methyl}-7,8-dihydro-6H-spiro[[1,3]oxazolo[5,4-f]quinazoline-9,1'-cyclohexane]-7-one

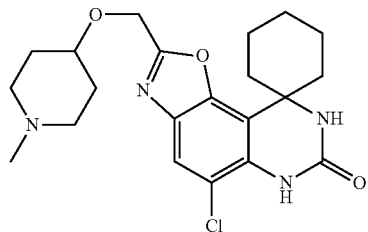 [SMILES: CN1CCC(OCc2nc3cc(Cl)c4c(c3o2)C2(CCCCC2)NC(=O)N4)CC1]

¹H NMR (400 MHz, CD₃OD) δ 7.74-7.69 (m, 1H), 4.90 (s, 2H), 4.05 (br s, 1H), 3.59 (d, J=13.1 Hz, 1H), 3.44-3.36 (m, 2H), 3.09 (br s, 1H), 2.95-2.86 (m, 3H), 2.44-2.21 (m, 4H), 2.08-1.96 (m, 3H), 1.89-1.71 (m, 6H), 1.52-1.35 (m, 1H). [M+H]=419.2.

Example 179.-Example 221. were prepared in a manner analogous to Example 7, with the appropriate starting material substitutions.

Example 179. 5-Chloro-N-[2-(dimethylamino)ethyl]-7-oxo-7,8-dihydro-6H-spiro[[1,3]oxazolo[5,4-f]quinazoline-9,1'-cyclohexane]-2-carboxamide

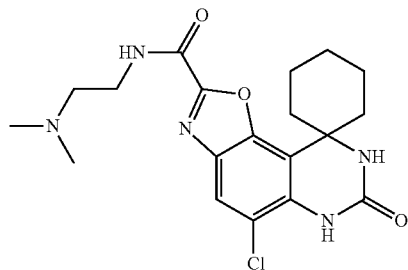 [SMILES: CN(C)CCNC(=O)c1nc2cc(Cl)c3c(c2o1)C1(CCCCC1)NC(=O)N3]

¹H NMR (400 MHz, CD₃OD) δ 7.86-7.82 (m, 1H), 3.85 (t, J=5.8 Hz, 2H), 3.44 (t, J=5.7 Hz, 2H), 3.01 (s, 6H), 2.41 (dt, J=5.1, 12.9 Hz, 2H), 2.02 (d, J=13.0 Hz, 2H), 1.90-1.66 (m, 5H), 1.61-1.44 (m, 1H). [M+H]=406.2.

Example 180. 5-Chloro-2-(morpholine-4-carbonyl)-7,8-dihydro-6H-spiro[[1,3]oxazolo[5,4-f]quinazoline-9,1'-cyclohexane]-7-one

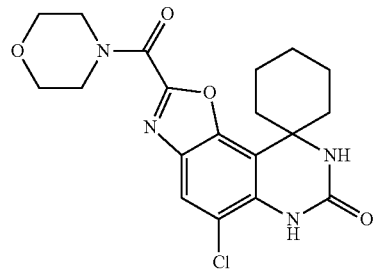

¹H NMR (400 MHz, CDCl₃) δ 7.77 (s, 1H), 7.54 (s, 1H), 6.50 (br s, 1H), 4.31-4.20 (m, 2H), 3.95-3.77 (m, 6H), 2.49-2.35 (m, 2H), 2.06 (d, J=12.7 Hz, 2H), 1.90-1.75 (m, 3H), 1.74-1.57 (m, 2H), 1.55-1.35 (m, 1H). [M+H]=405.2.

Example 181. 5-Chloro-N,N-dimethyl-7-oxo-7,8-dihydro-6H-spiro[[1,3]oxazolo[5,4-f]quinazoline-9,1'-cyclohexane]-2-carboxamide

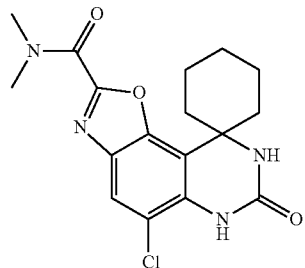 [SMILES: CN(C)C(=O)c1nc2cc(Cl)c3c(c2o1)C1(CCCCC1)NC(=O)N3]

¹H NMR (400 MHz, DMSO-d6) δ 8.59 (s, 1H), 7.96 (s, 1H), 7.44 (s, 1H), 3.33 (s, 3H), 3.08 (s, 3H), 2.28-2.10 (m, 2H), 1.98-1.78 (m, 4H), 1.71 (d, J=12.2 Hz, 1H), 1.56 (d, J=11.9 Hz, 2H), 1.26 (d, J=12.3 Hz, 1H). [M+H]=363.1.

Example 182. 5-Chloro-2-(4-methylpiperazine-1-carbonyl)-7,8-dihydro-6H-spiro[[1,3]oxazolo[5,4-f]quinazoline-9,1'-cyclohexane]-7-one

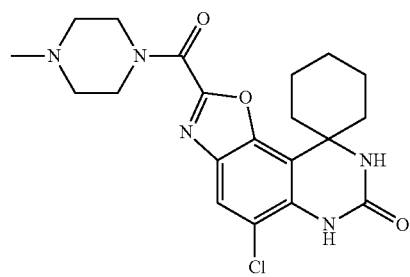

¹H NMR (400 MHz, DMSO-d6) δ 8.61 (s, 1H), 7.96 (s, 1H), 7.46 (s, 1H), 3.98-3.84 (m, 2H), 3.69 (br s, 2H), 2.41 (d, J=4.3 Hz, 4H), 2.25-2.13 (m, 5H), 1.95-1.81 (m, 4H), 1.71 (d, J=12.3 Hz, 1H), 1.56 (d, J=11.9 Hz, 2H), 1.33-1.19 (m, 1H). [M+H]=418.5.

Example 183. 5-Chloro-N-(2-methoxyethyl)-7-oxo-7,8-dihydro-6H-spiro[[1,3]oxazolo[5,4-f]quinazoline-9,1'-cyclohexane]-2-carboxamide

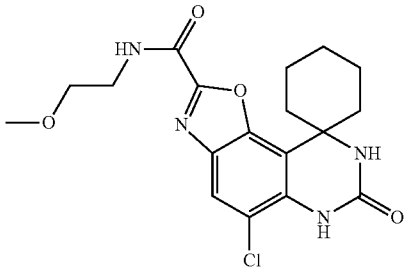 [SMILES: COCCNC(=O)c1nc2cc(Cl)c3c(c2o1)C1(CCCCC1)NC(=O)N3]

¹H NMR (400 MHz, CDCl₃) δ 7.74 (s, 1H), 7.54 (br s, 1H), 7.25 (s, 1H), 5.66 (br s, 1H), 3.71 (q, J=5.4 Hz, 2H), 3.64-3.59 (m, 2H), 3.44 (s, 3H), 2.39 (dt, J=3.9, 13.3 Hz, 2H), 2.04 (d, J=13.1 Hz, 2H), 1.82 (d, J=11.1 Hz, 3H), 1.69-1.46 (m, 3H). [M+H]=393.1.

Example 184. 5-Chloro-2-[(1S,4S)-2-oxa-5-azabicyclo[2.2.1]heptane-5-carbonyl]-7,8-dihydro-6H-spiro[[1,3]oxazolo[5,4-f]quinazoline-9,1'-cyclohexane]-7-one

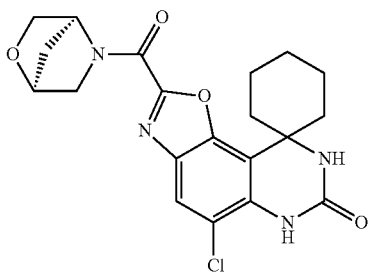 [SMILES: O=C1Nc2c(Cl)cc3nc(C(=O)N4C[C@@H]5C[C@H]4CO5)oc3c2C2(CCCCC2)N1]

¹H NMR (400 MHz, CDCl₃) δ 7.78 (s, 1H), 7.46 (br s, 1H), 6.25 (br s, 1H), 5.98-5.14 (m, 1H), 4.78 (s, 1H), 4.21-3.91 (m, 3H), 3.72 (d, J=10.8 Hz, 1H), 2.41 (t, J=13.5 Hz, 2H), 2.05 (d, J=14.7 Hz, 4H), 1.82 (d, J=16.5 Hz, 3H), 1.64 (q, J=13.7 Hz, 2H), 1.51 (br s, 1H). [M+H]=417.1.

Example 185. 5-Chloro-N-(2-methoxyethyl)-N-methyl-7-oxo-7,8-dihydro-6H-spiro[[1,3]oxazolo[5,4-f]quinazoline-9,1'-cyclohexane]-2-carboxamide

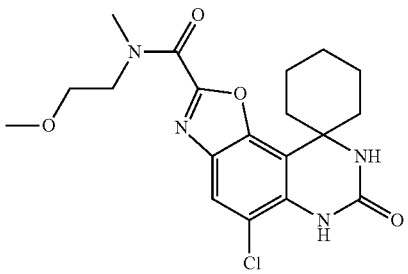 [SMILES: COCCN(C)C(=O)c1nc2cc(Cl)c3c(c2o1)C1(CCCCC1)NC(=O)N3]

¹H NMR (400 MHz, CDCl₃) δ 7.75 (d, J=9.4 Hz, 1H), 7.25 (br s, 1H), 5.71 (br s, 1H), 4.08 (t, J=5.3 Hz, 1H), 3.83-3.78 (m, 1H), 3.74-3.69 (m, 1H), 3.64 (t, J=5.3 Hz, 1H), 3.60-3.22 (m, 6H), 2.38 (dt, J=4.0, 13.4 Hz, 2H), 2.04 (d, J=13.3 Hz, 2H), 1.80 (d, J=13.1 Hz, 2H), 1.71-1.44 (m, 4H). [M+H]=407.2.

Example 186. 5-Chloro-N-methyl-N-(oxan-4-ylmethyl)-7-oxo-7,8-dihydro-6H-spiro[[1,3]oxazolo[5,4-f]quinazoline-9,1'-cyclohexane]-2-carboxamide

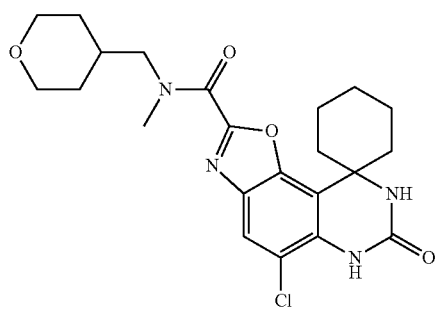 [SMILES: CN(CC1CCOCC1)C(=O)c1nc2cc(Cl)c3c(c2o1)C1(CCCCC1)NC(=O)N3]

¹H NMR (400 MHz, CDCl₃) δ 7.78 (d, J=3.2 Hz, 1H), 7.62 (s, 1H), 6.71 (br s, 1H), 4.07-3.97 (m, 2H), 3.87 (d, J=7.3 Hz, 1H), 3.58-3.51 (m, 3H), 3.48-3.34 (m, 2H), 3.22 (s, 1H), 2.45-2.32 (m, 2H), 2.19-1.98 (m, 3H), 1.92-1.75 (m, 3H), 1.73-1.56 (m, 4H), 1.54-1.28 (m, 3H). [M+H]=447.6.

Example 187. 5-Chloro-2-[(3R)-3-ethoxypyrrolidine-1-carbonyl]-7,8-dihydro-6H-spiro[[1,3]oxazolo[5,4-f]quinazoline-9,1'-cyclohexane]-7-one

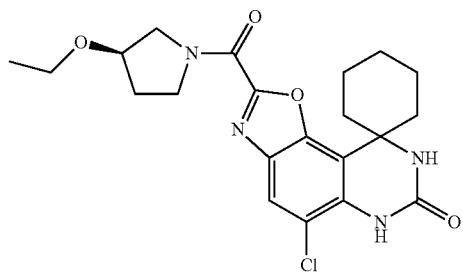 [SMILES: CCO[C@@H]1CCN(C(=O)c2nc3cc(Cl)c4c(c3o2)C2(CCCCC2)NC(=O)N4)C1]

¹H NMR (400 MHz, CDCl₃) δ 7.77 (d, J=2.1 Hz, 1H), 7.42 (s, 1H), 6.14 (br s, 1H), 4.36-4.09 (m, 3H), 3.95-3.72 (m, 2H), 3.61-3.50 (m, 2H), 2.47-2.35 (m, 2H), 2.29-1.99 (m, 4H), 1.90-1.76 (m, 3H), 1.70-1.57 (m, 2H), 1.51 (t, J=12.8 Hz, 1H), 1.24 (dt, J=5.7, 7.0 Hz, 3H). [M+H]=433.6.

Example 188. 2-{1-5-Chloro-7-oxo-7,8-dihydro-6H-spiro[[1,3]oxazolo[5,4-f]quinazoline-9,1'-cyclohexane]-2-yl-N-methylformamido}-N,N-dimethylacetamide

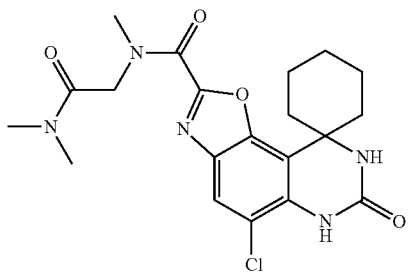 [SMILES: CN(C)C(=O)CN(C)C(=O)c1nc2cc(Cl)c3c(c2o1)C1(CCCCC1)NC(=O)N3]

¹H NMR (400 MHz, CDCl₃) δ 7.81-7.68 (m, 1H), 7.51 (s, 1H), 6.38 (d, J=15.8 Hz, 1H), 4.95 (s, 1H), 4.40 (s, 1H), 3.64 (s, 2H), 3.26 (s, 1H), 3.16-3.07 (m, 3H), 3.05-2.99 (m, 3H), 2.48-2.34 (m, 2H), 2.09-1.98 (m, 2H), 1.91-1.75 (m, 3H), 1.71-1.57 (m, 2H), 1.48 (t, J=13.1 Hz, 1H). [M+H]=434.2.

Example 189. 3-{1-5-Chloro-7-oxo-7,8-dihydro-6H-spiro[[1,3]oxazolo[5,4-f]quinazoline-9,1'-cyclohexane]-2-yl-N-methylformamido}-N,N-dimethylpropanamide

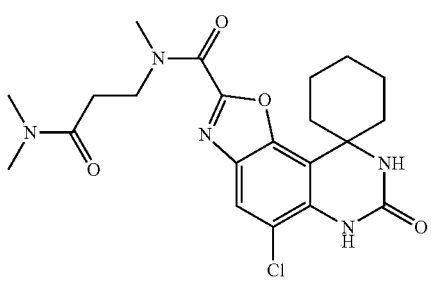 [SMILES: CN(C)C(=O)CCN(C)C(=O)c1nc2cc(Cl)c3c(c2o1)C1(CCCCC1)NC(=O)N3]

¹H NMR (400 MHz, CDCl₃) δ 7.75 (d, J=13.9 Hz, 1H), 7.35 (br s, 1H), 5.97 (br s, 1H), 4.18-4.11 (m, 1H), 3.91 (t, J=7.0 Hz, 1H), 3.58 (s, 2H), 3.21 (s, 1H), 3.09 (d, J=5.7 Hz, 3H), 2.99 (d, J=10.5 Hz, 3H), 2.90-2.78 (m, 2H), 2.44-2.32 (m, 2H), 2.05 (d, J=13.6 Hz, 2H), 1.88-1.76 (m, 3H), 1.69-1.57 (m, 2H), 1.53-1.41 (m, 1H). [M+H]=448.3.

Example 190. 5-Chloro-2-[(2S)-2-(methoxymethyl)pyrrolidine-1-carbonyl]-7,8-dihydro-6H-spiro[[1,3]oxazolo[5,4-f]quinazoline-9,1'-cyclohexane]-7-one

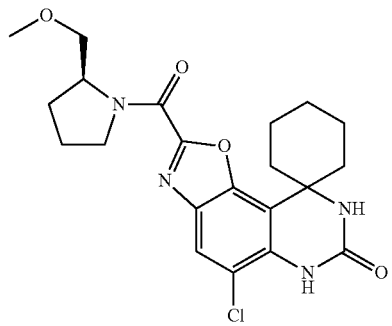 [SMILES: COC[C@@H]1CCCN1C(=O)c1nc2cc(Cl)c3c(c2o1)C1(CCCCC1)NC(=O)N3]

¹H NMR (400 MHz, CDCl₃) δ 7.81-7.71 (m, 1H), 7.43 (s, 1H), 6.19 (br s, 1H), 5.20-4.48 (m, 1H), 4.21-4.04 (m, 1H), 3.89-3.60 (m, 2H), 3.50-3.34 (m, 3H), 3.28-3.19 (m, 1H), 2.48-2.32 (m, 2H), 2.22-1.95 (m, 6H), 1.90-1.75 (m, 3H), 1.69-1.57 (m, 2H), 1.55-1.43 (m, 1H). [M+H]=432.0.

Example 191. methyl 2-{1-5-chloro-7-oxo-7,8-dihydro-6H-spiro[[1,3]oxazolo[5,4-f]quinazoline-9,1'-cyclohexane]-2-yl-N-methylformamido}acetate

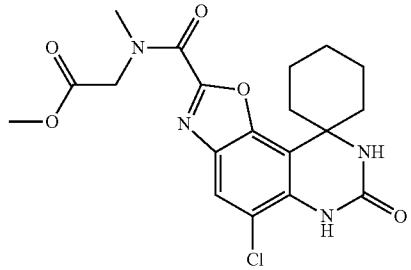 [SMILES: COC(=O)CN(C)C(=O)c1nc2cc(Cl)c3c(c2o1)C1(CCCCC1)NC(=O)N3]

¹H NMR (400 MHz, CDCl₃) δ 7.77 (d, J=19.8 Hz, 1H), 7.53 (br s, 1H), 6.44 (d, J=4.0 Hz, 1H), 4.86 (s, 1H), 4.35 (s, 1H), 3.82 (d, J=8.8 Hz, 3H), 3.65 (s, 1H), 3.27 (s, 2H), 2.40 (dt, J=4.2, 13.4 Hz, 2H), 2.04 (d, J=13.6 Hz, 2H), 1.81 (d, J=15.5 Hz, 3H), 1.72-1.57 (m, 2H), 1.55-1.43 (m, 1H). [M+H]=421.2.

Example 192. 5-Chloro-N-methyl-N-[2-(methylamino)ethyl]-7-oxo-7,8-dihydro-6H-spiro[[1,3]oxazolo[5,4-f]quinazoline-9,1'-cyclohexane]-2-carboxamide

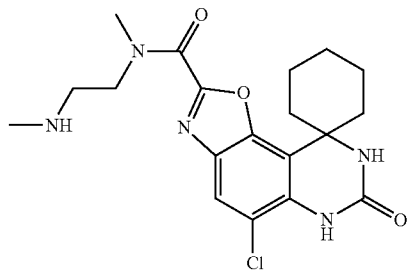 [SMILES: CNCCN(C)C(=O)c1nc2cc(Cl)c3c(c2o1)C1(CCCCC1)NC(=O)N3]

¹H NMR (400 MHz, DMSO-d6) δ 8.67 (s, 1H), 8.06-7.93 (m, 1H), 7.49 (s, 1H), 4.10 (t, J=6.1 Hz, 1H), 3.80 (t, J=5.9 Hz, 2H), 3.34-3.18 (m, 3H), 3.08 (s, 2H), 2.63 (t, J=5.1 Hz, 3H), 2.25-2.14 (m, 2H), 1.94-1.83 (m, 4H), 1.72 (d, J=12.8 Hz, 1H), 1.57 (d, J=13.3 Hz, 2H), 1.33-1.16 (m, 1H). [M+H]=406.2.

Example 193. 5-Chloro-N-[2-(dimethylamino)ethyl]-N-methyl-7-oxo-7,8-dihydro-6H-spiro[[1,3]oxazolo[5,4-f]quinazoline-9,1'-cyclohexane]-2-carboxamide

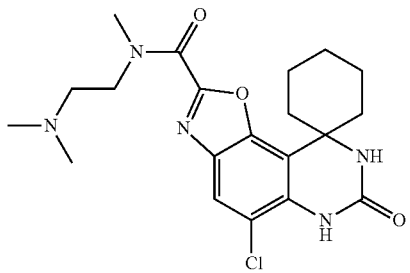 [SMILES: CN(C)CCN(C)C(=O)c1nc2cc(Cl)c3c(c2o1)C1(CCCCC1)NC(=O)N3]

¹H NMR (400 MHz, DMSO-d6) δ 8.66 (s, 1H), 8.02-7.99 (m, 1H), 7.53-7.44 (m, 1H), 4.17 (d, J=7.1 Hz, 1H), 3.88 (t, J=6.2 Hz, 1H), 3.47-3.37 (m, 2H), 3.12-3.04 (m, 1H), 2.91-2.87 (m, 6H), 2.26-2.13 (m, 2H), 1.98-1.81 (m, 4H), 1.72 (d, J=13.1 Hz, 1H), 1.57 (d, J=11.2 Hz, 2H), 1.34-1.16 (m, 3H). [M+H]=420.3.

Example 194. 5-Chloro-2-[4-(dimethylamino)piperidine-1-carbonyl]-7,8-dihydro-6H-spiro[[1,3]oxazolo[5,4-f]quinazoline-9,1'-cyclohexane]-7-one

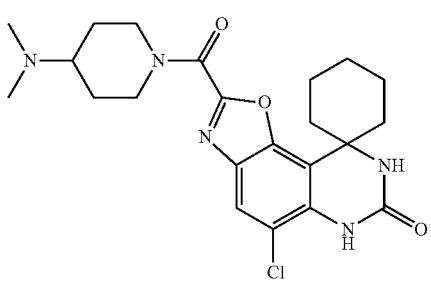 [SMILES: CN(C)C1CCN(C(=O)c2nc3cc(Cl)c4c(c3o2)C2(CCCCC2)NC(=O)N4)CC1]

¹H NMR (400 MHz, DMSO-d6) δ 8.65 (d, J=1.2 Hz, 1H), 7.97 (s, 1H), 7.48 (d, J=1.1 Hz, 1H), 4.82 (d, J=14.3 Hz, 1H), 4.63 (d, J=13.2 Hz, 1H), 3.59-3.53 (m, 1H), 3.25 (t, J=12.1 Hz, 1H), 2.97-2.86 (m, 1H), 2.78 (d, J=2.4 Hz, 6H), 2.28-2.06 (m, 4H), 1.88 (d, J=12.6 Hz, 4H), 1.77-1.65 (m, 3H), 1.56 (d, J=10.5 Hz, 2H), 1.25 (d, J=12.5 Hz, 1H). [M+H]=446.3.

Example 195. 5-Chloro-2-[4-(2,2,2-trifluoroethyl)piperazine-1-carbonyl]-7,8-dihydro-6H-spiro[[1,3]oxazolo[5,4-f]quinazoline-9,1'-cyclohexane]-7-one

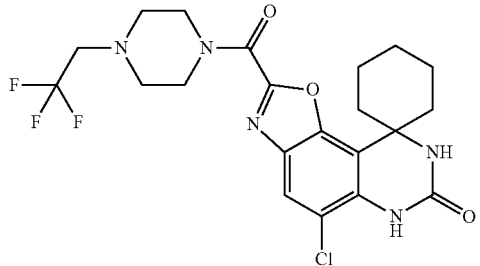 [SMILES: O=C1Nc2c(Cl)cc3nc(C(=O)N4CCN(CC(F)(F)F)CC4)oc3c2C2(CCCCC2)N1]

¹H NMR (400 MHz, DMSO-d6) δ 8.62 (s, 1H), 7.97 (s, 1H), 7.46 (s, 1H), 4.03-3.90 (m, 2H), 3.72-3.64 (m, 2H), 3.29 (q, J=10.1 Hz, 2H), 2.75 (d, J=4.8 Hz, 4H), 2.25-2.12 (m, 2H), 1.97-1.80 (m, 4H), 1.71 (d, J=13.0 Hz, 1H), 1.56 (d, J=11.0 Hz, 2H), 1.26 (d, J=13.0 Hz, 1H). [M+H]=486.3.

Example 196. 5-Chloro-2-[4-(2-methoxyethyl)piperazine-1-carbonyl]-7,8-dihydro-6H-spiro[[1,3]oxazolo[5,4-f]quinazoline-9,1'-cyclohexane]-7-one

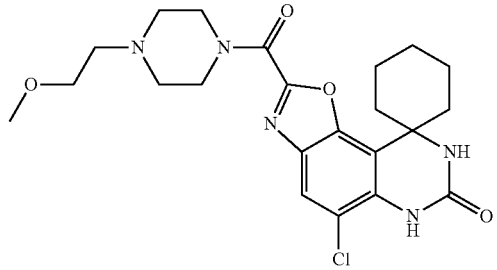 [SMILES: COCCN1CCN(C(=O)c2nc3cc(Cl)c4c(c3o2)C2(CCCCC2)NC(=O)N4)CC1]

¹H NMR (400 MHz, CDCl₃) δ 7.74 (s, 1H), 7.23 (s, 1H), 5.64 (br s, 1H), 4.20 (br s, 2H), 3.91 (br s, 2H), 3.58 (br s, 2H), 3.40 (s, 3H), 2.68 (br s, 6H), 2.37 (dt, J=4.0, 13.4 Hz, 2H), 2.04 (d, J=13.0 Hz, 2H), 1.80 (d, J=12.6 Hz, 3H), 1.68-1.40 (m, 3H). [M+H]=462.3.

Example 197. 2-[(8aR)-octahydropyrrolo[1,2-a]piperazine-2-carbonyl]-5-chloro-7,8-dihydro-6H-spiro[[1,3]oxazolo[5,4-f]quinazoline-9,1'-cyclohexane]-7-one

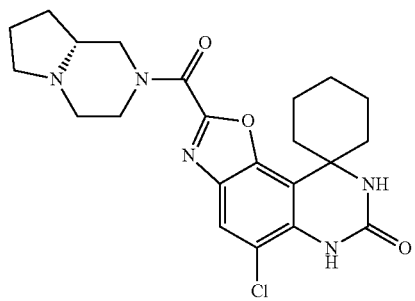 [SMILES: O=C1Nc2c(Cl)cc3nc(C(=O)N4CCN5CCC[C@@H]5C4)oc3c2C2(CCCCC2)N1]

¹H NMR (400 MHz, DMSO-d6) δ 8.61 (s, 1H), 7.97 (d, J=4.2 Hz, 1H), 7.46 (s, 1H), 4.69-4.41 (m, 2H), 3.16-2.92 (m, 3H), 2.73-2.59 (m, 1H), 2.29-2.05 (m, 4H), 2.03-1.81 (m, 6H), 1.71 (d, J=12.3 Hz, 3H), 1.56 (d, J=13.1 Hz, 2H), 1.46-1.14 (m, 2H). [M+H]=444.4.

Example 198. 5-Chloro-N-methyl-N-(oxan-4-yl)-7-oxo-7,8-dihydro-6H-spiro[[1,3]oxazolo[5,4-f]quinazoline-9,1'-cyclohexane]-2-carboxamide

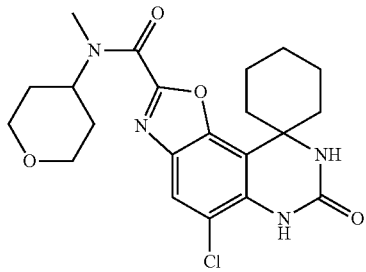 [SMILES: CN(C(=O)c1nc2cc(Cl)c3c(c2o1)C1(CCCCC1)NC(=O)N3)C1CCOCC1]

¹H NMR (400 MHz, CDCl₃) δ 7.79 (d, J=8.4 Hz, 1H), 7.53 (s, 1H), 6.46 (s, 1H), 4.91-4.68 (m, 1H), 4.11 (dt, J=4.3, 11.6 Hz, 2H), 3.65-3.52 (m, 1H), 3.45 (t, J=11.2 Hz, 1H), 3.37-3.08 (m, 3H), 2.39 (tt, J=4.5, 13.4 Hz, 2H), 2.11-1.92 (m, 4H), 1.91-1.74 (m, 5H), 1.72-1.57 (m, 2H), 1.48 (dtd, J=4.2, 8.6, 16.9 Hz, 1H). [M+H]=433.2.

Example 199. 5-Chloro-2-(3-methoxypyrrolidine-1-carbonyl)-7,8-dihydro-6H-spiro[[1,3]oxazolo[5,4-f]quinazoline-9,1'-cyclohexane]-7-one

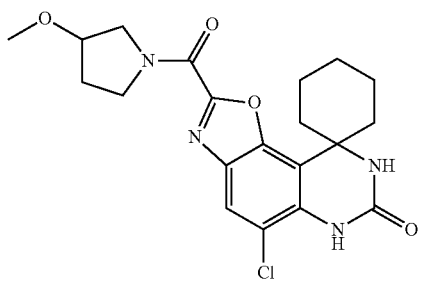 [SMILES: COC1CCN(C(=O)c2nc3cc(Cl)c4c(c3o2)C2(CCCCC2)NC(=O)N4)C1]

¹H NMR (400 MHz, CDCl₃) δ 7.78 (s, 1H), 7.40 (s, 1H), 6.10 (br s, 1H), 4.37-4.26 (m, 1H), 4.16-4.05 (m, 2H), 3.99-3.69 (m, 2H), 3.39 (d, J=4.0 Hz, 3H), 2.51-2.34 (m, 3H), 2.32-1.98 (m, 3H), 1.87-1.76 (m, 3H), 1.70-1.45 (m, 3H). [M+H]=419.2.

Example 200. 5-Chloro-2-[(3R)-3-methoxypiperidine-1-carbonyl]-7,8-dihydro-6H-spiro[[1,3]oxazolo[5,4-f]quinazoline-9,1'-cyclohexane]-7-one

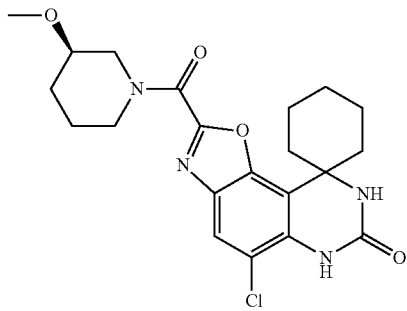 [SMILES: CO[C@@H]1CCCN(C(=O)c2nc3cc(Cl)c4c(c3o2)C2(CCCCC2)NC(=O)N4)C1]

¹H NMR (400 MHz, DMSO-d6) δ 8.61 (br s, 1H), 7.97 (d, J=2.2 Hz, 1H), 7.46 (s, 1H), 4.03-3.71 (m, 4H), 3.45-3.35 (m, 1H), 3.33-3.08 (m, 3H), 2.25-2.10 (m, 2H), 1.98-1.62 (m, 8H), 1.61-1.41 (m, 3H), 1.26 (d, J=13.4 Hz, 1H). [M+H]=433.2.

Example 201. 5-Chloro-N-(oxan-3-yl)-7-oxo-7,8-dihydro-6H-spiro[[1,3]oxazolo[5,4-f]quinazoline-9,1'-cyclohexane]-2-carboxamide

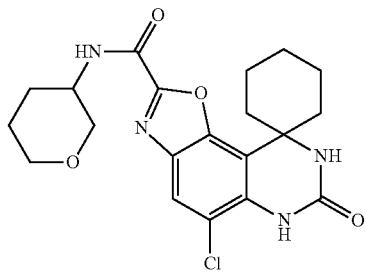 [SMILES: O=C1Nc2c(Cl)cc3nc(C(=O)NC4CCCOC4)oc3c2C2(CCCCC2)N1]

¹H NMR (400 MHz, DMSO-d6) δ 9.03 (d, J=8.2 Hz, 1H), 8.64 (s, 1H), 7.92 (s, 1H), 7.46 (s, 1H), 4.00-3.85 (m, 1H), 3.82-3.70 (m, 2H), 3.29-3.21 (m, 2H), 2.28-2.14 (m, 2H), 1.87 (d, J=12.1 Hz, 5H), 1.71 (t, J=9.0 Hz, 3H), 1.64-1.50 (m, 3H), 1.38-1.20 (m, 1H). [M+H]=419.2.

Example 202. 5-Chloro-2-[(3S)-3-methoxypyrrolidine-1-carbonyl]-7,8-dihydro-6H-spiro[[1,3]oxazolo[5,4-f]quinazoline-9,1'-cyclohexane]-7-one

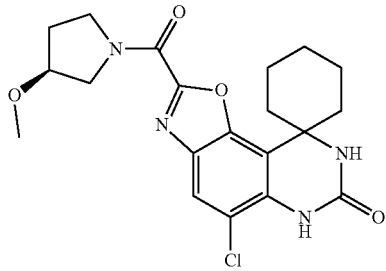 [SMILES: CO[C@H]1CCN(C(=O)c2nc3cc(Cl)c4c(c3o2)C2(CCCCC2)NC(=O)N4)C1]

¹H NMR (400 MHz, DMSO-d6) δ 8.61 (s, 1H), 7.97 (d, J=3.5 Hz, 1H), 7.46 (s, 1H), 4.17-4.02 (m, 2H), 4.00-3.84 (m, 1H), 3.76-3.61 (m, 2H), 3.27 (d, J=11.1 Hz, 3H), 2.30-2.14 (m, 2H), 2.14-1.96 (m, 2H), 1.95-1.80 (m, 4H), 1.72 (d, J=12.7 Hz, 1H), 1.57 (d, J=10.8 Hz, 2H), 1.26 (d, J=9.9 Hz, 1H). [M+H]=419.2.

Example 203. 5-Chloro-2-[(3R)-3-(methoxymethyl)pyrrolidine-1-carbonyl]-7,8-dihydro-6H-spiro[[1,3]oxazolo[5,4-f]quinazoline-9,1'-cyclohexane]-7-one

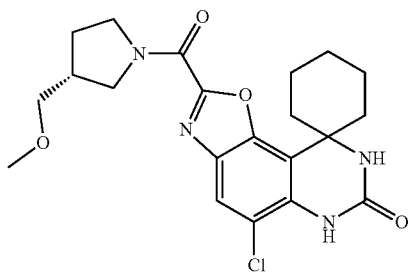 [SMILES: COC[C@@H]1CCN(C(=O)c2nc3cc(Cl)c4c(c3o2)C2(CCCCC2)NC(=O)N4)C1]

¹H NMR (400 MHz, DMSO-d6) δ 8.61 (s, 1H), 7.98 (d, J=14.5 Hz, 1H), 7.46 (s, 1H), 4.21-4.04 (m, 1H), 3.97-3.85 (m, 1H), 3.77-3.63 (m, 2H), 3.53 (td, J=8.1, 12.7 Hz, 2H), 3.27 (d, J=9.4 Hz, 3H), 2.63-2.53 (m, 1H), 2.30-2.14 (m, 2H), 2.11-1.97 (m, 1H), 1.95-1.81 (m, 4H), 1.79-1.63 (m, 2H), 1.61-1.49 (m, 2H), 1.27 (d, J=12.1 Hz, 1H). [M+H]=433.2.

Example 204. 5-Chloro-2-[(3S)-3-(methoxymethyl)pyrrolidine-1-carbonyl]-7,8-dihydro-6H-spiro[[1,3]oxazolo[5,4-f]quinazoline-9,1'-cyclohexane]-7-one

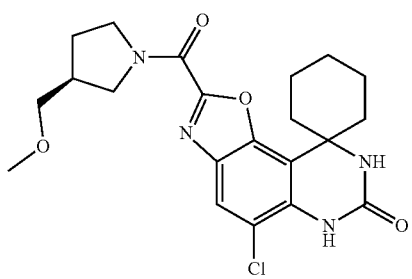 [SMILES: COC[C@H]1CCN(C(=O)c2nc3cc(Cl)c4c(c3o2)C2(CCCCC2)NC(=O)N4)C1]

¹H NMR (400 MHz, DMSO-d6) δ 8.61 (s, 1H), 7.98 (d, J=14.5 Hz, 1H), 7.46 (s, 1H), 4.20-4.04 (m, 1H), 3.97-3.87 (m, 1H), 3.76-3.63 (m, 2H), 3.59-3.48 (m, 2H), 3.27 (d, J=9.5 Hz, 3H), 2.63-2.54 (m, 1H), 2.29-2.14 (m, 2H), 2.11-1.95 (m, 1H), 1.95-1.81 (m, 4H), 1.79-1.62 (m, 2H), 1.57 (d, J=12.5 Hz, 2H), 1.27 (d, J=12.5 Hz, 1H). [M+H]=433.2.

Example 205. 5-Chloro-7-oxo-N-[2-(trifluoromethoxy)ethyl]-7,8-dihydro-6H-spiro[[1,3]oxazolo[5,4-f]quinazoline-9,1'-cyclohexane]-2-carboxamide

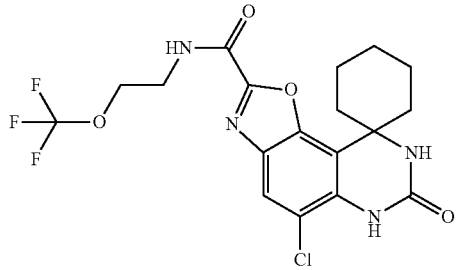 [SMILES: O=C1Nc2c(Cl)cc3nc(C(=O)NCCOC(F)(F)F)oc3c2C2(CCCCC2)N1]

¹H NMR (400 MHz, DMSO-d6) δ 9.40 (t, J=5.7 Hz, 1H), 8.65 (s, 1H), 7.95 (s, 1H), 7.46 (s, 1H), 4.24 (t, J=5.4 Hz, 2H), 3.62 (q, J=5.5 Hz, 2H), 2.30-2.15 (m, 2H), 1.88 (d, J=12.1 Hz, 4H), 1.72 (d, J=12.5 Hz, 1H), 1.57 (d, J=12.2 Hz, 2H), 1.37-1.19 (m, 1H). [M+H]=447.1.

Example 206. 5-Chloro-2-[(3R)-3-methoxypyrrolidine-1-carbonyl]-7,8-dihydro-6H-spiro[[1,3]oxazolo[5,4-f]quinazoline-9,1'-cyclohexane]-7-one

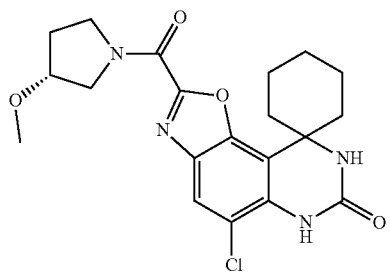 [SMILES: CO[C@@H]1CCN(C(=O)c2nc3cc(Cl)c4c(c3o2)C2(CCCCC2)NC(=O)N4)C1]

¹H NMR (400 MHz, CDCl₃) δ 7.77 (d, J=8.7 Hz, 1H), 7.47-7.38 (m, 1H), 6.20 (br s, 1H), 4.39-4.24 (m, 1H), 4.18-4.05 (m, 2H), 4.02-3.68 (m, 2H), 3.39 (d, J=4.0 Hz, 3H), 2.47-2.20 (m, 2H), 2.10-1.99 (m, 3H), 1.92-1.75 (m, 3H), 1.71-1.57 (m, 3H), 1.53-1.41 (m, 1H). [M+H]=419.2.

Example 207. 5-Chloro-2-(4-ethylpiperazine-1-carbonyl)-7,8-dihydro-6H-spiro[[1,3]oxazolo[5,4-f]quinazoline-9,1'-cyclohexane]-7-one

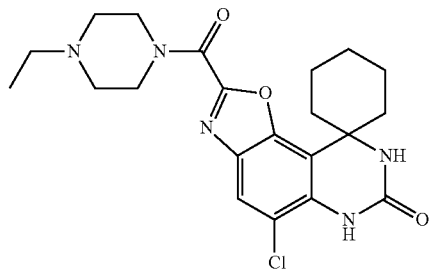

¹H NMR (400 MHz, DMSO-d6) δ 8.68 (s, 1H), 7.98 (s, 1H), 7.50 (s, 1H), 4.98 (br s, 1H), 4.59 (d, J=12.2 Hz, 1H), 3.61 (br s, 4H), 3.23-3.06 (m, 4H), 2.26-2.11 (m, 2H), 1.96-1.80 (m, 4H), 1.72 (d, J=12.1 Hz, 1H), 1.57 (d, J=11.1 Hz, 2H), 1.25 (t, J=7.3 Hz, 4H). [M+H]=432.3.

Example 208. 5-Chloro-2-[4-(propan-2-yl)piperazine-1-carbonyl]-7,8-dihydro-6H-spiro[[1,3]oxazolo[5,4-f]quinazoline-9,1'-cyclohexane]-7-one

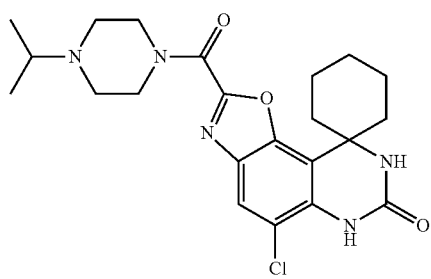

¹H NMR (400 MHz, CDCl₃) δ 7.74 (s, 1H), 7.27 (s, 1H), 5.74 (s, 1H), 4.25-4.09 (m, 2H), 3.89 (br s, 2H), 2.88-2.57 (m, 5H), 2.37 (dt, J=3.9, 13.4 Hz, 2H), 2.10-1.98 (m, 2H), 1.90-1.75 (m, 3H), 1.61 (q, J=13.6 Hz, 2H), 1.54-1.39 (m, 1H), 1.11 (d, J=6.0 Hz, 6H). [M+H]=446.0.

Example 209. 5-Chloro-2-[4-(2,2-difluoroethyl)piperazine-1-carbonyl]-7,8-dihydro-6H-spiro[[1,3]oxazolo[5,4-f]quinazoline-9,1'-cyclohexane]-7-one

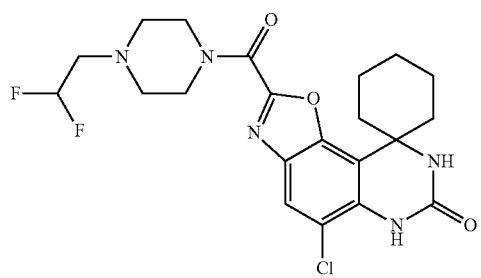

¹H NMR (400 MHz, CDCl₃) δ 7.75 (s, 1H), 7.26 (s, 1H), 6.20-5.80 (m, 1H), 5.69 (br s, 1H), 4.23 (br s, 2H), 3.91 (br s, 2H), 2.96-2.73 (m, 6H), 2.37 (dt, J=4.0, 13.4 Hz, 2H), 2.04 (d, J=12.8 Hz, 2H), 1.87-1.75 (m, 2H), 1.68-1.41 (m, 4H). [M+H]=468.3.

Example 210. 2-[(8aS)-Octahydropyrrolo[1,2-a]piperazine-2-carbonyl]-5-chloro-7,8-dihydro-6H-spiro[[1,3]oxazolo[5,4-f]quinazoline-9,1'-cyclohexane]-7-one

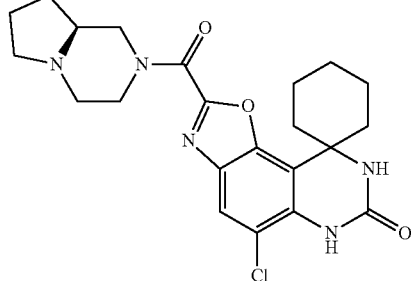

¹H NMR (400 MHz, DMSO-d6) δ 8.68 (s, 1H), 7.99 (s, 1H), 7.50 (s, 1H), 5.29-4.67 (m, 1H), 4.60-4.38 (m, 1H), 4.25-3.89 (m, 3H), 3.41-3.12 (m, 3H), 3.02 (br s, 1H), 2.27-1.78 (m, 10H), 1.72 (d, J=13.2 Hz, 1H), 1.57 (d, J=11.1 Hz, 2H), 1.32-1.17 (m, 1H). [M+H]=444.4.

Example 211. 5-Chloro-2-(piperazine-1-carbonyl)-7,8-dihydro-6H-spiro[[1,3]oxazolo[5,4-f]quinazoline-9,1'-cyclohexane]-7-one

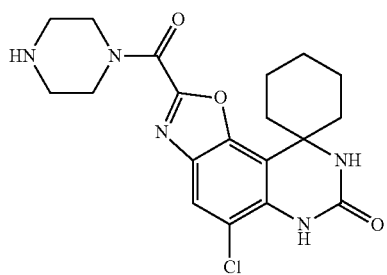 [SMILES: O=C1Nc2c(Cl)cc3nc(C(=O)N4CCNCC4)oc3c2C2(CCCCC2)N1]

¹H NMR (400 MHz, DMSO-d6) δ 8.91 (br s, 1H), 8.68 (s, 1H), 7.98 (s, 1H), 7.50 (s, 1H), 4.27 (br s, 2H), 3.89 (br s, 2H), 3.27 (br s, 4H), 2.29-2.13 (m, 2H), 1.88 (d, J=12.0 Hz, 4H), 1.72 (d, J=11.9 Hz, 1H), 1.63-1.50 (m, 2H), 1.25 (d, J=12.5 Hz, 1H). [M+H]=404.3.

Example 212. 5-Chloro-7-oxo-N-[(3R)-oxolan-3-ylmethyl]-7,8-dihydro-6H-spiro[[1,3]oxazolo[5,4-f]quinazoline-9,1'-cyclohexane]-2-carboxamide

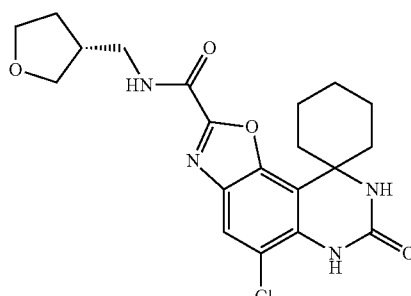

¹H NMR (400 MHz, CDCl₃) δ 7.74 (s, 1H), 7.46-7.37 (m, 2H), 6.00 (s, 1H), 3.97 (dt, J=5.4, 8.3 Hz, 1H), 3.90 (dd, J=6.8, 8.8 Hz, 1H), 3.81 (q, J=8.0 Hz, 1H), 3.68 (dd, J=5.1, 8.9 Hz, 1H), 3.55 (t, J=6.6 Hz, 2H), 2.66 (td, J=6.5, 13.1 Hz, 1H), 2.40 (dt, J=3.9, 13.4 Hz, 2H), 2.21-2.11 (m, 1H), 2.03 (s, 1H), 1.89-1.78 (m, 3H), 1.77-1.70 (m, 1H), 1.69-1.59 (m, 2H), 1.59-1.45 (m, 2H). [M+H]=419.2.

Example 213. 5-Chloro-2-[4-(2-fluoroethyl)piperazine-1-carbonyl]-7,8-dihydro-6H-spiro[[1,3]oxazolo[5,4-f]quinazoline-9,1'-cyclohexane]-7-one

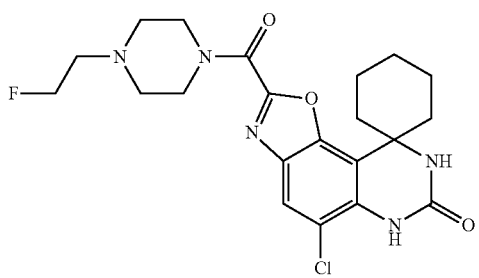 [SMILES: O=C1Nc2c(Cl)cc3nc(C(=O)N4CCN(CCF)CC4)oc3c2C2(CCCCC2)N1]

¹H NMR (400 MHz, CDCl₃) δ 7.74 (s, 1H), 7.32 (s, 1H), 5.86 (s, 1H), 4.69 (t, J=4.7 Hz, 1H), 4.57 (t, J=4.8 Hz, 1H), 4.28-4.15 (m, 2H), 3.98-3.84 (m, 2H), 2.83 (t, J=4.8 Hz, 1H), 2.76 (t, J=4.7 Hz, 1H), 2.71 (t, J=4.8 Hz, 4H), 2.37 (dt, J=4.0, 13.4 Hz, 2H), 2.03 (d, J=13.1 Hz, 2H), 1.87-1.76 (m, 2H), 1.70-1.55 (m, 2H), 1.54-1.41 (m, 1H), 1.32-1.21 (m, 1H). [M+H]=450.3.

Example 214. 5-Chloro-N-(2,2-difluorocyclopentyl)-7-oxo-7,8-dihydro-6H-spiro[[1,3]oxazolo[5,4-f]quinazoline-9,1'-cyclohexane]-2-carboxamide

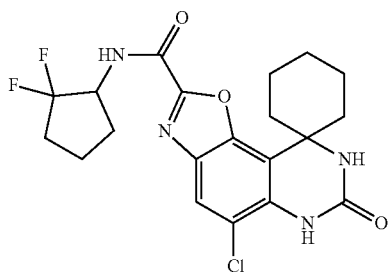 [SMILES: O=C1Nc2c(Cl)cc3nc(C(=O)NC4CCCC4(F)F)oc3c2C2(CCCCC2)N1]

¹H NMR (400 MHz, DMSO-d6) δ 9.35 (d, J=8.6 Hz, 1H), 8.66 (s, 1H), 7.95 (s, 1H), 7.47 (s, 1H), 4.62-4.48 (m, 1H), 2.27-2.05 (m, 5H), 2.02-1.79 (m, 6H), 1.76-1.65 (m, 2H), 1.58 (d, J=13.0 Hz, 2H), 1.38-1.22 (m, 1H). [M+H]=439.2.

Example 215. 5-Chloro-N-[4-(methoxymethyl)oxan-4-yl]-7-oxo-7,8-dihydro-6H-spiro[[1,3]oxazolo[5,4-f]quinazoline-9,1'-cyclohexane]-2-carboxamide

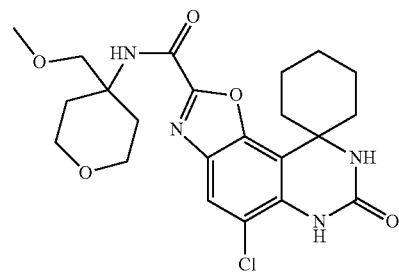 [SMILES: COCC1(NC(=O)c2nc3cc(Cl)c4c(c3o2)C2(CCCCC2)NC(=O)N4)CCOCC1]

¹H NMR (400 MHz, DMSO-d6) δ 8.64 (s, 1H), 8.39 (s, 1H), 7.94 (s, 1H), 7.46 (s, 1H), 3.73-3.65 (m, 2H), 3.62-3.53 (m, 4H), 3.28 (s, 3H), 2.34-2.16 (m, 4H), 1.87 (d, J=12.0 Hz, 4H), 1.75-1.53 (m, 5H), 1.27 (d, J=12.5 Hz, 1H). [M+H]=463.3.

Example 216. 5-Chloro-N-(3-fluorooxan-4-yl)-7-oxo-7,8-dihydro-6H-spiro[[1,3]oxazolo[5,4-f]quinazoline-9,1'-cyclohexane]-2-carboxamide

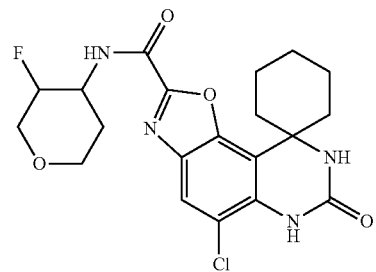 [SMILES: O=C1Nc2c(Cl)cc3nc(C(=O)NC4CCOCC4F)oc3c2C2(CCCCC2)N1]

¹H NMR (400 MHz, CDCl₃) δ 7.77 (s, 1H), 7.51 (d, J=8.4 Hz, 1H), 7.45 (br s, 1H), 6.20 (br s, 1H), 4.84-4.63 (m, 1H), 4.52-4.32 (m, 1H), 4.26 (t, J=13.2 Hz, 1H), 4.17-4.02 (m, 1H), 3.77-3.47 (m, 2H), 2.51-2.34 (m, 2H), 2.12 (d, J=12.2 Hz, 2H), 1.95-1.76 (m, 4H), 1.69-1.39 (m, 4H), 1.21-1.21 (m, 1H). [M+H]=437.2.

Example 217. 5-Chloro-N-(2,2-difluoro-3-hydroxypropyl)-7-oxo-7,8-dihydro-6H-spiro[[1,3]oxazolo[5,4-f]quinazoline-9,1'-cyclohexane]-2-carboxamide

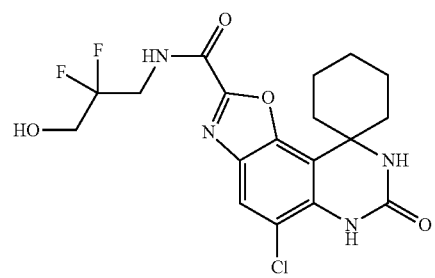 [SMILES: O=C1Nc2c(Cl)cc3nc(C(=O)NCC(F)(F)CO)oc3c2C2(CCCCC2)N1]

¹H NMR (400 MHz, CDCl₃) δ 7.77 (s, 1H), 7.70 (t, J=6.4 Hz, 1H), 7.50 (s, 1H), 6.24 (s, 1H), 4.01 (dt, J=6.7, 12.7 Hz,

2H), 3.83 (t, J=12.1 Hz, 2H), 3.25 (s, 1H), 2.38 (dt, J=4.0, 13.4 Hz, 2H), 2.06 (d, J=13.3 Hz, 2H), 1.91-1.76 (m, 3H), 1.72-1.47 (m, 3H). [M+H]=429.1.

Example 218. 5-Chloro-7-oxo-N-[(3S)-oxolan-3-ylmethyl]-7,8-dihydro-6H-spiro[[1,3]oxazolo[5,4-f]quinazoline-9,1'-cyclohexane]-2-carboxamide

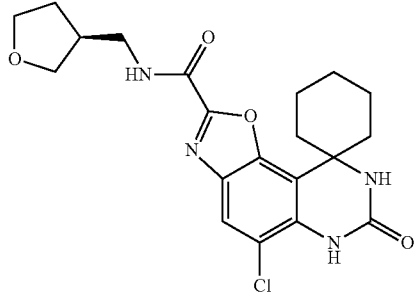 [SMILES: O=C1Nc2c(Cl)cc3nc(C(=O)NC[C@@H]4CCOC4)oc3c2C2(CCCCC2)N1]

¹H NMR (400 MHz, DMSO-d6) δ 9.36 (t, J=6.0 Hz, 1H), 8.64 (s, 1H), 7.93 (s, 1H), 7.46 (s, 1H), 3.81-3.58 (m, 4H), 3.33-3.23 (m, 3H), 2.29-2.16 (m, 2H), 2.01-1.80 (m, 5H), 1.77-1.51 (m, 4H), 1.39-1.22 (m, 1H). [M+H]=419.2.

Example 219. 5-Chloro-7-oxo-N-[(3S)-oxolan-3-yl]-7,8-dihydro-6H-spiro[[1,3]oxazolo[5,4-f]quinazoline-9,1'-cyclohexane]-2-carboxamide

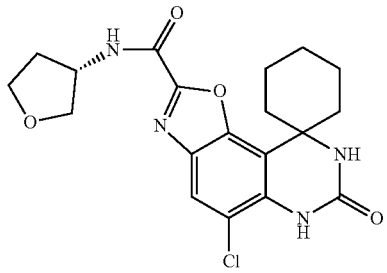 [SMILES: O=C1Nc2c(Cl)cc3nc(C(=O)N[C@H]4CCOC4)oc3c2C2(CCCCC2)N1]

¹H NMR (400 MHz, CDCl₃) δ 7.74 (s, 1H), 7.45 (s, 1H), 6.18 (br s, 1H), 4.81-4.68 (m, 1H), 4.13-4.01 (m, 1H), 4.00-3.77 (m, 4H), 2.47-2.34 (m, 2H), 2.08-2.00 (m, 3H), 1.89-1.76 (m, 4H), 1.71-1.49 (m, 3H). [M+H]=405.1.

Example 220. 5-Chloro-7-oxo-N-[(3R)-oxolan-3-yl]-7,8-dihydro-6H-spiro[[1,3]oxazolo[5,4-f]quinazoline-9,1'-cyclohexane]-2-carboxamide

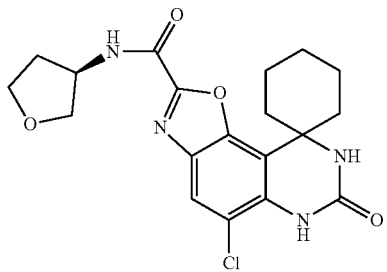 [SMILES: O=C1Nc2c(Cl)cc3nc(C(=O)N[C@@H]4CCOC4)oc3c2C2(CCCCC2)N1]

¹H NMR (400 MHz, CDCl₃) δ 7.73 (s, 1H), 7.44-7.33 (m, 2H), 5.95 (br s, 1H), 4.82-4.68 (m, 1H), 4.13-4.02 (m, 1H), 3.99-3.93 (m, 1H), 3.92-3.84 (m, 2H), 2.48-2.33 (m, 4H), 2.06 (br s, 1H), 1.90-1.75 (m, 3H), 1.71-1.42 (m, 4H). [M+H]=405.1.

Example 221. 2-[(8aS)-Octahydropyrrolo[1,2-a]piperazine-2-carbonyl]-5-chloro-4',4'-difluoro-7,8-dihydro-6H-spiro[[1,3]oxazolo[5,4-f]quinazoline-9,1'-cyclohexane]-7-one

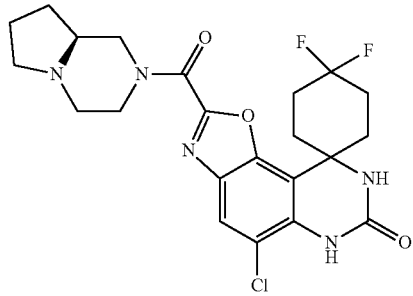 [SMILES: O=C1Nc2c(Cl)cc3nc(C(=O)N4CCN5CCC[C@H]5C4)oc3c2C2(CCC(F)(F)CC2)N1]

¹H NMR (400 MHz, CD₃OD) δ 7.92 (s, 1H), 3.93-3.42 (m, 5H), 3.22-3.02 (m, 2H), 2.73 (d, J=8.1 Hz, 2H), 2.47-1.99 (m, 12H). [M+H]=480.2.

Example 222.-Example 225. were prepared in a manner analogous to Example 8, with the appropriate starting material substitutions.

Example 222. 2-[(4,4-Difluoropiperidin-1-yl)methyl]-5-fluoro-7,8-dihydro-6H-spiro[[1,3]oxazolo[5,4-f]quinazoline-9,1'-cyclohexane]-7-one

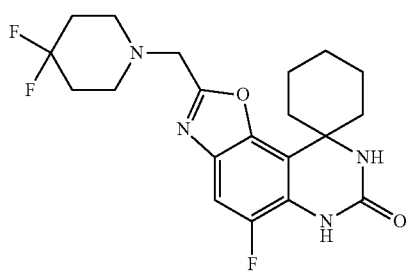 [SMILES: O=C1Nc2c(F)cc3nc(CN4CCC(F)(F)CC4)oc3c2C2(CCCCC2)N1]

¹H NMR (400 MHz, DMSO-d6) δ 9.31 (s, 1H), 7.60 (d, J=9.9 Hz, 1H), 7.25 (s, 1H), 4.35 (br s, 2H), 3.17-3.00 (m, 4H), 2.24-2.06 (m, 6H), 1.98-1.79 (m, 4H), 1.71 (d, J=11.7 Hz, 1H), 1.55 (d, J=13.9 Hz, 2H), 1.27 (d, J=12.8 Hz, 1H). [M+H]=409.1.

Example 223. 5-Fluoro-2-{[(2-methoxyethyl)amino]methyl}-7,8-dihydro-6H-spiro[[1,3]oxazolo[5,4-f]quinazoline-9,1'-cyclohexane]-7-one

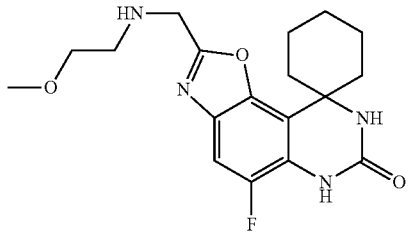 [SMILES: COCCNCc1nc2cc(F)c3c(c2o1)C1(CCCCC1)NC(=O)N3]

¹H NMR (400 MHz, DMSO-d6) δ 9.22 (s, 1H), 7.50 (d, J=10.0 Hz, 1H), 7.18 (s, 1H), 5.75 (s, 1H), 4.11 (q, J=5.3 Hz, 2H), 3.99 (s, 2H), 3.23 (s, 3H), 2.77 (t, J=5.6 Hz, 2H), 2.26-2.12 (m, 2H), 1.97-1.78 (m, 4H), 1.70 (d, J=12.1 Hz, 1H), 1.54 (d, J=13.3 Hz, 2H), 1.41-1.25 (m, 1H). [M+H]=363.1.

Example 224. 2-({5-Fluoro-7-oxo-7,8-dihydro-6H-spiro[[1,3]oxazolo[5,4-f]quinazoline-9,1'-cyclohexane]-2-ylmethyl}(methyl)amino)-N,N-dimethylacetamide

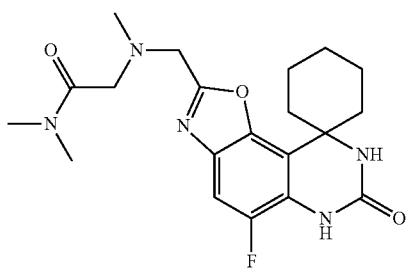

¹H NMR (400 MHz, DMSO-d6) δ 9.37 (s, 1H), 7.67 (d, J=9.8 Hz, 1H), 7.28 (s, 1H), 4.67 (br s, 2H), 4.32 (br s, 2H), 2.90 (d, J=19.3 Hz, 9H), 2.25-2.09 (m, 2H), 1.98-1.81 (m, 4H), 1.71 (d, J=12.0 Hz, 1H), 1.54 (d, J=13.3 Hz, 2H), 1.28 (d, J=13.2 Hz, 1H). [M+H]=404.4.

Example 225. 2-({5-Fluoro-7-oxo-7,8-dihydro-6H-spiro[[1,3]oxazolo[5,4-f]quinazoline-9,1'-cyclohexane]-2-ylmethyl}amino)-N,N-dimethylacetamide

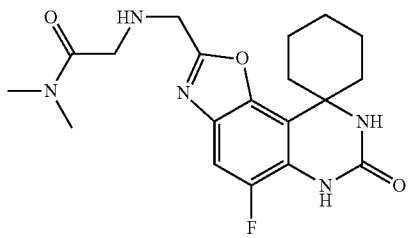 [SMILES: CN(C)C(=O)CNCc1nc2cc(F)c3c(c2o1)C1(CCCCC1)NC(=O)N3]

¹H NMR (400 MHz, DMSO-d6) δ 9.76 (br s, 1H), 9.36 (s, 1H), 7.66 (d, J=9.9 Hz, 1H), 7.27 (s, 1H), 4.58 (s, 2H), 4.24 (s, 2H), 2.94 (s, 3H), 2.92-2.89 (m, 3H), 2.29-2.14 (m, 2H), 1.96-1.78 (m, 4H), 1.71 (d, J=12.7 Hz, 1H), 1.54 (d, J=13.1 Hz, 2H), 1.31 (d, J=12.7 Hz, 1H). [M+H]=390.2.

Example 226.-Example 229. were prepared in a manner analogous to Example 10, with the appropriate starting material substitutions.

Example 226. 5-Chloro-4',4'-difluoro-2-({[(3S)-oxan-3-yl]amino}methyl)-7,8-dihydro-6H-spiro[[1,3]oxazolo[5,4-f]quinazoline-9,1'-cyclohexane]-7-one

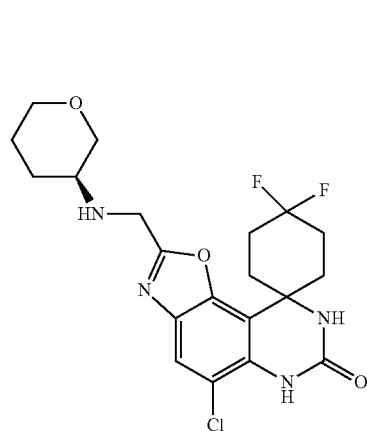 [SMILES: O=C1Nc2c(Cl)cc3nc(CN[C@H]4CCCOC4)oc3c2C2(CCC(F)(F)CC2)N1]

¹H NMR (400 MHz, DMSO-d6) δ 9.81-9.44 (m, 1H), 8.75 (s, 1H), 7.95 (s, 1H), 7.89 (s, 1H), 4.70 (d, J=3.8 Hz, 2H), 3.99-3.92 (m, 1H), 3.69 (d, J=11.5 Hz, 1H), 3.59 (dd, J=7.6, 11.7 Hz, 3H), 2.49-2.38 (m, 4H), 2.12 (br s, 1H), 2.01 (d, J=9.5 Hz, 4H), 1.85-1.73 (m, 2H), 1.59-1.47 (m, 1H). [M+H]=441.3.

Example 227. 5-Chloro-4',4'-difluoro-2-({[(3R)-oxolan-3-ylmethyl]amino}methyl)-7,8-dihydro-6H-spiro[[1,3]oxazolo[5,4-f]quinazoline-9,1'-cyclohexane]-7-one

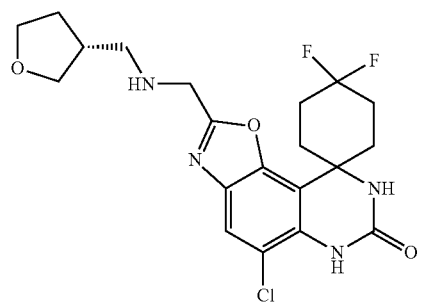 [SMILES: O=C1Nc2c(Cl)cc3nc(CNC[C@H]4CCOC4)oc3c2C2(CCC(F)(F)CC2)N1]

¹H NMR (400 MHz, CD₃OD) δ 7.84 (s, 1H), 4.72 (s, 2H), 4.00-3.90 (m, 2H), 3.86-3.77 (m, 1H), 3.62 (dd, J=5.7, 9.0 Hz, 1H), 3.36 (d, J=1.8 Hz, 2H), 2.76-2.63 (m, 3H), 2.49-2.06 (m, 8H), 1.77 (dd, J=6.7, 12.8 Hz, 1H). [M+H]=441.1.

Example 228. 5-Chloro-4',4'-difluoro-2-({[(3S)-oxolan-3-yl]amino}methyl)-7,8-dihydro-6H-spiro[[1,3]oxazolo[5,4-f]quinazoline-9,1'-cyclohexane]-7-one

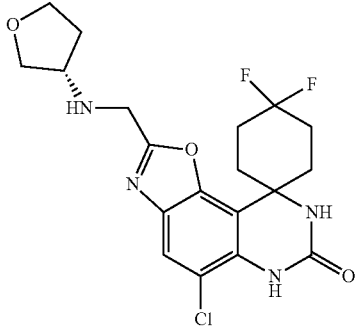 [SMILES: O=C1Nc2c(Cl)cc3nc(CN[C@H]4CCOC4)oc3c2C2(CCC(F)(F)CC2)N1]

¹H NMR (400 MHz, DMSO-d6) δ 9.75 (br s, 1H), 8.75 (s, 1H), 7.95 (s, 1H), 7.89 (s, 1H), 4.69 (s, 2H), 4.06 (br s, 1H), 3.99-3.88 (m, 2H), 3.80 (dd, J=6.1, 10.5 Hz, 1H), 3.71-3.64 (m, 1H), 2.49-2.39 (m, 3H), 2.36-2.19 (m, 1H), 2.14-1.90 (m, 6H). [M+H]=427.2.

Example 229. 5-Chloro-4',4'-difluoro-2-({[(3R)-oxan-3-yl]amino}methyl)-7,8-dihydro-6H-spiro[[1,3]oxazolo[5,4-f]quinazoline-9,1'-cyclohexane]-7-one

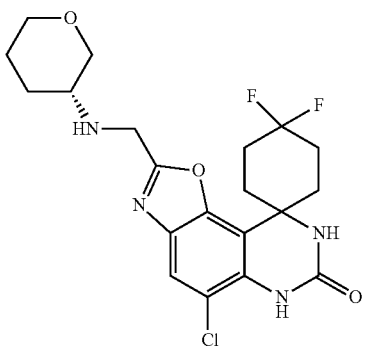 [SMILES: O=C1Nc2c(Cl)cc3nc(CN[C@@H]4CCCOC4)oc3c2C2(CCC(F)(F)CC2)N1]

¹H NMR (400 MHz, DMSO-d6) δ 9.60 (br s, 1H), 8.75 (s, 1H), 7.95 (s, 1H), 7.89 (s, 1H), 4.70 (d, J=3.8 Hz, 2H), 4.02-3.92 (m, 1H), 3.74-3.65 (m, 2H), 3.62-3.39 (m, 2H), 2.50-2.37 (m, 4H), 2.21-2.09 (m, 1H), 2.02 (d, J=8.8 Hz, 4H), 1.84-1.70 (m, 2H), 1.52 (dd, J=4.2, 8.9 Hz, 1H). [M+H]=441.2.

Example 230.-Example 239. were prepared in a manner analogous to Example 27, with the appropriate starting material substitutions.

Example 230. 5'-Chloro-2'-(4-methylpiperazine-1-carbonyl)-7',8'-dihydro-6'H-spiro[cyclohexane-1,9'-furo[2,3-f]quinazoline]-7'-one

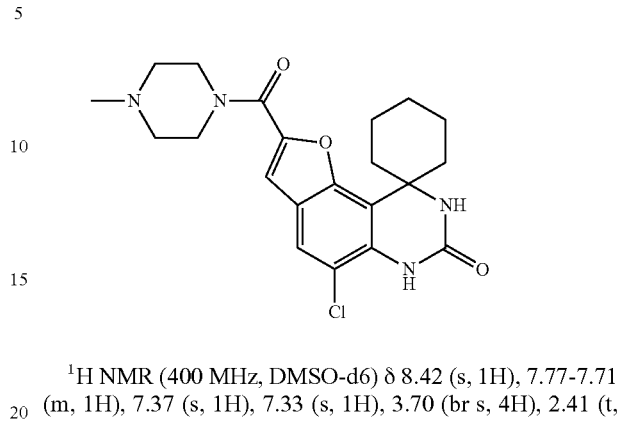

¹H NMR (400 MHz, DMSO-d6) δ 8.42 (s, 1H), 7.77-7.71 (m, 1H), 7.37 (s, 1H), 7.33 (s, 1H), 3.70 (br s, 4H), 2.41 (t, J=4.8 Hz, 4H), 2.36-2.26 (m, 2H), 2.24-2.21 (m, 3H), 2.23 (s, 3H), 1.96-1.80 (m, 4H), 1.72 (d, J=12.5 Hz, 1H), 1.56 (d, J=12.7 Hz, 2H), 1.31-1.21 (m, 1H). [M+H]=417.2.

Example 231. 5'-Chloro-2'-(4-ethylpiperazine-1-carbonyl)-7',8'-dihydro-6'H-spiro[cyclohexane-1,9'-furo[2,3-f]quinazoline]-7'-one

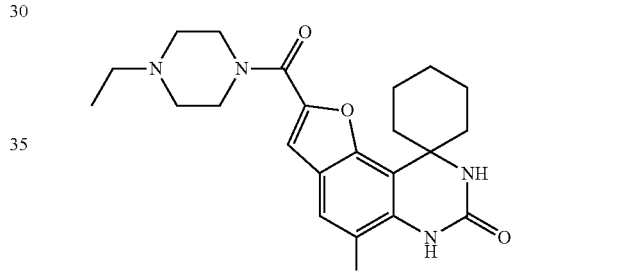

¹H NMR (400 MHz, DMSO-d6) δ 8.42 (s, 1H), 7.75 (s, 1H), 7.37 (s, 1H), 7.33 (s, 1H), 3.70 (br s, 4H), 2.48-2.44 (m, 4H), 2.42-2.36 (m, 2H), 2.35-2.27 (m, 2H), 1.95-1.83 (m, 4H), 1.72 (d, J=13.1 Hz, 1H), 1.56 (d, J=13.3 Hz, 2H), 1.26 (d, J=12.3 Hz, 1H), 1.03 (t, J=7.2 Hz, 3H). [M+H]=431.1.

Example 232. 5'-Chloro-N-(2-methoxyethyl)-N-methyl-7'-oxo-7',8'-dihydro-6'H-spiro[cyclohexane-1,9'-furo[2,3-f]quinazoline]-2'-carboxamide

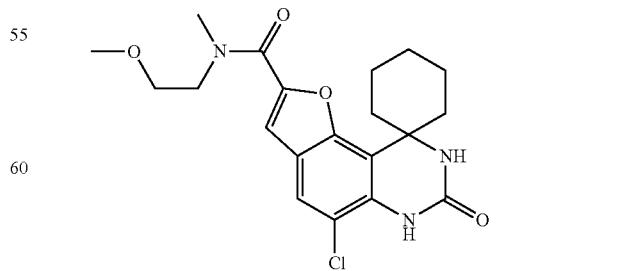

¹H NMR (400 MHz, DMSO-d6) δ 8.46-8.31 (m, 1H), 8.46-8.31 (m, 1H), 8.39 (br s, 1H), 7.75 (s, 1H), 7.36 (br s,

2H), 3.90-3.61 (m, 3H), 3.57 (t, J=5.3 Hz, 2H), 3.26 (br s, 3H), 3.03 (br s, 2H), 2.33 (br s, 2H), 1.93-1.80 (m, 5H), 1.71 (d, J=12.1 Hz, 1H), 1.56 (d, J=12.3 Hz, 2H), 1.26 (d, J=10.1 Hz, 1H). [M+H]=406.1.

Example 233. 5'-Chloro-2'-[4-(2-methoxyethyl)piperazine-1-carbonyl]-7',8'-dihydro-6'H-spiro[cyclohexane-1,9'-furo[2,3-f]quinazoline]-7'-one

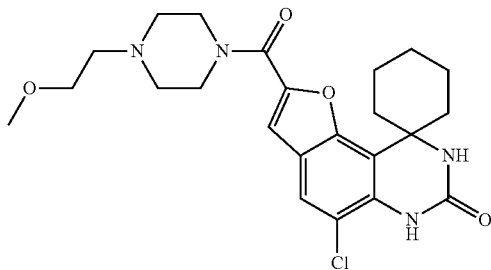 [SMILES: COCCN1CCN(C(=O)c2cc3cc(Cl)c4c(c3o2)C2(CCCCC2)NC(=O)N4)CC1]

¹H NMR (400 MHz, DMSO-d6) δ 8.42 (s, 1H), 7.81-7.67 (m, 1H), 7.37 (s, 1H), 7.33 (s, 1H), 3.68 (br s, 4H), 3.47 (t, J=5.6 Hz, 2H), 3.26-3.23 (m, 3H), 2.57-2.52 (m, 6H), 2.36-2.25 (m, 2H), 1.94-1.83 (m, 4H), 1.72 (d, J=12.7 Hz, 1H), 1.56 (d, J=13.3 Hz, 2H), 1.26 (d, J=13.3 Hz, 1H). [M+H]=461.2.

Example 234. 5'-Chloro-2'-(piperidine-1-carbonyl)-7',8'-dihydro-6'H-spiro[cyclohexane-1,9'-furo[2,3-f]quinazoline]-7'-one

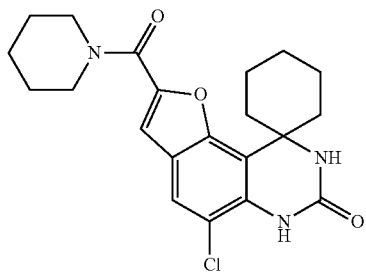 [SMILES: O=C1Nc2c(Cl)cc3cc(C(=O)N4CCCCC4)oc3c2C2(CCCCC2)N1]

¹H NMR (400 MHz, DMSO-d6) δ 8.40 (s, 1H), 7.74 (s, 1H), 7.36 (s, 1H), 7.30 (s, 1H), 3.66 (br s, 4H), 2.36-2.28 (m, 2H), 1.95-1.81 (m, 4H), 1.74-1.52 (m, 9H), 1.33-1.20 (m, 1H). [M+H]=402.2.

Example 235. 2'-(Azetidine-1-carbonyl)-5'-chloro-7',8'-dihydro-6'H-spiro[cyclohexane-1,9'-furo[2,3-f]quinazoline]-7'-one

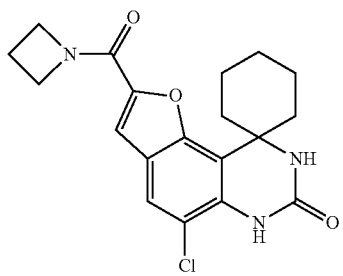 [SMILES: O=C1Nc2c(Cl)cc3cc(C(=O)N4CCC4)oc3c2C2(CCCCC2)N1]

¹H NMR (400 MHz, DMSO-d6) δ 8.41 (s, 1H), 7.76 (s, 1H), 7.41-7.37 (m, 2H), 4.62 (t, J=7.5 Hz, 2H), 4.09 (t, J=7.6 Hz, 2H), 2.42-2.32 (m, 3H), 1.96-1.79 (m, 4H), 1.70 (d, J=12.5 Hz, 1H), 1.56 (d, J=13.0 Hz, 2H), 1.30-1.22 (m, 4H). [M+H]=374.0.

Example 236. 5'-Chloro-2'-(pyrrolidine-1-carbonyl)-7',8'-dihydro-6'H-spiro[cyclohexane-1,9'-furo[2,3-f]quinazoline]-7'-one

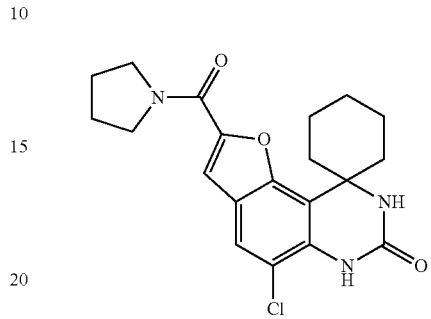

¹H NMR (400 MHz, DMSO-d6) δ 8.40 (s, 1H), 7.76 (s, 1H), 7.44-7.36 (m, 2H), 3.89 (t, J=6.6 Hz, 2H), 3.52 (t, J=6.8 Hz, 2H), 2.44-2.35 (m, 2H), 2.02-1.94 (m, 2H), 1.91-1.81 (m, 6H), 1.72 (d, J=11.9 Hz, 1H), 1.55 (d, J=12.8 Hz, 2H), 1.23 (d, J=13.1 Hz, 1H). [M+H]=388.0.

Example 237. 5'-Chloro-2'-(morpholine-4-carbonyl)-7',8'-dihydro-6'H-spiro[cyclohexane-1,9'-furo[2,3-f]quinazoline]-7'-one

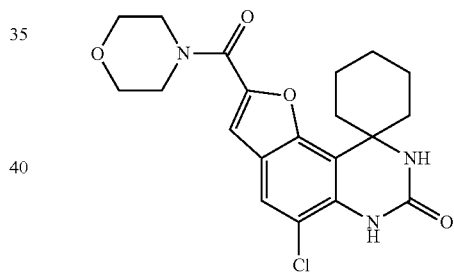

¹H NMR (400 MHz, DMSO-d6) δ 8.43 (s, 1H), 7.75 (s, 1H), 7.41-7.33 (m, 2H), 3.70 (br s, 8H), 2.35-2.26 (m, 2H), 1.92-1.80 (m, 4H), 1.72 (d, J=11.9 Hz, 1H), 1.56 (d, J=14.4 Hz, 2H), 1.31-1.19 (m, 1H). [M+H]=404.0.

Example 238. 5'-Chloro-2'-[4-(2,2,2-trifluoroethyl)piperazine-1-carbonyl]-7',8'-dihydro-6'H-spiro[cyclohexane-1,9'-furo[2,3-f]quinazoline]-7'-one

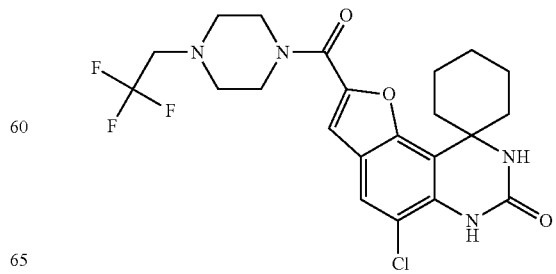

¹H NMR (400 MHz, DMSO-d6) δ 8.43 (br s, 1H), 7.75 (s, 1H), 7.38-7.30 (m, 2H), 3.71 (br s, 4H), 3.26-3.22 (m, 2H), 2.74 (br s, 4H), 2.32 (d, J=14.3 Hz, 2H), 1.85 (d, J=10.9 Hz, 4H), 1.72 (d, J=11.6 Hz, 1H), 1.56 (d, J=11.0 Hz, 2H), 1.25 (d, J=11.7 Hz, 1H). [M+H]=485.0.

Example 239. 5'-Chloro-2'-[4-(2,2-difluoroethyl)piperazine-1-carbonyl]-7',8'-dihydro-6'H-spiro[cyclohexane-1,9'-furo[2,3-f]quinazoline]-7'-one

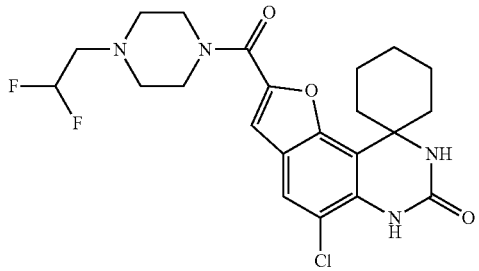

¹H NMR (400 MHz, DMSO-d6) δ 8.43 (s, 1H), 7.75 (s, 1H), 7.37 (s, 1H), 7.34 (s, 1H), 6.35-6.00 (m, 1H), 3.71 (br s, 4H), 2.87-2.78 (m, 2H), 2.88-2.77 (m, 3H), 2.82 (dt, J=4.2, 15.7 Hz, 3H), 2.67-2.62 (m, 4H), 2.36-2.26 (m, 2H), 1.95-1.83 (m, 4H), 1.72 (d, J=13.1 Hz, 1H), 1.56 (d, J=13.7 Hz, 2H), 1.26 (d, J=13.2 Hz, 1H). [M+H]=467.0.

Example 240.-Example 244. were prepared in a manner analogous to Example 29, with the appropriate starting material substitutions.

Example 240. 5'-Chloro-2'-[(1S,4S)-2-oxa-5-azabicyclo[2.2.1]heptan-5-ylmethyl]-7',8'-dihydro-6'H-spiro[cyclohexane-1,9'-furo[2,3-f]quinazoline]-7'-one

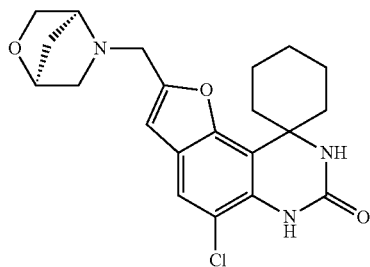

¹H NMR (400 MHz, DMSO-d6) δ 8.16 (s, 1H), 7.56 (s, 1H), 7.25 (s, 1H), 6.63 (s, 1H), 4.38 (s, 1H), 3.92 (d, J=7.7 Hz, 1H), 3.87 (d, J=5.1 Hz, 2H), 3.58-3.53 (m, 2H), 2.94-2.86 (m, 1H), 2.60 (d, J=9.8 Hz, 1H), 2.39-2.28 (m, 2H), 1.94-1.65 (m, 7H), 1.63-1.50 (m, 3H), 1.25 (d, J=13.4 Hz, 1H). [M+H]=402.1.

Example 241. 5'-Chloro-2'-(piperidin-1-ylmethyl)-7',8'-dihydro-6'H-spiro[cyclohexane-1,9'-furo[2,3-f]quinazoline]-7'-one

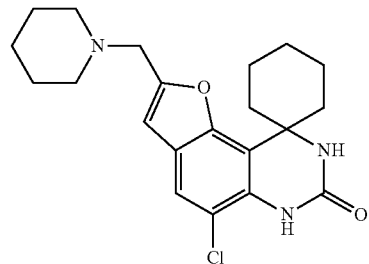 [SMILES: O=C1Nc2c(Cl)cc3cc(CN4CCCCC4)oc3c2C2(CCCCC2)N1]

¹H NMR (400 MHz, DMSO-d6) δ 8.15 (s, 1H), 7.57 (s, 1H), 7.26 (s, 1H), 6.63 (s, 1H), 3.68 (s, 2H), 2.46 (br s, 4H), 2.36 (dd, J=10.0, 13.9 Hz, 3H), 1.93-1.77 (m, 4H), 1.71 (d, J=12.2 Hz, 1H), 1.58-1.45 (m, 5H), 1.35 (br s, 2H), 1.25 (d, J=12.5 Hz, 1H). [M+H]=388.2.

Example 242. 5'-Chloro-2'-(morpholin-4-ylmethyl)-7',8'-dihydro-6'H-spiro[cyclohexane-1,9'-furo[2,3-f]quinazoline]-7'-one

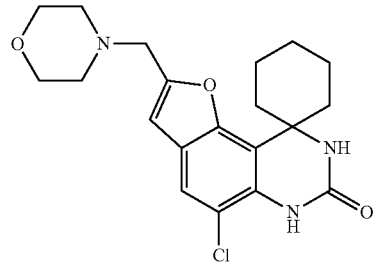 [SMILES: O=C1Nc2c(Cl)cc3cc(CN4CCOCC4)oc3c2C2(CCCCC2)N1]

¹H NMR (400 MHz, DMSO-d6) δ 8.17 (s, 1H), 7.62-7.55 (m, 1H), 7.27 (s, 1H), 6.67 (s, 1H), 3.72 (s, 2H), 3.62-3.55 (m, 4H), 2.48 (d, J=4.5 Hz, 4H), 2.41-2.27 (m, 2H), 1.92-1.79 (m, 4H), 1.71 (d, J=11.9 Hz, 1H), 1.55 (d, J=13.7 Hz, 2H), 1.34-1.20 (m, 1H). [M+H]=390.1.

Example 243. 5'-Chloro-2'-(pyrrolidin-1-ylmethyl)-7',8'-dihydro-6'H-spiro[cyclohexane-1,9'-furo[2,3-f]quinazoline]-7'-one

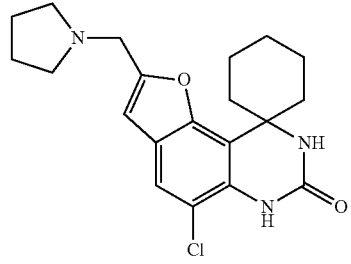 [SMILES: O=C1Nc2c(Cl)cc3cc(CN4CCCC4)oc3c2C2(CCCCC2)N1]

¹H NMR (400 MHz, DMSO-d6) δ 8.16 (s, 1H), 7.57 (s, 1H), 7.26 (s, 1H), 6.64 (s, 1H), 3.77 (s, 2H), 2.58 (br s, 4H), 2.40-2.31 (m, 2H), 1.94-1.78 (m, 5H), 1.70 (t, J=3.4 Hz, 4H), 1.54 (d, J=13.7 Hz, 2H), 1.24 (br s, 1H). [M+H]=373.9.

Example 244. 5'-chloro-2'-[(4-methylpiperazin-1-yl)methyl]-7',8'-dihydro-6'H-spiro[cyclohexane-1,9'-furo[2,3-f]quinazoline]-7'-one

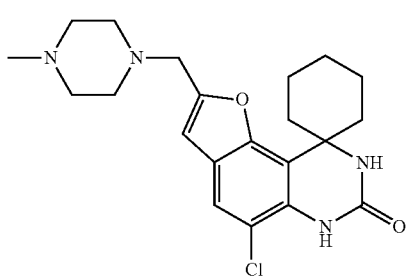 [SMILES: CN1CCN(Cc2cc3cc(Cl)c4c(c3o2)C2(CCCCC2)NC(=O)N4)CC1]

¹H NMR (400 MHz, DMSO-d6) δ 8.17 (s, 1H), 7.58 (s, 1H), 7.26 (s, 1H), 6.65 (s, 1H), 3.70 (s, 2H), 2.37-2.26 (m, 6H), 2.14 (s, 3H), 1.94-1.78 (m, 4H), 1.71 (d, J=12.6 Hz, 1H), 1.54 (d, J=14.3 Hz, 2H), 1.32-1.24 (m, 1H). [M+H]= 403.0.

Example 245.-Example 466. were prepared in a manner analogous to Example 28, with the appropriate starting material substitutions.

Example 245. 5'-Chloro-N-ethyl-7'-oxo-N-(propan-2-yl)-7',8'-dihydro-6'H-spiro[cyclohexane-1,9'-furo[2,3-f]quinazoline]-2'-carboxamide

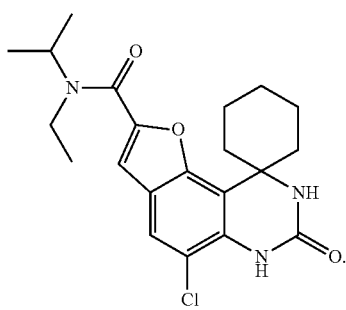

[M + H] = 404.4

Example 246. 5'-Chloro-7'-oxo-N-[2-(propan-2-yloxy)ethyl]-7',8'-dihydro-6'H-spiro[cyclohexane-1,9'-furo[2,3-f]quinazoline]-2'-carboxamide

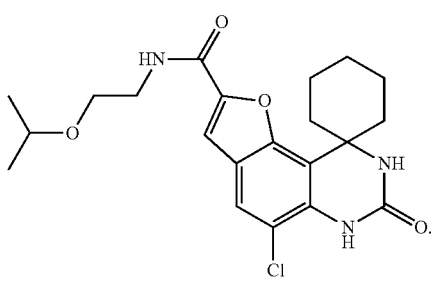

[M + H] = 420.4

Example 247. 5'-Chloro-2'-(4-methoxypiperidine-1-carbonyl)-7',8'-dihydro-6'H-spiro[cyclohexane-1,9'-furo[2,3-f]quinazoline]-7'-one

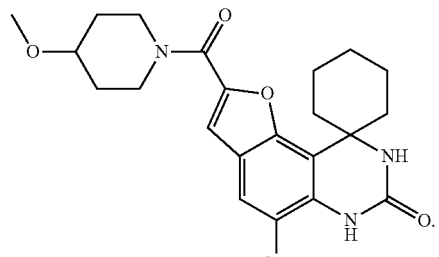

[M + H] = 432.6

Example 248. 5'-Chloro-N-[(4-fluorophenyl)methyl]-7'-oxo-7',8'-dihydro-6'H-spiro[cyclohexane-1,9'-furo[2,3-f]quinazoline]-2'-carboxamide

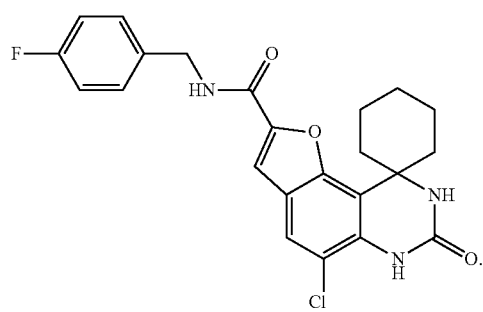

[M + H] = 442.4

Example 249. 5'-Chloro-N-(2-methoxyethyl)-7'-oxo-7',8'-dihydro-6'H-spiro[cyclohexane-1,9'-furo[2,3-f]quinazoline]-2'-carboxamide

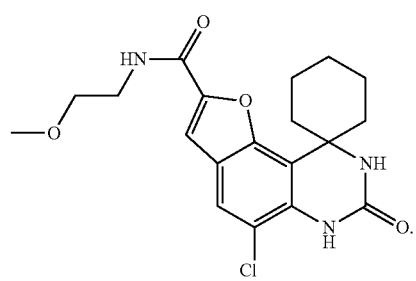

[M + H] = 392.4

Example 250. 5'-Chloro-N-methyl-N-(2-methylpropyl)-7'-oxo-7',8'-dihydro-6'H-spiro[cyclohexane-1,9'-furo[2,3-f]quinazoline]-2'-carboxamide

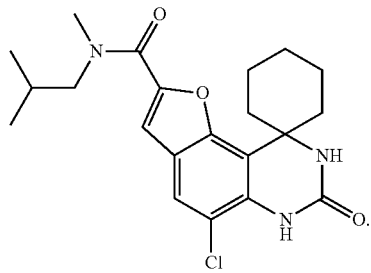

[M + H] = 404.4

Example 251. 5'-Chloro-N-cyclopentyl-N-methyl-7'-oxo-7',8'-dihydro-6'H-spiro[cyclohexane-1,9'-furo[2,3-f]quinazoline]-2'-carboxamide

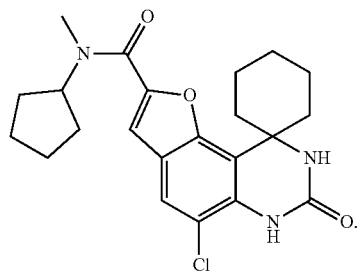

[M + H] = 416.4

Example 252. 5'-Chloro-N-(1-hydroxy-3-methylbutan-2-yl)-7'-oxo-7',8'-dihydro-6'H-spiro[cyclohexane-1,9'-furo[2,3-f]quinazoline]-2'-carboxamide

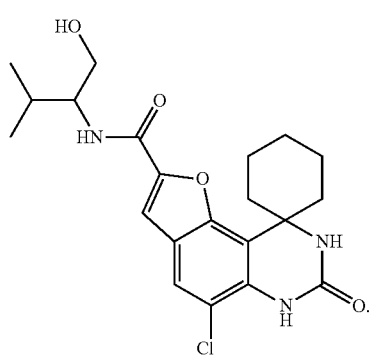

[M + H] = 420.4

Example 253. 5'-Chloro-N-(1-methylpiperidin-4-yl)-7'-oxo-7',8'-dihydro-6'H-spiro[cyclohexane-1,9'-furo[2,3-f]quinazoline]-2'-carboxamide

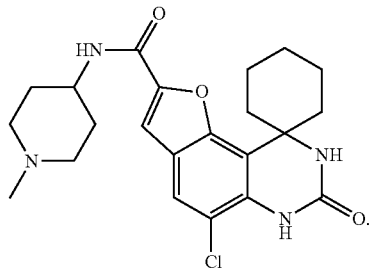

[M + H] = 431.4

Example 254. 5'-Chloro-N-[(2-fluorophenyl)methyl]-7'-oxo-7',8'-dihydro-6'H-spiro[cyclohexane-1,9'-furo[2,3-f]quinazoline]-2'-carboxamide

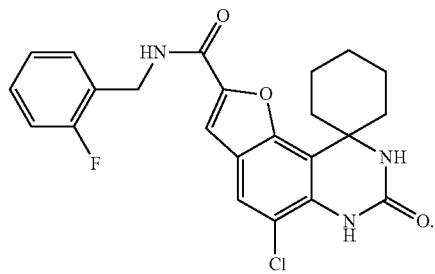

[M + H] = 442.4

Example 255. 5'-Chloro-2'-[4-(2-hydroxyethyl)piperazine-1-carbonyl]-7',8'-dihydro-6'H-spiro[cyclohexane-1,9'-furo[2,3-f]quinazoline]-7'-one

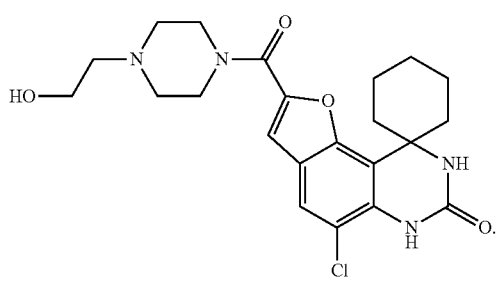

[M + H] = 447.4

Example 256. 5'-Chloro-N-(3-hydroxypropyl)-7'-oxo-7',8'-dihydro-6'H-spiro[cyclohexane-1,9'-furo[2,3-f]quinazoline]-2'-carboxamide

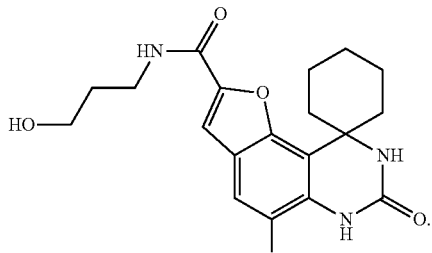

[M + H] = 392.4

Example 257. 5'-Chloro-N-(4-hydroxybutyl)-7'-oxo-7',8'-dihydro-6'H-spiro[cyclohexane-1,9'-furo[2,3-f]quinazoline]-2'-carboxamide

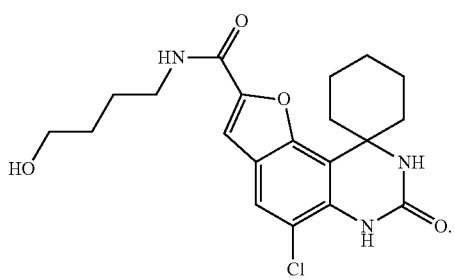

[M + H] = 406.3

Example 258. 5'-Chloro-N-(2-hydroxyethyl)-7'-oxo-N-propyl-7',8'-dihydro-6'H-spiro[cyclohexane-1,9'-furo[2,3-f]quinazoline]-2'-carboxamide

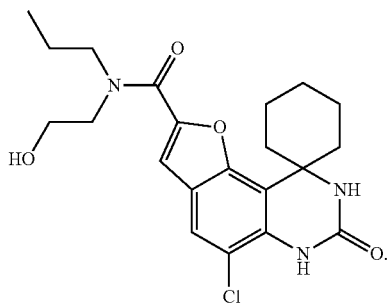

[M + H] = 420.4

Example 259. 5'-Chloro-7'-oxo-N-[2-(pyrrolidin-1-yl)ethyl]-7',8'-dihydro-6'H-spiro[cyclohexane-1,9'-furo[2,3-f]quinazoline]-2'-carboxamide

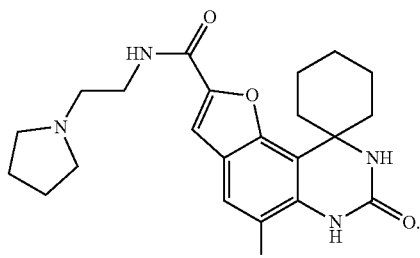

[M + H] = 431.4

Example 260. 5'-Chloro-N-[2-(dimethylamino)ethyl]-N-ethyl-7'-oxo-7',8'-dihydro-6'H-spiro[cyclohexane-1,9'-furo[2,3-f]quinazoline]-2'-carboxamide

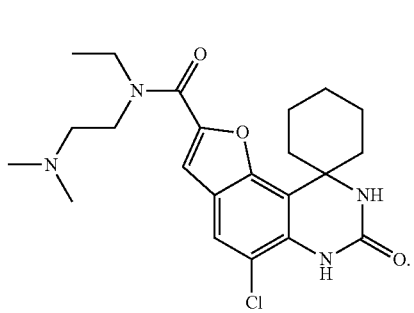

[M + H] = 433.5

Example 261. 5'-Chloro-N-[3-(1H-imidazol-1-yl)propyl]-7'-oxo-7',8'-dihydro-6'H-spiro[cyclohexane-1,9'-furo[2,3-f]quinazoline]-2'-carboxamide

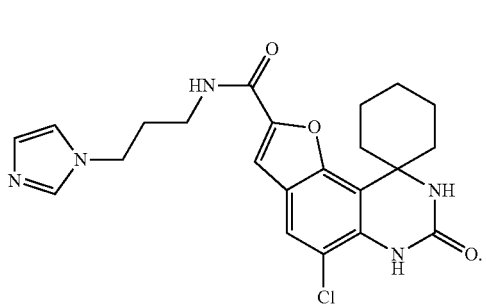

[M + H] = 442.4

Example 262. 5'-Chloro-N-(2-hydroxyethyl)-N-methyl-7'-oxo-7',8'-dihydro-6'H-spiro[cyclohexane-1,9'-furo[2,3-f]quinazoline]-2'-carboxamide

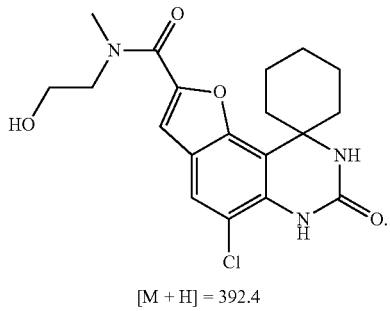 [SMILES: CN(CCO)C(=O)c1cc2cc(Cl)c3c(c2o1)C1(CCCCC1)NC(=O)N3]

[M + H] = 392.4

Example 263. 5'-Chloro-N-(2-hydroxybutyl)-7'-oxo-7',8'-dihydro-6'H-spiro[cyclohexane-1,9'-furo[2,3-f]quinazoline]-2'-carboxamide

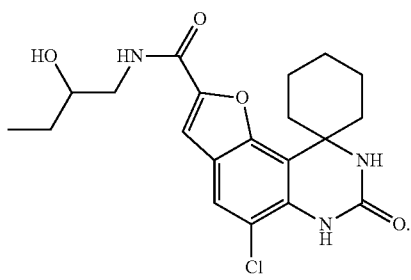

[M + H] = 406.5

Example 264. 5'-Chloro-N-[3-(dimethylamino)propyl]-N-methyl-7'-oxo-7',8'-dihydro-6'H-spiro[cyclohexane-1,9'-furo[2,3-f]quinazoline]-2'-carboxamide

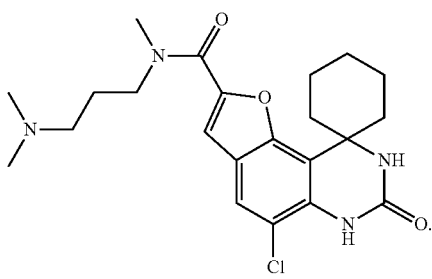

[M + H] = 433.5

Example 265. 2'-[(8aS)-octahydropyrrolo[1,2-a]piperazine-2-carbonyl]-5'-chloro-7',8'-dihydro-6'H-spiro[cyclohexane-1,9'-furo[2,3-f]quinazoline]-7'-one

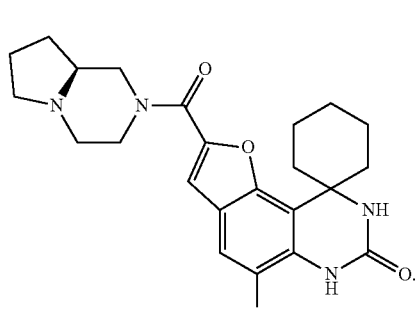

[M + H] = 443.4

Example 266. 5'-Chloro-N-methyl-7'-oxo-N-[2-(pyridin-2-yl)ethyl]-7',8'-dihydro-6'H-spiro[cyclohexane-1,9'-furo[2,3-f]quinazoline]-2'-carboxamide

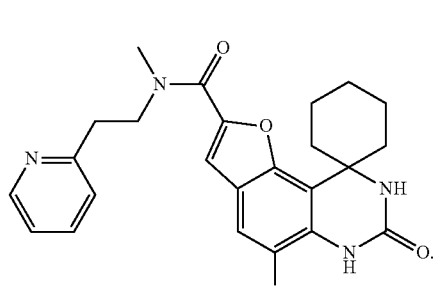

[M + H] = 453.4

Example 267. 5'-Chloro-N-(2-cyanoethyl)-N-methyl-7'-oxo-7',8'-dihydro-6'H-spiro[cyclohexane-1,9'-furo[2,3-f]quinazoline]-2'-carboxamide

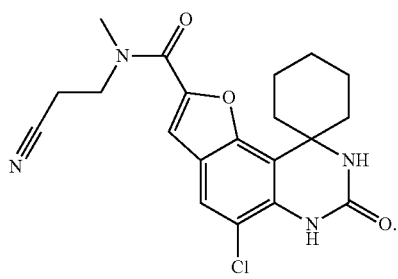

[M + H] = 401.4

Example 268. 5'-Chloro-N-(2-ethoxyethyl)-7'-oxo-7',8'-dihydro-6'H-spiro[cyclohexane-1,9'-furo[2,3-f]quinazoline]-2'-carboxamide

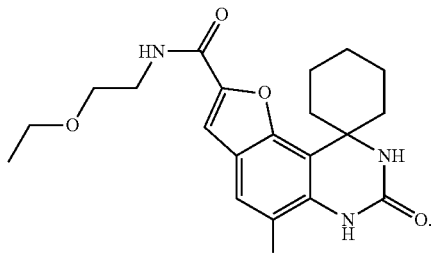

[M + H] = 406.4

Example 269. 5'-Chloro-7'-oxo-N-(oxolan-2-ylmethyl)-7',8'-dihydro-6'H-spiro[cyclohexane-1,9'-furo[2,3-f]quinazoline]-2'-carboxamide

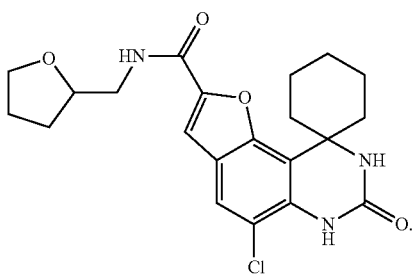

[M + H] = 418.4

Example 270. 5'-Chloro-N-(2-methoxyethyl)-7'-oxo-N-(propan-2-yl)-7',8'-dihydro-6'H-spiro[cyclohexane-1,9'-furo[2,3-f]quinazoline]-2'-carboxamide

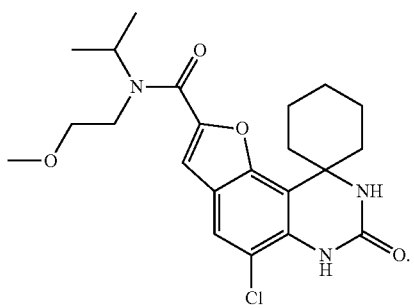

[M + H] = 434.5

Example 271. 5'-Chloro-7'-oxo-N-[2-(thiophen-2-yl)ethyl]-7',8'-dihydro-6'H-spiro[cyclohexane-1,9'-furo[2,3-f]quinazoline]-2'-carboxamide

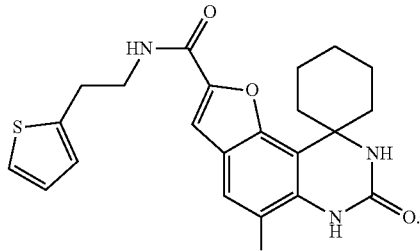

[M + H] = 444.4

Example 272. 5'-Chloro-N-cyclopentyl-7'-oxo-7',8'-dihydro-6'H-spiro[cyclohexane-1,9'-furo[2,3-f]quinazoline]-2'-carboxamide

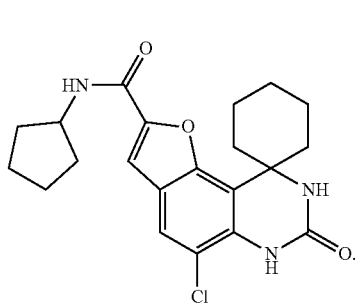

[M + H] = 402.3

Example 273. 5'-Chloro-N-ethyl-N-(2-hydroxyethyl)-7'-oxo-7',8'-dihydro-6'H-spiro[cyclohexane-1,9'-furo[2,3-f]quinazoline]-2'-carboxamide

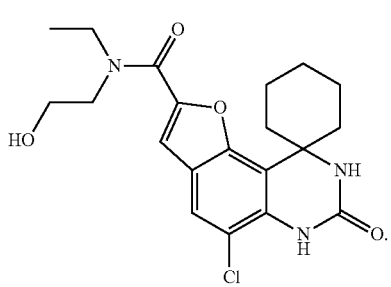

[M + H] = 406.4

Example 274. 5'-Chloro-2'-(3-hydroxypiperidine-1-carbonyl)-7',8'-dihydro-6'H-spiro[cyclohexane-1,9'-furo[2,3-f]quinazoline]-7'-one

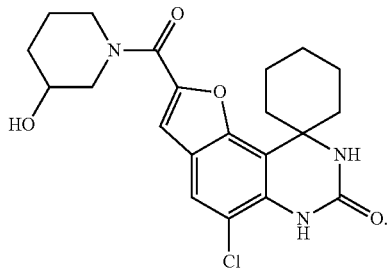

[M + H] = 418.4

Example 275. 5'-Chloro-7'-oxo-N-[2-(1H-pyrrol-1-yl)ethyl]-7',8'-dihydro-6'H-spiro[cyclohexane-1,9'-furo[2,3-f]quinazoline]-2'-carboxamide

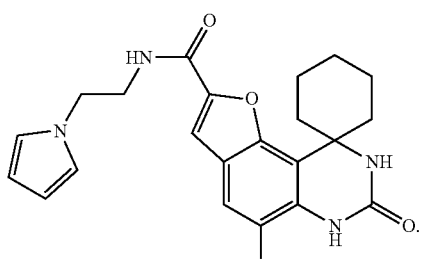

[M + H] = 427.4

Example 276. 5'-Chloro-N-methyl-N-(1-methylpyrrolidin-3-yl)-7'-oxo-7',8'-dihydro-6'H-spiro[cyclohexane-1,9'-furo[2,3-f]quinazoline]-2'-carboxamide

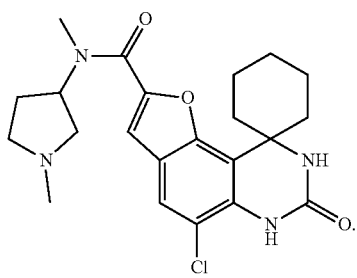

[M + H] = 431.4

Example 277. 5'-Chloro-N-(3-hydroxy-3-phenylpropyl)-N-methyl-7'-oxo-7',8'-dihydro-6'H-spiro[cyclohexane-1,9'-furo[2,3-f]quinazoline]-2'-carboxamide

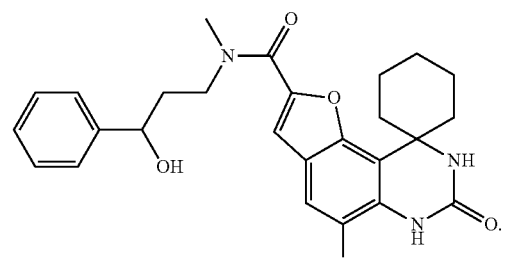

[M + H] = 482.5

Example 278. 5'-Chloro-2'-[3-(hydroxymethyl)-3-(2-methylpropyl)piperidine-1-carbonyl]-7',8'-dihydro-6'H-spiro[cyclohexane-1,9'-furo[2,3-f]quinazoline]-7'-one

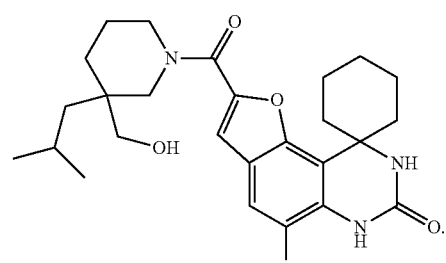

[M + H] = 488.5

Example 279. 5'-Chloro-N-[(2,3-dimethoxyphenyl)methyl]-N-methyl-7'-oxo-7',8'-dihydro-6'H-spiro[cyclohexane-1,9'-furo[2,3-f]quinazoline]-2'-carboxamide

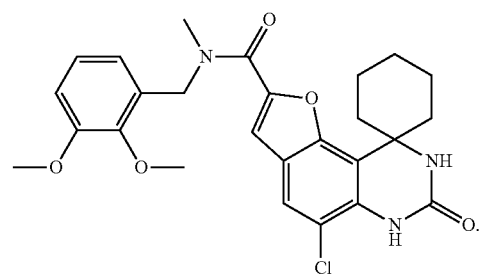

[M + H] = 498.4

Example 280. 5'-Chloro-2'-[2-(trifluoromethyl)-5H, 6H,7H,8H-imidazo[1,2-a]pyrazine-7-carbonyl]-7',8'-dihydro-6'H-spiro[cyclohexane-1,9'-furo[2,3-f]quinazoline]-7'-one

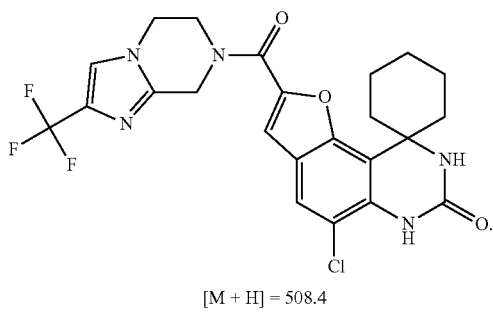 [SMILES: O=C1Nc2c(Cl)cc3cc(C(=O)N4CCn5cc(C(F)(F)F)nc5C4)oc3c2C2(CCCCC2)N1]

[M + H] = 508.4

Example 281. 5'-Chloro-N-[3-(morpholin-4-yl)propyl]-7'-oxo-7',8'-dihydro-6'H-spiro[cyclohexane-1,9'-furo[2,3-f]quinazoline]-2'-carboxamide

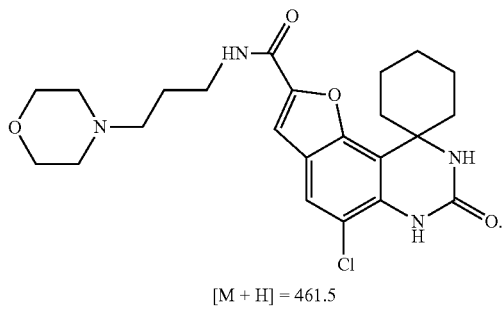 [SMILES: O=C1Nc2c(Cl)cc3cc(C(=O)NCCCN4CCOCC4)oc3c2C2(CCCCC2)N1]

[M + H] = 461.5

Example 282. 5'-Chloro-N-[(2-methoxyphenyl)methyl]-N-methyl-7'-oxo-7',8'-dihydro-6'H-spiro[cyclohexane-1,9'-furo[2,3-f]quinazoline]-2'-carboxamide

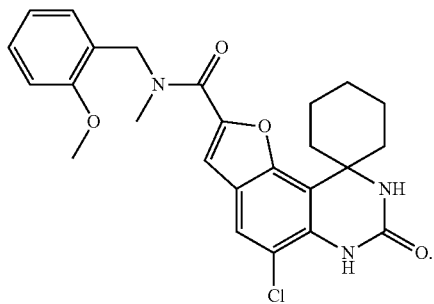

[M + H] = 468.5

Example 283. 5'-Chloro-2'-[3-(1H-imidazol-1-ylmethyl)piperidine-1-carbonyl]-7',8'-dihydro-6'H-spiro[cyclohexane-1,9'-furo[2,3-f]quinazoline]-7'-one

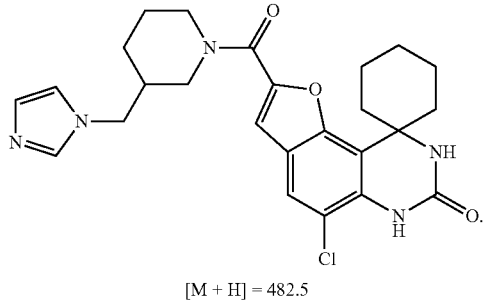 [SMILES: O=C1Nc2c(Cl)cc3cc(C(=O)N4CCCC(Cn5ccnc5)C4)oc3c2C2(CCCCC2)N1]

[M + H] = 482.5

Example 284. Ethyl 2-[4-({5'-chloro-7'-oxo-7',8'-dihydro-6'H-spiro[cyclohexane-1,9'-furo[2,3-f]quinazoline]-2'-yl}carbonyl)piperazin-1-yl]acetate

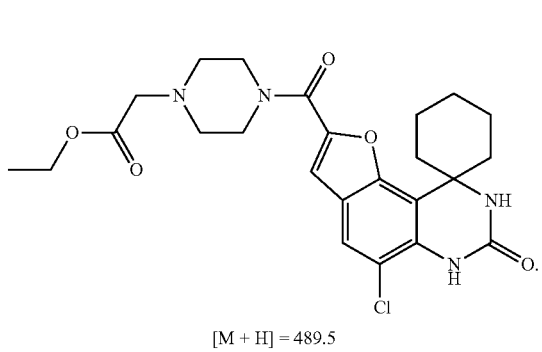 [SMILES: CCOC(=O)CN1CCN(C(=O)c2cc3cc(Cl)c4c(c3o2)C2(CCCCC2)NC(=O)N4)CC1]

[M + H] = 489.5

Example 285. 5'-Chloro-N-[(2,4-dimethoxyphenyl)methyl]-N-methyl-7'-oxo-7',8'-dihydro-6'H-spiro[cyclohexane-1,9'-furo[2,3-f]quinazoline]-2'-carboxamide

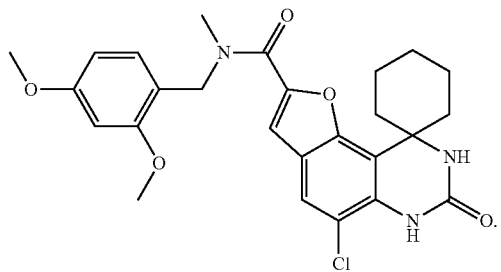

[M + H] = 498.4

Example 286. 5'-Chloro-N-[(3-methoxyphenyl)methyl]-N-methyl-7'-oxo-7',8'-dihydro-6'H-spiro[cyclohexane-1,9'-furo[2,3-f]quinazoline]-2'-carboxamide

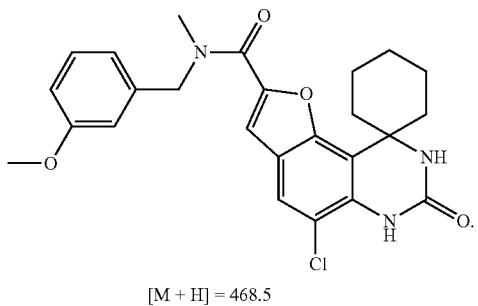 [SMILES: COc1cccc(CN(C)C(=O)c2cc3cc(Cl)c4c(c3o2)C2(CCCCC2)NC(=O)N4)c1]

[M + H] = 468.5

Example 287. 5'-Chloro-N-(2,2-dimethyloxan-4-yl)-N-ethyl-7'-oxo-7',8'-dihydro-6'H-spiro[cyclohexane-1,9'-furo[2,3-f]quinazoline]-2'-carboxamide

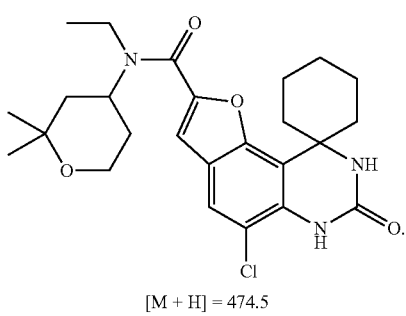 [SMILES: CCN(C(=O)c1cc2cc(Cl)c3c(c2o1)C1(CCCCC1)NC(=O)N3)C1CCOC(C)(C)C1]

[M + H] = 474.5

Example 288. 5'-Chloro-N-methyl-N-[(1-methyl-1H-1,3-benzodiazol-2-yl)methyl]-7'-oxo-7',8'-dihydro-6'H-spiro[cyclohexane-1,9'-furo[2,3-f]quinazoline]-2'-carboxamide

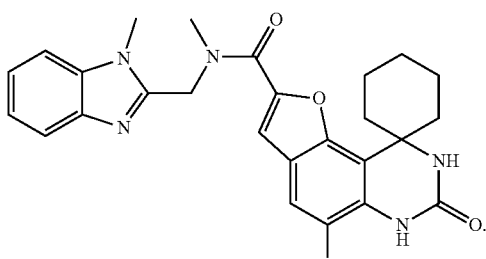

[M + H] = 492.5

Example 289. 5'-Chloro-N-[(3,5-dimethoxyphenyl)methyl]-N-methyl-7'-oxo-7',8'-dihydro-6'H-spiro[cyclohexane-1,9'-furo[2,3-f]quinazoline]-2'-carboxamide

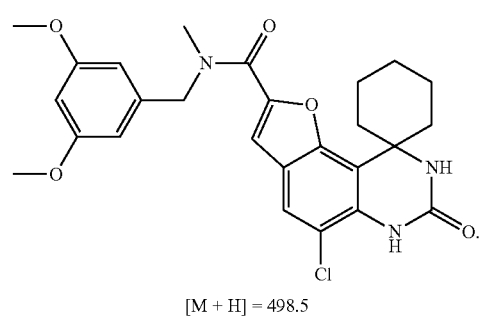 [SMILES: COc1cc(CN(C)C(=O)c2cc3cc(Cl)c4c(c3o2)C2(CCCCC2)NC(=O)N4)cc(OC)c1]

[M + H] = 498.5

Example 290. 5'-Chloro-2'-{5H,6H,7H,8H-imidazo[1,2-a]pyrazine-7-carbonyl}-7',8'-dihydro-6'H-spiro[cyclohexane-1,9'-furo[2,3-f]quinazoline]-7'-one

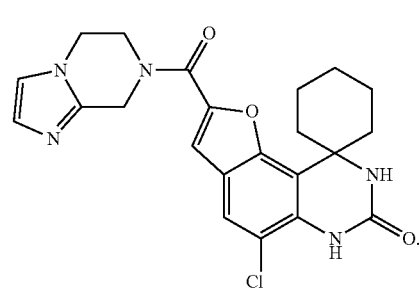

[M + H] = 440.4

Example 291. 5'-Chloro-2'-[2-(pyridin-2-yl)pyrrolidine-1-carbonyl]-7',8'-dihydro-6'H-spiro[cyclohexane-1,9'-furo[2,3-f]quinazoline]-7'-one

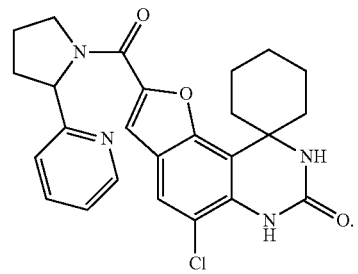

[M + H] = 465.5

Example 292. 5'-Chloro-N-(2-hydroxy-2-phenyl-ethyl)-N-methyl-7'-oxo-7',8'-dihydro-6'H-spiro[cyclohexane-1,9'-furo[2,3-f]quinazoline]-2'-carboxamide

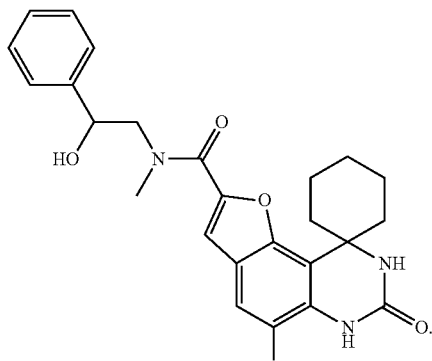

[M + H] = 468.4

Example 293. 5'-Chloro-N-[2-(2,3-dihydro-1H-indol-1-yl)ethyl]-7'-oxo-7',8'-dihydro-6'H-spiro[cyclohexane-1,9'-furo[2,3-f]quinazoline]-2'-carboxamide

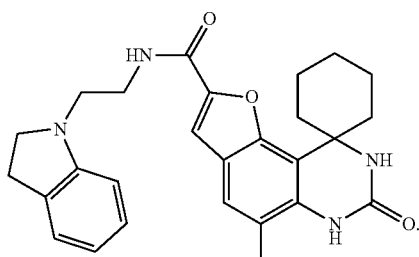

[M + H] = 479.5

Example 294. 5'-Chloro-N-[(2,3-dimethoxyphenyl)methyl]-7'-oxo-7',8'-dihydro-6'H-spiro[cyclohexane-1,9'-furo[2,3-f]quinazoline]-2'-carboxamide

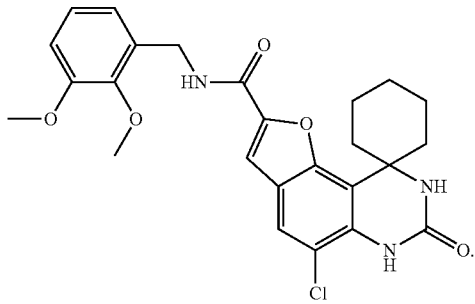

[M + H] = 484.5

Example 295. 5'-Chloro-N-methyl-N-[(5-methyl-1H-1,3-benzodiazol-2-yl)methyl]-7'-oxo-7',8'-dihydro-6'H-spiro[cyclohexane-1,9'-furo[2,3-f]quinazoline]-2'-carboxamide

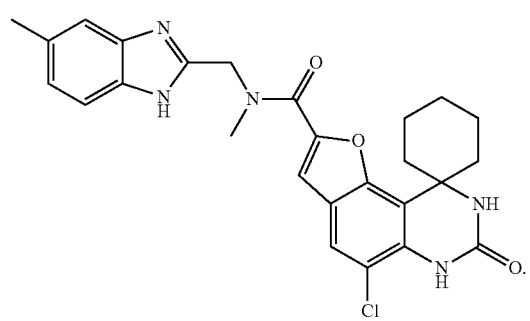

[M + H] = 492.5

Example 296. 5'-Chloro-N-methyl-7'-oxo-N-[3-(trimethyl-1H-pyrazol-4-yl)propyl]-7',8'-dihydro-6'H-spiro[cyclohexane-1,9'-furo[2,3-f]quinazoline]-2'-carboxamide

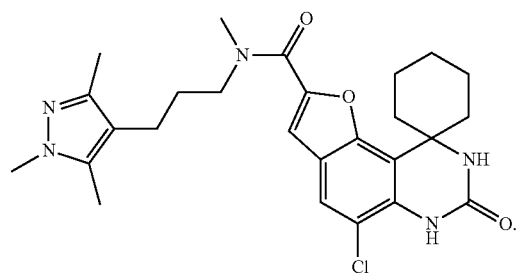

[M + H] = 498.5

Example 297. 5'-Chloro-2'-{octahydropyrrolo[1,2-a]piperazine-2-carbonyl}-7',8'-dihydro-6'H-spiro[cyclohexane-1,9'-furo[2,3-f]quinazoline]-7'-one

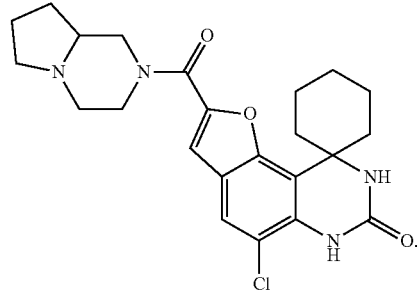

[M + H] = 443.5

Example 298. 5'-Chloro-N-(2,3-dihydro-1,4-benzo-dioxin-6-ylmethyl)-7'-oxo-7',8'-dihydro-6'H-spiro[cyclohexane-1,9'-furo[2,3-f]quinazoline]-2'-carboxamide

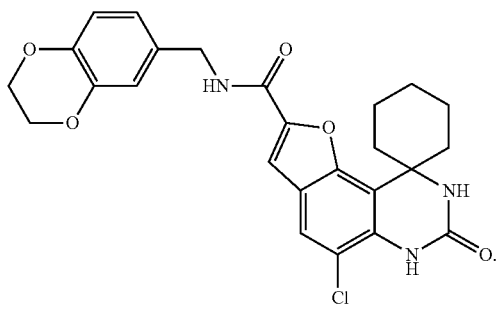

[M + H] = 482.4

Example 299. 5'-Chloro-N-[(5-cyclopropyl-1H-pyrazol-3-yl)methyl]-N-methyl-7'-oxo-7',8'-dihydro-6'H-spiro[cyclohexane-1,9'-furo[2,3-f]quinazoline]-2'-carboxamide

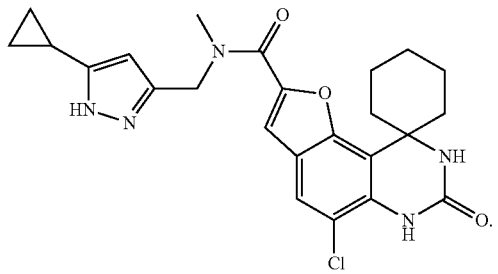

[M + H] = 468.5

Example 300. 5'-Chloro-N-[(2,4-dimethoxyphenyl)methyl]-7'-oxo-7',8'-dihydro-6'H-spiro[cyclohexane-1,9'-furo[2,3-f]quinazoline]-2'-carboxamide

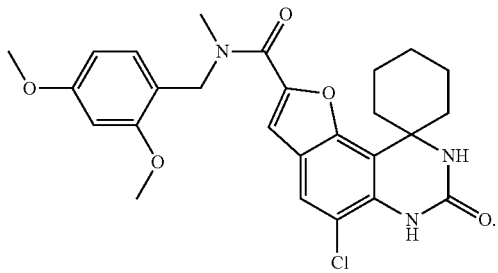

[M + H] = 484.4

Example 301. N-(1-benzylpyrrolidin-3-yl)-5'-chloro-7'-oxo-7',8'-dihydro-6'H-spiro[cyclohexane-1,9'-furo[2,3-f]quinazoline]-2'-carboxamide

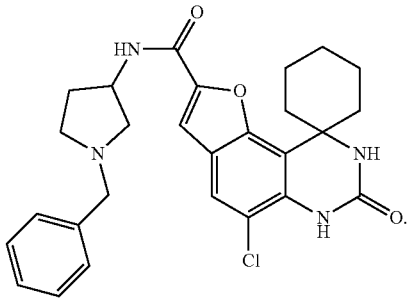

[M + H] = 493.5

Example 302. 5'-Chloro-N-[(2,3-difluoro-4-methoxyphenyl)methyl]-7'-oxo-7',8'-dihydro-6'H-spiro[cyclohexane-1,9'-furo[2,3-f]quinazoline]-2'-carboxamide

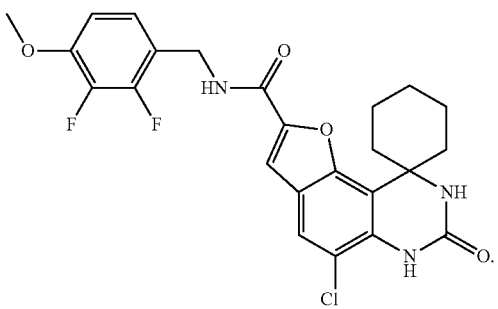

[M + H] = 490.3

Example 303. 5'-Chloro-N-{[4-(dimethylamino)phenyl]methyl}-7'-oxo-7',8'-dihydro-6'H-spiro[cyclohexane-1,9'-furo[2,3-f]quinazoline]-2'-carboxamide

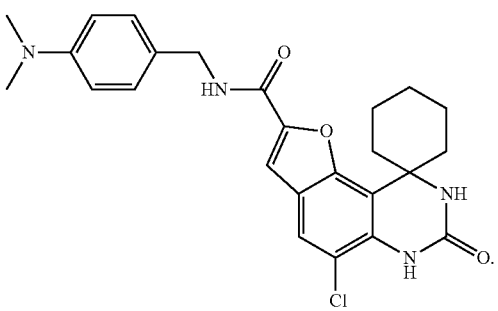

[M + H] = 467.4

Example 304. 5'-Chloro-N-[(1-methyl-1H-imidazol-2-yl)methyl]-7'-oxo-N-(propan-2-yl)-7',8'-dihydro-6'H-spiro[cyclohexane-1,9'-furo[2,3-f]quinazoline]-2'-carboxamide

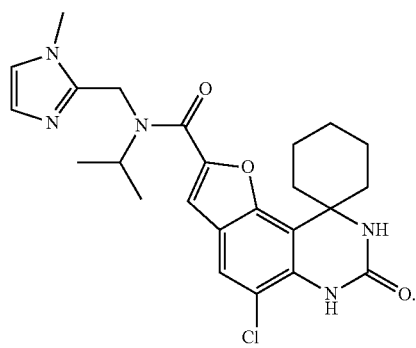

[M + H] = 470.5

Example 305. 5'-Chloro-2'-[4-(pyridin-4-yl)piperazine-1-carbonyl]-7',8'-dihydro-6'H-spiro[cyclohexane-1,9'-furo[2,3-f]quinazoline]-7'-one

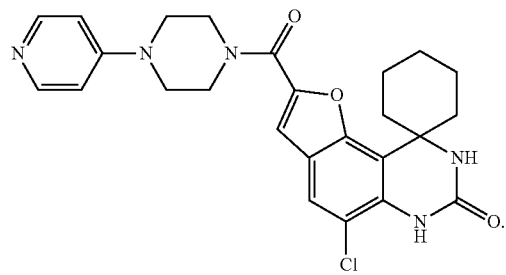

[M + H] = 480.4

Example 306. N-[(5-tert-Butyl-1H-pyrazol-3-yl)methyl]-5'-chloro-N-methyl-7'-oxo-7',8'-dihydro-6'H-spiro[cyclohexane-1,9'-furo[2,3-f]quinazoline]-2'-carboxamide

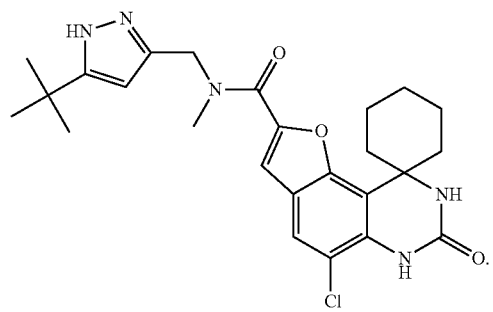

[M + H] = 484.5

Example 307. 2'-(4-Benzylpiperazine-1-carbonyl)-5'-chloro-7',8'-dihydro-6'H-spiro[cyclohexane-1,9'-furo[2,3-f]quinazoline]-7'-one

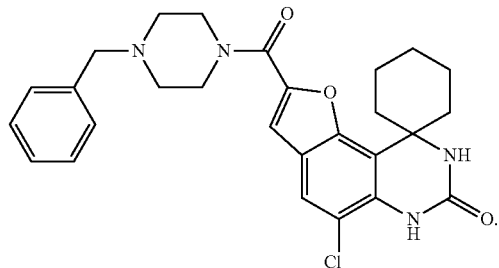

[M + H] = 493.5

Example 308. 5'-Chloro-N-[(1-methylpiperidin-4-yl)methyl]-7'-oxo-7',8'-dihydro-6'H-spiro[cyclohexane-1,9'-furo[2,3-f]quinazoline]-2'-carboxamide

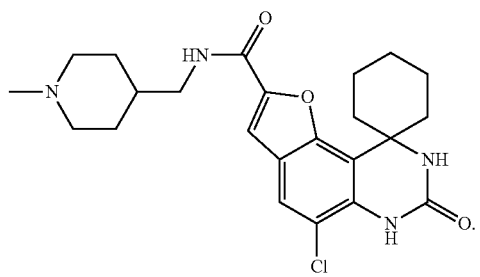

[M + H] = 445.5

Example 309. 5'-Chloro-2'-(3-methoxypiperidine-1-carbonyl)-7',8'-dihydro-6'H-spiro[cyclohexane-1,9'-furo[2,3-f]quinazoline]-7'-one

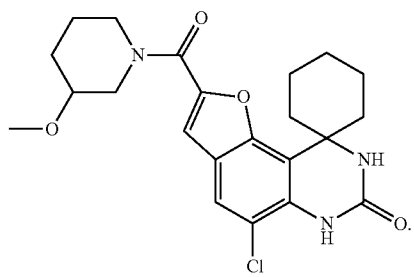

[M + H] = 432.4

Example 310. 5'-Chloro-N-methyl-7'-oxo-N-[(trimethyl-1H-pyrazol-4-yl)methyl]-7',8'-dihydro-6'H-spiro[cyclohexane-1,9'-furo[2,3-f]quinazoline]-2'-carboxamide

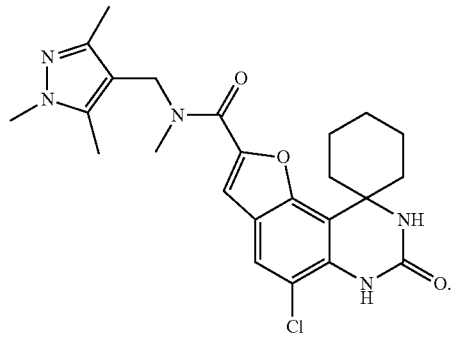

[M + H] = 470.5

Example 311. 5'-Chloro-2'-[4-(pyridin-2-yl)piperazine-1-carbonyl]-7',8'-dihydro-6'H-spiro[cyclohexane-1,9'-furo[2,3-f]quinazoline]-7'-one

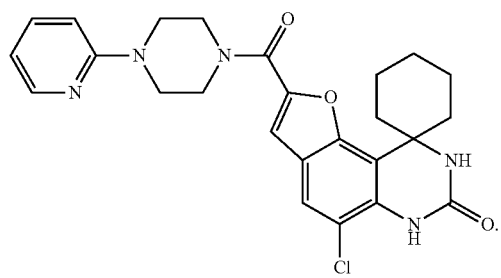

[M + H] = 480.5

Example 312. 5'-Chloro-N-[3-(3,5-dimethyl-1H-pyrazol-1-yl)propyl]-N-methyl-7'-oxo-7',8'-dihydro-6'H-spiro[cyclohexane-1,9'-furo[2,3-f]quinazoline]-2'-carboxamide

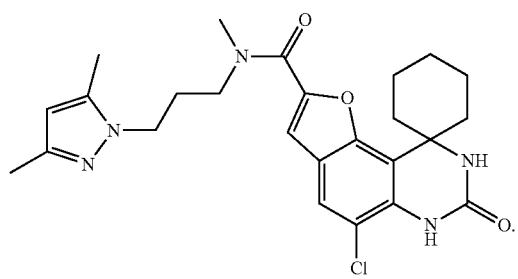

[M + H] = 484.5

Example 313. 5'-Chloro-2'-(4-methyl-2-phenylpiperazine-1-carbonyl)-7',8'-dihydro-6'H-spiro[cyclohexane-1,9'-furo[2,3-f]quinazoline]-7'-one

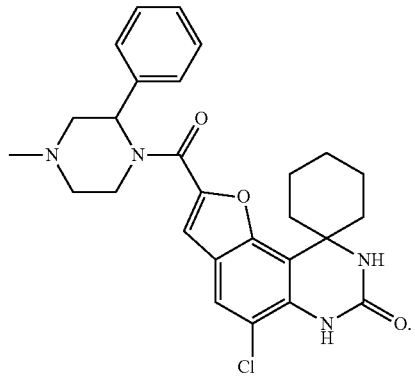

[M + H] = 493.5

Example 314. 5'-Chloro-2'-[3-(dimethyl amino)piperidine-1-carbonyl]-7',8'-dihydro-6'H-spiro[cyclohexane-1,9'-furo[2,3-f]quinazoline]-7'-one

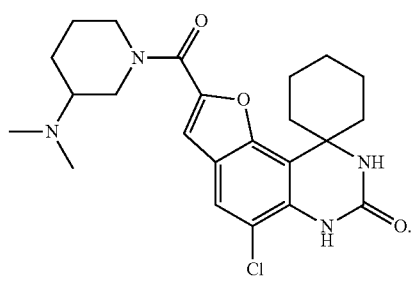

[M + H] = 445.5

Example 315. 5'-Chloro-N-[2-(morpholin-4-yl)ethyl]-7'-oxo-7',8'-dihydro-6'H-spiro[cyclohexane-1,9'-furo[2,3-f]quinazoline]-2'-carboxamide

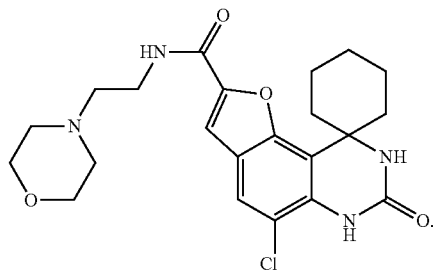

[M + H] = 447.4

Example 316. 5'-Chloro-7'-oxo-N-[2-(pyridin-3-yloxy)ethyl]-7',8'-dihydro-6'H-spiro[cyclohexane-1,9'-furo[2,3-f]quinazoline]-2'-carboxamide

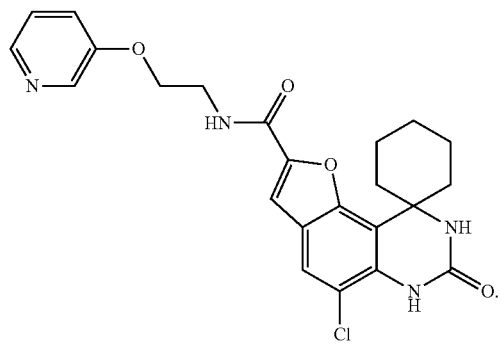

[M + H] = 445.4

Example 317. 5'-Chloro-N-[(2-fluoro-4-methoxyphenyl)methyl]-7'-oxo-7',8'-dihydro-6'H-spiro[cyclohexane-1,9'-furo[2,3-f]quinazoline]-2'-carboxamide

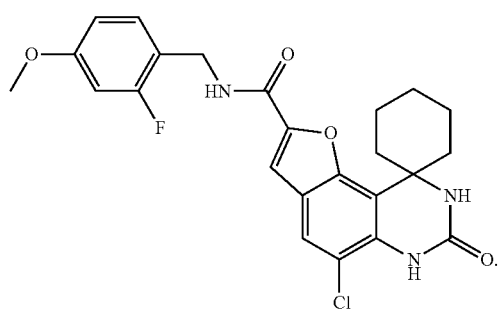

[M + H] = 472.4

Example 318. 1-({5'-Chloro-7'-oxo-7',8'-dihydro-6'H-spiro[cyclohexane-1,9'-furo[2,3-f]quinazoline]-2'-yl}carbonyl)azetidine-3-carbonitrile

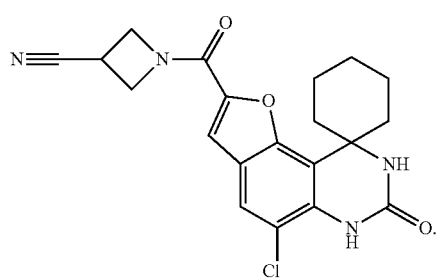

[M + H] = 399.3

Example 319. 5'-Chloro-2'-{3-phenyl-5H,6H,7H,8H-imidazo[1,2-a]pyrazine-7-carbonyl}-7',8'-dihydro-6'H-spiro[cyclohexane-1,9'-furo[2,3-f]quinazoline]-7'-one

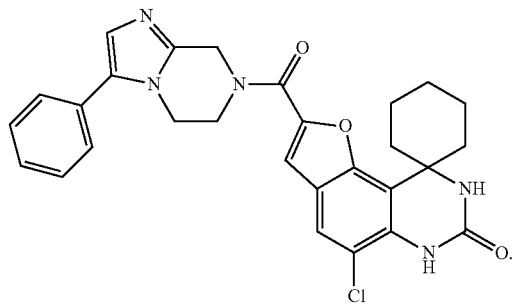

[M + H] = 516.4

Example 320. 5'-Chloro-7'-oxo-N-[2-(2-oxopyrrolidin-1-yl)ethyl]-7',8'-dihydro-6'H-spiro[cyclohexane-1,9'-furo[2,3-f]quinazoline]-2'-carboxamide

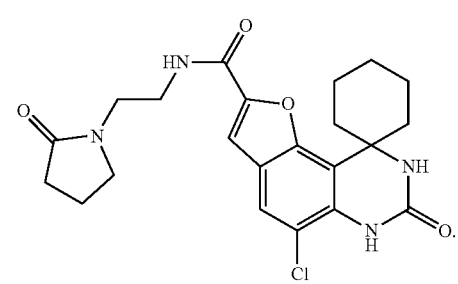

[M + H] = 445.4

Example 321. 5'-Chloro-7'-oxo-N-(2,2,6,6-tetramethyloxan-4-yl)-7',8'-dihydro-6'H-spiro[cyclohexane-1,9'-furo[2,3-f]quinazoline]-2'-carboxamide

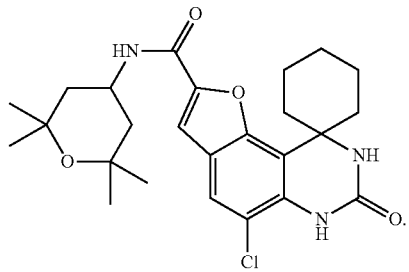

[M + H] = 474.5

Example 322. 2'-[(1R,5S)-3-azabicyclo[3.1.0]
hexane-3-carbonyl]-5'-chloro-7',8'-dihydro-6'H-spiro
[cyclohexane-1,9'-furo[2,3-f]quinazoline]-7'-one

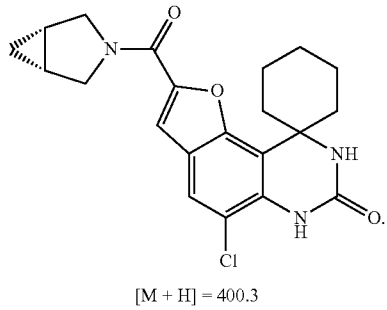 [SMILES: O=C1Nc2c(Cl)cc3cc(C(=O)N4C[C@H]5C[C@H]5C4)oc3c2C2(CCCCC2)N1]

[M + H] = 400.3

Example 323. 5'-Chloro-N-[2-(4-fluorophenoxy)
ethyl]-7'-oxo-7',8'-dihydro-6'H-spiro[cyclohexane-1,
9'-furo[2,3-f]quinazoline]-2'-carboxamide

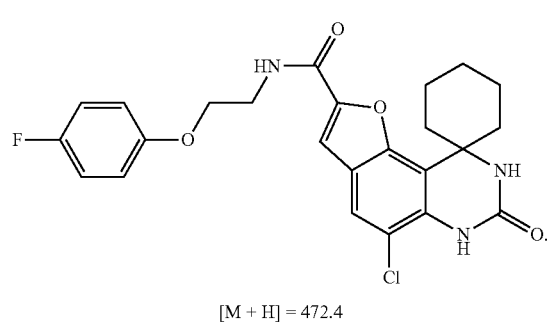 [SMILES: O=C1Nc2c(Cl)cc3cc(C(=O)NCCOc4ccc(F)cc4)oc3c2C2(CCCCC2)N1]

[M + H] = 472.4

Example 324. 5'-Chloro-7'-oxo-N-[2-(1H-pyrazol-1-
yl)ethyl]-7',8'-dihydro-6'H-spiro[cyclohexane-1,9'-
furo[2,3-f]quinazoline]-2'-carboxamide

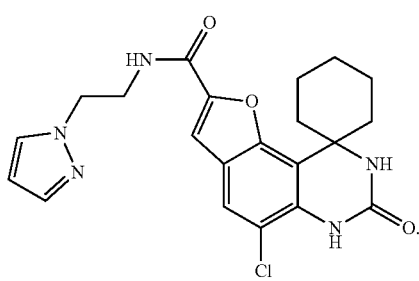

[M + H] = 428.4

Example 325. 5'-Chloro-N-[4-(4-hydroxypiperidin-
1-yl)phenyl]-7'-oxo-7',8'-dihydro-6'H-spiro[cyclo-
hexane-1,9'-furo[2,3-f]quinazoline]-2'-carboxamide

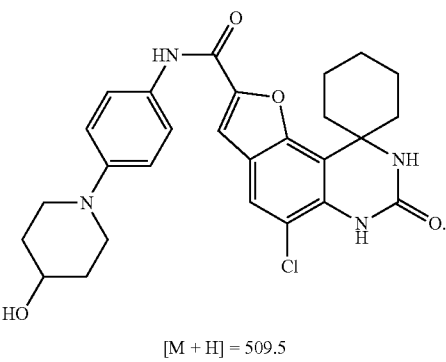 [SMILES: O=C1Nc2c(Cl)cc3cc(C(=O)Nc4ccc(N5CCC(O)CC5)cc4)oc3c2C2(CCCCC2)N1]

[M + H] = 509.5

Example 326. 5'-Chloro-N-(3,3-dimethyl-2-
oxobutyl)-7'-oxo-7',8'-dihydro-6'H-spiro[cyclo-
hexane-1,9'-furo[2,3-f]quinazoline]-2'-carboxamide

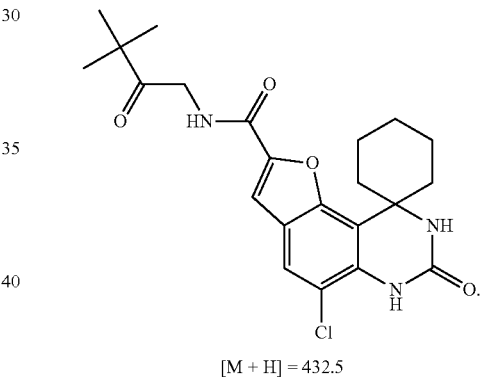

[M + H] = 432.5

Example 327. 5'-Chloro-N-(furan-2-ylmethyl)-N-
methyl-7'-oxo-7',8'-dihydro-6'H-spiro[cyclohexane-
1,9'-furo[2,3-f]quinazoline]-2'-carboxamide

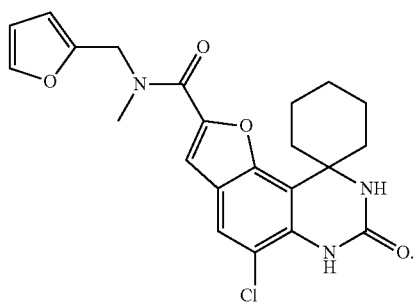

[M + H] = 428.4

Example 328. 5'-Chloro-2'-{4-[2-(dimethylamino)ethyl]piperidine-1-carbonyl}-7',8'-dihydro-6'H-spiro[cyclohexane-1,9'-furo[2,3-f]quinazoline]-7'-one

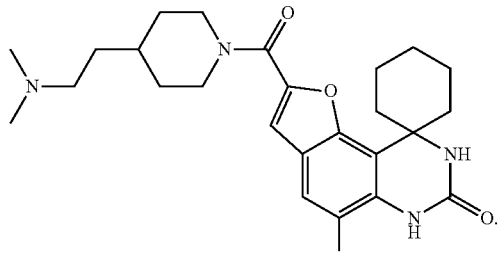

[M + H] = 473.5

Example 329. 5'-Chloro-2'-{4-(5-chloropyridin-2-yl)piperazine-1-carbonyl}-7',8'-dihydro-6'H-spiro[cyclohexane-1,9'-furo[2,3-f]quinazoline]-7'-one

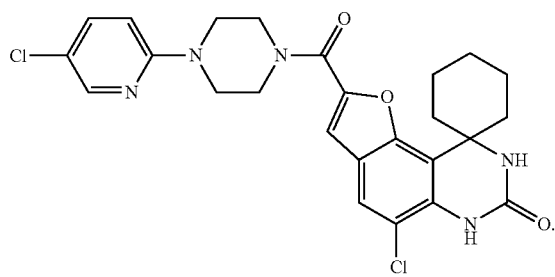

[M + H] = 514.4

Example 330. 5'-Chloro-N-[(2-methoxyphenyl)methyl]-7'-oxo-7',8'-dihydro-6'H-spiro[cyclohexane-1,9'-furo[2,3-f]quinazoline]-2'-carboxamide

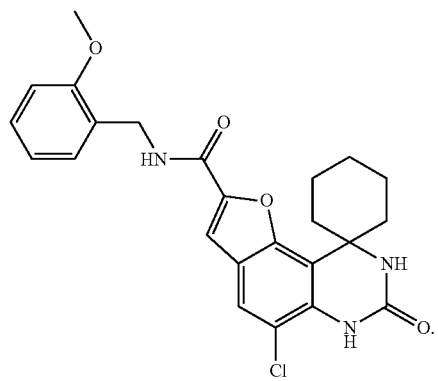

[M + H] = 454.5

Example 331. 5'-Chloro-N-(2-hydroxy-2-methylpropyl)-7'-oxo-7',8'-dihydro-6'H-spiro[cyclohexane-1,9'-furo[2,3-f]quinazoline]-2'-carboxamide

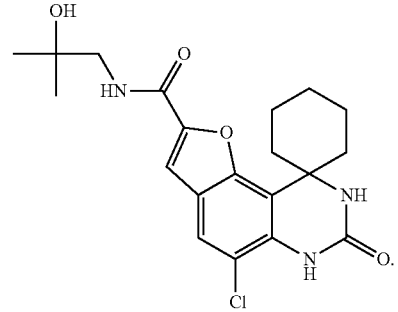

[M + H] = 406.4

Example 332. 5'-Chloro-N-[(4-cyanophenyl)methyl]-7'-oxo-7',8'-dihydro-6'H-spiro[cyclohexane-1,9'-furo[2,3-f]quinazoline]-2'-carboxamide

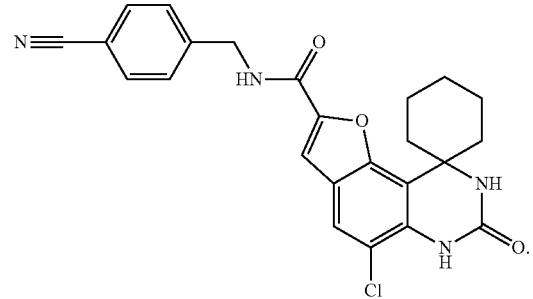

[M + H] = 449.4

Example 333. 5'-Chloro-2'-[3-oxo-4-(propan-2-yl)piperazine-1-carbonyl]-7',8'-dihydro-6'H-spiro[cyclohexane-1,9'-furo[2,3-f]quinazoline]-7'-one

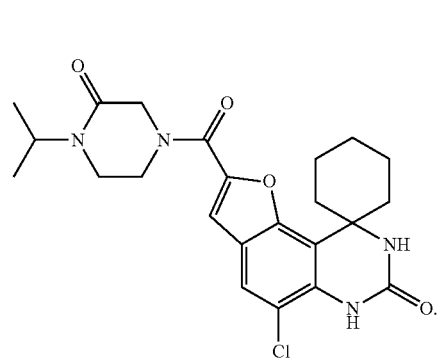

[M + H] = 459.4

Example 334. 5'-Chloro-N-{[5-(difluoromethoxy)pyridin-2-yl]methyl}-7'-oxo-7',8'-dihydro-6'H-spiro[cyclohexane-1,9'-furo[2,3-f]quinazoline]-2'-carboxamide

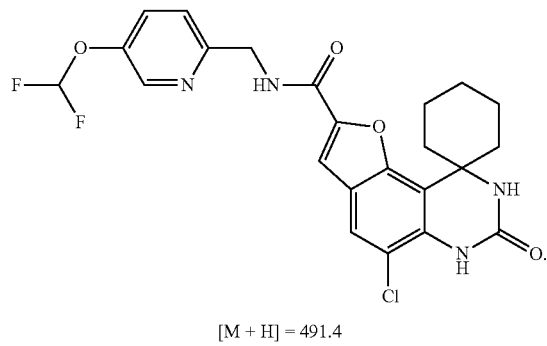 [SMILES: O=C1Nc2c(Cl)cc3cc(C(=O)NCc4ccc(OC(F)F)cn4)oc3c2C2(CCCCC2)N1]

[M + H] = 491.4

Example 335. 5'-Chloro-2'-[4-(oxetan-3-yl)piperazine-1-carbonyl]-7',8'-dihydro-6'H-spiro[cyclohexane-1,9'-furo[2,3-f]quinazoline]-7'-one

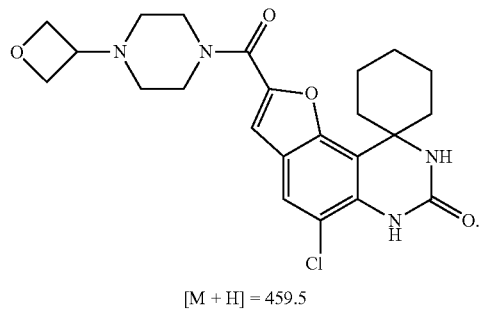 [SMILES: O=C1Nc2c(Cl)cc3cc(C(=O)N4CCN(C5COC5)CC4)oc3c2C2(CCCCC2)N1]

[M + H] = 459.5

Example 336. 5'-Chloro-N-[(1R,5S)-6,6-difluorobicyclo[3.1.0]hexan-3-yl]-7'-oxo-7',8'-dihydro-6'H-spiro[cyclohexane-1,9'-furo[2,3-f]quinazoline]-2'-carboxamide

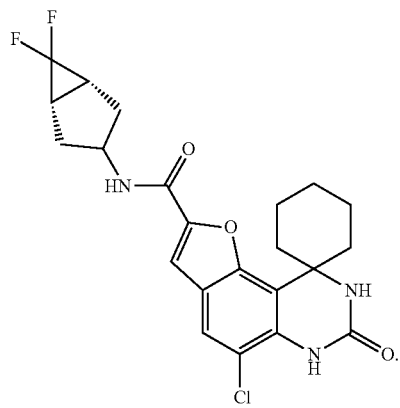

[M + H] = 450.5

Example 337. N-[2-(2H-1,3-benzodioxol-5-yl)ethyl]-5'-chloro-7'-oxo-7',8'-dihydro-6'H-spiro[cyclohexane-1,9'-furo[2,3-f]quinazoline]-2'-carboxamide

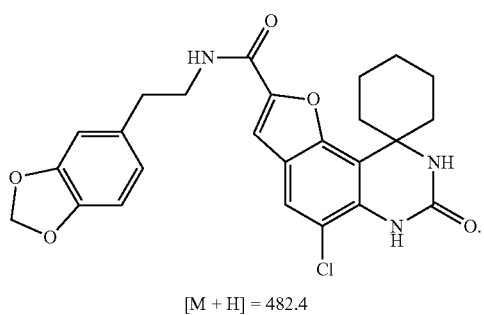 [SMILES: O=C1Nc2c(Cl)cc3cc(C(=O)NCCc4ccc5c(c4)OCO5)oc3c2C2(CCCCC2)N1]

[M + H] = 482.4

Example 338. 5'-Chloro-N-[(4-ethyl-4H-1,2,4-triazol-3-yl)methyl]-N-methyl-7'-oxo-7',8'-dihydro-6'H-spiro[cyclohexane-1,9'-furo[2,3-f]quinazoline]-2'-carboxamide

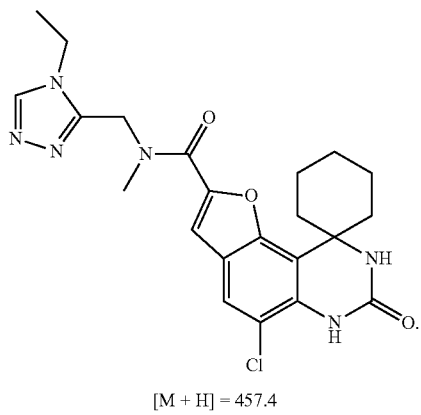 [SMILES: CCn1cnnc1CN(C)C(=O)c1cc2cc(Cl)c3c(c2o1)C1(CCCCC1)NC(=O)N3]

[M + H] = 457.4

Example 339. 5'-Chloro-N-[(4-cyano-3-fluorophenyl)methyl]-7'-oxo-7',8'-dihydro-6'H-spiro[cyclohexane-1,9'-furo[2,3-f]quinazoline]-2'-carboxamide

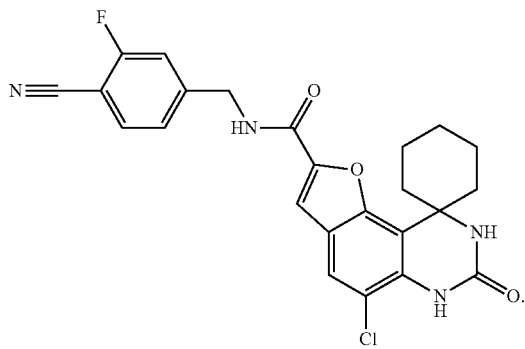

[M + H] = 467.4

Example 340. 2-{5'-Chloro-7'-oxo-7',8'-dihydro-6'H-spiro[cyclohexane-1,9'-furo[2,3-f]quinazoline]-2'-ylformamido}-N,N-diethylacetamide

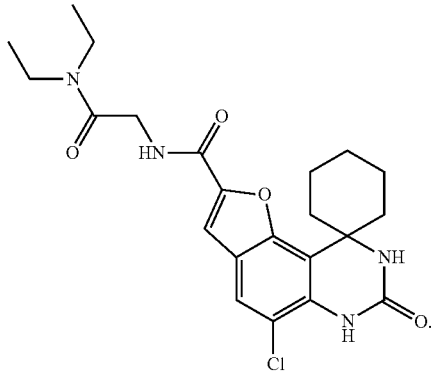

[M + H] = 447.4

Example 341. 5'-Chloro-2'-({6'-methyl-5',6'-dihydro-4'H-spiro[piperidine-4,7'-thieno[2,3-c]pyridine]-1-yl}carbonyl)-7',8'-dihydro-6'H-spiro[cyclohexane-1,9'-furo[2,3-f]quinazoline]-7'-one

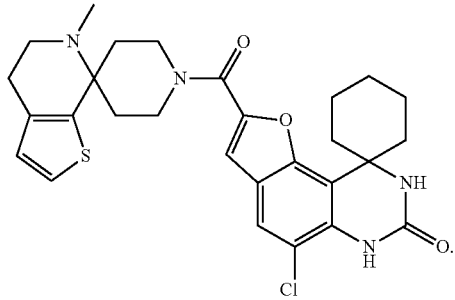

[M + H] = 539.5

Example 342. 5'-Chloro-N-[(6-methylpyridin-3-yl)methyl]-7'-oxo-7',8'-dihydro-6'H-spiro[cyclohexane-1,9'-furo[2,3-f]quinazoline]-2'-carboxamide

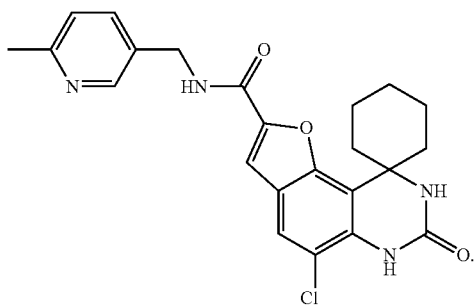

[M + H] = 439.4

Example 343. 5'-Chloro-7'-oxo-N-[(trimethyl-1H-imidazol-2-yl)methyl]-7',8'-dihydro-6'H-spiro[cyclohexane-1,9'-furo[2,3-f]quinazoline]-2'-carboxamide

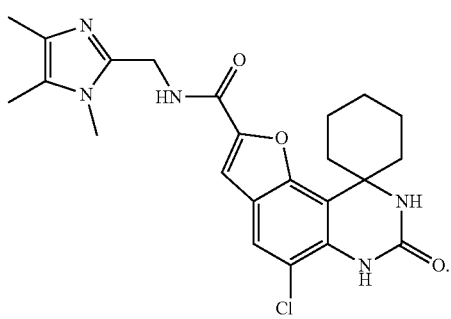

[M + H] = 456.5

Example 344. 5'-Chloro-N-[(5-methylpyridin-3-yl)methyl]-7'-oxo-7',8'-dihydro-6'H-spiro[cyclohexane-1,9'-furo[2,3-f]quinazoline]-2'-carboxamide

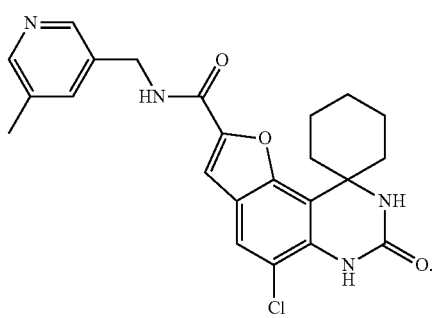

[M + H] = 439.4

Example 345. 5'-Chloro-N-methyl-7'-oxo-N-[(5-phenyl-1,2-oxazol-3-yl)methyl]-7',8'-dihydro-6'H-spiro[cyclohexane-1,9'-furo[2,3-f]quinazoline]-2'-carboxamide

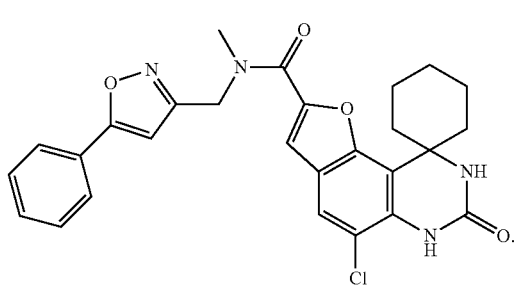

[M + H] = 505.5

Example 346. 2'-{6-Azaspiro[2.5]octane-6-carbonyl}-5'-chloro-7',8'-dihydro-6'H-spiro[cyclohexane-1,9'-furo[2,3-f]quinazoline]-7'-one

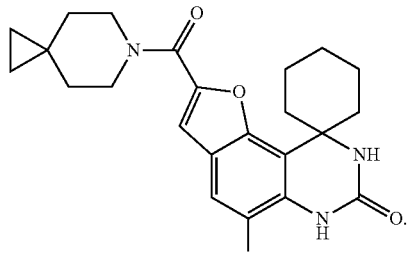

[M + H] = 428.4

Example 347. 5'-Chloro-N-[2-(oxan-4-yl)ethyl]-7'-oxo-7',8'-dihydro-6'H-spiro[cyclohexane-1,9'-furo[2,3-f]quinazoline]-2'-carboxamide

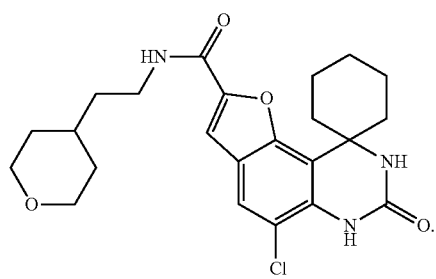

[M + H] = 446.5

Example 348. 5'-Chloro-2'-({6',7'-dihydro-5'H-spiro[piperidine-4,4'-thieno[3,2-c]pyridine]-1-yl}carbonyl)-7',8'-dihydro-6'H-spiro[cyclohexane-1,9'-furo[2,3-f]quinazoline]-7'-one

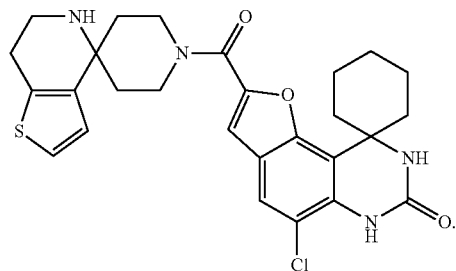

[M + H] = 525.4

Example 349. 5'-Chloro-N-(1-methoxy-2-methylpropan-2-yl)-7'-oxo-7',8'-dihydro-6'H-spiro[cyclohexane-1,9'-furo[2,3-f]quinazoline]-2'-carboxamide

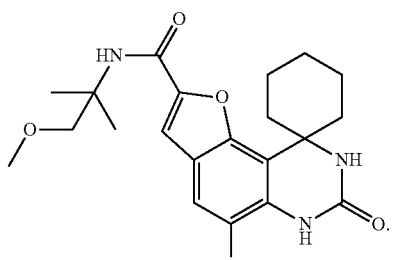

[M + H] = 420.5

Example 350. 5'-Chloro-7'-oxo-N-(1-(pyridin-3-yl)piperidin-4-yl)-7',8'-dihydro-6'H-spiro[cyclohexane-1,9'-furo[2,3-f]quinazoline]-2'-carboxamide

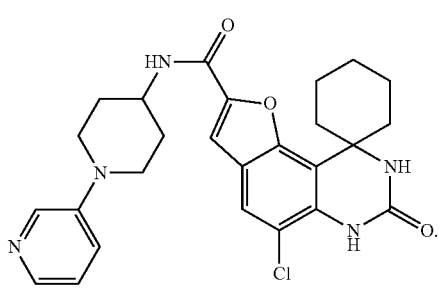

[M + H] = 494.5

Example 351. 5'-Chloro-2'-({3,4-dihydrospiro[2-benzopyran-1,4'-piperidine]-1'-yl}carbonyl)-7',8'-dihydro-6'H-spiro[cyclohexane-1,9'-furo[2,3-f]quinazoline]-7'-one

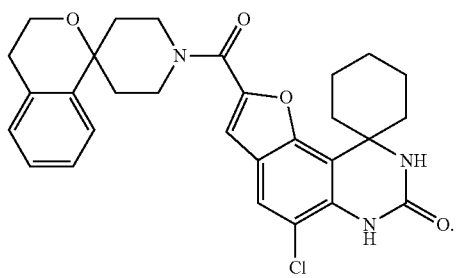

[M + H] = 520.4

Example 352. 5'-Chloro-7'-oxo-N-(2-phenoxyethyl)-7',8'-dihydro-6'H-spiro[cyclohexane-1,9'-furo[2,3-f]quinazoline]-2'-carboxamide

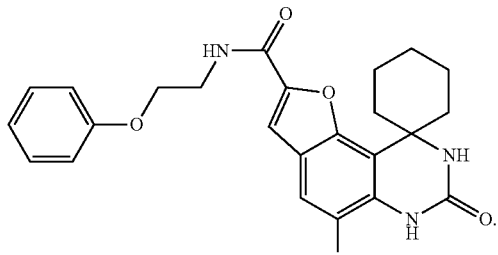

[M + H] = 454.4

Example 353. 3-{5'-Chloro-7'-oxo-7',8'-dihydro-6'H-spiro[cyclohexane-1,9'-furo[2,3-f]quinazoline]-2'-ylformamido}-N,N-dimethylpropanamide

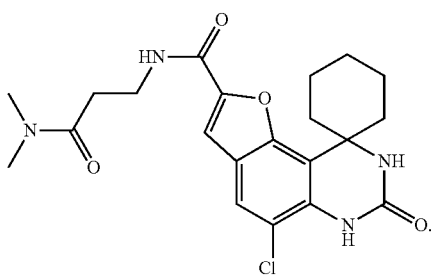

[M + H] = 433.4

Example 354. 5'-Chloro-N-[1-(methoxymethyl)cyclopropyl]-7'-oxo-7',8'-dihydro-6'H-spiro[cyclohexane-1,9'-furo[2,3-f]quinazoline]-2'-carboxamide

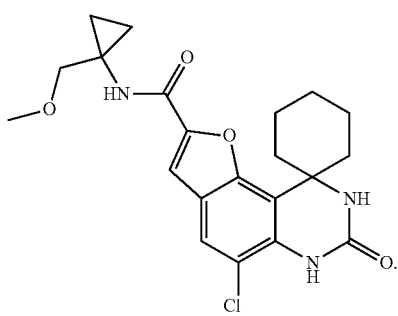

[M + H] = 418.4

Example 355. 5'-Chloro-N-[(3-fluoropyridin-4-yl)methyl]-7'-oxo-7',8'-dihydro-6'H-spiro[cyclohexane-1,9'-furo[2,3-f]quinazoline]-2'-carboxamide

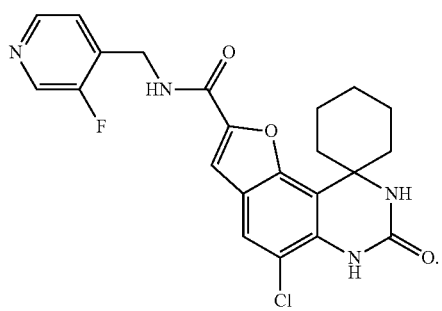

[M + H] = 443.4

Example 356. 5'-Chloro-N-(cyclobutylmethyl)-7'-oxo-N-(oxolan-2-ylmethyl)-7',8'-dihydro-6'H-spiro[cyclohexane-1,9'-furo[2,3-f]quinazoline]-2'-carboxamide

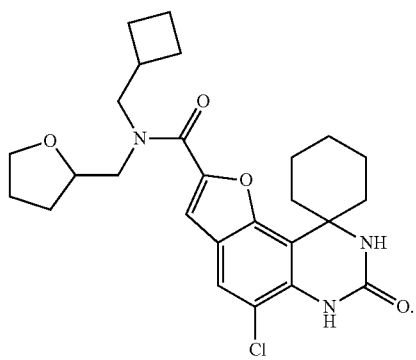

[M + H] = 486.5

Example 357. 5'-Chloro-2'-[4-(furan-2-ylmethyl)piperazine-1-carbonyl]-7',8'-dihydro-6'H-spiro[cyclohexane-1,9'-furo[2,3-f]quinazoline]-7'-one

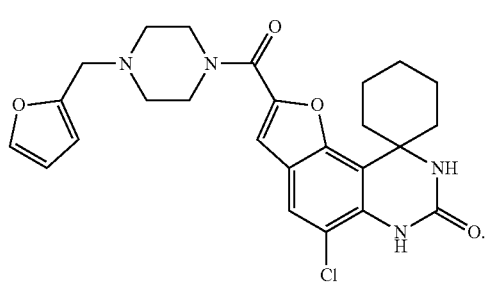

[M + H] = 483.4

Example 358. 5'-Chloro-N-[(1-methyl-1H-pyrazol-4-yl)methyl]-7'-oxo-7',8'-dihydro-6'H-spiro[cyclohexane-1,9'-furo[2,3-f]quinazoline]-2'-carboxamide

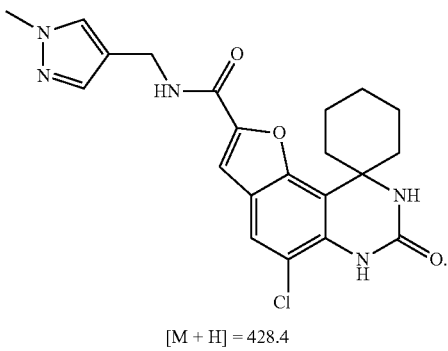 [SMILES: Cn1cc(CNC(=O)c2cc3cc(Cl)c4c(c3o2)C2(CCCCC2)NC(=O)N4)cn1]

[M + H] = 428.4

Example 359. 5'-Chloro-7'-oxo-N-[1-(pyridin-2-yl)cyclopropyl]-7',8'-dihydro-6'H-spiro[cyclohexane-1,9'-furo[2,3-f]quinazoline]-2'-carboxamide

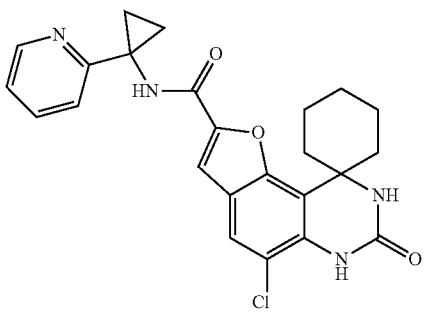

[M + H] = 451.4.

Example 360. 5'-Chloro-N-(4-methyloxan-4-yl)-7'-oxo-7',8'-dihydro-6'H-spiro[cyclohexane-1,9'-furo[2,3-f]quinazoline]-2'-carboxamide

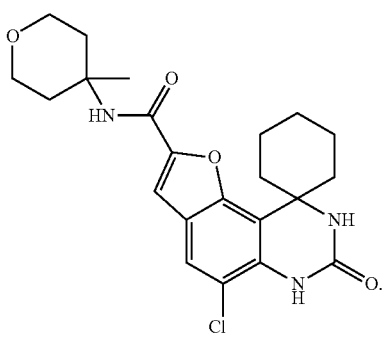

[M + H] = 432.4

Example 361. 5'-Chloro-N-{[1-(ethoxymethyl)cyclopropyl]methyl}-7'-oxo-7',8'-dihydro-6'H-spiro[cyclohexane-1,9'-furo[2,3-f]quinazoline]-2'-carboxamide

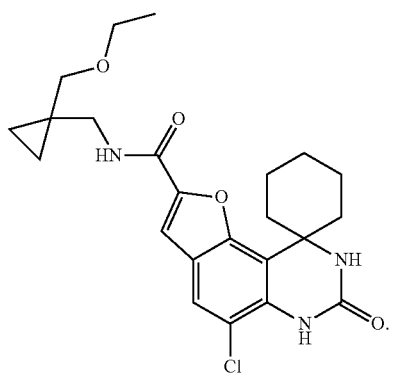

[M + H] = 446.5

Example 362. 2'-(4-Benzoylpiperazine-1-carbonyl)-5'-chloro-7',8'-dihydro-6'H-spiro[cyclohexane-1,9'-furo[2,3-f]quinazoline]-7'-one

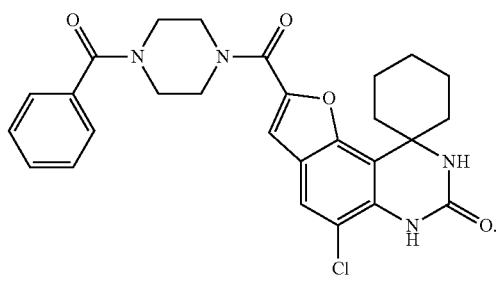

[M + H] = 507.4

Example 363. 2'-(4-{Bicyclo[2.2.1]heptan-2-yl}piperazine-1-carbonyl)-5'-chloro-7',8'-dihydro-6'H-spiro[cyclohexane-1,9'-furo[2,3-f]quinazoline]-7'-one

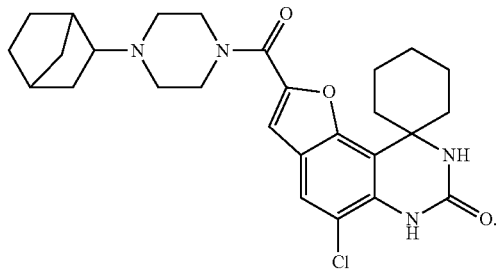

[M + H] = 497.5

Example 364. 5'-Chloro-N-[(1-methyl-1H-imidazol-5-yl)methyl]-7'-oxo-7',8'-dihydro-6'H-spiro[cyclohexane-1,9'-furo[2,3-f]quinazoline]-2'-carboxamide

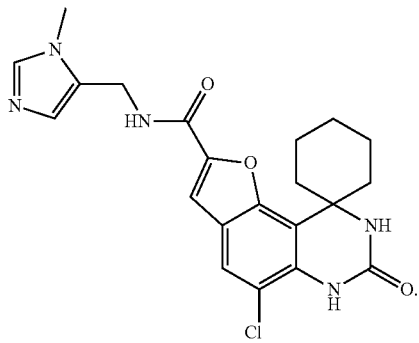

[M + H] = 428.4

Example 365. 5'-Chloro-7'-oxo-N-[2-oxo-2-(piperidin-1-yl)ethyl]-7',8'-dihydro-6'H-spiro[cyclohexane-1,9'-furo[2,3-f]quinazoline]-2'-carboxamide

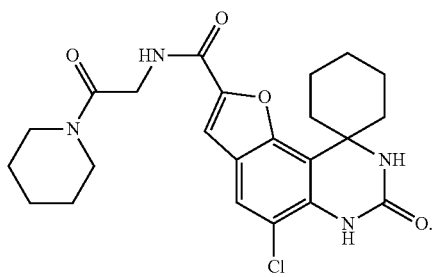

[M + H] = 459.4

Example 366. 5'-Chloro-2'-(3-hydroxyazetidine-1-carbonyl)-7',8'-dihydro-6'H-spiro[cyclohexane-1,9'-furo[2,3-f]quinazoline]-7'-one

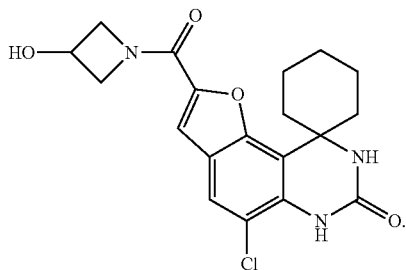

[M + H] = 390.4

Example 367. 5'-Chloro-7'-oxo-N-{[5-(trifluoromethyl)pyridin-2-yl]methyl}-7',8'-dihydro-6'H-spiro[cyclohexane-1,9'-furo[2,3-f]quinazoline]-2'-carboxamide

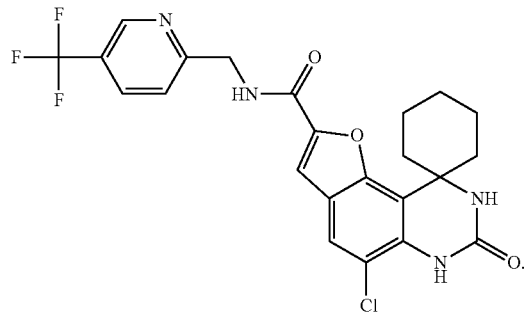

[M + H] = 493.4

Example 368. 5'-Chloro-N-[1-(oxan-4-yl)cyclopropyl]-7'-oxo-7',8'-dihydro-6'H-spiro[cyclohexane-1,9'-furo[2,3-f]quinazoline]-2'-carboxamide

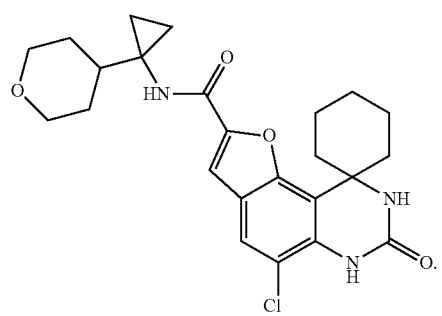

[M + H] = 458.4

Example 369. 5'-Chloro-N-methyl-7'-oxo-N-(prop-2-yn-1-yl)-7',8'-dihydro-6'H-spiro[cyclohexane-1,9'-furo[2,3-f]quinazoline]-2'-carboxamide

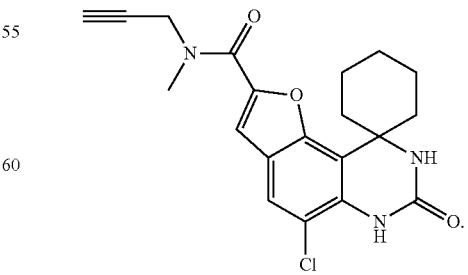

[M + H] = 386.4

Example 370. 5'-Chloro-N,N-diethyl-7'-oxo-7',8'-dihydro-6'H-spiro[cyclohexane-1,9'-furo[2,3-f]quinazoline]-2'-carboxamide

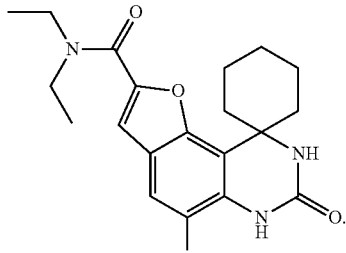

[M + H] = 390.4

Example 371. 5'-Chloro-N-(1-methyl-2-oxopiperidin-4-yl)-7'-oxo-7',8'-dihydro-6'H-spiro[cyclohexane-1,9'-furo[2,3-f]quinazoline]-2'-carboxamide

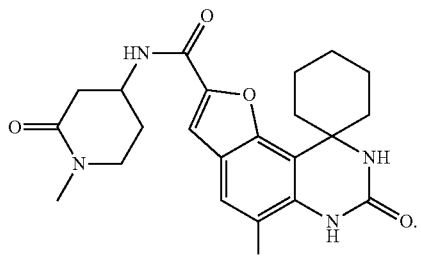

[M + H] = 445.4

Example 372. 5'-Chloro-2'-[(1R,5S,6S)-6-(pyridin-2-yl)-3-azabicyclo[3.1.0]hexane-3-carbonyl]-7',8'-dihydro-6'H-spiro[cyclohexane-1,9'-furo[2,3-f]quinazoline]-7'-one

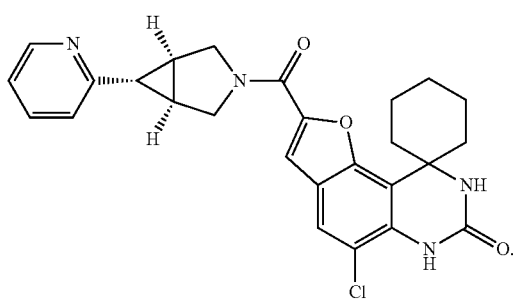

[M + H] = 477.5

Example 373. 5'-Chloro-N-[(6-fluoropyridin-2-yl)methyl]-7'-oxo-7',8'-dihydro-6'H-spiro[cyclohexane-1,9'-furo[2,3-f]quinazoline]-2'-carboxamide

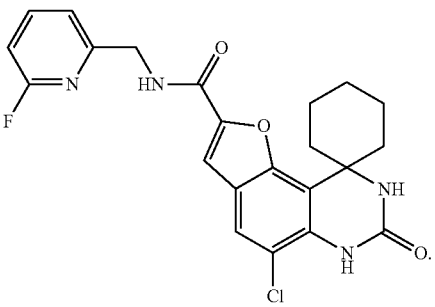

[M + H] = 443.4

Example 374. 5'-Chloro-N-ethyl-N-methyl-7'-oxo-7',8'-dihydro-6'H-spiro[cyclohexane-1,9'-furo[2,3-f]quinazoline]-2'-carboxamide

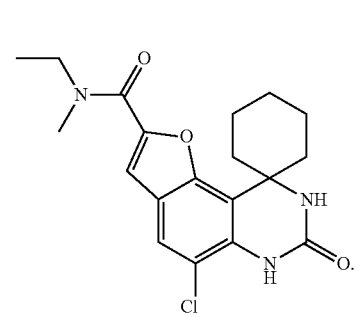

[M + H] = 376.4

Example 375. 5'-Chloro-2'-{6,6-dimethyl-3-azabicyclo[3.1.0]hexane-3-carbonyl}-7',8'-dihydro-6'H-spiro[cyclohexane-1,9'-furo[2,3-f]quinazoline]-7'-one

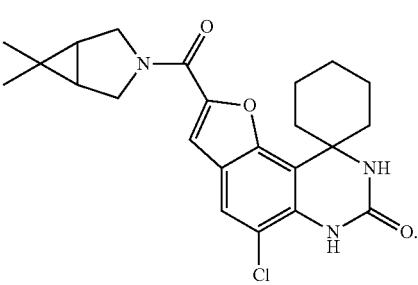

[M + H] = 428.5

Example 376. 5'-Chloro-2'-{7,7-difluoro-3-azabicyclo[4.1.0]heptane-3-carbonyl}-7',8'-dihydro-6'H-spiro[cyclohexane-1,9'-furo[2,3-f]quinazoline]-7'-one

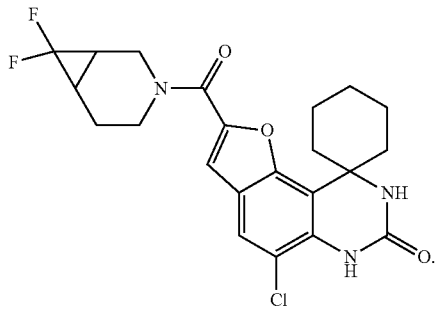

[M + H] = 450.4

Example 377. 5'-Chloro-2'-{6,6-difluoro-3-azabicyclo[3.1.0]hexane-3-carbonyl}-7',8'-dihydro-6'H-spiro[cyclohexane-1,9'-furo[2,3-f]quinazoline]-7'-one

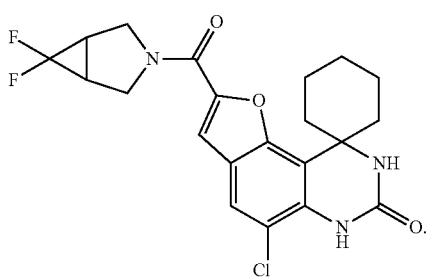

[M + H] = 436.4

Example 378. 5'-Chloro-7'-oxo-N-(2,2,2-trifluoroethyl)-7',8'-dihydro-6'H-spiro[cyclohexane-1,9'-furo[2,3-f]quinazoline]-2'-carboxamide

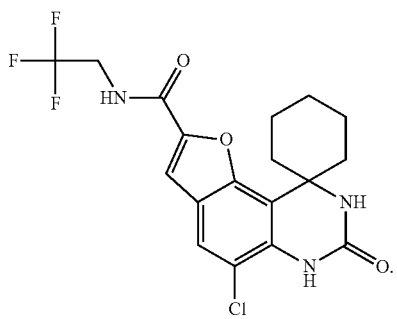

[M + H] = 416.3

Example 379. 5'-Chloro-7'-oxo-N-[(5-oxopyrrolidin-2-yl)methyl]-N-(propan-2-yl)-7',8'-dihydro-6'H-spiro[cyclohexane-1,9'-furo[2,3-f]quinazoline]-2'-carboxamide

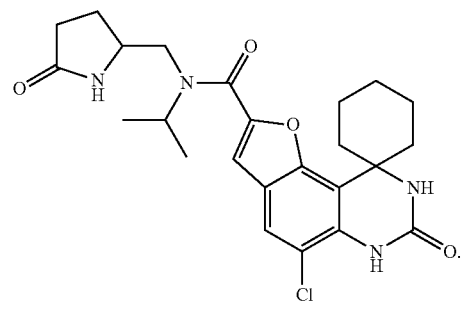

[M + H] = 473.5

Example 380. 5'-Chloro-N-[2-(2,3-dihydro-1-benzofuran-5-yl)ethyl]-7'-oxo-7',8'-dihydro-6'H-spiro[cyclohexane-1,9'-furo[2,3-f]quinazoline]-2'-carboxamide

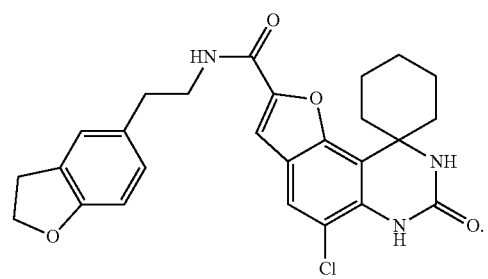

[M + H] = 480.4

Example 381. 5'-Chloro-N-(4,4-difluorocyclohexyl)-7'-oxo-7',8'-dihydro-6'H-spiro[cyclohexane-1,9'-furo[2,3-f]quinazoline]-2'-carboxamide

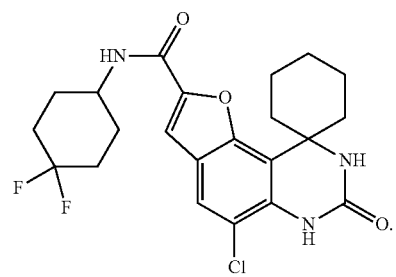

[M + H] = 452.4

Example 382. N-{bicyclo[1.1.1]pentan-1-yl}-5'-chloro-7'-oxo-7',8'-dihydro-6'H-spiro[cyclohexane-1,9'-furo[2,3-f]quinazoline]-2'-carboxamide

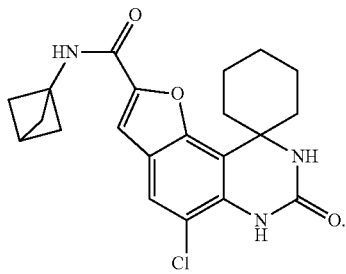

[M + H] = 400.4

Example 383. 5'-Chloro-N-[(1S,3R)-3-fluorocyclopentyl]-7'-oxo-7',8'-dihydro-6'H-spiro[cyclohexane-1,9'-furo[2,3-f]quinazoline]-2'-carboxamide

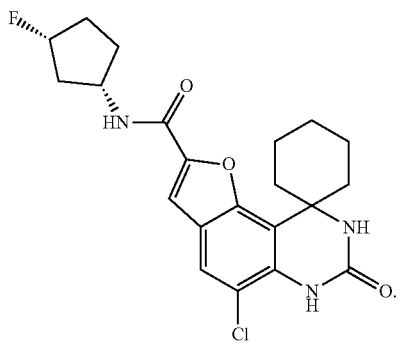

[M + H] = 420.3

Example 384. 5'-Chloro-N-methyl-7'-oxo-N-(prop-2-en-1-yl)-7',8'-dihydro-6'H-spiro[cyclohexane-1,9'-furo[2,3-f]quinazoline]-2'-carboxamide

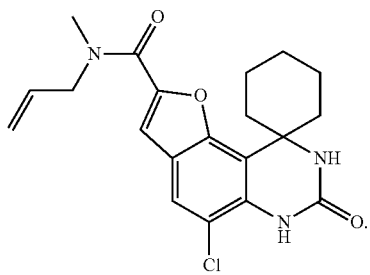

[M + H] = 388.4

Example 385. 5'-Chloro-7'-oxo-N-(prop-2-yn-1-yl)-7',8'-dihydro-6'H-spiro[cyclohexane-1,9'-furo[2,3-f]quinazoline]-2'-carboxamide

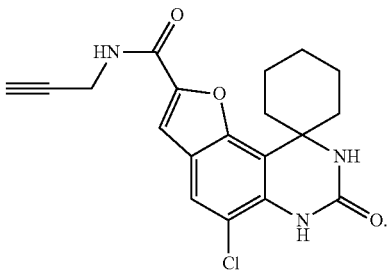

[M + H] = 372.3

Example 386. 5'-Chloro-2'-{2-ethyl-1-oxo-1H,2H,5H,6H,7H,8H-pyrido[3,4-d]pyridazine-6-carbonyl}-7',8'-dihydro-6'H-spiro[cyclohexane-1,9'-furo[2,3-f]quinazoline]-7'-one

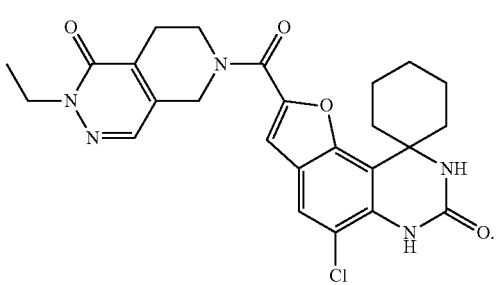

[M + H] = 496.4

Example 387. 5'-Chloro-N-(1,3-dihydro-2-benzofuran-5-ylmethyl)-7'-oxo-7',8'-dihydro-6'H-spiro[cyclohexane-1,9'-furo[2,3-f]quinazoline]-2'-carboxamide

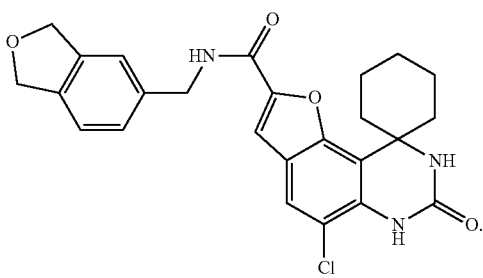

[M + H] = 466.4

Example 388. 5'-Chloro-N-[4-(methoxymethyl)oxan-4-yl]-7'-oxo-7',8'-dihydro-6'H-spiro[cyclohexane-1,9'-furo[2,3-f]quinazoline]-2'-carboxamide

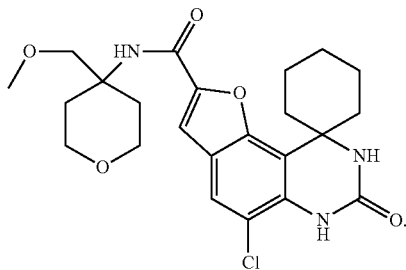

[M + H] = 462.4

Example 389. 5'-Chloro-N-cyclobutyl-7'-oxo-7',8'-dihydro-6'H-spiro[cyclohexane-1,9'-furo[2,3-f]quinazoline]-2'-carboxamide

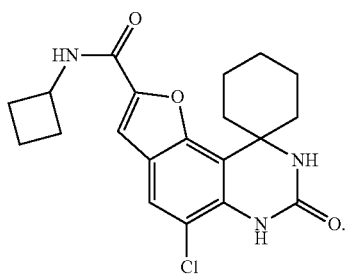

[M + H] = 388.3

Example 390. 5'-Chloro-2'-{9-propanoyl-2,9-diazaspiro[5.5]undecane-2-carbonyl}-7',8'-dihydro-6'H-spiro[cyclohexane-1,9'-furo[2,3-f]quinazoline]-7'-one

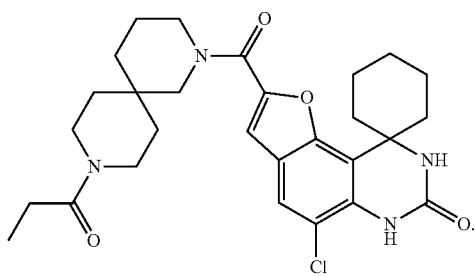

[M + H] = 527.5

Example 391. 5'-Chloro-N-methyl-7'-oxo-N-(propan-2-yl)-7',8'-dihydro-6'H-spiro[cyclohexane-1,9'-furo[2,3-f]quinazoline]-2'-carboxamide

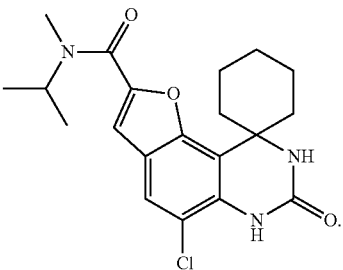

[M + H] = 390.4

Example 392. 5'-Chloro-2'-[(1R,5S,6S)-6-(2-methoxyphenyl)-3-azabicyclo[3.1.0]hexane-3-carbonyl]-7',8'-dihydro-6'H-spiro[cyclohexane-1,9'-furo[2,3-f]quinazoline]-7'-one

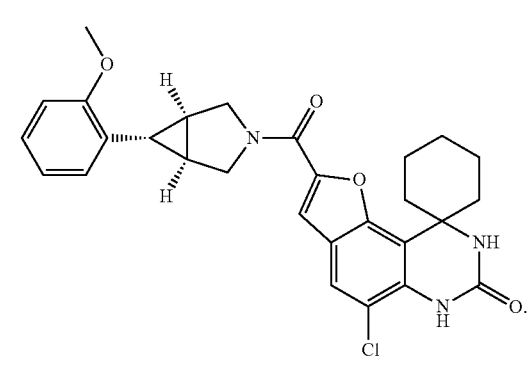

[M + H] = 506.4

Example 393. N-Butyl-5'-Chloro-7'-oxo-7',8'-dihydro-6'H-spiro[cyclohexane-1,9'-furo[2,3-f]quinazoline]-2'-carboxamide

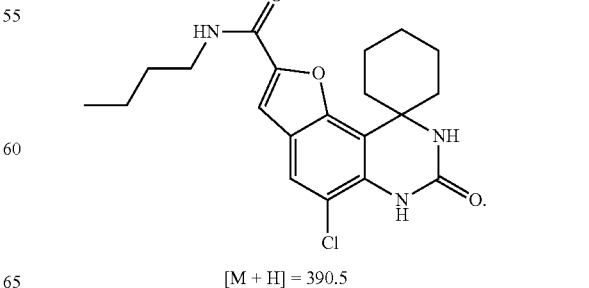

[M + H] = 390.5

Example 394. 5'-Chloro-2'-{8-ethoxy-2H,3H,4H, 5H-pyrido[3,2-f][1,4]oxazepine-4-carbonyl}-7',8'-dihydro-6'H-spiro[cyclohexane-1,9'-furo[2,3-f]quinazoline]-7'-one

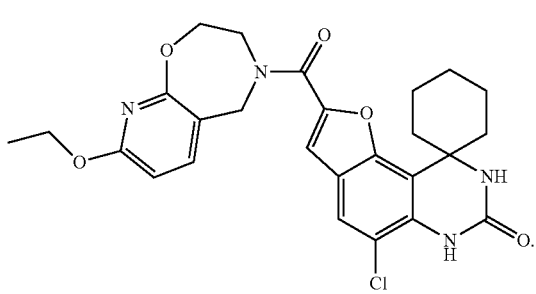

[M + H] = 511.4

Example 395. 5'-Chloro-7'-oxo-N-[2-(thiophen-3-yl)ethyl]-7',8'-dihydro-6'H-spiro[cyclohexane-1,9'-furo[2,3-f]quinazoline]-2'-carboxamide

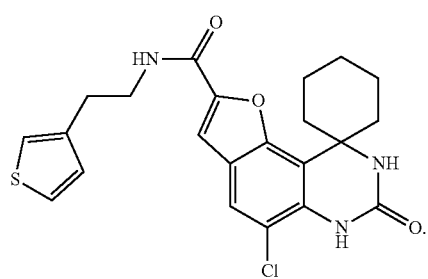

[M + H] = 444.4

Example 396. 5'-Chloro-N-(2-cyclobutyl-2,2-difluoroethyl)-7'-oxo-7',8'-dihydro-6'H-spiro[cyclohexane-1,9'-furo[2,3-f]quinazoline]-2'-carboxamide

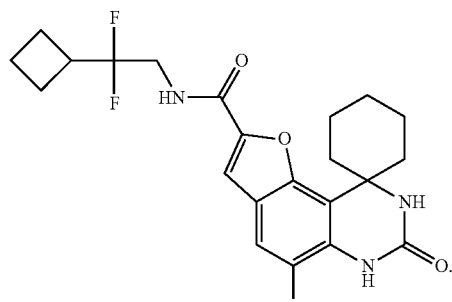

[M+H] = 452.4

Example 397. 5'-Chloro-N-methyl-7'-oxo-N-propyl-7',8'-dihydro-6'H-spiro[cyclohexane-1,9'-furo[2,3-f]quinazoline]-2'-carboxamide

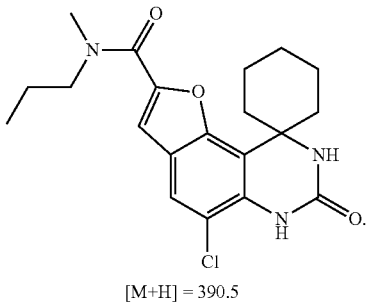 [SMILES: CCCN(C)C(=O)c1cc2cc(Cl)c3c(c2o1)C1(CCCCC1)NC(=O)N3]

[M+H] = 390.5

Example 398. (2R)-1-({5'-Chloro-7'-oxo-7',8'-dihydro-6'H-spiro[cyclohexane-1,9'-furo[2,3-f]quinazoline]-2'-yl}carbonyl)pyrrolidine-2-carboxylic acid

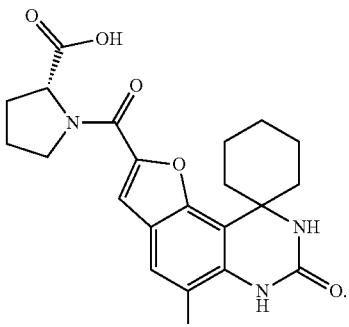

[M+H] = 432.4

Example 399. 5'-Chloro-2'-[(1R,6R)-7,7-difluoro-6-methyl-3-azabicyclo[4.1.0]heptane-3-carbonyl]-7',8'-dihydro-6'H-spiro[cyclohexane-1,9'-furo[2,3-f]quinazoline]-7'-one

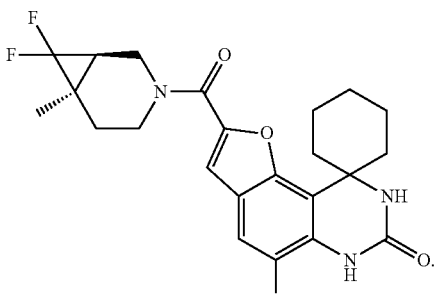

[M+H] = 464.4

Example 400. 5'-Chloro-N-methyl-7'-oxo-N-{[4-(propan-2-yl)-4H-1,2,4-triazol-3-yl]methyl}-7',8'-dihydro-6'H-spiro[cyclohexane-1,9'-furo[2,3-f]quinazoline]-2'-carboxamide

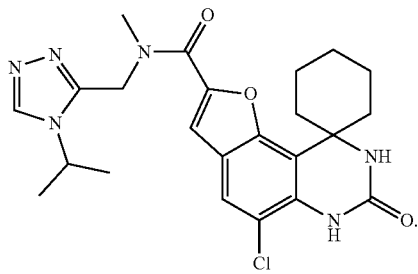

[M+H] = 471.4

Example 401. 5'-Chloro-2'-({4-oxo-3,4-dihydrospiro[1-benzopyran-2,3'-pyrrolidine]-1'-yl}carbonyl)-7',8'-dihydro-6'H-spiro[cyclohexane-1,9'-furo[2,3-f]quinazoline]-7'-one

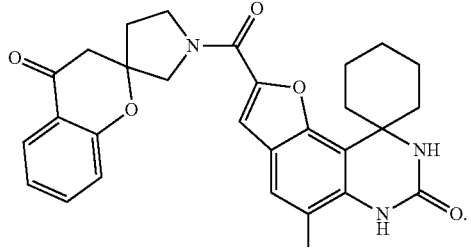

[M+H] = 520.6

Example 402. 5'-Chloro-N-cyclopropyl-7'-oxo-7',8'-dihydro-6'H-spiro[cyclohexane-1,9'-furo[2,3-f]quinazoline]-2'-carboxamide

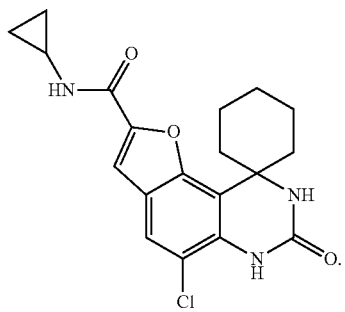

[M+H] = 374.4

Example 403. 5'-Chloro-N-ethyl-7'-oxo-N-propyl-7',8'-dihydro-6'H-spiro[cyclohexane-1,9'-furo[2,3-f]quinazoline]-2'-carboxamide

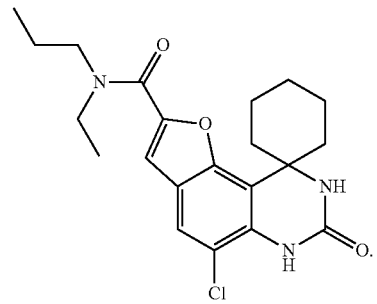

[M+H] = 404.5

Example 404. 5'-Chloro-7'-oxo-N-propyl-7',8'-dihydro-6'H-spiro[cyclohexane-1,9'-furo[2,3-f]quinazoline]-2'-carboxamide

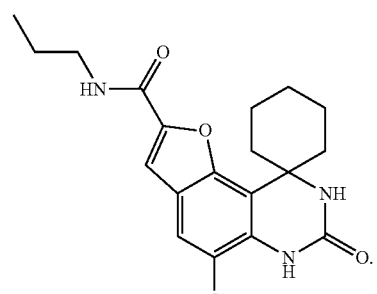

[M+H] = 376.4

Example 405. 5'-Chloro-N-methyl-7'-oxo-N-(thiophen-3-ylmethyl)-7',8'-dihydro-6'H-spiro[cyclohexane-1,9'-furo[2,3-f]quinazoline]-2'-carboxamide

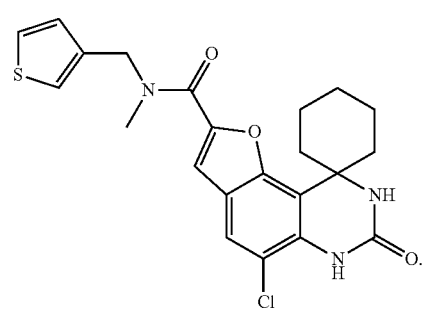

[M+H] = 444.4

Example 406. 1-({5'-Chloro-7'-oxo-7',8'-dihydro-6'H-spiro[cyclohexane-1,9'-furo[2,3-f]quinazoline]-2'-yl}carbonyl)piperidine-4-carbonitrile

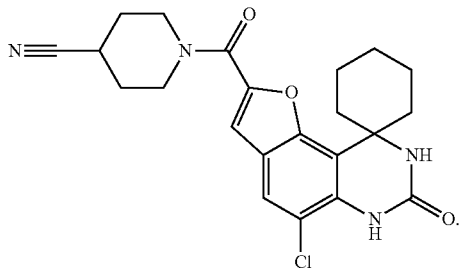

[M+H] = 427.5

Example 407. 5'-Chloro-2'-[3-(dimethylamino)pyrrolidine-1-carbonyl]-7',8'-dihydro-6'H-spiro[cyclohexane-1,9'-furo[2,3-f]quinazoline]-7'-one

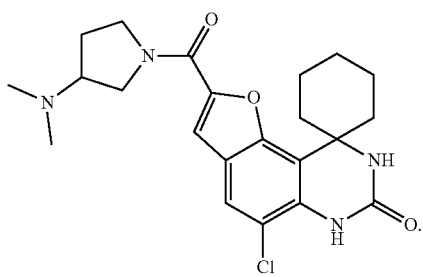

[M+H] = 431.4

Example 408. N-Benzyl-5'-chloro-N-methyl-7'-oxo-7',8'-dihydro-6'H-spiro[cyclohexane-1,9'-furo[2,3-f]quinazoline]-2'-carboxamide

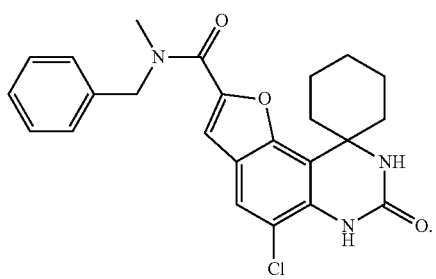

[M+H] = 438.5

Example 409. 5'-Chloro-N-methyl-7'-oxo-N-(thiophen-2-ylmethyl)-7',8'-dihydro-6'H-spiro[cyclohexane-1,9'-furo[2,3-f]quinazoline]-2'-carboxamide

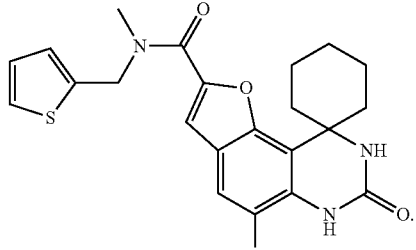

[M+H] = 444.5

Example 410. 5'-Chloro-N-[(3-methoxyphenyl)methyl]-7'-oxo-7',8'-dihydro-6'H-spiro[cyclohexane-1,9'-furo[2,3-f]quinazoline]-2'-carboxamide

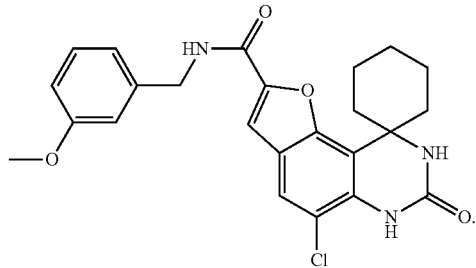

[M+H] = 454.4

Example 411. 5'-Chloro-2'-(3-hydroxypyrrolidine-1-carbonyl)-7',8'-dihydro-6'H-spiro[cyclohexane-1,9'-furo[2,3-f]quinazoline]-7'-one

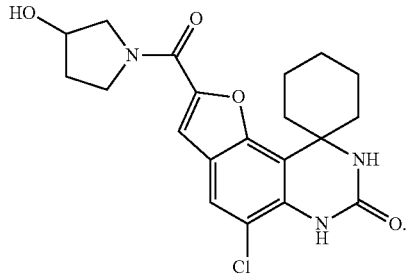

[M + H] = 404.4

Example 412. 5'-Chloro-7'-oxo-N,N-bis(propan-2-yl)-7',8'-dihydro-6'H-spiro[cyclohexane-1,9'-furo[2,3-f]quinazoline]-2'-carboxamide

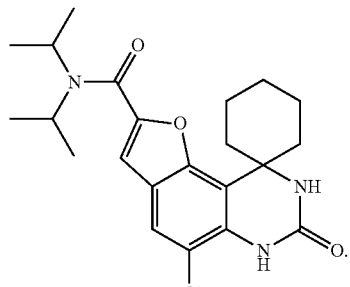

[M + H] = 418.4

Example 413. 5'-Chloro-N-[2-(furan-2-yl)ethyl]-7'-oxo-7',8'-dihydro-6'H-spiro[cyclohexane-1,9'-furo[2,3-f]quinazoline]-2'-carboxamide

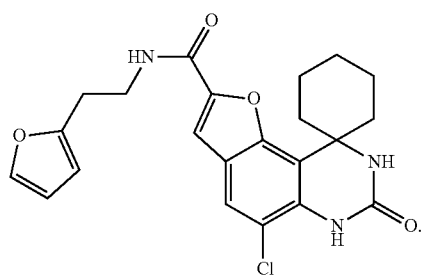

[M + H] = 428.4

Example 414. 5'-Chloro-2'-[2-(hydroxymethyl)piperidine-1-carbonyl]-7',8'-dihydro-6'H-spiro[cyclohexane-1,9'-furo[2,3-f]quinazoline]-7'-one

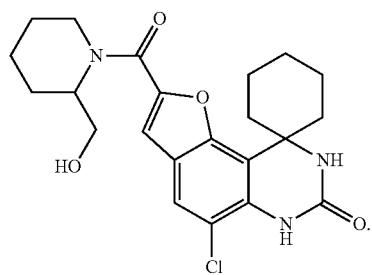

[M + H] = 432.4

Example 415. 5'-Chloro-2'-[4-(propan-2-yl)piperazine-1-carbonyl]-7',8'-dihydro-6'H-spiro[cyclohexane-1,9'-furo[2,3-f]quinazoline]-7'-one

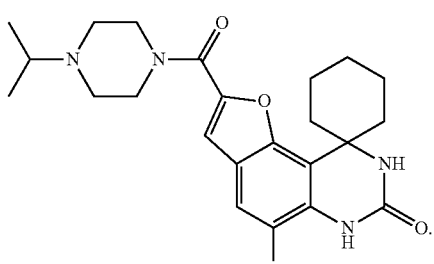

[M + H] = 445.5

Example 416. 5'-Chloro-2'-[2-(furan-2-yl)pyrrolidine-1-carbonyl]-7',8'-dihydro-6'H-spiro[cyclohexane-1,9'-furo[2,3-f]quinazoline]-7'-one

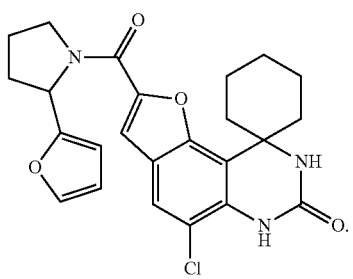

[M + H] = 454.4

Example 417. 5'-Chloro-N-(3-methylbutyl)-7'-oxo-7',8'-dihydro-6'H-spiro[cyclohexane-1,9'-furo[2,3-f]quinazoline]-2'-carboxamide

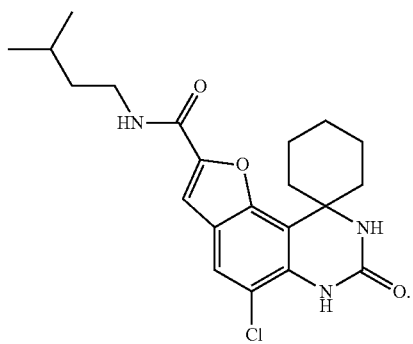

[M + H] = 404.4

Example 418. 5'-Chloro-N-(2-cyanoethyl)-N-ethyl-7'-oxo-7',8'-dihydro-6'H-spiro[cyclohexane-1,9'-furo[2,3-f]quinazoline]-2'-carboxamide

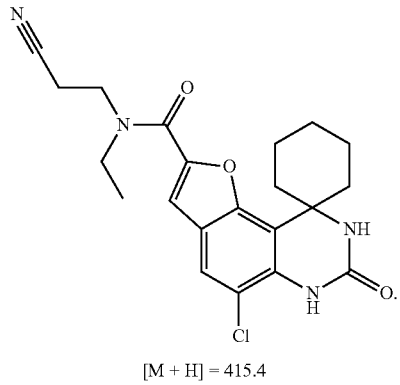 [SMILES: CCN(CCC#N)C(=O)c1cc2cc(Cl)c3c(c2o1)C1(CCCCC1)NC(=O)N3]

[M + H] = 415.4

Example 419. 5'-Chloro-N-methyl-7'-oxo-N-(pyridin-2-ylmethyl)-7',8'-dihydro-6'H-spiro[cyclohexane-1,9'-furo[2,3-f]quinazoline]-2'-carboxamide

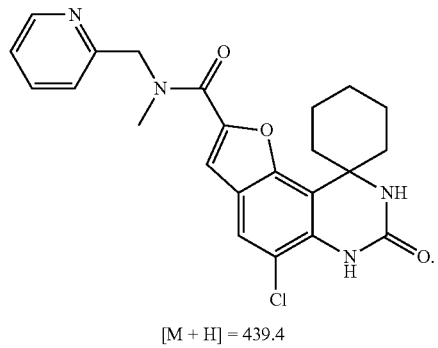 [SMILES: CN(Cc1ccccn1)C(=O)c1cc2cc(Cl)c3c(c2o1)C1(CCCCC1)NC(=O)N3]

[M + H] = 439.4

Example 420. 5'-Chloro-7'-oxo-N-[3-(pyrrolidin-1-yl)propyl]-7',8'-dihydro-6'H-spiro[cyclohexane-1,9'-furo[2,3-f]quinazoline]-2'-carboxamide

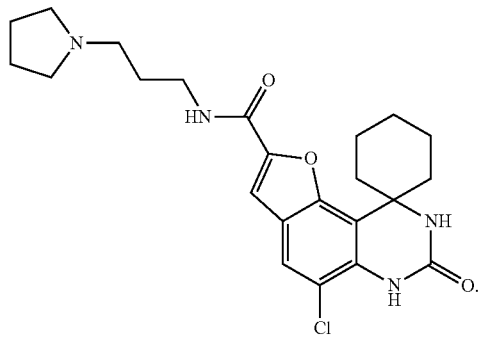

[M + H] = 445.5

Example 421. 5'-Chloro-7'-oxo-N-(pentan-3-yl)-7',8'-dihydro-6'H-spiro[cyclohexane-1,9'-furo[2,3-f]quinazoline]-2'-carboxamide

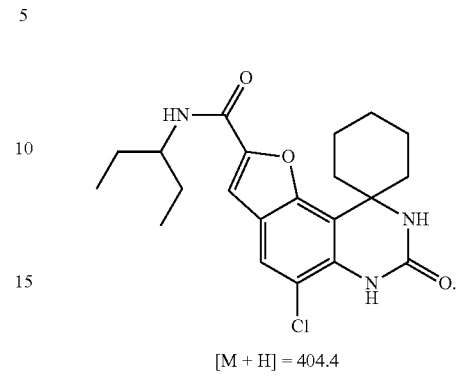

[M + H] = 404.4

Example 422. 2'-(Azepane-1-carbonyl)-5'-chloro-7',8'-dihydro-6'H-spiro[cyclohexane-1,9'-furo[2,3-f]quinazoline]-7'-one

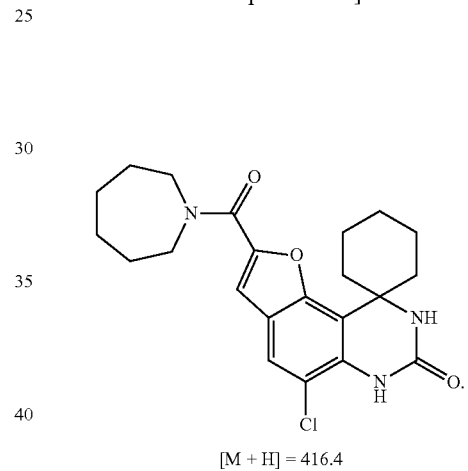

[M + H] = 416.4

Example 423. 5'-Chloro-N-[2-(1H-imidazol-1-yl)ethyl]-7'-oxo-7',8'-dihydro-6'H-spiro[cyclohexane-1,9'-furo[2,3-f]quinazoline]-2'-carboxamide

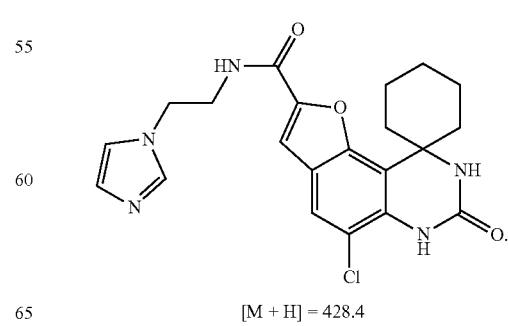

[M + H] = 428.4

Example 424. 5'-Chloro-2'-[(2R,6S)-2,6-dimethyl-morpholine-4-carbonyl]-7',8'-dihydro-6'H-spiro[cyclohexane-1,9'-furo[2,3-f]quinazoline]-7'-one

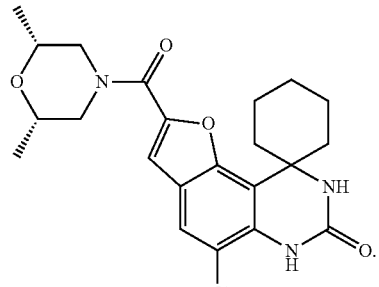

[M + H] = 432.5

Example 425. 5'-Chloro-N-methyl-7'-oxo-N-(pyridin-3-ylmethyl)-7',8'-dihydro-6'H-spiro[cyclohexane-1,9'-furo[2,3-f]quinazoline]-2'-carboxamide

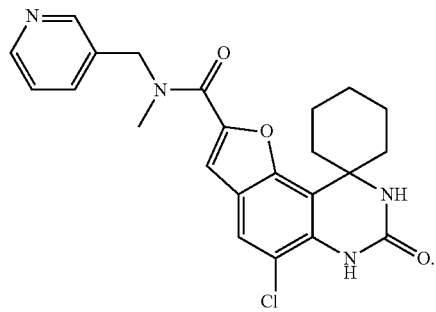

[M + H] = 439.4

Example 426. 5'-Chloro-N-methyl-N-(1-methylpiperidin-4-yl)-7'-oxo-7',8'-dihydro-6'H-spiro[cyclohexane-1,9'-furo[2,3-f]quinazoline]-2'-carboxamide

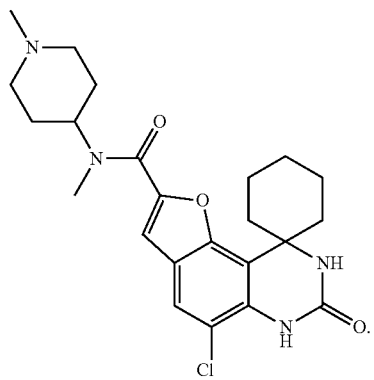

[M+H] = 445.5

Example 427. 5'-Chloro-N-[(3-ethyl-1,2-oxazol-5-yl)methyl]-N-methyl-7'-oxo-7',8'-dihydro-6'H-spiro[cyclohexane-1,9'-furo[2,3-f]quinazoline]-2'-carboxamide

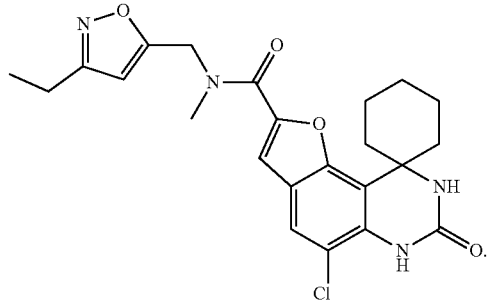

[M+H] = 457.4

Example 428. 5'-Chloro-N-(3-methylbutan-2-yl)-7'-oxo-7',8'-dihydro-6'H-spiro[cyclohexane-1,9'-furo[2,3-f]quinazoline]-2'-carboxamide

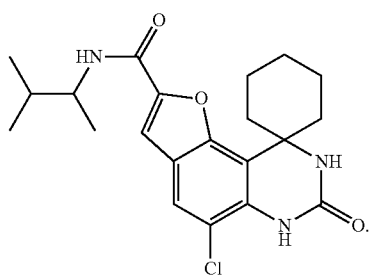

[M+H] = 404.4

Example 429. 5'-Chloro-2'-(3-methylpiperidine-1-carbonyl)-7',8'-dihydro-6'H-spiro[cyclohexane-1,9'-furo[2,3-f]quinazoline]-7'-one

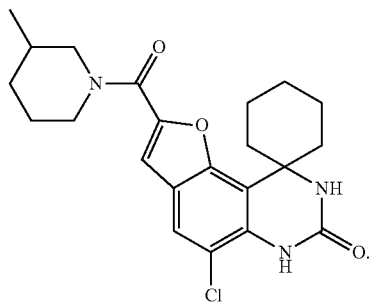

[M+H] = 416.4

Example 430. 5'-Chloro-N-[2-(dimethylamino)ethyl]-N-methyl-7'-oxo-7',8'-dihydro-6'H-spiro[cyclohexane-1,9'-furo[2,3-f]quinazoline]-2'-carboxamide

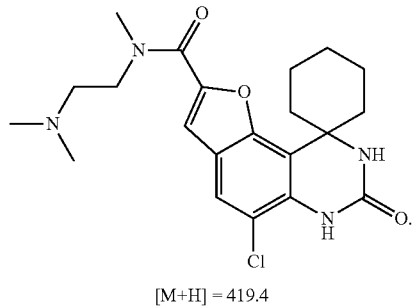 [SMILES: CN(C)CCN(C)C(=O)c1cc2cc(Cl)c3c(c2o1)C1(CCCCC1)NC(=O)N3]

[M+H] = 419.4

Example 431. 5'-Chloro-2'-(2,2-dimethylmorpholine-4-carbonyl)-7',8'-dihydro-6'H-spiro[cyclohexane-1,9'-furo[2,3-f]quinazoline]-7'-one

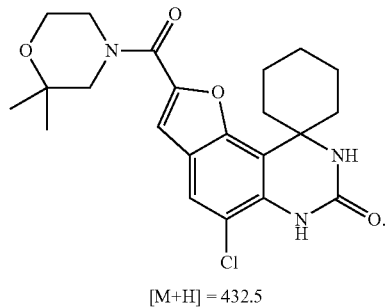 [SMILES: CC1(C)CN(C(=O)c2cc3cc(Cl)c4c(c3o2)C2(CCCCC2)NC(=O)N4)CCO1]

[M+H] = 432.5

Example 432. 5'-Chloro-N-[(3-hydroxyphenyl)methyl]-7'-oxo-7',8'-dihydro-6'H-spiro[cyclohexane-1,9'-furo[2,3-f]quinazoline]-2'-carboxamide

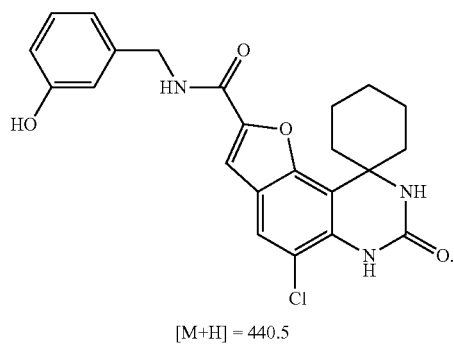 [SMILES: O=C1Nc2c(Cl)cc3cc(C(=O)NCc4cccc(O)c4)oc3c2C2(CCCCC2)N1]

[M+H] = 440.5

Example 433. 5'-Chloro-2'-[4-(dimethylamino)piperidine-1-carbonyl]-7',8'-dihydro-6'H-spiro[cyclohexane-1,9'-furo[2,3-f]quinazoline]-7'-one

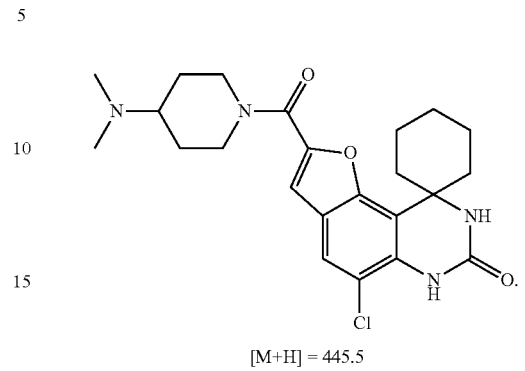

[M+H] = 445.5

Example 434. 5'-Chloro-7'-oxo-N-[3-(2-oxopyrrolidin-1-yl)propyl]-7',8'-dihydro-6'H-spiro[cyclohexane-1,9'-furo[2,3-f]quinazoline]-2'-carboxamide

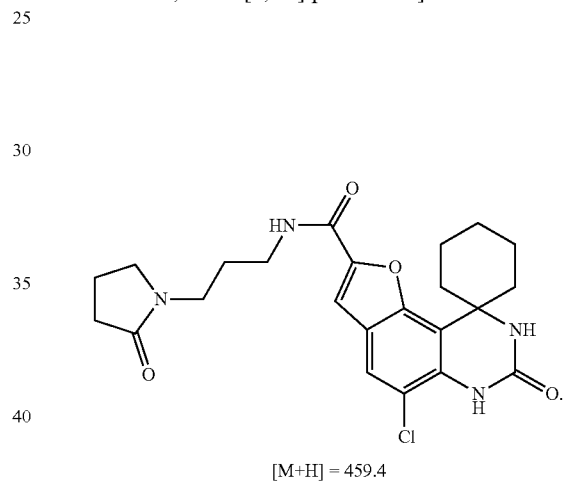

[M+H] = 459.4

Example 435. 5'-Chloro-2'-(4-methylpiperidine-1-carbonyl)-7',8'-dihydro-6'H-spiro[cyclohexane-1,9'-furo[2,3-f]quinazoline]-7'-one

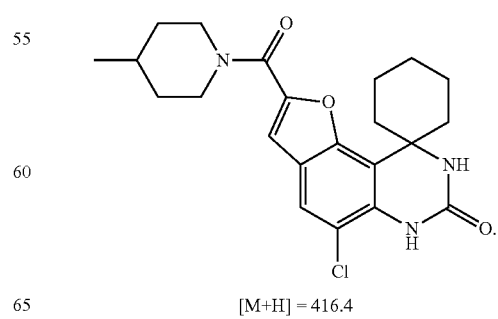

[M+H] = 416.4

Example 436. 5'-Chloro-7'-oxo-N-(thiophen-3-ylmethyl)-7',8'-dihydro-6'H-spiro[cyclohexane-1,9'-furo[2,3-f]quinazoline]-2'-carboxamide

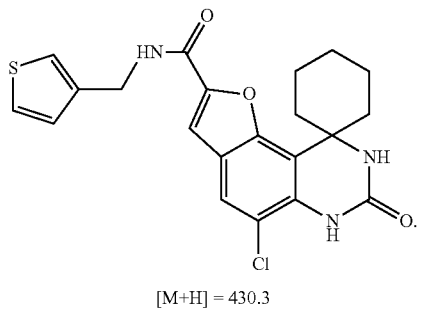 [SMILES: O=C1Nc2c(Cl)cc3cc(C(=O)NCc4ccsc4)oc3c2C2(CCCCC2)N1]

[M+H] = 430.3

Example 437. 5'-Chloro-N-[(3-fluorophenyl)methyl]-7'-oxo-7',8'-dihydro-6'H-spiro[cyclohexane-1,9'-furo[2,3-f]quinazoline]-2'-carboxamide

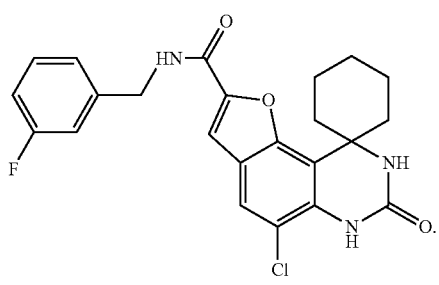

[M+H] = 442.4

Example 438. N-Benzyl-5'-chloro-N-(2-hydroxyethyl)-7'-oxo-7',8'-dihydro-6'H-spiro[cyclohexane-1,9'-furo[2,3-f]quinazoline]-2'-carboxamide

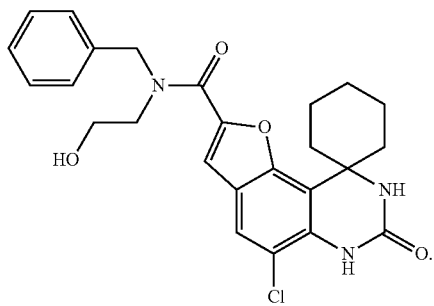

[M+H] = 468.4

Example 439. 5'-Chloro-N-[2-(3,5-dimethyl-1H-pyrazol-4-yl)ethyl]-N-methyl-7'-oxo-7',8'-dihydro-6'H-spiro[cyclohexane-1,9'-furo[2,3-f]quinazoline]-2'-carboxamide

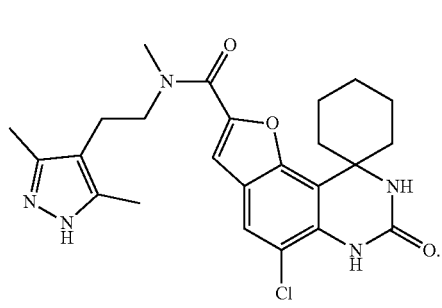

[M+H] = 470.5

Example 440. 5'-Chloro-2'-(4-cyclohexylpiperazine-1-carbonyl)-7',8'-dihydro-6'H-spiro[cyclohexane-1,9'-furo[2,3-f]quinazoline]-7'-one

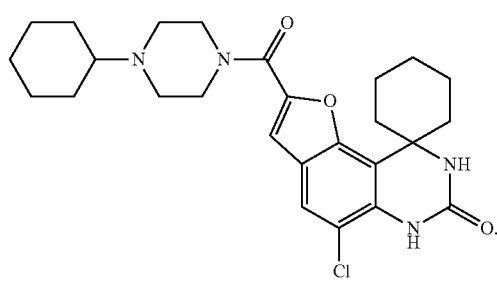

[M+H] = 485.5

Example 441. 5'-Chloro-2'-(4-hydroxy-4-phenylpiperidine-1-carbonyl)-7',8'-dihydro-6'H-spiro[cyclohexane-1,9'-furo[2,3-f]quinazoline]-7'-one

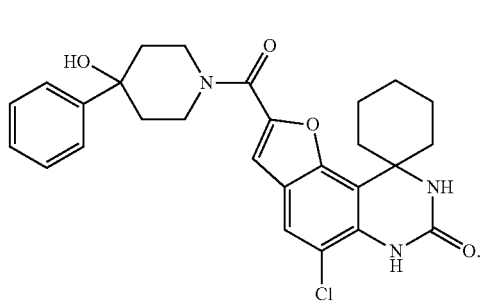

[M + H] = 494.5

Example 442. 5'-Chloro-2'-[4-(oxolane-2-carbonyl)piperazine-1-carbonyl]-7',8'-dihydro-6'H-spiro[cyclohexane-1,9'-furo[2,3-f]quinazoline]-7'-one

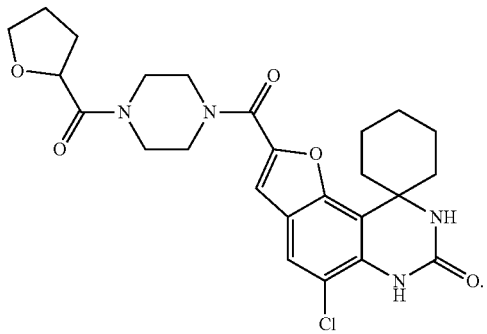

[M + H] = 501.4

Example 443. 5'-Chloro-2'-{4-[(dimethylamino)methyl]piperidine-1-carbonyl}-7',8'-dihydro-6'H-spiro[cyclohexane-1,9'-furo[2,3-f]quinazoline]-7'-one

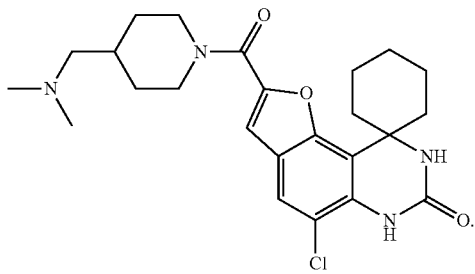

[M + H] = 459.5

Example 444. 1-({5'-Chloro-7'-oxo-7',8'-dihydro-6'H-spiro[cyclohexane-1,9'-furo[2,3-f]quinazoline]-2'-yl}carbonyl)-N-methylpiperidine-4-carboxamide

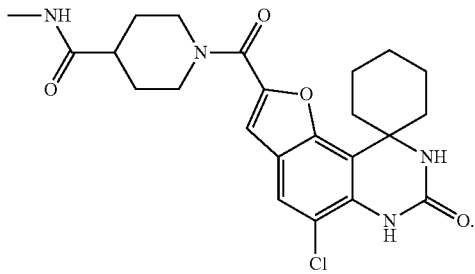

[M + H] = 459.5

Example 445. 5'-Chloro-N-[2-(4-methoxyphenyl)ethyl]-7'-oxo-7',8'-dihydro-6'H-spiro[cyclohexane-1,9'-furo[2,3-f]quinazoline]-2'-carboxamide

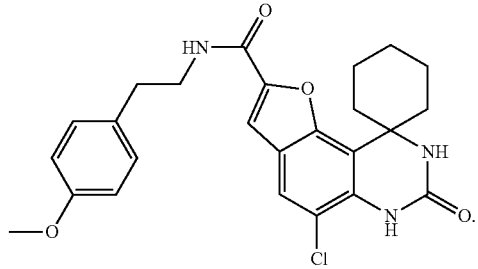

[M + H] = 468.4

Example 446. 5'-Chloro-N-[2-(dimethyl-1,2-oxazol-4-yl)ethyl]-N-methyl-7'-oxo-7',8'-dihydro-6'H-spiro[cyclohexane-1,9'-furo[2,3-f]quinazoline]-2'-carboxamide

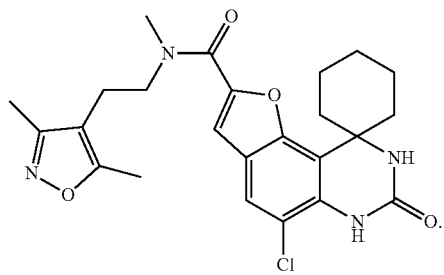

[M + H] = 471.5

Example 447. 5'-Chloro-2'-[4-(1,3-thiazol-2-yl)piperazine-1-carbonyl]-7',8'-dihydro-6'H-spiro[cyclohexane-1,9'-furo[2,3-f]quinazoline]-7'-one

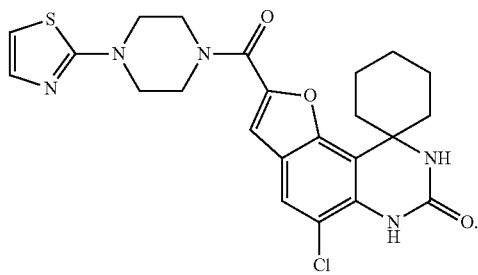

[M + H] = 486.4

Example 448. 5'-Chloro-N-{[4-(1H-imidazol-1-yl)phenyl]methyl}-N-methyl-7'-oxo-7',8'-dihydro-6'H-spiro[cyclohexane-1,9'-furo[2,3-f]quinazoline]-2'-carboxamide

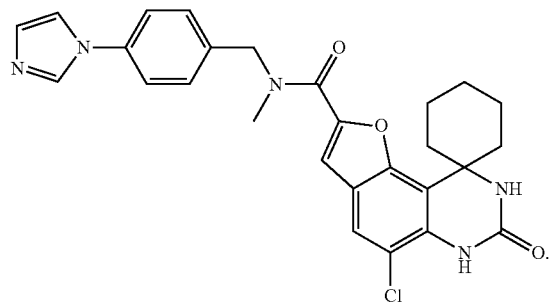

[M + H] = 504.4

Example 449. 2'-(4-tert-Butylpiperazine-1-carbonyl)-5'-chloro-7',8'-dihydro-6'H-spiro[cyclohexane-1,9'-furo[2,3-f]quinazoline]-7'-one

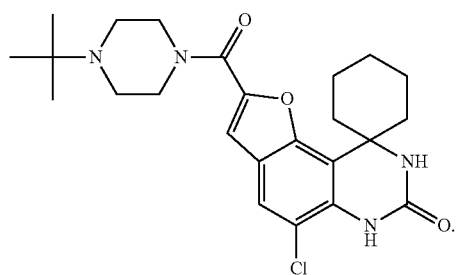

[M + H] = 495.5

Example 450. 5'-Chloro-N-[2-(3-methoxyphenyl)ethyl]-7'-oxo-7',8'-dihydro-6'H-spiro[cyclohexane-1,9'-furo[2,3-f]quinazoline]-2'-carboxamide

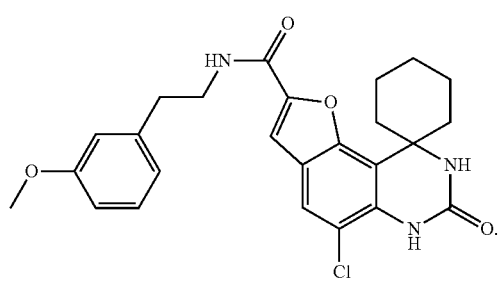

[M + H] = 468.5

Example 451. 5'-Chloro-2'-[4-(pyrrolidin-1-yl)piperidine-1-carbonyl]-7',8'-dihydro-6'H-spiro[cyclohexane-1,9'-furo[2,3-f]quinazoline]-7'-one

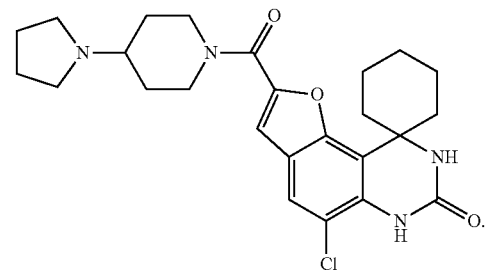

[M + H] = 471.5

Example 452. 5'-Chloro-N-(2,3-dihydro-1,4-benzodioxin-2-ylmethyl)-7'-oxo-7',8'-dihydro-6'H-spiro[cyclohexane-1,9'-furo[2,3-f]quinazoline]-2'-carboxamide

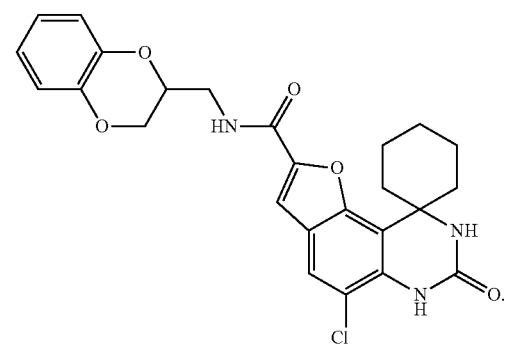

[M + H] = 482.4

Example 453. 5'-Chloro-2'-[4-(morpholin-4-yl)piperidine-1-carbonyl]-7',8'-dihydro-6'H-spiro[cyclohexane-1,9'-furo[2,3-f]quinazoline]-7'-one

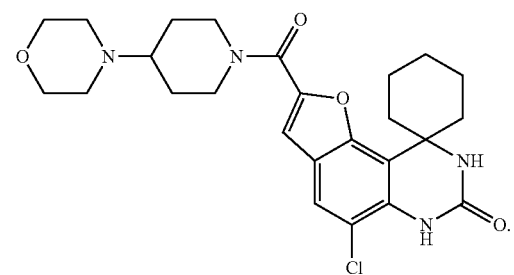

[M + H] = 487.5

Example 454. 5'-Chloro-2'-[4-(3-methoxyphenyl)piperazine-1-carbonyl]-7',8'-dihydro-6'H-spiro[cyclohexane-1,9'-furo[2,3-f]quinazoline]-7'-one

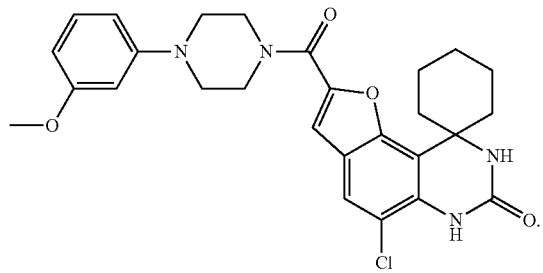

[M + H] = 509.4

Example 455. 5'-Chloro-7'-oxo-N-[1-(propan-2-yl)piperidin-4-yl]-7',8'-dihydro-6'H-spiro[cyclohexane-1,9'-furo[2,3-f]quinazoline]-2'-carboxamide

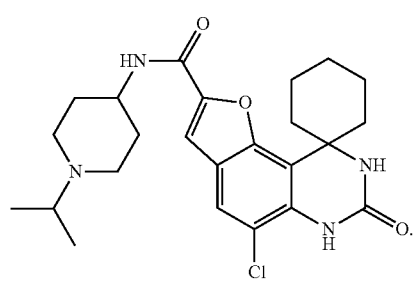

[M + H] = 459.5

Example 456. 5'-Chloro-N-(1-hydroxy-3-phenylpropan-2-yl)-7'-oxo-7',8'-dihydro-6'H-spiro[cyclohexane-1,9'-furo[2,3-f]quinazoline]-2'-carboxamide

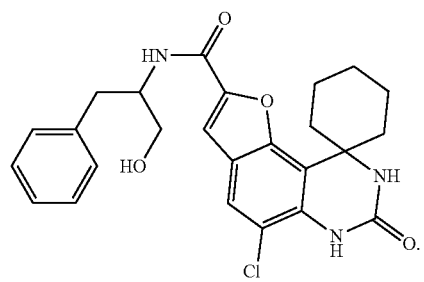

[M+H] = 468.4

Example 457. N-(2H-1,3-Benzodioxol-5-ylmethyl)-5'-chloro-N-methyl-7'-oxo-7',8'-dihydro-6'H-spiro[cyclohexane-1,9'-furo[2,3-f]quinazoline]-2'-carboxamide

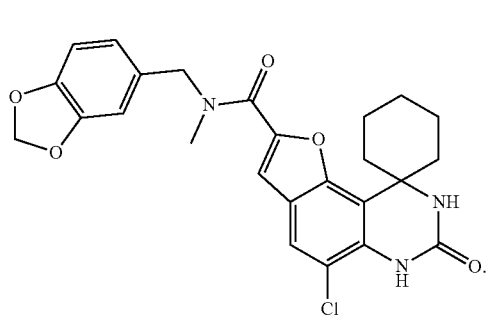

[M+H] = 482.4

Example 458. Methyl 3-[1-({5'-chloro-7'-oxo-7',8'-dihydro-6'H-spiro[cyclohexane-1,9'-furo[2,3-f]quinazoline]-2'-yl}carbonyl)piperidin-2-yl]propanoate

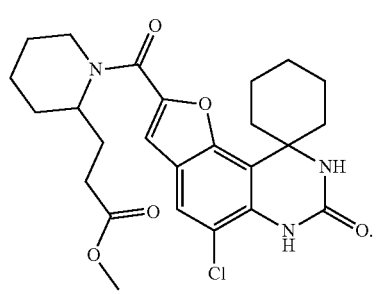

[M+H] = 488.5

Example 459. 5'-Chloro-2'-(4-cyclopentylpiperazine-1-carbonyl)-7',8'-dihydro-6'H-spiro[cyclohexane-1,9'-furo[2,3-f]quinazoline]-7'-one

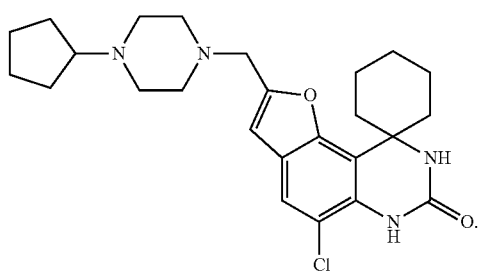

[M+H] = 471.5

Example 460. 5'-Chloro-2'-[4-(2-methylpropanoyl)piperazine-1-carbonyl]-7',8'-dihydro-6'H-spiro[cyclohexane-1,9'-furo[2,3-f]quinazoline]-7'-one

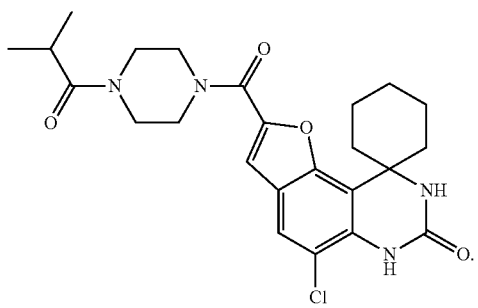

[M+H] = 473.5

Example 461. N-Benzyl-5'-chloro-N-(3-hydroxypropyl)-7'-oxo-7',8'-dihydro-6'H-spiro[cyclohexane-1,9'-furo[2,3-f]quinazoline]-2'-carboxamide

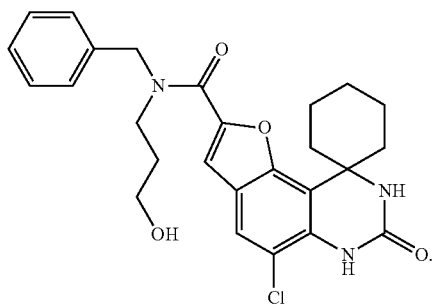

[M+H] = 482.4

Example 462. 5'-Chloro-N-(2-methoxyethyl)-7'-oxo-N-(thiophen-2-ylmethyl)-7',8'-dihydro-6'H-spiro[cyclohexane-1,9'-furo[2,3-f]quinazoline]-2'-carboxamide

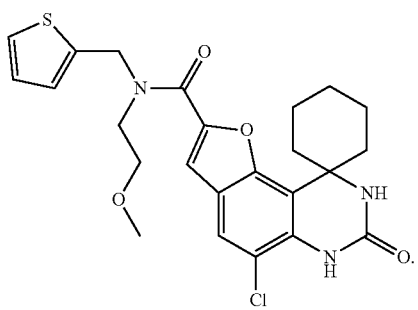

[M+H] = 488.5

Example 463. 5'-Chloro-N-[2-(dimethylamino)ethyl]-7'-oxo-7',8'-dihydro-6'H-spiro[cyclohexane-1,9'-furo[2,3-f]quinazoline]-2'-carboxamide

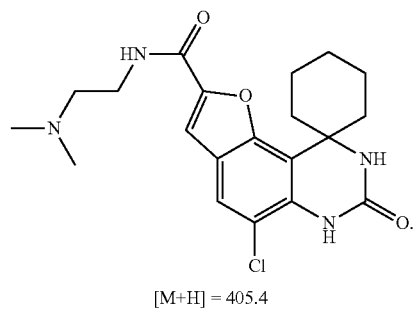 [SMILES: CN(C)CCNC(=O)c1cc2cc(Cl)c3c(c2o1)C1(CCCCC1)NC(=O)N3]

[M+H] = 405.4

Example 464. 5'-Chloro-2'-{5H,6H,7H-pyrrolo[3,4-b]pyridine-6-carbonyl}-7',8'-dihydro-6'H-spiro[cyclohexane-1,9'-furo[2,3-f]quinazoline]-7'-one

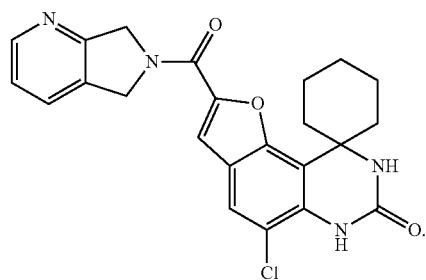

[M+H] = 437.4

Example 465. 5'-Chloro-N-cyclohexyl-N-(2-hydroxyethyl)-7'-oxo-7',8'-dihydro-6'H-spiro[cyclohexane-1,9'-furo[2,3-f]quinazoline]-2'-carboxamide

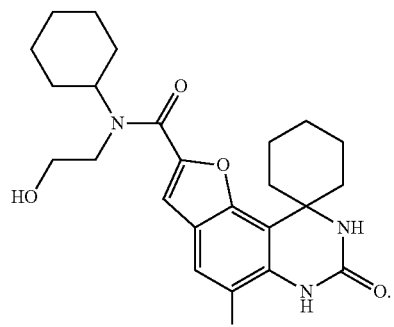

[M+H] = 460.5

Example 466. 5'-Chloro-N-[2-(dimethyl-1,3-thiazol-2-yl)ethyl]-7'-oxo-7',8'-dihydro-6'H-spiro[cyclohexane-1,9'-furo[2,3-f]quinazoline]-2'-carboxamide

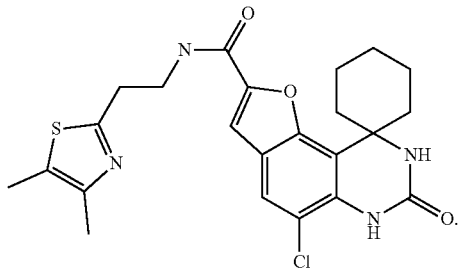

[M+H] = 473.4

Example 467.-Example 572. were prepared in a manner analogous to Example 30, with the appropriate starting material substitutions.

Example 467. 5'-Chloro-2'-({[(3R,4R)-3-methoxyoxan-4-yl]amino}methyl)-7',8'-dihydro-6'H-spiro[cyclohexane-1,9'-furo[2,3-f]quinazoline]-7'-one

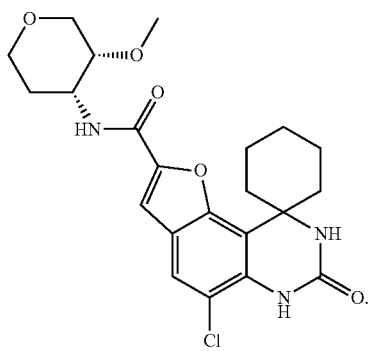

[M+H] = 434.2

Example 468. 5'-Chloro-2'-{[2-(2-hydroxyethyl)piperidin-1-yl]methyl}-7',8'-dihydro-6'H-spiro[cyclohexane-1,9'-furo[2,3-f]quinazoline]-7'-one

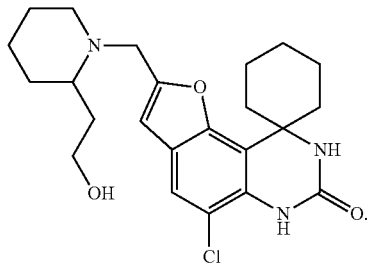

[M+H] = 432.2

Example 469. 5'-Chloro-2'-[(3-oxopiperazin-1-yl)methyl]-7',8'-dihydro-6'H-spiro[cyclohexane-1,9'-furo[2,3-f]quinazoline]-7'-one

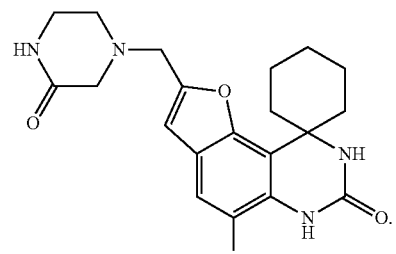

[M+H] = 403.2

Example 470. 5'-Chloro-2'-({[(1-methyl-1H-pyrazol-3-yl)methyl]amino}methyl)-7',8'-dihydro-6'H-spiro[cyclohexane-1,9'-furo[2,3-f]quinazoline]-7'-one

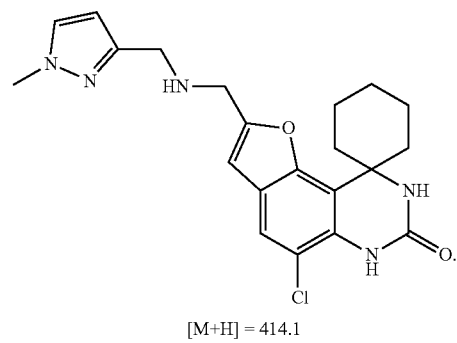 [SMILES: Cn1ccc(CNCc2cc3cc(Cl)c4c(c3o2)C2(CCCCC2)NC(=O)N4)n1]

[M+H] = 414.1

Example 471. 5'-Chloro-2'-{[(2-methoxyethyl)(propan-2-yl)amino]methyl}-7',8'-dihydro-6'H-spiro[cyclohexane-1,9'-furo[2,3-f]quinazoline]-7'-one

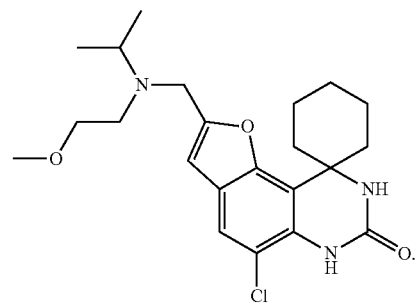

[M + H] = 420.2

Example 472. 1-{5'-Chloro-7'-oxo-7',8'-dihydro-6'H-spiro[cyclohexane-1,9'-furo[2,3-f]quinazoline]-2'-ylmethyl}piperidine-4-carbonitrile

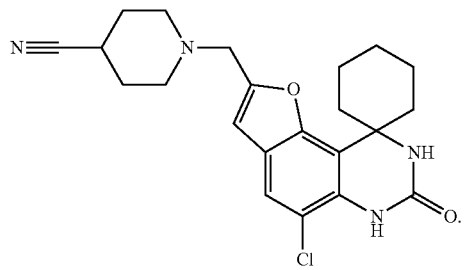

[M + H] = 413.2

Example 473. 5'-Chloro-2'-{[(2-hydroxyethyl)(propan-2-yl)amino]methyl}-7',8'-dihydro-6'H-spiro[cyclohexane-1,9'-furo[2,3-f]quinazoline]-7'-one

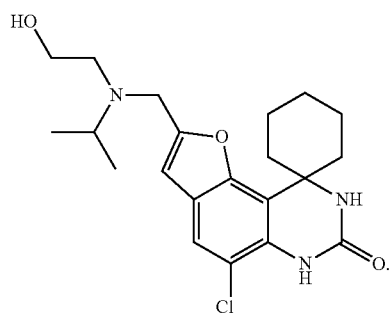

[M + H] = 406.2

Example 474. 5'-Chloro-2'-{[4-(pyridin-4-yl)piperazin-1-yl]methyl}-7',8'-dihydro-6'H-spiro[cyclohexane-1,9'-furo[2,3-f]quinazoline]-7'-one

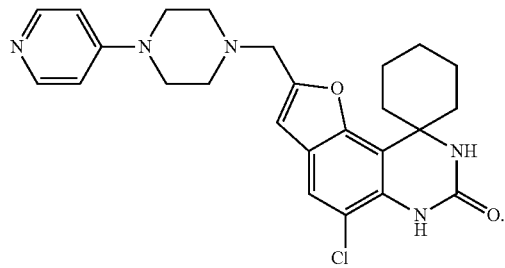

[M + H] = 466.2

Example 475. 5'-Chloro-2'-({[2-(1H-pyrazol-1-yl)ethyl]amino}methyl)-7',8'-dihydro-6'H-spiro[cyclohexane-1,9'-furo[2,3-f]quinazoline]-7'-one

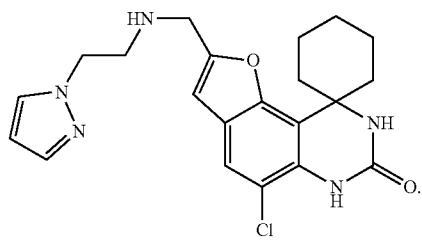

[M + H] = 414.3

Example 476. 5'-Chloro-2'-{[(oxan-4-yl)amino]methyl}-7',8'-dihydro-6'H-spiro[cyclohexane-1,9'-furo[2,3-f]quinazoline]-7'-one

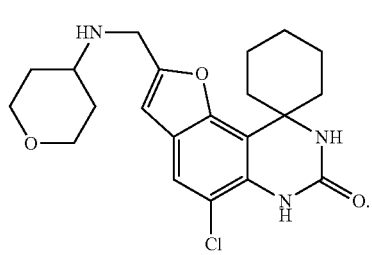

[M + H] = 404.2

Example 477. 2'-[(8aS)-Octahydropyrrolo[1,2-a]piperazin-2-ylmethyl]-5'-chloro-7',8'-dihydro-6'H-spiro[cyclohexane-1,9'-furo[2,3-f]quinazoline]-7'-one

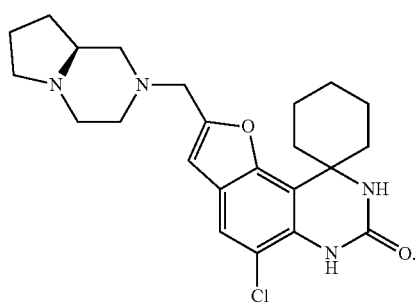

[M + H] = 492.2

Example 478. 5'-Chloro-2'-{[(oxolan-2-ylmethyl)amino]methyl}-7',8'-dihydro-6'H-spiro[cyclohexane-1,9'-furo[2,3-f]quinazoline]-7'-one

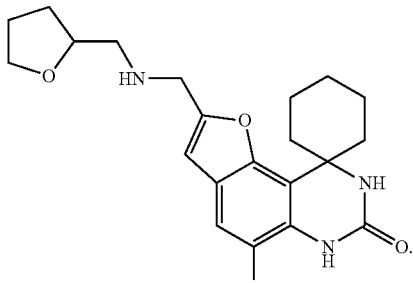

[M + H] = 404.1

Example 479. 3-({5'-Chloro-7'-oxo-7',8'-dihydro-6'H-spiro[cyclohexane-1,9'-furo[2,3-f]quinazoline]-2'-ylmethyl}(ethyl)amino)propanenitrile

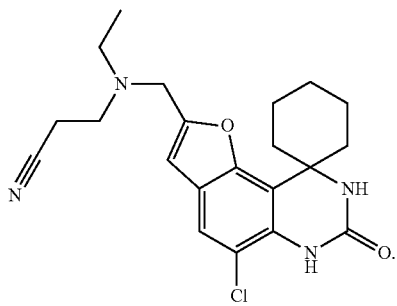

[M + H] = 401.2

Example 480. 5'-Chloro-2'-{[(pyridin-2-ylmethyl)amino]methyl}-7',8'-dihydro-6'H-spiro[cyclohexane-1,9'-furo[2,3-f]quinazoline]-7'-one

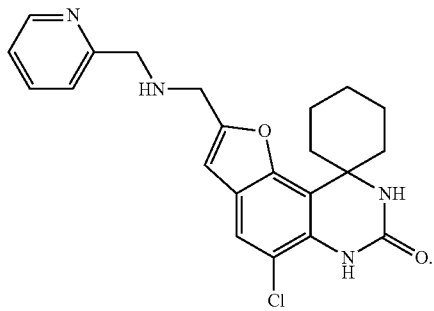

[M + H] = 411.2

Example 481. 5'-Chloro-2'-{[2-(hydroxymethyl)pyrrolidin-1-yl]methyl}-7',8'-dihydro-6'H-spiro[cyclohexane-1,9'-furo[2,3-f]quinazoline]-7'-one

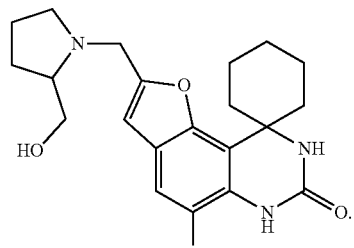

[M + H] = 404.2

Example 482. 5'-Chloro-2'-{[(2-methanesulfonylethyl)amino]methyl}-7',8'-dihydro-6'H-spiro[cyclohexane-1,9'-furo[2,3-f]quinazoline]-7'-one

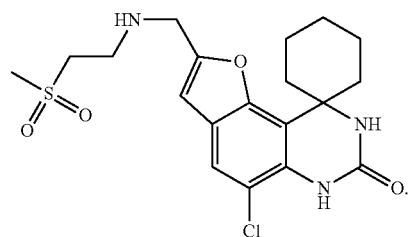

[M + H] = 426.2

Example 483. 2'-{[Benzyl(2-hydroxyethyl)amino]methyl}-5'-chloro-7',8'-dihydro-6'H-spiro[cyclohexane-1,9'-furo[2,3-f]quinazoline]-7'-one

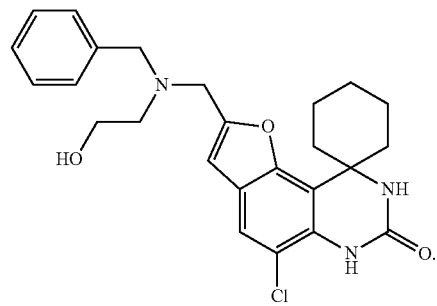

[M + H] = 454.2

Example 484. 5'-Chloro-2'-{[(furan-2-ylmethyl)(methyl)amino]methyl}-7',8'-dihydro-6'H-spiro[cyclohexane-1,9'-furo[2,3-f]quinazoline]-7'-one

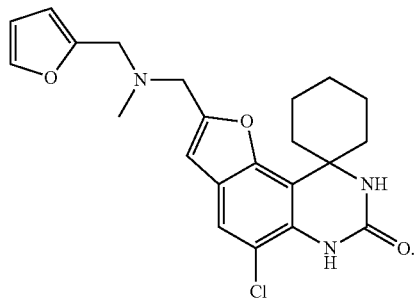

[M + H] = 414.2

Example 485. 5'-Chloro-2'-[(4-methoxypiperidin-1-yl)methyl]-7',8'-dihydro-6'H-spiro[cyclohexane-1,9'-furo[2,3-f]quinazoline]-7'-one

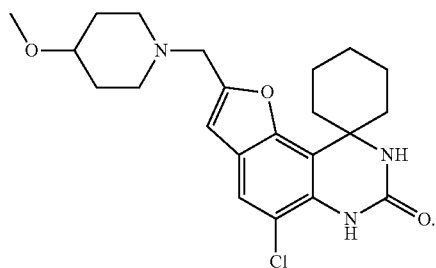

[M + H] = 418.1

Example 486. 2'-[(4-Acetyl-1,4-diazepan-1-yl)methyl]-5'-chloro-7',8'-dihydro-6'H-spiro[cyclohexane-1,9'-furo[2,3-f]quinazoline]-7'-one

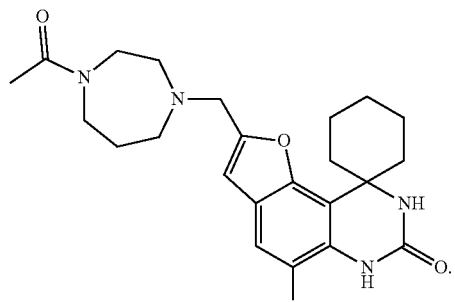

[M + H] = 445.2

Example 487. 5'-Chloro-2'-{[4-(2-hydroxyethyl)piperazin-1-yl]methyl}-7',8'-dihydro-6'H-spiro[cyclohexane-1,9'-furo[2,3-f]quinazoline]-7'-one

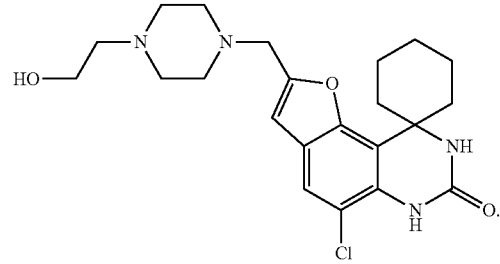

[M + H] = 433.2

Example 488. 5'-Chloro-2'-({4-[(dimethylamino)methyl]piperidin-1-yl}methyl)-7',8'-dihydro-6'H-spiro[cyclohexane-1,9'-furo[2,3-f]quinazoline]-7'-one

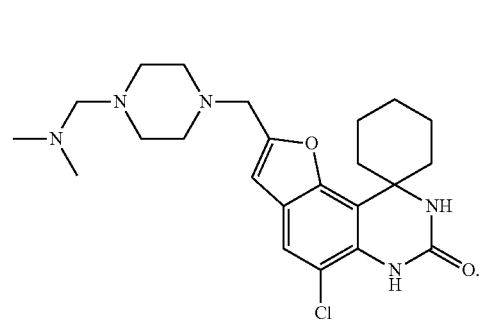

[M + H] = 445.2

Example 489. 5'-Chloro-2'-{[4-(oxolane-2-carbonyl)piperazin-1-yl]methyl}-7',8'-dihydro-6'H-spiro[cyclohexane-1,9'-furo[2,3-f]quinazoline]-7'-one

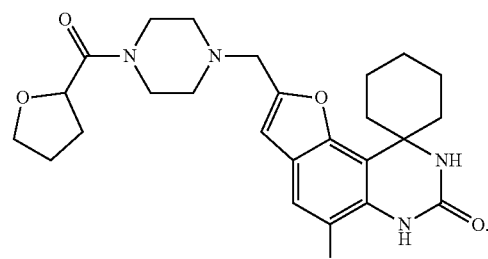

[M + H] = 487.2

Example 490. 5'-Chloro-2'-({[(5-oxopyrrolidin-2-yl)methyl](propan-2-yl)amino}methyl)-7',8'-dihydro-6'H-spiro[cyclohexane-1,9'-furo[2,3-f]quinazoline]-7'-one

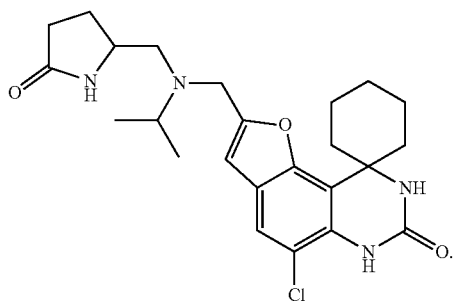

[M + H] = 459.2

Example 491. 5'-Chloro-2'-{5H,6H,7H,8H-imidazo[1,2-a]pyrazin-7-ylmethyl}-7',8'-dihydro-6'H-spiro[cyclohexane-1,9'-furo[2,3-f]quinazoline]-7'-one

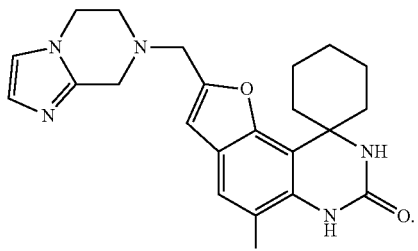

[M + H] = 426.2

Example 492. 5'-Chloro-2'-({[3-(2-oxopyrrolidin-1-yl)propyl]amino}methyl)-7',8'-dihydro-6'H-spiro[cyclohexane-1,9'-furo[2,3-f]quinazoline]-7'-one

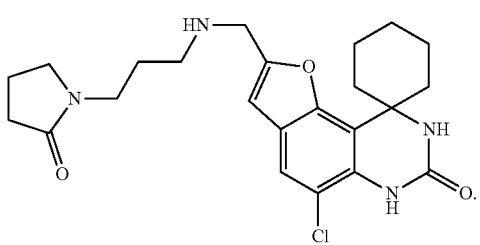

[M + H] = 445.2

Example 493. 1-{5'-Chloro-7'-oxo-7',8'-dihydro-6'H-spiro[cyclohexane-1,9'-furo[2,3-f]quinazoline]-2'-ylmethyl}-N-methylpiperidine-4-carboxamide

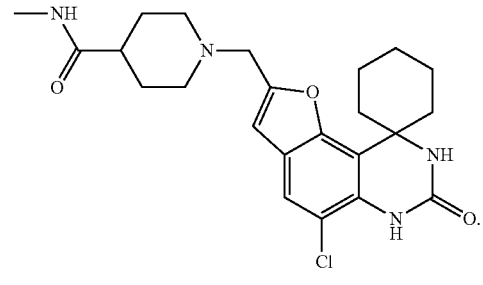

[M + H] = 445.4

Example 494. 5'-Chloro-2'-{[(3-hydroxypropyl)(methyl)amino]methyl}-7',8'-dihydro-6'H-spiro[cyclohexane-1,9'-furo[2,3-f]quinazoline]-7'-one

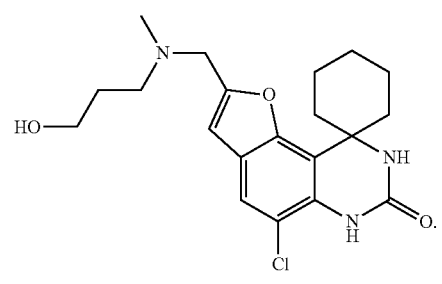

[M + H] = 392.2

Example 495. 5'-Chloro-2'-[(4-hydroxy-4-phenylpiperidin-1-yl)methyl]-7',8'-dihydro-6'H-spiro[cyclohexane-1,9'-furo[2,3-f]quinazoline]-7'-one

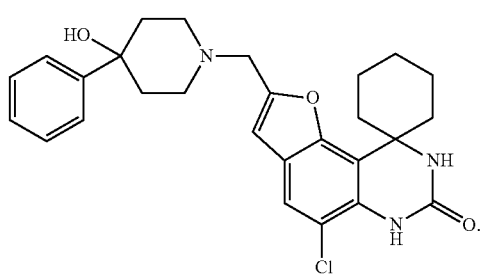

[M + H] = 480.2

Example 496. 1-{5'-Chloro-7'-oxo-7',8'-dihydro-6'H-spiro[cyclohexane-1,9'-furo[2,3-f]quinazoline]-2'-ylmethyl}piperidine-3-carboxamide

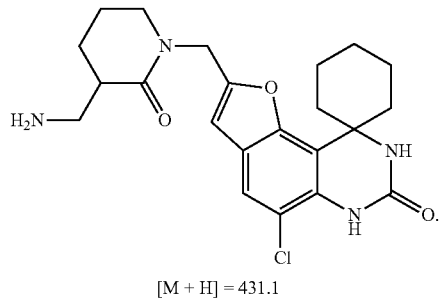 [SMILES: NCC1CCCN(Cc2cc3cc(Cl)c4c(c3o2)C2(CCCCC2)NC(=O)N4)C1=O]

[M + H] = 431.1

Example 497. 3-({5'-Chloro-7'-oxo-7',8'-dihydro-6'H-spiro[cyclohexane-1,9'-furo[2,3-f]quinazoline]-2'-ylmethyl}(methyl)amino)-N-methylpropanamide

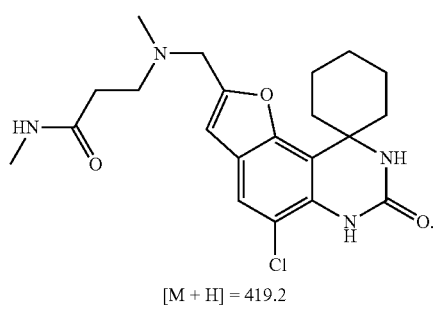 [SMILES: CNC(=O)CCN(C)Cc1cc2cc(Cl)c3c(c2o1)C1(CCCCC1)NC(=O)N3]

[M + H] = 419.2

Example 498. 5'-Chloro-2'-{[(1R,5S,6S)-6-(hydroxymethyl)-3-azabicyclo[3.1.0]hexan-3-yl]methyl}-7',8'-dihydro-6'H-spiro[cyclohexane-1,9'-furo[2,3-f]quinazoline]-7'-one

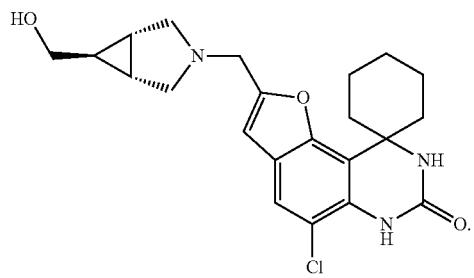

[M + H] = 416.2

Example 499. 5'-Chloro-2'-{[ethyl(2-hydroxyethyl)amino]methyl}-7',8'-dihydro-6'H-spiro[cyclohexane-1,9'-furo[2,3-f]quinazoline]-7'-one

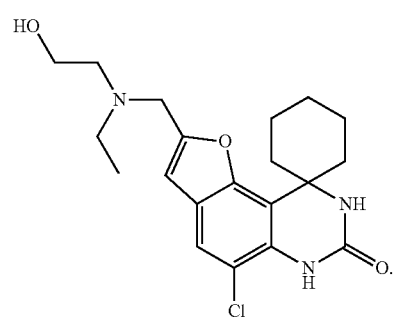

[M + H] = 392.2

Example 500. 5'-Chloro-2'-{[(2-hydroxyethyl)(methyl)amino]methyl}-7',8'-dihydro-6'H-spiro[cyclohexane-1,9'-furo[2,3-f]quinazoline]-7'-one

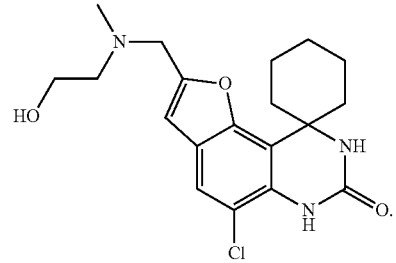

[M + H] = 378.2

Example 501. 5'-Chloro-2'-{(3-hydroxypiperidin-1-yl)methyl}-7',8'-dihydro-6'H-spiro[cyclohexane-1,9'-furo[2,3-f]quinazoline]-7'-one

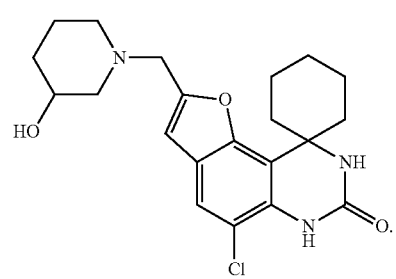

[M + H] = 404.2

Example 502. 5'-Chloro-2'-{[4-(2-hydroxyethyl)piperidin-1-yl]methyl}-7',8'-dihydro-6'H-spiro[cyclohexane-1,9'-furo[2,3-f]quinazoline]-7'-one

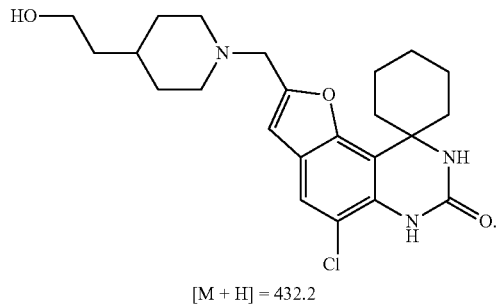 [SMILES: O=C1Nc2c(Cl)cc3cc(CN4CCC(CCO)CC4)oc3c2C2(CCCCC2)N1]

[M + H] = 432.2

Example 503. 5'-Chloro-2'-{[(2R,6S)-2,6-dimethylmorpholin-4-yl]methyl}-7',8'-dihydro-6'H-spiro[cyclohexane-1,9'-furo[2,3-f]quinazoline]-7'-one

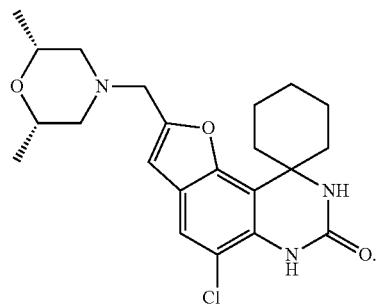

[M + H] = 418.3

Example 504. 5'-Chloro-2'-({[(4-ethyl-4H-1,2,4-triazol-3-yl)methyl](methyl)amino}methyl)-7',8'-dihydro-6'H-spiro[cyclohexane-1,9'-furo[2,3-f]quinazoline]-7'-one

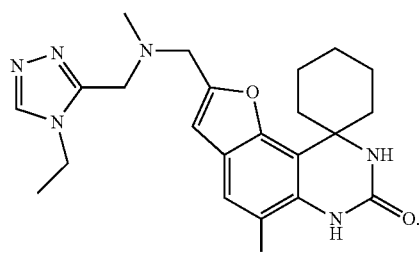

[M + H] = 443.2

Example 505. 5'-Chloro-2'-{2-oxa-6-azaspiro[3.5]nonan-6-ylmethyl}-7',8'-dihydro-6'H-spiro[cyclohexane-1,9'-furo[2,3-f]quinazoline]-7'-one

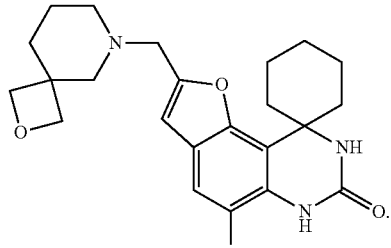

[M + H] = 430.2

Example 506. 5'-Chloro-2'-{[ethyl(propan-2-yl)amino]methyl}-7',8'-dihydro-6'H-spiro[cyclohexane-1,9'-furo[2,3-f]quinazoline]-7'-one

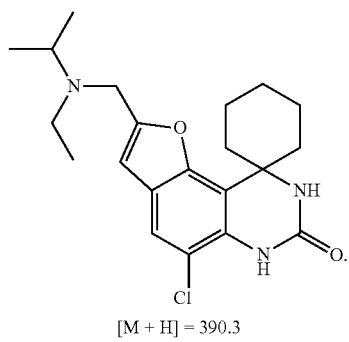 [SMILES: CCN(Cc1cc2cc(Cl)c3c(c2o1)C1(CCCCC1)NC(=O)N3)C(C)C]

[M + H] = 390.3

Example 507. 5'-Chloro-2'-({[(5-cyclopropyl-1H-pyrazol-3-yl)methyl](methyl)amino}methyl)-7',8'-dihydro-6'H-spiro[cyclohexane-1,9'-furo[2,3-f]quinazoline]-7'-one

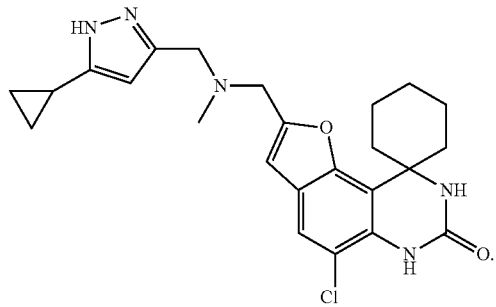

[M + H] = 454.2

Example 508. 5'-Chloro-2'-({[3-(dimethylamino)propyl](methyl)amino}methyl)-7',8'-dihydro-6'H-spiro[cyclohexane-1,9'-furo[2,3-f]quinazoline]-7'-one

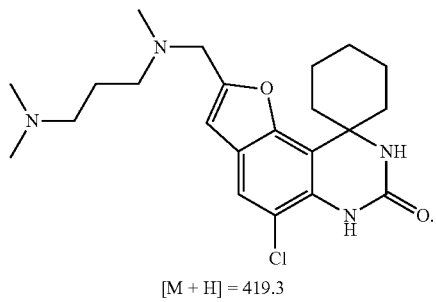 [SMILES: CN(C)CCCN(C)Cc1cc2cc(Cl)c3c(c2o1)C1(CCCCC1)NC(=O)N3]

[M + H] = 419.3

Example 509. 5'-Chloro-2'-{[3-(dimethylamino)pyrrolidin-1-yl]methyl}-7',8'-dihydro-6'H-spiro[cyclohexane-1,9'-furo[2,3-f]quinazoline]-7'-one

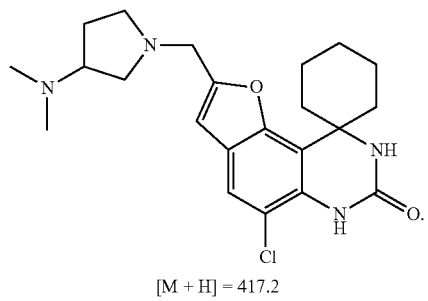 [SMILES: CN(C)C1CCN(Cc2cc3cc(Cl)c4c(c3o2)C2(CCCCC2)NC(=O)N4)C1]

[M + H] = 417.2

Example 510. 2-(4-{5'-Chloro-7'-oxo-7',8'-dihydro-6'H-spiro[cyclohexane-1,9'-furo[2,3-f]quinazoline]-2'-ylmethyl}piperazin-1-yl)pyridine-3-carbonitrile

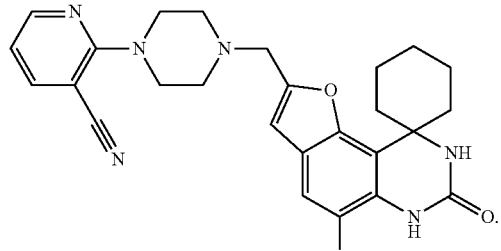

[M + H] = 491.2

Example 511. 5'-Chloro-2'-{[3-(1H-imidazol-1-ylmethyl)piperidin-1-yl]methyl}-7',8'-dihydro-6'H-spiro[cyclohexane-1,9'-furo[2,3-f]quinazoline]-7'-one

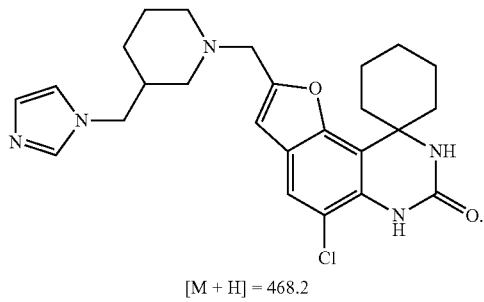 [SMILES: O=C1Nc2c(Cl)cc3cc(CN4CCCC(Cn5ccnc5)C4)oc3c2C2(CCCCC2)N1]

[M + H] = 468.2

Example 512. 5'-Chloro-2'-{[4-hydroxy-4-(thiophen-2-yl)piperidin-1-yl]methyl}-7',8'-dihydro-6'H-spiro[cyclohexane-1,9'-furo[2,3-f]quinazoline]-7'-one

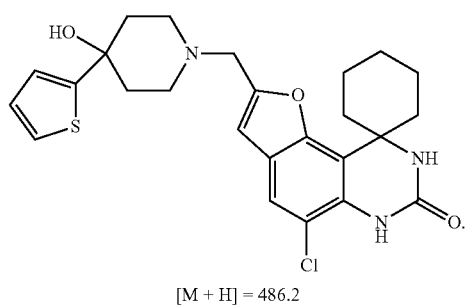 [SMILES: O=C1Nc2c(Cl)cc3cc(CN4CCC(O)(c5cccs5)CC4)oc3c2C2(CCCCC2)N1]

[M + H] = 486.2

Example 513. 5'-Chloro-2'-{[4-(2-methoxyethyl)piperazin-1-yl]methyl}-7',8'-dihydro-6'H-spiro[cyclohexane-1,9'-furo[2,3-f]quinazoline]-7'-one

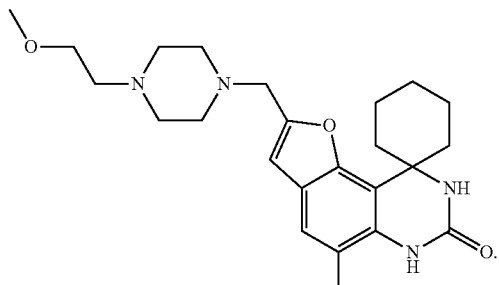

[M + H] = 447.2

Example 514. 5'-Chloro-2'-{[methyl(pyridin-3-ylmethyl)amino]methyl}-7',8'-dihydro-6'H-spiro[cyclohexane-1,9'-furo[2,3-f]quinazoline]-7'-one

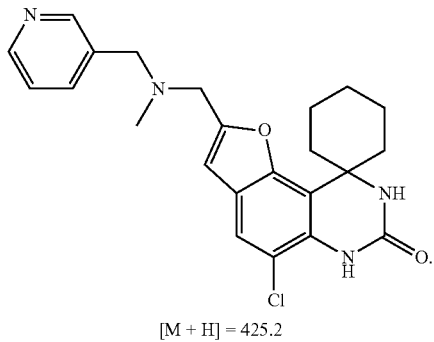 [SMILES: CN(Cc1cccnc1)Cc1cc2cc(Cl)c3c(c2o1)C1(CCCCC1)NC(=O)N3]

[M + H] = 425.2

Example 515. 4-{5'-Chloro-7'-oxo-7',8'-dihydro-6'H-spiro[cyclohexane-1,9'-furo[2,3-f]quinazoline]-2'-ylmethyl}-thiomorpholine-1,1-dione

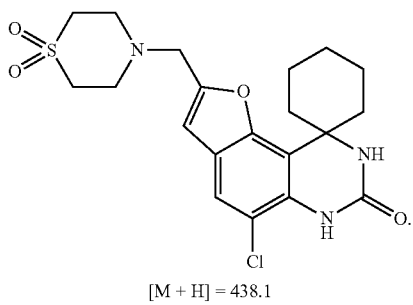 [SMILES: O=C1Nc2c(Cl)cc3cc(CN4CCS(=O)(=O)CC4)oc3c2C2(CCCCC2)N1]

[M + H] = 438.1

Example 516. 5'-Chloro-2'-{[(4-hydroxy-2-methylbutan-2-yl)amino]methyl}-7',8'-dihydro-6'H-spiro[cyclohexane-1,9'-furo[2,3-f]quinazoline]-7'-one

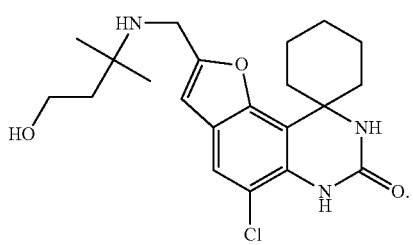

[M + H] = 406.2

Example 517. 4-{5'-Chloro-7'-oxo-7',8'-dihydro-6'H-spiro[cyclohexane-1,9'-furo[2,3-f]quinazoline]-2'-ylmethyl}piperazine-1-carbaldehyde

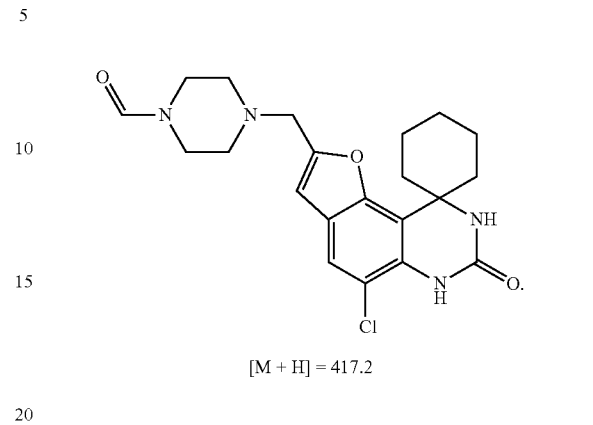

[M + H] = 417.2

Example 518. 5'-Chloro-2'-{[4-(morpholin-4-yl)piperidin-1-yl]methyl}-7',8'-dihydro-6'H-spiro[cyclohexane-1,9'-furo[2,3-f]quinazoline]-7'-one

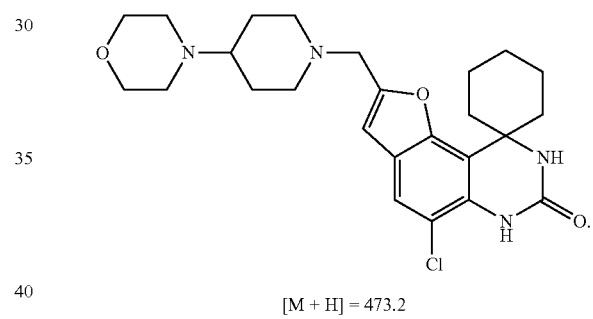

[M + H] = 473.2

Example 519. 4-{5'-Chloro-7'-oxo-7',8'-dihydro-6'H-spiro[cyclohexane-1,9'-furo[2,3-f]quinazoline]-2'-ylmethyl}-N,N-dimethylpiperazine-1-carboxamide

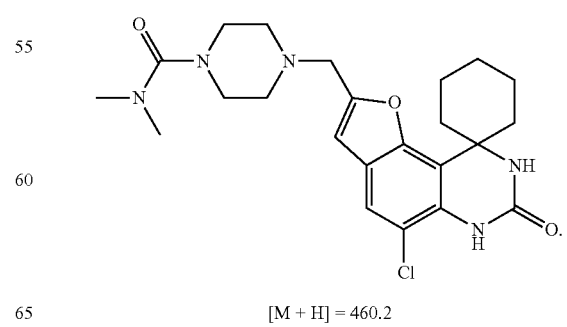

[M + H] = 460.2

Example 520. 5'-Chloro-2'-[({[4-(propan-2-yl)-4H-1,2,4-triazol-3-yl]methyl}amino)methyl]-7',8'-dihydro-6'H-spiro[cyclohexane-1,9'-furo[2,3-f]quinazoline]-7'-one

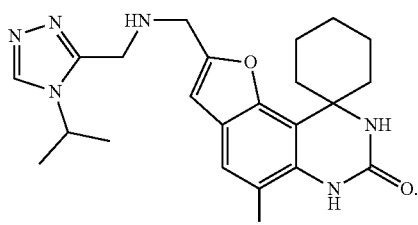

[M + H] = 443.1

Example 521. 5'-Chloro-2'-{[3-(trifluoromethyl)-5H,6H,7H,8H-[1,2,4]triazolo[4,3-a]pyrazin-7-yl]methyl}-7',8'-dihydro-6'H-spiro[cyclohexane-1,9'-furo[2,3-f]quinazoline]-7'-one

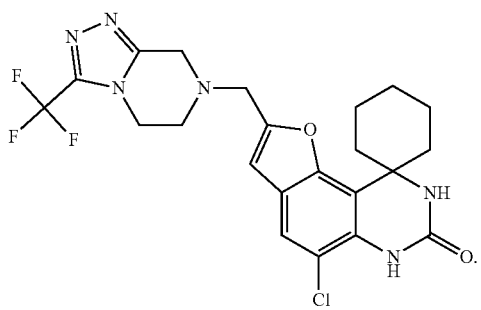

[M + H] = 495.1

Example 522. 1-{5'-Chloro-7'-oxo-7',8'-dihydro-6'H-spiro[cyclohexane-1,9'-furo[2,3-f]quinazoline]-2'-ylmethyl}azetidine-3-carbonitrile

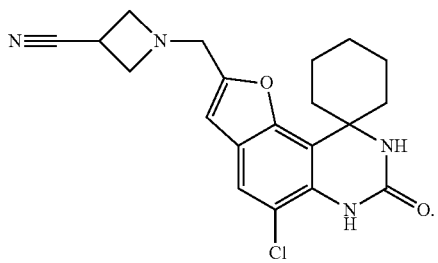

[M + H] = 385.1

Example 523. 4-({5'-Chloro-7'-oxo-7',8'-dihydro-6'H-spiro[cyclohexane-1,9'-furo[2,3-f]quinazoline]-2'-ylmethyl}amino)-thiane-1,1-dione

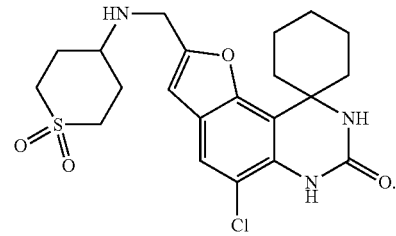

[M + H] = 452.1

Example 524. 5'-Chloro-2'-[(4-methanesulfonylpiperazin-1-yl)methyl]-7',8'-dihydro-6'H-spiro[cyclohexane-1,9'-furo[2,3-f]quinazoline]-7'-one

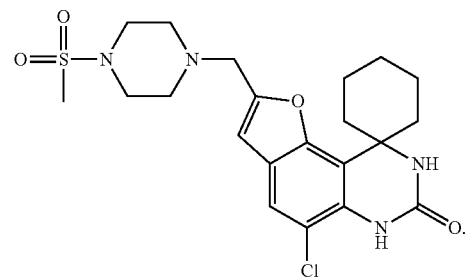

[M + H] = 466.8

Example 525. Ethyl 7-{5'-chloro-7'-oxo-7',8'-dihydro-6'H-spiro[cyclohexane-1,9'-furo[2,3-f]quinazoline]-2'-ylmethyl}-5H,6H,7H,8H-imidazo[1,2-a]pyrazine-2-carboxylate

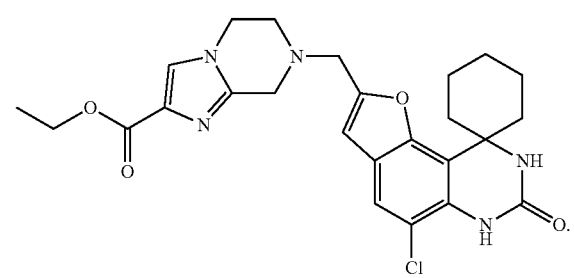

[M + H] = 498.2

Example 526. 2'-{6-Azaspiro[2.5]octan-6-ylmethyl}-5'-chloro-7',8'-dihydro-6'H-spiro[cyclohexane-1,9'-furo[2,3-f]quinazoline]-7'-one

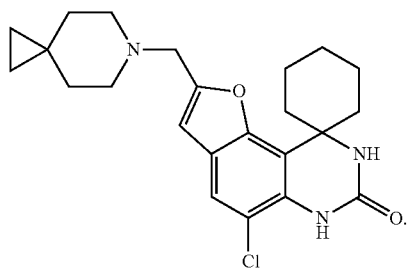

[M + H] = 414.2

Example 527. 5'-Chloro-2'-{[(2,2,2-trifluoroethyl)amino]methyl}-7',8'-dihydro-6'H-spiro[cyclohexane-1,9'-furo[2,3-f]quinazoline]-7'-one

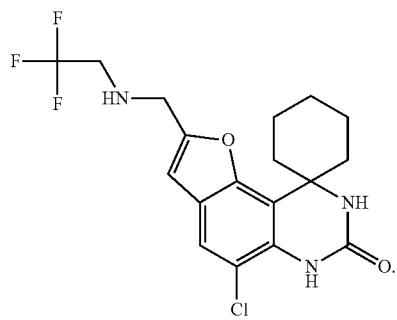

[M + H] = 402.2

Example 528. 5'-Chloro-2'-{octahydropyrrolo[1,2-a]piperazin-2-ylmethyl}-7',8'-dihydro-6'H-spiro[cyclohexane-1,9'-furo[2,3-f]quinazoline]-7'-one

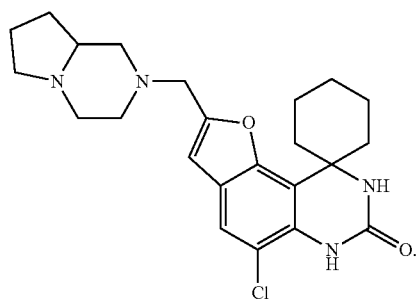

[M + H] = 429.3

Example 529. 5'-Chloro-2'-{[4-(furan-2-ylmethyl)piperazin-1-yl]methyl}-7',8'-dihydro-6'H-spiro[cyclohexane-1,9'-furo[2,3-f]quinazoline]-7'-one

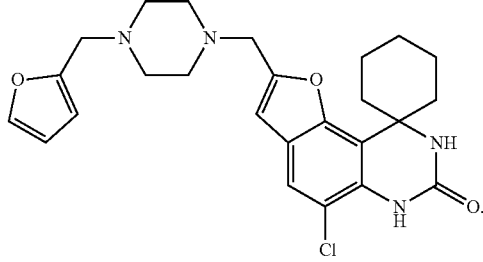

[M + H] = 469.2

Example 530. 5'-Chloro-2'-{[methyl(propan-2-yl)amino]methyl}-7',8'-dihydro-6'H-spiro[cyclohexane-1,9'-furo[2,3-f]quinazoline]-7'-one

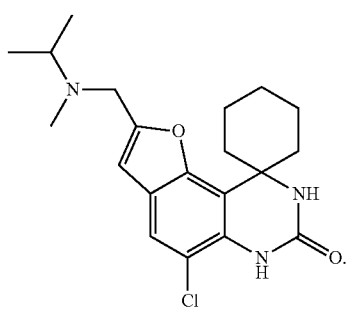

[M + H] = 376.5

Example 531. 3-({5'-Chloro-7'-oxo-7',8'-dihydro-6'H-spiro[cyclohexane-1,9'-furo[2,3-f]quinazoline]-2'-ylmethyl}amino)-thiolane-1,1-dione

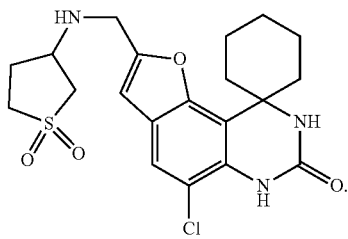

[M + H] = 438.1

Example 532. 5'-Chloro-2'-{[4-(pyridin-3-ylmethyl)piperazin-1-yl]methyl}-7',8'-dihydro-6'H-spiro[cyclohexane-1,9'-furo[2,3-f]quinazoline]-7'-one

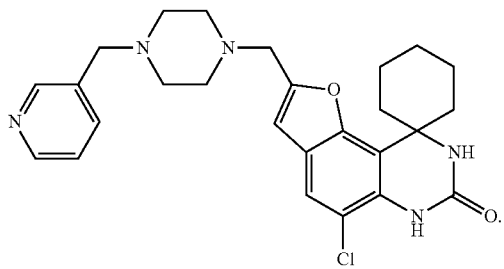

[M + H] = 480.5

Example 533. 5'-Chloro-2'-[(4-methyl-1,4-diazepan-1-yl)methyl]-7',8'-dihydro-6'H-spiro[cyclohexane-1,9'-furo[2,3-f]quinazoline]-7'-one

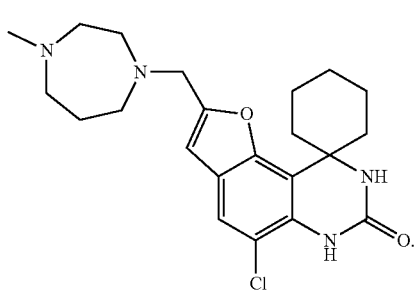

[M + H] = 417.2

Example 534. 5'-Chloro-2'-{[4-(dimethylamino)piperidin-1-yl]methyl}-7',8'-dihydro-6'H-spiro[cyclohexane-1,9'-furo[2,3-f]quinazoline]-7'-one

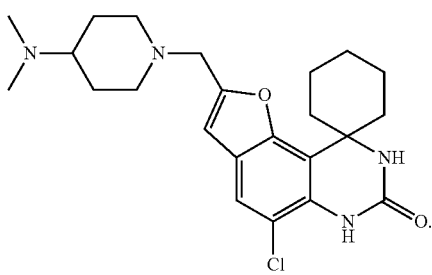

[M + H] = 431.2

Example 535. 5'-Chloro-2'-({methyl[(trimethyl-1H-pyrazol-4-yl)methyl]amino}methyl)-7',8'-dihydro-6'H-spiro[cyclohexane-1,9'-furo[2,3-f]quinazoline]-7'-one

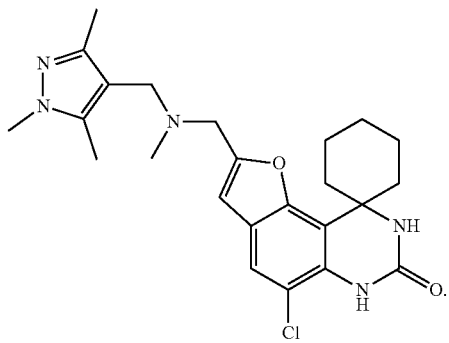

[M + H] = 456.2

Example 536. 5'-Chloro-2'-{[3-oxo-4-(propan-2-yl)piperazin-1-yl]methyl}-7',8'-dihydro-6'H-spiro[cyclohexane-1,9'-furo[2,3-f]quinazoline]-7'-one

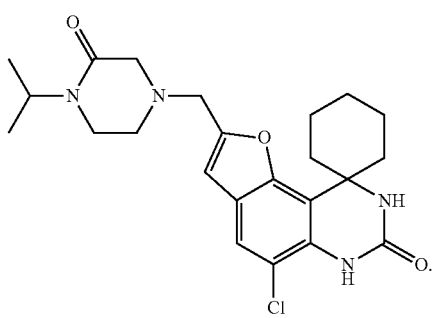

[M + H] = 445.2

Example 537. 5'-Chloro-2'-{[[(2,2-dimethyloxan-4-yl)(ethyl)amino]methyl}-7',8'-dihydro-6'H-spiro[cyclohexane-1,9'-furo[2,3-f]quinazoline]-7'-one

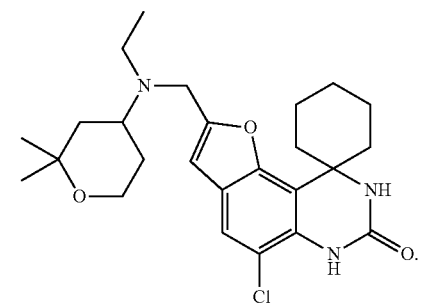

[M + H] = 460.2

Example 538. 5'-Chloro-2'-{[4-(pyrrolidine-1-carbonyl)piperazin-1-yl]methyl}-7',8'-dihydro-6'H-spiro[cyclohexane-1,9'-furo[2,3-f]quinazoline]-7'-one

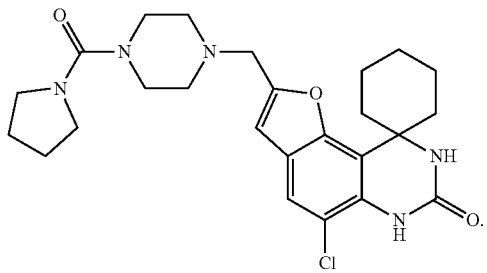

[M + H] = 486.2

Example 539. 5'-Chloro-2'-{[(1,3-oxazol-5-ylmethyl)amino]methyl}-7',8'-dihydro-6'H-spiro[cyclohexane-1,9'-furo[2,3-f]quinazoline]-7'-one

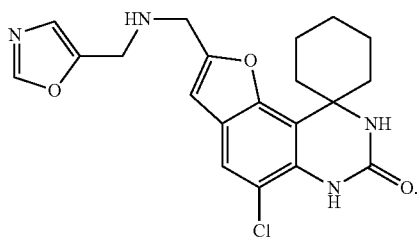

[M + H] = 401.1

Example 540. 5'-Chloro-2'-[(propylamino)methyl]-7',8'-dihydro-6'H-spiro[cyclohexane-1,9'-furo[2,3-f]quinazoline]-7'-one

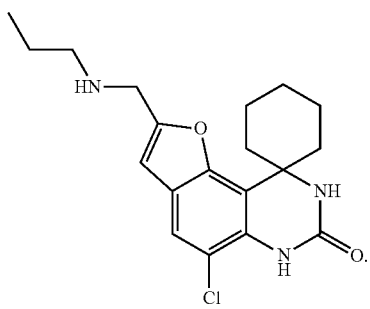

[M + H] = 362.2

Example 541. 5'-Chloro-2'-({[(1-methyl-1H-pyrazol-5-yl)methyl]amino}methyl)-7',8'-dihydro-6'H-spiro[cyclohexane-1,9'-furo[2,3-f]quinazoline]-7'-one

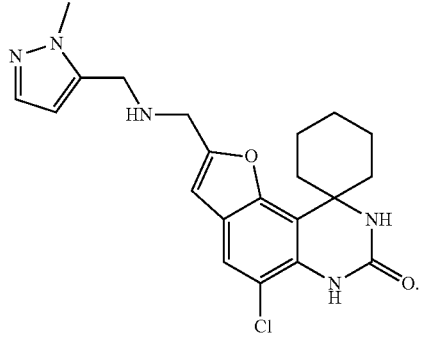

[M + H] = 414.2

Example 542. 5'-Chloro-2'-{[4-(oxetan-3-yl)piperazin-1-yl]methyl}-7',8'-dihydro-6'H-spiro[cyclohexane-1,9'-furo[2,3-f]quinazoline]-7'-one

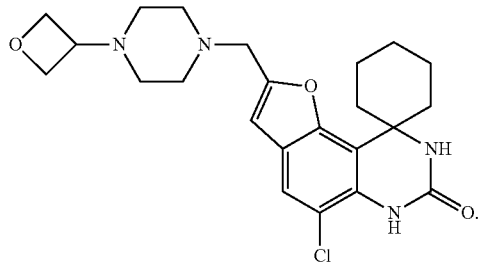

[M + H] = 445.2

Example 543. 5'-Chloro-2'-({methyl[2-(pyridin-2-yl)ethyl]amino}methyl)-7',8'-dihydro-6'H-spiro[cyclohexane-1,9'-furo[2,3-f]quinazoline]-7'-one

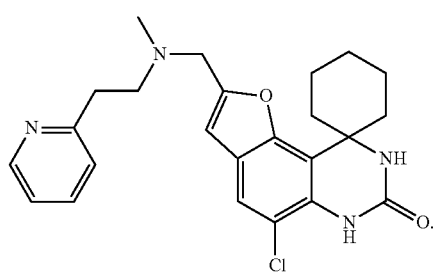

[M + H] = 439.2

Example 544. 5'-Chloro-2'-{[(2-methoxyethyl)(methyl)amino]methyl}-7',8'-dihydro-6'H-spiro[cyclohexane-1,9'-furo[2,3-f]quinazoline]-7'-one

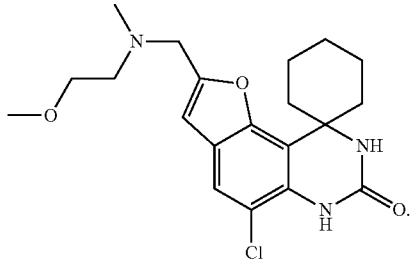

[M + H] = 392.2

Example 545. 5'-Chloro-2'-{5H,6H,7H-pyrrolo[3,4-b]pyridin-6-ylmethyl}-7',8'-dihydro-6'H-spiro[cyclohexane-1,9'-furo[2,3-f]quinazoline]-7'-one

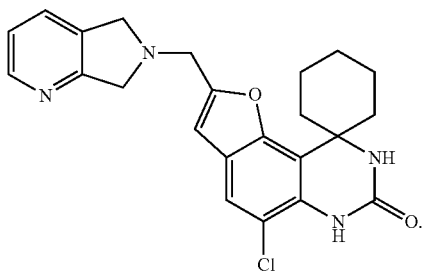

[M + H] = 423.2

Example 546. 5'-Chloro-2'-({[2-(3,5-dimethyl-1H-pyrazol-4-yl)ethyl](methyl)amino}methyl)-7',8'-dihydro-6'H-spiro[cyclohexane-1,9'-furo[2,3-f]quinazoline]-7'-one

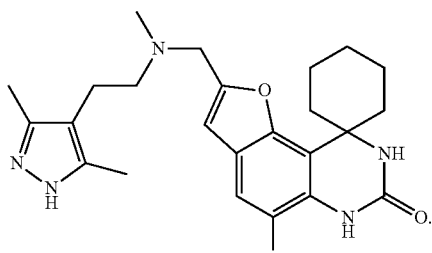

[M + H] = 456.2

Example 547. 5'-Chloro-2'-({[2-(dimethylamino)ethyl](ethyl)amino}methyl)-7',8'-dihydro-6'H-spiro[cyclohexane-1,9'-furo[2,3-f]quinazoline]-7'-one

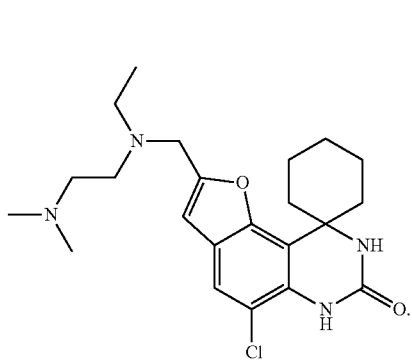

[M + H] = 419.2

Example 548. 5'-Chloro-2'-[(3-hydroxypyrrolidin-1-yl)methyl]-7',8'-dihydro-6'H-spiro[cyclohexane-1,9'-furo[2,3-f]quinazoline]-7'-one

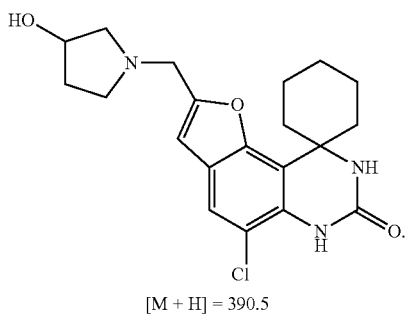 [SMILES: O=C1Nc2c(Cl)cc3cc(CN4CCC(O)C4)oc3c2C2(CCCCC2)N1]

[M + H] = 390.5

Example 549. 5'-Chloro-2'-[({[6-(morpholin-4-yl)pyridin-3-yl]methyl}amino)methyl]-7',8'-dihydro-6'H-spiro[cyclohexane-1,9'-furo[2,3-f]quinazoline]-7'-one

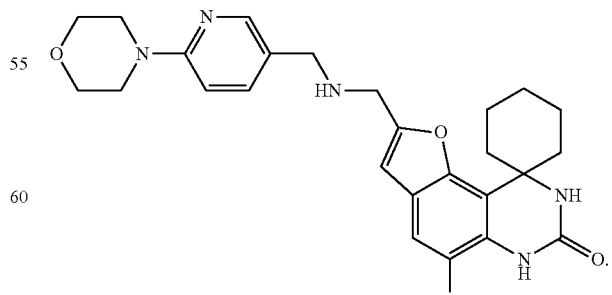

[M + H] = 496.2

Example 550. 5'-Chloro-2'-{[methyl(propyl)amino]
methyl}-7',8'-dihydro-6'H-spiro[cyclohexane-1,9'-
furo[2,3-f]quinazoline]-7'-one

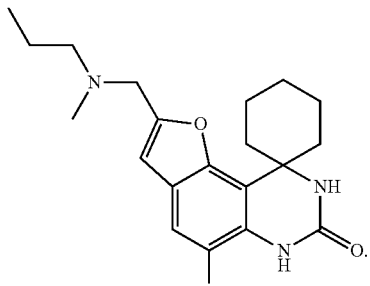

[M + H] = 376.1

Example 551. 5'-Chloro-2'-({[3-(3,5-dimethyl-1H-
pyrazol-1-yl)propyl](methyl)amino}methyl)-7',8'-
dihydro-6'H-spiro[cyclohexane-1,9'-furo[2,3-f]qui-
nazoline]-7'-one

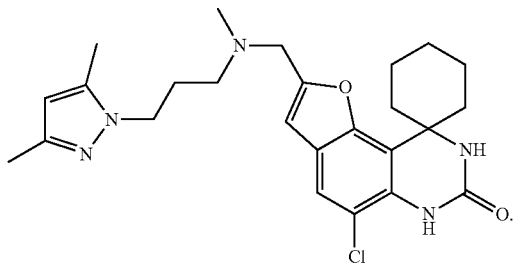

[M + H] = 470.2

Example 552. 5'-Chloro-2'-[(2,2-dimethylmorpho-
lin-4-yl)methyl]-7',8'-dihydro-6'H-spiro[cyclo-
hexane-1,9'-furo[2,3-f]quinazoline]-7'-one

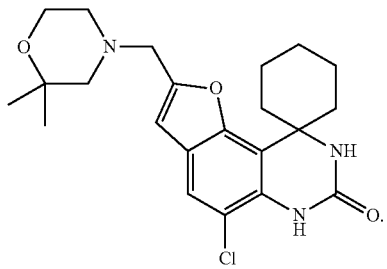

[M + H] = 418.2

Example 553. 5'-Chloro-2'-[(4-ethylpiperazin-1-yl)
methyl]-7',8'-dihydro-6'H-spiro[cyclohexane-1,9'-
furo[2,3-f]quinazoline]-7'-one

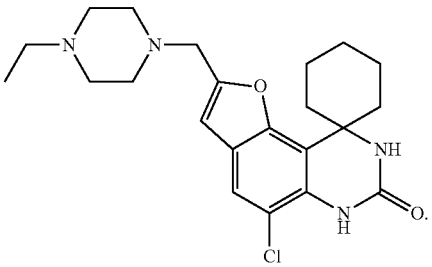

[M + H] = 417.2

Example 554. 5'-Chloro-2'-({[(3-ethyl-1,2-oxazol-5-
yl)methyl](methyl)amino}methyl)-7',8'-dihydro-6'H-
spiro[cyclohexane-1,9'-furo[2,3-f]quinazoline]-7'-
one

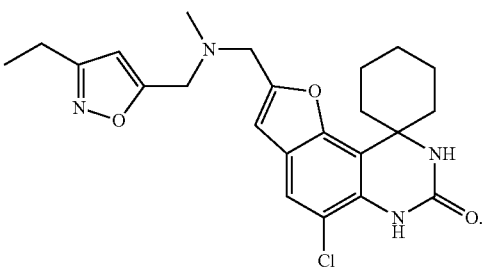

[M + H] = 443.2

Example 555. 5'-Chloro-2'-{[methyl(pyridin-2-ylm-
ethyl)amino]methyl}-7',8'-dihydro-6'H-spiro[cyclo-
hexane-1,9'-furo[2,3-f]quinazoline]-7'-one

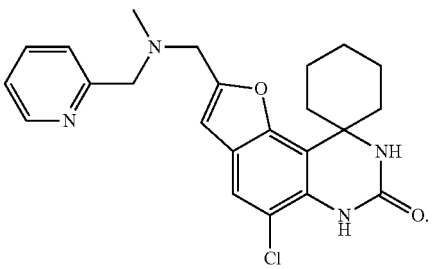

[M + H] = 425.2

Example 556. 1-{5'-Chloro-7'-oxo-7',8'-dihydro-6'H-spiro[cyclohexane-1,9'-furo[2,3-f]quinazoline]-2'-ylmethyl}piperidine-4-carboxamide

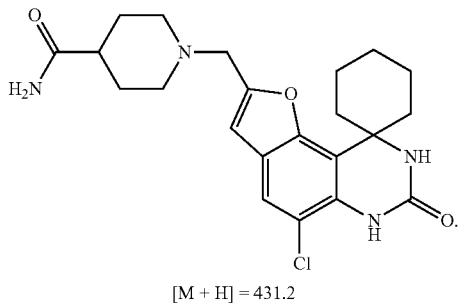 [SMILES: NC(=O)C1CCN(Cc2cc3cc(Cl)c4c(c3o2)C2(CCCCC2)NC(=O)N4)CC1]

[M + H] = 431.2

Example 557. 5'-Chloro-2'-({[2-(2-oxopyrrolidin-1-yl)ethyl]amino}methyl)-7',8'-dihydro-6'H-spiro[cyclohexane-1,9'-furo[2,3-f]quinazoline]-7'-one

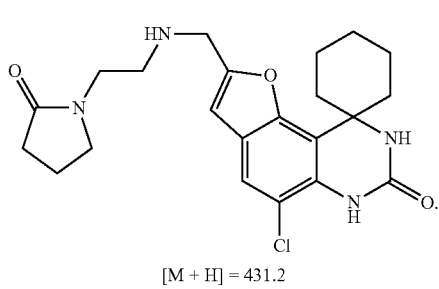 [SMILES: O=C1Nc2c(Cl)cc3cc(CNCCN4CCCC4=O)oc3c2C2(CCCCC2)N1]

[M + H] = 431.2

Example 558. 5'-Chloro-2'-[({[1-(ethoxymethyl)cyclopropyl]methyl}amino)methyl]-7',8'-dihydro-6'H-spiro[cyclohexane-1,9'-furo[2,3-f]quinazoline]-7'-one

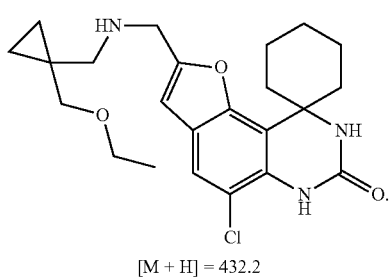 [SMILES: CCOCC1(CNCc2cc3cc(Cl)c4c(c3o2)C2(CCCCC2)NC(=O)N4)CC1]

[M + H] = 432.2

Example 559. 5'-Chloro-2'-({[2-(dimethyl-1,2-oxazol-4-yl)ethyl](methyl)amino}methyl)-7',8'-dihydro-6'H-spiro[cyclohexane-1,9'-furo[2,3-f]quinazoline]-7'-one

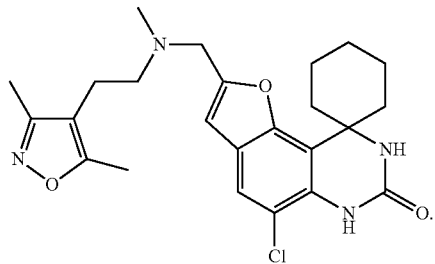

[M + H] = 457.6

Example 560. N-(1-{5'-Chloro-7'-oxo-7',8'-dihydro-6'H-spiro[cyclohexane-1,9'-furo[2,3-f]quinazoline]-2'-ylmethyl}piperidin-4-yl)acetamide

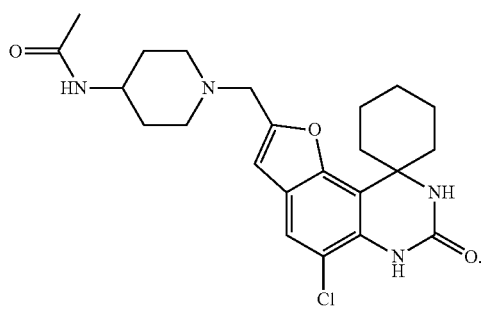

[M + H] = 445.2

Example 561. 5'-Chloro-2'-{[2-(hydroxymethyl)piperidin-1-yl]methyl}-7',8'-dihydro-6'H-spiro[cyclohexane-1,9'-furo[2,3-f]quinazoline]-7'-one

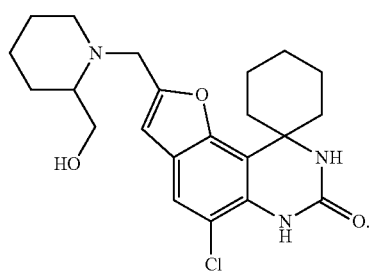

[M+H] = 418.2

Example 562. 5'-Chloro-2'-{[methyl(1-methylpiperidin-4-yl)amino]methyl}-7',8'-dihydro-6'H-spiro[cyclohexane-1,9'-furo[2,3-f]quinazoline]-7'-one

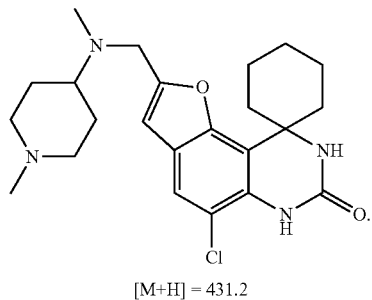 [SMILES: CN1CCC(N(C)Cc2cc3cc(Cl)c4c(c3o2)C2(CCCCC2)NC(=O)N4)CC1]

[M+H] = 431.2

Example 563. 5'-Chloro-2'-({6,6-dimethyl-3-azabicyclo[3.1.0]hexan-3-yl}methyl)-7',8'-dihydro-6'H-spiro[cyclohexane-1,9'-furo[2,3-f]quinazoline]-7'-one

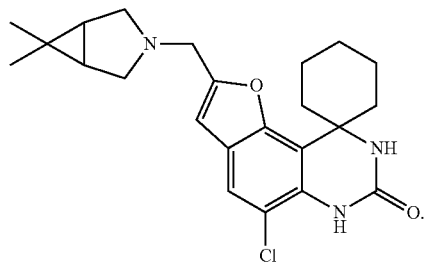

[M+H] = 414.2

Example 564. 5'-Chloro-2'-({[(1-methyl-1H-imidazol-2-yl)methyl]amino}methyl)-7',8'-dihydro-6'H-spiro[cyclohexane-1,9'-furo[2,3-f]quinazoline]-7'-one

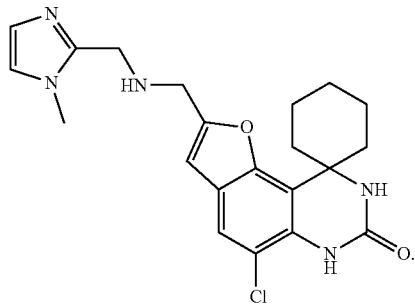

[M+H] = 414.2

Example 565. 5'-Chloro-2'-{[3-(hydroxymethyl)piperidin-1-yl]methyl}-7',8'-dihydro-6'H-spiro[cyclohexane-1,9'-furo[2,3-f]quinazoline]-7'-one

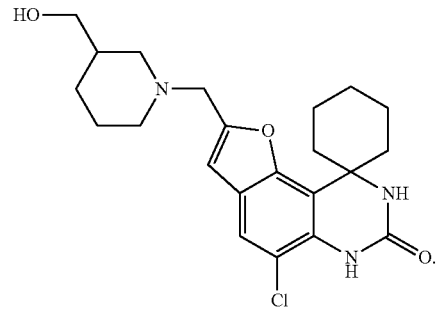

[M+H] = 418.2

Example 566. 5'-Chloro-2'-{[(2-hydroxyethyl)(propyl)amino]methyl}-7',8'-dihydro-6'H-spiro[cyclohexane-1,9'-furo[2,3-f]quinazoline]-7'-one

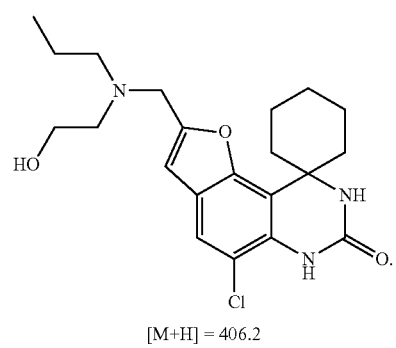 [SMILES: CCCN(CCO)Cc1cc2cc(Cl)c3c(c2o1)C1(CCCCC1)NC(=O)N3]

[M+H] = 406.2

Example 567. Ethyl 2-({5'-chloro-7'-oxo-7',8'-dihydro-6'H-spiro[cyclohexane-1,9'-furo[2,3-f]quinazoline]-2'-ylmethyl}(methyl)amino)acetate

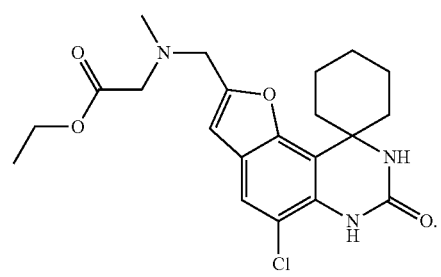

[M+H] = 420.3

Example 568. 2'-[(3-Aminopyrrolidin-1-yl)methyl]-5'-chloro-7',8'-dihydro-6'H-spiro[cyclohexane-1,9'-furo[2,3-f]quinazoline]-7'-one

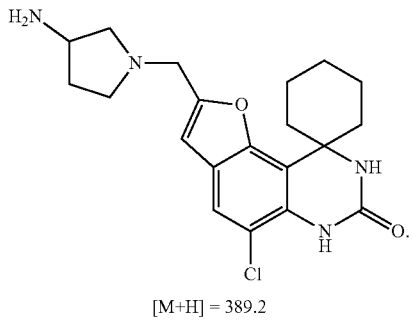 [SMILES: NC1CCN(Cc2cc3cc(Cl)c4c(c3o2)C2(CCCCC2)NC(=O)N4)C1]

[M+H] = 389.2

Example 569. N-[2-({5'-Chloro-7'-oxo-7',8'-dihydro-6'H-spiro[cyclohexane-1,9'-furo[2,3-f]quinazoline]-2'-ylmethyl}amino)ethyl]acetamide

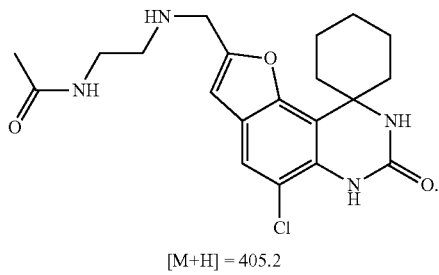 [SMILES: CC(=O)NCCNCc1cc2cc(Cl)c3c(c2o1)C1(CCCCC1)NC(=O)N3]

[M+H] = 405.2

Example 570. 5'-Chloro-2'-{[4-(hydroxymethyl)piperidin-1-yl]methyl}-7',8'-dihydro-6'H-spiro[cyclohexane-1,9'-furo[2,3-f]quinazoline]-7'-one

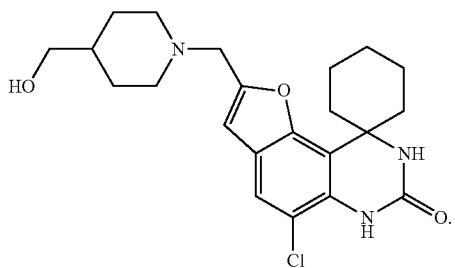

[M+H] = 418.2

Example 571. 5'-Chloro-2'-{[(piperidin-3-yl)amino]methyl}-7',8'-dihydro-6'H-spiro[cyclohexane-1,9'-furo[2,3-f]quinazoline]-7'-one

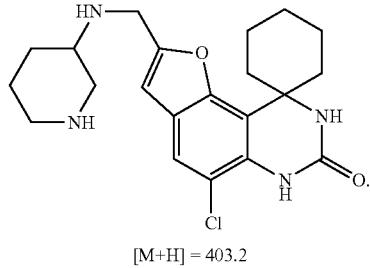 [SMILES: O=C1Nc2c(Cl)cc3cc(CNC4CCCNC4)oc3c2C2(CCCCC2)N1]

[M+H] = 403.2

Example 572. 5'-Chloro-2'-{[(pyrrolidin-3-yl)amino]methyl}-7',8'-dihydro-6'H-spiro[cyclohexane-1,9'-furo[2,3-f]quinazoline]-7'-one

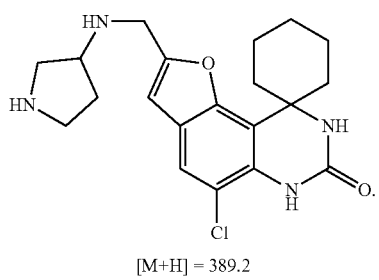 [SMILES: O=C1Nc2c(Cl)cc3cc(CNC4CCNC4)oc3c2C2(CCCCC2)N1]

[M+H] = 389.2

Example 573. 2'-Benzoyl-5'-chloro-7',8'-dihydro-6'H-spiro[cyclohexane-1,9'-furo[2,3-f]quinazoline]-7'-one

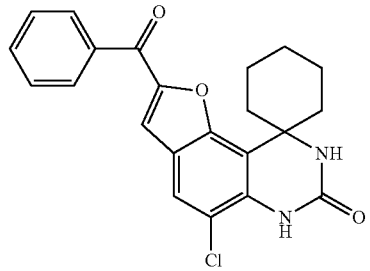 [SMILES: O=C1Nc2c(Cl)cc3cc(C(=O)c4ccccc4)oc3c2C2(CCCCC2)N1]

To a 25 mL vial was added 8'-chloro-5'-hydroxy-2'-oxo-2',3'-dihydro-1'H-spiro[cyclohexane-1,4'-quinazoline]-6'-carbaldehyde (150 mg, 0.51 mmol) and 2-bromo-1-phenylethanone (152 mg, 0.76 mmol) in DMF (10 mL), followed by potassium carbonate (211 mg, 1.53 mmol) in one portion, then the reaction was heated at 100° C. for approximately 30 minutes, then at 135° C., for an additional 90 min. The reaction mixture was then cooled to rt then diluted with H₂O (50 mL) and extracted with EtOAc (2×50 mL). The combined organics were washed with H₂O (2×25 mL), dried over Na₂SO₄, then concentrated under vacuum. The crude product was washed with Heptanes/EtOAc (~10:1), filtered and dried to give the title product as a light brown solid (85 mg, 42.3%). ¹H NMR (400 MHz, DMSO-d6) δ 8.59 (s, 1H), 8.00 (d, J=7.6 Hz, 2H), 7.88 (s, 1H), 7.75-7.70 (m, 2H), 7.64-7.59 (m, 2H), 7.46 (s, 1H), 2.44-2.38 (m, 2H), 1.88 (br s, 3H), 1.74 (br s, 1H), 1.56 (d, J=12.3 Hz, 2H), 1.25 (br s, 1H), 0.86 (t, J=6.7 Hz, 1H). [M+H]=394.9.

Example 574. 5'-Chloro-2'-(pyridine-4-carbonyl)-7',8'-dihydro-6'H-spiro[cyclohexane-1,9'-furo[2,3-f]quinazoline]-7'-one

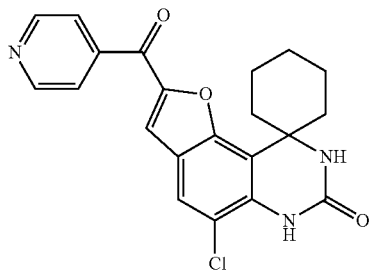 [SMILES: O=C1Nc2c(Cl)cc3cc(C(=O)c4ccncc4)oc3c2C2(CCCCC2)N1]

The title compound was prepared in a manner analogous to Example 573, with the appropriate starting material substitutions.

¹H NMR (400 MHz, DMSO-d6) δ 8.86 (d, J=5.9 Hz, 2H), 8.65 (s, 1H), 7.89 (s, 1H), 7.87-7.83 (m, 2H), 7.80 (s, 1H), 7.48 (s, 1H), 2.43-2.33 (m, 2H), 1.92-1.83 (m, 4H), 1.72 (d, J=11.5 Hz, 1H), 1.56 (d, J=14.5 Hz, 2H), 1.24 (br s, 1H). [M+H]=395.9.

Example 575. 2'-Acetyl-5'-chloro-7',8'-dihydro-6'H-spiro[cyclohexane-1,9'-furo[2,3-f]quinazoline]-7'-one

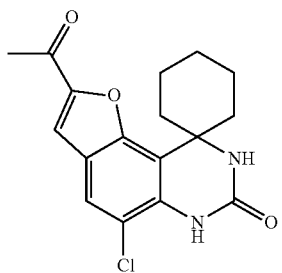 [SMILES: CC(=O)c1cc2cc(Cl)c3c(c2o1)C1(CCCCC1)NC(=O)N3]

The title compound was prepared in a manner analogous to Example 573, with the appropriate starting material substitutions.

¹H NMR (400 MHz, DMSO-d6) δ 8.53 (s, 1H), 7.86 (d, J=1.5 Hz, 1H), 7.77 (d, J=1.5 Hz, 1H), 7.41 (s, 1H), 2.54 (d, J=1.3 Hz, 3H), 2.42-2.35 (m, 2H), 1.92-1.84 (m, 4H), 1.74 (br s, 1H), 1.58 (br s, 2H), 1.29 (d, J=13.9 Hz, 1H). [M+H]=333.0.

Example 576-Example 583 were prepared in a manner analogous to Example 29, with the appropriate starting material substitutions.

Example 576. 5'-Chloro-2'-({[(3S,4R)-3-methoxyoxan-4-yl]amino}methyl)-7',8'-dihydro-6'H-spiro[cyclohexane-1,9'-furo[2,3-f]quinazoline]-7'-one

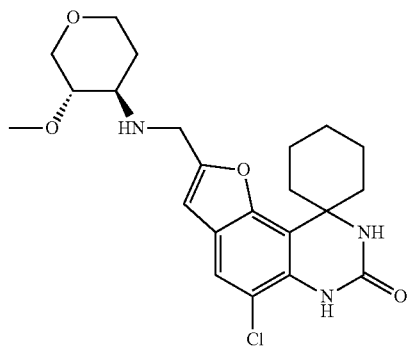 [SMILES: CO[C@@H]1COCC[C@H]1NCc1cc2cc(Cl)c3c(c2o1)C1(CCCCC1)NC(=O)N3]

¹H NMR (400 MHz, DMSO-d6) δ 8.14 (s, 1H), 7.56 (s, 1H), 7.24 (s, 1H), 6.63 (s, 1H), 4.02-3.85 (m, 4H), 3.82-3.75 (m, 1H), 3.31 (s, 3H), 3.28-3.17 (m, 2H), 3.02-2.94 (m, 2H), 2.56 (d, J=4.0 Hz, 2H), 2.46-2.32 (m, 4H), 2.01-1.80 (m, 6H), 1.75-1.67 (m, 1H), 1.70 (d, J=12.6 Hz, 1H), 1.54 (d, J=13.1 Hz, 2H), 1.36-1.26 (m, 2H). [M+H]=433.9.

Example 577. 5'-Chloro-2'-{[(3-fluorooxan-4-yl)amino]methyl}-7',8'-dihydro-6'H-spiro[cyclohexane-1,9'-furo[2,3-f]quinazoline]-7'-one

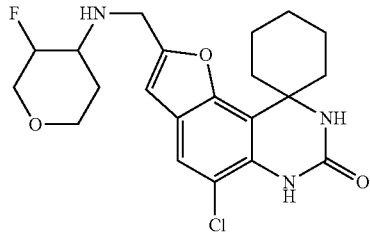

¹H NMR (400 MHz, DMSO-d6) δ 8.15 (s, 1H), 7.59-7.51 (m, 1H), 7.24 (s, 1H), 6.65 (s, 1H), 4.81-4.60 (m, 1H), 4.00-3.81 (m, 4H), 3.46 (d, J=13.3 Hz, 1H), 3.38-3.34 (m, 1H), 2.89-2.75 (m, 1H), 2.34 (t, J=13.0 Hz, 3H), 1.94-1.80 (m, 4H), 1.67 (br s, 2H), 1.54 (d, J=12.3 Hz, 3H), 1.28 (d, J=13.4 Hz, 1H). [M+H]=421.9.

Example 578. 5'-Chloro-2'-({[(3R)-oxolan-3-yl]amino}methyl)-7',8'-dihydro-6'H-spiro[cyclohexane-1,9'-furo[2,3-f]quinazoline]-7'-one

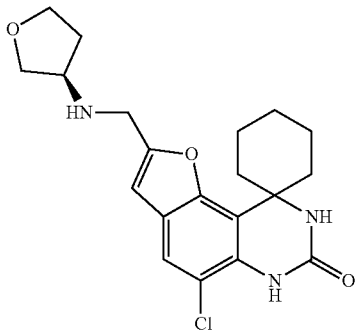

¹H NMR (400 MHz, DMSO-d6) δ 8.14 (s, 1H), 7.56 (s, 1H), 7.23 (s, 1H), 6.63 (s, 1H), 3.83 (s, 2H), 3.79-3.61 (m, 4H), 3.44 (dd, J=4.2, 8.6 Hz, 1H), 3.36 (br s, 1H), 2.40-2.32 (m, 2H), 1.98-1.87 (m, 2H), 1.81 (t, J=12.6 Hz, 3H), 1.73-1.65 (m, 2H), 1.54 (d, J=14.2 Hz, 2H), 1.35-1.22 (m, 1H). [M+H]=390.5.

Example 579. 5'-Chloro-2'-({[(3S)-oxolan-3-yl]amino}methyl)-7',8'-dihydro-6'H-spiro[cyclohexane-1,9'-furo[2,3-f]quinazoline]-7'-one

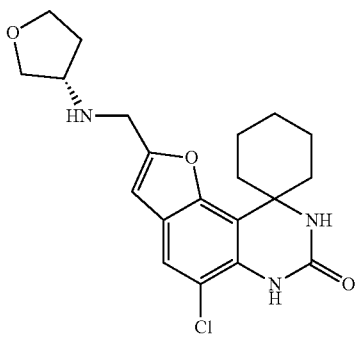 [SMILES: O=C1Nc2c(Cl)cc3cc(CN[C@H]4CCOC4)oc3c2C2(CCCCC2)N1]

¹H NMR (400 MHz, DMSO-d6) δ 8.14 (s, 1H), 7.56 (s, 1H), 7.23 (s, 1H), 6.63 (s, 1H), 3.83 (s, 2H), 3.79-3.61 (m, 4H), 3.44 (dd, J=4.2, 8.6 Hz, 1H), 3.36 (br s, 1H), 2.40-2.32 (m, 2H), 1.98-1.87 (m, 2H), 1.81 (t, J=12.6 Hz, 3H), 1.73-1.65 (m, 2H), 1.54 (d, J=14.2 Hz, 2H), 1.35-1.22 (m, 1H). [M+H]=390.5.

Example 580. 5'-Chloro-2'-({[(3R,4S)-3-methoxyoxan-4-yl]amino}methyl)-7',8'-dihydro-6'H-spiro[cyclohexane-1,9'-furo[2,3-f]quinazoline]-7'-one

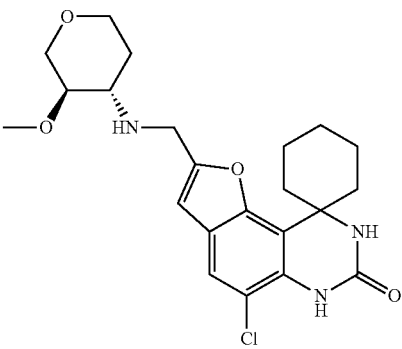 [SMILES: CO[C@H]1COCC[C@@H]1NCc1cc2cc(Cl)c3c(c2o1)C1(CCCCC1)NC(=O)N3]

¹H NMR (400 MHz, DMSO-d6) δ 8.13 (s, 1H), 7.57 (s, 1H), 7.24 (s, 1H), 6.63 (s, 1H), 4.01-3.87 (m, 3H), 3.78 (d, J=11.5 Hz, 1H), 3.31 (s, 3H), 3.25-3.18 (m, 1H), 3.04-2.94 (m, 2H), 2.60-2.55 (m, 2H), 2.44-2.36 (m, 2H), 2.01-1.79 (m, 5H), 1.72 (br s, 1H), 1.53 (d, J=13.3 Hz, 2H), 1.36-1.23 (m, 2H). [M+H]=433.9.

Example 581. 5'-Chloro-2'-({[(3S,4R)-3-methoxyoxan-4-yl]amino}methyl)-7',8'-dihydro-6'H-spiro[cyclohexane-1,9'-furo[2,3-f]quinazoline]-7'-one ¹H NMR (400 MHz, DMSO-d6) δ 8.13 (s, 1H), 7.57 (s, 1H), 7.24 (s, 1H), 6.63 (s, 1H), 4.01-3.87 (m, 3H), 3.78 (d, J=11.5 Hz, 1H), 3.31 (s, 3H), 3.25-3.18 (m, 1H), 3.04-2.94 (m, 2H), 2.60-2.55 (m, 2H), 2.44-2.36 (m, 2H), 2.01-1.79 (m, 5H), 1.72 (br s, 1H), 1.53 (d, J=13.3 Hz, 2H), 1.36-1.23 (m, 2H). [M+H]=433.9.

Example 582. 5'-Chloro-2'-{[(2-methoxyethyl)amino]methyl}-7',8'-dihydro-6'H-spiro[cyclohexane-1,9'-furo[2,3-f]quinazoline]-7'-one

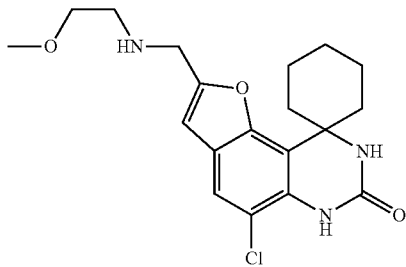 [SMILES: COCCNCc1cc2cc(Cl)c3c(c2o1)C1(CCCCC1)NC(=O)N3]

$^1$H NMR (400 MHz, DMSO-d6) δ 8.17-8.07 (m, 1H), 7.56 (s, 1H), 7.23 (s, 1H), 6.61 (s, 1H), 3.84 (s, 2H), 3.40 (t, J=5.7 Hz, 2H), 3.24 (s, 3H), 2.73 (t, J=5.6 Hz, 2H), 2.42-2.32 (m, 2H), 1.93-1.77 (m, 4H), 1.69 (d, J=11.6 Hz, 1H), 1.54 (d, J=14.5 Hz, 2H), 1.35-1.25 (m, 1H). [M+H]=378.5.

Example 583. 5'-Chloro-2'-{[(oxetan-3-yl)amino]methyl}-7',8'-dihydro-6'H-spiro[cyclohexane-1,9'-furo[2,3-f]quinazoline]-7'-one

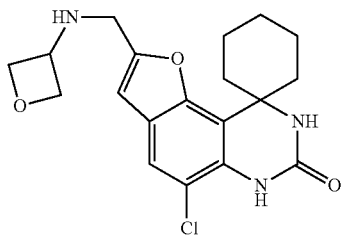 [SMILES: O=C1Nc2c(Cl)cc3cc(CNC4COC4)oc3c2C2(CCCCC2)N1]

$^1$H NMR (400 MHz, DMSO-d6) δ 8.15 (s, 1H), 7.56 (s, 1H), 7.22 (s, 1H), 6.61 (s, 1H), 4.55 (t, J=6.6 Hz, 2H), 4.27 (t, J=6.2 Hz, 2H), 3.94 (br s, 2H), 3.78 (br s, 2H), 3.06 (br s, 1H), 2.37 (d, J=9.4 Hz, 2H), 1.91-1.81 (m, 4H), 1.72 (br s, 1H), 1.56 (d, J=12.1 Hz, 2H), 1.32 (d, J=12.7 Hz, 1H). [M+H]=376.5.

PHARMACOLOGICAL EXAMPLES

The present disclosure will be further illustrated by the following pharmacological examples. These examples are understood to be exemplary only and are not intended to limit the scope of the invention disclosed herein.

Enzymatic Assay

PDE7 inhibition was determined by an IMAP TR-FRET assay using PDE7B. The IMAP TR-FRET PDE assay was optimized for concentration of enzyme, FAM-cAMP substrate, reducing agent, DMSO tolerance, and incubation time.

First, PDE7 inhibitor compounds in 10 mM DMSO stock were serially diluted in 100% DMSO. Next, into each well of a solid white 1536 well plate (Corning) was dispensed 12.8 pg of N-terminal truncated recombinant human PDE7B enzyme (91-450aa, prep #DBVC-D04614, made in-house by structural biology) in 2.5 μL IMAP BSA reaction buffer (Molecular Devices, Sunnyvale, Calif.) containing 1 mM DTT (Sigma Aldrich.) After a brief centrifugation, 30 nL of serially diluted compounds in DMSO were added by transfer from 1 mM stock using a Kalypsys 1536 Pintool. Plates were incubated for 5 minutes at room temperature before dispensing 1.5 μL of 134 nM 5-carboxy fluorescein (FAM)-labeled cAMP (Molecular Devices, Sunnyvale, Calif.) for a final concentration of 50 nM. After a brief centrifugation, the plates were incubated for 15 minutes at room temperature. The assay was terminated by adding 5 μL IMAP binding reagent/Tb complex (Molecular Devices, Sunnyvale, Calif.) to each well.

Plates were incubated 1 hour at room temperature and read on a Viewlux multimode plate reader (Perkin Elmer). The instrument was set to excite using the DUG11 filter and measure using 490/10 nm and 520/10 nm filters. Ratios of acceptor and donor were then calculated.

Data Analysis

For $IC_{50}$ calculations, the values of % efficacy versus a series of compound concentrations were then plotted using non-linear regression analysis of sigmoidal dose-response curves generated with the equation Y=B+(T−B)/1+10((Log $EC_{50}$−X)×Hill Slope), where Y=percent activity, B=minimum percent efficacy, T=maximum percent efficacy, X=logarithm of compound and Hill Slope=slope factor or Hill coefficient. The $IC_{50}$ value was determined by the concentration causing a half-maximal percent efficacy.

Results

Table 2 presents the negative log of the half-maximal molar inhibitory concentration ($pIC_{50}$), with respect to PDE7b activity, for the compounds disclosed herein.

TABLE 1

| PDE7b ($pIC_{50}$) | Example Numbers |
|---|---|
| >8 | 37, 43, 51, 64, 79, 123, 176, 189, 225, 323, 332, 334, 336, 369, 378, 427, 433, 492, 545, 557, 581 |
| 7-8 | 2, 4, 5, 6, 7, 15, 16, 17, 19, 20, 21, 22, 26, 27, 28, 30, 31, 34, 35, 36, 38, 39, 40, 41, 42, 44, 45, 46, 47, 48, 49, 52, 53, 54, 55, 56, 57, 58, 60, 61, 62, 65, 66, 67, 71, 73, 74, 75, 76, 77, 78, 80, 81, 82, 83, 84, 85, 86, 87, 88, 89, 91, 92, 103, 104, 105, 107, 109, 110, 111, 115, 116, 117, 118, 119, 121, 124, 125, 127, 128, 129, 130, 131, 132, 133, 134, 135, 136, 137, 138, 141, 143, 144, 145, 146, 147, 148, 149, 150, 151, 152, 153, 154, 155, 158, 160, 161, 162, 163, 164, 165, 166, 167, 169, 170, 171, 172, 173, 174, 175, 177, 181, 182, 183, 184, 185, 186, 187, 188, 190, 191, 194, 195, 196, 197, 198, 199, 200, 201, 202, 203, 204, 205, 206, 207, 208, 209, 210, 211, 212, 213, 215, 217, 218, 219, 220, 224, 230, 231, 232, 233, 234, 235, 236, 237, 238, 239, 240, 242, 245, 246, 250, 252, 255, 256, 257, 258, 261, 262, 263, |

TABLE 1-continued

| PDE7b (pIC$_{50}$) | Example Numbers |
|---|---|
|  | 265, 266, 267, 268, 269, 270, 273, 274, 275, 277, 278, 279, 280, 281, 282, 283, 284, 285, 286, 287, 288, 290, 291, 292, 294, 295, 296, 297, 299, 301, 303, 304, 306, 307, 309, 310, 311, 312, 313, 316, 317, 319, 320, 321, 322, 324, 325, 326, 327, 328, 331, 333, 335, 337, 340, 341, 342, 343, 344, 347, 348, 349, 350, 352, 354, 355, 356, 357, 358, 359, 360, 361, 362, 363, 364, 367, 368, 370, 371, 372, 373, 374, 376, 377, 379, 381, 382, 384, 385, 387, 388, 390, 391, 393, 397, 399, 401, 403, 404, 405, 406, 410, 411, 412, 413, 414, 415, 416, 417, 418, 419, 421, 422, 424, 425, 428, 429, 431, 434, 436, 438, 439, 440, 441, 442, 443, 444, 445, 446, 447, 448, 450, 452, 453, 456, 457, 458, 460, 461, 462, 465, 466, 467, 470, 475, 480, 482, 485, 486, 491, 496, 497, 503, 504, 511, 517, 519, 520, 522, 523, 531, 535, 538, 541, 543, 546, 551, 552, 559, 564, 569, 575, 576, 577, 578, 579, 580, 583 |
| 6-7 | 1, 3, 8, 9, 10, 11, 13, 14, 18, 23, 24, 25, 29, 32, 33, 50, 59, 63, 68, 69, 70, 72, 90, 93, 94, 95, 96, 97, 98, 99, 100, 101, 102, 106, 108, 112, 113, 114, 120, 122, 126, 139, 140, 142, 156, 157, 159, 168, 178, 179, 180, 192, 193, 214, 216, 221, 222, 223, 226, 227, 228, 229, 241, 243, 244, 247, 248, 249, 251, 253, 254, 259, 260, 264, 271, 272, 276, 289, 293, 298, 300, 302, 305, 308, 314, 315, 318, 329, 330, 338, 339, 345, 346, 351, 353, 365, 366, 375, 380, 383, 386, 389, 392, 394, 395, 396, 398, 400, 402, 407, 408, 409, 420, 423, 426, 430, 432, 435, 437, 449, 451, 454, 455, 459, 463, 464, 468, 469, 471, 472, 473, 474, 476, 477, 478, 479, 481, 483, 484, 487, 489, 490, 493, 494, 495, 498, 499, 500, 501, 502, 505, 507, 508, 509, 510, 512, 513, 514, 515, 516, 521, 524, 525, 526, 527, 528, 529, 530, 532, 533, 536, 537, 539, 540, 542, 544, 547, 548, 549, 550, 553, 554, 555, 556, 558, 560, 561, 565, 566, 567, 568, 570, 571, 572, 574, 574, 582 |
| <6 | 12, 323, 369, 433, 488, 506, 518, 534, 562, 563 |

PDE7 Selectivity of Compounds

Assay Conditions

The selectivity of compounds of the present invention was determined using a panel of recombinant human PDEs and an in vitro enzymatic assay (BPS Bioscience). Series of dilutions of each test compound were prepared with 10% DMSO in assay buffer and 5 µL of the dilution was added to a 50 µL reaction so that the final concentration of DMSO is 1% in all of the reactions.

The enzymatic reactions were conducted at room temperature for 60 minutes in a 50 µL mixture containing PDE assay buffer, 100 nM FAM-cAMP, or 100 nM FAM-cGMP, a recombinant PDE enzyme and the test compound.

After the enzymatic reaction, 100 µL of a binding solution (1:100 dilution of the binding agent with the binding agent diluent) was added to each reaction and the reaction was performed at room temperature for 60 minutes.

Fluorescence intensity was measured at an excitation of 485 nm and an emission of 528 nm using a Tecan Infinite M1000 microplate reader.

Data Analysis

PDE activity assays were performed in duplicate at each concentration. Fluorescence intensity is converted to fluorescence polarization using the Tecan Magellan6 software. The fluorescence polarization data were analyzed using the computer software, GraphPad Prism. The fluorescence polarization (FPt) in absence of the compound in each data set was defined as 100% activity. In the absence of PDE and the compound, the value of fluorescent polarization (FPb) in each data set was defined as 0% activity. The percent activity in the presence of the compound was calculated according to the following equation: % activity=(FP−FPb)/(FPt−FPb)×100%, where FP=the fluorescence polarization in the presence of the compound.

For IC$_{50}$ calculations, the values of % activity versus a series of compound concentrations were then plotted using non-linear regression analysis of Sigmoidal dose-response curve generated with the equation Y=B+(T−B)/1+10((Log EC50−X)×Hill Slope), where Y=percent activity, B=minimum percent activity, T=maximum percent activity, X=logarithm of compound and Hill Slope=slope factor or Hill coefficient. The IC$_{50}$ value was determined by the concentration causing a half-maximal percent activity.

Results

Exemplary compounds of the present invention displayed selectivity for PDE7 enzymes versus isoforms from many, if not all, other PDE families.

BIOLOGICAL EXAMPLES

The present disclosure will be further illustrated by the following biological examples. These examples are understood to be exemplary only, and not to limit the scope of the invention disclosed herein.

Biological Example 1

Effect of shRNA Mediated Knockdown of PDE7B on Memory Formation

The role of PDE7 in memory formation in animals was evaluated by RNA interference.

Procedures shRNA

Several shRNAs were screened for their ability to knockdown PDE7B in Neuro2a cells, resulting in the identification of shRNA PDE7b-28, which efficiently reduced PDE7B. This shRNA was packaged into AAV5 for in vivo expression in mouse brain. shRNA targeting PDE7B or control was expressed from a U6 promoter and a GFP reporter gene (to monitor in vivo transduction by AAV5) was expressed from a CBA (chick beta-actin) promoter contained in the same AAV5 virus. An shRNA targeting GFP was used to control for non-specific effects of viral transduction and shRNA expression on memory formation.

Subjects

Young-adult (13-15 weeks old) B6129SF1/Tac (Taconic Farms) male mice were utilized for contextual conditioning.

Upon arrival, mice were group-housed (4 mice) in standard laboratory cages and maintained on a 12:12 hour light-dark cycle. Experiments were always conducted during the light phase of the cycle.

After virus injection, group housing was maintained for the duration of the experiment. Mice received food and water ad libitum except when being trained or tested. They were maintained and bred under standard conditions, consistent with National Institutes of Health (NIH) guidelines and approved by the Institutional Animal Care and Use Committee.

Animal Surgery

For virus injections, mice were anesthetized with a Ketamine/Xylazine anesthetic, core body temperature maintained throughout the surgery using a heat blanket, and an ophthalmic ointment applied. Bregma and lambda were leveled to the same plane, as were two points 2 mm of each side of the midline. For HC injections, holes were drilled at stereotactic coordinates AP=−1.5 mm, Lateral=±1.5 mm and the injection cannula was lowered 1.75 mm below the surface of the skull. One μL of virus was injected bilaterally at a rate of 0.5 μL/min, and after 1 min the cannula was pulled up to −1.5 mm and another 1 μL was injected. After an additional 1 min the cannula was removed. After injection, a thin layer of bone wax was applied to limit efflux from the injection site and drying of the tissue. The skin was closed above the scalp, post-surgery care was provided, and mice were allowed to recover for 10-21 d prior to experimentation.

Fear Conditioning

Rationale

Contextual fear conditioning is a form of associative learning in which animals learn to recognize a training environment (conditioned stimulus, CS) that has been previously paired with an aversive stimulus such as foot shock (unconditioned stimulus, US). When exposed to the same context at a later time, conditioned animals show a variety of conditional fear responses, including freezing behavior. See, e.g., Fanselow, *Behav. Neurosci.* 1984, 98, 269-277; Fanselow, *Behav. Neurosci.* 1984, 98, 79-95; Phillips and LeDoux, *Behav. Neurosci.* 1992, 106, 274-285.

Contextual conditioning has been used to investigate the neural substrates mediating fear-motivated learning. See, e.g., Phillips and LeDoux, 1992, *Behav. Neurosci.* 106, 274-285; Kim et al., 1993, *Behav. Neurosci.* 107, 1093-1098. Previous studies in mice and rats provided evidence for functional interaction between hippocampal and non-hippocampal systems during contextual conditioning training. See, e.g., Maren et al., 1997, *Behav. Brain Res.* 88, 261-274; Maren et al., 1997, *Neurobiol. Learn. Mem.* 67, 142-149; Frankland et al., 1998, *Behav. Neurosci.* 112, 863-874. Specifically, post-training lesions of the hippocampus (but not pre-training lesions) greatly reduced contextual fear, implying that: 1) the hippocampus is essential for contextual memory but not for contextual learning per se and 2) in the absence of the hippocampus during training, non-hippocampal systems can support contextual conditioning.

Contextual conditioning has been extensively used to study the impact of various mutations on hippocampus-dependent learning and memory and strain differences in mice. See, e.g., Bourtchouladze et al., 1994, *Cell* 79, 59-68; Bourtchouladze et al., 1998, *Learn Mem.* 5, 365-374; Kogan et al., 1997, *Curr. Biol.* 7, 1-11; Silva et al., 1996, *Current Biology* 6, 1509-1518; Abel et al., 1997, *Cell* 88, 615-626; Giese et al., 1998. *Science* 279, 870-873; Logue et al., 1997, *Neuroscience* 80, 1075-1086; Chen et al., 1996, *Behav. Neurosci.* 110, 1177-1180; Nguyen et al., 2000, *Learn Mem.* 7, 170-179.

Because robust learning can be triggered with a few minutes training session, contextual conditioning has been especially useful to study the biology of temporally distinct processes of short- and long-term memory. See, e.g., Kim et al., *Behav. Neurosci.* 1993, 107, 1093-1098; Abel et al., *Cell* 1997, 88, 615-626; Bourtchouladze et al., *Cell* 1994, 79, 59-68; Bourtchouladze et al., *Learn. Mem.* 1998, 5, 365-374. As such, contextual conditioning provides an excellent model to evaluate the role of various novel genes in hippocampal-dependent memory formation.

Protocol

Previous investigations had established that training with 2×CS-US pairings induces sub-maximal (weak) memory in mice. See, e.g., U.S.2009/0053140 (siRNA); Peters et al., 2009, *Genes Brain Behav.* 8, 320-329; Tully et al., 2003, *Nat. Rev. Drug Discov.* 2, 267-77; Bourtchouladze et al., 1998, *Learn. Mem.* 5, 365-374.

An automated fear conditioning system (Coulbourn Instruments) was used for contextual conditioning. Mice were placed in the conditioning chamber and allowed to explore for 2 min. A total of two foot-shocks was delivered (0.2 mA, 2 s duration) with an inter-trial interval of 1 min. Freezing was scored for 30 s after the last foot-shock (immediate freezing). Mice were then returned to their home-cage. Memory was tested after 24 h (LTM) by reexposing the mice to the chamber in which they were trained. To assess contextual memory, freezing behavior was scored for 3 min.

Statistical Analyses

All behavioral experiments were designed and performed in a balanced fashion: First, for each experimental condition (e.g., injection with a specific shRNA) a similar number of experimental and control mice were used. Second, each experimental condition was replicated several times and replicate days were added to generate final number of subjects. Third, each session was video recorded and scored automatically. The experimenter was unaware (blind) to the treatment the subjects during training and testing.

Data were analyzed by ANOVA followed by contrast analysis using JMP software. Except where indicated, all values in the text and figures are expressed as mean+SEM.

Results

Contextual Memory

When tested in contextual fear conditioning with 2 CS-US pairings to induce weak (sub-maximal) contextual memory, mice injected with shRNA pde7b-28 packed into AAV5 exhibited significantly more freezing behavior 24 hours after training, compared to GFP control shRNA-injected mice.

This result shows that PDE7B is a negative regulator of memory formation in the hippocampus, a temporal lobe structure that is critical to memory formation in mice as well as in humans. Importantly, PDE7B-28 shRNA induced a 'gain of function"—that is, enhancement of contextual memory formation. Hence these results indicate that PDE7 is a valid target for enhancing cognition, and memory specifically. Augmentation of memory and brain plasticity by PDE7 inhibition may benefit a variety of conditions, including the treatment of neurological disorders disclosed herein, such as mental and psychiatric disorders, cognitive disorders, movement disorders, and neurodegenerative disorders.

Biological Example 2

Effect of Exemplary Compounds on Memory

The studies here evaluated the effect of exemplary compounds of the present disclosure on memory in rats.

Methods

Subjects

Male, Long Evans rats (350-380 g, Envigo Inc., or Taconic Biosciences, Inc.) were used for rat object recognition and contextual fear conditioning tasks. Rats were housed in standard cages in groups of two and maintained on a 12:12 hour light-dark cycle. Experiments were conducted during the light phase of the cycle. The animals received food and water ad libitum except during training and testing. All procedures were consistent with National Institutes of Health (NIH) guidelines and approved by the Dart Neuroscience LLC Institutional Animal Care and Use Committee.

Drug Administration

PDE7 inhibitors were dosed in a Vehicle containing 10% NMP, 50% PEG400 and 40% $H_2O$ and adjusted to pH 2.7 using HCl. Animals were dosed orally 60 minutes prior to training.

Contextual Fear Conditioning

Protocol

Contextual conditioning was carried out using an automated fear conditioning system (Med Associates Inc.). Rats were placed in the conditioning chamber and allowed to explore for 2 min. A total of two foot-shocks was delivered (0.4 mA, 2 s duration; "weak training") with an inter-shock interval of 1 min. A 5 foot-shocks group (0.4 mA, 2 s duration, "strong training") was used as positive control. After the final foot-shock, rats remained in the chamber for 30 sec and then were removed to their home cage. The weak training conditions generate sub-maximal, or weak, memory in control rats, thereby allowing one to evaluate whether a PDE7 inhibitor of the present disclosure can enhance memory formation.

Memory was assessed 24 h after training by placing the rat back into the training context and in the absence of a foot-shock measuring the percent time freezing during the 3 minute re-exposure to the chamber.

Object Recognition Memory

Rationale

Novel Object Recognition (NOR) is an assay of recognition learning and memory, which takes advantage of the spontaneous preference of rodents to investigate a novel object compared with a familiar one.

The NOR test has been employed extensively to assess the potential cognitive-enhancing properties of novel compounds derived from high-throughput screening. Object recognition is an ethologically relevant memory task that does not result from negative reinforcement (i.e. foot-shock). This task relies on the natural curiosity of rodents to explore novel objects in their environments more than familiar ones. (Antunes and Bial, 2012, Cogn. Process. 13, 93-110). For an object to be "familiar," the animal must have attended to it before and remembered that experience. Hence, animals with better memory will attend to and explore a new object more than an object familiar to them. During testing, the animal is presented with the training object and a second, novel one. Memory of the training object renders it familiar to the animal, and it then spends more time exploring the new novel object rather than the familiar one. See Bourtchouladze et al., 2003, Proc. Natl. Acad. Sci. USA 100, 10518-10522.

Studies indicate that the NOR procedure involves several brain regions, including the hippocampus and perirhinal cortex. Recent neuroimaging studies in humans have also demonstrated that object recognition memory depends on the prefrontal cortex (PFC). See Delbert et al., 1999, Neurology 52, 1413-1417. Consistent with these findings, rats with PFC lesions show poor working memory when they are required to discriminate between familiar and novel objects. See Mitchell, 1998, Behav. Brain Res. 97, 107-113. Other studies with monkeys and rodents suggest that the hippocampus is important for novel object recognition. See, e.g., Teng et al., 2000, J. Neurosci 20, 3853-3863; Cohen et al., 2015, Beh. Brain Res. 285, 105-117; Clark et al., 2000, J. Neurosci, 20, 8853-8860; Broadbent et al., 2010, Learning Mem. 17, 5-11. Hence, object recognition provides an excellent behavioral model to evaluate drug-compound effects on memory tasks associated with function of the hippocampus and cortex.

Protocol

The novel object recognition task was performed similarly to that described by Bevins and Besheer, 2006, Nat. Protocol. 1, 1306-1311, using a standard novel object recognition system for rats (Stoelting Co.). Objects were placed in a central location in the test arena, testing was carried out in low light, and time exploring objects was assessed using the automated Ethovision animal tracking Software.

For 3 consecutive days, rats were habituated to handling and the empty training arena for 7 min. The next day, rats were treated with vehicle or drug 60 min before training and were then placed into the arena and allowed to explore either two grey blocks or two white balls (~4 cm in width/diameter) for 3 min. Approximately 24 h after training, rats were placed back into the arena that now contained one familiar object and one novel object (white ball is replaced with a grey block and vice versa) and the time spent exploring each object was measured. Memory was scored by calculation of a discrimination index $((T_N-T_F)/(T_N+T_F))*100$; between group comparison).

Statistical Analyses

All behavioral experiments were designed and performed in a balanced fashion: (i) For each experimental condition (e.g., a specific dose-effect) an equal number of experimental and control rats were used; (ii) Each experimental condition was replicated several times, and (iii) The location of the novel object was counterbalanced across animals and treatment groups. In each experiment, the experimenter was unaware (blind) to the treatment of the subjects during training and testing. Animals that did not explore the objects for at least 5 seconds during the training and test phases were excluded from the analysis. Data were analyzed by ANOVA using JMP software, followed by contrast analysis comparing treatment groups to vehicle.

Results

Exemplary compounds of the disclosure were found to significantly enhance 24 hour memory in the object recognition assay. Control experiments showed that compound administration did not significantly affect the cumulative distance traveled or the total exploration time. Significant effects were seen at either 0.3 mg/kg or 1.0 mg depending on the drug.

Exemplary compounds of the disclosure were also found to enhance contextual memory in the fear conditioning assay. Significant effects were seen at several concentrations, depending on the compound, in the range of 0.1-3.0 mg/kg.

Biological Example 3

Enhanced Sensorimotor Performance in a Rat Stroke Model

The efficacy of compounds of the disclosure to enhance sensorimotor recovery after stroke can be tested in various animal models, including the well-established rodent stroke model based on cortical ischemia and motor impairment. (e.g., Berry et al., 2005, Restor. Neuro. Neurosci. 23, 251-256; Iaci et al., 2013, Stroke 44, 1942-1950; Iaci et al., 2016, J. Neurosci. Res. 94, 253-265).

Accordingly baseline levels of motor performance were established in rats by performing blinded assessments of sensorimotor function one day before surgery to induce focal cerebral infarction. Surgery was carried out via permanent middle cerebral artery occlusion (pMCAO) using a modification of the method of Tamura et al., 1986, No To Shinkei. 38, 747-751. Following surgery, animals were assigned to either control groups (vehicle alone) or experimental groups (corresponding to different drug doses) in a manner ensuring an equivalent level of impairment across treatment conditions. Lesion volume resulting from surgical infarction was measured using standard lesion reconstruction methods.

Daily administration of drug (or vehicle alone) began 24-hours after surgery. Animals were tested 1-hour after dosing on days 1, 3, 7 and 14 in the following sensorimotor tasks:

1. Forelimb and Hindlimb Placing: The forelimb placing test scored the rat's ability to place its forelimb on a tabletop in response to whisker, visual, tactile, or proprioceptive stimulation. The hindlimb placing test scored the rat's ability to place its hindlimb on the tabletop in response to tactile and proprioceptive stimulation. Together, these tests reflect function and recovery in the sensorimotor systems. Separate subscores were obtained for each mode of sensory input (half-point designations possible), and added to give total scores (for the forelimb placing test: 0=normal, 12=maximally impaired; for the hindlimb-placing test: 0=normal; 6=maximally impaired). Tests were performed 1 day before surgery (day −1) and then on days 1, 3, 7, and 14 after pMCAO.

2. Body Swing Test: Each rat was held along the vertical axis (defined as no more than 10° to either the left or the right side)≈1 inch from the base of its tail and elevated an inch above a table surface. A swing was recorded whenever the rat moved its head out of the vertical axis to either side. The rat had to return to the vertical position for the next swing to be counted. Thirty (30) total swings were counted. This test reflects symmetry of striatal function, and a normal rat typically has an equal number of swings to either side. After focal ischemia, a rat tends to swing to the contralateral (left) side.

The efficacy of each compound is assessed by comparing the rate and level of sensorimotor recovery in drug treated and vehicle treated animals. Compared to vehicle alone, exemplary compounds of the disclosure are able to enhance motor recovery in a dose dependent manner.

Biological Example 4

Enhanced Motor Rehabilitation in Post-Stroke Human Subjects

A randomized, double-blind, placebo-controlled, 6-week study uses standard stroke rehabilitation outcome measures to evaluate the effect of compositions of the present disclosure on motor recovery and function in post-stroke subjects undergoing rehabilitative therapy for upper extremity motor deficits following ischemic stroke.

Approximately equal numbers of post-stroke subjects are enrolled in two groups based on time since the ischemic event: Group 1, Subacute: between 2 and 6 weeks post-stroke; and Group 2, Chronic: greater than 6 weeks post-stroke. Subacute and chronic stroke subjects are randomized to receive (in addition to upper extremity rehabilitative therapy) either active ingredient or placebo, to be taken once daily in the morning at approximately the same time each day for 4 consecutive weeks. Blood samples for PK-related evaluations are also collected from stroke subjects at specified times over the course of the study.

Prior to dosing, subjects are assessed for baseline performance in multiple functional tests, which can include FMA-UE, AMAT-9, Stroke Impact Scale (SIS, hand domain), grip strength, index finger tapping, somatosensory evoked potential (SSEP), and 9-hole peg test. Subjects are subsequently assessed for performance in the functional tasks at weeks 1, 2, 3, 4, and 6.

Drug efficacy is evaluated by comparing the degree of improvement in upper extremity motor function as well as other motor and functional measures in subjects receiving the active ingredient versus those receiving placebo at weeks 1, 2, 3, and 4. The persistence of any improvement is determined by analyzing motor and functional data at the week 6 follow-up point. Compared to vehicle alone, compositions of the present disclosure significantly enhance motor recovery in subacute and chronic stroke patients, with recovery persisting at 42 days.

What is claimed is:
1. A compound of Formula (I):

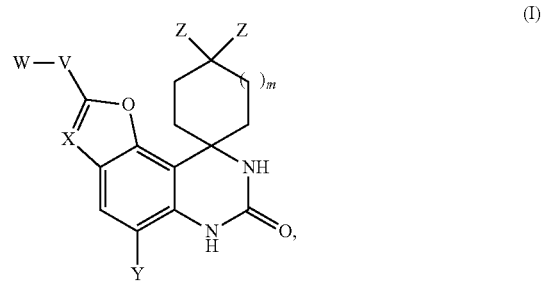

or pharmaceutically acceptable salt thereof,
wherein,
X is —CH or —N;
Y is selected from the group consisting of: —H, halo, and —C$_{1-4}$alkyl;
each Z is independently selected from the group consisting of: —H, -halo, and —C$_{1-4}$alkyl;
V is selected from the group consisting of: a bond, —(CH$_2$)$_m$—, —(CH$_2$)$_m$O(CH$_2$)$_n$—, —(CH$_2$)$_m$O(CH$_2$)$_n$C(O)—, —(CH$_2$)$_M$N[(CH$_2$)$_N$R$^{14}$]—, —(CH$_2$)$_m$C(O)O—, —(CH$_2$)$_m$C(O)—, —(CH$_2$)$_m$C(O)N[(CH$_2$)$_n$R$^{14}$]—, -L$^1$-L$^2$-, -L$^1$-L$^2$-L$^3$-, -L$^1$-L$^2$-L$^3$-L$^4$-, and -L$^1$-L$^5$;
each m is independently 0, 1, 2 or 3;
each n is independently 0, 1, 2 or 3;
L$^1$ is —C(O)(CH$_2$)$_m$—, —[C(R$^{14}$)$_2$]$_m$— or —(CH$_2$)$_m$—;
L$^2$ is —N[(CH$_2$)$_n$R$^{14}$]— or —N((CH$_2$)$_n$R$^{14}$)(CH$_2$)$_p$—;

$L^3$ is selected from the group consisting of $-(CH_2)_m-C_{3-7}cycloalkyl$, $-[C((CH_2)_nR^{1B})_2]_m[C((CH_2)_nR^{1C})_2]_n-$, $-[N[(CH_2)_mR^{1A}](CH_2)_n]-$, $-[(CH_2)_mN((CH_2)_nR^{1A})(CH_2)_p]-$, $-[(CH_2)_mC(O)N((CH_2)_nR^{1B})(CH_2)_p]-$, $-(CH_2)_mC(O)-$, $-[C(R^{1A})_2]_m-$ and $-[(CH_2)_pO]-$;

$L^4$ is selected from the group consisting of $-(CH_2)_mC(O)-$, $-(CH_2)_mO-$, $-C_{1-6}alkyl$, $-C_{3-7}cycloalkyl$, heteroaryl, aryl, 3-10 membered heterocycloalkyl, and $-CH(OH)-$, said $-C_{1-6}alkyl$, $-C_{3-7}cycloalkyl$, heteroaryl, aryl, and 3-10 membered heterocycloalkyl each optionally substituted with one to four $R^{2A}$;

$L^5$ is selected from the group consisting of $-C(O)(CH_2)_mN[(CH_2)_nR^{1B}]-$, $-C(O)(CH_2)_m-$, $-CH(OH)-$ and $-(CH_2)_mC(O)O-$;

each p is independently 0, 1, 2 or 3;

each $R^{1A}$ is independently selected from the group consisting of: $-H$, $-OH$, $-CN$, halo, $-C_{1-6}alkyl$, $-C_{2-6}$ alkenyl, $-C_{2-6}alkynyl$, $-C_{3-7}cycloalkyl$, aryl, heteroaryl, 3-15 membered heterocycloalkyl, $-C_{1-6}$ haloalkyl, and $-C_{1-6}alkoxy$, said $-C_{3-7}cycloalkyl$, aryl, heteroaryl, 3-15 membered heterocycloalkyl, $-C_{1-6}haloalkyl$, and $-C_{1-6}alkoxy$ each optionally substituted with one to four $R^{2A}$;

each $R^{1B}$ is independently selected from the group consisting of: $-H$, $-OH$, $-CN$, halo, $-C_{1-6}alkyl$, $-C_{2-6}$ alkenyl, $-C_{2-6}alkynyl$, $-C_{3-7}cycloalkyl$, aryl, heteroaryl, 3-15 membered heterocycloalkyl, $-C_{1-6}$ haloalkyl, and $-C_{1-6}alkoxy$, said $-C_{3-7}cycloalkyl$, aryl, heteroaryl, 3-15 membered heterocycloalkyl, $-C_{1-6}haloalkyl$, and $-C_{1-6}alkoxy$ each optionally substituted with one to four $R^{2A}$;

each $R^{1C}$ is independently selected from the group consisting of: $-H$, $-OH$, $-CN$, halo, $-C_{1-6}alkyl$, $-C_{2-6}$ alkenyl, $-C_{2-6}alkynyl$, $-C_{3-7}cycloalkyl$, aryl, heteroaryl, 3-15 membered heterocycloalkyl, $-C_{1-6}$ haloalkyl, and $-C_{1-6}alkoxy$, said $-C_{3-7}cycloalkyl$, aryl, heteroaryl, 3-15 membered heterocycloalkyl, $-C_{1-6}haloalkyl$, and $-C_{1-6}alkoxy$ each optionally substituted with one to four $R^{2A}$;

W is selected from the group consisting of: $-H$, -halo, $-OH$, $-CN$, $-C_{1-6}alkyl$, $-C_{1-6}haloalkyl$, aryl, heteroaryl, 3-15 membered heterocycloalkyl, $-C_{3-7}cycloalkyl$, $-SO_2C_{1-6}alkyl$, $-(CH_2)_mR^{1A}$, $-(CH_2)_mN(R^{1B})_2$, $-(CH_2)_mO(CH_2)_nR^{1A}$, $-(CH_2)_mS(CH_2)_nR^{1A}$, $-(CH_2)_mC(O)C_{1-6}alkyl$, $-(CH_2)_mC(O)heterocycloalkyl$, $-(CH_2)_mC(O)OH$, $-(CH_2)_mC(O)OC_{1-6}alkyl$, $-(CH_2)_mC(O)NH_2$, $-(CH_2)_mC(O)N(C_{1-4}alkyl)_2$, and $-(CH_2)_mC(O)NH(C_{1-4}alkyl)$, said aryl, heteroaryl, 3-15 membered heterocycloalkyl, and $-C_{3-7}cycloalkyl$, each optionally substituted with one to five $R^{3A}$;

each $R^{2A}$ is independently selected from the group consisting of: halo, $-CN$, $=O$, $-OH$, $-SO_2C_{1-6}alkyl$, $-C_{1-6}alkyl$, $-C_{1-6}alkoxy$, $-C_{1-6}haloalkyl$, aryl, heteroaryl, 3-15 membered heterocycloalkyl, $-C_{3-7}cycloalkyl$, $-(CH_2)_mN(C_{1-4}alkyl)_2$, $-OCH_2(CH_2)_mR^{2AA}$, $-CH_2(CH_2)_mR^{2AA}$, $-C_{1-6}alkyl-OH$, $-C_{1-6}haloalkylOH$, $-C_{1-6}haloalkyl-C_{3-7}cycloalkyl$, $-C_{2-6}$ alkenyl, $-C_{2-6}alkynyl$, $-C(O)C(CH_3)_3$, $-OC_{3-7}cycloalkyl$, $-C(O)C_{1-6}alkyl$, $-C(O)aryl$, $-C(O)heterocycloalkyl$, $-C(O)OC_{1-6}alkyl$, $-C(O)R^{2AA}$, $-NHC(O)R^{2AA}$, $-C(O)NH(C_{1-4}alkyl)$, $-C(O)N(C_{1-4}alkyl)_2$, $-CH_2CH(OH)C_{3-7}cycloalkyl$, $-C(CH_3)_2OH$, $-N(R^{2AA})_2$, $-C(CH_3)_2CH_2OCH_3$, $-CH(CH_3)C(O)N(C_{1-4}alkyl)_2$, and $-CH_2CF_2C_{3-7}cycloalkyl$, said aryl, heteroaryl, 3-15 membered heterocycloalkyl, and $-C_{3-7}cycloalkyl$, each optionally substituted with one to five substituents each independently selected from the group consisting of: $-CN$, $=O$, $-OH$, $-SO_2C_{1-6}alkyl$, $-C_{1-6}alkyl$, $-C_{1-6}alkoxy$, $-C_{1-6}haloalkyl$, aryl, heteroaryl, 3-15 membered heterocycloalkyl, $-C_{3-7}cycloalkyl$, $-N(C_{1-4}alkyl)_2$, $-NH(C_{1-4}alkyl)$, $-C_{2-6}alkenyl$, $-C_{2-6}alkynyl$, $-C(O)C(CH_3)_3$, $-OC_{3-7}cycloalkyl$, $-C(O)C_{1-6}alkyl$, $-C(O)aryl$, $-C(O)heterocycloalkyl$, $-C(O)OC_{1-6}alkyl$, $-C(O)N(C_{1-4}alkyl)_2$, $-CH_2CH(OH)C_{3-7}cycloalkyl$, and $-C(CH_3)_2OH$;

each $R^{3A}$ is independently selected from the group consisting of: halo, $-CN$, $=O$, $-OH$, $-SO_2C_{1-6}alkyl$, $-C_{1-6}alkyl$, $-C_{1-6}alkoxy$, $-C_{1-6}haloalkyl$, aryl, heteroaryl, 3-15 membered heterocycloalkyl, $-C_{3-7}cycloalkyl$, $-(CH_2)_mN(C_{1-4}alkyl)_2$, $-OCH_2(CH_2)_mR^{3AA}$, $-CH_2(CH_2)_mR^{3AA}$, $-C_{1-6}alkyl-OH$, $-C_{1-6}haloalkylOH$, $-C_{1-6}haloalkyl-C_{3-7}cycloalkyl$, $-C_{2-6}$ alkenyl, $-C_{2-6}alkynyl$, $-C(O)C(CH_3)_3$, $-OC_{3-7}cycloalkyl$, $-C(O)C_{1-6}alkyl$, $-C(O)aryl$, $-C(O)heterocycloalkyl$, $-C(O)OC_{1-6}alkyl$, $-C(O)R^{3AA}$, $-NHC(O)R^{3AA}$, $-C(O)NH(C_{1-4}alkyl)$, $-C(O)N(C_{1-4}alkyl)_2$, $-CH_2CH(OH)C_{3-7}cycloalkyl$, $-C(CH_3)_2OH$, $-N(R^{3AA})_2$, $-C(CH_3)_2CH_2OCH_3$, $-CH(CH_3)C(O)N(C_{1-4}alkyl)_2$, and $-CH_2CF_2C_{3-7}cycloalkyl$, said aryl, heteroaryl, 3-15 membered heterocycloalkyl, and $-C_{3-7}cycloalkyl$, each optionally substituted with one to five substituents each independently selected from the group consisting of: $-CN$, $=O$, $-OH$, $-SO_2C_{1-6}$ alkyl, $-C_{1-6}alkyl$, $-C_{1-6}alkoxy$, $-C_{1-6}haloalkyl$, aryl, heteroaryl, 3-15 membered heterocycloalkyl, $-C_{3-7}cycloalkyl$, $-N(C_{1-4}alkyl)_2$, $-NH(C_{1-4}alkyl)$, $-C_{2-6}alkenyl$, $-C_{2-6}alkynyl$, $-C(O)C(CH_3)_3$, $-OC_{3-7}cycloalkyl$, $-C(O)C_{1-6}alkyl$, $-C(O)aryl$, $-C(O)heterocycloalkyl$, $-C(O)OC_{1-6}alkyl$, $-C(O)N(C_{1-4}alkyl)_2$, $-CH_2CH(OH)C_{3-7}cycloalkyl$, and $-C(CH_3)_2OH$;

each $R^{2AA}$ is independently selected from the group consisting of: $-H$, $-OH$, $-SO_2C_{1-6}alkyl$, halo, $-CN$, $-C_{1-6}alkoxy$, $-C_{1-6}haloalkyl$, $-N(C_{1-4}alkyl)_2$, $-NH(C_{1-4}alkyl)$, $-NH_2$, aryl, heteroaryl, 3-15 membered heterocycloalkyl, $-C_{2-6}alkenyl$, $-C_{2-6}alkynyl$, $-C_{3-7}cycloalkyl$, $-C(O)C_{1-6}alkyl$, $-C(O)heterocycloalkyl$, $-C(O)OC_{1-6}alkyl$, $-C(O)N(C_{1-4}alkyl)_2$, and $-C(O)aryl$; and each $R^{3AA}$ is independently selected from the group consisting of: $-H$, $-OH$, $-SO_2C_{1-6}alkyl$, halo, $-CN$, $-C_{1-6}alkoxy$, $-C_{1-6}haloalkyl$, $-N(C_{1-4}alkyl)_2$, $-NH(C_{1-4}alkyl)$, $-NH_2$, aryl, heteroaryl, 3-15 membered heterocycloalkyl, $-C_{2-6}alkenyl$, $-C_{2-6}alkynyl$, $-C_{3-7}cycloalkyl$, $-C(O)C_{1-6}alkyl$, $-C(O)heterocycloalkyl$, $-C(O)OC_{1-6}alkyl$, $-C(O)N(C_{1-4}alkyl)_2$, and $-C(O)aryl$.

2. A compound of Formula (II):

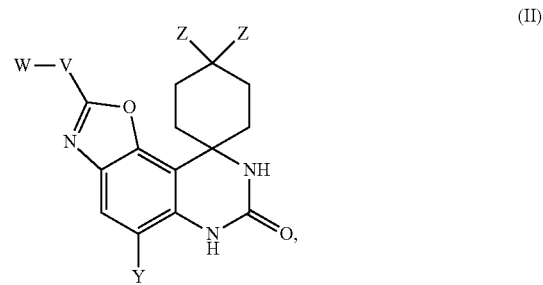

(II)

or pharmaceutically acceptable salt thereof,
wherein,
Y is selected from the group consisting of: —H, —F, —Cl, —Br, and —C$_{1-4}$alkyl;
Z is selected from the group consisting of: —H, —F, and —C$_{1-4}$alkyl;
V is selected from the group consisting of: a bond, —CH$_2$—, —C(O)—, and —NR$^a$—, where R$^a$ is —H, —C$_{1-6}$alkyl, —C$_{1-6}$haloalkyl, —C$_{3-7}$cycloalkyl, or —CH$_2$CH$_2$OC$_{1-6}$alkyl; and
W is selected from the group consisting of:
—H, -halo, —C$_{1-6}$alkyl, —C$_{1-6}$haloalkyl, —CH$_2$OC$_{1-5}$alkyl, —CH$_2$OH, —CH$_2$CH$_2$OH, —CH$_2$CH$_2$OCH$_3$, —C(O)C$_{1-6}$alkyl, —C(O)C$_{3-7}$cycloalkyl, —C(O)OC$_{1-4}$ alkyl, —C$_{3-7}$cycloalkyl, said —C$_{3-7}$cycloalkyl optionally substituted with one or more -halo or —C$_{1-6}$ alkyl, —C$_{1-6}$aryl, —C$_{1-6}$heteroaryl, said aryl or heteroaryl optionally substituted, —OH, —OC$_{1-6}$alkyl, —OCH$_2$CH$_2$OCH$_3$, —OCH$_2$C(O)N(CH$_3$)$_2$, —O-tetrahydropyranyl, —Opiperidinyl, optionally substituted heterocycloalkyl, and —N(R$^b$)$_2$,
where each R$^b$ is independently selected from the group consisting of: —H, —C$_{1-6}$alkyl, —C$_{1-6}$alkyl-OH, —C$_{1-6}$halo alkyl, —C$_{1-6}$haloalkylOH, —C$_{1-6}$haloalkyl-C$_{3-7}$cycloalkyl, —C$_{3-7}$cycloalkyl, —CH$_2$-alkenyl, —CH$_2$-alkynyl, —CH$_2$C$_{3-7}$cycloalkyl, —CH$_2$C(O)C(CH$_3$)$_3$, —CH$_2$C(O)C$_{1-6}$alkyl, —CH$_2$C(O)heterocycloalkyl, —CH$_2$C(O)OC$_{1-6}$alkyl, —CH$_2$C(O)N(C$_{1-4}$alkyl)$_2$, —CH$_2$CH(OH)C$_{3-7}$cycloalkyl, —C(CH$_3$)$_2$OH, —C(CH$_3$)$_2$CH$_2$OCH$_3$, —CH(CH$_3$)C(O)N(C$_{1-4}$alkyl)$_2$, —CH$_2$CF$_2$C$_{3-7}$cycloalkyl, —CH$_2$CH$_2$—R$^c$, and —(CH$_2$)$_n$—R$^d$,
where R$^c$ is —C$_{2-6}$alkynyl, —C$_{3-7}$cycloalkyl, —OH, —O—C$_{1-6}$alkyl, —OC(CH$_3$)$_2$, —O—C$_{1-6}$halo alkyl, —Ophenyl, —Opyridyl, —CH$_2$N(CH$_3$)$_2$, —C(O)NHCH$_3$, —C(O)N(CH$_3$)$_2$, —CN, —NHCH$_3$, —N(CH$_3$)$_2$, —NHC(O)CH$_3$, or —SO$_2$CH$_3$,
where R$^d$ is —C$_{3-7}$cycloalkyl, —C$_{3-7}$halocycloalkyl, heterocycloalkyl, aryl, or heteroaryl, each optionally substituted with up to 4 substituents each independently selected from the group consisting of: halo, —C$_{1-6}$ alkyl, —C$_{1-6}$halo alkyl, —C$_{3-7}$cycloalkyl, —OH, —OC$_{1-6}$alkyl, —O—C$_{1-6}$haloalkyl, —O-phenyl, —Opyridyl, —CH$_2$OH, —CH$_2$OCH$_3$, —CH$_2$OCH$_2$CH$_3$, —CN, —N(CH$_3$)$_2$, —N(CH$_3$)benzyl, heteroaryl, heterocycloalkyl, phenyl, or benzyl,
where n is 0, 1, 2 or 3;
or, alternatively, both R$^b$ come together to form a 4-15-membered, monocyclic, bicyclic or tricyclic ring, optionally containing up to 3 additional heteroatoms each independently selected from O (oxygen), N (nitrogen) and S (sulfur), said 4-15-membered monocyclic, bicyclic or tricyclic ring optionally substituted with one to 4 R$^{b1}$ where each R$^{b1}$ is independently selected from the group consisting of halo, —C$_{1-6}$alkyl, —C$_{1-6}$haloalkyl, —C$_{1-6}$haloalkyl-C$_{3-7}$cycloalkyl, —C$_{3-7}$cycloalkyl, bicyclo[2.2.1]heptane, —C$_{1-6}$alkyl-OH, —C(CH$_3$)$_2$OH, —CH$_2$OC$_{1-6}$alkyl, —CH$_2$C(O)OCH$_2$CH$_3$, —CH$_2$CH$_2$OC$_{1-6}$alkyl, —CH$_2$CH$_2$OC$_{1-6}$halo alkyl, —CH$_2$CH$_2$C(O)OCH$_3$, —OH, —OC$_{1-6}$alkyl, —OCH$_2$—C$_{3-7}$cycloalkyl, —OCH$_2$CH$_2$OCH$_3$, ═O, —CH$_2$N(CH$_3$)$_2$, —CH$_2$CH$_2$N(CH$_3$)$_2$, —C(O)C$_{1-6}$ alkyl, —C(O)H, —C(O)OH, —C(O)OC$_{1-6}$alkyl, —C(O)NH$_2$, —C(O)NHCH$_3$, —C(O)N(CH$_3$)$_2$, —CN, —NH$_2$, —NHC(O)CH$_3$, —N(CH$_3$)$_2$, —SO$_2$CH$_3$, oxetane, pyrrolidine, morpholine, furan, thiazole, pyridyl, phenyl, thiophene, —CH$_2$imidazole, —CH$_2$furan, —CH$_2$-thiophene, —CH$_2$pyridyl, benzyl, —C(O)-tetrahydrofuran, —C(O)pyrrole, or —C(O)phenyl.

3. A compound of Formula (III):

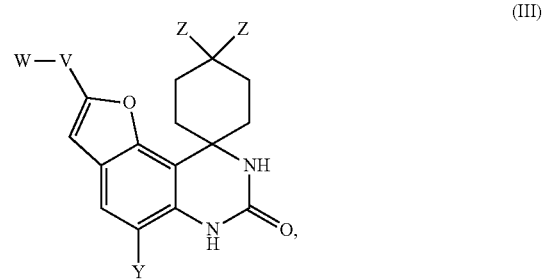

(III)

or pharmaceutically acceptable salt thereof,
wherein,
Y is selected from the group consisting of: —H, —F, —Cl, —Br, and —C$_{1-4}$alkyl;
Z is selected from the group consisting of: —H, —F and —CH$_3$;
V is selected from the group consisting of: a bond, —CH$_2$—, —C(O)—, and —NR$^a$—, where R$^a$ is —H, —C$_{1-6}$alkyl, —C$_{1-6}$haloalkyl, —C$_{3-7}$cycloalkyl, and —CH$_2$CH$_2$OC$_{1-6}$alkyl; and
W is selected from the group consisting of:
—H, halo, —C$_{1-6}$alkyl, —C$_{1-6}$haloalkyl, —CH$_2$OC$_{1-5}$alkyl, —CH$_2$OH, —CH$_2$CH$_2$OH, —CH$_2$CH$_2$OCH$_3$, —C(O)C$_{1-6}$alkyl, —C(O)C$_{3-7}$cycloalkyl, —C(O)OC$_{1-4}$ alkyl, —C$_{3-7}$cycloalkyl, said —C$_{3-7}$cycloalkyl optionally substituted with one or more halo or —C$_{1-6}$alkyl, —C$_{1-6}$aryl, —C$_{1-6}$heteroaryl, said aryl or heteroaryl optionally substituted, —OH, —OC$_{1-6}$alkyl, —OCH$_2$CH$_2$OCH$_3$, —OCH$_2$C(O)N(CH$_3$)$_2$, —O-tetrahydropyranyl, —Opiperidinyl, optionally substituted heterocycloalkyl, and —N(R$^b$)$_2$,
where each R$^b$ is independently selected from the group consisting of: —H, —C$_{1-6}$alkyl, —C$_{1-6}$alkyl-OH, —C$_{1-6}$halo alkyl, —C$_{1-6}$haloalkylOH, —C$_{1-6}$haloalkyl-C$_{3-7}$cycloalkyl, —C$_{3-7}$cycloalkyl, —CH$_2$-alkenyl, —CH$_2$-alkynyl, —CH$_2$C$_{3-7}$cycloalkyl, —CH$_2$C(O)C(CH$_3$)$_3$, —CH$_2$C(O)C$_{1-6}$alkyl, —CH$_2$C(O)heterocycloalkyl, —CH$_2$C(O)OC$_{1-6}$alkyl, —CH$_2$C(O)N(C$_{1-4}$alkyl)$_2$, —CH$_2$CH(OH)C$_{3-7}$cycloalkyl, —C(CH$_3$)$_2$OH, —C(CH$_3$)$_2$CH$_2$OCH$_3$, —CH(CH$_3$)C(O)N(C$_{1-4}$alkyl)$_2$, —CH$_2$CF$_2$C$_{3-7}$cycloalkyl, —CH$_2$CH$_2$—R$^c$, and —(CH$_2$)$_n$—R$^d$,
where R$^c$ is —C$_{2-6}$alkynyl, —C$_{3-7}$cycloalkyl, —OH, —O—C$_{1-6}$alkyl, —OC(CH$_3$)$_2$, —O—C$_{1-6}$haloalkyl, —Ophenyl, —Opyridyl, —CH$_2$N(CH$_3$)$_2$, —C(O)NHCH$_3$, —C(O)N(CH$_3$)$_2$, —CN, —NHCH$_3$, —N(CH$_3$)$_2$, —NHC(O)CH$_3$, or —SO$_2$CH$_3$,
where R$^d$ is cyclopropyl, cyclobutyl, cyclopentyl, cyclohexyl, bicyclo[1.1.1]pentane, bicyclo[3.1.0]hexane, —C$_{3-7}$halocycloalkyl, oxetane, pyrrolidine, pyrrolidinone, piperidine, piperidinone, tetrahydropyranyl, tetrahydrofuranyl, oxepane, morpholine, 3-azabicyclo[3.1.0]hexane, tetrahydrothiophene-1,1-dioxide, tetrahydro-2H-thiopyran-1,1-dioxide, thiomorpholine-1,1-dioxide, tetrahydrothiophene 1,1-dioxide, 1,3-dihydroisobenzofuran, benzofuran, indoline, benzodioxine, benzodioxole, phenyl, benzyl, —CH$_2$phenyl, —CH$_2$CH$_2$CH$_2$phenyl, furan, pyrrole, pyrazole, imidazole, triazole, isoxazole, oxazole, thiazole, pyridine, pyrimidine, thiophene, pyrrolopyridine, or benzimidazole, said $R^d$ optionally substituted with up to 4 substituents each independently selected from the group consisting of: halo, —$C_{1-6}$alkyl, —$C_{1-6}$haloalkyl, -cyclopropyl, —OH, —O$C_{1-6}$alkyl, —O—$C_{1-6}$haloalkyl, —O-phenyl, —O-pyridyl, —$CH_2$OH, —$CH_2OCH_3$, —$CH_2OCH_2CH_3$, —CN, —$N(CH_3)_2$, —$N(CH_3)$benzyl, heteroaryl, heterocycloalkyl, phenyl, or benzyl, where n is 0, 1, 2 or 3;

or, alternatively, both $R^b$ come together to form a monocyclic, bicyclic or tricyclic ring selected from the group consisting of: azetidine, pyrrole, pyrrolidine, pyrrolidinone, piperazine, piperazinone, piperidine, piperidinone, azepane, morpholine, 1-oxa-8-azaspiro[4.5]decan-3-one, 2-oxa-5-azabicyclo[2.2.1]heptane, 2-oxa-7-azaspiro[3.5]nonane, 2-oxa-8-azaspiro[4.5]decane, 2-oxa-8-azaspiro[4.5]decan-1-one, -6-oxa-9-azaspiro[4.5]decane, 7-oxa-2-azaspiro[3.5]nonane, octahydropyrrolo[3,4-c]pyrrole, octahydropyrrolo[1,2-a]pyrazine, oxaazabicyclo[2.2.1]heptane, thiomorpholine-1,1-dioxide, diazepane, 2,3,4,5-tetrahydropyrido[2,3-f][1,4]oxazepine, 5,6,7,8-tetrahydro[1,2,4]triazolo[4,3-a]pyrazine, 5,6,7,8-tetrahydroimidazo[1,2-a]pyrazine, 5,6,7,8-tetrahydropyrido[3,4-d]pyridazin-1(2H)-one, azaspiro[2.5]octane, azabicyclo[3.1.0]hexane, azabicyclo[4.1.0]heptane, diazaspiro[5.5]undecane, tetrahydroimidazopyrazine, dihydropyrrolopyridine, spiro[chroman-2,3'-pyrrolidin]-4-one, Spiro[isochroman-1,4'-piperidine], 6',7'-dihydro-5'H-spiro[piperidine-4,4'-thieno[3,2-c]pyridine], and 5',6'-dihydro-4'H-spiro[piperidine-4,7'-thieno[2,3-c]pyridine]), each optionally substituted with up to 4 substituents each independently selected from the group consisting of: halo, —$C_{1-6}$alkyl, —$C_{1-6}$haloalkyl, —$C_{1-6}$haloalkyl-$C_{3-7}$cycloalkyl, —$C_{3-7}$cycloalkyl, bicyclo[2.2.1]heptane, —$C_{1-6}$alkyl-OH, —$C(CH_3)_2$OH, —$CH_2OC_{1-6}$alkyl, —$CH_2C(O)OCH_2CH_3$, —$CH_2CH_2OC_{1-6}$alkyl, —$CH_2CH_2OC_{1-6}$haloalkyl, —$CH_2CH_2C(O)OCH_3$, —OH, —$OC_{1-6}$alkyl, —$OCH_2$—$C_{3-7}$cycloalkyl, —$OCH_2CH_2OCH_3$, =O, —$CH_2N(CH_3)_2$, —$CH_2CH_2N(CH_3)_2$, —$C(O)C_{1-6}$alkyl, —C(O)H, —C(O)OH, —$C(O)OC_{1-6}$alkyl, —$C(O)CH_3$, —$C(O)NH_2$, —$C(O)NHCH_3$, —$C(O)N(CH_3)_2$, —CN, —$NH_2$, —$NHC(O)CH_3$, —$N(CH_3)_2$, —$SO_2CH_3$, oxetane, pyrrolidine, morpholine, furan, thiazole, pyridyl, phenyl, thiophene, —$CH_2$imidazole, —$CH_2$furan, —$CH_2$-thiophene, —$CH_2$pyridyl, benzyl, —C(O)-tetrahydrofuran, —C(O)pyrrole or —C(O)phenyl.

4. A compound as in claim 2, having the structure of Formula (IIa):

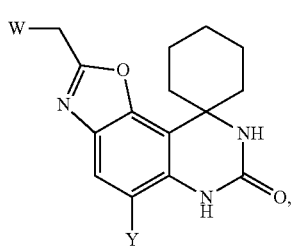

(IIa)

or a pharmaceutically acceptable salt thereof, wherein,

Y is selected from the group consisting of: —H, —F, —Cl, —Br, and —$CH_3$; and

W is —$N(R^b)_2$, where each $R^b$ is independently selected from the group consisting of: —H, —$C_{1-6}$alkyl, —$C_{1-6}$alkylOH, —$C_{1-6}$ haloalkyl, —$C_{1-6}$haloalkylOH, —$C_{1-6}$haloalkyl-$C_{3-7}$cycloalkyl, —$C_{3-7}$cycloalkyl, —$CH_2$-alkenyl, —$CH_2$-alkynyl, —$CH_2C_{3-7}$cycloalkyl, —$CH_2C(O)C(CH_3)_3$, —$CH_2C(O)C_{1-6}$alkyl, —$CH_2C(O)$heterocloalkyl, —$CH_2C(O)OC_{1-6}$alkyl, —$CH_2C(O)N(C_{1-6}$alkyl$)_2$, —$CH_2CH(OH)C_{3-7}$cycloalkyl, —$C(CH_3)_2OH$, —$C(CH_3)_2CH_2OCH_3$, —$CH(CH_3)C(O)N(C_{1-4}$alkyl$)_2$, —$CH_2CF_2C_{3-7}$cycloalkyl, —$CH_2CH_{2-12}c$ and —$(CH_2)_n$—$R^d$, where $R^c$ is —$C_{2-6}$alkynyl, —$C_{3-7}$cycloalkyl, —OH, —O—$C_{1-6}$alkyl, —$OC(CH_3)_2$, —O—$C_{1-6}$haloalkyl, —Ophenyl, —Opyridyl, —$CH_2N(CH_3)_2$, —C(O)NHCH_3, —$C(O)N(CH_3)_2$, —CN, —$NHCH_3$, —$N(CH_3)_2$, —$NHC(O)CH_3$, or —$SO_2CH_3$, where $R^d$ is —$C_{3-7}$cycloalkyl, —$C_{3-7}$halocycloalkyl, heterocycloalkyl, aryl, or -heteroaryl, each optionally substituted with up to 4 substituents each independently selected from the group consisting of: halo, —$C_{1-6}$alkyl, —$C_{1-6}$haloalkyl, —$C_{3-7}$cycloalkyl, —OH, —$OC_{1-6}$alkyl, —O—$C_{1-6}$haloalkyl, —O-phenyl, —O-pyridyl, —$CH_2OH$, —$CH_2OCH_3$, —$CH_2OCH_2CH_3$, —CN, —$N(CH_3)_2$, —$N(CH_3)$benzyl, heteroaryl, heterocycloalkyl, morpholine, phenyl, or benzyl, where n is 0, 1, 2 or 3;

or, alternatively, both $R^b$ come together to form a 4-15-membered, monocyclic, bicyclic or tricyclic ring, optionally containing up to 3 additional heteroatoms each independently selected from O (oxygen), N (nitrogen) and S (sulfur), said 4-15-membered monocyclic, bicyclic or tricyclic ring optionally substituted with up to 4 substituents each independently selected from the group consisting of: halo, —$C_{1-6}$alkyl, —$C_{1-6}$halo alkyl, —$C_{1-6}$haloalkyl-$C_{3-7}$cycloalkyl, —$C_{3-7}$cycloalkyl, -bicyclo[2.2.1]heptane, —$C_{1-6}$alkyl-OH, —$C(CH_3)_2OH$, —$CH_2OC_{1-6}$alkyl, —$CH_2C(O)OCH_3$, —$CH_2CH_2OC_{1-6}$alkyl, —$CH_2CH_2OC_{1-6}$haloalkyl, —$CH_2CH_2C(O)OCH_3$, —OH, —$OC_{1-6}$alkyl, —$OCH_2$—$C_{3-7}$cycloalkyl, —$OCH_2CH_2OCH_3$, =O, —$CH_2N(CH_3)_2$, —$CH_2CH_2N(CH_3)_2$, —$C(O)C_{1-6}$ alkyl, —C(O)H, —C(O)OH, —$C(O)OC_{1-6}$alkyl, —$C(O)CH_3$, —$C(O)NH_2$, —$C(O)NHCH_3$, —$C(O)N(CH_3)_2$, —CN, —$NH_2$, —$NHC(O)CH_3$, —$N(CH_3)_2$, —$SO_2CH_3$, oxetane, pyrrolidine, morpholine, furan, thiazole, pyridyl, phenyl, thiophene, —$CH_2$imidazole, —$CH_2$furan, —$CH_2$-thiophene, —$CH_2$pyridyl, benzyl, —C(O)-tetrahydrofuran, —C(O)pyrrole or —C(O) phenyl.

5. A compound as in claim 2, having the structure of Formula (IIb):

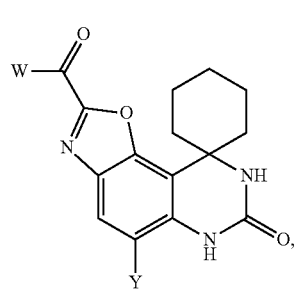

(IIb)

or a pharmaceutically acceptable salt thereof, wherein,

Y is selected from the group consisting of: —H, —F, —Cl, —Br, and —CH$_3$; and

W is —N(R$^b$)$_2$, where each R$^b$ is independently selected from the group consisting of: —H, —C$_{1-6}$alkyl, —C$_{1-6}$alkyl-OH, —C$_{1-6}$halo alkyl, —C$_{1-6}$haloalkylOH, —C$_{1-6}$haloalkyl-C$_{3-7}$cycloalkyl, —C$_{3-7}$cycloalkyl, —CH$_2$-alkenyl, —CH$_2$-alkynyl, —CH$_2$C$_{3-7}$cycloalkyl, —CH$_2$C(O)C(CH$_3$)$_3$, —CH$_2$C(O)C$_{1-6}$alkyl, —CH$_2$C(O)heterocycloalkyl, —CH$_2$C(O)OC$_{1-6}$alkyl, —CH$_2$C(O)N(C$_{1-4}$alkyl)$_2$, —CH$_2$CH(OH)C$_{3-7}$cycloalkyl, —C(CH$_3$)$_2$OH, —C(CH$_3$)$_2$CH$_2$OCH$_3$, —CH(CH$_3$)C(O)N(C$_{1-4}$alkyl)$_2$, —CH$_2$CF$_2$C$_{3-7}$cycloalkyl, —CH$_2$CH$_2$-12c and —(CH$_2$)$_n$—R$^d$, where R$^c$ is —C$_{2-6}$alkynyl, —C$_{3-7}$cycloalkyl, —OH, —O—C$_{1-6}$alkyl, —OC(CH$_3$)$_2$, —O—C$_{1-6}$haloalkyl, —Ophenyl, —Opyridyl, —CH$_2$N(CH$_3$)$_2$, —C(O)NHCH$_3$, —C(O)N(CH$_3$)$_2$, —CN, —NHCH$_3$, —N(CH$_3$)$_2$, —NHC(O)CH$_3$, or —SO$_2$CH$_3$, where R$^d$ is —C$_{3-7}$cycloalkyl, —C$_{3-7}$halocycloalkyl, heterocycloalkyl, aryl, or heteroaryl, each optionally substituted with up to 4 substituents each independently selected from the group consisting of: halo, —C$_{1-6}$alkyl, —C$_{1-6}$halo alkyl, —C$_{3-7}$cycloalkyl, —OH, —OC$_{1-6}$alkyl, —O—C$_{1-6}$haloalkyl, —O-phenyl, —O-pyridyl, —CH$_2$OH, —CH$_2$OCH$_3$, —CH$_2$OCH$_2$CH$_3$, —CN, —N(CH$_3$)$_2$, —N(CH$_3$)benzyl, heteroaryl, heterocycloalkyl, morpholine, aryl, phenyl, or benzyl, where n is 0, 1, 2 or 3;

or, alternatively, both R$^b$ come together to form a 4-15-membered, monocyclic, bicyclic or tricyclic ring, optionally containing up to 3 additional heteroatoms each independently selected from O (oxygen), N (nitrogen) and S (sulfur), said 4-15-membered monocyclic, bicyclic or tricyclic ring optionally substituted with up to 4 substituents each independently selected from the group consisting of: halo, —C$_{1-6}$alkyl, —C$_{1-6}$halo alkyl, —C$_{1-6}$haloalkyl-C$_{3-7}$cycloalkyl, —C$_{3-7}$cycloalkyl, bicyclo[2.2.1]heptane, —C$_{1-6}$alkyl-OH, —C(CH$_3$)$_2$ OH, —CH$_2$OC$_{1-6}$alkyl, —CH$_2$C(O)OCH$_2$CH$_3$, —CH$_2$CH$_2$OC$_{1-6}$alkyl, —CH$_2$CH$_2$OC$_{1-6}$haloalkyl, —CH$_2$CH$_2$C(O)OCH$_3$, —OH, —OC$_{1-6}$alkyl, —OCH$_2$—C$_{3-7}$cycloalkyl, —OCH$_2$CH$_2$OCH$_3$, =O, —CH$_2$N(CH$_3$)$_2$, —CH$_2$CH$_2$N(CH$_3$)$_2$, —C(O)C$_{1-6}$ alkyl, —C(O)H, —C(O)OH, —C(O)OC$_{1-6}$alkyl, —C(O)CH$_3$, —C(O)NH$_2$, —C(O)NHCH$_3$, —C(O)N(CH$_3$)$_2$, —CN, —NH$_2$, —NHC(O)CH$_3$, —N(CH$_3$)$_2$, —SO$_2$CH$_3$, oxetane, pyrrolidine, morpholine, furan, thiazole, pyridyl, phenyl, thiophene, —CH$_2$imidazole, —CH$_2$furan, —CH$_2$-thiophene, —CH$_2$pyridyl, benzyl, —C(O)-tetrahydrofuran, —C(O)pyrrole or —C(O)phenyl.

6. A compound as in claim 3, having the structure of Formula (IIIa):

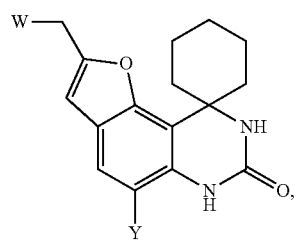

(IIIa)

or pharmaceutically acceptable salt thereof, wherein,

Y is selected from the group consisting of: —H, —F, —Cl, —Br, and —CH$_3$; and

W is —N(R$^b$)$_2$, where each R$^b$ is independently selected from the group consisting of: —H, —C$_{1-6}$alkyl, —C$_{1-6}$alkyl-OH, —C$_{1-6}$halo alkyl, —C$_{1-6}$haloalkylOH, —C$_{1-6}$haloalkyl-C$_{3-7}$cycloalkyl, —C$_{3-7}$cycloalkyl, —CH$_2$-alkenyl, —CH$_2$-alkynyl, —CH$_2$C$_{3-7}$cycloalkyl, —CH$_2$C(O)C(CH$_3$)$_3$, —CH$_2$C(O)C$_{1-6}$alkyl, —CH$_2$C(O)heterocycloalkyl, —CH$_2$C(O)OC$_{1-6}$alkyl, —CH$_2$C(O)N(C$_{1-4}$alkyl)$_2$, —CH$_2$CH(OH)C$_{3-7}$cycloalkyl, —C(CH$_3$)$_2$OH, —C(CH$_3$)$_2$CH$_2$OCH$_3$, —CH(CH$_3$)C(O)N(C$_{1-4}$alkyl)$_2$, —CH$_2$CF$_2$C$_{3-7}$cycloalkyl, —CH$_2$CH$_2$—R$^c$, and —(CH$_2$)$_n$—R$^d$, where R$^c$ is —C$_{2-6}$alkynyl, —C$_{3-7}$cycloalkyl, —OH, —O—C$_{1-6}$alkyl, —OC(CH$_3$)$_2$, —O—C$_{1-6}$haloalkyl, —Ophenyl, —Opyridyl, —CH$_2$N(CH$_3$)$_2$, —C(O)NHCH$_3$, —C(O)N(CH$_3$)$_2$, —CN, —NHCH$_3$, —N(CH$_3$)$_2$, —NHC(O)CH$_3$, or —SO$_2$CH$_3$, where R$^d$ is —C$_{3-7}$cycloalkyl, —C$_{3-7}$halocycloalkyl, aryl, or heteroaryl, each optionally substituted with up to 4 substituents each independently selected from the group consisting of: halo, —C$_{1-6}$alkyl, —C$_{1-6}$halo alkyl, —C$_{3-7}$cycloalkyl, —OH, —OC$_{1-6}$alkyl, —O—C$_{1-6}$haloalkyl, —O-phenyl, —O-pyridyl, —CH$_2$OH, —CH$_2$OCH$_3$, —CH$_2$OCH$_2$CH$_3$, —CN, —N(CH$_3$)$_2$, —N(CH$_3$)benzyl, heteroaryl, heterocycloalkyl, phenyl, or benzyl, where n is 0, 1, 2 or 3;

or, alternatively, both R$^b$ come together to form a 4-15-membered, monocyclic, bicyclic or tricyclic ring, optionally containing up to 3 additional heteroatoms each independently selected from O (oxygen), N (nitrogen) and S (sulfur), said 4-15-membered monocyclic, bicyclic or tricyclic ring optionally substituted with up to 4 substituents each independently selected from the group consisting of: halo, —C$_{1-6}$alkyl, —C$_{1-6}$halo alkyl, —C$_{1-6}$haloalkyl-C$_{3-7}$cycloalkyl, —C$_{3-7}$cycloalkyl, bicyclo[2.2.1]heptane, —C$_{1-6}$alkyl-OH, —C(CH$_3$)$_2$ OH, —CH$_2$OC$_{1-6}$alkyl, —CH$_2$C(O)OCH$_2$CH$_3$, —CH$_2$CH$_2$OC$_{1-6}$alkyl, —CH$_2$CH$_2$OC$_{1-6}$haloalkyl, —CH$_2$CH$_2$C(O)OCH$_3$, —OH, —OC$_{1-6}$alkyl, —OCH$_2$—C$_{3-7}$cycloalkyl, —OCH$_2$CH$_2$OCH$_3$, =O, —CH$_2$N(CH$_3$)$_2$, —CH$_2$CH$_2$N(CH$_3$)$_2$, —C(O)C$_{1-6}$ alkyl, —C(O)H, —C(O)OH, —C(O)OC$_{1-6}$alkyl, —C(O)CH$_3$, —C(O)NH$_2$, —C(O)NHCH$_3$, —C(O)N(CH$_3$)$_2$, —CN, —NH$_2$, —NHC(O)CH$_3$, —N(CH$_3$)$_2$, —SO$_2$CH$_3$, oxetane, pyrrolidine, morpholine, furan, thiazole, pyridyl, phenyl, thiophene, —CH$_2$imidazole, —CH$_2$furan, —CH$_2$-thiophene, —CH$_2$pyridyl, benzyl, —C(O)-tetrahydrofuran, —C(O)pyrrole or —C(O)phenyl.

7. A compound as in claim 3, having the structure of Formula (IIIb):

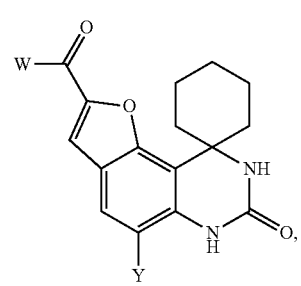

(IIIb)

or pharmaceutically acceptable salt thereof, wherein,

Y is selected from the group consisting of: —H, —F, —Cl, —Br, and —CH₃; and

W is —C₁₋₆aryl, —C₁₋₆heteroaryl, said aryl or heteroaryl optionally substituted, or —N(R^b)₂, where each R^b is independently selected from the group consisting of: —H, —C₁₋₆alkyl, —C₁₋₆alkyl-OH, —C₁₋₆halo alkyl, —C₁₋₆haloalkylOH, —C₁₋₆haloalkyl-C₃₋₇cycloalkyl, —C₃₋₇cycloalkyl, —CH₂-alkenyl, —CH₂-alkynyl, —CH₂C₃₋₇cycloalkyl, —CH₂C(O)C(CH₃)₃, —CH₂C(O)C₁₋₆alkyl, —CH₂C(O)heterocycloalkyl, —CH₂C(O)OC₁₋₆alkyl, —CH₂C(O)N(C₁₋₄alkyl)₂, —CH₂CH(OH)C₃₋₇cycloalkyl, —C(CH₃)₂OH, —C(CH₃)₂CH₂OCH₃, —CH(CH₃)C(O)N(C₁₋₄alkyl)₂, —CH₂CF₂C₃₋₇cycloalkyl, —CH₂CH₂—R^c, and —(CH₂)ₙ—R^d, where R^c is —C₂₋₆alkynyl, —C₃₋₇cycloalkyl, —OH, —O—C₁₋₆alkyl, —OC(CH₃)₂, —O—C₁₋₆haloalkyl, —Ophenyl, —Opyridyl, —CH₂N(CH₃)₂, —C(O)NHCH₃, —C(O)N(CH₃)₂, —CN, —NHCH₃, —N(CH₃)₂, —NHC(O)CH₃, or —SO₂CH₃, where R^d is —C₃₋₇cycloalkyl, —C₃₋₇halocycloalkyl, heterocycloalkyl, aryl, or heteroaryl, each optionally substituted with up to 4 substituents each independently selected from the group consisting of: halo, —C₁₋₆alkyl, —C₁₋₆haloalkyl, —C₃₋₇cycloalkyl, —OH, —OC₁₋₆alkyl, —O—C₁₋₆haloalkyl, —O-phenyl, —O-pyridyl, —CH₂OH, —CH₂OCH₃, —CH₂OCH₂CH₃, —CN, —N(CH₃)₂, —N(CH₃)benzyl, heteroaryl, heterocycloalkyl, morpholine, phenyl, or benzyl, where n is 0, 1, 2 or 3;

or, alternatively, both R^b come together to form a 4-15-membered, monocyclic, bicyclic or tricyclic ring, optionally containing up to 3 additional heteroatoms each independently selected from O (oxygen), N (nitrogen) and S (sulfur), said 4-15-membered monocyclic, bicyclic or tricyclic ring optionally substituted with up to 4 substituents each independently selected from the group consisting of: halo, —C₁₋₆alkyl, —C₁₋₆haloalkyl, —C₁₋₆haloalkyl-C₃₋₇cycloalkyl, —C₃₋₇cycloalkyl, -bicyclo[2.2.1]heptane, —C₁₋₆alkyl-OH, —C(CH₃)₂OH, —CH₂OC₁₋₆alkyl, —CH₂C(O)OCH₂CH₃, —CH₂CH₂OC₁₋₆alkyl, —CH₂CH₂OC₁₋₆haloalkyl, —CH₂CH₂C(O)OCH₃, —OH, —OC₁₋₆alkyl, —OCH₂—C₃₋₇cycloalkyl, —OCH₂CH₂OCH₃, =O, —CH₂N(CH₃)₂, —CH₂CH₂N(CH₃)₂, —C(O)C₁₋₆alkyl, —C(O)H, —C(O)OH, —C(O)OC₁₋₆alkyl, —C(O)CH₃, —C(O)NH₂, —C(O)NHCH₃, —C(O)N(CH₃)₂, —CN, —NH₂, —NHC(O)CH₃, —N(CH₃)₂, —SO₂CH₃, oxetane, pyrrolidine, morpholine, furan, thiazole, pyridyl, phenyl, thiophene, —CH₂imidazole, —CH₂furan, —CH₂-thiophene, —CH₂pyridyl, benzyl, —C(O)-tetrahydrofuran, —C(O)pyrrole or —C(O)phenyl.

8. A compound as in claim 1, or pharmaceutically acceptable salt thereof, wherein W is selected from the group consisting of: azetidine, pyrrole, pyrrolidine, pyrrolidinone, piperazine, piperazinone, piperidine, piperidinone, azepane, morpholine, 1-oxa-8-azaspiro[4.5]decan-3-one, 2-oxa-5-azabicyclo[2.2.1]heptane, 2-oxa-7-azaspiro[3.5]nonane, -2-oxa-8-azaspiro[4.5]decane, 2-oxa-8-azaspiro[4.5]decan-1-one, 6-oxa-9-azaspiro[4.5]decane, 7-oxa-2-azaspiro[3.5]nonane, octahydropyrrolo[3,4-c]pyrrole, octahydropyrrolo[1,2-a]pyrazine, oxaazabicyclo[2.2.1]heptane, thiomorpholine-1,1-dioxide, diazepane, 2,3,4,5-tetrahydropyrido[2,3-f][1,4]oxazepine, 5,6,7,8-tetrahydro[1,2,4]triazolo[4,3-a]pyrazine, 5,6,7,8-tetrahydroimidazo [1,2-a]pyrazine, 5,6,7,8-tetrahydropyrido[3,4-d]pyridazin-1(2H)-one, azaspiro[2.5]octane, azabicyclo[3.1.0]hexane, azabicyclo[4.1.0]heptane, diazaspiro[5.5]undecane, tetrahydroimidazopyrazine, dihydropyrrolopyridine, spiro[chroman-2,3'-pyrrolidin]-4-one, spiro[isochroman-1,4'-piperidine], 6',7'-dihydro-5'H-spiro[piperidine-4,4'-thieno[3,2-c]pyridine], and 5',6'-dihydro-4'H-spiro[piperidine-4,7'-thieno[2,3-c]pyridine], each optionally substituted with up to 4 substituents each independently selected from the group consisting of: halo, —C₁₋₆alkyl, —C₁₋₆haloalkyl, —C₁₋₆haloalkyl-C₃₋₇cycloalkyl, —C₃₋₇cycloalkyl, -bicyclo[2.2.1]heptane, —C₁₋₆alkyl-OH, —C(CH₃)₂OH, —CH₂OC₁₋₆alkyl, —CH₂C(O)OCH₂CH₃, —CH₂CH₂OC₁₋₆alkyl, —CH₂CH₂OC₁₋₆haloalkyl, —CH₂CH₂C(O)OCH₃, —OH, —OC₁₋₆alkyl, —OCH₂—C₃₋₇cycloalkyl, —OCH₂CH₂OCH₃, =O, —CH₂N(CH₃)₂, —CH₂CH₂N(CH₃)₂, —C(O)C₁₋₆alkyl, —C(O)H, —C(O)OH, —C(O)OC₁₋₆alkyl, —C(O)CH₃, —C(O)NH₂, —C(O)NHCH₃, —C(O)N(CH₃)₂, —CN, —NH₂, —NHC(O)CH₃, —N(CH₃)₂, —SO₂CH₃, oxetane, pyrrolidine, morpholine, furan, thiazole, pyridyl, phenyl, thiophene, —CH₂imidazole, —CH₂furan, —CH₂-thiophene, —CH₂pyridyl, benzyl, —C(O)-tetrahydrofuran, —C(O)pyrrole or —C(O)phenyl.

9. A compound as in claim 1, or pharmaceutically acceptable salt thereof, wherein W is halo, —C₁₋₆alkyl, —C₁₋₆haloalkyl or —C₃₋₇cycloalkyl; said —C₃₋₇cycloalkyl optionally substituted with one or more halo or —C₁₋₆alkyl.

10. A compound as in claim 1, or pharmaceutically acceptable salt thereof, wherein W is selected from the group consisting of: halo, —C₁₋₆alkyl, —C₁₋₆haloalkyl, —CH₂OC₁₋₅alkyl, —CH₂OH, —CH₂CH₂OH, —CH₂CH₂OCH₃, —C(O)C₁₋₆alkyl, —C(O)C₃₋₇cycloalkyl, —C(O)OC₁₋₄alkyl, —C₃₋₇cycloalkyl, said —C₃₋₇cycloalkyl optionally substituted with one or more halo or —C₁₋₆alkyl, optionally substituted —C₁₋₆aryl, optionally substituted —C₁₋₆heteroaryl, —OH, —OC₁₋₆alkyl, —OCH₂CH₂OCH₃, —OCH₂C(O)N(CH₃)₂, —O-tetrahydropyranyl, —Opiperidinyl, and —N(R^b)₂, where each R^b is independently selected from the group consisting of: —H, —C₁₋₆alkyl, —C₁₋₆alkyl-OH, —C₁₋₆haloalkyl, —C₁₋₆haloalkylOH, —C₁₋₆haloalkyl-C₃₋₇cycloalkyl, —C₃₋₇cycloalkyl, —CH₂-alkenyl, —CH₂-alkynyl, —CH₂C₃₋₇cycloalkyl, —CH₂C(O)C(CH₃)₃, —CH₂C(O)C₁₋₆alkyl, —CH₂C(O)heterocycloalkyl, —CH₂C(O)OC₁₋₆alkyl, —CH₂C(O)N(C₁₋₄alkyl)₂, —CH₂CH(OH)C₃₋₇cycloalkyl, —C(CH₃)₂OH, —C(CH₃)₂CH₂OCH₃, —CH(CH₃)C(O)N(C₁₋₄alkyl)₂, —CH₂CF₂C₃₋₇cycloalkyl, —CH₂CH₂—R^c, where R^c is —C₂₋₆alkynyl, —C₃₋₇cycloalkyl, —OH, —O—C₁₋₆alkyl, —OC(CH₃)₂, —O—C₁₋₆haloalkyl, —Ophenyl, —Opyridyl, —CH₂N(CH₃)₂, —C(O)NHCH₃, —C(O)N(CH₃)₂, —CN, —NHCH₃, —N(CH₃)₂, —NHC(O)CH₃, or —SO₂CH₃, and —(CH₂)ₙ—R^d, where R^d is —C₃₋₇cycloalkyl, —C₃₋₇halocycloalkyl, heterocycloalkyl, aryl, or heteroaryl, each optionally substituted with up to 4 substituents each independently selected from the group consisting of: halo, —C₁₋₆alkyl, —C₁₋₆haloalkyl, —C₃₋₇cycloalkyl, —OH, —OC₁₋₆alkyl, —O—C₁₋₆haloalkyl, —O-phenyl, —O-pyridyl, —CH₂OH, —CH₂OCH₃, —CH₂OCH₂CH₃, —CN, —N(CH₃)₂, —N(CH₃)benzyl, heteroaryl, heterocycloalkyl, phenyl, or benzyl, where n is 0, 1, 2 or 3; or, alternatively, both R^b come together to form a 4-15-membered, monocyclic, bicyclic or tricyclic ring, optionally containing up to 3 additional heteroatoms each independently selected from O (oxygen), N (nitrogen) and S (sulfur), said 4-15-membered monocyclic, bicyclic or tricyclic ring optionally substituted with up to 4 substituents each independently selected from the group consisting of: halo, —$C_{1-6}$alkyl, —$C_{1-6}$haloalkyl, —$C_{1-6}$haloalkyl-$C_{3-7}$cycloalkyl, —$C_{3-7}$cycloalkyl, -bicyclo[2.2.1]heptane, —$C_{1-6}$alkyl-OH, —$CH_2OC_{1-6}$alkyl, —$CH_2C(O)$ $OCH_2CH_3$, —$CH_2CH_2OC_{1-6}$alkyl, —$CH_2CH_2OC_{1-6}$ haloalkyl, —$CH_2CH_2C(O)OCH_3$, —OH, —$OC_{1-6}$alkyl, —$OCH_2$—$C_{3-7}$cycloalkyl, —$OCH_2CH_2OCH_3$, =O, —$CH_2N(CH_3)_2$, —$CH_2CH_2N(CH_3)_2$, —$C(O)C_{1-6}$alkyl, —C(O)H, —C(O)OH, —$C(O)OC_{1-6}$alkyl, —$C(O)CH_3$, —$C(O)NH_2$, —$C(O)NHCH_3$, —$C(O)N(CH_3)_2$, —CN, —$NH_2$, —$NHC(O)CH_3$, —$N(CH_3)_2$, —$SO_2CH_3$, oxetane, pyrrolidine, morpholine, furan, thiazole, pyridyl, phenyl, thiophene, —$CH_2$imidazole, —$CH_2$furan, —$CH_2$-thiophene, —$CH_2$pyridyl, benzyl, —C(O)-tetrahydrofuran, —C(O)pyrrole or —C(O)phenyl.

11. A compound as in claim 1, or pharmaceutically acceptable salt thereof, wherein W is selected from the group consisting of: halo, —$C_{1-6}$alkyl, —$C_{1-6}$haloalkyl, —$CH_2OC_{1-5}$alkyl, —$CH_2OH$, —$CH_2CH_2OH$, —$CH_2CH_2OCH_3$, —$C(O)C_{1-6}$alkyl, —$C(O)C_{3-7}$cycloalkyl, —$C(O)OC_{1-4}$alkyl, —$C_{3-7}$cycloalkyl, said —$C_{3-7}$cycloalkyl optionally substituted with one or more halo or —$C_{1-6}$alkyl, —$C_{1-6}$aryl, —$C_{1-6}$heteroaryl, said aryl or heteroaryl optionally substituted, —OH, —$OC_{1-6}$alkyl, —$CH_2CH_2OCH_3$, —$OCH_2C(O)N(CH_3)_2$, —O-tetrahydropyranyl, —Opiperidinyl, and —$N(R^b)_2$, where each $R^b$ is independently selected from the group consisting of: —H, —$C_{1-6}$alkyl, —$C_{1-6}$alkyl-OH, —$C_{1-6}$haloalkyl, —$C_{1-6}$haloalkylOH, —$C_{1-6}$haloalkyl-$C_{3-7}$cycloalkyl, —$C_{3-7}$cycloalkyl, —$CH_2$-alkenyl, —$CH_2$-alkynyl, —$CH_2C_{3-7}$cycloalkyl, —$CH_2C(O)$ $C(CH_3)_3$, —$CH_2C(O)C_{1-6}$alkyl, —$CH_2C(O)$piperidine, —$CH_2C(O)OC_{1-6}$alkyl, —$CH_2C(O)N(C_{1-4}$alkyl$)_2$, —$CH_2CH(OH)C_{3-7}$cycloalkyl, —$C(CH_3)_2OH$, —$C(CH_3)_2$ $CH_2OCH_3$, —$CH(CH_3)C(O)N(C_{1-4}$alkyl$)_2$, —$CH_2CF_2C_{3-7}$ cycloalkyl, —$CH_2CH_2$—$R^c$, where $R^c$ is —$C_{2-6}$alkynyl, —$C_{3-7}$cycloalkyl, —OH, —O—$C_{1-6}$alkyl, —$OC(CH_3)_2$, —O—$C_{1-6}$haloalkyl, —Ophenyl, —Opyridyl, —$CH_2N$ $(CH_3)_2$, —$C(O)NHCH_3$, —$C(O)N(CH_3)_2$, —CN, —$NHCH_3$, —$N(CH_3)_2$, —$NHC(O)CH_3$, or —$SO_2CH_3$, and —$(CH_2)_n$—$R^d$, where $R^d$ is cyclopropyl, cyclobutyl, cyclopentyl, cyclohexyl, bicyclo[1.1.1]pentane, bicyclo[3.1.0]hexane, —$C_{3-7}$halocycloalkyl, oxetane, pyrrolidine, pyrrolidinone, piperidine, piperidinone, tetrahydropyranyl, tetrahydrofuranyl, oxepane, morpholine, 3-azabicyclo [3.1.0]hexane, tetrahydrothiophene-1,1-dioxide, tetrahydro-2H-thiopyran-1,1-dioxide, thiomorpholine-1,1-dioxide, tetrahydrothiophene-1,1-dioxide, 1,3-dihydroisobenzofuran, benzofuran, indoline, benzodioxine, benzodioxole, phenyl, benzyl, —$CH_2CH_2$phenyl, —$CH_2CH_2CH_2$phenyl, furan, pyrrole, pyrazole, imidazole, triazole, isoxazole, oxazole, thiazole, pyridine, pyrimidine, thiophene, pyrrolopyridine, benzimidazole, said $R^d$ optionally substituted with up to 4 substituents each independently selected from the group consisting of: —F, —$C_{1-6}$alkyl, —$C_{1-6}$haloalkyl, cyclopropyl, —OH, —$OC_{1-6}$alkyl, —O—$C_{1-6}$haloalkyl, —O-phenyl, —O-pyridyl, —$CH_2OH$, —$CH_2OCH_3$, —$CH_2OCH_2CH_3$, —CN, —$N(CH_3)_2$, —$N(CH_3)$benzyl, heteroaryl, heterocycloalkyl, morpholine, phenyl, pyrrolidinone, hydroxypiperidine, benzyl, imidazole, pyridine, where n is 0, 1, 2 or 3; or, alternatively, both $R^b$ come together to form a monocyclic, bicyclic or tricyclic ring selected from the group consisting of: azetidine, pyrrole, pyrrolidine, pyrrolidinone, piperazine, piperazinone, piperidine, piperidinone, azepane, morpholine, 1-oxa-8-azaspiro[4.5]decan-3-one, 2-oxa-5-azabicyclo[2.2.1]heptane, 2-oxa-7-azaspiro [3.5]nonane, 2-oxa-8-azaspiro[4.5]decane, 2-oxa-8-azaspiro [4.5]decan-1-one, 6-oxa-9-azaspiro[4.5]decane, 7-oxa-2-azaspiro[3.5]nonane, octahydropyrrolo[3,4-c]pyrrole, octahydropyrrolo[1,2-a]pyrazine, oxaazabicyclo[2.2.1]heptane, thiomorpholine-1,1-dioxide, diazepane, 2,3,4,5-tetrahydropyrido[2,3-f][1,4]oxazepine, 5,6,7,8-tetrahydro[1,2,4] triazolo[4,3-a]pyrazine, 5,6,7,8-tetrahydroimidazo [1,2-a] pyrazine, 5,6,7,8-tetrahydropyrido[3,4-d]pyridazin-1(2H)-one, azaspiro[2.5]octane, azabicyclo[3.1.0]hexane, azabicyclo[4.1.0]heptane, diazaspiro[5.5]undecane, tetrahydroimidazopyrazine, dihydropyrrolopyridine, spiro[chroman-2,3'-pyrrolidin]-4-one, spiro[isochroman-1,4'-piperidine], 6',7'-dihydro-5'H-spiro[piperidine-4,4'-thieno[3,2-c] pyridine], and 5',6'-dihydro-4'H-spiro[piperidine-4,7'-thieno [2,3-c]pyridine], said 4-15-membered monocyclic, bicyclic or tricyclic ring optionally substituted with up to 4 substituents each independently selected from the group consisting of: halo, —$C_{1-6}$alkyl, —$Ci_{-6}$haloalkyl, —$C_{1-6}$haloalkyl-$C_{3-7}$ cycloalkyl, —$C_{3-7}$cycloalkyl, bicyclo[2.2.1]heptane, —$C_{1-6}$alkyl-OH, —$C(CH_3)_2OH$, —$CH_2OC_{1-6}$alkyl, —$CH_2C(O)OCH_2CH_3$, —$CH_2CH_2OC_{1-6}$alkyl, —$CH_2CH_2OC_{1-6}$haloalkyl, —$CH_2CH_2C(O)OCH_3$, —OH, —$OC_{1-6}$alkyl, —$OCH_2$—$C_{3-7}$cycloalkyl, —$OCH_2CH_2OCH_3$, =O, —$CH_2N(CH_3)_2$, —$CH_2CH_2N$ $(CH_3)_2$, —$C(O)C_{1-6}$alkyl, —C(O)H, —C(O)OH, —$C(O)$ $OC_{1-6}$alkyl, —$C(O)CH_3$, —$C(O)NH_2$, —$C(O)NHCH_3$, —$C(O)N(CH_3)_2$, —CN, —$NH_2$, —$NHC(O)CH_3$, —$N(CH_3)_2$, —$SO_2CH_3$, oxetane, pyrrolidine, morpholine, furan, thiazole, pyridyl, phenyl, thiophene, —$CH_2$imidazole, —$CH_2$furan, —$CH_2$-thiophene, —$CH_2$pyridyl, benzyl, —C(O)-tetrahydrofuran, —C(O)pyrrole or —C(O)phenyl.

12. A compound as in claim 1, or pharmaceutically acceptable salt thereof, wherein W is —$N(R^b)_2$, where each $R^b$ is independently selected from the group consisting of: —H, —$C_{1-6}$alkyl, —$C_{1-6}$alkyl-OH, —$C_{1-6}$haloalkyl, —$C_{1-6}$haloalkylOH, —$C_{1-6}$haloalkyl-$C_{3-7}$cycloalkyl, —$C_{3-7}$cycloalkyl, —$CH_2$-alkenyl, —$CH_2$-alkynyl, —$CH_2C_{3-7}$cycloalkyl, —$CH_2C(O)C(CH_3)_3$, —$CH_2C(O)C_{1-6}$alkyl, —$CH_2C(O)$piperidine, —$CH_2C(O)OC_{1-6}$alkyl, —$CH_2C(O)$ $N(C_{1-4}$alkyl$)_2$, —$CH_2CH(OH)C_{3-7}$cycloalkyl, —$C(CH_3)_2$ OH, —$C(CH_3)_2CH_2OCH_3$, —$CH(CH_3)C(O)N(C_{1-4}$alkyl$)_2$, —$CH_2CF_2C_{3-7}$cycloalkyl, —$CH_2CH_2$—$R^c$, where $R^c$ is —$C_{2-6}$alkynyl, —$C_{3-7}$cycloalkyl, —OH, —O—$C_{1-6}$alkyl, —$OC(CH_3)_2$, —O—$C_{1-6}$haloalkyl, —Ophenyl, —Opyridyl, —$CH_2N(CH_3)_2$, —$C(O)NHCH_3$, —$C(O)N$ $(CH_3)_2$, —CN, —$NHCH_3$, —$N(CH_3)_2$, —$NHC(O)CH_3$, or —$SO_2CH_3$, and —$(CH_2)_n$—$R^d$, where $R^d$ is cyclopropyl, cyclobutyl, cyclopentyl, cyclohexyl, bicyclo[1.1.1]pentane, bicyclo[3.1.0]hexane), —$C_{3-7}$halocycloalkyl, oxetane, pyrrolidine, pyrrolidinone, piperidine, piperidinone, tetrahydropyranyl, tetrahydrofuranyl, oxepane, morpholine, 3-azabicyclo[3.1.0]hexane, tetrahydrothiophene-1,1-dioxide, tetrahydro-2H-thiopyran-1,1-dioxide, thiomorpholine-1,1-dioxide, tetrahydrothiophene-1,1-dioxide, 1,3-dihydroisobenzofuran, benzofuran, indoline, benzodioxine, benzodioxole, phenyl, benzyl, —$CH_2CH_2$phenyl, —$CH_2CH_2CH_2$phenyl, furan, pyrrole, pyrazole, imidazole, triazole, isoxazole, oxazole, thiazole, pyridine, pyrimidine, thiophene, pyrrolopyridine, benzimidazole, said $R^d$ optionally substituted with up to 4 substituents each independently selected from the group consisting of: —F, —$C_{1-6}$alkyl, —$C_{1-6}$haloalkyl, cyclopropyl, —OH, —$OC_{1-6}$alkyl, —O—$C_{1-6}$haloalkyl, —O-phenyl, —O-pyridyl, —$CH_2OH$, —$CH_2OCH_3$, —$CH_2OCH_2CH_3$, —CN, or —$N(CH_3)_2$, —$N(CH_3)$benzyl, heteroaryl, heterocycloalkyl, morpholine, phenyl, pyrrolidinone, hydroxypiperidine, benzyl, imidazole, pyridine, where n is 0, 1, 2 or 3.

13. A compound as in claim 1, or pharmaceutically acceptable salt thereof, wherein W is —$N(R^b)_2$, where both R$^b$ come together to form a monocyclic, bicyclic or tricyclic ring selected from the group consisting of: azetidine, pyrrole, pyrrolidine, pyrrolidinone, piperazine, piperazinone, piperidine, piperidinone, azepane, morpholine, 1-oxa-8-azaspiro[4.5]decan-3-one, 2-oxa-5-azabicyclo[2.2.1]heptane, 2-oxa-7-azaspiro[3.5]nonane, -2-oxa-8-azaspiro[4.5]decane, 2-oxa-8-azaspiro[4.5]decan-1-one, 6-oxa-9-azaspiro[4.5]decane, 7-oxa-2-azaspiro[3.5]nonane, octahydropyrrolo[3,4-c]pyrrole, octahydropyrrolo[1,2-a]pyrazine, oxaazabicyclo[2.2.1]heptane, thiomorpholine-1,1-dioxide, diazepane, 2,3,4,5-tetrahydropyrido[2,3-f][1,4]oxazepine, 5,6,7,8-tetrahydro[1,2,4]triazolo[4,3-a]pyrazine, 5,6,7,8-tetrahydroimidazo[1,2-c]pyrazine, 5,6,7,8-tetrahydropyrido[3,4-d]pyridazin-1(2H)-one, azaspiro[2.5]octane, azabicyclo[3.1.0]hexane, azabicyclo[4.1.0]heptane, diazaspiro[5.5]undecane, tetrahydroimidazopyrazine, dihydropyrrolopyridine, spiro[chroman-2,3'-pyrrolidin]-4-one, spiro[isochroman-1,4'-piperidine], 6',7'-dihydro-5'H-spiro[piperidine-4,4'-thieno]3,2-c[pyridine], and 5',6'-dihydro-4'H-spiro[piperidine-4,7'-thieno]2,3-c[pyridine], said monocyclic, bicyclic or tricyclic ring optionally substituted with up to 4 substituents each independently selected from the group consisting of: halo, —C$_{1-6}$alkyl, —C$_{1-6}$haloalkyl, —C$_{1-6}$haloalkyl-C$_{3-7}$cycloalkyl, —C$_{3-7}$cycloalkyl, -bicyclo[2.2.1]heptane, —C$_{1-6}$alkyl-OH, —C(CH$_3$)$_2$OH, —CH$_2$OC$_{1-6}$alkyl, —CH$_2$C(O)OCH$_2$CH$_3$, —CH$_2$CH$_2$OC$_{1-6}$ alkyl, —CH$_2$CH$_2$OC$_{1-6}$haloalkyl, —CH$_2$CH$_2$C(O)OCH$_3$, —OH, —OC$_{1-6}$alkyl, —OCH$_2$—C$_{3-7}$cycloalkyl, —OCH$_2$CH$_2$OCH$_3$, =O, —CH$_2$N(CH$_3$)$_2$, —CH$_2$CH$_2$N(CH$_3$)$_2$, —C(O)C$_{1-6}$alkyl, —C(O)H, —C(O) OH, —C(O)OC$_{1-6}$alkyl, —C(O)CH$_3$, —C(O)NH$_2$, —C(O) NHCH$_3$, —C(O)N(CH$_3$)$_2$, —CN, —NH$_2$, —NHC(O)CH$_3$, —N(CH$_3$)$_2$, —SO$_2$CH$_3$, oxetane, pyrrolidine, morpholine, furan, thiazole, pyridyl, phenyl, thiophene, —CH$_2$imidazole, —CH$_2$furan, —CH$_2$-thiophene, —CH$_2$pyridyl, benzyl, —C(O)-tetrahydrofuran, —C(O)pyrrole or —C(O)phenyl.

14. A compound as in claim 1, or pharmaceutically acceptable salt thereof, wherein W is selected from the group consisting of: —C$_{1-6}$alkyl, —C$_{1-6}$haloalkyl, —C$_{3-7}$cycloalkyl, —C(O)C$_{1-6}$alkyl, —C(O)C$_{3-7}$cycloalkyl, and —CH$_2$CH$_2$OCH$_3$.

15. A compound as in claim 1, or pharmaceutically acceptable salt thereof, wherein V is a bond and W is halo, —C$_{1-3}$alkyl, —C$_{1-3}$haloalkyl or —C$_{3-5}$cycloalkyl, said —C$_{3-5}$cycloalkyl optionally substituted with one or more halo or —C$_{1-3}$alkyl.

16. A compound as in claim 1, or pharmaceutically acceptable salt thereof, wherein V is —CH$_2$— and W is: —N(R$^b$)$_2$, where each R$^b$ is independently selected from the group consisting of: —H, —C$_{1-6}$alkyl, —C$_{1-6}$alkyl-OH, —C$_{1-6}$haloalkyl, —C$_{1-6}$haloalkylOH, —C$_{1-6}$haloalkyl-C$_{3-7}$cycloalkyl, —C$_{3-7}$cycloalkyl, —CH$_2$-alkenyl, —CH$_2$-alkynyl, —CH$_2$C$_{3-7}$cycloalkyl, —CH$_2$C(O)C(CH$_3$)$_3$, —CH$_2$C(O)C$_{1-6}$alkyl, —CH$_2$C(O)heterocycloalkyl, —CH$_2$C(O)OC$_{1-6}$alkyl, —CH$_2$C(O)N(C$_{1-4}$alkyl)$_2$, —CH$_2$CH(OH)C$_{3-7}$cycloalkyl, —C(CH$_3$)$_2$OH, —C(CH$_3$)$_2$CH$_2$OCH$_3$, —CH(CH$_3$)C(O)N(C$_{1-4}$alkyl)$_2$, —CH$_2$CF$_2$C$_{3-7}$cycloalkyl, —CH$_2$CH$_2$—R$^c$, where R$^c$ is —C$_{2-6}$alkynyl, —C$_{3-7}$cycloalkyl, —OH, —O—C$_{1-6}$alkyl, —OC(CH$_3$)$_2$, —O—C$_{1-6}$haloalkyl, —Ophenyl, —Opyridyl, —CH$_2$N(CH$_3$)$_2$, —C(O)NHCH$_3$, —C(O)N(CH$_3$)$_2$, —CN, —NHCH$_3$, —N(CH$_3$)$_2$, —NHC(O)CH$_3$, or —SO$_2$CH$_3$, and —(CH$_2$)$_n$—R$^d$, where R$^d$ is —C$_{3-7}$cycloalkyl, —C$_{3-7}$halocycloalkyl, heterocycloalkyl, aryl, or heteroaryl, each optionally substituted with up to 4 substituents each independently selected from the group consisting of: halo, —C$_{1-6}$alkyl, —C$_{1-6}$haloalkyl, —C$_{3-7}$cycloalkyl, —OH, —OC$_{1-6}$alkyl, —O—C$_{1-6}$haloalkyl, —O-phenyl, —O-pyridyl, —CH$_2$OH, —CH$_2$OCH$_3$, —CH$_2$OCH$_2$CH$_3$, —CN, —N(CH$_3$)$_2$, —N(CH$_3$)benzyl, heteroaryl, heterocycloalkyl, phenyl, or benzyl, where n is 0, 1, 2 or 3; or, alternatively, both R$^b$ come together to form a 4-15-membered, monocyclic, bicyclic or tricyclic ring, optionally containing up to 3 additional heteroatoms each independently selected from O (oxygen), N (nitrogen) and S (sulfur), said 4-15-membered monocyclic, bicyclic or tricyclic ring optionally substituted with up to 4 substituents each independently selected from the group consisting of: halo, —C$_{1-6}$alkyl, —C$_{1-6}$haloalkyl, —C$_{1-6}$haloalkyl-C$_{3-7}$cycloalkyl, —C$_{3-7}$cycloalkyl, bicyclo[2.2.1]heptane, —C$_{1-6}$alkyl-OH, —C(CH$_3$)$_2$OH, —CH$_2$OC$_{1-6}$alkyl, —CH$_2$C(O)OCH$_2$CH$_3$, —CH$_2$CH$_2$OC$_{1-6}$alkyl, —CH$_2$CH$_2$OC$_{1-6}$haloalkyl, —CH$_2$CH$_2$C(O)OCH$_3$, —OH, —OC$_{1-6}$alkyl, —OCH$_2$—C$_{3-7}$cycloalkyl, —OCH$_2$CH$_2$OCH$_3$, =O, —CH$_2$N(CH$_3$)$_2$, —CH$_2$CH$_2$N(CH$_3$)$_2$, —C(O)C$_{1-6}$alkyl, —C(O)H, —C(O)OH, —C(O)OC$_{1-6}$alkyl, —C(O)CH$_3$, —C(O)NH$_2$, —C(O)NHCH$_3$, —C(O)N(CH$_3$)$_2$, —CN, —NH$_2$, —NHC(O)CH$_3$, —N(CH$_3$)$_2$, —SO$_2$CH$_3$, oxetane, pyrrolidine, morpholine, furan, thiazole, pyridyl, phenyl, thiophene, —CH$_2$imidazole, —CH$_2$furan, —CH$_2$-thiophene, —CH$_2$pyridyl, benzyl, —C(O)-tetrahydrofuran, —C(O)pyrrole or —C(O)phenyl.

17. A compound as in claim 16, or pharmaceutically acceptable salt thereof, wherein W is selected from the group consisting of: halo, —C$_{1-6}$alkyl, —C$_{1-6}$haloalkyl, —CH$_2$OC$_{1-5}$alkyl, —CH$_2$OH, —CH$_2$CH$_2$OH, —CH$_2$CH$_2$OCH$_3$, —C(O)C$_{1-6}$alkyl, —C(O)C$_{3-7}$cycloalkyl, —C(O)OC$_{1-4}$alkyl, —C$_{3-7}$cycloalkyl, said —C$_{3-7}$cycloalkyl optionally substituted with one or more halo or —C$_{1-6}$alkyl, optionally substituted —C$_{1-6}$aryl, optionally substituted —C$_{1-6}$heteroaryl, —OH, —OC$_{1-6}$alkyl, —OCH$_2$CH$_2$OCH$_3$, —OCH$_2$C(O)N(CH$_3$)$_2$, —O-tetrahydropyranyl, —Opiperidinyl, and —N(R$^b$)$_2$, where each R$^b$ is independently selected from the group consisting of: —H, —C$_{1-6}$alkyl, —C$_{1-6}$alkyl-OH, —C$_{1-6}$haloalkyl, —C$_{1-6}$haloalkylOH, —C$_{1-6}$haloalkyl-C$_{3-7}$cycloalkyl, —C$_{3-7}$cycloalkyl, —CH$_2$-alkenyl, —CH$_2$-alkynyl, —CH$_2$C$_{3-7}$cycloalkyl, —CH$_2$C(O)C(CH$_3$)$_3$, —CH$_2$C(O)C$_{1-6}$alkyl, —CH$_2$C(O)piperidine, —CH$_2$C(O)OC$_{1-6}$alkyl, —CH$_2$C(O)N(C$_{1-4}$alkyl)$_2$, —CH$_2$CH(OH)C$_{3-7}$cycloalkyl, —C(CH$_3$)$_2$OH, —C(CH$_3$)$_2$CH$_2$OCH$_3$, —CH(CH$_3$)C(O)N(C$_{1-4}$alkyl)$_2$, —CH$_2$CF$_2$C$_{3-7}$cycloalkyl, —CH$_2$CH$_{2-12}$c, where R$^c$ is —C$_{2-6}$alkynyl, —C$_{3-7}$cycloalkyl, —OH, —O—C$_{1-6}$alkyl, —OC(CH$_3$)$_2$, —O—C$_{1-6}$haloalkyl, —Ophenyl, —Opyridyl, —CH$_2$N(CH$_3$)$_2$, —C(O)NHCH$_3$, —C(O)N(CH$_3$)$_2$, —CN, —NHCH$_3$, —N(CH$_3$)$_2$, —NHC(O)CH$_3$, or —SO$_2$CH$_3$, and —(CH$_2$)$_n$—R$^d$, where R$^d$ is cyclopropyl, cyclobutyl, cyclopentyl, cyclohexyl, bicyclo[1.1.1]pentane, bicyclo[3.1.0]hexane, —C$_{3-7}$halocycloalkyl, oxetane, pyrrolidine, pyrrolidinone, piperidine, piperidinone, tetrahydropyranyl, tetrahydrofuranyl, oxepane, morpholine, 3-azabicyclo[3.1.0]hexane, tetrahydrothiophene-1,1-dioxide, tetrahydro-2H-thiopyran-1,1-dioxide, thiomorpholine-1,1-dioxide, tetrahydrothiophene-1,1-dioxide, 1,3-dihydroisobenzofuran, benzofuran, indoline, benzodioxine, benzodioxole, phenyl, benzyl, —CH$_2$CH$_2$phenyl, —CH$_2$CH$_2$CH$_2$phenyl, furan, pyrrole, pyrazole, imidazole, triazole, isoxazole, oxazole, thiazole, pyridine, pyrimidine, thiophene, pyrrolopyridine, benzimidazole, said R$^d$ optionally substituted with up to 4 substituents each independently selected from the group consisting of: —F, —C$_{1-6}$alkyl, —C$_{1-6}$haloalkyl, cyclopropyl, —OH, —OC$_{1-6}$alkyl, —O—C$_{1-6}$haloalkyl, —O-phenyl, —O-pyridyl, —CH$_2$OH, —CH$_2$OCH$_3$, —CH$_2$OCH$_2$CH$_3$, —CN, —N(CH$_3$)$_2$, —N(CH$_3$)benzyl, heteroaryl, heterocycloalkyl, morpholine, phenyl, pyrrolidinone, hydroxypiperidine, phenyl, benzyl, imidazole, pyridine, where n is 0, 1, 2 or 3; or, alternatively, both $R^b$ come together to form a monocyclic, bicyclic or tricyclic ring selected from the group consisting of: azetidine, pyrrole, pyrrolidine, pyrrolidinone, piperazine, piperazinone, piperidine, piperidinone, azepane, morpholine, 1-oxa-8-azaspiro[4.5]decan-3-one, 2-oxa-5-azabicyclo[2.2.1]heptane, 2-oxa-7-azaspiro[3.5]nonane, 2-oxa-8-azaspiro[4.5]decane, 2-oxa-8-azaspiro[4.5]decan-1-one, 6-oxa-9-azaspiro[4.5]decane, 7-oxa-2-azaspiro[3.5]nonane, octahydropyrrolo[3,4-c]pyrrole, octahydropyrrolo[1,2-a]pyrazine, oxaazabicyclo[2.2.1]heptane, thiomorpholine-1,1-dioxide, diazepane, 2,3,4,5-tetrahydropyrido[2,3-f][1,4]oxazepine, 5,6,7,8-tetrahydro[1,2,4]triazolo[4,3-a]pyrazine, 5,6,7,8-tetrahydroimidazo [1,2-a]pyrazine, 5,6,7,8-tetrahydropyrido[3,4-d]pyridazin-1(2H)-one, azaspiro[2.5]octane, azabicyclo[3.1.0]hexane, azabicyclo[4.1.0]heptane, diazaspiro[5.5]undecane, tetrahydroimidazopyrazine, dihydropyrrolopyridine, spiro[chroman-2,3'-pyrrolidin]-4-one, spiro[isochroman-1,4'-piperidine], 6',7'-dihydro-5'H-spiro[piperidine-4,4'-thieno[3,2-c]pyridine], 5',6'-dihydro-4'H-spiro[piperidine-4,7'-thieno[2,3-c]pyridine], said monocyclic, bicyclic or tricyclic ring optionally substituted with up to 4 substituents each independently selected from the group consisting of: halo, —$C_{1-6}$ alkyl, —$C_{1-6}$haloalkyl, —$C_{1-6}$haloalkyl-$C_{3-7}$cycloalkyl, —$C_{3-7}$cycloalkyl, bicyclo[2.2.1]heptane, —$C_{1-6}$alkyl-OH, —C($CH_3$)$_2$OH, —$CH_2$O$C_{1-6}$alkyl, —$CH_2$C(O)OCH$_2$CH$_3$, —CH$_2$CH$_2$O$C_{1-6}$alkyl, —CH$_2$CH$_2$O$C_{1-6}$haloalkyl, —CH$_2$CH$_2$C(O)OCH$_3$, —OH, —O$C_{1-6}$alkyl, —OCH$_2$—$C_{3-7}$cycloalkyl, —OCH$_2$CH$_2$OCH$_3$, =O, —CH$_2$N(CH$_3$)$_2$, —CH$_2$CH$_2$N(CH$_3$)$_2$, —C(O)$C_{1-6}$alkyl, —C(O)H, —C(O)OH, —C(O)O$C_{1-6}$alkyl, —C(O)NH$_2$, —C(O)NHCH$_3$, —C(O)N(CH$_3$)$_2$, —CN, —NH$_2$, —NHC(O)CH$_3$, —N(CH$_3$)$_2$, —SO$_2$CH$_3$, oxetane, pyrrolidine, morpholine, furan, thiazole, pyridyl, phenyl, thiophene, —CH$_2$imidazole, —CH$_2$furan, —CH$_2$-thiophene, —CH$_2$pyridyl, benzyl, —C(O)-tetrahydrofuran, —C(O)pyrrole and —C(O)phenyl.

18. A compound as in claim 16, or pharmaceutically acceptable salt thereof, wherein W is —N($R^b$)$_2$, where each $R^b$ is independently selected from the group consisting of: —H, —$C_{1-6}$alkyl, —$C_{1-6}$alkyl-OH, —$C_{1-6}$haloalkyl, —$C_{1-6}$haloalkylOH, —$C_{1-6}$haloalkyl-$C_{3-7}$cycloalkyl, —$C_{3-7}$cycloalkyl, —CH$_2$-alkenyl, —CH$_2$-alkynyl, —CH$_2$$C_{3-7}$cycloalkyl, —CH$_2$C(O)C(CH$_3$)$_3$, —CH$_2$C(O)$C_{1-6}$alkyl, —CH$_2$C(O)piperidine, —CH$_2$C(O)O$C_{1-6}$alkyl, —CH$_2$C(O)N($C_{1-4}$alkyl)$_2$, —CH$_2$CH(OH)$C_{3-7}$cycloalkyl, —C(CH$_3$)$_2$OH, —C(CH$_3$)$_2$CH$_2$OCH$_3$, —CH(CH$_3$)C(O)N($C_{1-4}$alkyl)$_2$, —CH$_2$CF$_2$$C_{3-7}$cycloalkyl, —CH$_2$CH$_2$—$R^c$, where $R^c$ is —$C_{2-6}$alkynyl, —$C_{3-7}$cycloalkyl, —OH, —O—$C_{1-6}$alkyl, —OC(CH$_3$)$_2$, —O—$C_{1-6}$haloalkyl, —Ophenyl, —Opyridyl, —CH$_2$N(CH$_3$)$_2$, —C(O)NHCH$_3$, —C(O)N(CH$_3$)$_2$, —CN, —NHCH$_3$, —N(CH$_3$)$_2$, —NHC(O)CH$_3$, or —SO$_2$CH$_3$, and —(CH$_2$)$_n$—$R^d$, where $R^d$ is cyclopropyl, cyclobutyl, cyclopentyl, cyclohexyl, bicyclo[1.1.1]pentane, bicyclo[3.1.0]hexane, —$C_{3-7}$halocycloalkyl, oxetane, pyrrolidine, pyrrolidinone, piperidine, piperidinone, tetrahydropyranyl, tetrahydrofuranyl, oxepane, morpholine, 3-azabicyclo[3.1.0]hexane, tetrahydrothiophene-1,1-dioxide, tetrahydro-2H-thiopyran-1,1-dioxide, thiomorpholine-1,1-dioxide, tetrahydrothiophene-1,1-dioxide, 1,3-dihydroisobenzofuran, benzofuran, indoline, benzodioxine, benzodioxole, phenyl, benzyl, —CH$_2$CH$_2$phenyl, —CH$_2$CH$_2$CH$_2$phenyl, furan, pyrrole, pyrazole, imidazole, triazole, isoxazole, oxazole, thiazole, pyridine, pyrimidine, thiophene, pyrrolopyridine, benzimidazole, said $R^d$ optionally substituted with up to 4 substituents each independently selected from the group consisting of: —F, —$C_{1-6}$alkyl, —$C_{1-6}$haloalkyl, cyclopropyl, —OH, —O$C_{1-6}$alkyl, —O—$C_{1-6}$haloalkyl, —O— phenyl, —O-pyridyl, —CH$_2$OH, —CH$_2$OCH$_3$, —CH$_2$OCH$_2$CH$_3$, —CN, —N(CH$_3$)$_2$, —N(CH$_3$)benzyl, heteroaryl, heterocycloalkyl, morpholine, pyrrolidinone, hydroxypiperidine, phenyl, benzyl, imidazole, or pyridine, where n is 0, 1, 2 or 3.

19. A compound as in claim 16, or pharmaceutically acceptable salt thereof, wherein W is —N($R^b$)$_2$, where both $R^b$ come together to form a monocyclic, bicyclic or tricyclic ring selected from the group consisting of: azetidine, pyrrole, pyrrolidine, pyrrolidinone, piperazine, piperazinone, piperidine, piperidinone, azepane, morpholine, 1-oxa-8-azaspiro[4.5]decan-3-one, 2-oxa-5-azabicyclo[2.2.1]heptane, 2-oxa-7-azaspiro[3.5]nonane, 2-oxa-8-azaspiro[4.5]decane, 2-oxa-8-azaspiro[4.5]decan-1-one, 6-oxa-9-azaspiro[4.5]decane, 7-oxa-2-azaspiro[3.5]nonane, octahydropyrrolo[3,4-c]pyrrole, octahydropyrrolo[1,2-a]pyrazine, oxaazabicyclo[2.2.1]heptane, thiomorpholine-1,1-dioxide, diazepane, 2,3,4,5-tetrahydropyrido[2,3-f][1,4]oxazepine, 5,6,7,8-tetrahydro[1,2,4]triazolo[4,3-a]pyrazine, 5,6,7,8-tetrahydroimidazo [1,2-a]pyrazine, 5,6,7,8-tetrahydropyrido[3,4-d]pyridazin-1(2H)-one, azaspiro[2.5]octane, azabicyclo[3.1.0]hexane, azabicyclo[4.1.0]heptane, diazaspiro[5.5]undecane, tetrahydroimidazopyrazine, dihydropyrrolopyridine, spiro[chroman-2,3'-pyrrolidin]-4-one, spiro[isochroman-1,4'-piperidine], 6',7'-dihydro-5'H-spiro [piperidine-4,4'-thieno[3,2-c]pyridine], and 5',6'-dihydro-4'H-spiro[piperidine-4,7'-thieno[2,3-c]pyridine], said monocyclic, bicyclic or tricyclic ring optionally substituted with up to 4 substituents each independently selected from the group consisting of: halo, —$C_{1-6}$alkyl, —$C_{1-6}$haloalkyl, —$C_{1-6}$haloalkyl-$C_{3-7}$cycloalkyl, —$C_{3-7}$cycloalkyl, bicyclo[2.2.1]heptane, —$C_{1-6}$alkyl-OH, —C(CH$_3$)$_2$OH, —CH$_2$O$C_{1-6}$alkyl, —CH$_2$C(O)OCH$_2$CH$_3$, —CH$_2$CH$_2$O$C_{1-6}$ alkyl, —CH$_2$CH$_2$O$C_{1-6}$haloalkyl, —CH$_2$CH$_2$C(O)OCH$_3$, —OH, —O$C_{1-6}$alkyl, —OCH$_2$—$C_{3-7}$cycloalkyl, —OCH$_2$CH$_2$OCH$_3$, =O, —CH$_2$N(CH$_3$)$_2$, —CH$_2$CH$_2$N(CH$_3$)$_2$, —C(O)$C_{1-6}$alkyl, —C(O)H, —C(O)OH, —C(O)O$C_{1-6}$alkyl, —C(O)CH$_3$, —C(O)NH$_2$, —C(O)NHCH$_3$, —C(O)N(CH$_3$)$_2$, —CN, —NH$_2$, —NHC(O)CH$_3$, —N(CH$_3$)$_2$, —SO$_2$CH$_3$, oxetane, pyrrolidine, morpholine, furan, thiazole, pyridyl, phenyl, thiophene, —CH$_2$imidazole, —CH$_2$furan, —CH$_2$-thiophene, —CH$_2$pyridyl, benzyl, —C(O)-tetrahydrofuran, —C(O)pyrrole, or —C(O)phenyl.

20. A compound as in claim 1, or pharmaceutically acceptable salt thereof, wherein W is selected from the group consisting of: halo, —$C_{1-6}$alkyl, —$C_{1-6}$haloalkyl, —CH$_2$O$C_{1-5}$alkyl, —CH$_2$OH, —CH$_2$CH$_2$OH, —CH$_2$CH$_2$OCH$_3$, —C(O)$C_{1-6}$alkyl, —C(O)$C_{3-7}$cycloalkyl, —C(O)O$C_{1-4}$alkyl, —$C_{3-7}$cycloalkyl, said —$C_{3-7}$cycloalkyl optionally substituted with one or more halo or —$C_{1-6}$alkyl, optionally substituted —$C_{1-6}$aryl, optionally substituted —$C_{1-6}$heteroaryl, —OH, —O$C_{1-6}$alkyl, —OCH$_2$CH$_2$OCH$_3$, —OCH$_2$C(O)N(CH$_3$)$_2$, —O— tetrahydropyranyl, —Opiperidinyl, and —N($R^b$)$_2$, where each $R^b$ is independently selected from the group consisting of: —H, —$C_{1-6}$alkyl, —$C_{1-6}$alkyl-OH, —$C_{1-6}$haloalkyl, —$C_{1-6}$haloalkylOH, —$C_{1-6}$haloalkyl-$C_{3-7}$cycloalkyl, —$C_{3-7}$cycloalkyl, —CH$_2$-alkenyl, —CH$_2$-alkynyl, —CH$_2$$C_{3-7}$cycloalkyl, —CH$_2$C(O)C(CH$_3$)$_3$, —CH$_2$C(O)$C_{1-6}$alkyl, —CH$_2$C(O)heterocycloalkyl, —CH$_2$C(O)O$C_{1-6}$alkyl, —CH$_2$C(O)N($C_{1-4}$alkyl)$_2$, —CH$_2$CH(OH)$C_{3-7}$cycloalkyl, —C(CH$_3$)$_2$OH, —C(CH$_3$)$_2$CH$_2$OCH$_3$, —CH(CH$_3$)C(O)N($C_{1-4}$alkyl)$_2$, —CH$_2$CF$_2$$C_{3-7}$cycloalkyl, —CH$_2$CH$_2$—$R^c$, where $R^c$ is —$C_{2-6}$alkynyl, —$C_{3-7}$cycloalkyl, —OH, —O—$C_{1-6}$alkyl, —OC(CH$_3$)$_2$, —O—$C_{1-6}$haloalkyl, —Ophenyl, —Opyridyl, —CH$_2$N(CH$_3$)$_2$, —C(O)NHCH$_3$, —C(O)N(CH$_3$)$_2$, —CN, —NHCH$_3$, —N(CH$_3$)$_2$, —NHC(O)CH$_3$, or —SO$_2$CH$_3$, and —(CH$_2$)$_n$—R$^d$, where R$^d$ is —$C_{3-7}$cycloalkyl, —$C_{3-7}$halocycloalkyl, heterocycloalkyl, aryl, and heteroaryl, each optionally substituted with up to 4 substituents each independently selected from the group consisting of: halo, —$C_{1-6}$alkyl, —$C_{1-6}$haloalkyl, —$C_{3-7}$cycloalkyl, —OH, —OC$_{1-6}$alkyl, —O—$C_{1-6}$haloalkyl, —O-phenyl, —O-pyridyl, —CH$_2$OH, —CH$_2$OCH$_3$, —CH$_2$OCH$_2$CH$_3$, —CN, —N(CH$_3$)$_2$, —N(CH$_3$)benzyl, heteroaryl, heterocycloalkyl, phenyl, or benzyl, where n is 0, 1, 2 or 3; or, alternatively, both R$^b$ come together to form a 4-15-membered, monocyclic, bicyclic or tricyclic ring, optionally containing up to 3 additional heteroatoms each independently selected from O (oxygen), N (nitrogen) and S (sulfur), said 4-15-membered monocyclic, bicyclic or tricyclic ring optionally substituted with up to 4 substituents each independently selected from the group consisting of: halo, —$C_{1-6}$alkyl, —$C_{1-6}$haloalkyl, —$C_{1-6}$haloalkyl-$C_{3-7}$cycloalkyl, —$C_{3-7}$cycloalkyl, -bicyclo[2.2.1]heptane, —$C_{1-6}$alkyl-OH, —C(CH$_3$)$_2$OH, —CH$_2$OC$_{1-6}$alkyl, —CH$_2$C(O)OCH$_2$CH$_3$, —CH$_2$CH$_2$OC$_{1-6}$alkyl, —CH$_2$CH$_2$OC$_{1-6}$haloalkyl, —CH$_2$CH$_2$C(O)OCH$_3$, —OH, —OC$_{1-6}$alkyl, —OCH$_2$—$C_{3-7}$cycloalkyl, —OCH$_2$CH$_2$OCH$_3$, =O, —CH$_2$N(CH$_3$)$_2$, —CH$_2$CH$_2$N(CH$_3$)$_2$, —C(O)C$_{1-6}$alkyl, —C(O)H, —C(O)OH, —C(O)OC$_{1-6}$alkyl, —C(O)CH$_3$, —C(O)NH$_2$, —C(O)NHCH$_3$, —C(O)N(CH$_3$)$_2$, —CN, —NH$_2$, —NHC(O)CH$_3$, —N(CH$_3$)$_2$, —SO$_2$CH$_3$, oxetane, pyrrolidine, morpholine, furan, thiazole, pyridyl, phenyl, thiophene, —CH$_2$imidazole, —CH$_2$furan, —CH$_2$-thiophene, —CH$_2$pyridyl, benzyl, —C(O)-tetrahydrofuran, —C(O)pyrrole, or —C(O)phenyl.

21. A compound as in claim 20, or pharmaceutically acceptable salt thereof, wherein W is selected from the group consisting of: halo, —$C_{1-6}$alkyl, —$C_{1-6}$haloalkyl, —CH$_2$OC$_{1-5}$alkyl, —CH$_2$OH, —CH$_2$CH$_2$OH, —CH$_2$CH$_2$OCH$_3$, —C(O)C$_{1-6}$alkyl, —C(O)C$_{3-7}$cycloalkyl, —C(O)OC$_{1-4}$alkyl, —$C_{3-7}$cycloalkyl, said —$C_{3-7}$cycloalkyl optionally substituted with one or more halo or —$C_{1-6}$alkyl, optionally substituted —$C_{1-6}$aryl, optionally substituted —$C_{1-6}$heteroaryl, —OH, —OC$_{1-6}$alkyl, —OCH$_2$CH$_2$OCH$_3$, —OCH$_2$C(O)N(CH$_3$)$_2$, —O-tetrahydropyranyl, —Opiperidinyl, and —N(R$^b$)$_2$ where each R$^b$ is independently selected from the group consisting of: —H, —$C_{1-6}$alkyl, —$C_{1-6}$alkyl-OH, —$C_{1-6}$halo alkyl, —$C_{1-6}$haloalkylOH, —$C_{1-6}$haloalkyl-$C_{3-7}$cycloalkyl, —$C_{3-7}$cycloalkyl, —CH$_2$-alkenyl, —CH$_2$-alkynyl, —CH$_2$C$_{3-7}$cycloalkyl, —CH$_2$C(O)C(CH$_3$)$_3$, —CH$_2$C(O)C$_{1-6}$alkyl, —CH$_2$C(O)piperidine, —CH$_2$C(O)OC$_{1-6}$alkyl, —CH$_2$C(O)N(C$_{1-4}$alkyl)$_2$, —CH$_2$CH(OH)C$_{3-7}$cycloalkyl, —C(CH$_3$)$_2$OH, —C(CH$_3$)$_2$CH$_2$OCH$_3$, —CH(CH$_3$)C(O)N(C$_{1-4}$alkyl)$_2$, —CH$_2$CF$_2$C$_{3-7}$cycloalkyl, —CH$_2$CH$_2$—R$^c$, where R$^c$ is —$C_{2-6}$alkynyl, —$C_{3-7}$cycloalkyl, —OH, —O—$C_{1-6}$alkyl, —OC(CH$_3$)$_2$, —O—$C_{1-6}$haloalkyl, —Ophenyl, —Opyridyl, —CH$_2$N(CH$_3$)$_2$, —C(O)NHCH$_3$, —C(O)N(CH$_3$)$_2$, —CN, —NHCH$_3$, —N(CH$_3$)$_2$, —NHC(O)CH$_3$, or —SO$_2$CH$_3$, and —(CH$_2$)$_n$—R$^d$, where R$^d$ is cyclopropyl, cyclobutyl, cyclopentyl, cyclohexyl, bicyclo[1.1.1]pentane, bicyclo[3.1.0]hexane), —$C_{3-7}$halocycloalkyl, oxetane, pyrrolidine, pyrrolidinone, piperidine, piperidinone, tetrahydropyranyl, tetrahydrofuranyl, oxepane, morpholine, 3-azabicyclo[3.1.0]hexane, tetrahydrothiophene-1,1-dioxide, tetrahydro-2H-thiopyran-1,1-dioxide, thiomorpholine-1,1-dioxide, tetrahydrothiophene-1,1-dioxide, 1,3-dihydroisobenzofuran, benzofuran, indoline, benzodioxine, benzodioxole, phenyl, benzyl, —CH$_2$CH$_2$phenyl, —CH$_2$CH$_2$CH$_2$phenyl, furan, pyrrole, pyrazole, imidazole, triazole, isoxazole, oxazole, thiazole, pyridine, pyrimidine, thiophene, pyrrolopyridine, benzimidazole, said R$^d$ optionally substituted with up to 4 substituents each independently selected from the group consisting of: —F, —$C_{1-6}$alkyl, —$C_{1-6}$haloalkyl, cyclopropyl, —OH, —OC$_{1-6}$alkyl, —O—$C_{1-6}$haloalkyl, —O-phenyl, —O-pyridyl, —CH$_2$OH, —CH$_2$OCH$_3$, —CH$_2$OCH$_2$CH$_3$, —CN, —N(CH$_3$)$_2$, —N(CH$_3$)benzyl, heteroaryl, heterocycloalkyl, morpholine, pyrrolidinone, hydroxypiperidine, phenyl, benzyl, imidazole, or pyridine, where n is 0, 1, 2 or 3; or, alternatively, both R$^b$ come together to form a monocyclic, bicyclic or tricyclic ring selected from the group consisting of: azetidine, pyrrole, pyrrolidine, pyrrolidinone, piperazine, piperazinone, piperidine, piperidinone, azepane, morpholine, 1-oxa-8-azaspiro[4.5]decan-3-one, 2-oxa-5-azabicyclo[2.2.1]heptane, 2-oxa-7-azaspiro[3.5]nonane, 2-oxa-8-azaspiro[4.5]decane, 2-oxa-8-azaspiro[4.5]decan-1-one, 6-oxa-9-azaspiro[4.5]decane, 7-oxa-2-azaspiro[3.5]nonane, octahydropyrrolo[3,4-c]pyrrole, octahydropyrrolo[1,2-a]pyrazine, oxaazabicyclo[2.2.1]heptane, thiomorpholine-1,1-dioxide, diazepane, 2,3,4,5-tetrahydropyrido[2,3-f][1,4]oxazepine, 5,6,7,8-tetrahydro[1,2,4]triazolo[4,3-a]pyrazine, 5,6,7,8-tetrahydroimidazo[1,2-a]pyrazine, 5,6,7,8-tetrahydropyrido[3,4-d]pyridazin-1 (2H)-one, azaspiro[2.5]octane, azabicyclo[3.1.0]hexane, azabicyclo[4.1.0]heptane, diazaspiro[5.5]undecane, tetrahydroimidazopyrazine, dihydropyrrolopyridine, spiro[chroman-2,3'-pyrrolidin]-4-one, spiro[isochroman-1,4'-piperidine], 6',7'-dihydro-5'H-spiro[piperidine-4,4'-thieno[3,2-c]pyridine], 5',6'-dihydro-4'H-spiro[piperidine-4,7'-thieno[2,3-c]pyridine], said monocyclic, bicyclic or tricyclic ring optionally substituted with up to 4 substituents each independently selected from the group consisting of: halo, —$C_{1-6}$ alkyl, —$C_{1-6}$haloalkyl, —$C_{1-6}$haloalkyl-$C_{3-7}$cycloalkyl, —$C_{3-7}$cycloalkyl, bicyclo[2.2.1]heptane, —$C_{1-6}$alkyl-OH, —C(CH$_3$)$_2$OH, —CH$_2$OC$_{1-6}$alkyl, —CH$_2$C(O)OCH$_2$CH$_3$, —CH$_2$CH$_2$OC$_{1-6}$alkyl, —CH$_2$CH$_2$OC$_{1-6}$haloalkyl, —CH$_2$CH$_2$C(O)OCH$_3$, —OH, —OC$_{1-6}$alkyl, —OCH$_2$—$C_{3-7}$cycloalkyl, —OCH$_2$CH$_2$OCH$_3$, =O, —CH$_2$N(CH$_3$)$_2$, —CH$_2$CH$_2$N(CH$_3$)$_2$, —C(O)C$_{1-6}$alkyl, —C(O)H, —C(O)OH, —C(O)OC$_{1-6}$alkyl, —C(O)CH$_3$, —C(O)NH$_2$, —C(O)NHCH$_3$, —C(O)N(CH$_3$)$_2$, —CN, —NH$_2$, —NHC(O)CH$_3$, —N(CH$_3$)$_2$, —SO$_2$CH$_3$, oxetane, pyrrolidine, morpholine, furan, thiazole, pyridyl, phenyl, thiophene, —CH$_2$imidazole, —CH$_2$furan, —CH$_2$-thiophene, —CH$_2$pyridyl, benzyl, —C(O)-tetrahydrofuran, —C(O)pyrrole and —C(O)phenyl.

22. A compound as in claim 20, or pharmaceutically acceptable salt thereof, wherein W is —N(R$^b$)$_2$, where each R$^b$ is independently selected from the group consisting of: —H, —$C_{1-6}$alkyl, —$C_{1-6}$alkyl-OH, —$C_{1-6}$haloalkyl, —$C_{1-6}$haloalkylOH, —$C_{1-6}$haloalkyl-$C_{3-7}$cycloalkyl, —$C_{3-7}$cycloalkyl, —CH$_2$-alkenyl, —CH$_2$-alkynyl, —CH$_2$C$_{3-7}$cycloalkyl, —CH$_2$C(O)C(CH$_3$)$_3$, —CH$_2$C(O)C$_{1-6}$alkyl, —CH$_2$C(O)piperidine, —CH$_2$C(O)OC$_{1-6}$alkyl, —CH$_2$C(O)N(C$_{1-4}$alkyl)$_2$, —CH$_2$CH(OH)C$_{3-7}$cycloalkyl, —C(CH$_3$)$_2$OH, —C(CH$_3$)$_2$CH$_2$OCH$_3$, —CH(CH$_3$)C(O)N(C$_{1-4}$alkyl)$_2$, —CH$_2$CF$_2$C$_{3-7}$cycloalkyl, —CH$_2$CH$_2$—R$^c$, where R$^c$ is —$C_{2-6}$alkynyl, —$C_{3-7}$cycloalkyl, —OH, —O—$C_{1-6}$alkyl, —OC(CH$_3$)$_2$, —O—$C_{1-6}$haloalkyl, —Ophenyl, —Opyridyl, —CH$_2$N(CH$_3$)$_2$, —C(O)NHCH$_3$, —C(O)N(CH$_3$)$_2$, —CN, —NHCH$_3$, —N(CH$_3$)$_2$, —NHC(O)CH$_3$, or —SO$_2$CH$_3$, and —(CH$_2$)$_n$—R$^d$, where R$^d$ is cyclopropyl, cyclobutyl, cyclopentyl, cyclohexyl, bicyclo[1.1.1]pentane, bicyclo[3.1.0]hexane, —$C_{3-7}$halocycloalkyl, oxetane, pyrrolidine, pyrrolidinone, piperidine, piperidinone, tetrahydropyranyl, tetrahydrofuranyl, oxepane, morpholine, 3-azabicyclo[3.1.0]hexane, tetrahydrothiophene-1,1-dioxide, tetrahydro-2H-thiopyran-1,1-dioxide, thiomorpholine-1,1-dioxide, tetrahydrothiophene-1,1-dioxide, 1,3-dihydroisobenzofuran, benzofuran, indoline, benzodioxine, benzodioxole, phenyl, benzyl, —CH$_2$CH$_2$phenyl, —CH$_2$CH$_2$CH$_2$phenyl, furan, pyrrole, pyrazole, imidazole, triazole, isoxazole, oxazole, thiazole, pyridine, pyrimidine, thiophene, pyrrolopyridine, benzimidazole, said R$^d$ optionally substituted with up to 4 substituents each independently selected from the group consisting of: —F, —C$_{1-6}$alkyl, —C$_{1-6}$haloalkyl, cyclopropyl, —OH, —OC$_{1-6}$alkyl, —O—C$_{1-6}$haloalkyl, —O-phenyl, —O-pyridyl, —CH$_2$OH, —CH$_2$OCH$_3$, —CH$_2$OCH$_2$CH$_3$, —CN, —N(CH$_3$)$_2$, —N(CH$_3$)benzyl, heteroaryl, heterocycloalkyl, morpholine, pyrrolidinone, hydroxypiperidine, phenyl, benzyl, imidazole, or pyridine, where n is 0, 1, 2 or 3.

23. A compound as in claim 20, or pharmaceutically acceptable salt thereof, wherein W is —N(R$^b$)$_2$, where both R$^b$ come together to form a monocyclic, bicyclic or tricyclic ring selected from the group consisting of: azetidine, pyrrole, pyrrolidine, pyrrolidinone, piperazine, piperazinone, piperidine, piperidinone, azepane, morpholine, 1-oxa-8-azaspiro[4.5]decan-3-one, 2-oxa-5-azabicyclo[2.2.1]heptane, 2-oxa-7-azaspiro[3.5]nonane, 2-oxa-8-azaspiro[4.5]decane, 2-oxa-8-azaspiro[4.5]decan-1-one, 6-oxa-9-azaspiro[4.5]decane, 7-oxa-2-azaspiro[3.5]nonane, octahydropyrrolo[3,4-c]pyrrole, octahydropyrrolo[1,2-a]pyrazine, oxaazabicyclo[2.2.1]heptane, thiomorpholine-1,1-dioxide, diazepane, 2,3,4,5-tetrahydropyrido[2,3-f][1,4]oxazepine, 5,6,7,8-tetrahydro[1,2,4]triazolo[4,3-a]pyrazine, 5,6,7,8-tetrahydroimidazo[1,2-a]pyrazine, 5,6,7,8-tetrahydropyrido[3,4-d]pyridazin-1(2H)-one, azaspiro[2.5]octane, azabicyclo[3.1.0]hexane, azabicyclo[4.1.0]heptane, diazaspiro[5.5]undecane, tetrahydroimidazopyrazine, dihydropyrrolopyridine, spiro[chroman-2,3'-pyrrolidin]-4-one, spiro[isochroman-1,4'-piperidine], 6',7'-dihydro-5'H-spiro[piperidine-4,4'-thieno[3,2-c]pyridine], and 5',6'-dihydro-4'H-spiro[piperidine-4,7'-thieno[2,3-c]pyridine], said 4-15-membered monocyclic, bicyclic or tricyclic ring optionally substituted with up to 4 substituents each independently selected from the group consisting of: halo, —C$_{1-6}$alkyl, —C$_{1-6}$haloalkyl, —C$_{1-6}$haloalkyl-C$_{3-7}$cycloalkyl, —C$_{3-7}$cycloalkyl, bicyclo[2.2.1]heptane, —C$_{1-6}$alkyl-OH, —C(CH$_3$)$_2$ OH, —CH$_2$OC$_{1-6}$alkyl, —CH$_2$C(O)OCH$_2$CH$_3$, —CH$_2$CH$_2$OC$_{1-6}$alkyl, —CH$_2$CH$_2$OC$_{1-6}$haloalkyl, —CH$_2$CH$_2$C(O)OCH$_3$, —OH, —OC$_{1-6}$alkyl, —OCH$_2$—C$_{3-7}$cycloalkyl, —OCH$_2$CH$_2$OCH$_3$, =O, —CH$_2$N(CH$_3$)$_2$, —CH$_2$CH$_2$N(CH$_3$)$_2$, —C(O)C$_{1-6}$alkyl, —C(O)H, —C(O)OH, —C(O)OC$_{1-6}$alkyl, —C(O)CH$_3$, —C(O)NH$_2$, —C(O)NHCH$_3$, —C(O)N(CH$_3$)$_2$, —CN, —NH$_2$, —NHC(O)CH$_3$, —N(CH$_3$)$_2$, —SO$_2$CH$_3$, oxetane, pyrrolidine, morpholine, furan, thiazole, pyridyl, phenyl, thiophene, —CH$_2$imidazole, —CH$_2$furan, —CH$_2$-thiophene, —CH$_2$pyridyl, benzyl, —C(O)-tetrahydrofuran, —C(O)pyrrole or —C(O)phenyl.

24. A compound selected from the group consisting of:
methyl 5-chloro-7-oxo-7,8-dihydro-6H-spiro[[1,3]oxazolo[5,4-f]quinazoline-9,1'-cyclohexane]-2-carboxylate;
5-chloro-7-oxo-7,8-dihydro-6H-spiro[[1,3]oxazolo[5,4-f]quinazoline-9,1'-cyclohexane]-2-carboxylic acid;
5-chloro-2-(chloromethyl)-7,8-dihydro-6H-spiro[[1,3]oxazolo[5,4-f]quinazoline-9,1'-cyclohexane]-7-one;
5-chloro-2-{[(2-methoxyethyl)amino]methyl}-7,8-dihydro-6H-spiro[[1,3]oxazolo[5,4-f]quinazoline-9,1'-cyclohexane]-7-one;
5-chloro-2-[(2-methoxyethoxy)methyl]-7,8-dihydro-6H-spiro[[1,3]oxazolo[5,4-f]quinazoline-9,1'-cyclohexane]-7-one;
ethyl 2-{5-chloro-7-oxo-7,8-dihydro-6H-spiro[[1,3]oxazolo[5,4f]quinazoline-9,1'-cyclohexane]-2-yl}acetate;
5-chloro-2-(4-methoxypiperidine-1-carbonyl)-7,8-dihydro-6H-spiro[[1,3]oxazolo[5,4-f]quinazoline-9,1'-cyclohexane]-7-one;
5-fluoro-2-[(3-methoxyazetidin-1-yl)methyl]-7,8-dihydro-6H-spiro[[1,3]oxazolo[5,4-f]quinazoline-9,1'-cyclohexane]-7-one;
methyl 5-chloro-4',4'-difluoro-7-oxo-7,8-dihydro-6H-spiro[[1,3]oxazolo[5,4-f]quinazoline-9,1'-cyclohexane]-2-carboxylate;
5-chloro-4',4'-difluoro-2-[(4-methylpiperazin-1-yl)methyl]-7,8-dihydro-6H-spiro[[1,3]oxazolo[5,4-f]quinazoline-9,1'-cyclohexane]-7-one;
5-chloro-4',4'-difluoro-2-methyl-7,8-dihydro-6H-spiro[[1,3]oxazolo[5,4-f]quinazoline-9,1'-cyclohexane]-7-one;
5-chloro-2,4',4'-trimethyl-7,8-dihydro-6H-spiro[[1,3]oxazolo[5,4-f]quinazoline-9,1'-cyclohexane]-7-one;
5-chloro-7,8-dihydro-6H-spiro[[1,3]oxazolo[5,4-f]quinazoline-9,1'-cyclohexane]-7-one;
5-chloro-2-methyl-7,8-dihydro-6H-spiro[[1,3]oxazolo[5,4-f]quinazoline-9,1'-cyclohexane]-7-one;
5-chloro-2-ethyl-7,8-dihydro-6H-spiro[[1,3]oxazolo[5,4-f]quinazoline-9,1'-cyclohexane]-7-one;
5-chloro-2-propyl-7,8-dihydro-6H-spiro[[1,3]oxazolo[5,4-f]quinazoline-9,1'-cyclohexane]-7-one;
5-chloro-2-(propan-2-yl)-7,8-dihydro-6H-spiro[[1,3]oxazolo[5,4-f]quinazoline-9,1'-cyclohexane]-7-one;
5-chloro-2-cyclopropyl-7,8-dihydro-6H-spiro[[1,3]oxazolo[5,4-f]quinazoline-9,1'-cyclohexane]-7-one;
5-chloro-2-(methoxymethyl)-7,8-dihydro-6H-spiro[[1,3]oxazolo[5,4-f]quinazoline-9,1'-cyclohexane]-7-one;
5-chloro-2-(hydroxymethyl)-7,8-dihydro-6H-spiro[[1,3]oxazolo[5,4-f]quinazoline-9,1'-cyclohexane]-7-one;
5-chloro-2-(2-methoxyethyl)-7,8-dihydro-6H-spiro[[1,3]oxazolo[5,4-f]quinazoline-9,1'-cyclohexane]-7-one;
5-chloro-2-(2-hydroxyethyl)-7,8-dihydro-6H-spiro[[1,3]oxazolo[5,4-f]quinazoline-9,1'-cyclohexane]-7-one;
N-[5-chloro-7-oxo-7,8-dihydro-6H-spiro[[1,3]oxazolo[5,4-f]quinazoline-9,1'-cyclohexane]-2-yl]acetamide;
2-[bis(2-methoxyethyl)amino]-5-chloro-7,8-dihydro-6H-spiro[[1,3]oxazolo[5,4-f]quinazoline-9,1'-cyclohexane]-7-one;
5-chloro-7-oxo-7,8-dihydro-6H-spiro[[1,3]oxazolo[5,4-f]quinazoline-9,1'-cyclohexane]-2-carboxamide;
5-chloro-2-[(dimethylamino)methyl]-7,8-dihydro-6H-spiro[[1,3]oxazolo[5,4-f]quinazoline-9,1'-cyclohexane]-7-one;
5-chloro-2-[(4-methylpiperazin-1-yl)methyl]-7,8-dihydro-6H-spiro[[1,3]oxazolo[5,4-f]quinazoline-9,1'-cyclohexane]-7-one;
5-chloro-2-(morpholin-4-ylmethyl)-7,8-dihydro-6H-spiro[[1,3]oxazolo[5,4-f]quinazoline-9,1'-cyclohexane]-7-one;
5-chloro-2-[(4-hydroxypiperidin-1-yl)methyl]-7,8-dihydro-6H-spiro[[1,3]oxazolo[5,4-f]quinazoline-9,1'-cyclohexane]-7-one;
5-chloro-2-[(methylamino)methyl]-7,8-dihydro-6H-spiro[[1,3]oxazolo[5,4-f]quinazoline-9,1'-cyclohexane]-7-one;
5-chloro-2-[(cyclopropylamino)methyl]-7,8-dihydro-6H-spiro[[1,3]oxazolo[5,4-f]quinazoline-9,1'-cyclohexane]-7-one;

5-chloro-2-(piperazin-1-ylmethyl)-7,8-dihydro-6H-spiro[[1,3]oxazolo[5,4-f]quinazoline-9,1'-cyclohexane]-7-one;

5-chloro-2-(pyrrolidin-1-ylmethyl)-7,8-dihydro-6H-spiro[[1,3]oxazolo[5,4-f]quinazoline-9,1'-cyclohexane]-7-one;

5-chloro-2-{[(propan-2-yl)amino]methyl}-7,8-dihydro-6H-spiro[[1,3]oxazolo[5,4-f]quinazoline-9,1'-cyclohexane]-7-one;

5-chloro-2-[(ethylamino)methyl]-7,8-dihydro-6H-spiro[[1,3]oxazolo[5,4-f]quinazoline-9,1'-cyclohexane]-7-one;

5-chloro-2-{[(2-hydroxyethyl)amino]methyl}-7,8-dihydro-6H-spiro[[1,3]oxazolo[5,4-f]quinazoline-9,1'-cyclohexane]-7-one;

5-chloro-2-[(4,4-difluoropiperidin-1-yl)methyl]-7,8-dihydro-6H-spiro[[1,3]oxazolo[5,4-f]quinazoline-9,1'-cyclohexane]-7-one;

5-chloro-2-{[(2,2,2-trifluoroethyl)amino]methyl}-7,8-dihydro-6H-spiro[[1,3]oxazolo[5,4-f]quinazoline-9,1'-cyclohexane]-7-one;

5-chloro-2-{[(2-hydroxyethyl)(methyl)amino]methyl}-7,8-dihydro-6H-spiro[[1,3]oxazolo[5,4-f]quinazoline-9,1'-cyclohexane]-7-one;

5-chloro-2-[(3,3-difluoroazetidin-1-yl)methyl]-7,8-dihydro-6H-spiro[[1,3]oxazolo[5,4-f]quinazoline-9,1'-cyclohexane]-7-one;

5-chloro-2-[(3,3-difluoropyrrolidin-1-yl)methyl]-7,8-dihydro-6H-spiro[[1,3]oxazolo[5,4-f]quinazoline-9,1'-cyclohexane]-7-one;

2-[(4-acetylpiperazin-1-yl)methyl]-5-chloro-7,8-dihydro-6H-spiro[[1,3]oxazolo[5,4-f]quinazoline-9,1'-cyclohexane]-7-one;

5-chloro-2-[(4-propanoylpiperazin-1-yl)methyl]-7,8-dihydro-6H-spiro[[1,3]oxazolo[5,4-f]quinazoline-9,1'-cyclohexane]-7-one;

5-chloro-2-{2-oxa-8-azaspiro[4.5]decan-8-ylmethyl}-7,8-dihydro-6H-spiro[[1,3]oxazolo[5,4-f]quinazoline-9,1'-cyclohexane]-7-one;

5-chloro-2-{[4-(oxetan-3-yl)piperazin-1-yl]methyl}-7,8-dihydro-6H-spiro[[1,3]oxazolo[5,4-f]quinazoline-9,1'-cyclohexane]-7-one;

2-({5-chloro-7-oxo-7,8-dihydro-6H-spiro[[1,3]oxazolo[5,4-f]quinazoline-9,1'-cyclohexane]-2-ylmethyl}amino)-N,N-dimethylacetamide;

tert-butyl 2-[({5-chloro-7-oxo-7,8-dihydro-6H-spiro[[1,3]oxazolo[5,4-f]quinazoline-9,1'-cyclohexane]-2-ylmethyl}amino)methyl]piperidine-1-carboxylate;

5-chloro-2-({[(3,5-difluoropyridin-2-yl)methyl]amino}methyl)-7,8-dihydro-6H-spiro[[1,3]oxazolo[5,4-f]quinazoline-9,1'-cyclohexane]-7-one;

5-chloro-2-{[(piperidin-2-ylmethyl)amino]methyl}-7,8-dihydro-6H-spiro[[1,3]oxazolo[5,4-f]quinazoline-9,1'-cyclohexane]-7-one;

5-chloro-2-({[2-oxo-2-(piperidin-1-yl)ethyl]amino}methyl)-7,8-dihydro-6H-spiro[[1,3]oxazolo[5,4-f]quinazoline-9,1'-cyclohexane]-7-one;

2-({5-chloro-7-oxo-7,8-dihydro-6H-spiro[[1,3]oxazolo[5,4-f]quinazoline-9,1'-cyclohexane]-2-ylmethyl}amino)-N-ethyl-N-methylacetamide;

5-chloro-2-[(4-methyl-3-oxopiperazin-1-yl)methyl]-7,8-dihydro-6H-spiro[[1,3]oxazolo[5,4-f]quinazoline-9,1'-cyclohexane]-7-one;

5-chloro-2-[(4-ethyl-3-oxopiperazin-1-yl)methyl]-7,8-dihydro-6H-spiro[[1,3]oxazolo[5,4-f]quinazoline-9,1'-cyclohexane]-7-one;

5-chloro-2-{[(pyridin-2-ylmethyl)amino]methyl}-7,8-dihydro-6H-spiro[[1,3]oxazolo[5,4-f]quinazoline-9,1'-cyclohexane]-7-one;

5-chloro-2-{[(pyrimidin-2-ylmethyl)amino]methyl}-7,8-dihydro-6H-spiro[[1,3]oxazolo[5,4-f]quinazoline-9,1'-cyclohexane]-7-one;

5-chloro-2-({[(5-methoxypyridin-3-yl)methyl]amino}methyl)-7,8-dihydro-6H-spiro[[1,3]oxazolo[5,4-f]quinazoline-9,1'-cyclohexane]-7-one;

5-chloro-2-[(2,4-dimethyl-3-oxopiperazin-1-yl)methyl]-7,8-dihydro-6H-spiro[[1,3]oxazolo[5,4-f]quinazoline-9,1'-cyclohexane]-7-one;

ethyl 1-{5-chloro-7-oxo-7,8-dihydro-6H-spiro[[1,3]oxazolo[5,4-f]quinazoline-9,1'-cyclohexane]-2-ylmethyl}piperidine-4-carboxylate;

5-chloro-2-({1-oxo-2-oxa-8-azaspiro[4.5]decan-8-yl}methyl)-7,8-dihydro-6H-spiro[[1,3]oxazolo[5,4-f]quinazoline-9,1'-cyclohexane]-7-one;

2-[(4-acetylpiperidin-1-yl)methyl]-5-chloro-7,8-dihydro-6H-spiro[[1,3]oxazolo[5,4-f]quinazoline-9,1'-cyclohexane]-7-one;

methyl 1-{5-chloro-7-oxo-7,8-dihydro-6H-spiro[[1,3]oxazolo[5,4-f]quinazoline-9,1'-cyclohexane]-2-ylmethyl}piperidine-4-carboxylate;

5-chloro-2-({[(5-fluoropyridin-2-yl)methyl]amino}methyl)-7,8-dihydro-6H-spiro[[1,3]oxazolo[5,4-f]quinazoline-9,1'-cyclohexane]-7-one;

5-chloro-2-{[3-(2-methylpropoxy)azetidin-1-yl]methyl}-7,8-dihydro-6H-spiro[[1,3]oxazolo[5,4-f]quinazoline-9,1'-cyclohexane]-7-one;

5-chloro-2-[(4-ethoxypiperidin-1-yl)methyl]-7,8-dihydro-6H-spiro[[1,3]oxazolo[5,4-f]quinazoline-9,1'-cyclohexane]-7-one;

5-chloro-2-{[4-(cyclopropylmethoxy)piperidin-1-yl]methyl}-7,8-dihydro-6H-spiro[[1,3]oxazolo[5,4-f]quinazoline-9,1'-cyclohexane]-7-one;

5-chloro-2-{[4-hydroxy-4-(trifluoromethyl)piperidin-1-yl]methyl}-7,8-dihydro-6H-spiro[[1,3]oxazolo[5,4-f]quinazoline-9,1'-cyclohexane]-7-one;

5-chloro-2-{[4-(propan-2-yloxy)piperidin-1-yl]methyl}-7,8-dihydro-6H-spiro[[1,3]oxazolo[5,4-f]quinazoline-9,1'-cyclohexane]-7-one;

5-chloro-2-[(3-fluoroazetidin-1-yl)methyl]-7,8-dihydro-6H-spiro[[1,3]oxazolo[5,4-f]quinazoline-9,1'-cyclohexane]-7-one;

5-chloro-2-[(3-methoxyazetidin-1-yl)methyl]-7,8-dihydro-6H-spiro[[1,3]oxazolo[5,4-f]quinazoline-9,1'-cyclohexane]-7-one;

5-chloro-2-{[3-(methoxymethyl)azetidin-1-yl]methyl}-7,8-dihydro-6H-spiro[[1,3]oxazolo[5,4-f]quinazoline-9,1'-cyclohexane]-7-one;

5-chloro-2-{7-oxa-2-azaspiro[3.5]nonan-2-ylmethyl}-7,8-dihydro-6H-spiro[[1,3]oxazolo[5,4-f]quinazoline-9,1'-cyclohexane]-7-one;

5-chloro-2-[(4-methoxy-4-methylpiperidin-1-yl)methyl]-7,8-dihydro-6H-spiro[[1,3]oxazolo[5,4-f]quinazoline-9,1'-cyclohexane]-7-one;

5-chloro-2-({3-oxo-1-oxa-8-azaspiro[4.5]decan-8-yl}methyl)-7,8-dihydro-6H-spiro[[1,3]oxazolo[5,4-f]quinazoline-9,1'-cyclohexane]-7-one;

2-({5-chloro-7-oxo-7,8-dihydro-6H-spiro[[1,3]oxazolo[5,4-f]quinazoline-9,1'-cyclohexane]-2-ylmethyl}(methyl)amino)-N,N-dimethylacetamide;

5-chloro-2-({[(6-methylpyridin-3-yl)methyl]amino}methyl)-7,8-dihydro-6H-spiro[[1,3]oxazolo[5,4-f]quinazoline-9,1'-cyclohexane]-7-one;

5-chloro-2-{[methyl(oxan-4-ylmethyl)amino]methyl}-7,8-dihydro-6H-spiro[[1,3]oxazolo[5,4-f]quinazoline-9,1'-cyclohexane]-7-one;

5-chloro-2-({methyl[(3-methyloxetan-3-yl)methyl]amino}methyl)-7,8-dihydro-6H-spiro[[1,3]oxazolo[5,4-f]quinazoline-9,1'-cyclohexane]-7-one;

5-chloro-2-({[(3-fluorooxetan-3-yl)methyl]amino}methyl)-7,8-dihydro-6H-spiro[[1,3]oxazolo[5,4-f]quinazoline-9,1'-cyclohexane]-7-one;

5-chloro-2-{[(oxan-4-ylmethyl)amino]methyl}-7,8-dihydro-6H-spiro[[1,3]oxazolo[5,4-f]quinazoline-9,1'-cyclohexane]-7-one;

5-chloro-2-{2-oxa-7-azaspiro[3.5]nonan-7-ylmethyl}-7,8-dihydro-6H-spiro[[1,3]oxazolo[5,4-f]quinazoline-9,1'-cyclohexane]-7-one;

5-chloro-2-({[(3-methyloxetan-3-yl)methyl]amino}methyl)-7,8-dihydro-6H-spiro[[1,3]oxazolo[5,4-f]quinazoline-9,1'-cyclohexane]-7-one;

5-chloro-2-{2-oxa-5-azabicyclo[2.2.1]heptan-5-ylmethyl}-7,8-dihydro-6H-spiro[[1,3]oxazolo[5,4-f]quinazoline-9,1'-cyclohexane]-7-one;

5-chloro-2-{[methyl(2,2,2-trifluoroethyl)amino]methyl}-7,8-dihydro-6H-spiro[[1,3]oxazolo[5,4-f]quinazoline-9,1'-cyclohexane]-7-one;

5-chloro-2-{[(oxetan-3-ylmethyl)amino]methyl}-7,8-dihydro-6H-spiro[[1,3]oxazolo[5,4-f]quinazoline-9,1'-cyclohexane]-7-one;

5-chloro-2-[(4-oxopiperidin-1-yl)methyl]-7,8-dihydro-6H-spiro[[1,3]oxazolo[5,4-f]quinazoline-9,1'-cyclohexane]-7-one;

5-chloro-2-({[(2-methoxyphenyl)methyl]amino}methyl)-7,8-dihydro-6H-spiro[[1,3]oxazolo[5,4-f]quinazoline-9,1'-cyclohexane]-7-one;

5-chloro-2-({[(2,4-dimethoxyphenyl)methyl]amino}methyl)-7,8-dihydro-6H-spiro[[1,3]oxazolo[5,4-f]quinazoline-9,1'-cyclohexane]-7-one;

5-chloro-2-{[4-(propan-2-yl)piperazin-1-yl]methyl}-7,8-dihydro-6H-spiro[[1,3]oxazolo[5,4-f]quinazoline-9,1'-cyclohexane]-7-one;

5-chloro-2-[(3,3,4-trimethylpiperazin-1-yl)methyl]-7,8-dihydro-6H-spiro[[1,3]oxazolo[5,4-f]quinazoline-9,1'-cyclohexane]-7-one;

5-chloro-2-{[2-(hydroxymethyl)piperidin-1-yl]methyl}-7,8-dihydro-6H-spiro[[1,3]oxazolo[5,4-f]quinazoline-9,1'-cyclohexane]-7-one;

5-chloro-2-({[1-(hydroxymethyl)cyclopentyl]amino}methyl)-7,8-dihydro-6H-spiro[[1,3]oxazolo[5,4-f]quinazoline-9,1'-cyclohexane]-7-one;

5-chloro-2-{[(2R)-2-(hydroxymethyl)pyrrolidin-1-yl]methyl}-7,8-dihydro-6H-spiro[[1,3]oxazolo[5,4-f]quinazoline-9,1'-cyclohexane]-7-one;

5-chloro-2-[(2-methylpiperidin-1-yl)methyl]-7,8-dihydro-6H-spiro[[1,3]oxazolo[5,4-f]quinazoline-9,1'-cyclohexane]-7-one;

5-chloro-2-{[2-(2-methylpropyl)morpholin-4-yl]methyl}-7,8-dihydro-6H-spiro[[1,3]oxazolo[5,4-f]quinazoline-9,1'-cyclohexane]-7-one;

5-chloro-2-{[(2-cyclobutyl-2,2-difluoroethyl)amino]methyl}-7,8-dihydro-6H-spiro[[1,3]oxazolo[5,4-f]quinazoline-9,1'-cyclohexane]-7-one;

5-chloro-2-[(3-ethylmorpholin-4-yl)methyl]-7,8-dihydro-6H-spiro[[1,3]oxazolo[5,4-f]quinazoline-9,1'-cyclohexane]-7-one;

5-chloro-2-{[(2-cyclohexyl-2-hydroxyethyl)amino]methyl}-7,8-dihydro-6H-spiro[[1,3]oxazolo[5,4-f]quinazoline-9,1'-cyclohexane]-7-one;

5-chloro-2-{6-oxa-9-azaspiro[4.5]decan-9-ylmethyl}-7,8-dihydro-6H-spiro[[1,3]oxazolo[5,4-f]quinazoline-9,1'-cyclohexane]-7-one;

5-chloro-2-({[1-(oxan-2-yl)ethyl]amino}methyl)-7,8-dihydro-6H-spiro[[1,3]oxazolo[5,4-f]quinazoline-9,1'-cyclohexane]-7-one;

5-chloro-2-{[(oxan-2-ylmethyl)amino]methyl}-7,8-dihydro-6H-spiro[[1,3]oxazolo[5,4-f]quinazoline-9,1'-cyclohexane]-7-one;

5-chloro-2-{[(3-methyl-2-oxobutyl)amino]methyl}-7,8-dihydro-6H-spiro[[1,3]oxazolo[5,4-f]quinazoline-9,1'-cyclohexane]-7-one;

5-chloro-2-{[(4,4-difluorocyclohexyl)amino]methyl}-7,8-dihydro-6H-spiro[[1,3]oxazolo[5,4-f]quinazoline-9,1'-cyclohexane]-7-one;

5-chloro-2-({[(1r,4r)-4-methoxycyclohexyl]amino}methyl)-7,8-dihydro-6H-spiro[[1,3]oxazolo[5,4-f]quinazoline-9,1'-cyclohexane]-7-one;

5-chloro-2-[(1R,4R)-2-oxa-5-azabicyclo[2.2.1]heptan-5-ylmethyl]-7,8-dihydro-6H-spiro[[1,3]oxazolo[5,4-f]quinazoline-9,1'-cyclohexane]-7-one;

5-chloro-2-[(1S,4S)-2-oxa-5-azabicyclo[2.2.1]heptan-5-ylmethyl]-7,8-dihydro-6H-spiro[[1,3]oxazolo[5,4-f]quinazoline-9,1'-cyclohexane]-7-one;

5-chloro-2-[(3-methoxy-3-methylazetidin-1-yl)methyl]-7,8-dihydro-6H-spiro[[1,3]oxazolo[5,4-f]quinazoline-9,1'-cyclohexane]-7-one;

5-chloro-2-[(4-methoxypiperidin-1-yl)methyl]-7,8-dihydro-6H-spiro[[1,3]oxazolo[5,4-f]quinazoline-9,1'-cyclohexane]-7-one;

5-chloro-2-{[4-(dimethylamino)piperidin-1-yl]methyl}-7,8-dihydro-6H-spiro[[1,3]oxazolo[5,4-f]quinazoline-9,1'-cyclohexane]-7-one;

5-chloro-2-({5-methyl-octahydropyrrolo[3,4-c]pyrrol-2-yl}methyl)-7,8-dihydro-6H-spiro[[1,3]oxazolo[5,4-f]quinazoline-9,1'-cyclohexane]-7-one;

5-chloro-2-{[(2R)-2-(methoxymethyl)pyrrolidin-1-yl]methyl}-7,8-dihydro-6H-spiro[[1,3]oxazolo[5,4-f]quinazoline-9,1'-cyclohexane]-7-one;

5-chloro-2-{[3-(hydroxymethyl)pyrrolidin-1-yl]methyl}-7,8-dihydro-6H-spiro[[1,3]oxazolo[5,4-f]quinazoline-9,1'-cyclohexane]-7-one;

5-chloro-2-{[(3R)-3-methoxypiperidin-1-yl]methyl}-7,8-dihydro-6H-spiro[[1,3]oxazolo[5,4-f]quinazoline-9,1'-cyclohexane]-7-one;

5-chloro-2-{[(3S)-3-methoxypiperidin-1-yl]methyl}-7,8-dihydro-6H-spiro[[1,3]oxazolo[5,4-f]quinazoline-9,1'-cyclohexane]-7-one;

5-chloro-2-{[(3R)-3-ethoxypyrrolidin-1-yl]methyl}-7,8-dihydro-6H-spiro[[1,3]oxazolo[5,4-f]quinazoline-9,1'-cyclohexane]-7-one;

5-chloro-2-{[(3R)-3-(2-hydroxypropan-2-yl)pyrrolidin-1-yl]methyl}-7,8-dihydro-6H-spiro[[1,3]oxazolo[5,4-f]quinazoline-9,1'-cyclohexane]-7-one;

5-chloro-2-{[(3R)-3-hydroxypyrrolidin-1-yl]methyl}-7,8-dihydro-6H-spiro[[1,3]oxazolo[5,4-f]quinazoline-9,1'-cyclohexane]-7-one;

5-chloro-2-({[2-(dimethylamino)ethyl](methyl)amino}methyl)-7,8-dihydro-6H-spiro[[1,3]oxazolo[5,4-f]quinazoline-9,1'-cyclohexane]-7-one;

3-({5-chloro-7-oxo-7,8-dihydro-6H-spiro[[1,3]oxazolo[5,4-f]quinazoline-9,1'-cyclohexane]-2-ylmethyl}(methyl)amino)-N,N-dimethylpropanamide;

5-chloro-2-({methyl[2-(morpholin-4-yl)ethyl]amino}methyl)-7,8-dihydro-6H-spiro[[1,3]oxazolo[5,4-f]quinazoline-9,1'-cyclohexane]-7-one;

5-chloro-2-[(3-methoxypyrrolidin-1-yl)methyl]-7,8-dihydro-6H-spiro[[1,3]oxazolo[5,4-f]quinazoline-9,1'-cyclohexane]-7-one;

5-chloro-2-{[4-(2,2,2-trifluoroethyl)piperazin-1-yl]methyl}-7,8-dihydro-6H-spiro[[1,3]oxazolo[5,4-f]quinazoline-9,1'-cyclohexane]-7-one;

methyl 2-({5-chloro-7-oxo-7,8-dihydro-6H-spiro[[1,3]oxazolo[5,4-f]quinazoline-9,1'-cyclohexane]-2-ylmethyl}(methyl)amino)acetate;

2-[(8aR)-octahydropyrrolo[1,2-a]piperazin-2-ylmethyl]-5-chloro-7,8-dihydro-6H-spiro[[1,3]oxazolo[5,4-f]quinazoline-9,1'-cyclohexane]-7-one;

5-chloro-2-{[methyl(oxan-4-yl)amino]methyl}-7,8-dihydro-6H-spiro[[1,3]oxazolo[5,4-f]quinazoline-9,1'-cyclohexane]-7-one;

methyl 1-{5-chloro-7-oxo-7,8-dihydro-6H-spiro[[1,3]oxazolo[5,4-f]quinazoline-9,1'-cyclohexane]-2-ylmethyl}piperidine-3-carboxylate;

methyl 2-({5-chloro-7-oxo-7,8-dihydro-6H-spiro[[1,3]oxazolo[5,4-f]quinazoline-9,1'-cyclohexane]-2-ylmethyl}amino)acetate;

5-chloro-2-{[(3S)-3-methoxypyrrolidin-1-yl]methyl}-7,8-dihydro-6H-spiro[[1,3]oxazolo[5,4-f]quinazoline-9,1'-cyclohexane]-7-one;

5-chloro-2-{[(oxan-3-yl)amino]methyl}-7,8-dihydro-6H-spiro[[1,3]oxazolo[5,4-f]quinazoline-9,1'-cyclohexane]-7-one;

5-chloro-2-{[(3R)-3-methoxypyrrolidin-1-yl]methyl}-7,8-dihydro-6H-spiro[[1,3]oxazolo[5,4-f]quinazoline-9,1'-cyclohexane]-7-one;

5-chloro-2-{[(3S)-3-(methoxymethyl)pyrrolidin-1-yl]methyl}-7,8-dihydro-6H-spiro[[1,3]oxazolo[5,4-f]quinazoline-9,1'-cyclohexane]-7-one;

5-chloro-2-{[(3R)-3-(methoxymethyl)pyrrolidin-1-yl]methyl}-7,8-dihydro-6H-spiro[[1,3]oxazolo[5,4-f]quinazoline-9,1'-cyclohexane]-7-one;

methyl (3R)-1-{5-chloro-7-oxo-7,8-dihydro-6H-spiro[[1,3]oxazolo[5,4-f]quinazoline-9,1'-cyclohexane]-2-ylmethyl}piperidine-3-carboxylate;

5-chloro-2-({[2-(trifluoromethoxy)ethyl]amino}methyl)-7,8-dihydro-6H-spiro[[1,3]oxazolo[5,4-f]quinazoline-9,1'-cyclohexane]-7-one;

5-chloro-2-[(4-ethylpiperazin-1-yl)methyl]-7,8-dihydro-6H-spiro[[1,3]oxazolo[5,4-f]quinazoline-9,1'-cyclohexane]-7-one;

5-chloro-2-{[3-(dimethylamino)pyrrolidin-1-yl]methyl}-7,8-dihydro-6H-spiro[[1,3]oxazolo[5,4-f]quinazoline-9,1'-cyclohexane]-7-one;

2-({5-chloro-7-oxo-7,8-dihydro-6H-spiro[[1,3]oxazolo[5,4-f]quinazoline-9,1'-cyclohexane]-2-ylmethyl}amino)-N,N-diethylacetamide;

(2S)-2-({5-chloro-7-oxo-7,8-dihydro-6H-spiro[[1,3]oxazolo[5,4-f]quinazoline-9,1'-cyclohexane]-2-ylmethyl}amino)-N,N-dimethylpropanamide;

(2R)-2-({5-chloro-7-oxo-7,8-dihydro-6H-spiro[[1,3]oxazolo[5,4-f]quinazoline-9,1'-cyclohexane]-2-ylmethyl}amino)-N,N-dimethylpropanamide;

5-chloro-2-({[2-oxo-2-(pyrrolidin-1-yl)ethyl]amino}methyl)-7,8-dihydro-6H-spiro[[1,3]oxazolo[5,4-f]quinazoline-9,1'-cyclohexane]-7-one;

5-chloro-2-{[(oxan-4-yl)amino]methyl}-7,8-dihydro-6H-spiro[[1,3]oxazolo[5,4-f]quinazoline-9,1'-cyclohexane]-7-one;

5-chloro-2-[({3-oxabicyclo[3.1.0]hexan-6-yl}amino)methyl]-7,8-dihydro-6H-spiro[[1,3]oxazolo[5,4-f]quinazoline-9,1'-cyclohexane]-7-one;

5-chloro-2-{[(oxepan-4-yl)amino]methyl}-7,8-dihydro-6H-spiro[[1,3]oxazolo[5,4-f]quinazoline-9,1'-cyclohexane]-7-one;

5-chloro-2-{[(oxolan-3-ylmethyl)amino]methyl}-7,8-dihydro-6H-spiro[[1,3]oxazolo[5,4-f]quinazoline-9,1'-cyclohexane]-7-one;

5-chloro-2-{[(3,3-difluoro-2-hydroxypropyl)amino]methyl}-7,8-dihydro-6H-spiro[[1,3]oxazolo[5,4-f]quinazoline-9,1'-cyclohexane]-7-one;

5-chloro-2-{[(4-cyclopropyloxan-4-yl)amino]methyl}-7,8-dihydro-6H-spiro[[1,3]oxazolo[5,4-f]quinazoline-9,1'-cyclohexane]-7-one;

5-chloro-2-{[(2,6-dimethyloxan-4-yl)amino]methyl}-7,8-dihydro-6H-spiro[[1,3]oxazolo[5,4-f]quinazoline-9,1'-cyclohexane]-7-one;

5-chloro-2-({[(3S)-oxan-3-yl]amino}methyl)-7,8-dihydro-6H-spiro[[1,3]oxazolo[5,4-f]quinazoline-9,1'-cyclohexane]-7-one;

5-chloro-2-({[(3S)-oxolan-3-yl]amino}methyl)-7,8-dihydro-6H-spiro[[1,3]oxazolo[5,4-f]quinazoline-9,1'-cyclohexane]-7-one;

5-chloro-2-{[(3-methyloxolan-3-yl)amino]methyl}-7,8-dihydro-6H-spiro[[1,3]oxazolo[5,4-f]quinazoline-9,1'-cyclohexane]-7-one;

5-chloro-2-({[(3R)-oxolan-3-yl]amino}methyl)-7,8-dihydro-6H-spiro[[1,3]oxazolo[5,4-f]quinazoline-9,1'-cyclohexane]-7-one;

5-chloro-2-{[4-(2-methoxyethoxy)piperidin-1-yl]methyl}-7,8-dihydro-6H-spiro[[1,3]oxazolo[5,4-f]quinazoline-9,1'-cyclohexane]-7-one;

2-[(8aS)-octahydropyrrolo[1,2-a]piperazin-2-ylmethyl]-5-chloro-7,8-dihydro-6H-spiro[[1,3]oxazolo[5,4-f]quinazoline-9,1'-cyclohexane]-7-one;

methyl (3R)-1-{5-chloro-7-oxo-7,8-dihydro-6H-spiro[[1,3]oxazolo[5,4-f]quinazoline-9,1'-cyclohexane]-2-ylmethyl}pyrrolidine-3-carboxylate;

5-chloro-2-{[4-(2,2-difluoroethyl)piperazin-1-yl]methyl}-7,8-dihydro-6H-spiro[[1,3]oxazolo[5,4-f]quinazoline-9,1'-cyclohexane]-7-one;

5-chloro-2-({[(3-methyloxolan-3-yl)methyl]amino}methyl)-7,8-dihydro-6H-spiro[[1,3]oxazolo[5,4-f]quinazoline-9,1'-cyclohexane]-7-one;

5-chloro-2-({[(3R)-oxan-3-yl]amino}methyl)-7,8-dihydro-6H-spiro[[1,3]oxazolo[5,4-f]quinazoline-9,1'-cyclohexane]-7-one;

5-chloro-2-({[(3R)-oxolan-3-ylmethyl]amino}methyl)-7,8-dihydro-6H-spiro[[1,3]oxazolo[5,4-f]quinazoline-9,1'-cyclohexane]-7-one;

5-chloro-2-{[(3-fluorooxan-4-yl)amino]methyl}-7,8-dihydro-6H-spiro[[1,3]oxazolo[5,4-f]quinazoline-9,1'-cyclohexane]-7-one;

5-chloro-2-{[(2,2-difluoro-3-hydroxypropyl)amino]methyl}-7,8-dihydro-6H-spiro[[1,3]oxazolo[5,4-f]quinazoline-9,1'-cyclohexane]-7-one;

5-chloro-2-{[(2,2-difluorocyclopentyl)amino]methyl}-7,8-dihydro-6H-spiro[[1,3]oxazolo[5,4-f]quinazoline-9,1'-cyclohexane]-7-one;

5-chloro-2-({[4-(methoxymethyl)oxan-4-yl]amino}methyl)-7,8-dihydro-6H-spiro[[1,3]oxazolo[5,4-f]quinazoline-9,1'-cyclohexane]-7-one;

5-chloro-2-({[(3S)-oxolan-3-ylmethyl]amino}methyl)-7,8-dihydro-6H-spiro[[1,3]oxazolo[5,4-f]quinazoline-9,1'-cyclohexane]-7-one;

5-chloro-4',4'-difluoro-2-[(1S,4S)-2-oxa-5-azabicyclo[2.2.1]heptan-5-ylmethyl]-7,8-dihydro-6H-spiro[[1,3]oxazolo[5,4-f]quinazoline-9,1'-cyclohexane]-7-one;

5-chloro-4',4'-difluoro-2-({[(3S)-oxolan-3-ylmethyl]amino}methyl)-7,8-dihydro-6H-spiro[[1,3]oxazolo[5,4-f]quinazoline-9,1'-cyclohexane]-7-one;

5-chloro-2-{[(1,3-oxazol-2-ylmethyl)amino]methyl}-7,8-dihydro-6H-spiro[[1,3]oxazolo[5,4-f]quinazoline-9,1'-cyclohexane]-7-one;

5-chloro-2-{[(1,3-oxazol-5-ylmethyl)amino]methyl}-7,8-dihydro-6H-spiro[[1,3]oxazolo[5,4-f]quinazoline-9,1'-cyclohexane]-7-one;

5-chloro-2-({[2-(1,2-oxazol-3-yl)ethyl]amino}methyl)-7,8-dihydro-6H-spiro[[1,3]oxazolo[5,4-f]quinazoline-9,1'-cyclohexane]-7-one;

5-chloro-2-{[(1,3-oxazol-4-ylmethyl)amino]methyl}-7,8-dihydro-6H-spiro[[1,3]oxazolo[5,4-f]quinazoline-9,1'-cyclohexane]-7-one;

5-chloro-2-({[(1-methyl-1H-pyrazol-3-yl)methyl]amino}methyl)-7,8-dihydro-6H-spiro[[1,3]oxazolo[5,4-f]quinazoline-9,1'-cyclohexane]-7-one;

5-chloro-2-{[(1,2-oxazol-5-ylmethyl)amino]methyl}-7,8-dihydro-6H-spiro[[1,3]oxazolo[5,4-f]quinazoline-9,1'-cyclohexane]-7-one;

2-{5-chloro-7-oxo-7,8-dihydro-6H-spiro[[1,3]oxazolo[5,4-f]quinazoline-9,1'-cyclohexane]-2-ylmethoxy}-N,N-dimethylacetamide;

5-chloro-2-[(oxan-4-yloxy)methyl]-7,8-dihydro-6H-spiro[[1,3]oxazolo[5,4-f]quinazoline-9,1'-cyclohexane]-7-one;

5-chloro-2-{[(1-methylpiperidin-4-yl)oxy]methyl}-7,8-dihydro-6H-spiro[[1,3]oxazolo[5,4-f]quinazoline-9,1'-cyclohexane]-7-one;

5-chloro-N-[2-(dimethylamino)ethyl]-7-oxo-7,8-dihydro-6H-spiro[[1,3]oxazolo[5,4-f]quinazoline-9,1'-cyclohexane]-2-carboxamide;

5-chloro-2-(morpholine-4-carbonyl)-7,8-dihydro-6H-spiro[[1,3]oxazolo[5,4-f]quinazoline-9,1'-cyclohexane]-7-one;

5-chloro-N,N-dimethyl-7-oxo-7,8-dihydro-6H-spiro[[1,3]oxazolo[5,4-f]quinazoline-9,1'-cyclohexane]-2-carboxamide;

5-chloro-2-(4-methylpiperazine-1-carbonyl)-7,8-dihydro-6H-spiro[[1,3]oxazolo[5,4-f]quinazoline-9,1'-cyclohexane]-7-one;

5-chloro-N-(2-methoxyethyl)-7-oxo-7,8-dihydro-6H-spiro[[1,3]oxazolo[5,4-f]quinazoline-9,1'-cyclohexane]-2-carboxamide;

5-chloro-2-[(1S,4S)-2-oxa-5-azabicyclo[2.2.1]heptane-5-carbonyl]-7,8-dihydro-6H-spiro[[1,3]oxazolo[5,4-f]quinazoline-9,1'-cyclohexane]-7-one;

5-chloro-N-(2-methoxyethyl)-N-methyl-7-oxo-7,8-dihydro-6H-spiro[[1,3]oxazolo[5,4-f]quinazoline-9,1'-cyclohexane]-2-carboxamide;

5-chloro-N-methyl-N-(oxan-4-ylmethyl)-7-oxo-7,8-dihydro-6H-spiro[[1,3]oxazolo[5,4-f]quinazoline-9,1'-cyclohexane]-2-carboxamide;

5-chloro-2-[(3R)-3-ethoxypyrrolidine-1-carbonyl]-7,8-dihydro-6H-spiro[[1,3]oxazolo[5,4-f]quinazoline-9,1'-cyclohexane]-7-one;

2-{1-5-chloro-7-oxo-7,8-dihydro-6H-spiro[[1,3]oxazolo[5,4-f]quinazoline-9,1'-cyclohexane]-2-yl-N-methylformamido}-N,N-dimethylacetamide;

3-{1-5-chloro-7-oxo-7,8-dihydro-6H-spiro[[1,3]oxazolo[5,4-f]quinazoline-9,1'-cyclohexane]-2-yl-N-methylformamido}-N,N-dimethylpropanamide;

5-chloro-2-[(2S)-2-(methoxymethyl)pyrrolidine-1-carbonyl]-7,8-dihydro-6H-spiro[[1,3]oxazolo[5,4-f]quinazoline-9,1'-cyclohexane]-7-one;

methyl 2-{1-5-chloro-7-oxo-7,8-dihydro-6H-spiro[[1,3]oxazolo[5,4-f]quinazoline-9,1'-cyclohexane-2-yl-N-methylformamido}acetate;

5-chloro-N-methyl-N-[2-(methylamino)ethyl]-7-oxo-7,8-dihydro-6H-spiro[[1,3]oxazolo[5,4-f]quinazoline-9,1'-cyclohexane]-2-carboxamide;

5-chloro-N-[2-(dimethylamino)ethyl]-N-methyl-7-oxo-7,8-dihydro-6H-spiro[[1,3]oxazolo[5,4-f]quinazoline-9,1'-cyclohexane]-2-carboxamide;

5-chloro-2-[4-(dimethylamino)piperidine-1-carbonyl]-7,8-dihydro-6H-spiro[[1,3]oxazolo[5,4-f]quinazoline-9,1'-cyclohexane]-7-one;

5-chloro-2-[4-(2,2,2-trifluoroethyl)piperazine-1-carbonyl]-7,8-dihydro-6H-spiro[[1,3]oxazolo[5,4-f]quinazoline-9,1'-cyclohexane]-7-one;

5-chloro-2-[4-(2-methoxyethyl)piperazine-1-carbonyl]-7,8-dihydro-6H-spiro[[1,3]oxazolo[5,4-f]quinazoline-9,1'-cyclohexane]-7-one;

2-[(8aR)-octahydropyrrolo[1,2-a]piperazine-2-carbonyl]-5-chloro-7,8-dihydro-6H-spiro[[1,3]oxazolo[5,4-f]quinazoline-9,1'-cyclohexane]-7-one;

5-chloro-N-methyl-N-(oxan-4-yl)-7-oxo-7,8-dihydro-6H-spiro[[1,3]oxazolo[5,4-f]quinazoline-9,1'-cyclohexane]-2-carboxamide;

5-chloro-2-(3-methoxypyrrolidine-1-carbonyl)-7,8-dihydro-6H-spiro[[1,3]oxazolo[5,4-f]quinazoline-9,1'-cyclohexane]-7-one;

5-chloro-2-[(3R)-3-methoxypiperidine-1-carbonyl]-7,8-dihydro-6H-spiro[[1,3]oxazolo[5,4-f]quinazoline-9,1'-cyclohexane]-7-one;

5-chloro-N-(oxan-3-yl)-7-oxo-7,8-dihydro-6H-spiro[[1,3]oxazolo[5,4-f]quinazoline-9,1'-cyclohexane]-2-carboxamide;

5-chloro-2-[(3S)-3-methoxypyrrolidine-1-carbonyl]-7,8-dihydro-6H-spiro[[1,3]oxazolo[5,4-f]quinazoline-9,1'-cyclohexane]-7-one;

5-chloro-2-[(3R)-3-(methoxymethyl)pyrrolidine-1-carbonyl]-7,8-dihydro-6H-spiro[[1,3]oxazolo[5,4-f]quinazoline-9,1'-cyclohexane]-7-one;

5-chloro-2-[(3S)-3-(methoxymethyl)pyrrolidine-1-carbonyl]-7,8-dihydro-6H-spiro[[1,3]oxazolo[5,4-f]quinazoline-9,1'-cyclohexane]-7-one;

5-chloro-7-oxo-N-[2-(trifluoromethoxy)ethyl]-7,8-dihydro-6H-spiro[[1,3]oxazolo[5,4-f]quinazoline-9,1'-cyclohexane]-2-carboxamide;

5-chloro-2-[(3R)-3-methoxypyrrolidine-1-carbonyl]-7,8-dihydro-6H-spiro[[1,3]oxazolo[5,4-f]quinazoline-9,1'-cyclohexane]-7-one;

5-chloro-2-(4-ethylpiperazine-1-carbonyl)-7,8-dihydro-6H-spiro[[1,3]oxazolo[5,4-f]quinazoline-9,1'-cyclohexane]-7-one;

5-chloro-2-[4-(propan-2-yl)piperazine-1-carbonyl]-7,8-dihydro-6H-spiro[[1,3]oxazolo[5,4-f]quinazoline-9,1'-cyclohexane]-7-one;

5-chloro-2-[4-(2,2-difluoroethyl)piperazine-1-carbonyl]-7,8-dihydro-6H-spiro[[1,3]oxazolo[5,4-f]quinazoline-9,1'-cyclohexane]-7-one;

2-[(8aS)-octahydropyrrolo[1,2-a]piperazine-2-carbonyl]-5-chloro-7,8-dihydro-6H-spiro[[1,3]oxazolo[5,4-f]quinazoline-9,1'-cyclohexane]-7-one;

5-chloro-2-(piperazine-1-carbonyl)-7,8-dihydro-6H-spiro[[1,3]oxazolo[5,4-f]quinazoline-9,1'-cyclohexane]-7-one;

5-chloro-7-oxo-N-[(3R)-oxolan-3-ylmethyl]-7,8-dihydro-6H-spiro[[1,3]oxazolo[5,4-f]quinazoline-9,1'-cyclohexane]-2-carboxamide;

5-chloro-2-[4-(2-fluoroethyl)piperazine-1-carbonyl]-7,8-dihydro-6H-spiro[[1,3]oxazolo[5,4-f]quinazoline-9,1'-cyclohexane]-7-one;

5-chloro-N-(2,2-difluorocyclopentyl)-7-oxo-7,8-dihydro-6H-spiro[[1,3]oxazolo[5,4-f]quinazoline-9,1'-cyclohexane]-2-carboxamide;

5-chloro-N-[4-(methoxymethyl)oxan-4-yl]-7-oxo-7,8-dihydro-6H-spiro[[1,3]oxazolo[5,4-f]quinazoline-9,1'-cyclohexane]-2-carboxamide;

5-chloro-N-(3-fluorooxan-4-yl)-7-oxo-7,8-dihydro-6H-spiro[[1,3]oxazolo[5,4-f]quinazoline-9,1'-cyclohexane]-2-carboxamide;

5-chloro-N-(2,2-difluoro-3-hydroxypropyl)-7-oxo-7,8-dihydro-6H-spiro[[1,3]oxazolo[5,4-f]quinazoline-9,1'-cyclohexane]-2-carboxamide;

5-chloro-7-oxo-N-[(3S)-oxolan-3-ylmethyl]-7,8-dihydro-6H-spiro[[1,3]oxazolo[5,4-f]quinazoline-9,1'-cyclohexane]-2-carboxamide;

5-chloro-7-oxo-N-[(3S)-oxolan-3-yl]-7,8-dihydro-6H-spiro[[1,3]oxazolo[5,4-f]quinazoline-9,1'-cyclohexane]-2-carboxamide;

5-chloro-7-oxo-N-[(3R)-oxolan-3-yl]-7,8-dihydro-6H-spiro[[1,3]oxazolo[5,4-f]quinazoline-9,1'-cyclohexane]-2-carboxamide;

2-[(8aS)-octahydropyrrolo[1,2-a]piperazine-2-carbonyl]-5-chloro-4',4'-difluoro-7,8-dihydro-6H-spiro[[1,3]oxazolo[5,4-f]quinazoline-9,1'-cyclohexane]-7-one;

2-[(4,4-difluoropiperidin-1-yl)methyl]-5-fluoro-7,8-dihydro-6H-spiro[[1,3]oxazolo[5,4-f]quinazoline-9,1'-cyclohexane]-7-one;

5-fluoro-2-{[(2-methoxyethyl)amino]methyl}-7,8-dihydro-6H-spiro[[1,3]oxazolo[5,4-f]quinazoline-9,1'-cyclohexane]-7-one;

2-({5-fluoro-7-oxo-7,8-dihydro-6H-spiro[[1,3]oxazolo[5,4-f]quinazoline-9,1'-cyclohexane]-2-ylmethyl}(methyl)amino)-N,N-dimethylacetamide;

2-({5-fluoro-7-oxo-7,8-dihydro-6H-spiro[[1,3]oxazolo[5,4-f]quinazoline-9,1'-cyclohexane]-2-ylmethyl}amino)-N,N-dimethylacetamide;

5-chloro-4',4'-difluoro-2-({[(3S)-oxan-3-yl]amino}methyl)-7,8-dihydro-6H-spiro[[1,3]oxazolo[5,4-f]quinazoline-9,1'-cyclohexane]-7-one;

5-chloro-4',4'-difluoro-2-({[(3R)-oxolan-3-ylmethyl]amino}methyl)-7,8-dihydro-6H-spiro[[1,3]oxazolo[5,4-f]quinazoline-9,1'-cyclohexane]-7-one;

5-chloro-4',4'-difluoro-2-({[(3S)-oxolan-3-yl]amino}methyl)-7,8-dihydro-6H-spiro[[1,3]oxazolo[5,4-f]quinazoline-9,1'-cyclohexane]-7-one;

5-chloro-4',4'-difluoro-2-({[(3R)-oxan-3-yl]amino}methyl)-7,8-dihydro-6H-spiro[[1,3]oxazolo[5,4-f]quinazoline-9,1'-cyclohexane]-7-one;

and pharmaceutically acceptable salts thereof; or
a compound selected from the group consisting of
methyl 5-chloro-7-oxo-7,8-dihydro-6H-spiro[[1,3]oxazolo[5,4-f]quinazoline-9,1'-cyclohexane]-2-carboxylate;

5-chloro-7-oxo-7,8-dihydro-6H-spiro[[1,3]oxazolo[5,4-f]quinazoline-9,1'-cyclohexane]-2-carboxamide;

5-chloro-N-[2-(dimethylamino)ethyl]-7-oxo-7,8-dihydro-6H-spiro[[1,3]oxazolo[5,4-f]quinazoline-9,1'-cyclohexane]-2-carboxamide;

5-chloro-2-(morpholine-4-carbonyl)-7,8-dihydro-6H-spiro[[1,3]oxazolo[5,4-f]quinazoline-9,1'-cyclohexane]-7-one;

5-chloro-7-oxo-7,8-dihydro-6H-spiro[[1,3]oxazolo[5,4-f]quinazoline-9,1'-cyclohexane]-2-carboxylic acid;

5-chloro-N,N-dimethyl-7-oxo-7,8-dihydro-6H-spiro[[1,3]oxazolo[5,4-f]quinazoline-9,1'-cyclohexane]-2-carboxamide;

5-chloro-2-(4-methylpiperazine-1-carbonyl)-7,8-dihydro-6H-spiro[[1,3]oxazolo[5,4-f]quinazoline-9,1'-cyclohexane]-7-one;

5-chloro-2-(4-methoxypiperidine-1-carbonyl)-7,8-dihydro-6H-spiro[[1,3]oxazolo[5,4-f]quinazoline-9,1'-cyclohexane]-7-one;

5-chloro-N-(2-methoxyethyl)-7-oxo-7,8-dihydro-6H-spiro[[1,3]oxazolo[5,4-f]quinazoline-9,1'-cyclohexane]-2-carboxamide;

5-chloro-2-[(1 S,4S)-2-oxa-5-azabicyclo[2.2.1]heptane-5-carbonyl]-7,8-dihydro-6H-spiro[[1,3]oxazolo[5,4-f]quinazoline-9,1'-cyclohexane]-7-one;

5-chloro-N-(2-methoxyethyl)-N-methyl-7-oxo-7,8-dihydro-6H-spiro[[1,3]oxazolo[5,4-f]quinazoline-9,1'-cyclohexane]-2-carboxamide;

5-chloro-N-methyl-N-(oxan-4-ylmethyl)-7-oxo-7,8-dihydro-6H-spiro[[1,3]oxazolo[5,4-f]quinazoline-9,1'-cyclohexane]-2-carboxamide;

5-chloro-2-[(3R)-3-ethoxypyrrolidine-1-carbonyl]-7,8-dihydro-6H-spiro[[1,3]oxazolo[5,4-f]quinazoline-9,1'-cyclohexane]-7-one;

2-{1-5-chloro-7-oxo-7,8-dihydro-6H-spiro[[1,3]oxazolo[5,4-f]quinazoline-9,1'-cyclohexane]-2-yl-N-methylformamido}-N,N-dimethylacetamide;

3-{1-5-chloro-7-oxo-7,8-dihydro-6H-spiro[[1,3]oxazolo[5,4-f]quinazoline-9,1'-cyclohexane]-2-yl-N-methylformamido}-N,N-dimethylpropanamide;

5-chloro-2-[(2S)-2-(methoxymethyl)pyrrolidine-1-carbonyl]-7,8-dihydro-6H-spiro[[1,3]oxazolo[5,4-f]quinazoline-9,1'-cyclohexane]-7-one;

methyl 2-{1-5-chloro-7-oxo-7,8-dihydro-6H-spiro[[1,3]oxazolo[5,4-f]quinazoline-9,1'-cyclohexane]-2-yl-N-methylformamido}acetate;

5-chloro-N-methyl-N-[2-(methylamino)ethyl]-7-oxo-7,8-dihydro-6H-spiro[[1,3]oxazolo[5,4-f]quinazoline-9,1'-cyclohexane]-2-carboxamide;

5-chloro-N-[2-(dimethylamino)ethyl]-N-methyl-7-oxo-7,8-dihydro-6H-spiro[[1,3]oxazolo[5,4-f]quinazoline-9,1'-cyclohexane]-2-carboxamide;

5-chloro-2-[4-(dimethylamino)piperidine-1-carbonyl]-7,8-dihydro-6H-spiro[[1,3]oxazolo[5,4-f]quinazoline-9,1'-cyclohexane]-7-one;

5-chloro-2-[4-(2,2,2-trifluoroethyl)piperazine-1-carbonyl]-7,8-dihydro-6H-spiro[[1,3]oxazolo[5,4-f]quinazoline-9,1'-cyclohexane]-7-one;

5-chloro-2-[4-(2-methoxyethyl)piperazine-1-carbonyl]-7,8-dihydro-6H-spiro[[1,3]oxazolo[5,4-f]quinazoline-9,1'-cyclohexane]-7-one;

2-[(8aR)-octahydropyrrolo[1,2-a]piperazine-2-carbonyl]-5-chloro-7,8-dihydro-6H-spiro[[1,3]oxazolo[5,4-f]quinazoline-9,1'-cyclohexane]-7-one;

5-chloro-N-methyl-N-(oxan-4-yl)-7-oxo-7,8-dihydro-6H-spiro[[1,3]oxazolo[5,4-f]quinazoline-9,1'-cyclohexane]-2-carboxamide;

5-chloro-2-(3-methoxypyrrolidine-1-carbonyl)-7,8-dihydro-6H-spiro[[1,3]oxazolo[5,4-f]quinazoline-9,1'-cyclohexane]-7-one;

5-chloro-2-[(3R)-3-methoxypiperidine-1-carbonyl]-7,8-dihydro-6H-spiro[[1,3]oxazolo[5,4-f]quinazoline-9,1'-cyclohexane]-7-one;

5-chloro-N-(oxan-3-yl)-7-oxo-7,8-dihydro-6H-spiro[[1,3]oxazolo[5,4-f]quinazoline-9,1'-cyclohexane]-2-carboxamide;

5-chloro-2-[(3S)-3-methoxypyrrolidine-1-carbonyl]-7,8-dihydro-6H-spiro[[1,3]oxazolo[5,4-f]quinazoline-9,1'-cyclohexane]-7-one;
5-chloro-2-[(3R)-3-(methoxymethyl)pyrrolidine-1-carbonyl]-7,8-dihydro-6H-spiro[[1,3]oxazolo[5,4-f]quinazoline-9,1'-cyclohexane];
5-chloro-2-[(3S)-3-(methoxymethyl)pyrrolidine-1-carbonyl]-7,8-dihydro-6H-spiro[[1,3]oxazolo[5,4-f]quinazoline-9,1'-cyclohexane];
5-chloro-7-oxo-N-[2-(trifluoromethoxy)ethyl]-7,8-dihydro-6H-spiro[[1,3]oxazolo[5,4-f]quinazoline-9,1'-cyclohexane]-2-carboxamide;
5-chloro-2-[(3R)-3-methoxypyrrolidine-1-carbonyl]-7,8-dihydro-6H-spiro[[1,3]oxazolo[5,4-f]quinazoline-9,1'-cyclohexane]-7-one;
5-chloro-2-(4-ethylpiperazine-1-carbonyl)-7,8-dihydro-6H-spiro[[1,3]oxazolo[5,4-f]quinazoline-9,1'-cyclohexane]-7-one;
5-chloro-2-[4-(propan-2-yl)piperazine-1-carbonyl]-7,8-dihydro-6H-spiro[[1,3]oxazolo[5,4-f]quinazoline-9,1'-cyclohexane]-7-one;
5-chloro-2-[4-(2,2-difluoroethyl)piperazine-1-carbonyl]-7,8-dihydro-6H-spiro[[1,3]oxazolo[5,4-f]quinazoline-9,1'-cyclohexane]-7-one;
2-[(8aS)-octahydropyrrolo[1,2-a]piperazine-2-carbonyl]-5-chloro-7,8-dihydro-6H-spiro[[1,3]oxazolo[5,4-f]quinazoline-9,1'-cyclohexane]-7-one;
5-chloro-2-(piperazine-1-carbonyl)-7,8-dihydro-6H-spiro[[1,3]oxazolo[5,4-f]quinazoline-9,1'-cyclohexane]-7-one;
5-chloro-7-oxo-N-[(3R)-oxolan-3-ylmethyl]-7,8-dihydro-6H-spiro[[1,3]oxazolo[5,4-f]quinazoline-9,1'-cyclohexane]-2-carboxamide;
5-chloro-2-[4-(2-fluoroethyl)piperazine-1-carbonyl]-7,8-dihydro-6H-spiro[[1,3]oxazolo[5,4-f]quinazoline-9,1'-cyclohexane]-7-one;
5-chloro-N-(2,2-difluorocyclopentyl)-7-oxo-7,8-dihydro-6H-spiro[[1,3]oxazolo[5,4-f]quinazoline-9,1'-cyclohexane]-2-carboxamide;
5-chloro-N-[4-(methoxymethyl)oxan-4-yl]-7-oxo-7,8-dihydro-6H-spiro[[1,3]oxazolo[5,4-f]quinazoline-9,1'-cyclohexane]-2-carboxamide;
5-chloro-N-(3-fluorooxan-4-yl)-7-oxo-7,8-dihydro-6H-spiro[[1,3]oxazolo[5,4-f]quinazoline-9,1'-cyclohexane]-2-carboxamide;
5-chloro-N-(2,2-difluoro-3-hydroxypropyl)-7-oxo-7,8-dihydro-6H-spiro[[1,3]oxazolo[5,4-f]quinazoline-9,1'-cyclohexane]-2-carboxamide;
5-chloro-7-oxo-N-[(3S)-oxolan-3-ylmethyl]-7,8-dihydro-6H-spiro[[1,3]oxazolo[5,4-f]quinazoline-9,1'-cyclohexane]-2-carboxamide;
5-chloro-7-oxo-N-[(3S)-oxolan-3-yl]-7,8-dihydro-6H-spiro[[1,3]oxazolo[5,4-f]quinazoline-9,1'-cyclohexane]-2-carboxamide;
5-chloro-7-oxo-N-[(3R)-oxolan-3-yl]-7,8-dihydro-6H-spiro[[1,3]oxazolo[5,4-f]quinazoline-9,1'-cyclohexane]-2-carboxamide;
methyl 5-chloro-4',4'-difluoro-7-oxo-7,8-dihydro-6H-spiro[[1,3]oxazolo[5,4-f]quinazoline-9,1'-cyclohexane]-2-carboxylate;
2-[(8aS)-octahydropyrrolo[1,2-a]piperazine-2-carbonyl]-5-chloro-4',4'-difluoro-7,8-dihydro-6H-spiro[[1,3]oxazolo[5,4-f]quinazoline-9,1'-cyclohexane]-7-one;
and pharmaceutically acceptable salts thereof; or
a compound selected from the group consisting of:
5-chloro-2-methyl-7,8-dihydro-6H-spiro[[1,3]oxazolo[5,4-f]quinazoline-9,1'-cyclohexan]-7-one;
5-chloro-2-(chloromethyl)-7,8-dihydro-6H-spiro[[1,3]oxazolo[5,4-f]quinazoline-9,1'-cyclohexan]-7-one;
5-chloro-2-(methoxymethyl)-7,8-dihydro-6H-spiro[[1,3]oxazolo[5,4-f]quinazoline-9,1'-cyclohexan]-7-one;
5-chloro-2-(hydroxymethyl)-7,8-dihydro-6H-spiro[[1,3]oxazolo[5,4-f]quinazoline-9,1'-cyclohexan]-7-one;
5-chloro-2-propyl-7,8-dihydro-6H-spiro[[1,3]oxazolo[5,4-f]quinazoline-9,1'-cyclohexan]-7-one;
5-chloro-2-ethyl-7,8-dihydro-6H-spiro[[1,3]oxazolo[5,4-f]quinazoline-9,1'-cyclohexan]-7-one;
5-chloro-2-[(dimethylamino)methyl]-7,8-dihydro-6H-spiro[[1,3]oxazolo[5,4-f]quinazoline-9,1'-cyclohexan]-7-one;
5-chloro-2-[(4-methylpiperazin-1-yl)methyl]-7,8-dihydro-6H-spiro[[1,3]oxazolo[5,4-f]quinazoline-9,1'-cyclohexan]-7-one;
5-chloro-2-[(morpholin-4-yl)methyl]-7,8-dihydro-6H-spiro[[1,3]oxazolo[5,4-f]quinazoline-9,1'-cyclohexan]-7-one;
5-chloro-2-[(4-hydroxypiperidin-1-yl)methyl]-7,8-dihydro-6H-spiro[[1,3]oxazolo[5,4-f]quinazoline-9,1'-cyclohexan]-7-one;
5-chloro-2-[(methylamino)methyl]-7,8-dihydro-6H-spiro[[1,3]oxazolo[5,4-f]quinazoline-9,1'-cyclohexan]-7-one;
5-chloro-2-[(cyclopropylamino)methyl]-7,8-dihydro-6H-spiro[[1,3]oxazolo[5,4-f]quinazoline-9,1'-cyclohexan]-7-one;
5-chloro-2-[(piperazin-1-yl)methyl]-7,8-dihydro-6H-spiro[[1,3]oxazolo[5,4-f]quinazoline-9,1'-cyclohexan]-7-one;
5-chloro-2-[(pyrrolidin-1-yl)methyl]-7,8-dihydro-6H-spiro[[1,3]oxazolo[5,4-f]quinazoline-9,1'-cyclohexan]-7-one;
5-chloro-2-(2-methoxyethyl)-7,8-dihydro-6H-spiro[[1,3]oxazolo[5,4-f]quinazoline-9,1'-cyclohexan]-7-one;
5-chloro-2-(2-hydroxyethyl)-7,8-dihydro-6H-spiro[[1,3]oxazolo[5,4-f]quinazoline-9,1'-cyclohexan]-7-one;
5-chloro-2-{[(2-methoxyethyl)amino]methyl}-7,8-dihydro-6H-spiro[[1,3]oxazolo[5,4-f]quinazoline-9,1'-cyclohexan]-7-one;
5-chloro-2-{[(propan-2-yl)amino]methyl}-7,8-dihydro-6H-spiro[[1,3]oxazolo[5,4-f]quinazoline-9,1'-cyclohexan]-7-one;
5-chloro-2-[(ethylamino)methyl]-7,8-dihydro-6H-spiro[[1,3]oxazolo[5,4-f]quinazoline-9,1'-cyclohexan]-7-one;
5-chloro-2-{[(2-hydroxyethyl)amino]methyl}-7,8-dihydro-6H-spiro[[1,3]oxazolo[5,4-f]quinazoline-9,1'-cyclohexan]-7-one;
5-chloro-2-[(4,4-difluoropiperidin-1-yl)methyl]-7,8-dihydro-6H-spiro[[1,3]oxazolo[5,4-f]quinazoline-9,1'-cyclohexan]-7-one;
5-chloro-2-{[(2,2,2-trifluoroethyl)amino]methyl}-7,8-dihydro-6H-spiro[[1,3]oxazolo[5,4-f]quinazoline-9,1'-cyclohexan]-7-one;
5-chloro-2-{[(2-hydroxyethyl)(methyl)amino]methyl}-7,8-dihydro-6H-spiro[[1,3]oxazolo[5,4-f]quinazoline-9,1'-cyclohexan]-7-one;
5-chloro-2-[(3,3-difluoroazetidin-1-yl)methyl]-7,8-dihydro-6H-spiro[[1,3]oxazolo[5,4-f]quinazoline-9,1'-cyclohexan]-7-one;
5-chloro-2-[(3,3-difluoropyrrolidin-1-yl)methyl]-7,8-dihydro-6H-spiro[[1,3]oxazolo[5,4-f]quinazoline-9,1'-cyclohexan]-7-one;

2-[(4-acetylpiperazin-1-yl)methyl]-5-chloro-7,8-dihydro-6H-spiro[[1,3]oxazolo[5,4-f]quinazoline-9,1'-cyclohexan]-7-one;

5-chloro-2-[(4-propanoylpiperazin-1-yl)methyl]-7,8-dihydro-6H-spiro[[1,3]oxazolo[5,4-f]quinazoline-9,1'-cyclohexan]-7-one;

5-chloro-2-({2-oxa-8-azaspiro[4.5]decan-8-yl}methyl)-7,8-dihydro-6H-spiro[[1,3]oxazolo[5,4-f]quinazoline-9,1'-cyclohexan]-7-one;

5-chloro-2-{[4-(oxetan-3-yl)piperazin-1-yl]methyl}-7,8-dihydro-6H-spiro[[1,3]oxazolo[5,4-f]quinazoline-9,1'-cyclohexan]-7-one;

2-[({5-chloro-7-oxo-7,8-dihydro-6H-spiro[[1,3]oxazolo[5,4-f]quinazoline-9,1'-cyclohexan]-2-yl}methyl)amino]-N,N-dimethylacetamide;

tert-butyl 2-{[({5-chloro-7-oxo-7,8-dihydro-6H-spiro[[1,3]oxazolo[5,4-f]quinazoline-9,1'-cyclohexan]-2-yl}methyl)amino]methyl}piperidine-1-carboxylate;

5-chloro-2-({[(3,5-difluoropyridin-2-yl)methyl]amino}methyl)-7,8-dihydro-6H-spiro[[1,3]oxazolo[5,4-f]quinazoline-9,1'-cyclohexan]-7-one;

5-chloro-2-({[(piperidin-2-yl)methyl]amino}methyl)-7,8-dihydro-6H-spiro[[1,3]oxazolo[5,4-f]quinazoline-9,1'-cyclohexan]-7-one;

5-chloro-2-({[2-oxo-2-(piperidin-1-yl)ethyl]amino}methyl)-7,8-dihydro-6H-spiro[[1,3]oxazolo[5,4-f]quinazoline-9,1'-cyclohexan]-7-one;

2-[({5-chloro-7-oxo-7,8-dihydro-6H-spiro[[1,3]oxazolo[5,4-f]quinazoline-9,1'-cyclohexan]-2-yl}methyl)amino]-N-ethyl-N-methylacetamide;

5-chloro-2-[(4-methyl-3-oxopiperazin-1-yl)methyl]-7,8-dihydro-6H-spiro[[1,3]oxazolo[5,4-f]quinazoline-9,1'-cyclohexan]-7-one;

5-chloro-2-[(4-ethyl-3-oxopiperazin-1-yl)methyl]-7,8-dihydro-6H-spiro[[1,3]oxazolo[5,4-f]quinazoline-9,1'-cyclohexan]-7-one;

5-chloro-2-({[(pyridin-2-yl)methyl]amino}methyl)-7,8-dihydro-6H-spiro[[1,3]oxazolo[5,4-f]quinazoline-9,1'-cyclohexan]-7-one;

5-chloro-2-({[(pyrimidin-2-yl)methyl]amino}methyl)-7,8-dihydro-6H-spiro[[1,3]oxazolo[5,4-f]quinazoline-9,1'-cyclohexan]-7-one;

5-chloro-2-({[(5-methoxypyridin-3-yl)methyl]amino}methyl)-7,8-dihydro-6H-spiro[[1,3]oxazolo[5,4-f]quinazoline-9,1'-cyclohexan]-7-one;

5-chloro-2-[(2,4-dimethyl-3-oxopiperazin-1-yl)methyl]-7,8-dihydro-6H-spiro[[1,3]oxazolo[5,4-f]quinazoline-9,1'-cyclohexan]-7-one;

ethyl 1-({5-chloro-7-oxo-7,8-dihydro-6H-spiro[[1,3]oxazolo[5,4f]quinazoline-9,1'-cyclohexan]-2-yl}methyl)piperidine-4-carboxylate;

5-chloro-2-({1-oxo-2-oxa-8-azaspiro[4.5]decan-8-yl}methyl)-7,8-dihydro-6H-spiro[[1,3]oxazolo[5,4-f]quinazoline-9,1'-cyclohexan]-7-one;

2-[(4-acetylpiperidin-1-yl)methyl]-5-chloro-7,8-dihydro-6H-spiro[[1,3]oxazolo[5,4-f]quinazoline-9,1'-cyclohexan]-7-one;

methyl 1-({5-chloro-7-oxo-7,8-dihydro-6H-spiro[[1,3]oxazolo[5,4f]quinazoline-9,1'-cyclohexan]-2-yl}methyl)piperidine-4-carboxylate;

5-chloro-2-({[(5-fluoropyridin-2-yl)methyl]amino}methyl)-7,8-dihydro-6H-spiro[[1,3]oxazolo[5,4-f]quinazoline-9,1'-cyclohexan]-7-one;

5-chloro-2-{[3-(2-methylpropoxy)azetidin-1-yl]methyl}-7,8-dihydro-6H-spiro[[1,3]oxazolo[5,4-f]quinazoline-9,1'-cyclohexan]-7-one;

5-chloro-2-[(4-ethoxypiperidin-1-yl)methyl]-7,8-dihydro-6H-spiro[[1,3]oxazolo[5,4-f]quinazoline-9,1'-cyclohexan]-7-one;

5-chloro-2-{[4-(cyclopropylmethoxy)piperidin-1-yl]methyl}-7,8-dihydro-6H-spiro[[1,3]oxazolo[5,4-f]quinazoline-9,1'-cyclohexan]-7-one;

5-chloro-2-{[4-hydroxy-4-(trifluoromethyl)piperidin-1-yl]methyl}-7,8-dihydro-6H-spiro[[1,3]oxazolo[5,4-f]quinazoline-9,1'-cyclohexan]-7-one;

5-chloro-2-{[4-(propan-2-yloxy)piperidin-1-yl]methyl}-7,8-dihydro-6H-spiro[[1,3]oxazolo[5,4-f]quinazoline-9,1'-cyclohexan]-7-one;

5-chloro-2-[(3-fluoroazetidin-1-yl)methyl]-7,8-dihydro-6H-spiro[[1,3]oxazolo[5,4-f]quinazoline-9,1'-cyclohexan]-7-one;

5-chloro-2-[(3-methoxyazetidin-1-yl)methyl]-7,8-dihydro-6H-spiro[[1,3]oxazolo[5,4-f]quinazoline-9,1'-cyclohexan]-7-one;

5-chloro-2-{[3-(methoxymethyl)azetidin-1-yl]methyl}-7,8-dihydro-6H-spiro[[1,3]oxazolo[5,4-f]quinazoline-9,1'-cyclohexan]-7-one;

5-chloro-2-({7-oxa-2-azaspiro[3.5]nonan-2-yl}methyl)-7,8-dihydro-6H-spiro[[1,3]oxazolo[5,4-f]quinazoline-9,1'-cyclohexan]-7-one;

5-chloro-2-[(4-methoxy-4-methylpiperidin-1-yl)methyl]-7,8-dihydro-6H-spiro[[1,3]oxazolo[5,4-f]quinazoline-9,1'-cyclohexan]-7-one;

5-chloro-2-({3-oxo-1-oxa-8-azaspiro[4.5]decan-8-yl}methyl)-7,8-dihydro-6H-spiro[[1,3]oxazolo[5,4-f]quinazoline-9,1'-cyclohexan]-7-one;

2-[({5-chloro-7-oxo-7,8-dihydro-6H-spiro[[1,3]oxazolo[5,4-f]quinazoline-9,1'-cyclohexan]-2-yl}methyl)(methyl)amino]-N,N-dimethylacetamide;

5-chloro-2-({[(6-methylpyridin-3-yl)methyl]amino}methyl)-7,8-dihydro-6H-spiro[[1,3]oxazolo[5,4-f]quinazoline-9,1'-cyclohexan]-7-one;

5-chloro-2-({methyl[(oxan-4-yl)methyl]amino}methyl)-7,8-dihydro-6H-spiro[[1,3]oxazolo[5,4-f]quinazoline-9,1'-cyclohexan]-7-one;

5-chloro-2-({methyl[(3-methyloxetan-3-yl)methyl]amino}methyl)-7,8-dihydro-6H-spiro[[1,3]oxazolo[5,4-f]quinazoline-9,1'-cyclohexan]-7-one;

5-chloro-2-({[(3-fluorooxetan-3-yl)methyl]amino}methyl)-7,8-dihydro-6H-spiro[[1,3]oxazolo[5,4-f]quinazoline-9,1'-cyclohexan]-7-one;

5-chloro-2-({[(oxan-4-yl)methyl]amino}methyl)-7,8-dihydro-6H-spiro[[1,3]oxazolo[5,4-f]quinazoline-9,1'-cyclohexan]-7-one;

5-chloro-2-({2-oxa-7-azaspiro[3.5]nonan-7-yl}methyl)-7,8-dihydro-6H-spiro[[1,3]oxazolo[5,4-f]quinazoline-9,1'-cyclohexan]-7-one;

5-chloro-2-({[(3-methyloxetan-3-yl)methyl]amino}methyl)-7,8-dihydro-6H-spiro[[1,3]oxazolo[5,4-f]quinazoline-9,1'-cyclohexan]-7-one;

5-chloro-2-({2-oxa-5-azabicyclo[2.2.1]heptan-5-yl}methyl)-7,8-dihydro-6H-spiro[[1,3]oxazolo[5,4-f]quinazoline-9,1'-cyclohexan]-7-one;

5-chloro-2-{[methyl(2,2,2-trifluoroethyl)amino]methyl}-7,8-dihydro-6H-spiro[[1,3]oxazolo[5,4-f]quinazoline-9,1'-cyclohexan]-7-one;

5-chloro-2-({[(oxetan-3-yl)methyl]amino}methyl)-7,8-dihydro-6H-spiro[[1,3]oxazolo[5,4-f]quinazoline-9,1'-cyclohexan]-7-one;

5-chloro-2-[(4-oxopiperidin-1-yl)methyl]-7,8-dihydro-6H-spiro[[1,3]oxazolo[5,4-f]quinazoline-9,1'-cyclohexan]-7-one;

5-chloro-2-({[(2-methoxyphenyl)methyl]amino}methyl)-7,8-dihydro-6H-spiro[[1,3]oxazolo[5,4-f]quinazoline-9,1'-cyclohexan]-7-one;

5-chloro-2-({[(2,4-dimethoxyphenyl)methyl]amino}methyl)-7,8-dihydro-6H-spiro[[1,3]oxazolo[5,4-f]quinazoline-9,1'-cyclohexan]-7-one;

5-chloro-2-{[4-(propan-2-yl)piperazin-1-yl]methyl}-7,8-dihydro-6H-spiro[[1,3]oxazolo[5,4-f]quinazoline-9,1'-cyclohexan]-7-one;

5-chloro-2-[(3,3,4-trimethylpiperazin-1-yl)methyl]-7,8-dihydro-6H-spiro[[1,3]oxazolo[5,4-f]quinazoline-9,1'-cyclohexan]-7-one;

5-chloro-2-{[2-(hydroxymethyl)piperidin-1-yl]methyl}-7,8-dihydro-6H-spiro[[1,3]oxazolo[5,4-f]quinazoline-9,1'-cyclohexan]-7-one;

5-chloro-2-({[1-(hydroxymethyl)cyclopentyl]amino}methyl)-7,8-dihydro-6H-spiro[[1,3]oxazolo[5,4-f]quinazoline-9,1'-cyclohexan]-7-one;

5-chloro-2-{[(2R)-2-(hydroxymethyl)pyrrolidin-1-yl]methyl}-7,8-dihydro-6H-spiro[[1,3]oxazolo[5,4-f]quinazoline-9,1'-cyclohexan]-7-one;

5-chloro-2-[(2-methylpiperidin-1-yl)methyl]-7,8-dihydro-6H-spiro[[1,3]oxazolo[5,4-f]quinazoline-9,1'-cyclohexan]-7-one;

5-chloro-2-{[2-(2-methylpropyl)morpholin-4-yl]methyl}-7,8-dihydro-6H-spiro[[1,3]oxazolo[5,4-f]quinazoline-9,1'-cyclohexan]-7-one;

5-chloro-2-{[(2-cyclobutyl-2,2-difluoroethyl)amino]methyl}-7,8-dihydro-6H-spiro[[1,3]oxazolo[5,4-f]quinazoline-9,1'-cyclohexan]-7-one;

5-chloro-2-[(3-ethylmorpholin-4-yl)methyl]-7,8-dihydro-6H-spiro[[1,3]oxazolo[5,4-f]quinazoline-9,1'-cyclohexan]-7-one;

5-chloro-2-{[(2-cyclohexyl-2-hydroxyethyl)amino]methyl}-7,8-dihydro-6H-spiro[[1,3]oxazolo[5,4-f]quinazoline-9,1'-cyclohexan]-7-one;

5-chloro-2-({6-oxa-9-azaspiro[4.5]decan-9-yl}methyl)-7,8-dihydro-6H-spiro[[1,3]oxazolo[5,4-f]quinazoline-9,1'-cyclohexan]-7-one;

5-chloro-2-({[1-(oxan-2-yl)ethyl]amino}methyl)-7,8-dihydro-6H-spiro[[1,3]oxazolo[5,4-f]quinazoline-9,1'-cyclohexan]-7-one;

5-chloro-2-({[(oxan-2-yl)methyl]amino}methyl)-7,8-dihydro-6H-spiro[[1,3]oxazolo[5,4-f]quinazoline-9,1'-cyclohexan]-7-one;

5-chloro-2-[(2-methoxyethoxy)methyl]-7,8-dihydro-6H-spiro[[1,3]oxazolo[5,4-f]quinazoline-9,1'-cyclohexan]-7-one;

ethyl 2-{5-chloro-7-oxo-7,8-dihydro-6H-spiro[[1,3]oxazolo[5,4-f]quinazoline-9,1'-cyclohexan]-2-yl}acetate;

2-[(4,4-difluoropiperidin-1-yl)methyl]-5-fluoro-7,8-dihydro-6H-spiro[[1,3]oxazolo[5,4-f]quinazoline-9,1'-cyclohexan]-7-one;

5-fluoro-2-{[(2-methoxyethyl)amino]methyl}-7,8-dihydro-6H-spiro[[1,3]oxazolo[5,4-f]quinazoline-9,1'-cyclohexan]-7-one;

5-chloro-2-{[(3-methyl-2-oxobutyl)amino]methyl}-7,8-dihydro-6H-spiro[[1,3]oxazolo[5,4-f]quinazoline-9,1'-cyclohexan]-7-one;

5-fluoro-2-[(3-methoxyazetidin-1-yl)methyl]-7,8-dihydro-6H-spiro[[1,3]oxazolo[5,4-f]quinazoline-9,1'-cyclohexan]-7-one;

5-chloro-2-{[(4,4-difluorocyclohexyl)amino]methyl}-7,8-dihydro-6H-spiro[[1,3]oxazolo[5,4-f]quinazoline-9,1'-cyclohexan]-7-one;

5-chloro-2-({[(1R,4R)-4-methoxycyclohexyl]amino}methyl)-7,8-dihydro-6H-spiro[[1,3]oxazolo[5,4-f]quinazoline-9,1'-cyclohexan]-7-one;

5-chloro-2-{[(1R,4R)-2-oxa-5-azabicyclo[2.2.1]heptan-5-yl]methyl}-7,8-dihydro-6H-spiro[[1,3]oxazolo[5,4-f]quinazoline-9,1'-cyclohexan]-7-one;

5-chloro-2-{[(1S,4S)-2-oxa-5-azabicyclo[2.2.1]heptan-5-yl]methyl}-7,8-dihydro-6H-spiro[[1,3]oxazolo[5,4-f]quinazoline-9,1'-cyclohexan]-7-one;

5-chloro-2-[(3-methoxy-3-methylazetidin-1-yl)methyl]-7,8-dihydro-6H-spiro[[1,3]oxazolo[5,4-f]quinazoline-9,1'-cyclohexan]-7-one;

5-chloro-2-[(4-methoxypiperidin-1-yl)methyl]-7,8-dihydro-6H-spiro[[1,3]oxazolo[5,4-f]quinazoline-9,1'-cyclohexan]-7-one;

5-chloro-2-{[4-(dimethylamino)piperidin-1-yl]methyl}-7,8-dihydro-6H-spiro[[1,3]oxazolo[5,4-f]quinazoline-9,1'-cyclohexan]-7-one;

5-chloro-2-({5-methyl-octahydropyrrolo[3,4-c]pyrrol-2-yl}methyl)-7,8-dihydro-6H-spiro[[1,3]oxazolo[5,4-f]quinazoline-9,1'-cyclohexan]-7-one;

5-chloro-2-{[(2R)-2-(methoxymethyl)pyrrolidin-1-yl]methyl}-7,8-dihydro-6H-spiro[[1,3]oxazolo[5,4-f]quinazoline-9,1'-cyclohexan]-7-one;

5-chloro-2-{[3-(hydroxymethyl)pyrrolidin-1-yl]methyl}-7,8-dihydro-6H-spiro[[1,3]oxazolo[5,4-f]quinazoline-9,1'-cyclohexan]-7-one;

5-chloro-2-{[(3R)-3-methoxypiperidin-1-yl]methyl}-7,8-dihydro-6H-spiro[[1,3]oxazolo[5,4-f]quinazoline-9,1'-cyclohexan]-7-one;

5-chloro-2-{[(3S)-3-methoxypiperidin-1-yl]methyl}-7,8-dihydro-6H-spiro[[1,3]oxazolo[5,4-f]quinazoline-9,1'-cyclohexan]-7-one;

5-chloro-2-{[(3R)-3-ethoxypyrrolidin-1-yl]methyl}-7,8-dihydro-6H-spiro[[1,3]oxazolo[5,4-f]quinazoline-9,1'-cyclohexan]-7-one;

5-chloro-2-{[(3R)-3-(2-hydroxypropan-2-yl)pyrrolidin-1-yl]methyl}-7,8-dihydro-6H-spiro[[1,3]oxazolo[5,4-f]quinazoline-9,1'-cyclohexan]-7-one;

5-chloro-2-{[(3R)-3-hydroxypyrrolidin-1-yl]methyl}-7,8-dihydro-6H-spiro[[1,3]oxazolo[5,4-f]quinazoline-9,1'-cyclohexan]-7-one;

5-chloro-2-({[2-(dimethylamino)ethyl](methyl)amino}methyl)-7,8-dihydro-6H-spiro[[1,3]oxazolo[5,4-f]quinazoline-9,1'-cyclohexan]-7-one;

3-[({5-chloro-7-oxo-7,8-dihydro-6H-spiro[[1,3]oxazolo[5,4-f]quinazoline-9,1'-cyclohexan]-2-yl}methyl)(methyl)amino]-N,N-dimethylpropanamide;

5-chloro-2-({methyl[2-(morpholin-4-yl)ethyl]amino}methyl)-7,8-dihydro-6H-spiro[[1,3]oxazolo[5,4-f]quinazoline-9,1'-cyclohexan]-7-one 5-chloro-2-[(3-methoxypyrrolidin-1-yl)methyl]-7,8-dihydro-6H-spiro[[1,3]oxazolo[5,4-f]quinazoline-9,1'-cyclohexan]-7-one;

5-chloro-2-{[4-(2,2,2-trifluoroethyl)piperazin-1-yl]methyl}-7,8-dihydro-6H-spiro[[1,3]oxazolo[5,4-f]quinazoline-9,1'-cyclohexan]-7-one;

methyl 2-[({5-chloro-7-oxo-7,8-dihydro-6H-spiro[[1,3]oxazolo[5,4f]quinazoline-9,1'-cyclohexan]-2-yl}methyl)(methyl)amino]acetate;

2-{[(8aR)-octahydropyrrolo[1,2-a]pyrazin-2-yl]methyl}-5-chloro-7,8-dihydro-6H-spiro[[1,3]oxazolo[5,4-f]quinazoline-9,1'-cyclohexan]-7-one;

5-chloro-2-{[methyl(oxan-4-yl)amino]methyl}-7,8-dihydro-6H-spiro[[1,3]oxazolo[5,4-f]quinazoline-9,1'-cyclohexan]-7-one;

methyl 1-({5-chloro-7-oxo-7,8-dihydro-6H-spiro[[1,3]oxazolo[5,4-f]quinazoline-9,1'-cyclohexan]-2-yl}methyl)piperidine-3-carboxylate;

methyl 2-[({5-chloro-7-oxo-7,8-dihydro-6H-spiro[[1,3]oxazolo[5,4-f]quinazoline-9,1'-cyclohexan]-2-yl}methyl)amino]acetate;

5-chloro-2-{[(3S)-3-methoxypyrrolidin-1-yl]methyl}-7,8-dihydro-6H-spiro[[1,3]oxazolo[5,4-f]quinazoline-9,1'-cyclohexan]-7-one;

5-chloro-2-{[(oxan-3-yl)amino]methyl}-7,8-dihydro-6H-spiro[[1,3]oxazolo[5,4-f]quinazoline-9,1'-cyclohexan]-7-one;

5-chloro-2-{[(3R)-3-methoxypyrrolidin-1-yl]methyl}-7,8-dihydro-6H-spiro[[1,3]oxazolo[5,4-f]quinazoline-9,1'-cyclohexan]-7-one;

5-chloro-2-{[(3S)-3-(methoxymethyl)pyrrolidin-1-yl]methyl}-7,8-dihydro-6H-spiro[[1,3]oxazolo[5,4-f]quinazoline-9,1'-cyclohexan]-7-one;

5-chloro-2-{[(3R)-3-(methoxymethyl)pyrrolidin-1-yl]methyl}-7,8-dihydro-6H-spiro[[1,3]oxazolo[5,4-f]quinazoline-9,1'-cyclohexan]-7-one;

methyl (3R)-1-({5-chloro-7-oxo-7,8-dihydro-6H-spiro[[1,3]oxazolo[5,4-f]quinazoline-9,1'-cyclohexan]-2-yl}methyl)piperidine-3-carboxylate;

2-({5-chloro-7-oxo-7,8-dihydro-6H-spiro[[1,3]oxazolo[5,4-f]quinazoline-9,1'-cyclohexan]-2-yl}methoxy)-N,N-dimethylacetamide;

5-chloro-2-[(oxan-4-yloxy)methyl]-7,8-dihydro-6H-spiro[[1,3]oxazolo[5,4-f]quinazoline-9,1'-cyclohexan]-7-one;

5-chloro-2-({[2-(trifluoromethoxy)ethyl]amino}methyl)-7,8-dihydro-6H-spiro[[1,3]oxazolo[5,4-f]quinazoline-9,1'-cyclohexan]-7-one;

5-chloro-2-[(4-ethylpiperazin-1-yl)methyl]-7,8-dihydro-6H-spiro[[1,3]oxazolo[5,4-f]quinazoline-9,1'-cyclohexan]-7-one;

5-chloro-2-{[3-(dimethylamino)pyrrolidin-1-yl]methyl}-7,8-dihydro-6H-spiro[[1,3]oxazolo[5,4-f]quinazoline-9,1'-cyclohexan]-7-one;

2-({5-chloro-7-oxo-7,8-dihydro-6H-spiro[[1,3]oxazolo[5,4-f]quinazoline-9,1'-cyclohexan]-2-yl}methyl)amino]-N,N-diethylacetamide;

(2S)-2-[({5-chloro-7-oxo-7,8-dihydro-6H-spiro[[1,3]oxazolo[5,4-f]quinazoline-9,1'-cyclohexan]-2-yl}methyl)amino]-N,N-dimethylpropanamide;

(2R)-2-[({5-chloro-7-oxo-7,8-dihydro-6H-spiro[[1,3]oxazolo[5,4-f]quinazoline-9,1'-cyclohexan]-2-yl}methyl)amino]-N,N-dimethylpropanamide;

5-chloro-2-({[2-oxo-2-(pyrrolidin-1-yl)ethyl]amino}methyl)-7,8-dihydro-6H-spiro[[1,3]oxazolo[5,4-f]quinazoline-9,1'-cyclohexan]-7-one;

5-chloro-2-{[(oxan-4-yl)amino]methyl}-7,8-dihydro-6H-spiro[[1,3]oxazolo[5,4-f]quinazoline-9,1'-cyclohexan]-7-one;

5-chloro-2-[({3-oxabicyclo[3.1.0]hexan-6-yl}amino)methyl]-7,8-dihydro-6H-spiro[[1,3]oxazolo[5,4-f]quinazoline-9,1'-cyclohexan]-7-one;

5-chloro-2-{[(oxepan-4-yl)amino]methyl}-7,8-dihydro-6H-spiro[[1,3]oxazolo[5,4-f]quinazoline-9,1'-cyclohexan]-7-one;

5-chloro-2-({[(oxolan-3-yl)methyl]amino}methyl)-7,8-dihydro-6H-spiro[[1,3]oxazolo[5,4-f]quinazoline-9,1'-cyclohexan]-7-one;

5-chloro-2-{[(3,3-difluoro-2-hydroxypropyl)amino]methyl}-7,8-dihydro-6H-spiro[[1,3]oxazolo[5,4-f]quinazoline-9,1'-cyclohexan]-7-one;

5-chloro-2-{[(4-cyclopropyloxan-4-yl)amino]methyl}-7,8-dihydro-6H-spiro[[1,3]oxazolo[5,4-f]quinazoline-9,1'-cyclohexan]-7-one;

5-chloro-2-{[(2,6-dimethyloxan-4-yl)amino]methyl}-7,8-dihydro-6H-spiro[[1,3]oxazolo[5,4-f]quinazoline-9,1'-cyclohexan]-7-one;

5-chloro-2-({[(3S)-oxan-3-yl]amino}methyl)-7,8-dihydro-6H-spiro[[1,3]oxazolo[5,4-f]quinazoline-9,1'-cyclohexan]-7-one;

5-chloro-2-({[(3S)-oxolan-3-yl]amino}methyl)-7,8-dihydro-6H-spiro[[1,3]oxazolo[5,4-f]quinazoline-9,1'-cyclohexan]-7-one;

5-chloro-2-{[(3-methyloxolan-3-yl)amino]methyl}-7,8-dihydro-6H-spiro[[1,3]oxazolo[5,4-f]quinazoline-9,1'-cyclohexan]-7-one;

5-chloro-2-({[(3R)-oxolan-3-yl]amino}methyl)-7,8-dihydro-6H-spiro[[1,3]oxazolo[5,4-f]quinazoline-9,1'-cyclohexan]-7-one;

5-chloro-2-{[4-(2-methoxyethoxy)piperidin-1-yl]methyl}-7,8-dihydro-6H-spiro[[1,3]oxazolo[5,4-f]quinazoline-9,1'-cyclohexan]-7-one;

2-{[(8aS)-octahydropyrrolo[1,2-a]pyrazin-2-yl]methyl}-5-chloro-7,8-dihydro-6H-spiro[[1,3]oxazolo[5,4-f]quinazoline-9,1'-cyclohexan]-7-one;

methyl (3R)-1-({5-chloro-7-oxo-7,8-dihydro-6H-spiro[[1,3]oxazolo[5,4-f]quinazoline-9,1'-cyclohexan]-2-yl}methyl)pyrrolidine-3-carboxylate;

5-chloro-2-{[4-(2,2-difluoroethyl)piperazin-1-yl]methyl}-7,8-dihydro-6H-spiro[[1,3]oxazolo[5,4-f]quinazoline-9,1'-cyclohexan]-7-one;

5-chloro-2-({[(3-methyloxolan-3-yl)methyl]amino}methyl)-7,8-dihydro-6H-spiro[[1,3]oxazolo[5,4-f]quinazoline-9,1'-cyclohexan]-7-one;

5-chloro-2-({[(3R)-oxan-3-yl]amino}methyl)-7,8-dihydro-6H-spiro[[1,3]oxazolo[5,4-f]quinazoline-9,1'-cyclohexan]-7-one;

5-chloro-2-[({[(3R)-oxolan-3-yl]methyl}amino)methyl]-7,8-dihydro-6H-spiro[[1,3]oxazolo[5,4-f]quinazoline-9,1'-cyclohexan]-7-one;

5-chloro-2-{[(3-fluorooxan-4-yl)amino]methyl}-7,8-dihydro-6H-spiro[[1,3]oxazolo[5,4-f]quinazoline-9,1'-cyclohexan]-7-one;

5-chloro-2-{[(2,2-difluoro-3-hydroxypropyl)amino]methyl}-7,8-dihydro-6H-spiro[[1,3]oxazolo[5,4-f]quinazoline-9,1'-cyclohexan]-7-one;

5-chloro-2-{[(2,2-difluorocyclopentyl)amino]methyl}-7,8-dihydro-6H-spiro[[1,3]oxazolo[5,4-f]quinazoline-9,1'-cyclohexan]-7-one;

5-chloro-2-({[4-(methoxymethyl)oxan-4-yl]amino}methyl)-7,8-dihydro-6H-spiro[[1,3]oxazolo[5,4-f]quinazoline-9,1'-cyclohexan]-7-one;

5-chloro-2-[({[(3S)-oxolan-3-yl]methyl}amino)methyl]-7,8-dihydro-6H-spiro[[1,3]oxazolo[5,4-f]quinazoline-9,1'-cyclohexan]-7-one;

5-chloro-2-({[(1,3-oxazol-2-yl)methyl]amino}methyl)-7,8-dihydro-6H-spiro[[1,3]oxazolo[5,4-f]quinazoline-9,1'-cyclohexan]-7-one;

5-chloro-4',4'-difluoro-2-methyl-7,8-dihydro-6H-spiro[[1,3]oxazolo[5,4-f]quinazoline-9,1'-cyclohexan]-7-one;

5-chloro-2-{[(1-methylpiperidin-4-yl)oxy]methyl}-7,8-dihydro-6H-spiro[[1,3]oxazolo[5,4-f]quinazoline-9,1'-cyclohexan]-7-one;

2-[({5-fluoro-7-oxo-7,8-dihydro-6H-spiro[[1,3]oxazolo[5,4-f]quinazoline-9,1'-cyclohexan]-2-yl}methyl)(methyl)amino]-N,N-dimethylacetamide;

2-[({5-fluoro-7-oxo-7,8-dihydro-6H-spiro[[1,3]oxazolo [5,4-f]quinazoline-9,1'-cyclohexan]-2-yl}methyl) amino]-N,N-dimethylacetamide;

5-chloro-4',4'-difluoro-2-{[(1S,4S)-2-oxa-5-azabicyclo [2.2.1]heptan-5-yl]methyl}-7,8-dihydro-6H-spiro[[1, 3]oxazolo[5,4-f]quinazoline-9,1'-cyclohexan]-7-one;

5-chloro-4',4'-difluoro-2-[({[(3S)-oxolan-3-yl] methyl}amino)methyl]-7,8-dihydro-6H-spiro[[1,3] oxazolo[5,4-f]quinazoline-9,1'-cyclohexan]-7-one;

5-chloro-2,4',4'-trimethyl-7,8-dihydro-6H-spiro[[1,3] oxazolo[5,4-f]quinazoline-9,1'-cyclohexan]-7-one;

5-chloro-4',4'-difluoro-2-({[(3S)-oxan-3-yl] amino}methyl)-7,8-dihydro-6H-spiro[[1,3]oxazolo[5, 4-f]quinazoline-9,1'-cyclohexan]-7-one;

5-chloro-4',4'-difluoro-2-[(4-methylpiperazin-1-yl) methyl]-7,8-dihydro-6H-spiro[[1,3]oxazolo[5,4-f]qui nazoline-9,1'-cyclohexan]-7-one;

5-chloro-4',4'-difluoro-2-[({[(3R)-oxolan-3-yl] methyl}amino)methyl]-7,8-dihydro-6H-spiro[[1,3] oxazolo[5,4-f]quinazoline-9,1'-cyclohexan]-7-one;

5-chloro-4',4'-difluoro-2-({[(3S)-oxan-3-yl] amino}methyl)-7,8-dihydro-6H-spiro[[1,3]oxazolo[5, 4-f]quinazoline-9,1'-cyclohexan]-7-one;

5-chloro-4',4'-difluoro-2-({[(3R)-oxan-3-yl] amino}methyl)-7,8-dihydro-6H-spiro[[1,3]oxazolo[5, 4-f]quinazoline-9,1'-cyclohexan]-7-one;

5-chloro-2-({[(1,3-oxazol-5-yl)methyl]amino}methyl)-7, 8-dihydro-6H-spiro[[1,3]oxazolo[5,4-f]quinazoline-9, 1'-cyclohexan]-7-one;

5-chloro-2-({[2-(1,2-oxazol-3-yl)ethyl]amino}methyl)-7, 8-dihydro-6H-spiro[[1,3]oxazolo[5,4-f]quinazoline-9, 1'-cyclohexan]-7-one;

5-chloro-2-({[(1,3-oxazol-4-yl)methyl]amino}methyl)-7, 8-dihydro-6H-spiro[[1,3]oxazolo[5,4-f]quinazoline-9, 1'-cyclohexan]-7-one;

5-chloro-2-({[(1-methyl-1H-pyrazol-3-yl)methyl] amino}methyl)-7,8-dihydro-6H-spiro[[1,3]oxazolo[5, 4-f]quinazoline-9,1'-cyclohexan]-7-one;

5-chloro-2-({[(1,2-oxazol-5-yl)methyl]amino}methyl)-7, 8-dihydro-6H-spiro[[1,3]oxazolo[5,4-f]quinazoline-9, 1'-cyclohexan]-7-one;

and pharmaceutically acceptable salts thereof; or

5'-chloro-7'-(hydroxymethyl)-7',8'-dihydro-6'H-spiro[cy clohexane-1,9'-furo[2,3-f]quinazoline]-7'-one;

5'-chloro-7'-[4-(2-fluoroethyl)piperazine-1-carbonyl]-7', 8'-dihydro-6'H-spiro[cyclohexane-1,9'-furo[2,3-f]qui nazoline]-7'-one;

N-{2-[benzyl(methyl)amino]ethyl}-5'-chloro-N-methyl-7'-oxo-7',8'-dihydro-6'H-spiro[cyclohexane-1,9'-furo [2,3-f]quinazoline]-2'-carboxamide;

5'-chloro-2'-{[4-(propan-2-yl)piperazin-1-yl]methyl}-7', 8'-dihydro-6'H-spiro[cyclohexane-1,9'-furo[2 3-f]qui nazoline]-7'-one;

5'-chloro-2'-{[methyl({[4-(propan-2-yl)-4H-1,2,4-triazol-3-yl]methyl})amino]methyl}-7',8'-dihydro-6'H-spiro [cyclohexane-1,9'-furo[2,3-]quinazoline]-7'-one;

5'-chloro-2'-(4-methylpiperazine-1-carbonyl)-7',8'-di hydro-6'H-spiro[cyclohexane-1,9'-furo[2,3-f]quinazo line]-7'-one;

5'-chloro-2'-(4-ethylpiperazine-1-carbonyl)-7',8'-dihydro-6'H-spiro[cyclohexane-1,9'-furo[2,3-f]quinazoline]-7'-one;

5'-chloro-N-(2-methoxyethyl)-N-methyl-7'-oxo-7',8'-di hydro-6'H-spiro[cyclohexane-1,9'-furo[2,3-f]quinazo line]-2'-carboxamide;

5'-chloro-2'-[4-(2-methoxyethyl)piperazine-1-carbonyl]-7',8'-dihydro-6'H-spiro[cyclohexane-1,9'-furo[2,3-f] quinazoline]-7'-one;

5'-chloro-7'-(piperidine-1-carbonyl)-7',8'-dihydro-6'H-spiro[cyclohexane-1,9'-furo[2,3-f]quinazoline]-7'-one;

2'-(azetidine-1-carbonyl)-5'-chloro-7',8'-dihydro-6'H-spiro[cyclohexane-1,9'-furo[2,3-f]quinazoline]-7'-one;

5'-chloro-7'-(pyrrolidine-1-carbonyl)-7',8'-dihydro-6'H-spiro[cyclohexane-1,9'-furo[2,3-f]quinazoline]-7'-one;

5'-chloro-7'-(morpholine-4-carbonyl)-7',8'-dihydro-6'H-spiro[cyclohexane-1,9'-furo[2,3-f]quinazoline]-7'-one;

5'-chloro-2'-[4-(2,2,2-trifluoroethyl)piperazine-1-carbo nyl]-7',8'-dihydro-6'H-spiro[cyclohexane-1,9'-furo[2, 3-f]quinazoline]-7'-one;

5'-chloro-2'-[4-(2,2-difluoroethyl)piperazine-1-carbo nyl]-7',8'-dihydro-6'H-spiro[cyclohexane-1,9'-furo[2, 3-f]quinazoline]-7'-one;

5'-chloro-2'-[(1S,4S)-2-oxa-5-azabicyclo[2.2.1]heptan-5-ylmethyl]-7',8'-dihydro-6'H-spiro[cyclohexane-1,9'-furo[2,3-f]quinazoline]-7'-one;

5'-chloro-2'-(piperidin-1-ylmethyl)-7',8'-dihydro-6'H-spiro[cyclohexane-1,9'-furo[2,3-f]quinazoline]-7'-one;

5'-chloro-2'-(morpholin-4-ylmethyl)-7',8'-dihydro-6'H-spiro[cyclohexane-1,9'-furo[2,3-f]quinazoline]-7'-one;

5'-chloro-2'-(pyrrolidin-1-ylmethyl)-7',8'-dihydro-6'H-spiro[cyclohexane-1,9'-furo[2,3-f]quinazoline]-7'-one;

5'-chloro-2'-[(4-methylpiperazin-1-yl)methyl]-7',8'-di hydro-6'H-spiro[cyclohexane-1,9'-furo[2,3-f]quinazo line]-7'-one;

5'-chloro-N-ethyl-7'-oxo-N-(propan-2-yl)-7',8'-dihydro-6'H-spiro[cyclohexane-1,9'-furo[2,3-f]quinazoline]-2'-carboxamide;

5'-chloro-7'-oxo-N-[2-(propan-2-yloxy)ethyl]-7',8'-di hydro-6'H-spiro[cyclohexane-1,9'-furo[2,3-f]quinazo line]-2'-carboxamide;

5'-chloro-2'-(4-methoxypiperidine-1-carbonyl)-7',8'-di hydro-6'H-spiro[cyclohexane-1,9'-furo[2,3-f]quinazo line]-7'-one;

5'-chloro-N-[(4-fluorophenyl)methyl]-7'-oxo-7',8'-di hydro-6'H-spiro[cyclohexane-1,9'-furo[2,3-f]quinazo line]-2'-carboxamide;

5'-chloro-N-(2-methoxyethyl)-7'-oxo-7',8'-dihydro-6'H-spiro[cyclohexane-1,9'-furo[2,3-f]quinazoline]-7'-car boxamide;

5'-chloro-N-methyl-N-(2-methylpropyl)-7'-oxo-7',8'-di hydro-6'H-spiro[cyclohexane-1,9'-furo[2,3-f]quinazo line]-7'-carboxamide;

5'-chloro-N-cyclopentyl-N-methyl-7'-oxo-7',8'-dihydro-6'H-spiro[cyclohexane-1,9'-furo[2,3-f]quinazoline]-7'-carboxamide;

5'-chloro-N-(1-hydroxy-3-methylbutan-2-yl)-7'-oxo-7', 8'-dihydro-6'H-spiro[cyclohexane-1,9'-furo[2,3-f]qui nazoline]-2'-carboxamide;

5'-chloro-N-(1-methylpiperidin-4-yl)-7'-oxo-7',8'-di hydro-6'H-spiro[cyclohexane-1,9'-furo[2,3-f]quinazo line]-2'-carboxamide;

5'-chloro-N-[(2-fluorophenyl)methyl]-7'-oxo-7',8'-di hydro-6'H-spiro[cyclohexane-1,9'-furo[2,3-f]quinazo line]-2'-carboxamide;

5'-chloro-2'-[4-(2-hydroxyethyl)piperazine-1-carbonyl]-7',8'-dihydro-6'H-spiro[cyclohexane-1,9'-furo[2,3-f] quinazoline]-7'-one;

5'-chloro-N-(3-hydroxypropyl)-7'-oxo-7',8'-dihydro-6'H-spiro[cyclohexane-1,9'-furo[2,3-f]quinazoline]-2'-car boxamide;

5'-chloro-N-(4-hydroxybutyl)-7'-oxo-7',8'-dihydro-6'H-spiro[cyclohexane-1,9'-furo[2,3-f]quinazoline]-2'-carboxamide;

5'-chloro-N-(2-hydroxyethyl)-7'-oxo-N-propyl-7',8'-dihydro-6'H-spiro[cyclohexane-1,9'-furo[2,3-f]quinazoline]-2'-carboxamide;

5'-chloro-7'-oxo-N-[2-(pyrrolidin-1-yl)ethyl]-7',8'-dihydro-6'H-spiro[cyclohexane-1,9'-furo[2,3-f]quinazoline]-2'-carboxamide;

5'-chloro-N-[2-(dimethylamino)ethyl]-N-ethyl-7'-oxo-7',8'-dihydro-6'H-spiro[cyclohexane-1,9'-furo[2,3-f]quinazoline]-2'-carboxamide;

5'-chloro-N-[3-(1H-imidazol-1-yl)propyl]-7'-oxo-7',8'-dihydro-6'H-spiro[cyclohexane-1,9'-furo[2,3-f]quinazoline]-2'-carboxamide;

5'-chloro-N-(2-hydroxyethyl)-N-methyl-7'-oxo-7',8'-dihydro-6'H-spiro[cyclohexane-1,9'-furo[2,3-f]quinazoline]-2'-carboxamide;

5'-chloro-N-(2-hydroxybutyl)-7'-oxo-7',8'-dihydro-6'H-spiro[cyclohexane-1,9'-furo[2,3-f]quinazoline]-2'-carboxamide;

5'-chloro-N-[3-(dimethylamino)propyl]-N-methyl-7'-oxo-7',8'-dihydro-6'H-spiro[cyclohexane-1,9'-furo[2,3-f]quinazoline]-2'-carboxamide;

2'-[(8aS)-octahydropyrrolo[1,2-a]piperazine-2-carbonyl]-5'-chloro-7',8'-dihydro-6'H-spiro[cyclohexane-1,9'-furo[2,3-f]quinazoline]-7'-one;

5'-chloro-N-methyl-7'-oxo-N-[2-(pyridin-2-yl)ethyl]-7',8'-dihydro-6'H-spiro[cyclohexane-1,9'-furo[2,3-f]quinazoline]-2'-carboxamide;

5'-chloro-N-(2-cyanoethyl)-N-methyl-7'-oxo-7',8'-dihydro-6'H-spiro[cyclohexane-1,9'-furo[2,3-f]quinazoline]-2'-carboxamide;

5'-chloro-N-(2-ethoxyethyl)-7'-oxo-7',8'-dihydro-6'H-spiro[cyclohexane-1,9'-furo[2,3-f]quinazoline]-2'-carboxamide;

5'-chloro-7'-oxo-N-(oxolan-2-ylmethyl)-7',8'-dihydro-6'H-spiro[cyclohexane-1,9'-furo[2,3-f]quinazoline]-2'-carboxamide;

5'-chloro-N-(2-methoxyethyl)-7'-oxo-N-(propan-2-yl)-7',8'-dihydro-6'H-spiro[cyclohexane-1,9'-furo[2,3-f]quinazoline]-2'-carboxamide;

5'-chloro-7'-oxo-N-[2-(thiophen-2-yl)ethyl]-7',8'-dihydro-6'H-spiro[cyclohexane-1,9'-furo[2,3-f]quinazoline]-2'-carboxamide;

5'-chloro-N-cyclopentyl-7'-oxo-7',8'-dihydro-6'H-spiro[cyclohexane-1,9'-furo[2,3-f]quinazoline]-2'-carboxamide;

5'-chloro-N-ethyl-N-(2-hydroxyethyl)-7'-oxo-7',8'-dihydro-6'H-spiro[cyclohexane-1,9'-furo[2,3-f]quinazoline]-2'-carboxamide;

5'-chloro-2'-(3-hydroxypiperidine-1-carbonyl)-7',8'-dihydro-6'H-spiro[cyclohexane-1,9'-furo[2,3-f]quinazoline]-7'-one;

5'-chloro-7'-oxo-N-[2-(1H-pyrrol-1-yl)ethyl]-7',8'-dihydro-6'H-spiro[cyclohexane-1,9'-furo[2,3-f]quinazoline]-2'-carboxamide;

5'-chloro-N-methyl-N-(1-methylpyrrolidin-3-yl)-7'-oxo-7',8'-dihydro-6'H-spiro[cyclohexane-1,9'-furo[2,3-f]quinazoline]-2'-carboxamide;

5'-chloro-N-(3-hydroxy-3-phenylpropyl)-N-methyl-7'-oxo-7',8'-dihydro-6'H-spiro[cyclohexane-1,9'-furo[2,3-f]quinazoline]-2'-carboxamide;

5'-chloro-2'-[3-(hydroxymethyl)-3-(2-methylpropyl)piperidine-1-carbonyl]-7',8'-dihydro-6'H-spiro[cyclohexane-1,9'-furo[2,3-f]quinazoline]-7'-one;

5'-chloro-N-[(2,3-dimethoxyphenyl)methyl]-N-methyl-7'-oxo-7',8'-dihydro-6'H-spiro[cyclohexane-1,9'-furo[2,3-f]quinazoline]-7'-carboxamide;

5'-chloro-7'-[2-(trifluoromethyl)-5H,6H,7H,8H-imidazo[1,2-a]pyrazine-7-carbonyl]-7',8'-dihydro-6'H-spiro[cyclohexane-1,9'-furo[2,3-f]quinazoline]-7'-one;

5'-chloro-N-[3-(morpholin-4-yl)propyl]-7'-oxo-7',8'-dihydro-6'H-spiro[cyclohexane-1,9'-furo[2,3-f]quinazoline]-7'-carboxamide;

5'-chloro-N-[(2-methoxyphenyl)methyl]-N-methyl-7'-oxo-7',8'-dihydro-6'H-spiro[cyclohexane-1,9'-furo[2,3-f]quinazoline]-2'-carboxamide;

5'-chloro-2'-[3-(1H-imidazol-1-ylmethyl)piperidine-1-carbonyl]-7',8'-dihydro-6'H-spiro[cyclohexane-1,9'-furo[2,3-f]quinazoline]-7'-one;

ethyl 2-[4-({5'-chloro-7'-oxo-7',8'-dihydro-6'H-spiro[cyclohexane-1,9'-furo[2,3-f]quinazoline]-2'-yl}carbonyl)piperazin-1-yl]acetate;

5'-chloro-N-[(2,4-dimethoxyphenyl)methyl]-N-methyl-7'-oxo-7',8'-dihydro-6'H-spiro[cyclohexane-1,9'-furo[2,3-f]quinazoline]-2'-carboxamide;

5'-chloro-N-[(3-methoxyphenyl)methyl]-N-methyl-7'-oxo-7',8'-dihydro-6'H-spiro[cyclohexane-1,9'-furo[2,3-f]quinazoline]-2'-carboxamide;

5'-chloro-N-(2,2-dimethyloxan-4-yl)-N-ethyl-7'-oxo-7',8'-dihydro-6'H-spiro[cyclohexane-1,9'-furo[2,3-f]quinazoline]-2'-carboxamide;

5'-chloro-N-methyl-N-[(1-methyl-1H-1,3-benzodiazol-2-yl)methyl]-7'-oxo-7',8'-dihydro-6'H-spiro[cyclohexane-1,9'-furo[2,3-f]quinazoline]-2'-carboxamide;

5'-chloro-N-[(3,5-dimethoxyphenyl)methyl]-N-methyl-7'-oxo-7',8'-dihydro-6'H-spiro[cyclohexane-1,9'-furo[2,3-f]quinazoline]-2'-carboxamide;

5'-chloro-2'-{5H,6H,7H, 8H-imidazo [1,2-a]pyrazine-7-carbonyl}-7',8'-dihydro-6'H-spiro[cyclohexane-1,9'-furo[2,3-f]quinazoline]-7'-one;

5'-chloro-2'-[2-(pyridin-2-yl)pyrrolidine-1-carbonyl]-7',8'-dihydro-6'H-spiro[cyclohexane-1,9'-furo[2,3-f]quinazoline]-7'-one;

5'-chloro-N-(2-hydroxy-2-phenylethyl)-N-methyl-7'-oxo-7',8'-dihydro-6'H-spiro[cyclohexane-1,9'-furo[2,3-f]quinazoline]-2'-carboxamide;

5'-chloro-N-[2-(2,3-dihydro-1H-indol-1-yl)ethyl]-7'-oxo-7',8'-dihydro-6'H-spiro[cyclohexane-1,9'-furo[2,3-f]quinazoline]-2'-carboxamide;

5'-chloro-N-[(2,3-dimethoxyphenyl)methyl]-7'-oxo-7',8'-dihydro-6'H-spiro[cyclohexane-1,9'-furo[2,3-f]quinazoline]-2'-carboxamide;

5'-chloro-N-methyl-N-[(5-methyl-1H-1,3-benzodiazol-2-yl)methyl]-7'-oxo-7',8'-dihydro-6'H-spiro[cyclohexane-1,9'-furo[2,3-f]quinazoline]-2'-carboxamide;

5'-chloro-N-methyl-7'-oxo-N-[3-(trimethyl-1H-pyrazol-4-yl)propyl]-7',8'-dihydro-6'H-spiro[cyclohexane-1,9'-furo[2,3-f]quinazoline]-2'-carboxamide;

5'-chloro-2'-{octahydropyrrolo[1,2-a]piperazine-2-carbonyl}-7',8'-dihydro-6'H-spiro[cyclohexane-1,9'-furo[2,3-f]quinazoline]-7'-one;

5'-chloro-N-(2,3-dihydro-1,4-benzodioxin-6-ylmethyl)-7'-oxo-7',8'-dihydro-6'H-spiro[cyclohexane-1,9'-furo[2,3-f]quinazoline]-2'-carboxamide;

5'-chloro-N-[(5-cyclopropyl-1H-pyrazol-3-yl)methyl]-N-methyl-7'-oxo-7',8'-dihydro-6'H-spiro[cyclohexane-1,9'-furo[2,3-f]quinazoline]-2'-carboxamide;

5'-chloro-N-[(2,4-dimethoxyphenyl)methyl]-7'-oxo-7',8'-dihydro-6'H-spiro[cyclohexane-1,9'-furo[2,3-f]quinazoline]-2'-carboxamide;

N-(1-benzylpyrrolidin-3-yl)-5'-chloro-7'-oxo-7',8'-dihydro-6'H-spiro[cyclohexane-1,9'-furo[2,3-f]quinazoline]-2'-carboxamide;

5'-chloro-N-[(2,3-difluoro-4-methoxyphenyl)methyl]-7'-oxo-7',8'-dihydro-6'H-spiro[cyclohexane-1,9'-furo[2,3-f]quinazoline]-2'-carboxamide;

5'-chloro-N-{[4-(dimethylamino)phenyl]methyl}-7'-oxo-7',8'-dihydro-6'H-spiro[cyclohexane-1,9'-furo[2,3-f]quinazoline]-2'-carboxamide;

5'-chloro-N-[(1-methyl-1H-imidazol-2-yl)methyl]-7'-oxo-N-(propan-2-yl)-7',8'-dihydro-6'H-spiro[cyclohexane-1,9'-furo[2,3-f]quinazoline]-2'-carboxamide;

5'-chloro-2'-[4-(pyridin-4-yl)piperazine-1-carbonyl]-7',8'-dihydro-6'H-spiro[cyclohexane-1,9'-furo[2,3-f]quinazoline]-7'-one;

N-[(5-tert-butyl-1H-pyrazol-3-yl)methyl]-5'-chloro-N-methyl-7'-oxo-7',8'-dihydro-6'H-spiro[cyclohexane-1,9'-furo[2,3-f]quinazoline]-2'-carboxamide;

2'-(4-benzylpiperazine-1-carbonyl)-5'-chloro-7',8'-dihydro-6'H-spiro[cyclohexane-1,9'-furo[2,3-f]quinazoline]-7'-one;

5'-chloro-N-[(1-methylpiperidin-4-yl)methyl]-7'-oxo-7',8'-dihydro-6'H-spiro[cyclohexane-1,9'-furo[2,3-f]quinazoline]-2'-carboxamide;

5'-chloro-7'-(3-methoxypiperidine-1-carbonyl)-7',8'-dihydro-6'H-spiro[cyclohexane-1,9'-furo[2,3-f]quinazoline]-7'-one;

5'-chloro-N-methyl-7'-oxo-N-[(trimethyl-1H-pyrazol-4-yl)methyl]-7',8'-dihydro-6'H-spiro[cyclohexane-1,9'-furo[2,3-f]quinazoline]-2'-carboxamide;

5'-chloro-2'-[4-(pyridin-2-yl)piperazine-1-carbonyl]-7',8'-dihydro-6'H-spiro[cyclohexane-1,9'-furo[2,3-f]quinazoline]-7'-one;

5'-chloro-N-[3-(3,5-dimethyl-1H-pyrazol-1-yl)propyl]-N-methyl-7'-oxo-7',8'-dihydro-6'H-spiro[cyclohexane-1,9'-furo[2,3-f]quinazoline]-2'-carboxamide;

5'-chloro-2'-(4-methyl-2-phenylpiperazine-1-carbonyl)-7',8'-dihydro-6'H-spiro[cyclohexane-1,9'-furo[2,3-f]quinazoline]-7'-one;

5'-chloro-2'-[3-(dimethylamino)piperidine-1-carbonyl]-7',8'-dihydro-6'H-spiro[cyclohexane-1,9'-furo[2,3-f]quinazoline]-7'-one;

5'-chloro-N-[2-(morpholin-4-yl)ethyl]-7'-oxo-7',8'-dihydro-6'H-spiro[cyclohexane-1,9'-furo[2,3-f]quinazoline]-2'-carboxamide;

5'-chloro-7'-oxo-N-[2-(pyridin-3-yloxy)ethyl]-7',8'-dihydro-6'H-spiro[cyclohexane-1,9'-furo[2,3-f]quinazoline]-2'-carboxamide;

5'-chloro-N-[(2-fluoro-4-methoxyphenyl)methyl]-7'-oxo-7',8'-dihydro-6'H-spiro[cyclohexane-1,9'-furo[2,3-f]quinazoline]-2'-carboxamide;

1-({5'-chloro-7'-oxo-7',8'-dihydro-6'H-spiro[cyclohexane-1,9'-furo[2,3-f]quinazoline]-2'-yl}carbonyl)azetidine-3-carbonitrile;

5'-chloro-2'-{3-phenyl-5H,6H,7H,8H-imidazo[1,2-a]pyrazine-7-carbonyl}-7',8'-dihydro-6'H-spiro[cyclohexane-1,9'-furo[2,3-f]quinazoline]-7'-one;

5'-chloro-7'-oxo-N-[2-(2-oxopyrrolidin-1-yl)ethyl]-7',8'-dihydro-6'H-spiro[cyclohexane-1,9'-furo[2,3-f]quinazoline]-2'-carboxamide;

5'-chloro-7'-oxo-N-(2,2,6,6-tetramethyloxan-4-yl)-7',8'-dihydro-6'H-spiro[cyclohexane-1,9'-furo[2,3-f]quinazoline]-2'-carboxamide;

2'-[(1R,5S)-3-azabicyclo[3.1.0]hexane-3-carbonyl]-5'-chloro-7',8'-dihydro-6'H-spiro[cyclohexane-1,9'-furo[2,3-f]quinazoline]-7'-one;

5'-chloro-N-[2-(4-fluorophenoxy)ethyl]-7'-oxo-7',8'-dihydro-6'H-spiro[cyclohexane-1,9'-furo[2,3-f]quinazoline]-2'-carboxamide;

5'-chloro-7'-oxo-N-[2-(1H-pyrazol-1-yl)ethyl]-7',8'-dihydro-6'H-spiro[cyclohexane-1,9'-furo[2,3-f]quinazoline]-2'-carboxamide;

5'-chloro-N-[4-(4-hydroxypiperidin-1-yl)phenyl]-7'-oxo-7',8'-dihydro-6'H-spiro[cyclohexane-1,9'-furo[2,3-f]quinazoline]-2'-carboxamide;

5'-chloro-N-(3,3-dimethyl-2-oxobutyl)-7'-oxo-7',8'-dihydro-6'H-spiro[cyclohexane-1,9'-furo[2,3-f]quinazoline]-2'-carboxamide;

5'-chloro-N-(furan-2-ylmethyl)-N-methyl-7'-oxo-7',8'-dihydro-6'H-spiro[cyclohexane-1,9'-furo[2,3-f]quinazoline]-2'-carboxamide;

5'-chloro-2'-{4-[2-(dimethylamino)ethyl]piperidine-1-carbonyl}-7',8'-dihydro-6'H-spiro[cyclohexane-1,9'-furo[2,3-f]quinazoline]-7'-one;

5'-chloro-2'-[4-(5-chloropyridin-2-yl)piperazine-1-carbonyl]-7',8'-dihydro-6'H-spiro[cyclohexane-1,9'-furo[2,3-f]quinazoline]-7'-one;

5'-chloro-N-[(2-methoxyphenyl)methyl]-7'-oxo-7',8'-dihydro-6'H-spiro[cyclohexane-1,9'-furo[2,3-f]quinazoline]-2'-carboxamide;

5'-chloro-N-(2-hydroxy-2-methylpropyl)-7'-oxo-7',8'-dihydro-6'H-spiro[cyclohexane-1,9'-furo[2,3-f]quinazoline]-2'-carboxamide;

5'-chloro-N-[(4-cyanophenyl)methyl]-7'-oxo-7',8'-dihydro-6'H-spiro[cyclohexane-1,9'-furo[2,3-f]quinazoline]-2'-carboxamide;

5'-chloro-2'-[3-oxo-4-(propan-2-yl)piperazine-1-carbonyl]-7',8'-dihydro-6'H-spiro[cyclohexane-1,9'-furo[2,3-f]quinazoline]-7'-one;

5'-chloro-N-{[5-(difluoromethoxy)pyridin-2-yl]methyl}-7'-oxo-7',8'-dihydro-6'H-spiro[cyclohexane-1,9'-furo[2,3-f]quinazoline]-2'-carboxamide;

5'-chloro-2'-[4-(oxetan-3-yl)piperazine-1-carbonyl]-7',8'-dihydro-6'H-spiro[cyclohexane-1,9'-furo[2,3-f]quinazoline]-7'-one;

5'-chloro-N-[(1R,5S)-6,6-difluorobicyclo[3.1.0]hexan-3-yl]-7'-oxo-7',8'-dihydro-6'H-spiro[cyclohexane-1,9'-furo[2,3-f]quinazoline]-2'-carboxamide;

N-[2-(2H-1,3-benzodioxol-5-yl)ethyl]-5'-chloro-7'-oxo-7',8'-dihydro-6'H-spiro[cyclohexane-1,9'-furo[2,3-f]quinazoline]-2'-carboxamide;

5'-chloro-N-[(4-ethyl-4H-1,2,4-triazol-3-yl)methyl]-N-methyl-7'-oxo-7',8'-dihydro-6'H-spiro[cyclohexane-1,9'-furo[2,3-f]quinazoline]-2'-carboxamide;

5'-chloro-N-[(4-cyano-3-fluorophenyl)methyl]-7'-oxo-7',8'-dihydro-6'H-spiro[cyclohexane-1,9'-furo[2,3-f]quinazoline]-2'-carboxamide;

2-{5'-chloro-7'-oxo-7',8'-dihydro-6'H-spiro[cyclohexane-1,9'-furo[2,3-f]quinazoline]-7'-ylformamido}-N,N-diethylacetamide;

5'-chloro-7'-({6'-methyl-5',6'-dihydro-4'H-spiro[piperidine-4,7'-thieno[2,3-c]pyridine]-1-yl}carbonyl)-7',8'-dihydro-6'H-spiro[cyclohexane-1,9'-furo[2,3-f]quinazoline]-7'-one;

5'-chloro-N-[(6-methylpyridin-3-yl)methyl]-7'-oxo-7',8'-dihydro-6'H-spiro[cyclohexane-1,9'-furo[2,3-f]quinazoline]-2'-carboxamide;

5'-chloro-7'-oxo-N-[(trimethyl-1H-imidazol-2-yl)methyl]-7',8'-dihydro-6'H-spiro[cyclohexane-1,9'-furo[2,3-f]quinazoline]-2'-carboxamide;

5'-chloro-N-[(5-methylpyridin-3-yl)methyl]-7'-oxo-7',8'-dihydro-6'H-spiro[cyclohexane-1,9'-furo[2,3-f]quinazoline]-2'-carboxamide;

5'-chloro-N-methyl-7'-oxo-N-[(5-phenyl-1,2-oxazol-3-yl)methyl]-7',8'-dihydro-6'H-spiro[cyclohexane-1,9'-furo[2,3-f]quinazoline]-2'-carboxamide;

2'-{6-azaspiro[2.5]octane-6-carbonyl}-5'-chloro-7',8'-dihydro-6'H-spiro[cyclohexane-1,9'-furo[2,3-f]quinazoline]-7'-one;

5'-chloro-N-[2-(oxan-4-yl)ethyl]-7'-oxo-7',8'-dihydro-6'H-spiro[cyclohexane-1,9'-furo[2,3-f]quinazoline]-2'-carboxamide;

5'-chloro-2'-({6',7'-dihydro-5'H-spiro[piperidine-4,4'-thieno[3,2-c]pyridine]-1'-yl}carbonyl)-7',8'-dihydro-6'H-spiro[cyclohexane-1,9'-furo[2,3-f]quinazoline]-7'-one;

5'-chloro-N-(1-methoxy-2-methylpropan-2-yl)-7'-oxo-7',8'-dihydro-6'H-spiro[cyclohexane-1,9'-furo[2,3-f]quinazoline]-2'-carboxamide;

5'-chloro-7'-oxo-N-[1-(pyridin-3-yl)piperidin-4-yl]-7',8'-dihydro-6'H-spiro[cyclohexane-1,9'-furo[2,3-f]quinazoline]-2'-carboxamide;

5'-chloro-2'-({3,4-dihydrospiro[2-benzopyran-1,4'-piperidine]-1'-yl}carbonyl)-7',8'-dihydro-6'H-spiro[cyclohexane-1,9'-furo[2,3-f]quinazoline]-7'-one;

5'-chloro-7'-oxo-N-(2-phenoxyethyl)-7',8'-dihydro-6'H-spiro[cyclohexane-1,9'-furo[2,3-f]quinazoline]-2'-carboxamide;

3-{5'-chloro-7'-oxo-7',8'-dihydro-6'H-spiro[cyclohexane-1,9'-furo[2,3-f]quinazoline]-2'-ylformamido}-N,N-dimethylpropanamide;

5'-chloro-N-[1-(methoxymethyl)cyclopropyl]-7'-oxo-7',8'-dihydro-6'H-spiro[cyclohexane-1,9'-furo[2,3-f]quinazoline]-7'-carboxamide;

5'-chloro-N-[(3-fluoropyridin-4-yl)methyl]-7'-oxo-7',8'-dihydro-6'H-spiro[cyclohexane-1,9'-furo[2,3-f]quinazoline]-7'-carboxamide;

5'-chloro-N-(cyclobutylmethyl)-7'-oxo-N-(oxolan-2-ylmethyl)-7',8'-dihydro-6'H-spiro[cyclohexane-1,9'-furo[2,3-f]quinazoline]-7'-carboxamide;

5'-chloro-7'-[4-(furan-2-ylmethyl)piperazine-1-carbonyl]-7',8'-dihydro-6'H-spiro[cyclohexane-1,9'-furo[2,3-f]quinazoline]-7'-one;

5'-chloro-N-[(1-methyl-1H-pyrazol-4-yl)methyl]-7'-oxo-7',8'-dihydro-6'H-spiro[cyclohexane-1,9'-furo[2,3-f]quinazoline]-2'-carboxamide;

5'-chloro-7'-oxo-N-[1-(pyridin-2-yl)cyclopropyl]-7',8'-dihydro-6'H-spiro[cyclohexane-1,9'-furo[2,3-f]quinazoline]-2'-carboxamide;

5'-chloro-N-(4-methyloxan-4-yl)-7'-oxo-7',8'-dihydro-6'H-spiro[cyclohexane-1,9'-furo[2,3-f]quinazoline]-2'-carboxamide;

5'-chloro-N-{[1-(ethoxymethyl)cyclopropyl]methyl}-7'-oxo-7',8'-dihydro-6'H-spiro[cyclohexane-1,9'-furo[2,3-f]quinazoline]-2'-carboxamide;

2'-(4-benzoylpiperazine-1-carbonyl)-5'-chloro-7',8'-dihydro-6'H-spiro[cyclohexane-1,9'-furo[2,3-f]quinazoline]-7'-one;

2'-(4-{bicyclo[2.2.1]heptan-2-yl}piperazine-1-carbonyl)-5'-chloro-7',8'-dihydro-6'H-spiro[cyclohexane-1,9'-furo[2,3-f]quinazoline]-7'-one;

5'-chloro-N-[(1-methyl-1H-imidazol-5-yl)methyl]-7'-oxo-7',8'-dihydro-6'H-spiro[cyclohexane-1,9'-furo[2,3-f]quinazoline]-2'-carboxamide;

5'-chloro-7'-oxo-N-[2-oxo-2-(piperidin-1-yl)ethyl]-7',8'-dihydro-6'H-spiro[cyclohexane-1,9'-furo[2,3-f]quinazoline]-2'-carboxamide;

5'-chloro-2'-(3-hydroxyazetidine-1-carbonyl)-7',8'-dihydro-6'H-spiro[cyclohexane-1,9'-furo[2,3-f]quinazoline]-7'-one;

5'-chloro-7'-oxo-N-{[5-(trifluoromethyl)pyridin-2-yl]methyl}-7',8'-dihydro-6'H-spiro[cyclohexane-1,9'-furo[2,3-f]quinazoline]-2'-carboxamide;

5'-chloro-N-[1-(oxan-4-yl)cyclopropyl]-7'-oxo-7',8'-dihydro-6'H-spiro[cyclohexane-1,9'-furo[2,3-f]quinazoline]-2'-carboxamide;

5'-chloro-N-methyl-7'-oxo-N-(prop-2-yn-1-yl)-7',8'-dihydro-6'H-spiro[cyclohexane-1,9'-furo[2,3-f]quinazoline]-7'-carboxamide;

5'-chloro-N,N-diethyl-7'-oxo-7',8'-dihydro-6'H-spiro[cyclohexane-1,9'-furo[2,3-f]quinazoline]-7'-carboxamide;

5'-chloro-N-(1-methyl-2-oxopiperidin-4-yl)-7'-oxo-7',8'-dihydro-6'H-spiro[cyclohexane-1,9'-furo[2,3-f]quinazoline]-7'-carboxamide;

5'-chloro-2'-[(1R,5S,6S)-6-(pyridin-2-yl)-3-azabicyclo[3.1.0]hexane-3-carbonyl]-7',8'-dihydro-6'H-spiro[cyclohexane-1,9'-furo[2,3-f]quinazoline]-7'-one;

5'-chloro-N-[(6-fluoropyridin-2-yl)methyl]-7'-oxo-7',8'-dihydro-6'H-spiro[cyclohexane-1,9'-furo[2,3-f]quinazoline]-2'-carboxamide;

5'-chloro-N-ethyl-N-methyl-7'-oxo-7',8'-dihydro-6'H-spiro[cyclohexane-1,9'-furo[2,3-f]quinazoline]-2'-carboxamide;

5'-chloro-2'-{6,6-dimethyl-3-azabicyclo[3.1.0]hexane-3-carbonyl}-7',8'-dihydro-6'H-spiro[cyclohexane-1,9'-furo[2,3-f]quinazoline]-7'-one;

5'-chloro-2'-{7,7-difluoro-3-azabicyclo[4.1.0]heptane-3-carbonyl}-7',8'-dihydro-6'H-spiro[cyclohexane-1,9'-furo[2,3-f]quinazoline]-7'-one;

5'-chloro-2'-{6,6-difluoro-3-azabicyclo[3.1.0]hexane-3-carbonyl}-7',8'-dihydro-6'H-spiro[cyclohexane-1,9'-furo[2,3-f]quinazoline]-7'-one;

5'-chloro-7'-oxo-N-(2,2,2-trifluoroethyl)-7',8'-dihydro-6'H-spiro[cyclohexane-1,9'-furo[2,3-f]quinazoline]-2'-carboxamide;

5'-chloro-7'-oxo-N-[(5-oxopyrrolidin-2-yl)methyl]-N-(propan-2-yl)-7',8'-dihydro-6'H-spiro[cyclohexane-1,9'-furo[2,3-f]quinazoline]-2'-carboxamide;

5'-chloro-N-[2-(2,3-dihydro-1-benzofuran-5-yl)ethyl]-7'-oxo-7',8'-dihydro-6'H-spiro[cyclohexane-1,9'-furo[2,3-f]quinazoline]-2'-carboxamide;

5'-chloro-N-(4,4-difluorocyclohexyl)-7'-oxo-7',8'-dihydro-6'H-spiro[cyclohexane-1,9'-furo[2,3-f]quinazoline]-2'-carboxamide;

N-{bicyclo[1.1.1]pentan-1-yl}-5'-chloro-7'-oxo-7',8'-dihydro-6'H-spiro[cyclohexane-1,9'-furo[2,3-f]quinazoline]-2'-carboxamide;

5'-chloro-N-[(1S,3R)-3-fluorocyclopentyl]-7'-oxo-7',8'-dihydro-6'H-spiro[cyclohexane-1,9'-furo[2,3-f]quinazoline]-2'-carboxamide;

5'-chloro-N-methyl-7'-oxo-N-(prop-2-en-1-yl)-7',8'-dihydro-6'H-spiro[cyclohexane-1,9'-furo[2,3-f]quinazoline]-7'-carboxamide;

5'-chloro-7'-oxo-N-(prop-2-yn-1-yl)-7',8'-dihydro-6'H-spiro[cyclohexane-1,9'-furo[2,3-f]quinazoline]-7'-carboxamide;

5'-chloro-7'-{2-ethyl-1-oxo-1H,2H,5H,6H,7H,8H-pyrido[3,4-d]pyridazine-6-carbonyl}-7',8'-dihydro-6'H-spiro[cyclohexane-1,9'-furo[2,3-]quinazoline]-7'-one;

5'-chloro-N-(1,3-dihydro-2-benzofuran-5-ylmethyl)-7'-oxo-7',8'-dihydro-6'H-spiro[cyclohexane-1,9'-furo[2,3-f]quinazoline]-2'-carboxamide;

5'-chloro-N-[4-(methoxymethyl)oxan-4-yl]-7'-oxo-7',8'-dihydro-6'H-spiro[cyclohexane-1,9'-furo[2,3-]quinazoline]-2'-carboxamide;

5'-chloro-N-cyclobutyl-7'-oxo-7',8'-dihydro-6'H-spiro[cyclohexane-1,9'-furo[2,3-f]quinazoline]-2'-carboxamide;

5'-chloro-2'-{9-propanoyl-2,9-diazaspiro[5.5]undecane-2-carbonyl}-7',8'-dihydro-6'H-spiro[cyclohexane-1,9'-furo[2,3-f]quinazoline]-7'-one;

5'-chloro-N-methyl-7'-oxo-N-(propan-2-yl)-7',8'-dihydro-6'H-spiro[cyclohexane-1,9'-furo[2,3-f]quinazoline]-2'-carboxamide;

5'-chloro-2'-[(1R,5S,6S)-6-(2-methoxyphenyl)-3-azabicyclo[3.1.0]hexane-3-carbonyl]-7',8'-dihydro-6'H-spiro[cyclohexane-1,9'-furo[2,3-]quinazoline]-7'-one;

N-butyl-5'-chloro-7'-oxo-7',8'-dihydro-6'H-spiro[cyclohexane-1,9'-furo[2,3-f]quinazoline]-2'-carboxamide;

5'-chloro-2'-{8-ethoxy-2H,3H,4H,5H-pyrido[3,2-f][1,4]oxazepine-4-carbonyl}-7',8'-dihydro-6'H-spiro[cyclohexane-1,9'-furo[2,3-f]quinazoline]-7'-one;

5'-chloro-7'-oxo-N-[2-(thiophen-3-yl)ethyl]-7',8'-dihydro-6'H-spiro[cyclohexane-1,9'-furo[2,3-f]quinazoline]-2'-carboxamide;

5'-chloro-N-(2-cyclobutyl-2,2-difluoroethyl)-7'-oxo-7',8'-dihydro-6'H-spiro[cyclohexane-1,9'-furo[2,3-f]quinazoline]-2'-carboxamide;

5'-chloro-N-methyl-7'-oxo-N-propyl-7',8'-dihydro-6'H-spiro[cyclohexane-1,9'-furo[2,3-f]quinazoline]-2'-carboxamide;

(2R)-1-({5'-chloro-7'-oxo-7',8'-dihydro-6'H-spiro[cyclohexane-1,9'-furo[2,3-f]quinazoline]-2'-yl}carbonyl)pyrrolidine-2-carboxylic acid;

5'-chloro-7'-[(1R,6R)-7,7-difluoro-6-methyl-3-azabicyclo[4.1.0]heptane-3-carbonyl]-7',8'-dihydro-6'H-spiro[cyclohexane-1,9'-furo[2,3-f]quinazoline]-7'-one;

5'-chloro-N-methyl-7'-oxo-N-{[4-(propan-2-yl)-4H-1,2,4-triazol-3-yl]methyl}-7',8'-dihydro-6'H-spiro[cyclohexane-1,9'-furo[2,3-]quinazoline]-2'-carboxamide;

5'-chloro-7'-({4-oxo-3,4-dihydrospiro[1-benzopyran-2,3'-pyrrolidine]-1'-yl}carbonyl)-7',8'-dihydro-6'H-spiro[cyclohexane-1,9'-furo[2,3-f]quinazoline]-7'-one;

5'-chloro-N-cyclopropyl-7'-oxo-7',8'-dihydro-6'H-spiro[cyclohexane-1,9'-furo[2,3-f]quinazoline]-7'-carboxamide;

5'-chloro-N-ethyl-7'-oxo-N-propyl-7',8'-dihydro-6'H-spiro[cyclohexane-1,9'-furo[2,3-f]quinazoline]-2'-carboxamide;

5'-chloro-7'-oxo-N-propyl-7',8'-dihydro-6'H-spiro[cyclohexane-1,9'-furo[2,3-f]quinazoline]-2'-carboxamide;

5'-chloro-N-methyl-7'-oxo-N-(thiophen-3-ylmethyl)-7',8'-dihydro-6'H-spiro[cyclohexane-1,9'-furo[2,3-f]quinazoline]-2'-carboxamide;

1-({5'-chloro-7'-oxo-7',8'-dihydro-6'H-spiro[cyclohexane-1,9'-furo[2,3-f]quinazoline]-2'-yl}carbonyl)piperidine-4-carbonitrile;

5'-chloro-2'-[3-(dimethylamino)pyrrolidine-1-carbonyl]-7',8'-dihydro-6'H-spiro[cyclohexane-1,9'-furo[2,3-]quinazoline]-7'-one;

N-benzyl-5'-chloro-N-methyl-7'-oxo-7',8'-dihydro-6'H-spiro[cyclohexane-1,9'-furo[2,3-f]quinazoline]-2'-carboxamide;

5'-chloro-N-methyl-7'-oxo-N-(thiophen-2-ylmethyl)-7',8'-dihydro-6'H-spiro[cyclohexane-1,9'-furo[2,3-]quinazoline]-2'-carboxamide;

5'-chloro-N-[(3-methoxyphenyl)methyl]-7'-oxo-7',8'-dihydro-6'H-spiro[cyclohexane-1,9'-furo[2,3-f]quinazoline]-2'-carboxamide;

5'-chloro-2'-(3-hydroxypyrrolidine-1-carbonyl)-7',8'-dihydro-6'H-spiro[cyclohexane-1,9'-furo[2,3-f]quinazoline]-7'-one;

5'-chloro-7'-oxo-N,N-bis(propan-2-yl)-7',8'-dihydro-6'H-spiro[cyclohexane-1,9'-furo[2,3-f]quinazoline]-2'-carboxamide;

5'-chloro-N-[2-(furan-2-yl)ethyl]-7'-oxo-7',8'-dihydro-6'H-spiro[cyclohexane-1,9'-furo[2,3-f]quinazoline]-2'-carboxamide;

5'-chloro-7'-[2-(hydroxymethyl)piperidine-1-carbonyl]-7',8'-dihydro-6'H-spiro[cyclohexane-1,9'-furo[2,3-f]quinazoline]-7'-one;

5'-chloro-7'-[4-(propan-2-yl)piperazine-1-carbonyl]-7',8'-dihydro-6'H-spiro[cyclohexane-1,9'-furo[2,3-f]quinazoline]-7'-one;

5'-chloro-7'-[2-(furan-2-yl)pyrrolidine-1-carbonyl]-7',8'-dihydro-6'H-spiro[cyclohexane-1,9'-furo[2,3-f]quinazoline]-7'-one;

5'-chloro-N-(3-methylbutyl)-7'-oxo-7',8'-dihydro-6'H-spiro[cyclohexane-1,9'-furo[2,3-f]quinazoline]-2'-carboxamide;

5'-chloro-N-(2-cyanoethyl)-N-ethyl-7'-oxo-7',8'-dihydro-6'H-spiro[cyclohexane-1,9'-furo[2,3-f]quinazoline]-2'-carboxamide;

5'-chloro-N-methyl-7'-oxo-N-(pyridin-2-ylmethyl)-7',8'-dihydro-6'H-spiro[cyclohexane-1,9'-furo[2,3-]quinazoline]-2'-carboxamide;

5'-chloro-7'-oxo-N-[3-(pyrrolidin-1-yl)propyl]-7',8'-dihydro-6'H-spiro[cyclohexane-1,9'-furo[2,3-f]quinazoline]-2'-carboxamide;

5'-chloro-7'-oxo-N-(pentan-3-yl)-7',8'-dihydro-6'H-spiro[cyclohexane-1,9'-furo[2,3-f]quinazoline]-2'-carboxamide;

2'-(azepane-1-carbonyl)-5'-chloro-7',8'-dihydro-6'H-spiro[cyclohexane-1,9'-furo[2,3-f]quinazoline]-7'-one;

5'-chloro-N-[2-(1H-imidazol-1-yl)ethyl]-7'-oxo-7',8'-dihydro-6'H-spiro[cyclohexane-1,9'-furo[2,3-f]quinazoline]-2'-carboxamide;

5'-chloro-2'-[(2R,6S)-2,6-dimethylmorpholine-4-carbonyl]-7',8'-dihydro-6'H-spiro[cyclohexane-1,9'-furo[2,3-f]quinazoline]-7'-one;

5'-chloro-N-methyl-7'-oxo-N-(pyridin-3-ylmethyl)-7',8'-dihydro-6'H-spiro[cyclohexane-1,9'-furo[2,3-]quinazoline]-2'-carboxamide;

5'-chloro-N-methyl-N-(1-methylpiperidin-4-yl)-7'-oxo-7',8'-dihydro-6'H-spiro[cyclohexane-1,9'-furo[2,3-f]quinazoline]-2'-carboxamide;

5'-chloro-N-[(3-ethyl-1,2-oxazol-5-yl)methyl]-N-methyl-7'-oxo-7',8'-dihydro-6'H-spiro[cyclohexane-1,9'-furo[2,3-f]quinazoline]-2'-carboxamide;

5'-chloro-N-(3-methylbutan-2-yl)-7'-oxo-7',8'-dihydro-6'H-spiro[cyclohexane-1,9'-furo[2,3-f]quinazoline]-2'-carboxamide;

5'-chloro-7'-(3-methylpiperidine-1-carbonyl)-7',8'-dihydro-6'H-spiro[cyclohexane-1,9'-furo[2,3-f]quinazoline]-7'-one;

5'-chloro-N-[2-(dimethylamino)ethyl]-N-methyl-7'-oxo-7',8'-dihydro-6'H-spiro[cyclohexane-1,9'-furo[2,3-f]quinazoline]-2'-carboxamide;

5'-chloro-7'-(2,2-dimethylmorpholine-4-carbonyl)-7',8'-dihydro-6'H-spiro[cyclohexane-1,9'-furo[2,3-f]quinazoline]-7'-one;

5'-chloro-N-[(3-hydroxyphenyl)methyl]-7'-oxo-7',8'-dihydro-6'H-spiro[cyclohexane-1,9'-furo[2,3-f]quinazoline]-7'-carboxamide;

5'-chloro-7'-[4-(dimethylamino)piperidine-1-carbonyl]-7',8'-dihydro-6'H-spiro[cyclohexane-1,9'-furo[2,3-f]quinazoline]-7'-one;

5'-chloro-7'-oxo-N-[3-(2-oxopyrrolidin-1-yl)propyl]-7',8'-dihydro-6'H-spiro[cyclohexane-1,9'-furo[2,3-]quinazoline]-2'-carboxamide;

5'-chloro-2'-(4-methylpiperidine-1-carbonyl)-7',8'-dihydro-6'H-spiro[cyclohexane-1,9'-furo[2,3-f]quinazoline]-7'-one;

5'-chloro-7'-oxo-N-(thiophen-3-ylmethyl)-7',8'-dihydro-6'H-spiro[cyclohexane-1,9'-furo[2,3-f]quinazoline]-2'-carboxamide;

5'-chloro-N-[(3-fluorophenyl)methyl]-7'-oxo-7',8'-dihydro-6'H-spiro[cyclohexane-1,9'-furo[2,3-f]quinazoline]-2'-carboxamide;

N-benzyl-5'-chloro-N-(2-hydroxyethyl)-7'-oxo-7',8'-dihydro-6'H-spiro[cyclohexane-1,9'-furo[2,3-f]quinazoline]-2'-carboxamide;

5'-chloro-N-[2-(3,5-dimethyl-1H-pyrazol-4-yl)ethyl]-N-methyl-7'-oxo-7',8'-dihydro-6'H-spiro[cyclohexane-1,9'-furo[2,3-f]quinazoline]-2'-carboxamide;

5'-chloro-2'-(4-cyclohexylpiperazine-1-carbonyl)-7',8'-dihydro-6'H-spiro[cyclohexane-1,9'-furo[2,3-f]quinazoline]-7'-one;

5'-chloro-2'-(4-hydroxy-4-phenylpiperidine-1-carbonyl)-7',8'-dihydro-6'H-spiro[cyclohexane-1,9'-furo[2,3-f]quinazoline]-7'-one;

5'-chloro-2'-[4-(oxolane-2-carbonyl)piperazine-1-carbonyl]-7',8'-dihydro-6'H-spiro[cyclohexane-1,9'-furo[2,3-f]quinazoline]-7'-one;

5'-chloro-2'-{4-[(dimethylamino)methyl]piperidine-1-carbonyl}-7',8'-dihydro-6'H-spiro[cyclohexane-1,9'-furo[2,3-f]quinazoline]-7'-one;

1-({5'-chloro-7'-oxo-7',8'-dihydro-6'H-spiro[cyclohexane-1,9'-furo[2,3-f]quinazoline]-2'-yl}carbonyl)-N-methylpiperidine-4-carboxamide;

5'-chloro-N-[2-(4-methoxyphenyl)ethyl]-7'-oxo-7',8'-dihydro-6'H-spiro[cyclohexane-1,9'-furo[2,3-f]quinazoline]-2'-carboxamide;

5'-chloro-N-[2-(dimethyl-1,2-oxazol-4-yl)ethyl]-N-methyl-7'-oxo-7',8'-dihydro-6'H-spiro[cyclohexane-1,9'-furo[2,3-f]quinazoline]-2'-carboxamide;

5'-chloro-2'-[4-(1,3-thiazol-2-yl)piperazine-1-carbonyl]-7',8'-dihydro-6'H-spiro[cyclohexane-1,9'-furo[2,3-f]quinazoline]-7'-one;

5'-chloro-N-{[4-(1H-imidazol-1-yl)phenyl]methyl}-N-methyl-7'-oxo-7',8'-dihydro-6'H-spiro[cyclohexane-1,9'-furo[2,3-f]quinazoline]-2'-carboxamide;

2'-(4-tert-butylpiperazine-1-carbonyl)-5'-chloro-7',8'-dihydro-6'H-spiro[cyclohexane-1,9'-furo[2,3-f]quinazoline]-7'-one;

5'-chloro-N-[2-(3-methoxyphenyl)ethyl]-7'-oxo-7',8'-dihydro-6'H-spiro[cyclohexane-1,9'-furo[2,3-f]quinazoline]-2'-carboxamide;

5'-chloro-2'-[4-(pyrrolidin-1-yl)piperidine-1-carbonyl]-7',8'-dihydro-6'H-spiro[cyclohexane-1,9'-furo[2,3-f]quinazoline]-7'-one;

5'-chloro-N-(2,3-dihydro-1,4-benzodioxin-2-ylmethyl)-7'-oxo-7',8'-dihydro-6'H-spiro[cyclohexane-1,9'-furo[2,3-f]quinazoline]-2'-carboxamide;

5'-chloro-2'-[4-(morpholin-4-yl)piperidine-1-carbonyl]-7',8'-dihydro-6'H-spiro[cyclohexane-1,9'-furo[2,3-f]quinazoline]-7'-one;

5'-chloro-2'-[4-(3-methoxyphenyl)piperazine-1-carbonyl]-7',8'-dihydro-6'H-spiro[cyclohexane-1,9'-furo[2,3-f]quinazoline]-7'-one;

5'-chloro-7'-oxo-N-[1-(propan-2-yl)piperidin-4-yl]-7',8'-dihydro-6'H-spiro[cyclohexane-1,9'-furo[2,3-f]quinazoline]-2'-carboxamide;

5'-chloro-N-(1-hydroxy-3-phenylpropan-2-yl)-7'-oxo-7',8'-dihydro-6'H-spiro[cyclohexane-1,9'-furo[2,3-f]quinazoline]-2'-carboxamide;

N-(2H-1,3-benzodioxol-5-ylmethyl)-5'-chloro-N-methyl-7'-oxo-7',8'-dihydro-6'H-spiro[cyclohexane-1,9'-furo[2,3-f]quinazoline]-2'-carboxamide;

methyl 3-[1-({5'-chloro-7'-oxo-7',8'-dihydro-6'H-spiro[cyclohexane-1,9'-furo[2,3-f]quinazoline]-2'-yl}carbonyl)piperidin-2-yl]propanoate;

5'-chloro-7'-(4-cyclopentylpiperazine-1-carbonyl)-7',8'-dihydro-6'H-spiro[cyclohexane-1,9'-furo[2,3-f]quinazoline]-7'-one;

5'-chloro-7'-[4-(2-methylpropanoyl)piperazine-1-carbonyl]-7',8'-dihydro-6'H-spiro[cyclohexane-1,9'-furo[2,3-f]quinazoline]-7'-one;

N-benzyl-5'-chloro-N-(3-hydroxypropyl)-7'-oxo-7',8'-dihydro-6'H-spiro[cyclohexane-1,9'-furo[2,3-f]quinazoline]-7'-carboxamide;

5'-chloro-N-(2-methoxyethyl)-7'-oxo-N-(thiophen-2-ylmethyl)-7',8'-dihydro-6'H-spiro[cyclohexane-1,9'-furo[2,3-f]quinazoline]-2'-carboxamide;

5'-chloro-N-[2-(dimethylamino)ethyl]-7'-oxo-7',8'-dihydro-6'H-spiro[cyclohexane-1,9'-furo[2,3-f]quinazoline]-2'-carboxamide;

5'-chloro-2'-{5H,6H,7H-pyrrolo [3,4-b]pyridine-6-carbonyl}-7',8'-dihydro-6'H-spiro[cyclohexane-1,9'-furo[2,3-f]quinazoline]-7'-one;

5'-chloro-N-cyclohexyl-N-(2-hydroxyethyl)-7'-oxo-7',8'-dihydro-6'H-spiro[cyclohexane-1,9'-furo[2,3-f]quinazoline]-2'-carboxamide;

5'-chloro-N-[2-(dimethyl-1,3-thiazol-2-yl)ethyl]-7'-oxo-7',8'-dihydro-6'H-spiro[cyclohexane-1,9'-furo[2,3-f]quinazoline]-2'-carboxamide;

5'-chloro-2'-({[(3R,4R)-3-methoxyoxan-4-yl]amino}methyl)-7',8'-dihydro-6'H-spiro[cyclohexane-1,9'-furo[2,3-f]quinazoline]-7'-one;

5'-chloro-2'-{[2-(2-hydroxyethyl)piperidin-1-yl]methyl}-7',8'-dihydro-6'H-spiro[cyclohexane-1,9'-furo[2,3-f]quinazoline]-7'-one;

5'-chloro-2'-[(3-oxopiperazin-1-yl)methyl]-7',8'-dihydro-6'H-spiro[cyclohexane-1,9'-furo[2,3-f]quinazoline]-7'-one;

5'-chloro-2'-({[(1-methyl-1H-pyrazol-3-yl)methyl]amino}methyl)-7',8'-dihydro-6'H-spiro[cyclohexane-1,9'-furo[2,3-f]quinazoline]-7'-one;

5'-chloro-2'-{[(2-methoxyethyl)(propan-2-yl)amino]methyl}-7',8'-dihydro-6'H-spiro[cyclohexane-1,9'-furo[2,3-f]quinazoline]-7'-one;

1-{5'-chloro-7'-oxo-7',8'-dihydro-6'H-spiro[cyclohexane-1,9'-furo[2,3-f]quinazoline]-2'-ylmethyl}piperidine-4-carbonitrile;

5'-chloro-2'-{[(2-hydroxyethyl)(propan-2-yl)amino]methyl}-7',8'-dihydro-6'H-spiro[cyclohexane-1,9'-furo[2,3-f]quinazoline]-7'-one;

5'-chloro-2'-{[4-(pyridin-4-yl)piperazin-1-yl]methyl}-7',8'-dihydro-6'H-spiro[cyclohexane-1,9'-furo[2,3-f]quinazoline]-7'-one;

5'-chloro-2'-({[2-(1H-pyrazol-1-yl)ethyl]amino}methyl)-7',8'-dihydro-6'H-spiro[cyclohexane-1,9'-furo[2,3-f]quinazoline]-7'-one;

5'-chloro-2'-{[(oxan-4-yl)amino]methyl}-7',8'-dihydro-6'H-spiro[cyclohexane-1,9'-furo[2,3-f]quinazoline]-7'-one;

2'-[(8aS)-octahydropyrrolo[1,2-a]piperazin-2-ylmethyl]-5'-chloro-7',8'-dihydro-6'H-spiro[cyclohexane-1,9'-furo[2,3-f]quinazoline]-7'-one;

5'-chloro-2'-{[(oxolan-2-ylmethyl)amino]methyl}-7',8'-dihydro-6'H-spiro[cyclohexane-1,9'-furo[2,3-f]quinazoline]-7'-one;

3-({5'-chloro-7'-oxo-7',8'-dihydro-6'H-spiro[cyclohexane-1,9'-furo[2,3-f]quinazoline]-2'-ylmethyl}(ethyl)amino)propanenitrile;

5'-chloro-2'-{[(pyridin-2-ylmethyl)amino]methyl}-7',8'-dihydro-6'H-spiro[cyclohexane-1,9'-furo[2,3-f]quinazoline]-7'-one;

5'-chloro-2'-{[2-(hydroxymethyl)pyrrolidin-1-yl]methyl}-7',8'-dihydro-6'H-spiro[cyclohexane-1,9'-furo[2,3-f]quinazoline]-7'-one;

5'-chloro-2'-{[(2-methanesulfonylethyl)amino]methyl}-7',8'-dihydro-6'H-spiro[cyclohexane-1,9'-furo[2,3-f]quinazoline]-7'-one;

2'-{[benzyl(2-hydroxyethyl)amino]methyl}-5'-chloro-7',8'-dihydro-6'H-spiro[cyclohexane-1,9'-furo[2,3-f]quinazoline]-7'-one;

5'-chloro-2'-{[(furan-2-ylmethyl)(methyl)amino]methyl}-7',8'-dihydro-6'H-spiro[cyclohexane-1,9'-furo[2,3-f]quinazoline]-7'-one;

5'-chloro-2'-[(4-methoxypiperidin-1-yl)methyl]-7',8'-dihydro-6'H-spiro[cyclohexane-1,9'-furo[2,3-f]quinazoline]-7'-one;

2'-[(4-acetyl-1,4-diazepan-1-yl)methyl]-5'-chloro-7',8'-dihydro-6'H-spiro[cyclohexane-1,9'-furo[2,3-f]quinazoline]-7'-one;

5'-chloro-2'-{[4-(2-hydroxyethyl)piperazin-1-yl]methyl}-7',8'-dihydro-6'H-spiro[cyclohexane-1,9'-furo[2,3-f]quinazoline]-7'-one;

5'-chloro-2'-({4-[(dimethylamino)methyl]piperidin-1-yl}methyl)-7',8'-dihydro-6'H-spiro[cyclohexane-1,9'-furo[2,3-f]quinazoline]-7'-one;

5'-chloro-7'-{[4-(oxolane-2-carbonyl)piperazin-1-yl]methyl}-7',8'-dihydro-6'H-spiro[cyclohexane-1,9'-furo[2,3-f]quinazoline]-7'-one;

5'-chloro-2'-({[(5-oxopyrrolidin-2-yl)methyl](propan-2-yl)amino}methyl)-7',8'-dihydro-6'H-spiro[cyclohexane-1,9'-furo[2,3-f]quinazoline]-7'-one;

5'-chloro-2'-{5H,6H,7H,8H-imidazo[1,2-a]pyrazin-7-ylmethyl}-7',8'-dihydro-6'H-spiro[cyclohexane-1,9'-furo[2,3-f]quinazoline]-7'-one;

5'-chloro-2'-({[3-(2-oxopyrrolidin-1-yl)propyl]amino}methyl)-7',8'-dihydro-6'H-spiro[cyclohexane-1,9'-furo[2,3-f]quinazoline]-7'-one;

1-{5'-chloro-7'-oxo-7',8'-dihydro-6'H-spiro[cyclohexane-1,9'-furo[2,3-f]quinazoline]-2'-ylmethyl}-N-methylpiperidine-4-carboxamide;

5'-chloro-2'-{[(3-hydroxypropyl)(methyl)amino]methyl}-7',8'-dihydro-6'H-spiro[cyclohexane-1,9'-furo[2,3-f]quinazoline]-7'-one;

5'-chloro-2'-[(4-hydroxy-4-phenylpiperidin-1-yl)methyl]-7',8'-dihydro-6'H-spiro[cyclohexane-1,9'-furo[2,3-f]quinazoline]-7'-one;

1-{5'-chloro-7'-oxo-7',8'-dihydro-6'H-spiro[cyclohexane-1,9'-furo[2,3-f]quinazoline]-2'-ylmethyl}piperidine-3-carboxamide;

3-({5'-chloro-7'-oxo-7',8'-dihydro-6'H-spiro[cyclohexane-1,9'-furo[2,3-f]quinazoline]-2'-ylmethyl}(methyl)amino)-N-methylpropanamide;

5'-chloro-2'-[{(1R,5S,6S)-6-(hydroxymethyl)-3-azabicyclo[3.1.0]hexan-3-yl]methyl}-7',8'-dihydro-6'H-spiro[cyclohexane-1,9'-furo[2,3-f]quinazoline]-7'-one;

5'-chloro-2'-{[ethyl(2-hydroxyethyl)amino]methyl}-7',8'-dihydro-6'H-spiro[cyclohexane-1,9'-furo[2,3-f]quinazoline]-7'-one;

5'-chloro-2'-{[(2-hydroxyethyl)(methyl)amino]methyl}-7',8'-dihydro-6'H-spiro[cyclohexane-1,9'-furo[2,3-f]quinazoline]-7'-one;

5'-chloro-2'-[(3-hydroxypiperidin-1-yl)methyl]-7',8'-dihydro-6'H-spiro[cyclohexane-1,9'-furo[2,3-f]quinazoline]-7'-one;

5'-chloro-2'-{[4-(2-hydroxyethyl)piperidin-1-yl]methyl}-7',8'-dihydro-6'H-spiro[cyclohexane-1,9'-furo[2,3-f]quinazoline]-7'-one;

5'-chloro-2'-{[(2R,6S)-2,6-dimethylmorpholin-4-yl]methyl}-7',8'-dihydro-6'H-spiro[cyclohexane-1,9'-furo[2,3-f]quinazoline]-7'-one;

5'-chloro-2'-({[(4-ethyl-4H-1,2,4-triazol-3-yl)methyl](methyl)amino}methyl)-7',8'-dihydro-6'H-spiro[cyclohexane-1,9'-furo[2,3-f]quinazoline]-7'-one;

5'-chloro-7'-{2-oxa-6-azaspiro[3.5]nonan-6-ylmethyl}-7',8'-dihydro-6'H-spiro[cyclohexane-1,9'-furo[2,3-f]quinazoline]-7'-one;

5'-chloro-7'-{[ethyl(propan-2-yl)amino]methyl}-7',8'-dihydro-6'H-spiro[cyclohexane-1,9'-furo[2,3-f]quinazoline]-7'-one;

5'-chloro-2'-({[(5-cyclopropyl-1H-pyrazol-3-yl)methyl](methyl)amino}methyl)-7',8'-dihydro-6'H-spiro[cyclohexane-1,9'-furo[2,3-f]quinazoline]-7'-one;

5'-chloro-2'-({[3-(dimethylamino)propyl](methyl)amino}methyl)-7',8'-dihydro-6'H-spiro[cyclohexane-1,9'-furo[2,3-f]quinazoline]-7'-one;

5'-chloro-2'-{[3-(dimethylamino)pyrrolidin-1-yl]methyl}-7',8'-dihydro-6'H-spiro[cyclohexane-1,9'-furo[2,3-f]quinazoline]-7'-one;

2-(4-{5'-chloro-7'-oxo-7',8'-dihydro-6'H-spiro[cyclohexane-1,9'-furo[2,3-f]quinazoline]-2'-ylmethyl}piperazin-1-yl)pyridine-3-carbonitrile;

5'-chloro-2'-{[3-(1H-imidazol-1-ylmethyl)piperidin-1-yl]methyl}-7',8'-dihydro-6'H-spiro[cyclohexane-1,9'-furo[2,3-f]quinazoline]-7'-one;

5'-chloro-2'-{[4-hydroxy-4-(thiophen-2-yl)piperidin-1-yl]methyl}-7',8'-dihydro-6'H-spiro[cyclohexane-1,9'-furo[2,3-f]quinazoline]-7'-one;

5'-chloro-2'-{[4-(2-methoxyethyl)piperazin-1-yl]methyl}-7',8'-dihydro-6'H-spiro[cyclohexane-1,9'-furo[2,3-f]quinazoline]-7'-one;

5'-chloro-2'-{[methyl(pyridin-3-ylmethyl)amino]methyl}-7',8'-dihydro-6'H-spiro[cyclohexane-1,9'-furo[2,3-f]quinazoline]-7'-one;

4-{5'-chloro-7'-oxo-7',8'-dihydro-6'H-spiro[cyclohexane-1,9'-furo[2,3-f]quinazoline]-2'-ylmethyl}-thiomorpholine-1,1-dione;

5'-chloro-2'-{[(4-hydroxy-2-methylbutan-2-yl)amino]methyl}-7',8'-dihydro-6'H-spiro[cyclohexane-1,9'-furo[2,3-f]quinazoline]-7'-one;

4-{5'-chloro-7'-oxo-7',8'-dihydro-6'H-spiro[cyclohexane-1,9'-furo[2,3-f]quinazoline]-2'-ylmethyl}piperazine-1-carbaldehyde;

5'-chloro-2'-{[4-(morpholin-4-yl)piperidin-1-yl]methyl}-7',8'-dihydro-6'H-spiro[cyclohexane-1,9'-furo[2,3-f]quinazoline]-7'-one;

4-{5'-chloro-7'-oxo-7',8'-dihydro-6'H-spiro[cyclohexane-1,9'-furo[2,3-f]quinazoline]-2'-ylmethyl}-N,N-dimethylpiperazine-1-carboxamide;

5'-chloro-2'-[({[4-(propan-2-yl)-4H-1,2,4-triazol-3-yl]methyl}amino)methyl]-7',8'-dihydro-6'H-spiro[cyclohexane-1,9'-furo[2,3-f]quinazoline]-7'-one;

5'-chloro-2'-{[3-(trifluoromethyl)-5H,6H,7H,8H-[1,2,4]triazolo[4,3-a]pyrazin-7-yl]methyl}-7',8'-dihydro-6'H-spiro[cyclohexane-1,9'-furo[2,3-f]quinazoline]-7'-one;

1-{5'-chloro-7'-oxo-7',8'-dihydro-6'H-spiro[cyclohexane-1,9'-furo[2,3-f]quinazoline]-2'-ylmethyl}azetidine-3-carbonitrile;

4-({5'-chloro-7'-oxo-7',8'-dihydro-6'H-spiro[cyclohexane-1,9'-furo[2,3-f]quinazoline]-2'-ylmethyl}amino)-thiane-1,1-dione;

5'-chloro-2'-[(4-methanesulfonylpiperazin-1-yl)methyl]-7',8'-dihydro-6'H-spiro[cyclohexane-1,9'-furo[2,3-f]quinazoline]-7'-one;

ethyl 7-{5'-chloro-7'-oxo-7',8'-dihydro-6'H-spiro[cyclohexane-1,9'-furo[2,3-f]quinazoline]-2'-ylmethyl}-5H,6H,7H,8H-imidazo[1,2-a]pyrazine-2-carboxylate;

2'-{6-azaspiro[2.5]octan-6-ylmethyl}-5'-chloro-7',8'-dihydro-6'H-spiro[cyclohexane-1,9'-furo[2,3-f]quinazoline]-7'-one;

5'-chloro-2'-{[(2,2,2-trifluoroethyl)amino]methyl}-7',8'-dihydro-6'H-spiro[cyclohexane-1,9'-furo[2,3-f]quinazoline]-7'-one;

5'-chloro-2'-{octahydropyrrolo[1,2-a]piperazin-2-ylmethyl}-7',8'-dihydro-6'H-spiro[cyclohexane-1,9'-furo[2,3-f]quinazoline]-7'-one;

5'-chloro-2'-{[4-(furan-2-ylmethyl)piperazin-1-yl]methyl}-7',8'-dihydro-6'H-spiro[cyclohexane-1,9'-furo[2,3-f]quinazoline]-7'-one;

5'-chloro-2'-{[methyl(propan-2-yl)amino]methyl}-7',8'-dihydro-6'H-spiro[cyclohexane-1,9'-furo[2,3-f]quinazoline]-7'-one;

3-({5'-chloro-7'-oxo-7',8'-dihydro-6'H-spiro[cyclohexane-1,9'-furo[2,3-f]quinazoline]-2'-ylmethyl}amino)-thiolane-1,1-dione;

5'-chloro-2'-{[4-(pyridin-3-ylmethyl)piperazin-1-yl]methyl}-7',8'-dihydro-6'H-spiro[cyclohexane-1,9'-furo[2,3-f]quinazoline]-7'-one;

5'-chloro-2'-[(4-methyl-1,4-diazepan-1-yl)methyl]-7',8'-dihydro-6'H-spiro[cyclohexane-1,9'-furo[2,3-f]quinazoline]-7'-one;

5'-chloro-7'-{[4-(dimethylamino)piperidin-1-yl]methyl}-7',8'-dihydro-6'H-spiro[cyclohexane-1,9'-furo[2,3-f]quinazoline]-7'-one;

5'-chloro-7'-({methyl[(trimethyl-1H-pyrazol-4-yl)methyl]amino}methyl)-7',8'-dihydro-6'H-spiro[cyclohexane-1,9'-furo[2,3-f]quinazoline]-7'-one;

5'-chloro-7'-{[3-oxo-4-(propan-2-yl)piperazin-1-yl]methyl}-7',8'-dihydro-6'H-spiro[cyclohexane-1,9'-furo[2,3-f]quinazoline]-7'-one;

5'-chloro-7'-{[(2,2-dimethyloxan-4-yl)(ethyl)amino]methyl}-7',8'-dihydro-6'H-spiro[cyclohexane-1,9'-furo[2,3-f]quinazoline]-7'-one;

5'-chloro-2'-{[4-(pyrrolidine-1-carbonyl)piperazin-1-yl]methyl}-7',8'-dihydro-6'H-spiro[cyclohexane-1,9'-furo[2,3-f]quinazoline]-7'-one;

5'-chloro-2'-{[(1,3-oxazol-5-ylmethyl)amino]methyl}-7',8'-dihydro-6'H-spiro[cyclohexane-1,9'-furo[2,3-f]quinazoline]-7'-one;

5'-chloro-2'-[(propylamino)methyl]-7',8'-dihydro-6'H-spiro[cyclohexane-1,9'-furo[2,3-f]quinazoline]-7'-one;

5'-chloro-2'-({[(1-methyl-1H-pyrazol-5-yl)methyl]amino}methyl)-7',8'-dihydro-6'H-spiro[cyclohexane-1,9'-furo[2,3-f]quinazoline]-7'-one;

5'-chloro-2'-{[4-(oxetan-3-yl)piperazin-1-yl]methyl}-7',8'-dihydro-6'H-spiro[cyclohexane-1,9'-furo[2,3-f]quinazoline]-7'-one;

5'-chloro-2'-({methyl[2-(pyridin-2-yl)ethyl]amino}methyl)-7',8'-dihydro-6'H-spiro[cyclohexane-1,9'-furo[2,3-f]quinazoline]-7'-one;

5'-chloro-2'-{[(2-methoxyethyl)(methyl)amino]methyl}-7',8'-dihydro-6'H-spiro[cyclohexane-1,9'-furo[2,3-f]quinazoline]-7'-one;

5'-chloro-2'-{5H,6H,7H-pyrrolo[3,4-b]pyridin-6-ylmethyl}-7',8'-dihydro-6'H-spiro[cyclohexane-1,9'-furo[2,3-f]quinazoline]-7'-one;

5'-chloro-2'-({[2-(3,5-dimethyl-1H-pyrazol-4-yl)ethyl](methyl)amino}methyl)-7',8'-dihydro-6'H-spiro[cyclohexane-1,9'-furo[2,3-f]quinazoline]-7'-one;

5'-chloro-2'-({[2-(dimethylamino)ethyl](ethyl)amino}methyl)-7',8'-dihydro-6'H-spiro[cyclohexane-1,9'-furo[2,3-f]quinazoline]-7'-one;

5'-chloro-2'-[(3-hydroxypyrrolidin-1-yl)methyl]-7',8'-dihydro-6'H-spiro[cyclohexane-1,9'-furo[2,3-f]quinazoline]-7'-one;

5'-chloro-7'-[({6-(morpholin-4-yl)pyridin-3-yl]methyl}amino)methyl]-7',8'-dihydro-6'H-spiro[cyclohexane-1,9'-furo[2,3-f]quinazoline]-7'-one;

5'-chloro-7'-{[methyl(propyl)amino]methyl}-7',8'-dihydro-6'H-spiro[cyclohexane-1,9'-furo[2,3-f]quinazoline]-7'-one;

5'-chloro-2'-({[3-(3,5-dimethyl-1H-pyrazol-1-yl)propyl](methyl)amino}methyl)-7',8'-dihydro-6'H-spiro[cyclohexane-1,9'-furo[2,3-f]quinazoline]-7'-one;

5'-chloro-7'-[(2,2-dimethylmorpholin-4-yl)methyl]-7',8'-dihydro-6'H-spiro[cyclohexane-1,9'-furo[2,3-f]quinazoline]-7'-one;

5'-chloro-2'-[(4-ethylpiperazin-1-yl)methyl]-7',8'-dihydro-6'H-spiro[cyclohexane-1,9'-furo[2,3-f]quinazoline]-7'-one;

5'-chloro-2'-({[(3-ethyl-1,2-oxazol-5-yl)methyl](methyl)amino}methyl)-7',8'-dihydro-6'H-spiro[cyclohexane-1,9'-furo[2,3-f]quinazoline]-7'-one;

5'-chloro-2'-{[methyl(pyridin-2-ylmethyl)amino]methyl}-7',8'-dihydro-6'H-spiro[cyclohexane-1,9'-furo[2,3-f]quinazoline]-7'-one;

1-{5'-chloro-7'-oxo-7',8'-dihydro-6'H-spiro[cyclohexane-1,9'-furo[2,3-f]quinazoline]-2'-ylmethyl}piperidine-4-carboxamide;

5'-chloro-2'-({[2-(2-oxopyrrolidin-1-yl)ethyl]amino}methyl)-7',8'-dihydro-6'H-spiro[cyclohexane-1,9'-furo[2,3-f]quinazoline]-7'-one;

5'-chloro-2'-[({[1-(ethoxymethyl)cyclopropyl]methyl}amino)methyl]-7',8'-dihydro-6'H-spiro[cyclohexane-1,9'-furo[2,3-f]quinazoline]-7'-one;

5'-chloro-2'-({[2-(dimethyl-1,2-oxazol-4-yl)ethyl](methyl)amino}methyl)-7',8'-dihydro-6'H-spiro[cyclohexane-1,9'-furo[2,3-f]quinazoline]-7'-one;

N-(1-{5'-chloro-7'-oxo-7',8'-dihydro-6'H-spiro[cyclohexane-1,9'-furo[2,3-f]quinazoline]-2'-ylmethyl}piperidin-4-yl)acetamide;

5'-chloro-2'-{[2-(hydroxymethyl)piperidin-1-yl]methyl}-7',8'-dihydro-6'H-spiro[cyclohexane-1,9'-furo[2,3-f]quinazoline]-7'-one;

5'-chloro-2'-{[methyl(1-methylpiperidin-4-yl)amino]methyl}-7',8'-dihydro-6'H-spiro[cyclohexane-1,9'-furo[2,3-f]quinazoline]-7'-one;

5'-chloro-2'-({6,6-dimethyl-3-azabicyclo[3.1.0]hexan-3-yl}methyl)-7',8'-dihydro-6'H-spiro[cyclohexane-1,9'-furo[2,3-f]quinazoline]-7'-one;

5'-chloro-2'-({[(1-methyl-1H-imidazol-2-yl)methyl]amino}methyl)-7',8'-dihydro-6'H-spiro[cyclohexane-1,9'-furo[2,3-f]quinazoline]-7'-one;

5'-chloro-7'-{[3-(hydroxymethyl)piperidin-1-yl]methyl}-7',8'-dihydro-6'H-spiro[cyclohexane-1,9'-furo[2,3-f]quinazoline]-7'-one;

5'-chloro-7'-{[(2-hydroxyethyl)(propyl)amino]methyl}-7',8'-dihydro-6'H-spiro[cyclohexane-1,9'-furo[2,3-f]quinazoline]-7'-one;

ethyl 2-({5'-chloro-7'-oxo-7',8'-dihydro-6'H-spiro[cyclohexane-1,9'-furo[2,3-f]quinazoline]-2'-ylmethyl}(methyl)amino)acetate;

2'-[(3-aminopyrrolidin-1-yl)methyl]-5'-chloro-7',8'-dihydro-6'H-spiro[cyclohexane-1,9'-furo[2,3-f]quinazoline]-7'-one;

N-{2-({5'-chloro-7'-oxo-7',8'-dihydro-6'H-spiro[cyclohexane-1,9'-furo[2,3-f]quinazoline]-2'-ylmethyl}amino)ethyl}acetamide;

5'-chloro-2'-{[4-(hydroxymethyl)piperidin-1-yl]methyl}-7',8'-dihydro-6'H-spiro[cyclohexane-1,9'-furo[2,3-f]quinazoline]-7'-one;

5'-chloro-2'-{[(piperidin-3-yl)amino]methyl}-7',8'-dihydro-6'H-spiro[cyclohexane-1,9'-furo[2,3-f]quinazoline]-7'-one;

5'-chloro-2'-{[(pyrrolidin-3-yl)amino]methyl}-7',8'-dihydro-6'H-spiro[cyclohexane-1,9'-furo[2,3-f]quinazoline]-7'-one;

2'-benzoyl-5'-chloro-7',8'-dihydro-6'H-spiro[cyclohexane-1,9'-furo[2,3-f]quinazoline]-7'-one;

5'-chloro-2'-(pyridine-4-carbonyl)-7',8'-dihydro-6'H-spiro[cyclohexane-1,9'-furo[2,3-f]quinazoline]-7'-one;

2'-acetyl-5'-chloro-7',8'-dihydro-6'H-spiro[cyclohexane-1,9'-furo[2,3-]quinazoline]-7'-one;

5'-chloro-2'-({[(3S,4R)-3-methoxyoxan-4-yl]amino}methyl)-7',8'-dihydro-6'H-spiro[cyclohexane-1,9'-furo[2,3-f]quinazoline]-7'-one;

5'-chloro-2'-{[(3-fluorooxan-4-yl)amino]methyl}-7',8'-dihydro-6'H-spiro[cyclohexane-1,9'-furo[2,3-f]quinazoline]-7'-one;

5'-chloro-2'-({[(3R)-oxolan-3-yl]amino}methyl)-7',8'-dihydro-6'H-spiro[cyclohexane-1,9'-furo[2,3-f]quinazoline]-7'-one;

5'-chloro-2'-({[(3S)-oxolan-3-yl]amino}methyl)-7',8'-dihydro-6'H-spiro[cyclohexane-1,9'-furo[2,3-f]quinazoline]-7'-one;

5'-chloro-7'-({[(3R,4S)-3-methoxyoxan-4-yl]amino}methyl)-7',8'-dihydro-6'H-spiro[cyclohexane-1,9'-furo[2,3-f]quinazoline]-7'-one;

5'-chloro-7'-({[(3S,4R)-3-methoxyoxan-4-yl]amino}methyl)-7',8'-dihydro-6'H-spiro[cyclohexane-1,9'-furo[2,3-f]quinazoline]-7'-one;

5'-chloro-7'-{[(2-methoxyethyl)amino]methyl}-7',8'-dihydro-6'H-spiro[cyclohexane-1,9'-furo[2,3-f]quinazoline]-7'-one;

5'-chloro-2'-{[(oxetan-3-yl)amino]methyl}-7',8'-dihydro-6'H-spiro[cyclohexane-1,9'-furo[2,3-f]quinazoline]-7'-one;

and pharmaceutically acceptable salts thereof.

25. A pharmaceutical composition comprising a compound or pharmaceutically acceptable salt thereof of claim 1, and a pharmaceutically acceptable carrier.

26. A method of treating inhibiting or relieving a disorder or ameliorating a symptom of a disorder that includes having an aberrant or dysregulated signaling pathway mediated by PDE7 in a subject, the method comprising administering a compound of claim 1, or pharmaceutically acceptable salt thereof, to a subject in need thereof.

27. A compound of claim 1 selected from the group consisting of:

5-chloro-2-[(1S,4S)-2-oxa-5-azabicyclo[2.2.1]heptan-5-ylmethyl]-7,8-dihydro-6H-spiro[[1,3]oxazolo[5,4-f]quinazoline-9,1'-cyclohexane]-7-one;

5-chloro-2-[(3-methoxy-3-methylazetidin-1-yl)methyl]-7,8-dihydro-6H-spiro[[1,3]oxazolo[5,4-f]quinazoline-9,1'-cyclohexane]-7-one;

5-chloro-2-{[3-(hydroxymethyl)pyrrolidin-1-yl]methyl}-7,8-dihydro-6H-spiro[[1,3]oxazolo[5,4-f]quinazoline-9,1'-cyclohexane]-7-one;

5-chloro-2-({[2-(dimethylamino)ethyl](methyl)amino}methyl)-7,8-dihydro-6H-spiro[[1,3]oxazolo[5,4-f]quinazoline-9,1'-cyclohexane]-7-one;

5-chloro-2-{[methyl(oxan-4-yl)amino]methyl}-7,8-dihydro-6H-spiro[[1,3]oxazolo[5,4-f]quinazoline-9,1'-cyclohexane]-7-one; and pharmaceutically acceptable salts thereof.

28. A compound of claim 27, which is 5-chloro-2-[(1S,4S)-2-oxa-5-azabicyclo[2.2.1]heptan-5-ylmethyl]-7,8-dihydro-6H-spiro[[1,3]oxazolo[5,4-f]quinazoline-9,1'-cyclohexane]-7-one or a pharmaceutically acceptable salt thereof.

29. A compound of claim 27, which is 5-chloro-2-[(3-methoxy-3-methylazetidin-1-yl)methyl]-7,8-dihydro-6H-spiro[[1,3]oxazolo[5,4-f]quinazoline-9,1'-cyclohexane]-7-one or a pharmaceutically acceptable salt thereof.

30. A compound of claim 27, which is 5-chloro-2-{[3-(hydroxymethyl)pyrrolidin-1-yl]methyl}-7,8-dihydro-6H-spiro[[1,3]oxazolo[5,4-f]quinazoline-9,1'-cyclohexane]-7-one or a pharmaceutically acceptable salt thereof.

31. A compound of claim 27, which is 5-chloro-2-({[2-(dimethylamino)ethyl](methyl)amino}methyl)-7,8-dihydro-6H-spiro[[1,3]oxazolo [5,4-f]quinazoline-9,1'-cyclohexane]-7-one or a pharmaceutically acceptable salt thereof.

32. A compound of claim 27, which is 5-chloro-2-{[methyl(oxan-4-yl)amino]methyl}-7,8-dihydro-6H-spiro[[1,3]oxazolo[5,4-f]quinazoline-9,1'-cyclohexane]-7-one or a pharmaceutically acceptable salt thereof.

* * * * *

UNITED STATES PATENT AND TRADEMARK OFFICE
CERTIFICATE OF CORRECTION

PATENT NO. : 11,685,745 B2  Page 1 of 29
APPLICATION NO. : 16/629922
DATED : June 27, 2023
INVENTOR(S) : Vincent John Santora It is certified that error appears in the above-identified patent and that said Letters Patent is hereby corrected as shown below:

On the Title Page

Column 2 (Other Publications), Line 13, delete "pyrimidones" and insert -- pyrimidines --.

In the Specification

Column 7, Line 38, delete "C$_{2-6}$ alkynyl," and insert -- C$_{2-6}$alkynyl, --.

Column 8, Line 1-7 (approx.), delete "The term "phenyl" represents the following moiety:" and insert -- The term "phenyl" represents the following moiety: 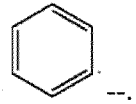 --.

Column 11, Line 7 (approx.), after " 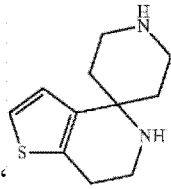 " insert -- . --.

Column 11, Line 57 (approx.), after " 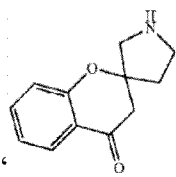 " insert -- . --.

Column 17, Line 57-58, delete "N-methyl-O-glucamine," and insert -- N-methyl-D-glucamine, --.

Column 18, Line 30, delete "demosine, isodemosine," and insert -- desmosine, isodesmosine, --.

Signed and Sealed this
Second Day of September, 2025

Coke Morgan Stewart
*Acting Director of the United States Patent and Trademark Office*

CERTIFICATE OF CORRECTION (continued)
U.S. Pat. No. 11,685,745 B2

Column 18, Line 42, delete "$C_{1-6}$ alkyl" and insert -- $C_{1-6}$alkyl --.

Column 18, Line 45, delete "$C_{1-3}$ alkyl" and insert -- $C_{1-3}$alkyl --.

Column 18, Line 46, delete "di($C_{1-6}$alkyeamines." and insert -- di($C_{1-2}$alkyl)amines. --.

Column 22, Line 32, delete "—$(CH_2)_mO(CH_2)_m$—," and insert -- —$(CH_2)_mO(CH_2)_n$—, --.

Column 22, Line 47, delete "—$C_{1-6}$ alkyl," and insert -- —$C_{1-6}$alkyl, --.

Column 22, Line 57-58, delete "—$C_{1-6}$ alkyl, —$C_{2-6}$ alkenyl, —$C_{2-6}$ alkynyl," and insert -- —$C_{1-6}$alkyl, —$C_{2-6}$alkenyl, —$C_{2-6}$alkynyl, --.

Column 22, Line 60, delete "—$C_{1-6}$ alkoxy," and insert -- —$C_{1-6}$alkoxy, --.

Column 22, Line 65-66, delete "—$C_{1-6}$ alkyl, —$C_{2-6}$ alkenyl, —$C_{2-6}$ alkynyl," and insert -- —$C_{1-6}$alkyl, —$C_{2-6}$alkenyl, —$C_{2-6}$alkynyl, --.

Column 23, Line 3, delete "—$C_{1-6}$ haloalkyl," and insert -- —$C_{1-6}$haloalkyl, --.

Column 23, Line 6-7, delete "—$C_{1-6}$ alkyl, —$C_{2-6}$ alkenyl, —$C_{2-6}$ alkynyl," and insert -- —$C_{1-6}$alkyl, —$C_{2-6}$alkenyl, —$C_{2-6}$alkynyl, --.

Column 23, Line 9, delete "—$C_{1-6}$ alkoxy," and insert -- —$C_{1-6}$alkoxy, --.

Column 23, Line 14, delete "—$C_{1-6}$ alkyl, —$C_{1-6}$ haloalkyl," and insert -- —$C_{1-6}$alkyl, —$C_{1-6}$haloalkyl, --.

Column 23, Line 17, delete "—$(CH_2)_mO(CH_2)_6R^{1A}$, —$(CH_2)_mS(CH_2)_6R^{1A}$," and insert -- —$(CH_2)_mO(CH_2)_nR^{1A}$, —$(CH_2)_mS(CH_2)_nR^{1A}$, --.

Column 23, Line 25, delete "—$SO_2C_{1-6}$ alkyl," and insert -- —$SO_2C_{1-6}$alkyl, --.

Column 23, Line 26, delete "—$C_{1-6}$ halo alkyl," and insert -- —$C_{1-6}$haloalkyl, --.

Column 23, Line 29-30, delete "—$C_{1-6}$ alkyl-OH, —$C_{1-6}$ haloalkylOH," and insert -- —$C_{1-6}$alkyl-OH, —$C_{1-6}$haloalkyl-OH --.

Column 23, Line 31, delete "—$C_{2-6}$ alkenyl," and insert -- —$C_{2-6}$alkenyl, --.

Column 23, Line 32, delete "—$C(O)C_{1-6}$ alkyl," and insert -- —$C(O)C_{1-6}$alkyl, --.

Column 23, Line 33, delete "—$C(O)OC_{1-6}$ alkyl," and insert -- —$C(O)OC_{1-6}$alkyl, --.

Column 23, Line 42, delete "—$SO_2C_{1-6}$ alkyl," and insert -- —$SO_2C_{1-6}$alkyl, --.

Column 23, Line 43, delete "—$C_{1-6}$ alkoxy," and insert -- —$C_{1-6}$alkoxy, --.

Column 23, Line 44, delete "3-membered" and insert -- 3-15 membered --.

Column 23, Line 45-46, delete "—$C_{2-6}$ alkenyl, —$C_{2-6}$ alkynyl," and insert -- —$C_{2-6}$alkenyl, —$C_{2-6}$alkynyl, --.

Column 23, Line 48, delete "—C(O)O$C_{1-6}$ alkyl," and insert -- —C(O)O$C_{1-6}$alkyl, --.

Column 23, Line 51, delete "—$SO_2C_{1-6}$ alkyl," and insert -- —$SO_2C_{1-6}$alkyl, --.

Column 23, Line 52, delete "—$C_{1-6}$ halo alkyl," and insert -- —$C_{1-6}$haloalkyl, --.

Column 23, Line 55-56, delete "—$C_{1-6}$ alkyl-OH, —$C_{1-6}$ haloalkylOH," and insert -- —$C_{1-6}$alkyl-OH, —$C_{1-6}$haloalkyl-OH --.

Column 23, Line 56-57, delete "—$C_{2-6}$ alkenyl, —$C_{2-6}$ alkynyl," and insert -- —$C_{2-6}$alkenyl, —$C_{2-6}$alkynyl, --.

Column 23, Line 58, delete "—C(O)$C_{1-6}$ alkyl," and insert -- —C(O)$C_{1-6}$alkyl, --.

Column 23, Line 59, delete "—C(O)O$C_{1-6}$ alkyl," and insert -- —C(O)O$C_{1-6}$alkyl, --.

Column 23-24, Line 67 (Column 23) , Line 1 (Column 24), delete "—$SO_2C_{1-6}$ alkyl," and insert -- —$SO_2C_{1-6}$alkyl, --.

Column 24, Line 1, delete "—$C_{1-6}$ alkoxy," and insert -- —$C_{1-6}$alkoxy, --.

Column 24, Line 4, delete "—$C_{2-6}$ alkenyl, —$C_{2-6}$ alkynyl," and insert -- —$C_{2-6}$alkenyl, —$C_{2-6}$alkynyl, --.

Column 24, Line 6, delete "—C(O)O$C_{1-6}$ alkyl," and insert -- —C(O)O$C_{1-6}$alkyl, --.

Column 24, Line 12 (approx.), delete "—$C_{1-6}$ alkoxy," and insert -- —$C_{1-6}$alkoxy, --.

Column 24, Line 14 (approx.), delete "—$C_{2-6}$ alkenyl, —$C_{2-6}$ alkynyl," and insert -- —$C_{2-6}$alkenyl, —$C_{2-6}$alkynyl, --.

Column 24, Line 15 (approx.), delete "—C(O)$C_{1-6}$ alkyl," and insert -- —C(O)$C_{1-6}$alkyl, --.

Column 24, Line 16 (approx.), delete "—C(O)O$C_{1-6}$ alkyl," and insert -- —C(O)O$C_{1-6}$alkyl, --.

Column 24, Line 19 (approx.), delete "—$SO_2C_{1-6}$ alkyl," and insert -- —$SO_2C_{1-6}$alkyl, --.

Column 24, Line 20 (approx.), delete "—$C_{1-6}$ alkoxy," and insert -- —$C_{1-6}$alkoxy, --.

Column 24, Line 23, delete "—C(O)1-6 alkyl," and insert -- —C(O)1-6alkyl, --.

Column 24, Line 24, delete "—C(O)OC$_{1-6}$ alkyl," and insert -- —C(O)OC$_{1-6}$alkyl, --.

Column 24, Line 35 (approx.), delete "—[C(R$^{1A}$)$_2$]$_m$N[(CH$_2$)$_n$R$^{1A}$][C(R$^{1B}$)$_2$]$_m$[C(R$^{1C}$)$_2$]," and insert -- —[C(R$^{1A}$)$_2$]$_m$N[(CH$_2$)$_n$R$^{1A}$][C(R$^{1B}$)$_2$]$_m$[C(R$^{1C}$)$_2$]$_n$— --.

Column 24, Line 48-49 (approx.), delete "—[(CH$_2$)$_m$N((CH$_2$)$_n$R$^{1A}$)(CH$_2$)$_p$[N[(CH$_2$)$_m$R$^{1A}$](CH$_2$)$_n$]—." and insert -- —[(CH$_2$)$_m$N((CH$_2$)$_n$R$^{1A}$)(CH$_2$)$_p$][[N(CH$_2$)$_m$N[(CH$_2$)$_n$R$^{1A}$](CH$_2$)$_p$]—. --.

Column 24, Line 52, delete "—C(O)(CH$_2$)$_m$N[(CH$_2$)—R$^{1A}$(CH$_2$)$_p$O—," and insert -- —C(O)(CH$_2$)$_m$N[(CH$_2$)$_n$—R$^{1A}$(CH$_2$)$_p$O—, --.

Column 24, Line 57-58, delete "—C(O)(CH$_2$)$_m$N[(CH$_2$)$_n$R$^{1A}$][N[(CH$_2$)$_m$R$^{A1}$](CH$_2$)$_n$]CH(OH)—," and insert -- —C(O)(CH$_2$)$_m$N[(CH$_2$)$_n$R$^{1A}$][N[(CH$_2$)$_m$R$^{1A}$](CH$_2$)$_n$]CH(OH)—, --.

Column 25, Line 49-50 (approx.), delete "C(O)NR$^{1A}$CH$_2$CH$_2$C(O)—," and insert -- —C(O)NR$^{1A}$CH$_2$CH$_2$C(O)—, --.

Column 25, Line 53-56 (approx.), delete "—CH$_2$NR$^{1A}$[(CH$_2$)$_n$N((CH$_2$)$_n$R$^{1A}$)(CH$_2$)$_n$]—CH$_2$NR$^{1A}$CH$_2$CH$_2$CH$_2$—, —CH$_2$N [CH$_2$R$^{1A}$)]2—," and insert -- —CH$_2$NR$^{1A}$[(CH$_2$)$_n$N(CH$_2$)$_n$R$^{1A}$)(CH$_2$)$_n$]—, —CH$_2$NR$^{1A}$CH$_2$CH$_2$CH$_2$—, —CH$_2$N[CH$_2$R$^{1A}$)]CH$_2$CH$_2$—, --.

Column 26, Line 18-19 (approx.), delete "—C$_{1-6}$ alkyl," and insert -- —C$_{1-6}$alkyl, --.

Column 26, Line 23, delete "—C(O)OC$_{1-6}$ alkyl," and insert -- —C(O)OC$_{1-6}$alkyl, --.

Column 26, Line 31, delete "—C$_{1-6}$ alkoxy," and insert -- —C$_{1-6}$alkoxy, --.

Column 26, Line 33, delete "—C$_{1-6}$ alkoxy," and insert -- —C$_{1-6}$alkoxy, --.

Column 26, Line 58, delete "—N[(CH$_2$)—R$^{1A}$]—" and insert -- —N[(CH$_2$)$_n$R$^{1A}$]— --.

Column 26, Line 62, delete "—(CH$_2$)$_m$O(CH$_2$)$_m$R$^{1A}$, —(CH$_2$)$_m$S(CH$_2$)$_6$R$^{1A}$," and insert -- —(CH$_2$)$_m$O(CH$_2$)$_n$R$^{1A}$, —(CH$_2$)$_m$S(CH$_2$)$_n$R$^{1A}$, --.

Column 26, Line 63-64, delete "—(CH$_2$)$_m$C(O)OC$_{1-6}$ alkyl," and insert -- —(CH$_2$)$_m$C(O)OC$_{1-6}$alkyl, --.

Column 27, Line 4, delete "—C$_{1-6}$ alkoxy," and insert -- —C$_{1-6}$alkoxy, --.

Column 27, Line 6, delete "—C$_{1-6}$ haloalkyl" and insert -- —C$_{1-6}$haloalkyl --.

Column 27, Line 13, delete "—C$_{1-6}$ alkyl-OH," and insert -- —C$_{1-6}$alkyl-OH, --.

Column 27, Line 13, delete "—C$_{1-6}$haloalkylOH," and insert -- —C$_{1-6}$haloalkyl-OH, --.

CERTIFICATE OF CORRECTION (continued)
U.S. Pat. No. 11,685,745 B2

Column 27, Line 14, delete "—$C_{2-6}$ alkenyl, —$C_{2-6}$ alkynyl," and insert -- —$C_{2-6}$alkenyl, —$C_{2-6}$alkynyl, --.

Column 27, Line 15, delete "—C(O)$C_{1-6}$ alkyl," and insert -- —C(O)$C_{1-6}$alkyl, --.

Column 27, Line 16, delete "—C(O)O$C_{1-6}$ alkyl," and insert -- —C(O)O$C_{1-6}$alkyl, --.

Column 27, Line 24-25, delete "—$SO_2C_{1-6}$ alkyl, —$C_{1-6}$ alkyl, —$C_{1-6}$ alkoxy, —$C_{1-6}$ haloalkyl," and insert -- —$SO_2C_{1-6}$alkyl, —$C_{1-6}$alkyl, —$C_{1-6}$alkoxy, —$C_{1-6}$haloalkyl, --.

Column 27, Line 27, delete "—$C_{2-6}$ alkenyl, —$C_{2-6}$ alkynyl," and insert -- —$C_{2-6}$alkenyl, —$C_{2-6}$alkynyl, --.

Column 27, Line 28, delete "—C(O)$C_{1-6}$ alkyl," and insert -- —C(O)$C_{1-6}$alkyl, --.

Column 27, Line 29, delete "—C(O)O$C_{1-6}$ alkyl," and insert -- —C(O)O$C_{1-6}$alkyl, --.

Column 27, Line 33, delete "—$SO_2C_{1-6}$ alkyl," and insert -- —$SO_2C_{1-6}$alkyl, --.

Column 27, Line 36, delete "—$C_{2-6}$ alkenyl, —$C_{2-6}$ alkynyl," and insert -- —$C_{2-6}$alkenyl, —$C_{2-6}$alkynyl, --.

Column 27, Line 37, delete "—C(O)$C_{1-6}$ alkyl," and insert -- —C(O)$C_{1-6}$alkyl, --.

Column 27, Line 38, delete "—C(O)O$C_{1-6}$ alkyl," and insert -- —C(O)O$C_{1-6}$alkyl, --.

Column 27, Line 46-47, delete "—C(O)O$C_{1-6}$ alkyl," and insert -- —C(O)O$C_{1-6}$alkyl, --.

Column 27, Line 52, delete "—$C_{1-6}$ alkoxy;" and insert -- —$C_{1-6}$alkoxy; --.

Column 28, Line 21-22, delete "3,4-dihydrospiro[2-benzopyran-1,4'-piperidine]-3-azabicyclo[4.1.0]heptan-3-yl," and insert -- 3,4-dihydrospiro[2-benzopyran-1,4'-piperidine]-1'-yl, 3-azabicyclo[4.1.0]heptan-3-yl, --.

Column 28, Line 24 (approx.), delete "6-aza spiro[3.5]nonan-6-yl," and insert -- 6-azaspiro[3.5]nonan-6-yl, --.

Column 28, Line 30 (approx.), delete "3-azabicyclo[3.1.0]hexanyl," and insert -- 3-azabicyclo[3.1.0]hexenyl, --.

Column 29, Line 25 (approx.), delete "—$C_1$," and insert -- —Cl, --.

Column 29, Line 30, delete "—$C_{1-6}$ alkyl," and insert -- —$C_{1-6}$alkyl, --.

Column 29, Line 31-32, delete "—$CH_2CH_2OC_{1-6}$ alkyl;" and insert -- —$CH_2CH_2OC_{1-6}$alkyl; --.

CERTIFICATE OF CORRECTION (continued)
U.S. Pat. No. 11,685,745 B2

Column 29, Line 34, delete "—$C_{1-6}$ alkyl, —$C_{1-6}$ haloalkyl," and insert -- —$C_{1-6}$alkyl, —$C_{1-6}$haloalkyl, --.

Column 29, Line 35-36, delete "—C(O)$C_{1-6}$ alkyl," and insert -- —C(O)$C_{1-6}$alkyl, --.

Column 29, Line 38-39, delete "—$C_{1-6}$ alkyl, —$C_{1-6}$ aryl, —$C_{1-6}$ heteroaryl," and insert -- —$C_{1-6}$alkyl, —$C_{1-6}$aryl, —$C_{1-6}$heteroaryl, --.

Column 29, Line 40, delete "—O$C_{1-6}$ alkyl," and insert -- —O$C_{1-6}$alkyl, --.

Column 29, Line 41-42, delete "—Otetrahydropyranyl, —Opiperidinyl," and insert -- —O-tetrahydropyranyl, —O-piperidinyl, --.

Column 29, Line 46, delete "—$C_{1-6}$haloalkylOH," and insert -- —$C_{1-6}$haloalkyl-OH, --.

Column 29, Line 49, delete "—$CH_2$C(O)$C_{1-6}$ alkyl," and insert -- —$CH_2$C(O)$C_{1-6}$alkyl, --.

Column 29, Line 50, delete "—$CH_2$C(O)O$C_{1-6}$ alkyl," and insert -- —$CH_2$C(O)O$C_{1-6}$alkyl, --.

Column 29, Line 55, delete "—$C_{2-6}$ alkynyl," and insert -- —$C_{2-6}$alkynyl, --.

Column 29, Line 56, delete "—O-$C_{1-6}$ alkyl," and insert -- —O-$C_{1-6}$alkyl, --.

Column 29, Line 56-57, delete "—O—$C_{1-6}$ haloalkyl," and insert -- —O—$C_{1-6}$haloalkyl, --.

Column 29, Line 57, delete "—Ophenyl, —Opyridyl," and insert -- —O-phenyl, —O-pyridyl, --.

Column 29, Line 61, delete "—$C_{3-7}$ halocycloalkyl," and insert -- —$C_{3-7}$halocycloalkyl, --.

Column 29, Line 66, delete "—O$C_{1-6}$ alkyl, —O—$C_{1-6}$ haloalkyl," and insert -- —O$C_{1-6}$alkyl, —O—$C_{1-6}$haloalkyl, --.

Column 30, Line 13-14 (approx.), delete "—$C_{1-6}$ haloalkyl, —$C_{1-6}$ haloalkyl" and insert -- —$C_{1-6}$haloalkyl, —$C_{1-6}$haloalkyl --.

Column 30, Line 16 (approx.), delete "—$CH_2$O$C_{1-6}$ alkyl," and insert -- —$CH_2$O$C_{1-6}$alkyl, --.

Column 30, Line 17-18 (approx.), delete "—$CH_2CH_2$O$C_{1-6}$ alkyl, —$CH_2CH_2$O$C_{1-6}$ haloalkyl," and insert -- —$CH_2CH_2$O$C_{1-6}$alkyl, —$CH_2CH_2$O$C_{1-6}$haloalkyl, --.

Column 30, Line 18-19 (approx.), delete "—O$C_{1-6}$ alkyl, —O$CH_2$-$C_{327}$cycloalkyl," and insert -- —O$C_{1-6}$alkyl, —O$CH_2$—$C_{3-7}$cycloalkyl, --.

Column 30, Line 20-21 (approx.), delete "—C(O)$C_{1-6}$ alkyl," and insert -- —C(O)$C_{1-6}$alkyl, --.

Column 30, Line 31, delete "W" and insert -- $R^b$ --.

Column 30, Line 32, delete "—$C_{1-6}$ alkyl," and insert -- —$C_{1-6}$alkyl, --.

Column 30, Line 33-34, delete "—$C_{1-6}$haloalkyl OH, —$C_{1-6}$ haloalkyl" and insert -- —$C_{1-6}$haloalkyl-OH, —$C_{1-6}$haloalkyl --.

Column 30, Line 36, delete "—$CH_2C(O)C_{1-6}$ alkyl," and insert -- —$CH_2C(O)C_{1-6}$alkyl, --.

Column 30, Line 37, delete "—$CH_2C(O)OC_{1-6}$ alkyl," and insert -- —$CH_2C(O)OC_{1-6}$alkyl, --.

Column 30, Line 42, delete "W" and insert -- $R^c$ --.

Column 30, Line 42, delete "—$C_{2-6}$ alkynyl," and insert -- —$C_{2-6}$alkynyl, --.

Column 30, Line 43, delete "—O—$C_{1-6}$ alkyl," and insert -- —O—$C_{1-6}$alkyl, --.

Column 30, Line 43-44, delete "—O—$C_{1-6}$ haloalkyl," and insert -- —O—$C_{1-6}$haloalkyl, --.

Column 30, Line 44, delete "—Ophenyl, —Opyridyl," and insert -- —Ophenyl, —Opyridyl, --.

Column 30, Line 64, delete "—$C_{1-6}$ haloalkyl," and insert -- —$C_{1-6}$haloalkyl, --.

Column 30, Line 65, delete "—$OC_{1-6}$ alkyl, —O—$C_{1-6}$ haloalkyl," and insert -- —$OC_{1-6}$alkyl, —O—$C_{1-6}$haloalkyl, --.

Column 31, Line 3, delete "W" and insert -- $R^b$ --.

Column 31, Line 31-32, delete "—$CH_2OC_{1-6}$ alkyl, —$CH_2C(O)$ $OCH_2CH_3$," and insert -- —$CH_2OC_{1-6}$alkyl, —$CH_2C(O)OCH_2CH_3$, --.

Column 31, Line 33, delete "—$CH_2CH_2OC_{1-6}$ haloalkyl," and insert -- —$CH_2CH_2OC_{1-6}$haloalkyl, --.

Column 31, Line 34, delete "—$OC_{1-6}$ alkyl," and insert -- —$OC_{1-6}$alkyl, --.

Column 31, Line 36, delete "—$C(O)C_{1-6}$ alkyl," and insert -- —$C(O)C_{1-6}$alkyl, --.

Column 32, Line 19, delete "—$C_1$," and insert -- —Cl, --.

Column 32, Line 22, delete "W" and insert -- $R^b$ --.

Column 32, Line 23-25, delete "—$C_{1-6}$ alkyl, —$C_{1-6}$ alkylOH, —$C_{1-6}$ haloalkyl, —$C_{1-6}$ haloalkylOH, —$C_{1-6}$ haloalkyl" and insert -- —$C_{1-6}$alkyl, —$C_{1-6}$alkyl-OH, —$C_{1-6}$haloalkyl, —$C_{1-6}$haloalkyl-OH, —$C_{1-6}$haloalkyl --.

Column 32, Line 27, delete "—$CH_2C(O)C_{1-6}$ alkyl," and insert -- —$CH_2C(O)C_{1-6}$alkyl, --.

Column 32, Line 28, delete "—CH$_2$C(O)OC$_{1-6}$ alkyl," and insert -- —CH$_2$C(O)OC$_{1-6}$alkyl, --.

Column 32, Line 32, delete "—(CH$_2$)R$^d$," and insert -- —(CH$_2$)$_n$-R$^d$, --.

Column 32, Line 33, delete "W" and insert -- R$^c$ --.

Column 32, Line 33, delete "—C$_{2-6}$ alkynyl," and insert -- —C$_{2-6}$alkynyl, --.

Column 32, Line 34, delete "—O—C$_{1-6}$ alkyl," and insert -- —O—C$_{1-6}$alkyl, --.

Column 32, Line 35, delete "—Ophenyl, —Opyridyl," and insert -- —O-phenyl, —O-pyridyl, --.

Column 32, Line 39, delete "—C$_{3-7}$ halocycloalkyl," and insert -- —C$_{3-7}$halocycloalkyl, --.

Column 32, Line 43, delete "—C$_{1-6}$ alkyl," and insert -- —C$_{1-6}$ alkyl, --.

Column 32, Line 44, delete "—OC$_{1-6}$ alkyl, —O—C$_{1-6}$ haloalkyl," and insert -- —OC$_{1-6}$alkyl, —O—C$_{1-6}$haloalkyl, --.

Column 32, Line 57-58, delete "—C$_{1-6}$ alkyl, —C$_{1-6}$ haloalkyl, —C$_{1-6}$ haloalkyl" and insert -- —C$_{1-6}$alkyl, —C$_{1-6}$haloalkyl, —C$_{1-6}$haloalkyl --.

Column 32, Line 59, delete "—C$_{1-6}$ alkyl-OH," and insert -- —C$_{1-6}$alkyl-OH, --.

Column 32, Line 60-61, delete "—CH$_2$OC$_{1-6}$ alkyl, —CH$_2$C(O)OCH$_2$CH$_3$, —CH$_2$CH$_2$OC$_{1-6}$ alkyl, —CH$_2$CH$_2$OC$_{1-6}$ haloalkyl," and insert -- —CH$_2$OC$_{1-6}$alkyl, —CH$_2$C(O)OCH$_2$CH$_3$, —CH$_2$CH$_2$OC$_{1-6}$alkyl, —CH$_2$CH$_2$OC$_{1-6}$haloalkyl, --.

Column 32, Line 62, delete "—OC$_{1-6}$ alkyl," and insert -- —OC$_{1-6}$alkyl, --.

Column 32, Line 64-65, delete "—C(O)C$_{1-6}$ alkyl," and insert -- —C(O)C$_{1-6}$alkyl, --.

Column 32, Line 65, delete "—C(O)OC$_{1-6}$ alkyl," and insert -- —C(O)OC$_{1-6}$alkyl, --.

Column 33, Line 26, delete "—C$_1$," and insert -- —Cl, --.

Column 33, Line 30-32, delete "—C$_{1-6}$ alkyl-OH, —C$_{1-6}$ haloalkyl, —C$_{1-6}$ haloalkylOH, —C$_{1-6}$ haloalkyl" and insert -- —C$_{1-6}$alkyl-OH, —C$_{1-6}$haloalkyl, —C$_{1-6}$haloalkyl-OH, —C$_{1-6}$haloalkyl --.

Column 33, Line 34, delete "—CH$_2$C(O)C$_{1-6}$ alkyl," and insert -- —CH$_2$C(O)C$_{1-6}$alkyl, --.

Column 33, Line 35, delete "—CH$_2$C(O)OC$_{1-6}$ alkyl," and insert -- —CH$_2$C(O)OC$_{1-6}$alkyl, --.

Column 33, Line 39, delete "—(CH$_2$)R$^d$," and insert -- —(CH$_2$)$_n$-R$^d$, --.

Column 33, Line 42, delete "—Ophenyl, —Opyridyl," and insert -- —O-phenyl, —O-pyridyl, --.

Column 33, Line 49, delete "—C$_{1-6}$ alkyl," and insert -- —C$_{1-6}$alkyl, --.

Column 33, Line 50, delete "—OC$_{1-6}$ alkyl, —O—C$_{1-6}$ haloalkyl" and insert -- —OC$_{1-6}$alkyl, —O—C$_{1-6}$haloalkyl --.

Column 33, Line 64, delete "—C$_{1-6}$ haloalkyl," and insert -- —C$_{1-6}$haloalkyl, --.

Column 33, Line 66, delete "—C(CH$_3$)$_2$ OH, —CH$_2$OC$_{1-6}$ alkyl," and insert -- —C(CH$_3$)$_2$ OH, —CH$_2$OC$_{1-6}$alkyl, --.

Column 34, Line 1, delete "—CH$_2$CH$_2$OC$_{1-6}$ alkyl, —CH$_2$CH$_2$OC$_{1-6}$ haloalkyl," and insert -- —CH$_2$CH$_2$OC$_{1-6}$alkyl, —CH$_2$CH$_2$OC$_{1-6}$haloalkyl, --.

Column 34, Line 2, delete "—OC$_{1-6}$ alkyl," and insert -- —OC$_{1-6}$alkyl, --.

Column 34, Line 4-5, delete "—C(O)C$_{1-6}$ alkyl," and insert -- —C(O)C$_{1-6}$alkyl, --.

Column 34, Line 35, delete "—C$_1$," and insert -- —Cl, --.

Column 34, Line 37, delete "—C$_{1-6}$ aryl," and insert -- —C$_{1-6}$aryl, --.

Column 34, Line 41-42, delete "—C$_{1-6}$haloalkyl OH, —C$_{1-6}$ haloalkyl" and insert -- —C$_{1-6}$haloalkyl-OH, —C$_{1-6}$haloalkyl --.

Column 34, Line 44, delete "—CH$_2$C(O)C$_{1-6}$ alkyl," and insert -- —CH$_2$C(O)C$_{1-6}$alkyl, --.

Column 34, Line 45, delete "—CH$_2$C(O)OC$_{1-6}$ alkyl," and insert -- —CH$_2$C(O)OC$_{1-6}$alkyl, --.

Column 34, Line 49, delete "—(CH$_2$)R$^d$," and insert -- —(CH$_2$)$_n$-R$^d$, --.

Column 34, Line 52, delete "—Ophenyl, —Opyridyl," and insert -- —O-phenyl, —O-pyridyl, --.

Column 34, Line 55, delete "—C$_{3-7}$ halocycloalkyl," and insert -- —C$_{3-7}$halocycloalkyl, --.

Column 34, Line 59, delete "—C$_{1-6}$ alkyl," and insert -- —C$_{1-6}$alkyl, --.

Column 34, Line 60, delete "—OC$_{1-6}$ alkyl, —O—C$_{1-6}$ haloalkyl," and insert -- —OC$_{1-6}$alkyl, —O—C$_{1-6}$haloalkyl, --.

Column 35, Line 6, delete "—C$_{1-6}$ alkyl, —C$_{1-6}$ haloalkyl, —C$_{1-6}$ haloalkyl" and insert -- —C$_{1-6}$alkyl, —C$_{1-6}$haloalkyl, —C$_{1-6}$haloalkyl --.

Column 35, Line 7-8, delete "—C$_{1-6}$ alkyl-OH," and insert -- —C$_{1-6}$alkyl-OH, --.

CERTIFICATE OF CORRECTION (continued)
U.S. Pat. No. 11,685,745 B2

Column 35, Line 8, delete "—$CH_2OC_{1-6}$ alkyl," and insert -- —$CH_2OC_{1-6}$ alkyl, --.

Column 35, Line 9-10, delete "—$CH_2CH_2OC_{1-6}$ haloalkyl, —$CH_2CH_2C(O)$ $OCH_3$," and insert -- —$CH_2CH_2OC_{1-6}$haloalkyl, —$CH_2CH_2C(O)OCH_3$, --.

Column 35, Line 10, delete "—$OC_{1-6}$ alkyl," and insert -- —$OC_{1-6}$alkyl, --.

Column 35, Line 12, delete "—$C(O)C_{1-6}$ alkyl," and insert -- —$C(O)C_{1-6}$alkyl, --.

Column 35, Line 13, delete "—$C(O)OC_{1-6}$ alkyl," and insert -- —$C(O)OC_{1-6}$alkyl, --.

Column 35, Line 42, delete "—$C_{1-6}$ alkyl," and insert -- —$C_{1-6}$alkyl, --.

Column 35, Line 44, delete "—$C_{1-6}$ alkyl-OH," and insert -- —$C_{1-6}$alkyl-OH, --.

Column 35, Line 45-46, delete "—$CH_2CH_2OC_{1-6}$ alkyl, —$CH_2CH_2OC_{1-6}$ halo alkyl," and insert -- —$CH_2CH_2OC_{1-6}$alkyl, —$CH_2CH_2OC_{1-6}$haloalkyl, --.

Column 35, Line 49, delete "—$C(O)C_{1-6}$ alkyl," and insert -- —$C(O)C_{1-6}$alkyl, --.

Column 35, Line 49-50, delete "—$C(O)OC_{1-6}$ alkyl," and insert -- —$C(O)OC_{1-6}$alkyl, --.

Column 35, Line 58-59, delete "—$C_{1-6}$ alkyl," and insert -- —$C_{1-6}$alkyl, --.

Column 35, Line 61, delete "—$C_{1-6}$ alkyl." and insert -- —$C_{1-6}$alkyl. --.

Column 35, Line 63, delete "—$C_{1-6}$ alkyl," and insert -- —$C_{1-6}$alkyl, --.

Column 35, Line 65, delete "—$C(O)C_{1-6}$ alkyl," and insert -- —$C(O)C_{1-6}$alkyl, --.

Column 36, Line 1, delete "—$C_{1-6}$ alkyl, —$C_{1-6}$ aryl," and insert -- —$C_{1-6}$alkyl, —$C_{1-6}$aryl, --.

Column 36, Line 3, delete "—$OC_{1-6}$ alkyl," and insert -- —$OC_{1-6}$alkyl, --.

Column 36, Line 7, delete "—$C_{1-6}$haloalkylOH," and insert -- —$C_{1-6}$haloalkyl-OH, --.

Column 36, Line 9-10, delete "—$CH_2C(O)C_{1-6}$ alkyl," and insert -- —$CH_2C(O)C_{1-6}$alkyl, --.

Column 36, Line 10-11, delete "—$CH_2C(O)OC_{1-6}$ alkyl," and insert -- —$CH_2C(O)OC_{1-6}$alkyl, --.

Column 36, Line 14, delete "—$CH_2CH_2$—Re" and insert -- —$CH_2CH_2$—$R^c$ --.

Column 36, Line 14, delete "—$C_{2-6}$ alkynyl," and insert -- —$C_{2-6}$alkynyl, --.

Column 36, Line 15, delete "—O—$C_{1-6}$ alkyl," and insert -- —O—$C_{1-6}$alkyl, --.

CERTIFICATE OF CORRECTION (continued)
U.S. Pat. No. 11,685,745 B2

Column 36, Line 15-16, delete "—O—C$_{1-6}$ haloalkyl," and insert -- —O—C$_{1-6}$haloalkyl, --.

Column 36, Line 16, delete "—Ophenyl, —Opyridyl," and insert -- —O-phenyl, —O-pyridyl, --.

Column 36, Line 34, delete "—C$_{1-6}$ haloalkyl," and insert -- —C$_{1-6}$haloalkyl, --.

Column 36, Line 36, delete "—CH$_2$OC$_{1-6}$ alkyl," and insert -- —CH$_2$OC$_{1-6}$alkyl, --.

Column 36, Line 37-38, delete "—CH$_2$CH$_2$OC$_{1-6}$ alkyl, —CH$_2$CH$_2$OC$_{1-6}$ haloalkyl," and insert -- —CH$_2$CH$_2$OC$_{1-6}$alkyl, —CH$_2$CH$_2$OC$_{1-6}$haloalkyl, --.

Column 36, Line 38, delete "—OC$_{1-6}$ alkyl," and insert -- —OC$_{1-6}$alkyl, --.

Column 36, Line 40, delete "—C(O)C$_{1-6}$ alkyl," and insert -- —C(O)C$_{1-6}$alkyl, --.

Column 36, Line 41, delete "—C(O)OC$_{1-6}$ alkyl," and insert -- —C(O)OC$_{1-6}$alkyl, --.

Column 36, Line 50, delete "—C$_{1-6}$ alkyl, —C$_{1-6}$ haloalkyl," and insert -- —C$_{1-6}$alkyl, —C$_{1-6}$haloalkyl, --.

Column 36, Line 52, delete "—C(O)C$_{1-6}$ alkyl," and insert -- —C(O)C$_{1-6}$alkyl, --.

Column 36, Line 54-55, delete "—C$_{1-6}$ alkyl, —C$_{1-6}$ aryl, —C$_{1-6}$ heteroaryl," and insert -- —C$_{1-6}$alkyl, —C$_{1-6}$aryl, —C$_{1-6}$heteroaryl, --.

Column 36, Line 56, delete "—OC$_{1-6}$ alkyl," and insert -- —OC$_{1-6}$alkyl, --.

Column 36, Line 58, delete "—Opiperidinyl," and insert -- —O-piperidinyl, --.

Column 36, Line 60-61, delete "—C$_{1-6}$haloalkylOH," and insert -- —C$_{1-6}$haloalkyl-OH, --.

Column 36, Line 63, delete "—CH$_2$C(O)C$_{1-6}$ alkyl," and insert -- —CH$_2$C(O)C$_{1-6}$alkyl, --.

Column 36, Line 64, delete "—CH$_2$C(O)OC$_{1-6}$ alkyl," and insert -- —CH$_2$C(O)OC$_{1-6}$alkyl, --.

Column 36, Line 67, delete "—CH$_2$CH$_2$—Re" and insert -- —CH$_2$CH$_2$—R$^c$ --.

Column 37, Line 1, delete "—C$_{2-6}$ alkynyl," and insert -- —C$_{2-6}$alkynyl, --.

Column 37, Line 1, delete "—O—C$_{1-6}$ alkyl," and insert -- —O—C$_{1-6}$alkyl, --.

Column 37, Line 2, delete "—O—C$_{1-6}$ haloalkyl," and insert -- —O—C$_{1-6}$haloalkyl, --.

Column 37, Line 2-3, delete "—Ophenyl, —Opyridyl," and insert -- —O-phenyl, —O-pyridyl, --.

Column 37, Line 5, delete "—(CH$_2$)R$^d$" and insert -- —(CH$_2$)$_n$-R$^d$ --.

Column 37, Line 19, after "—F," insert -- —$C_{1-6}$alkyl, —$C_{1-6}$haloalkyl, --.

Column 37, Line 42, delete "spiro[isochroman-1,4'-piperidine]6',7'" and insert -- spiro[isochroman-1,4'-piperidine], 6',7' --.

Column 37, Line 47-48, delete "—$C_{1-6}$ alkyl, —$C_{1-6}$ haloalkyl-$C_{3-7}$cycloalkyl," and insert -- —$C_{1-6}$alkyl, —$C_{1-6}$haloalkyl, —$C_{1-6}$haloalkyl-$C_{3-7}$cycloalkyl, --.

Column 37, Line 49, delete "—$C_{1-6}$ alkyl-OH," and insert -- —$C_{1-6}$alkyl-OH, --.

Column 37, Line 50, delete "—$CH_2OC_{1-6}$ alkyl," and insert -- —$CH_2OC_{1-6}$alkyl, --.

Column 37, Line 51, delete "—$CH_2CH_2OC_{1-6}$ alkyl, —$CH_2CH_2OC_{1-6}$ haloalkyl," and insert -- —$CH_2CH_2OC_{1-6}$alkyl, —$CH_2CH_2OC_{1-6}$haloalkyl, --.

Column 37, Line 52, delete "—$OC_{1-6}$ alkyl," and insert -- —$OC_{1-6}$alkyl, --.

Column 37, Line 54, delete "—$C(O)C_{1-6}$ alkyl," and insert -- —$C(O)C_{1-6}$alkyl, --.

Column 37, Line 55, delete "—$C(O)OC_{1-6}$ alkyl," and insert -- —$C(O)OC_{1-6}$alkyl, --.

Column 38, Line 10, delete "[3,4-c]" and insert -- [3,4-d] --.

Column 38, Line 20, delete "—$C_{1-6}$ alkyl," and insert -- —$C_{1-6}$alkyl, --.

Column 38, Line 20, delete "—$C_{1-6}$ halo alkyl" and insert -- —$C_{1-6}$haloalkyl --.

Column 38, Line 21-22, delete "—$C_{1-6}$ alkyl-OH," and insert -- —$C_{1-6}$alkyl-OH, --.

Column 38, Line 22, delete "—$CH_2OC_{1-6}$ alkyl," and insert -- —$CH_2OC_{1-6}$alkyl, --.

Column 38, Line 23-24, delete "—$CH_2CH_2OC_{1-6}$ alkyl, —$CH_2CH_2OC_{1-6}$ haloalkyl," and insert -- —$CH_2CH_2OC_{1-6}$alkyl, —$CH_2CH_2OC_{1-6}$haloalkyl, --.

Column 38, Line 24, delete "—$OC_{1-6}$ alkyl," and insert -- —$OC_{1-6}$alkyl, --.

Column 38, Line 26, delete "—$C(O)C_{1-6}$ alkyl," and insert -- —$C(O)C_{1-6}$alkyl, --.

Column 38, Line 27, delete "—$C(O)OC_{1-6}$ alkyl," and insert -- —$C(O)OC_{1-6}$alkyl, --.

Column 38, Line 36, delete "—$C_{1-6}$ alkyl, —$C_{1-6}$ haloalkyl," and insert -- —$C_{1-6}$alkyl, —$C_{1-6}$haloalkyl, --.

Column 38, Line 37, delete "—$C(O)C_{1-6}$ alkyl," and insert -- —$C(O)C_{1-6}$alkyl, --.

CERTIFICATE OF CORRECTION (continued)
U.S. Pat. No. 11,685,745 B2

Column 38, Line 40-41, delete "—$C_{1-6}$ alkyl, —$C_{1-6}$ haloalkyl," and insert -- —$C_{1-6}$alkyl, —$C_{1-6}$haloalkyl, --.

Column 38, Line 42-43, delete "—$C_{1-6}$ alkyl." and insert -- —$C_{1-6}$alkyl. --.

Column 38, Line 48, "—C(O)$C_{1-6}$ alkyl," and insert -- —C(O)$C_{1-6}$alkyl, --.

Column 38, Line 51, delete "—$C_{1-6}$ aryl," and insert -- —$C_{1-6}$aryl, --.

Column 38, Line 52, delete "—O$C_{1-6}$ alkyl," and insert -- —O$C_{1-6}$alkyl, --.

Column 38, Line 54, delete "—Opiperidinyl," and insert -- —O-piperidinyl, --.

Column 38, Line 56-57, delete "—$C_{1-6}$ haloalkyl, —$C_{1-6}$ haloalkylOH, —$C_{1-6}$ haloalkyl" and insert -- —$C_{1-6}$haloalkyl, —$C_{1-6}$haloalkyl-OH, —$C_{1-6}$haloalkyl --.

Column 38, Line 59, delete "—$CH_2$C(O)$C_{1-6}$ alkyl," and insert -- —$CH_2$C(O)$C_{1-6}$alkyl, --.

Column 38, Line 60, delete "—$CH_2$C(O)O$C_{1-6}$ alkyl," and insert -- —$CH_2$C(O)O$C_{1-6}$alkyl, --.

Column 38, Line 64, delete "—$C_{2-6}$ alkynyl," and insert -- —$C_{2-6}$alkynyl, --.

Column 38, Line 65, delete "—O—$C_{1-6}$ alkyl," and insert -- —O—$C_{1-6}$alkyl, --.

Column 38, Line 66, delete "—Ophenyl, —Opyridyl," and insert -- —O-phenyl, —O-pyridyl, --.

Column 39, Line 6-32, delete "—$C_{1-6}$ alkyl, —$C_{1-6}$ haloalkyl, —$C_{3-7}$cycloalkyl, —OH, —O$C_{1-6}$ alkyl, —O—$C_{1-6}$ haloalkyl, —O-phenyl, —O-pyridyl, —$CH_2$OH, —$CH_2$O$CH_3$, —$CH_2$O$CH_2$$CH_3$, heteroaryl, heterocycloalkyl, morphoLine, phenyl, —CN, —N($CH_3$)$_2$, —N($CH_3$)benzyl, heterocycloalkyl, aryl, or heteroaryl, where n is 0, 1, 2 or 3; or, alternatively, both $R^b$ come together to form a 4-15-membered, monocyclic, bicyclic or tricyclic ring, optionally containing up to 3 additional heteroatoms each independently selected from O (oxygen), N (nitrogen) and S (sulfur), said 4-15-membered monocyclic, bicyclic or tricyclic ring optionally substituted with up to 4 substituents each independently selected from the group consisting of: halo, —$C_{1-6}$alkyl, —$C_{1-6}$halo alkyl, —$C_{1-6}$haloalkyl-$C_{3-7}$cycloalkyl, —$C_{3-7}$cycloalkyl, bicyclo[2.2.1]heptane, —$C_{1-6}$alkyl-OH, —C($CH_3$)$_2$OH, —$CH_2$O$C_{1-6}$alkyl, —$CH_2$C(O)O$CH_2$$CH_3$, —$CH_2$$CH_2$O$C_{1-6}$ alkyl, —$CH_2$$CH_2$O$C_{1-6}$ halo alkyl, —$CH_2$$CH_2$C(O)O$CH_3$, —OH, —O$C_{1-6}$alkyl, —O$CH_2$—$C_{3-7}$cycloalkyl, —O$CH_2$$CH_2$O$CH_3$, =O, —$CH_2$N($CH_3$)$_2$, —$CH_2$$CH_2$N($CH_3$)$_2$, —C(O)$C_{1-6}$ alkyl, —C(O)H, —C(O)OH, —C(O)O$C_{1-6}$ alkyl, —C(O)$CH_3$, —C(O)$NH_2$, —C(O)NH$CH_3$, —C(O)N($CH_3$)$_2$, —CN, —$NH_2$, —NHC(O)$CH_3$, —N($CH_3$)$_2$, —$SO_2$$CH_3$, oxetane, pyrrolidine, morpholine, furan, thiazole, pyridyl, phenyl, thiophene, —$CH_2$imidazole, —$CH_2$furan, —$CH_2$-thiophene, —$CH_2$pyridyl, benzyl, —C(O)-tetrahydrofuran, —C(O)pyrrole or —C(O)phenyl." and insert the same on Column 39 Line 5, as the continuation of the same Paragraph.

Column 39, Line 6, delete "—$C_{1-6}$ alkyl, —$C_{1-6}$ haloalkyl," and insert -- —$C_{1-6}$alkyl,

CERTIFICATE OF CORRECTION (continued)
U.S. Pat. No. 11,685,745 B2

—$C_{1-6}$haloalkyl, --.

Column 39, Line 7, delete "—$OC_{1-6}$ alkyl, —O—$C_{1-6}$ haloalkyl," and insert -- —$OC_{1-6}$alkyl, —O—$C_{1-6}$haloalkyl --.

Column 39, Line 19, delete "—$C_{1-6}$halo alkyl," and insert -- —$C_{1-6}$haloalkyl, --.

Column 39, Line 22-23, delete "—$CH_2CH_2OC_{1-6}$ alkyl, —$CH_2CH_2OC_{1-6}$ halo alkyl," and insert -- —$CH_2CH_2OC_{1-6}$alkyl, —$CH_2CH_2OC_{1-6}$haloalkyl --.

Column 39, Line 25, delete "—$C(O)C_{1-6}$ alkyl," and insert -- —$C(O)C_{1-6}$alkyl, --.

Column 39, Line 26, delete "—$C(O)OC_{1-6}$ alkyl," and insert -- —$C(O)OC_{1-6}$alkyl, --.

Column 39, Line 35, delete "—$CH_2OC_{1-5}$ alkyl," and insert -- —$CH_2OC_{1-5}$alkyl, --.

Column 39, Line 36-37, delete "—$C(O)C_{1-6}$ alkyl," and insert -- —$C(O)C_{1-6}$alkyl, --.

Column 39, Line 40, delete "—$C_{1-6}$ hetero aryl," and insert -- —$C_{1-6}$heteroaryl, --.

Column 39, Line 41, delete "—$OC_{1-6}$ alkyl," and insert -- —$OC_{1-6}$alkyl, --.

Column 39, Line 42, delete "—Opiperidinyl," and insert --— O-piperidinyl, --.

Column 39, Line 45, delete "—$C_{1-6}$ haloalkylOH, —$C_{1-6}$ haloalkyl" and insert -- —$C_{1-6}$haloalkyl-OH, —$C_{1-6}$haloalkyl --.

Column 39, Line 47-48, delete "—$CH_2C(O)C_{1-6}$ alkyl," and insert -- —$CH_2C(O)C_{1-6}$alkyl, --.

Column 39, Line 48, delete "—$CH_2C(O)OC_{1-6}$ alkyl," and insert -- —$CH_2C(O)OC_{1-6}$alkyl, --.

Column 39, Line 51, delete "—$CH_2CH_2$—Re" and insert -- —$CH_2CH_2$—$R^c$ --.

Column 39, Line 52, delete "—$C_{2-6}$ alkynyl," and insert -- —$C_{2-6}$alkynyl, --.

Column 39, Line 53, delete "—O—$C_{1-6}$ alkyl," and insert -- —O—$C_{1-6}$alkyl, --.

Column 39, Line 53, delete "—O—$C_{1-6}$ haloalkyl," and insert -- —O—$C_{1-6}$haloalkyl, --.

Column 39, Line 54, delete "—Ophenyl, —Opyridyl," and insert -- —O-phenyl, —O-pyridyl, --.

Column 39, Line 56, delete "—$(CH_2)R^d$," and insert -- —$(CH_2)_n$-$R^d$, --.

Column 40, Line 3, after "$C_{1-6}$alkyl," insert -- —$C_{1-6}$haloalkyl, --.

Column 40, Line 4, delete "—O—$C_{1-6}$ halo alkyl," and insert -- —O—$C_{1-6}$alkyl, —O—$C_{1-6}$haloalkyl, --.

Column 40, Line 26, delete "spiro[isochroman-1,4'-piperidine]6',7'" and insert -- spiro[isochroman-1,4'-piperidine], 6',7' --.

Column 40, Line 31, after "$C_{1-6}$alkyl," insert -- —$C_{1-6}$haloalkyl, --.

Column 40, Line 33, delete "—$CH_2OC_{1-6}$ alkyl," and insert -- —$CH_2OC_{1-6}$alkyl, --.

Column 40, Line 34-35, delete delete "—$CH_2CH_2OC_{1-6}$ alkyl, —$CH_2CH_2OC_{1-6}$ haloalkyl," and insert -- —$CH_2CH_2OC_{1-6}$alkyl, —$CH_2CH_2OC_{1-6}$haloalkyl --.

Column 40, Line 35, delete "—$OC_{1-6}$ alkyl," and insert -- —$OC_{1-6}$alkyl, --.

Column 40, Line 37, delete "—$C(O)C_{1-6}$ alkyl," and insert -- —$C(O)C_{1-6}$alkyl, --.

Column 40, Line 38, delete "—$C(O)OC_{1-6}$ alkyl," and insert -- —$C(O)OC_{1-6}$alkyl, --.

Column 40, Line 48, delete "—$C_{1-6}$haloalkylOH," and insert -- —$C_{1-6}$haloalkyl-OH, --.

Column 40, Line 51, delete "—$CH_2C(O)C_{1-6}$ alkyl," and insert -- —$CH_2C(O)C_{1-6}$alkyl, --.

Column 40, Line 55, delete "—$CH_2CH_2$—Re" and insert -- —$CH_2CH_2$—$R^c$ --.

Column 40, Line 55, delete "-C2-6 alkynyl," and insert -- C2-6alkynyl, --.

Column 40, Line 56, delete "—O—$C_{1-6}$ alkyl," and insert -- —O—$C_{1-6}$alkyl, --.

Column 40, Line 57, delete "—O—$C_{1-6}$ haloalkyl," and insert -- —O—$C_{1-6}$haloalkyl, --.

Column 40, Line 57, delete "—Ophenyl, —Opyridyl," and insert -- —O-phenyl, —O-pyridyl, --.

Column 40, Line 60, delete "—$(CH_2)R^d$," and insert -- —$(CH_2)_n$-$R^d$, --.

Column 41, Line 37-38, after "—$C_{1-6}$alkyl," insert -- —$C_{1-6}$haloalkyl, --.

Column 41, Line 39, delete "—$C_{1-6}$ alkyl-OH," and insert -- —$C_{1-6}$alkyl-OH, --.

Column 41, Line 41, delete "—$CH_2CH_2OC_{1-6}$ alkyl, —$CH_2CH_2OC_{1-6}$ haloalkyl," and insert -- —$CH_2CH_2OC_{1-6}$alkyl, —$CH_2CH_2OC_{1-6}$haloalkyl, --.

Column 41, Line 42, delete "—$OC_{1-6}$ alkyl," and insert -- —$OC_{1-6}$alkyl, --.

Column 41, Line 44, delete "—$C(O)C_{1-6}$ alkyl," and insert -- —$C(O)C_{1-6}$alkyl, --.

Column 41, Line 45, delete "—C(O)OC$_{1-6}$ alkyl," and insert -- —C(O)OC$_{1-6}$alkyl, --.

Column 41, Line 54, after "—C$_{1-6}$alkyl," insert -- —C$_{1-6}$haloalkyl, --.

Column 41, Line 55, delete "—C(O)C$_{1-6}$ alkyl," and insert -- —C(O)C$_{1-6}$alkyl, --.

Column 41, Line 59, delete "—C$_{1-6}$hetero aryl," and insert -- —C$_{1-6}$heteroaryl, --.

Column 41, Line 59, after "—OH," insert -- —C$_{1-6}$ alkyl, --.

Column 41, Line 60-61, delete "—Opiperidinyl," and insert -- —O-piperidinyl, --.

Column 41, Line 62-63, delete "—C$_{1-6}$ haloalkylOH, —C$_{1-6}$ haloalkyl–C$_{3-7}$cycloalkyl," and insert -- —C$_{1-6}$alkyl, —C$_{1-6}$alkyl-OH, C$_{1-6}$haloalkyl, —C$_{1-6}$haloalkyl-OH, —C$_{1-6}$haloalkyl–C$_{3-7}$cycloalkyl, --.

Column 41, Line 65, delete "—CH$_2$C(O)C$_{1-6}$ alkyl," and insert -- —CH$_2$C(O)C$_{1-6}$alkyl, --.

Column 41, Line 66, delete "—CH$_2$C(O)OC$_{1-6}$ alkyl," and insert -- —CH$_2$C(O)OC$_{1-6}$alkyl, --.

Column 42, Line 3, delete "—C$_{2-6}$ alkynyl," and insert -- —C$_{2-6}$alkynyl, --.

Column 42, Line 3, delete "—O—C$_{1-6}$ alkyl," and insert -- —O—C$_{1-6}$alkyl, --.

Column 42, Line 4, after "—OC(CH$_3$)$_2$," insert -- —O—C$_{1-6}$haloalkyl, --.

Column 42, Line 4, delete "—Ophenyl, —Opyridyl," and insert -- —O-phenyl, —O-pyridyl, --.

Column 42, Line 7, delete "—C$_{3-7}$ halocycloalkyl," and insert -- —C$_{3-7}$halocycloalkyl, --.

Column 42, Line 10, after "—C$_{1-6}$alkyl," insert -- —C$_{1-6}$haloalkyl, --.

Column 42, Line 11, after "—OH," insert -- —C$_{1-6}$alkyl, --.

Column 42, Line 22, delete "—C$_{1-6}$ alkyl, —C$_{1-6}$ halo alkyl, —C$_{1-6}$ haloalkyl" and insert -- —C$_{1-6}$alkyl, —C$_{1-6}$haloalkyl, —C$_{1-6}$haloalkyl --.

Column 42, Line 23-24, delete "—C$_{1-6}$ alkyl-OH," and insert -- —C$_{1-6}$alkyl-OH, --.

Column 42, Line 25-26, delete "—CH$_2$CH$_2$OC$_{1-6}$ alkyl, —CH$_2$CH$_2$OC$_{1-6}$ haloalkyl," and insert -- —CH$_2$CH$_2$OC$_{1-6}$alkyl, —CH$_2$CH$_2$OC$_{1-6}$haloalkyl, --.

Column 42, Line 28, delete "—C(O)C$_{1-6}$ alkyl," and insert -- —C(O)C$_{1-6}$alkyl, --.

Column 42, Line 29, delete "—C(O)OC$_{1-6}$ alkyl," and insert -- —C(O)OC$_{1-6}$alkyl, --.

Column 42, Line 38, delete "—C$_1$," and insert -- —Cl, --.

CERTIFICATE OF CORRECTION (continued)
U.S. Pat. No. 11,685,745 B2

Column 42, Line 45, after "—H," insert -- —$C_{1-6}$alkyl, —$C_{1-6}$alkyl-OH, --.

Column 42, Line 46, delete "—$C_{1-6}$haloalkylOH," and insert -- —$C_{1-6}$haloalkyl-OH, --.

Column 42, Line 48-49, delete "—$CH_2C(O)C_{1-6}$ alkyl," and insert -- —$CH_2C(O)C_{1-6}$alkyl, --.

Column 42, Line 49-50, delete "—$CH_2C(O)OC_{1-6}$ alkyl," and insert -- —$CH_2C(O)OC_{1-6}$alkyl, --.

Column 42, Line 53, delete "—$C_{2-6}$ alkynyl," and insert -- —$C_{2-6}$alkynyl, --.

Column 42, Line 54, after "—OH," insert -- —O—$C_{1-6}$alkyl, --.

Column 42, Line 54, after "—$OC(CH_3)_2$," insert -- —O—$C_{1-6}$haloalkyl, --.

Column 42, Line 54, delete "—Ophenyl, —Opyridyl," and insert -- —O-phenyl, —O-pyridyl, --.

Column 42, Line 59, delete "—$C_{3-7}$ halocycloalkyl," and insert -- —$C_{3-7}$halocycloalkyl, --.

Column 43, Line 6, delete "—O—$C_{1-6}$ haloalkyl," and insert -- —O—$C_{1-6}$haloalkyl, --.

Column 43, Line 36, delete "—$C_{1-6}$ alkyl-OH," and insert -- —$C_{1-6}$alkyl-OH, --.

Column 43, Line 37, delete "—$CH_2OC_{1-6}$ alkyl," and insert -- —$CH_2OC_{1-6}$alkyl, --.

Column 43, Line 38, delete "—$CH_2CH_2OC_{1-6}$ alkyl, —$CH_2CH_2OC_{1-6}$ haloalkyl," and insert -- —$CH_2CH_2OC_{1-6}$alkyl, —$CH_2CH_2OC_{1-6}$haloalkyl, --.

Column 43, Line 39, delete "—$OC_{1-6}$ alkyl," and insert -- —$OC_{1-6}$alkyl, --.

Column 43, Line 41, delete "—$C(O)C_{1-6}$ alkyl," and insert -- —$C(O)C_{1-6}$alkyl, --.

Column 43, Line 42, delete "—$C(O)OC_{1-6}$ alkyl," and insert -- —$C(O)OC_{1-6}$alkyl, --.

Column 43, Line 52, delete "—$C_1$," and insert -- —Cl, --.

Column 43, Line 59, delete "—$C_{1-6}$haloalkylOH," and insert -- —$C_{1-6}$haloalkyl-OH, --.

Column 43, Line 62, delete "—$CH_2C(O)C_{1-6}$ alkyl," and insert -- —$CH_2C(O)C_{1-6}$alkyl, --.

Column 43, Line 63, delete "—$CH_2C(O)OC_{1-6}$ alkyl," and insert -- —$CH_2C(O)OC_{1-6}$alkyl, --.

Column 43, Line 67, delete "—$C_{2-6}$ alkynyl," and insert -- —$C_{2-6}$alkynyl, --.

Column 43-44, Line 67 (Column 43), Line 1 (Column 44), delete "—O—$C_{1-6}$ alkyl," and insert -- —O—$C_{1-6}$alkyl, --.

Column 44, Line 1-2, delete "—Ophenyl, —Opyridyl," and insert -- —O-phenyl, —O-pyridyl, --.

Column 44, Line 22, delete "—O—$C_{1-6}$ haloalkyl," and insert -- —O—$C_{1-6}$haloalkyl, --.

Column 44, Line 28, delete "—$C_1$," and insert -- —Cl, --.

Column 44, Line 58, delete "—$C_{1-6}$ alkyl, —$C_{1-6}$ haloalkyl," and insert -- —$C_{1-6}$alkyl, —$C_{1-6}$haloalkyl, --.

Column 44, Line 62, delete "—$CH_2CH_2OC_{1-6}$ alkyl, —$CH_2CH_2OC_{1-6}$ haloalkyl," and insert -- —$CH_2CH_2OC_{1-6}$alkyl, —$CH_2CH_2OC_{1-6}$haloalkyl, --.

Column 44, Line 63, delete "—$OC_{1-6}$ alkyl," and insert -- —$OC_{1-6}$alkyl, --.

Column 44, Line 65, delete "—$C(O)C_{1-6}$ alkyl," and insert -- —$C(O)C_{1-6}$alkyl, --.

Column 44, Line 66, delete "—$C(O)OC_{1-6}$ alkyl," and insert -- —$C(O)OC_{1-6}$alkyl, --.

Column 45, Line 9, delete "—$C_1$," and insert -- —Cl, --.

Column 45, Line 19, delete "—$C_{1-6}$ haloalkyl," and insert -- —$C_{1-6}$haloalkyl, --.

Column 45, Line 19-20, delete "—$C_{1-6}$ haloalkylOH," and insert -- —$C_{1-6}$haloalkyl-OH, --.

Column 45, Line 22, delete "—$CH_2C(O)C_{1-6}$ alkyl," and insert -- —$CH_2C(O)C_{1-6}$alkyl, --.

Column 45, Line 23, delete "—$CH_2C(O)OC_{1-6}$ alkyl," and insert -- —$CH_2C(O)OC_{1-6}$alkyl, --.

Column 45, Line 26, delete "—$CH_2CH_2$—Re" and insert -- —$CH_2CH_2$—$R^c$ --.

Column 45, Line 27, delete "—$C_{2-6}$ alkynyl," and insert -- —$C_{2-6}$alkynyl, --.

Column 45, Line 28, delete "—O—$C_{1-6}$ alkyl," and insert -- —O—$C_{1-6}$alkyl, --.

Column 45, Line 28, delete "—O—$C_{1-6}$ haloalkyl," and insert -- —O—$C_{1-6}$haloalkyl, --.

Column 45, Line 29, delete "—Ophenyl, —Opyridyl," and insert -- —O-phenyl, —O-pyridyl, --.

Column 45, Line 48, delete "—$C_{1-6}$ alkyl, —$C_{1-6}$ halo alkyl, —$C_{1-6}$ haloalkyl" and insert -- —$C_{1-6}$alkyl, —$C_{1-6}$haloalkyl, —$C_{1-6}$haloalkyl --.

Column 45, Line 51-52, delete "—$CH_2CH_2OC_{1-6}$ alkyl, —$CH_2CH_2OC_{1-6}$halo alkyl," and insert -- —$CH_2CH_2OC_{1-6}$alkyl, —$CH_2CH_2OC_{1-6}$haloalkyl, --.

Column 45, Line 52, after "—OH," insert -- — $OC_{1-6}$alkyl, --.

Column 45, Line 54, delete "—C(O)C$_{1-6}$ alkyl," and insert -- —C(O)C$_{1-6}$alkyl, --.

Column 46, Line 30, delete "C." and insert -- C$_{max}$ --.

Column 54, Line 16 (approx.), delete "Pharamacol." and insert -- Pharmacol --.

Column 55, Line 9 (approx.), delete "diseases." and insert -- diseases; --.

Column 64, Line 21, delete "times," and insert -- times. --.

Column 66, Line 59, delete "Physiol" and insert -- Physiol. --.

Column 67, Line 49, delete "mirtazapine" and insert -- mirtazapine. --.

Column 68, Line 62 (approx.), delete "nethylene" and insert -- methylene --.

Column 69, Line 65, delete "—C$_1$," and insert -- —Cl, --.

Column 71, Line 61, delete "-FH-" and insert -- -1′H- --.

Column 75, Line 4, delete "metheneamine," and insert -- methenamine, --.

Column 75, Line 65, delete "methanamine" and insert -- methenamine --.

Column 76, Line 3-4, delete "methanamine" and insert -- methenamine --.

Column 76, Line 8, delete "—C$_{1-6}$haloalkylOH," and insert -- —C$_{1-6}$haloalkyl-OH, --.

Column 76, Line 10-11, delete "—CH$_2$C(O)C$_{1-6}$ alkyl," and insert -- —CH$_2$C(O)C$_{1-6}$alkyl, --.

Column 76, Line 11-12, delete "—CH$_2$C(O)OC$_{1-6}$ alkyl," and insert -- —CH$_2$C(O)OC$_{1-6}$alkyl, --.

Column 76, Line 15, delete "—CH$_2$CH$_2$—Re," and insert -- —CH$_2$CH$_2$—R$^c$, --.

Column 76, Line 17, delete "—C$_{2-6}$ alkynyl," and insert -- —C$_{2-6}$alkynyl, --.

Column 76, Line 18, delete "—O—C$_{1-6}$ alkyl," and insert -- —O—C$_{1-6}$alkyl, --.

Column 76, Line 18, delete "—O—C$_{1-6}$ haloalkyl," and insert -- —O—C$_{1-6}$haloalkyl, --.

Column 76, Line 19, delete "—Ophenyl, —Opyridyl," and insert -- —O-phenyl, —O-pyridyl, --.

Column 76, Line 27, delete "methanamine" and insert -- methenamine --.

Column 76, Line 67, delete "—C$_{1-6}$ alkyl," and insert -- —C$_{1-6}$alkyl, --.

Column 77, Line 50, delete "—$C_{1-6}$ haloalkylOH, —$C_{1-6}$ haloalkyl" and insert -- —$C_{1-6}$haloalkyl-OH, —$C_{1-6}$haloalkyl --.

Column 78, Line 3-4, delete "—$CH_2C(O)OC_{1-6}$ alkyl," and insert -- —$CH_2C(O)OC_{1-6}$alkyl, --.

Column 78, Line 9 (approx.), delete "—$C_{2-6}$ alkynyl," and insert -- —$C_{2-6}$alkynyl, --.

Column 78, Line 9-10 (approx.), delete "—O—$C_{1-6}$ alkyl," and insert -- —O—$C_{1-6}$alkyl, --.

Column 78, Line 10-11 (approx.), delete "—Ophenyl, —Opyridyl," and insert -- —O-phenyl, —O-pyridyl, --.

Column 79, Line 63, delete "—$C_{1-6}$ alkyl," and insert -- —$C_{1-6}$alkyl, --.

Column 79, Line 64, delete "—$C_{1-6}$ alkyl-O—$C_{1-6}$ alkyl," and insert -- —$C_{1-6}$alkyl-O—$C_{1-6}$alkyl, --.

Column 80, Line 63, delete "—$C_1$," and insert -- —Cl, --.

Column 81, Line 4-5, delete "-6alkyl-O—$C_{1-6}$ alkyl," and insert -- —$C_{1-6}$alkyl-O—$C_{1-6}$alkyl, --.

Column 81, Line 64, after "—H," insert -- —$C_{1-6}$alkyl, --.

Column 82, Line 30, delete "$R^{19}$" and insert -- $R^{10}$ --.

Column 82, Line 38, delete "$R^{19}$" and insert -- $R^{10}$ --.

Column 83, Line 18, delete "lam," and insert -- μm, --.

Column 85, Line 55, delete "-F-H-" and insert -- -1′H- --.

Column 90, Line 24 (approx.), delete "(O %" and insert -- (0% --.

Column 91, Line 2, delete "[M+4]" and insert -- [M+H] --.

Column 91, Line 66, delete "(O %" and insert -- (0% --.

Column 98, Line 7, delete "(O %" and insert -- (0% --.

Column 107, Line 30, delete "[MAI]=" and insert -- [M+H]= --.

Column 163, Line 1, delete "-yl]" and insert -- -yl]amin0 } --.

Column 217, Line 54-64 (approx.), delete " 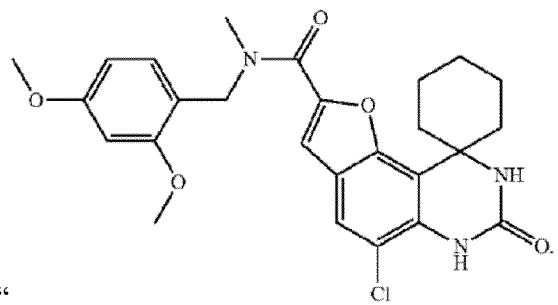 " and insert
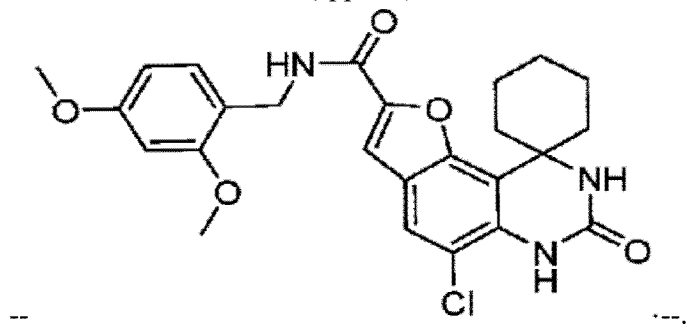
--                                                                                                               --.
Column 222, Line 26 (approx.), delete "(dimethyl amino)" and insert -- (dimethylamino) --.
Column 227, Line 22 (approx.), delete "{4" and insert -- [4 --.
Column 227, Line 23 (approx.), delete "carbonyl}" and insert -- carbonyl] --.
Column 234, Line 22 (approx.), delete "(1" and insert -- [1 --.
Column 234, Line 23 (approx.), delete "yl)" and insert -- yl] --.
Column 270, Line 54-64 (approx.), delete " 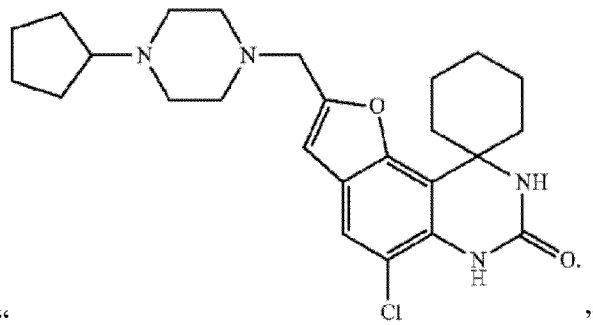 " and insert -- 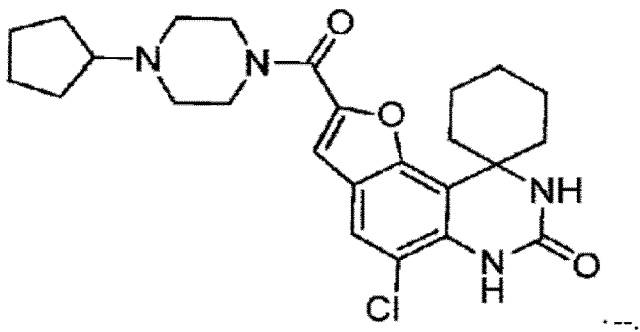 --.

Column 284, Line 49, delete "{(3" and insert -- [(3 --.

Column 284, Line 50, delete "methyl}" and insert -- methyl] --.

Column 315, Line 53, delete "Magellan6" and insert -- Magellan --.

Column 321, Line 10, delete "Neuro." and insert -- Neurol. --.

In the Clams

Column 322, Line 60, Claim 1, delete "—(CH$_2$)$_M$N[(CH$_2$)$_N$R$^{1A}$]—," and insert
-- —(CH$_2$)$_m$N[(CH$_2$)$_n$R$^{1A}$]—, --.

Column 323, Line 57-58, Claim 1, delete "—C$_{1-6}$haloalkylOH," and insert -- —C$_{1-6}$haloalkyl-OH, --.

Column 324, Line 15-16 (approx.), Claim 1, delete "—C$_{1-6}$haloalkylOH," and insert
-- —C$_{1-6}$haloalkyl-OH, --.

Column 325, Line 20, Claim 2, delete "—Opiperidinyl," and insert -- —O-piperidinyl, --.

Column 325, Line 24, Claim 2, delete "—C$_{1-6}$halo alkyl," and insert -- —C$_{1-6}$haloalkyl, --.

Column 325, Line 24, Claim 2, delete "—C$_{1-6}$haloalkylOH," and insert -- —C$_{1-6}$haloalkyl-OH, --.

Column 325, Line 34, Claim 2, delete "—O—C$_{1-6}$halo alkyl," and insert -- —O—C$_{1-6}$haloalkyl, --.

Column 325, Line 35, Claim 2, delete "—Ophenyl, —Opyridyl," and insert -- —O-phenyl,
—O-pyridyl, --.

Column 325, Line 42, Claim 2, delete "—C$_{1-6}$halo alkyl," and insert -- —C$_{1-6}$haloalkyl, --.

Column 325, Line 59-60, Claim 2, delete "—CH$_2$CH$_2$OC$_{1-6}$halo alkyl," and insert
-- —CH$_2$CH$_2$OC$_{1-6}$haloalkyl, --.

Column 326, Line 38, Claim 3, delete "—Opiperidinyl," and insert -- —O-piperidinyl, --.

CERTIFICATE OF CORRECTION (continued)
U.S. Pat. No. 11,685,745 B2

Column 326, Line 42, Claim 3, delete "—$C_{1-6}$halo alkyl," and insert -- —$C_{1-6}$haloalkyl, --.

Column 326, Line 42, Claim 3, delete "—$C_{1-6}$haloalkylOH," and insert -- —$C_{1-6}$haloalkyl-OH, --.

Column 326, Line 53, Claim 3, delete "—Ophenyl, —Opyridyl," and insert -- —O-phenyl, —O-pyridyl, --.

Column 327, Line 28, Claim 3, delete "Spiro" and insert -- spiro --.

Column 328, Line 3, Claim 4, delete "—$C_{1-6}$alkylOH," and insert -- —$C_{1-6}$alkyl-OH, --.

Column 328, Line 4, Claim 4, delete "—$C_{1-6}$haloalkylOH," and insert -- —$C_{1-6}$haloalkyl-OH, --.

Column 328, Line 8-9, Claim 4, delete "—$CH_2C(O)N(C_{1-6}alkyl)_2$," and insert -- —$CH_2C(O)N(C_{1-4}alkyl)_2$, --.

Column 328, Line 11, Claim 4, delete "—$CH_2CH_{2-12}c$" and insert -- —$CH_2CH_2-R^c$ --.

Column 328, Line 15, Claim 4, delete "—Ophenyl, —Opyridyl," and insert -- —O-phenyl, —O-pyridyl, --.

Column 328, Line 35-36, Claim 4, delete "—$C_{1-6}$halo alkyl," and insert -- —$C_{1-6}$haloalkyl, --.

Column 329, Line 7, Claim 5, delete "—$C_{1-6}$halo alkyl," and insert -- —$C_{1-6}$haloalkyl, --.

Column 329, Line 7, Claim 5, delete "—$C_{1-6}$haloalkylOH," and insert -- —$C_{1-6}$haloalkyl-OH, --.

Column 329, Line 14, Claim 5, delete "—$CH_2CH_{2-12}c$" and insert -- —$CH_2CH_2-R^c$ --.

Column 329, Line 18, Claim 5, delete "—Ophenyl, —Opyridyl," and insert -- —O-phenyl, —O-pyridyl, --.

Column 329, Line 25 (approx.), Claim 5, delete "—$C_{1-6}$halo alkyl," and insert -- —$C_{1-6}$haloalkyl, --.

Column 329, Line 37-38 (approx.), Claim 5, delete "—$C_{1-6}$halo alkyl," and insert -- —$C_{1-6}$haloalkyl, --.

Column 329, Line 53, Claim 6, delete "(Ma):" and insert -- (IIIa): --.

Column 330, Line 7, Claim 6, delete "—$C_{1-6}$halo alkyl," and insert -- —$C_{1-6}$haloalkyl, --.

Column 330, Line 7, Claim 6, delete "—$C_{1-6}$haloalkylOH," and insert -- —$C_{1-6}$haloalkyl-OH, --.

Column 330, Line 17, Claim 6, delete "—Ophenyl, —Opyridyl," and insert -- —O-phenyl, —O-pyridyl, --.

Column 330, Line 24 (approx.), Claim 6, delete "—$C_{1-6}$halo alkyl," and insert -- —$C_{1-6}$haloalkyl, --.

Column 330, Line 36-37, Claim 6, delete "—$C_{1-6}$halo alkyl," and insert -- —$C_{1-6}$haloalkyl, --.

Column 331, Line 7, Claim 7, delete "—$C_{1-6}$halo alkyl," and insert -- —$C_{1-6}$haloalkyl, --.

Column 331, Line 8, Claim 7, delete "—$C_{1-6}$haloalkylOH," and insert -- —$C_{1-6}$haloalkyl-OH, --.

Column 331, Line 19, Claim 7, delete "—Ophenyl, —Opyridyl," and insert -- —O-phenyl, —O-pyridyl, --.

Column 332, Line 39, Claim 10, delete "—Opiperidinyl," and insert -- —O-piperidinyl, --.

Column 332, Line 41-42, Claim 10, delete "—$C_{1-6}$haloalkylOH," and insert -- —$C_{1-6}$haloalkyl-OH, --.

Column 332, Line 50-51, Claim 10, delete "—Ophenyl, —Opyridyl," and insert -- —O-phenyl, —O-pyridyl, --.

Column 333, Line 25-26, Claim 11, delete "—Opiperidinyl," and insert -- —O-piperidinyl, --.

Column 333, Line 28, Claim 11, delete "—$C_{1-6}$haloalkylOH," and insert -- —$C_{1-6}$haloalkyl-OH, --.

Column 333, Line 37, Claim 11, delete "—Ophenyl, —Opyridyl," and insert -- —O-phenyl, —O-pyridyl, --.

Column 334, Line 15 (approx.), Claim 11, delete "—Ci-6haloalkyl," and insert -- —$C_{1-6}$haloalkyl, --.

Column 334, Line 33-34, Claim 12, delete "—$C_{1-6}$haloalkylOH," and insert -- —$C_{1-6}$haloalkyl-OH, --.

Column 334, Line 42-43, Claim 12, delete "—Ophenyl, —Opyridyl," and insert -- —O-phenyl, —O-pyridyl, --.

Column 335, Line 6-7, Claim 13, delete "-2-oxa-8-azaspiro[4.5]decane," and insert -- 2-oxa-8-azaspiro[4.5]decane, --.

Column 335, Line 13, Claim 13, delete "5,6,7,8-tetrahydroimidazo[1,2-c]pyrazine," and insert -- 5,6,7,8-tetrahydroimidazo[1,2-α]pyrazine, --.

Column 335, Line 19, Claim 13, delete "thieno]3,2-c[pyridine]," and insert -- thieno[3,2-c]pyridine], --.

Column 335, Line 20, Claim 13, delete "]2,3-c[pyridine]," and insert -- [2,3-c]pyridine], --.

Column 335, Line 35, Claim 13, delete "—$CH_2$-thiophene," and insert -- —$CH_2$thiophene, --.

Column 335, Line 36, Claim 13, delete "—C(O)-tetrahydrofuran," and insert

-- —C(O)tetrahydrofuran, --.

Column 335, Line 52, Claim 16, delete "—$C_{1-6}$haloalkylOH," and insert -- —$C_{1-6}$haloalkyl-OH, --.

Column 335, Line 61, Claim 16, delete "—Ophenyl, —Opyridyl," and insert -- —O-phenyl, —O-pyridyl, --.

Column 336, Line 36, Claim 17, delete "—Opiperidinyl," and insert -- —O-piperidinyl, --.

Column 336, Line 38-39, Claim 17, delete "—$C_{1-6}$haloalkylOH," and insert -- —$C_{1-6}$haloalkyl-OH, --.

Column 336, Line 45, Claim 17, delete "—$CH_2CH_{2-12}c$," and insert -- —$CH_2CH_2$-$R^c$, --.

Column 336, Line 47, Claim 17, delete "—Ophenyl, —Opyridyl," and insert -- —O-phenyl, —O-pyridyl, --.

Column 337, Line 43-44, Claim 18, delete "—$C_{1-6}$haloalkylOH," and insert -- —$C_{1-6}$haloalkyl-OH, --.

Column 337, Line 52-53, Claim 18, delete "—Ophenyl, —Opyridyl," and insert -- —O-phenyl, —O-pyridyl, --.

Column 338, Line 58, Claim 20, delete "—Opiperidinyl," and insert -- —O-piperidinyl, --.

Column 338, Line 60-61, Claim 20, delete "—$C_{1-6}$haloalkylOH," and insert -- —$C_{1-6}$haloalkyl-OH, --.

Column 339, Line 2-3, Claim 20, delete "—Ophenyl, —Opyridyl," and insert -- —O-phenyl, —O-pyridyl, --.

Column 339, Line 45, Claim 21, delete "—Opiperidinyl," and insert -- —O-piperidinyl, --.

Column 339, Line 47, Claim 21, delete "—$C_{1-6}$halo alkyl," and insert -- —$C_{1-6}$haloalkyl, --.

Column 339, Line 47-48, Claim 21, delete "—$C_{1-6}$haloalkylOH," and insert -- —$C_{1-6}$haloalkyl-OH, --.

Column 339, Line 56, Claim 21, delete "—Ophenyl, —Opyridyl," and insert -- —O-phenyl, —O-pyridyl, --.

Column 340, Line 52-53, Claim 22, delete "—$C_{1-6}$haloalkylOH," and insert -- —$C_{1-6}$haloalkyl-OH, --.

Column 340, Line 61-62, Claim 22, delete "—Ophenyl, —Opyridyl," and insert -- —O-phenyl, —O-pyridyl, --.

Column 342, Line 5, Claim 24, delete "[5,4f]" and insert -- [5,4-f] --.

Column 342, Line 43, Claim 24, delete "[5-" and insert -- {5- --.

Column 342, Line 44, Claim 24, delete "yl]" and insert -- yl} --.

Column 352, Line 14 (approx.), Claim 24, delete "[(1 S," and insert -- [(1S, --.

Column 355, Line 51, Claim 24, delete "[5,4f]" and insert -- [5,4-f] --.

Column 355, Line 60, Claim 24, delete "[5,4f]" and insert -- [5,4-f] --.

Column 358, Line 60, Claim 24, delete "[5,4f]" and insert -- [5,4-f] --.

Column 359, Line 41, Claim 24, delete "2-({5" and insert -- 2-[({5 --.

Column 361, Line 45, Claim 24, delete "-7'-" and insert -- -2'- --.

Column 361, Line 47, Claim 24, delete "-7'-" and insert -- -2'- --.

Column 361, Line 54, Claim 24, delete "[2 3-f]" and insert -- [2,3-f] --.

Column 362, Line 4 (approx.), Claim 24, delete "-7'-" and insert -- -2'- --.

Column 362, Line 8 (approx.), Claim 24, delete "-7'-" and insert -- -2'- --.

Column 362, Line 10 (approx.), Claim 24, delete "-7'-" and insert -- -2'- --.

Column 362, Line 45, Claim 24, delete "-7'-" and insert -- -2'- --.

Column 362, Line 49, Claim 24, delete "-7'-" and insert -- -2'- --.

Column 362, Line 51, Claim 24, delete "-7'-" and insert -- -2'- --.

Column 364, Line 3, Claim 24, delete "-7'-" and insert -- -2'- --.

Column 364, Line 4, Claim 24, delete "-7'-" and insert -- -2'- --.

Column 364, Line 9, Claim 24, delete "-7'-" and insert -- -2'- --.

Column 364, Line 35, Claim 24, delete "{5H,6H,7H, 8H-imidazo" and insert -- {5H,6H,7H,8H-imidazo --.

Column 365, Line 26, Claim 24, delete "-7'-" and insert -- -2'- --.

Column 366, Line 51, Claim 24, delete "-7'-" and insert -- -2'- --.

Column 366, Line 53, Claim 24, delete "-7'-" and insert -- -2'- --.

Column 366, Line 55, Claim 24, delete "-7'-" and insert -- -2'- --.

Column 366, Line 61, Claim 24, delete "-7'-" and insert -- -2'- --.

Column 367, Line 31, Claim 24, delete "-7'-" and insert -- -2'- --.

Column 367, Line 34, Claim 24, delete "-7'-" and insert -- -2'- --.

Column 367, Line 37, Claim 24, delete "-7'-" and insert -- -2'- --.

Column 367, Line 44, Claim 24, delete "-7'-" and insert -- -2'- --.

Column 368, Line 9 (approx.), Claim 24, delete "-7'-" and insert -- -2'- --.

Column 368, Line 11 (approx.), Claim 24, delete "-7'-" and insert -- -2'- --.

Column 368, Line 16 (approx.), Claim 24, delete "-7'-" and insert -- -2'- --.

Column 368, Line 55, Claim 24, delete "-7'-" and insert -- -2'- --.

Column 368, Line 57, Claim 24, delete "-7'-" and insert -- -2'- --.

Column 368, Line 59, Claim 24, delete "-7'-" and insert -- -2'- --.

Column 368, Line 61, Claim 24, delete "[2,3-]" and insert -- [2,3-f] --.

Column 368, Line 66, Claim 24, delete "[2,3-]" and insert -- [2,3-f] --.

Column 369, Line 12, Claim 24, delete "[2,3-]" and insert -- [2,3-f] --.

Column 369, Line 30, Claim 24, delete "-7'-" and insert -- -2'- --.

Column 369, Line 35, Claim 24, delete "[2,3-]" and insert -- [2,3-f] --.

Column 369, Line 36, Claim 24, delete "-7'-" and insert -- -2'- --.

Column 369, Line 40, Claim 24, delete "-7'-" and insert -- -2'- --.

Column 369, Line 54, Claim 24, delete "[2,3-]" and insert -- [2,3-f] --.

Column 369, Line 60, Claim 24, delete "[2,3-]" and insert -- [2,3-f] --.

Column 370, Line 7 (approx.), Claim 24, delete "-7'-" and insert -- -2'- --.

Column 370, Line 10 (approx.), In Claim 24, delete "-7'-" and insert -- -2'- --.

Column 370, Line 14 (approx.), In Claim 24, delete "-7'-" and insert -- -2'- --.

Column 370, Line 24, Claim 24, delete "[2,3-]" and insert -- [2,3-f] --.

Column 370, Line 42, Claim 24, delete "[2,3-]" and insert -- [2,3-f] --.

Column 370, Line 53, Claim 24, delete "-7'-" and insert -- -2'- --.

Column 370, Line 58, Claim 24, delete "-7'-" and insert -- -2'- --.

Column 370, Line 59, Claim 24, delete "-7'-" and insert -- -2'- --.

Column 370, Line 64, Claim 24, delete "-7'-" and insert -- -2'- --.

Column 370, Line 65, Claim 24, delete "-7'-" and insert -- -2'- --.

Column 371, Line 2, Claim 24, delete "[2,3-]" and insert -- [2,3-f] --.

Column 371, Line 37, Claim 24, delete "-7'-" and insert -- -2'- --.

Column 371, Line 40, Claim 24, delete "-7'-" and insert -- -2'- --.

Column 372, Line 10 (approx.), Claim 24, delete "-7'-" and insert -- -2'- --.

Column 372, Line 13 (approx.), Claim 24, delete "-7'-" and insert -- -2'- --.

Column 372, Line 19 (approx.), Claim 24, delete "-7'-" and insert -- -2'- --.

Column 373, Line 35, Claim 24, delete "-7'-" and insert -- -2'- --.

Column 373, Line 62, Claim 24, delete "[{(1R," and insert -- {[(1R, --.

Column 374, Line 17, Claim 24, delete "-7'-" and insert -- -2'- --.

Column 374, Line 20, Claim 24, delete "-7'-" and insert -- -2'- --.

Column 375, Line 39, Claim 24, delete "-7'-" and insert -- -2'- --.

Column 375, Line 42, Claim 24, delete "-7'-" and insert -- -2'- --.

Column 375, Line 45, Claim 24, delete "-7'-" and insert -- -2'- --.

Column 375, Line 48, Claim 24, delete "-7'-" and insert -- -2'- --.

Column 376, Line 17 (approx.), Claim 24, delete "-7'-" and insert -- -2'- --.

CERTIFICATE OF CORRECTION (continued)
U.S. Pat. No. 11,685,745 B2

Column 376, Line 20 (approx.), Claim 24, delete "-7'-" and insert -- -2'- --.

Column 376, Line 26, Claim 24, delete "-7'-" and insert -- -2'- --.

Column 376, Line 65, Claim 24, delete "-7'-" and insert -- -2'- --.

Column 377, Line 1, Claim 24, delete "-7'-" and insert -- -2'- --.

Column 377, Line 10, Claim 24, delete "{2" and insert -- [2 --.

Column 377, Line 12, Claim 24, delete "ethyl}" and insert -- ethyl] --.

Column 377, Line 27, Claim 24, delete "[2,3-]" and insert -- [2,3-f] --.

Column 377, Line 40, Claim 24, delete "-7'-" and insert -- -2'- --.

Column 377, Line 43, Claim 24, delete "-7'-" and insert -- -2'- --.

Column 377, Line 46, Claim 24, delete "-7'-" and insert -- -2'- --.